(12) United States Patent
Kim et al.

(10) Patent No.: US 11,999,952 B2
(45) Date of Patent: Jun. 4, 2024

(54) ARTIFICIALLY-MANIPULATED NEOVASCULARIZATION REGULATORY SYSTEM

(71) Applicants: TOOLGEN INCORPORATED, Seoul (KR); SEOUL NATIONAL UNIVERSITY R&DB FOUNDATION, Seoul (KR); SEOUL NATIONAL UNIVERSITY HOSPITAL, Seoul (KR)

(72) Inventors: Jeong Hun Kim, Seoul (KR); Sung Wook Park, Seoul (KR); Seokjoong Kim, Seoul (KR); Dong Woo Song, Seoul (KR)

(73) Assignees: TOOLGEN INCORPORATED, Seoul (KR); SEOUL NATIONAL UNIVERSITY R&DB FOUNDATION, Seoul (KR); SEOUL NATIONAL UNIVERSITY HOSPITAL, Seoul (KR); INSTITUTE FOR BASIC SCIENCE, Daejeon (KR)

( * ) Notice: Subject to any disclaimer, the term of this patent is extended or adjusted under 35 U.S.C. 154(b) by 253 days.

(21) Appl. No.: 17/236,660

(22) Filed: Apr. 21, 2021

(65) Prior Publication Data
US 2021/0254054 A1 Aug. 19, 2021

Related U.S. Application Data

(63) Continuation of application No. 15/953,141, filed on Apr. 13, 2018, now abandoned, which is a continuation of application No. PCT/KR2017/009078, filed on Aug. 21, 2017.

(60) Provisional application No. 62/376,998, filed on Aug. 19, 2016.

(51) Int. Cl.
| | | |
|---|---|---|
| *C12N 15/00* | (2006.01) | |
| *A61K 9/00* | (2006.01) | |
| *A61K 38/46* | (2006.01) | |
| *A61K 48/00* | (2006.01) | |
| *C07K 14/47* | (2006.01) | |
| *C07K 14/515* | (2006.01) | |
| *C07K 14/52* | (2006.01) | |
| *C12N 9/22* | (2006.01) | |
| *C12N 15/11* | (2006.01) | |
| *C12N 15/113* | (2010.01) | |
| *C12N 15/86* | (2006.01) | |

(52) U.S. Cl.
CPC .......... *C12N 15/11* (2013.01); *A61K 9/0048* (2013.01); *A61K 38/465* (2013.01); *A61K 48/00* (2013.01); *A61K 48/005* (2013.01); *C07K 14/4702* (2013.01); *C07K 14/515* (2013.01); *C07K 14/52* (2013.01); *C12N 9/22* (2013.01); *C12N 15/113* (2013.01); *C12N 15/1136* (2013.01); *C12N 15/86* (2013.01); *A01K 2227/105* (2013.01); *A01K 2267/03* (2013.01); *C12N 2310/20* (2017.05); *C12N 2750/14143* (2013.01); *Y02A 50/30* (2018.01)

(58) Field of Classification Search
CPC ........ C12N 15/11; C12N 9/22; C12N 15/113; C12N 15/1136; C12N 15/86; C12N 2310/20; C12N 2750/14143; A61K 9/0048; A61K 38/465; A61K 48/00; A61K 48/005; C07K 14/4702; C07K 14/515; C07K 14/52; Y02A 50/30; A01K 2227/105; A01K 2267/03
See application file for complete search history.

(56) References Cited

U.S. PATENT DOCUMENTS

| | | |
|---|---|---|
| 8,889,418 B2 | 11/2014 | Zhang et al. |
| 2009/0192104 A1 | 7/2009 | McSwiggen et al. |
| 2014/0273234 A1* | 9/2014 | Zhang ............ C12N 9/96 435/320.1 |
| 2015/0203872 A1 | 7/2015 | Zhang |
| 2015/0232881 A1 | 8/2015 | Glucksmann et al. |

(Continued)

FOREIGN PATENT DOCUMENTS

| | | |
|---|---|---|
| CN | 105658805 A | 6/2016 |
| EP | 3492096 A1 | 6/2019 |

(Continued)

OTHER PUBLICATIONS

Kim et al in "In vivo genome editing with a small Cas9 orthologue derived from Campylobacter jejuni" (Nature Communications, published Feb. 21, 2017; pp. 1-12). (Year: 2017).*

(Continued)

*Primary Examiner* — Catherine S Hibbert
(74) *Attorney, Agent, or Firm* — Harness, Dickey & Pierce, P.L.C.

(57) ABSTRACT

The present invention relates to an artificially manipulated neovascularization-associated factor for regulating neovascularization and a use thereof. More particularly, the present invention relates to a system for artificially regulating neovascularization, which includes an artificially manipulated neovascularization-associated factor for regulating neovascularization and/or a composition for artificially manipulating the neovascularization-associated factor. In a specific aspect, a neovascularization regulatory system including a neovascularization-associated factor such as artificially manipulated VEGFA, HIF1A, ANGPT2, EPAS1, or ANGPTL4 and/or an expression product thereof is provided.

11 Claims, 21 Drawing Sheets

Specification includes a Sequence Listing.

(56) References Cited

U.S. PATENT DOCUMENTS

| | | | |
|---|---|---|---|
| 2016/0201089 A1 | 7/2016 | Gersbach et al. | |
| 2016/0215300 A1 | 7/2016 | May et al. | |
| 2017/0065636 A1* | 3/2017 | Moriarity | C12N 9/96 |
| 2017/0137801 A1 | 5/2017 | Liras et al. | |
| 2020/0405639 A1* | 12/2020 | Zhang | C12N 15/63 |

FOREIGN PATENT DOCUMENTS

| | | | | |
|---|---|---|---|---|
| JP | 2007-528736 A | 10/2007 | | |
| JP | 2016/521555 A | 7/2016 | | |
| JP | 2016/523564 A | 8/2016 | | |
| KR | 2017-0068400 A | 6/2017 | | |
| WO | WO-2005/089224 A2 | 9/2005 | | |
| WO | WO-2008/109381 A2 | 9/2008 | | |
| WO | WO-2008/154482 A2 | 12/2008 | | |
| WO | WO-2008154482 A2 * | 12/2008 | | C12N 15/1136 |
| WO | WO-2008/154482 A3 | 4/2009 | | |
| WO | WO-2010/078517 A2 | 7/2010 | | |
| WO | WO-2010/078517 A3 | 10/2010 | | |
| WO | WO-2012/100172 A2 | 7/2012 | | |
| WO | WO-2012/100172 A3 | 10/2012 | | |
| WO | WO-2014/144288 A1 | 9/2014 | | |
| WO | WO-2014/197748 A2 | 12/2014 | | |
| WO | WO-2014/204729 A1 | 12/2014 | | |
| WO | WO-2015/048577 A2 | 4/2015 | | |
| WO | WO-2015/070083 A1 | 5/2015 | | |
| WO | WO-2015-089462 A1 | 6/2015 | | |
| WO | WO-2016/021973 A1 | 2/2016 | | |
| WO | WO-2017/099494 A1 | 6/2017 | | |
| WO | WO-2017/099494 A8 | 8/2017 | | |

OTHER PUBLICATIONS

Kim et al Supplemental Information for "In vivo genome editing with a small Cas9 orthologue derived from Campylobacter jejuni" (Nature Communications, published Feb. 21, 2017; pp. 1-12). (Year: 2017).*
Score report for SEQ ID No. 20 to Lu & Liang in WO2008154482. (Year: 2008).*
Yiu, et al. (2016) "Genomic Disruption of VEGF-A Expression in Human Retinal Pigment Epithelial Cells Using CRISPR-Cas9 Endonuclease." *Investigative Ophthalmology & Visual Science* (IOVS) vol. 57(No. 13):5490-5497.
International Search Report, dated Dec. 15, 2017 in PCT/KR2017/009078 (WO2018034554) with English translation.
John G Doench et al: "Optimized sgRNA design to maximize activity and minimize off-target effects of CRISPR-Cas9", Nature Biotechnology, vol. 34, No. 2, Jan. 18, 2016, pp. 184-191 & John G Doench et al, "Optimized sgRNA design to maximize activity and minimize off-target effects of CRISPR-Cas9-Supplementary table 21, excerpt", Jan. 18, 2016.
Ines Fonfara et al, "Phylogeny of Cas9 determines functional exchaneability of dual-RNA and Cas9 among orthologous ttype II CRISPR-Cas systems", Nucleic acids research acvance access, vol. 42, No. 4, Nov. 22, 2013, pp. 2577-2590.
S. Chen et al, "Global microRNA depletion suppresses tumor angiogenesis", Genes and Development, vol. 28, No. 10, May 1, 2014, pp. 1054-1067.
Partial Supplementary Search Report issued in the corresponding European Patent Application No. 17841736.6, dated Mar. 4, 2020.
ARVO Annual Meeting Abstract, Abstract No. 1159, May 1, 2016.
Office Action issued in the corresponding Japanese Patent Application No. 2019-510289, dated Feb. 27, 2020.
Decision to Reject issued in the corresponding Korean Patent Application No. 10-2017- 0105303, dated Mar. 26, 2020.

Kim E et al, "In vivo genome editing with a small Cas9 orthologue derived from Campylobacter jejuni", Nature Communications, vol. 8, article No. 14500, Feb. 27, 2017.
Decision to Grant issued in the corresponding KR Patent Application No. 10-2017-0105303, dated May 21, 2020.
Partial Search Report issued in the corresponding European Patent Application No. 17841736.6.
Decision to Reject issued in the corresponding Korean Patent Application No. 10-2017-0105303.
Office Action issued in the corresponding Japanese Patent Application No. 2019-510289.
Decision to Grant issued in the corresponding KR Patent Application No. 10-2017-0105303.
Search Report and Written Opinion issued in the corresponding Singapore Patent Application No. 11201901306X, dated Jun. 1, 2020.
John G Doench et al, "Optimized sgRNA design to maximize activity and minimize off-target effects of CRISPR-Cas9-Supplementary table 22, excerpt", Nature Biotechnology, Jan. 18, 2016.
Shiruyeh Schokrpur et al, "CRISPR-Mediated VHL Knockout Generates an Improved Model for Metastattic Renal Cell Carcinoma", Scientific Reports, vol. 6, No. 1, Jun. 30, 2016.
Shiruyeh Schokrpur et al, "Supplementary Information—CRISPR-Mediated VHL Knockout Generates an Improved Model for Metastatic Renal Cell Carcinoma", Scientific Reports, Jun. 30, 2016.
Milica Vukovic et al, "Hif-1? and Hif-2? synergize to suppress AML development but are dispensable for disease maintenance", The Journal of Experimental Medicine, vol. 212, No. 13, Dec. 14, 2015, pp. 2223-2234.
Philip M. Elks et al, "Exploring the HIFs, buts and maybes of hypoxia signalling in disease: lessons from zebrafish models", Disease Models & Mechanisms, vol. 8, No. 11, Oct. 28, 2015, pp. 1349-1360.
Aswani Dutt Vadlapudi et al, "Hypoxia-Inducible Factor-1 (HIF-1): A Potential Target for Intervention in Ocular Neovascular Diseases", Current Drug Targets, vol. 14, No. 8, May 2013, pp. 919-935.
Subhani Saima et al, "HIF inhibitors for ischemic retinopathies and cancers: options beyond anti-VEGF therapies", Angiogenesis, Kluwer, Dordrecht, Nl, vol. 19, No. 3, May 4, 2016, pp. 257-273.
Extended European Search Report issued in the corresponding European Patent Application No. 17841736.6, dated Jun. 17, 2020.
Office Action from corresponding Korean Patent Application No. 10-2020-0090852, dated Sep. 16, 2020.
Office Action from corresponding Japanese Patent Application No. 2019-510289, dated Nov. 17, 2020.
Glenn Yiu et al, "Genomic Disruption of VEGF in Human Retinal Pigment Epithelial Cells using CRISPR-Cas9 Endonuclease", Investigative Ophthalmology & Visual Science Sep. 2016, vol. 57, 1159.
Office Action (Non-Final) from corresponding U.S. Appl. No. 15/953,141, dated Oct. 2, 2018.
Office Action (Final) from corresponding U.S. Appl. No. 15/953,141, dated Mar. 14, 2019.
Extended European Search Report from corresponding European Patent Application No. 21210792.4, dated May 17, 2022.
Office Action from corresponding Chinese Patent Application No. 201780064951.7, dated May 23, 2022.
Office Action from corresponding Japanese Patent Application No. 2021-212083 dated Jan. 31, 2023.
Notice of Acceptance from corresponding Australian Patent Application No. 2017313616, dated Nov. 15, 2022.
Golias T, et al. Hypoxic repression of pyruvate dehydrogenase activity is necessary for metabolic reprogramming and growth of model tumours. Scientific reports. Aug. 8, 2016;6(1):1-1.
Office Action from corresponding European Patent Application No. 21210792.4, dated Mar. 27, 2024.

* cited by examiner

| Gene | No. | Species | RGEN Target | Mismatch | | | More than minimum frequency | Insertions | Deletions | Indel ratio (%) |
| --- | --- | --- | --- | --- | --- | --- | --- | --- | --- | --- |
| | | | | 0 bp | 1 bp | 2 bp | | | | |
| VEGFA | 1 | Human | GTAGAGCAGCAAGCAAGGCTC (SEQ ID NO: 1) | 1 | 0 | 0 | 13619 | 3 | 206 | 1.535 |
| VEGFA | 2 | Human | CTTTCTGTCCTCAGTGGTCCCA (SEQ ID NO: 2) | 1 | 0 | 0 | 44326 | 128 | 396 | 1.182 |
| VEGFA | 3 | Human | GAGACCCTGGTGGACATCTTCC (SEQ ID NO: 3) | 1 | 0 | 0 | 85413 | 884 | 3266 | 4.859 |
| VEGFA | 4 | Human | TTCCAGGAGTACCCTGATGAGA (SEQ ID NO: 4) | 1 | 0 | 0 | 60920 | 1188 | 13853 | 24.690 |
| VEGFA | 5 | Human | TTGAAGATGTACTCGATCTCAT (SEQ ID NO: 5) | 1 | 0 | 0 | 46994 | 68 | 165 | 0.496 |
| VEGFA | 6 | Human | AGGGGCACACAGGATGGCTTGA (SEQ ID NO: 6) | 1 | 0 | 0 | 38858 | 10 | 7 | 0.44 |
| VEGFA | 7 | Human | AGCAGCCCCGCATCGCATCAG (SEQ ID NO: 7) | 1 | 0 | 0 | 16605 | 684 | 6441 | 42.939 |
| VEGFA | 8 | Human | GCAGCAGCCCCGCATCGCATC (SEQ ID NO: 8) | 1 | 0 | 0 | 36464 | 29 | 54 | 0.228 |
| VEGFA | 9 | Human | GTGGATGTTGGACTCCTCAGTGG (SEQ ID NO: 9) | 1 | 0 | 0 | 61570 | 6313 | 38511 | 72.802 |
| VEGFA | 10 | Human | TGGTGATGTTGGACTCCTCAGT (SEQ ID NO: 10) | 1 | 0 | 0 | 41580 | 3087 | 21321 | 58.701 |
| VEGFA | 11 | Human | CATGGTGATGTTGGACTCCTCA (SEQ ID NO: 11) | 1 | 0 | 0 | 42569 | 382 | 2057 | 5.730 |
| VEGFA | 12 | Human | ATGTCGGATCAAACCTCACCAAG (SEQ ID NO: 12) | 1 | 0 | 0 | 63996 | 24 | 357 | 0.595 |
| VEGFA | 13 | Human | CACATAGGAGAGATGAGCTTCC (SEQ ID NO: 13) | 1 | 0 | 0 | 52511 | 11 | 77 | 0.168 |

FIG. 16

| Gene | No. | Species | RGEN Target | Mismatch 0 bp | Mismatch 1 bp | Mismatch 2 bp | More than minimum frequency | Insertions | Deletions | Indel ratio (%) |
|---|---|---|---|---|---|---|---|---|---|---|
| HIF1A | 1 | Human | ACTGTACCAGCATCCAGAAGTTT (SEQ ID NO: 14) | 1 | 0 | 0 | 59642 | 2152 | 1087 | 5.4324234 |
| HIF1A | 2 | Human | ATTTGGATATTGAAGATGACAT (SEQ ID NO: 15) | 1 | 0 | 0 | 61221 | 0 | 21 | 0.03430196 |
| HIF1A | 3 | Human | ATTACATTCTGATAAIGTGA (SEQ ID NO: 16) | 1 | 0 | 0 | 63190 | 0 | 7 | 0.011 |
| HIF1A | 4 | Human | ATGTGTTTACAGTTGAACTAA (SEQ ID NO: 17) | 1 | 0 | 0 | 11164 | 4 | 5 | 0.081 |
| HIF1A | 5 | Human | CTGTGTCCAGTTAGTTCAAACT (SEQ ID NO: 18) | 1 | 0 | 0 | 14828 | 641 | 2033 | 17.9559 |
| HIF1A | 6 | Human | ATGGTCACATGGATGAGTAAAA (SEQ ID NO: 19) | 1 | 0 | 0 | 12607 | 248 | 3189 | 27.255 |
| HIF1A | 7 | Human | CATGAGGGAAATGAGAGAAATGC (SEQ ID NO: 20) | 1 | 0 | 0 | 13033 | 1772 | 5744 | 57.771 |
| HIF1A | 8 | Human | CCCAGTGAGAAAGGGAAGAA (SEQ ID NO: 21) | 1 | 0 | 0 | 10165 | 0 | 0 | 0.000 |
| HIF1A | 9 | Human | TTGTGAAAAGGGTAAAGAACA (SEQ ID NO: 22) | 1 | 0 | 0 | 19888 | 35 | 229 | 1.327 |
| HIF1A | 10 | Human | ATAGTTGTTCCTCGGCTAGTTA (SEQ ID NO: 23) | 1 | 0 | 0 | 31783 | 62 | 66 | 0.403 |
| HIF1A | 11 | Human | TCATAGTTCTTCCTCGGCTAGT (SEQ ID NO: 24) | 1 | 0 | 0 | 25063 | 5 | 8 | 0.052 |
| HIF1A | 12 | Human | TGTTCTTCATACACAAGGTATTG (SEQ ID NO: 25) | 1 | 0 | 0 | 67151 | 8 | 53 | 0.091 |
| HIF1A | 13 | Human | TACGTGAATGTGGCCTGTGCAG (SEQ ID NO: 26) | 1 | 0 | 0 | 41784 | 2090 | 21711 | 56.9603 |
| HIF1A | 14 | Human | CTGLACAGECCACATTCACGTA (SEQ ID NO: 27) | 1 | 0 | 0 | 51781 | 140 | 171 | 0.601 |
| HIF1A | 15 | Human | CTGAGGTTGGTTACTGTTGGTA (SEQ ID NO: 28) | 1 | 0 | 0 | 42355 | 137 | 738 | 2.066 |
| HIF1A | 16 | Human | CAGGTCATAAGGTGGTTCTTAT (SEQ ID NO: 29) | 1 | 0 | 0 | 42693 | 607 | 3281 | 9.107 |
| HIF1A | 17 | Human | ACCAAGCAGGTCATAGGTGGTT (SEQ ID NO: 30) | 1 | 0 | 0 | 58575 | 0 | 4 | 0.007 |
| HIF1A | 18 | Human | TTAGATAGCAAGACTTTCCTCA (SEQ ID NO: 31) | 1 | 0 | 0 | 58810 | 1028 | 2437 | 5.795 |

FIG. 17

```
Homo_I03E04       TCATCCATGTGACCATGAGGAAATGAGAGAAATGCTTACACACAGAAATG

Macaque_I03E04    TCATCCATGTGACCATGAGGAAATGAGAGAAATGCTTACACACAGAAATG

Marmoset_I03E04   TCATCCATGTGACCATGAGGAAATGAGAGAAATGCTTACACACAGAAATG

Pig_I03E04        TCATCCGTGCGACCATGAGGAAATGAGAGAAATGCTTACACACAGAAATG

Dog_I03E04        TCATCCATGTGACCATGAGGAAATGAGAGAAATGCTTACACACAGAAATG

Mouse_I03E04      TCATCCATGTGACCATGAGGAAATGAGAGAAATGCTTACACACAGAAATG

| Gene | No. | Species | RGEN Target | Mismatch | | | More than minimum frequency | Insertions | Deletions | Indel ratio (%) |
|---|---|---|---|---|---|---|---|---|---|---|
| | | | | 0 bp | 1 bp | 2 bp | | | | |
| ANGPT2 | 1 | Human | TCAGGTCCAGCATGGTCCTGC (SEQ ID NO: 32) | 1 | 0 | 0 | 40481 | 0 | 20 | 0.049 |
| ANGPT2 | 2 | Human | CGGCGGCGTCCTCTGCACAGCA (SEQ ID NO: 33) | 1 | 0 | 0 | 25828 | 1018 | 3294 | 16.695 |
| ANGPT2 | 3 | Human | GCTGTGCAGAGGACGCGCCGC (SEQ ID NO: 34) | 1 | 0 | 0 | 32576 | 3733 | 13686 | 50.465 |
| ANGPT2 | 4 | Human | ATCGTATTCGAGCGGCGGTCC (SEQ ID NO: 35) | 1 | 0 | 0 | 48216 | 30 | 56 | 0.178 |
| ANGPT2 | 5 | Human | GATGTCTCCAGCACTTGCAGC (SEQ ID NO: 36) | 1 | 0 | 0 | 38396 | 0 | 0 | 0.000 |
| ANGPT2 | 6 | Human | AGTGCTGGAGAACATCATGAAA (SEQ ID NO: 37) | 1 | 0 | 0 | 47931 | 854 | 12527 | 28.123 |
| ANGPT2 | 7 | Human | ACAACATGAAGAAGAAATGGT (SEQ ID NO: 38) | 1 | 0 | 0 | 24395 | 1370 | 10712 | 49.527 |
| ANGPT2 | 8 | Human | AAAATGGTAGAAGAATAGACAGAA (SEQ ID NO: 39) | 1 | 0 | 0 | 23618 | 296 | 983 | 5.193 |
| ANGPT2 | 9 | Human | TTCTATCATCACAGACCCGTCTGG (SEQ ID NO: 40) | 1 | 0 | 0 | 36732 | 17 | 15 | 0.087 |
| ANGPT2 | 10 | Human | AAGTTCAAGTCTCGTGGTCTGA (SEQ ID NO: 41) | 1 | 0 | 0 | 35259 | 95 | 374 | 1.330 |
| ANGPT2 | 11 | Human | ACGAGACTTGAACTTCAGCTCT (SEQ ID NO: 42) | 3 | 0 | 0 | 28139 | 7 | 95 | 0.362 |
| ANGPT2 | 12 | Human | AAGAAGGTGCTAGCTATGGAAAG (SEQ ID NO: 43) | 1 | 0 | 0 | 17482 | 210 | 4907 | 29.273 |
| ANGPT2 | 13 | Human | CATGATGTGCTTGTCTTCCATA (SEQ ID NO: 44) | 1 | 0 | 0 | 7694 | 0 | 3 | 0.039 |

FIG. 19

| Gene | No. | Species | RGEN Target | Mismatch | | | More than minimum frequency | Insertions | Deletions | Indel ratio (%) |
|---|---|---|---|---|---|---|---|---|---|---|
| | | | | 0 bp | 1 bp | 2 bp | | | | |
| EPAS1 | 1 | Human | AACACCTCCGTCCTTGCTCC (SEQ ID NO: 45) | 1 | 0 | 0 | 66871 | 370 | 2024 | 3.580 |
| EPAS1 | 2 | Human | GAAGCTGACCAGCAGATGGACA (SEQ ID NO: 46) | 1 | 0 | 0 | 22285 | 53 | 0 | 0.238 |
| EPAS1 | 3 | Human | GCAATGAAACCCTCCAAGGCTT (SEQ ID NO: 47) | 1 | 0 | 0 | 20616 | 556 | 11383 | 57.911 |
| EPAS1 | 4 | Human | AAAACATCAGCAAGTTCATGGG (SEQ ID NO: 48) | 1 | 0 | 0 | 43752 | 565 | 1817 | 5.444 |
| EPAS1 | 5 | Human | GCAAGTTCATGGGACTTACACA (SEQ ID NO: 49) | 1 | 0 | 0 | 42717 | 2201 | 24304 | 62.048 |
| EPAS1 | 6 | Human | GGTCGCAGGGATGAGTGAAGTC (SEQ ID NO: 50) | 1 | 0 | 0 | 76378 | 3576 | 33124 | 48.050 |
| EPAS1 | 7 | Human | GCGGGACTTCTTCATGAGGATG (SEQ ID NO: 51) | 1 | 0 | 0 | 87392 | 0 | 3 | 0.003 |
| EPAS1 | 8 | Human | GAAGTGCACGGTCACCAACAGA (SEQ ID NO: 52) | 1 | 0 | 0 | 66339 | 180 | 909 | 1.642 |
| EPAS1 | 9 | Human | ACAGTACGGCCCTCTGTTGGTGA (SEQ ID NO: 53) | 1 | 0 | 0 | 81266 | 571 | 3786 | 5.361 |
| EPAS1 | 10 | Human | TCCAGGTGGCTGACTTGAAGTT (SEQ ID NO: 54) | 1 | 0 | 0 | 72666 | 1733 | 12723 | 19.894 |
| EPAS1 | 11 | Human | CAGGACAGCAGGGGCTCCTTGT (SEQ ID NO: 55) | 1 | 0 | 0 | 14079 | 737 | 6225 | 49.450 |
| EPAS1 | 12 | Human | TAGCCCCATGCTTTGCGAGCA (SEQ ID NO: 56) | 1 | 0 | 0 | 34753 | 18 | 12 | 0.086 |

FIG. 20

| Gene | No. | Species | RGEN Target | Mismatch | | | Indel ratio (%) |
|---|---|---|---|---|---|---|---|
| | | | | 0 bp | 1 bp | 2 bp | |
| ANGPTL4 | 1 | Human | GCATCAGGGCTGCCCCGGCCGT (SEQ ID NO: 57) | 1 | 0 | 0 | 0.152 |
| ANGPTL4 | 2 | Human | GCATCAGGGCTGCCCCGGCCGT (SEQ ID NO: 58) | 1 | 0 | 0 | 0.024 |
| ANGPTL4 | 3 | Human | GGACGCAAAGCGCGGCGACTTG (SEQ ID NO: 59) | 1 | 0 | 0 | 0.006 |
| ANGPTL4 | 4 | Human | TCCTGGGACGAGATGAATGTCC (SEQ ID NO: 60) | 1 | 0 | 0 | 0.137 |
| ANGPTL4 | 5 | Human | CTGCAGCTCGGCCAGGGGCTGC (SEQ ID NO: 61) | 1 | 0 | 0 | 0.000 |
| ANGPTL4 | 6 | Human | CCAGGGGCTGCGCGAACACGCG (SEQ ID NO: 62) | 1 | 0 | 0 | 0.000 |
| ANGPTL4 | 7 | Human | CCCTCGGTTCCCTGACAGGCGG (SEQ ID NO: 63) | 1 | 0 | 0 | 1.383 |
| ANGPTL4 | 8 | Human | ACCCTGAGGTCCTTCACAGCCT (SEQ ID NO: 64) | 1 | 0 | 0 | 9.746 |
| ANGPTL4 | 9 | Human | TTCCACAAGGTGGCCCAGCAGC (SEQ ID NO: 65) | 1 | 0 | 0 | 0.298 |
| ANGPTL4 | 10 | Human | CAGCAGCAGCGGCACCTGGAGA (SEQ ID NO: 66) | 1 | 0 | 0 | 4.803 |
| ANGPTL4 | 11 | Human | TCCTAGTTTGGCCTCCTGGACC (SEQ ID NO: 67) | 1 | 0 | 0 | 5.192 |
| ANGPTL4 | 12 | Human | GACCCGGCTCACAATGTCAGCC (SEQ ID NO: 68) | 1 | 0 | 0 | 0.000 |
| ANGPTL4 | 13 | Human | GCTGTTGCGGTCCCCCGTGATG (SEQ ID NO: 69) | 1 | 0 | 0 | 0.041 |
| ANGPTL4 | 14 | Human | GGCGTTGCCATCCCAGTCCCGC (SEQ ID NO: 70) | 1 | 0 | 0 | 0.000 |
| ANGPTL4 | 15 | Human | AACGCCGAGTTGCTGCAGTTCT (SEQ ID NO: 71) | 1 | 0 | 0 | 0.000 |
| ANGPTL4 | 16 | Human | ATAGGCCGTGTCCTCGCCACCC (SEQ ID NO: 72) | 1 | 0 | 0 | 0.000 |
| ANGPTL4 | 17 | Human | GTTCTCCGTGCACCTGGGTGGC (SEQ ID NO: 73) | 1 | 0 | 0 | 6.136 |
| ANGPTL4 | 18 | Human | ACACGGCCTATAGCCTGCAGCT (SEQ ID NO: 74) | 1 | 0 | 0 | 0.000 |
| ANGPTL4 | 19 | Human | CCACCGTCCCACCCAGCGGCCT (SEQ ID NO: 75) | 1 | 0 | 0 | 0.150 |
| ANGPTL4 | 20 | Human | GTGATCCTGGTCCCAAGTGGAG (SEQ ID NO: 76) | 1 | 0 | 0 | 13.605 |
| ANGPTL4 | 21 | Human | GACCCCGGCAGGAGGCTGGTGG (SEQ ID NO: 77) | 1 | 0 | 0 | 2.379 |
| ANGPTL4 | 22 | Human | TGCAGCCATTCCAACCTCAACG (SEQ ID NO: 78) | 1 | 0 | 0 | 0.245 |
| ANGPTL4 | 23 | Human | TGCCGCTGCTGTGGGATGGAGC (SEQ ID NO: 79) | 1 | 0 | 0 | 13.909 |

FIG. 21

ARTIFICIALLY-MANIPULATED NEOVASCULARIZATION REGULATORY SYSTEM

CROSS-REFERENCE TO RELATED APPLICATION

This application is a continuation application of U.S. Application Ser. No. 15/953,141, filed on 13 Apr. 2018, which is a continuation application of International Patent Application No. PCT/KR2017/009078, filed 21 Aug. 2017, which claims the priority and the benefit of U.S. Provisional Patent Application No. 62/376,998, filed on Aug. 19, 2016, the disclosures of which are incorporated herein by reference in their entirety.

SEQUENCE LISTING

This application contains references to amino acid sequences and/or nucleic acid sequences which have been submitted concurrently herewith as the sequence listing text file entitled "000017uscob_SequenceListing.TXT", file size 243,072 bytes, created on 22 Dec. 2023. The aforementioned sequence listing is hereby incorporated by reference in its entirety pursuant to 37 C.F.R. § 1.52(e)(5).

FIELD

The present invention relates to an artificially manipulated neovascularization-associated factor for regulating neovascularization and a use thereof. More particularly, the present invention relates to a system capable of artificially regulating neovascularization, which includes an artificially manipulated neovascularization-associated factor for regulating neovascularization and/or a composition able to be used in artificial manipulation of the neovascularization-associated factor.

BACKGROUND

Excessive neovascularization found in many cases of severe diseases occurs in diseases such as cancer, macular degeneration, diabetic retinopathy, arthritis and psoriasis. In such a state, new blood vessels are provided to tissue with a disease, resulting in destroyed normal tissue, and in the case of cancer, new blood vessels allow tumor cells to enter the circulation system and thus settle in another organ (tumor metastasis).

Particularly, since cancer cells receive nutrients through neovascularization and are metastasized to another organ, neovascularization is essential for growth and metastasis of cancer. It has been known that there is an actual close relationship between the density of capillaries generated in cancer tissue and probability of cancer metastasis in various types of cancer. In addition, rheumatoid arthritis, which is the representative disease among inflammatory diseases, is caused by an autoimmune disorder, however, during the development of the disease, chronic inflammation generated in the synovial cavity between joints leads to neovascularization, resulting in destroyed cartilage. Various ophthalmologic diseases leading to blindness in several million people in the world every year are also caused by neovascularization. As a representative example, diabetic blindness is a diabetic complication, and refers to an invasion of capillaries generated in the retina to the vitreous body through neovascularization, ending up in blindness. Therefore, neovascularization inhibitory substances may be usefully employed as therapeutic agents and preventive agents for various diseases such as cancer, rheumatoid arthritis and diabetic blindness, in which continuous neovascularization occurs.

Meanwhile, conventionally, inhibition of signaling of vascular endothelial growth factors (VEGFs) in order to inhibit neovascularization had been actively studied. However, in the conventional art, initially, neovascularization seemed to be inhibited, and then there was a side effect in which cancer cells became more aggressive because the pathway of an anticancer agent to the cancer cells was also inhibited.

As such, while a variety of studies to treat diseases induced by neovascularization are progressing, there is almost no fundamental method for treating such a disease. Particularly, there is no method for treating a severe disease such as cancer or cancer metastasis caused by neovascularization, blindness caused by retinal or corneal degeneration, and therefore, there is an urgent demand for developing such a fundamental method for treating a neovascularization-associated disease.

SUMMARY

Technical Problem

To solve the above problems, the present invention relates to an artificially manipulated neovascularization system, which has an improved neovascularizing effect. More particularly, the present invention relates to an artificially manipulated neovascularization-associated factor and a neovascularization system which has a function artificially modified by the factor.

The present invention also relates to a neovascularization-associated factor genetically manipulated or modified for a specific purpose.

As an exemplary embodiment, the present invention is directed to providing an artificially manipulated neovascularization-regulating system.

As an exemplary embodiment, the present invention is directed to providing an artificially manipulated neovascularization-associated factor and an expression product thereof.

As an exemplary embodiment, the present invention is directed to providing a composition for manipulating a gene to manipulate a neovascularization-associated factor and a method for utilizing the same.

As an exemplary embodiment, the present invention is directed to providing a method for regulating neovascularization.

As an exemplary embodiment, the present invention is directed to providing a pharmaceutical composition for treating a neovascularization-associated disease and various uses thereof.

As an exemplary embodiment, the present invention is directed to providing an artificially manipulated neovascularization-associated factor, for example, VEGFA, HIF1A, ANGPT2, EPAS1, ANGPTL4, etc., and/or expression products thereof.

As an exemplary embodiment, the present invention is directed to providing a composition for manipulating a gene to enable artificial manipulation of a neovascularization-associated factor, for example, VEGFA, HIF1A, ANGPT2, EPAS1, ANGPTL4, etc.

As an exemplary embodiment, the present invention is directed to providing a therapeutic use of an artificially manipulated neovascularization-associated factor, for example, VEGFA, HIF1A, ANGPT2, EPAS1, ANGPTL4, etc., and/or a composition for manipulating a gene to enable the artificial manipulation.

As an exemplary embodiment, the present invention is directed to providing an additional use of an artificially manipulated neovascularization-associated factor, for example, VEGFA, HIF1A, ANGPT2, EPAS1, ANGPTL4, etc., and/or a composition for manipulating a gene to enable the artificial manipulation.

Technical Solution

To solve these problems, the present invention relates to a system for artificially regulating neovascularization, which includes an artificially manipulated neovascularization-associated factor for regulating neovascularization and/or a composition for artificially manipulating the neovascularization-associated factor.

The present invention provides an artificially manipulated neovascularization-associated factor for a specific purpose.

The term "neovascularization-associated factor" encompasses a variety of non-natural, artificially manipulated substances capable of having a neovascularization regulating function, which directly participate in or indirectly affect neovascularization. The substances may be DNA, RNA, genes, peptides, polypeptides or proteins. For example, the substances may be genetically manipulated or modified genes or proteins expressed in an immune cells. The neovascularization-associated factor may promote or increase neovascularization, or conversely, suppress or inhibit neovascularization.

In addition, it may induce, activate or inactivate a neovascularization environment or a neovascularization-inhibiting environment.

In an exemplary embodiment of the present invention, the neovascularization-associated factor may be, for example, an artificially manipulated VEGFA gene, HIF1A gene, ANGPT2 gene, EPAS1 gene or ANGPTL4 gene.

In an exemplary embodiment of the present invention, the neovascularization-associated factor may include two or more artificially manipulated genes. For example, two or more genes selected from the group consisting of a VEGFA gene, an HIF1A gene, an ANGPT2 gene, an EPAS1 gene and an ANGPTL4 gene may be artificially manipulated.

Therefore, in an exemplary embodiment of the present invention, one or more artificially manipulated neovascularization-associated factors selected from the group consisting of a VEGFA gene, an HIF1A gene, an ANGPT2 gene, an EPAS1 gene and an ANGPTL4 gene, which have undergone modification in a nucleic acid sequence, are provided.

The modification in a nucleic acid sequence may be non-limitedly, artificially manipulated by a guide nucleic acid-editor protein complex.

The term "guide nucleic acid-editor protein complex" refers to a complex formed through the interaction between a guide nucleic acid and an editor protein, and the nucleic acid-protein complex includes the guide nucleic acid and the editor protein.

The guide nucleic acid-editor protein complex may serve to modify a subject. The subject may be a target nucleic acid, a gene, a chromosome or a protein.

For example, the gene may be a neovascularization-associated factor, artificially manipulated by a guide nucleic acid-editor protein complex, wherein the neovascularization-associated factor artificially manipulated includes one or more modifications of nucleic acids which is at least one of a deletion or insertion of one or more nucleotides, a substitution with one or more nucleotides different from a wild-type gene, and an insertion of one or more foreign nucleotide, in a proto-spacer-adjacent motif (PAM) sequence in a nucleic acid sequence constituting the neovascularization-associated factor or in a continuous 1 bp to 50 bp the base sequence region adjacent to the 5' end and/or 3' end thereof, or a chemical modification of one or more nucleotides in a nucleic acid sequence constituting the neovascularization-associated factor.

The modification of nucleic acids may occur in a promoter region of the gene.

The modification of nucleic acids may occur in an exon region of the gene. In one exemplary embodiment, 50% of the modifications may occur in the upstream section of the coding regions of the gene.

The modification of nucleic acids may occur in an intron region of the gene.

The modification of nucleic acids may occur in an enhancer region of the gene.

The PAM sequence may be, for example, one or more of the following sequences (described in the 5' to 3' direction):
NGG (N is A, T, C or G);
NNNNRYAC (each of N is independently A, T, C or G, R is A or G, and Y is C or T);
NNAGAAW (each of N is independently A, T, C or G, and W is A or T);
NNNNGATT (each of N is independently A, T, C or G);
NNGRR(T) (each of N is independently A, T, C or G, R is A or G); and
TTN (N is A, T, C or G).

The editor protein may be derived from *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becsii, Candidatus Desulforudis, Clostridium botulinum, Clostridium difficile, Finegoldia magna, Natranaerobius thermophilus, Pelotomaculum thermopropionicum, Acidithiobacillus callus, Acidithiobacillus ferrooxidans, Allochromatium vinosum, Marinobacter* sp., *Nitrosococcus halophilus, Nitrosococcus watsonii, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus,* or *Acaryochloris marina*.

In one exemplary embodiment, the editor protein may be one or more selected from the group consisting of a *Streptococcus pyogenes*-derived Cas9 protein, a *Campylobacter jejuni*-derived Cas9 protein, a *Streptococcus thermophilus*-derived Cas9 protein, a *Streptococcus aureus*-derived Cas9 protein, a *Neisseria meningitidis*-derived Cas9 protein, and a Cpf1 protein. As an example, the editor protein may be a *Streptococcus pyogenes*-derived Cas9 protein or a *Campylobacter jejuni*-derived Cas9 protein.

In addition, in another embodiment, the present invention provides a guide nucleic acid, which is capable of forming a complementary bond with respect to target sequences of SEQ ID NOs: 1 to 1522, for example, SEQ ID Nos: 1 to 79 in the nucleic acid sequences of one or more genes selected from the group consisting of a VEGFA gene, an HIF1A gene, an ANGPT2 gene, an EPAS1 gene and an ANGPTL4 gene, respectively.

The guide nucleic acid may form a complementary bond with a part of nucleic acid sequences of one or more genes selected from the group consisting of a VEGFA gene, an HIF1A gene, an ANGPT2 gene, an EPAS1 gene and an ANGPTL4 gene. It may create 0 to 5, 0 to 4, 0 to 3, or 0 to 2 mismatches. As an exemplary example, the guide nucleic acid may be nucleotides forming a complementary bond with one or more of the target sequences of SEQ ID NOs: 1 to 1522, for example, SEQ ID NOs: 1 to 79, respectively.

For example, the present invention may provide one or more guide nucleic acids selected from the group as described below:
  a guide nucleic acid capable of forming a complementary bond with respect to the target sequences of SEQ ID NOs: 3, 4, 7, 9, 10 and 11 in the nucleic acid sequence of the VEGFA gene, respectively;
  a guide nucleic acid capable of forming a complementary bond with respect to the target sequences of SEQ ID NOs: 14, 18, 19, 20, 26, 29 and 31 in the nucleic acid sequence of the HIF1A gene, respectively;
  a guide nucleic acid capable of forming a complementary bond with respect to the target sequences of SEQ ID NOs: 33, 34, 37, 38, 39 and 43 in the nucleic acid sequence of the ANGPT2 gene, respectively;
  a guide nucleic acid capable of forming a complementary bond with respect to the target sequences of SEQ ID NOs: 47, 48, 49, 50, 53, 54 and 55 in the nucleic acid sequence of the EPAS1 gene, respectively; and
  a guide nucleic acid capable of forming a complementary bond with respect to the target sequences of SEQ ID NOs: 64, 66, 67, 73, 76 and 79 in the nucleic acid sequence of the ANGPTL4 gene, respectively.

The guide nucleic acid may be non-limitedly 18 to 25 bp, 18 to 24 bp, 18 to 23 bp, 19 to 23 bp, or 20 to 23 bp nucleotides.

In addition, the present invention provides a composition for gene manipulation, which may be employed in artificial manipulation of a neovascularization-associated factor for a specific purpose.

The composition for gene manipulation may include a guide nucleic acid-editor protein complex or a nucleic acid sequence encoding the same.

The composition for gene manipulation may include:
  (a) a guide nucleic acid capable of forming a complementary bond with respect to each of target sequences of SEQ ID NOs: 1 to 1522, for example, SEQ ID NOs: 1 to 79 in the nucleic acid sequences of one or more genes selected from the group consisting of a VEGFA gene, an HIF1A gene, an ANGPT2 gene, an EPAS1 gene and an ANGPTL4 gene, respectively or a nucleic acid sequence encoding the guide nucleic acid;
  (b) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Streptococcus aureus*-derived Cas9 protein, a *Neisseria meningitidis*-derived Cas9 protein, and a Cpf1 protein or a nucleic acid sequence encoding the same.

In one exemplary embodiment, the guide nucleic acid may be a nucleic acid sequence which forms a complementary bond with respect to one or more of the target sequences of SEQ ID NOs: 3, 4, 7, 9, 10 and 11 (VEGFA), SEQ ID NOs: 14, 18, 19, 20, 26, 29 and 31 (HIF1A), SEQ ID NOs: 33, 34, 37, 38, 39 and 43 (ANGPT2), SEQ ID NOs: 47, 48, 49, 50, 53, 54 and 55 (EPAS1), and SEQ ID NOs: 64, 66, 67, 73, 76 and 79 (ANGPTL4), respectively.

In one exemplary embodiment, the composition for gene manipulation may be a viral vector system.

The viral vector may include one or more selected from the group consisting of a retrovirus, a lentivirus, an adenovirus, an adeno-associated virus (AAV), a vaccinia virus, a poxvirus and a herpes simplex virus.

In an exemplary embodiment, the present invention provides a method for artificially manipulating cells, which includes: introducing
  (a) a guide nucleic acid which is capable of forming a complementary bond with respect to the target sequences of SEQ ID NOs: 1 to 1522, for example, SEQ ID NOs: 1 to 79 in the nucleic acid sequences of one or more genes selected from the group consisting of a VEGFA gene, an HIF1A gene, an ANGPT2 gene, an EPAS1 gene and an ANGPTL4 gene, respectively, or a nucleic acid sequence encoding the same; and
  (b) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Streptococcus aureus*-derived Cas9 protein, a *Neisseria meningitidis*-derived Cas9 protein, and a Cpf1 protein, respectively, or a nucleic acid sequence encoding the same to cells.

The guide nucleic acid and the editor protein may be present in one or more vectors in the form of a nucleic acid sequence, or may be present in a complex formed by coupling the guide nucleic acid with the editor protein.

The introduction may be performed in vivo or ex vivo.

The introduction may be performed by one or more methods selected from electroporation, liposomes, plasmids, viral vectors, nanoparticles and a protein translocation domain (PTD) fusion protein method.

The viral vector may be one or more selected from the group consisting of a retrovirus, a lentivirus, an adenovirus, an adeno-associated virus (AAV), a vaccinia virus, a poxvirus and a herpes simplex virus.

In another exemplary embodiment, the present invention provides a pharmaceutical composition for treating a neovascularization-associated disease.

The pharmaceutical composition may include a composition for gene manipulation which may be employed in artificial manipulation of a neovascularization-associated factor.

The formulation of the composition for gene manipulation is the same as described above.

In an exemplary embodiment, the present invention provides a method for obtaining information about the sequences of target sites that are artificially manipulated from a subject by sequencing one or more genes selected from the group consisting of a VEGFA gene, an HIF1A gene, an ANGPT2 gene, an EPAS1 gene and an ANGPTL4 gene.

In addition, the present invention provides a method for constructing libraries using the information obtained thereby.

In an exemplary embodiment, the present invention provides a kit for gene manipulation, which includes the following components:
  (a) a guide nucleic acid capable of forming a complementary bond with respect to the target sequences of SEQ ID NOs: 1 to 1522, for example, SEQ ID NOs: 1 to 79 in the nucleic acid sequences of one or more genes selected from the group consisting of a VEGFA gene, an HIF1A gene, an ANGPT2 gene, an EPAS1 gene and an ANGPTL4 gene, respectively, or a nucleic acid sequence encoding the same; and (b) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Streptococcus aureus*-derived Cas9 protein, a *Neisseria meningitidis*-derived Cas9 protein, and a Cpf1 protein, respectively, or a nucleic acid sequence encoding the same.

The gene of interest may be artificially manipulated using such a kit.

In one exemplary embodiment, the present invention may provide a composition for treating a neovascularization-related disorder, which includes:

a guide nucleic acid capable of forming a complementary bond with one or more target sequences in the nucleic acid sequences of one or more genes selected from the group consisting of a VEGFA gene, an HIF1A gene, an ANGPT2 gene, an EPAS1 gene and an ANGPTL4 gene, respectively, or a nucleic acid sequence encoding the same; and an editor protein or a nucleic acid sequence encoding the same.

The target sequences may be one or more sequences of SEQ ID NOs: 1 to 1522, for example, SEQ ID NOs: 1 to 79.

In one exemplary embodiment, a *Campylobacter jejuni*-derived Cas9 protein may be employed as the editor protein.

In one exemplary embodiment, the neovascularization-related disorder may be ischemic retinopathy or retinopathy of prematurity.

In one exemplary embodiment, the present invention provides all aspects of uses of an artificially manipulated neovascularization-associated factor or a composition for gene manipulation which is employed in artificial manipulation of the neovascularization-associated factor for treating a disease in a target.

Targets for treatment may be mammals including primates such as humans, monkeys, etc., rodents such as mice, rats, etc., and the like.

Advantageous Effects

An artificially manipulated neovascularization-associated factor and a neovascularization system whose function is artificially modified thereby can be effectively used to treat a neovascularization-related disease, for example, a neovascularization-related ocular disease. The efficiency of the neovascularization system can be improved by modulation of a variety of in vivo mechanisms in which various neovascularization-associated factors are involved.

For example, one or more genes of a VEGFA gene, an HIF1A gene, an ANGPT2 gene, an EPAS1 gene and an ANGPTL4 gene can be utilized.

BRIEF DESCRIPTION OF DRAWINGS

FIG. 1 CjCas9 target sequences in Vegfa and Hif1a/HIF1A genes (the PAM sequence and the target sequence of sgRNA are marked with a dotted line and solid line, respectively) (TS14 5'-3' corresponds to SEQ ID NO: 1564; TS14 3'-5' corresponds to SEQ ID NO: 1565; TS5 5'-3' corresponds to SEQ ID NO: 1566; and TS5 3'-5' corresponds to 1567), FIG. 2 the all-in-one AAV vector encoding CjCas9 and an in vivo test schedule, FIG. 3 graphs of indel frequencies at Rosa26, Vegfa, and Hif1a target sites in RPE cells (Error bars=s.e.m. (a control not injected with AAV: n=4, AAV-CjCa9-injected test group: n=5), Student's t-tests, * $p<0.05$, *** $p<0.001$), FIG. 4 a graph of Vegfa expression levels measured by ELISA in RPE cells (Error bars=s.e.m. (a control not injected with AAV: n=4, AAV-CjCa9-injected test group: n=5), One-way ANOVA and Tukey post-hoc tests, * $p<0.05$, *** $p<0.001$), FIG. 5 graph of indel frequencies at off-target sites (the mismatched base sequence is marked with a solid line, and the PAM sequence is marked with a dotted line) (Vegfa-CjCas9 OT1 corresponds to SEQ ID NO: 1568; Vegfa-CjCas9 On corresponds to SEQ ID NO: 1569; Hif1a-CjCas9 corresponds OT2 to SEQ ID NO: 1570; Hif1a-CjCas9 OT1 corresponds to SEQ ID NO: 1571; and Hif1a-CjCas9 On corresponds to SEQ ID NO: 1572), FIG. 6 laser-induced CNV areas of eyeballs of mice injected with AAV9-CjCa9 targeting Rosa26, Vegfa, or Hif1a, stained with isolectin B4 (Scale bar=200 µm), and FIG. 7 a graph of the laser-induced CNV areas (%) (Error bars=s.e.m. (n=17-18), One-way ANOVA and Tukey post-hoc tests, * $p<0.05$,  $p<0.01$, * $p<0.001$, ns: not significant).

FIG. 9 images of opsin-positive areas corresponding to RPE cells expressing HA-tagged CjCas9 in Rosa26-, Vegfa-, or Hif1a-specific CjCas9-injected mice (Opsin: red, HA: green, and DAPI: blue, Scale bar=20 µm, ONL: outer nuclear layer, IS: inner segment of photoreceptor cells, OS: outer segment of photoreceptor cells); and FIG. 10 a graph of relative opsin-positive areas (%) (Error bars=s.e.m. (n=4), One-way ANOVA and Tukey post-hoc tests, * $p<0.05$).

FIG. 11a graph of indel frequencies at target sites of Rosa26, Vegfa and Hif1a in retinal cells (Error bars=s.e.m. (a control not injected with AAV: n=4, AAV-CjCa9-injected test group: n=5), Student's t-tests, * $p<0.05$,  $p<0.01$, * $p<0.001$), FIG. 12a graph of Vegfa expression levels in retinal cells, measured using ELISA (Error bars=s.e.m. (n=6-7), One-way ANOVA and Tukey post-hoc tests, * $p<0.05$, *** $p<0.001$).

FIG. 14 is an in vivo test schedule (a), images of the reducing effect on vascular leakage and blood leakage in mouse retinas injected with AAV2-CjCas9 targeting Vegfa (b), and FIG. 15 is a graph of relative vascular leakage (%) due to CjCas9 targeting Rosa26 or Vegfa.

FIG. 16 shows CjCas9 target site screening results and indel frequencies of human VEGFAs for gene manipulation.

FIGS. 17 and 18 show the result of CjCas9 target site screening of human HIF1As for gene manipulation: FIG. 17 CjCas9 target site screening results and indel frequencies of human HIF1As, and FIG. 18 target sites of HIF1As, conserved between various mammals (Homo 103E04 corresponds to SEQ ID NO: 1573; Macaque_103E04 corresponds to SEQ ID NO: 1574; Marmoset_103E04 corresponds to SEQ ID NO: 1575; Pig_103E04 corresponds to SEQ ID NO: 1576; Dog_103E04 corresponds to SEQ ID NO: 1577; and Mouse_103E04 corresponds to SEQ ID NO: 1578.

FIG. 19 shows CjCas9 target site screening results and indel frequencies of human ANGPT2s for gene manipulation.

FIG. 20 shows CjCas9 target site screening results and indel frequencies of human EPAS1s for gene manipulation.

FIG. 21 shows CjCas9 target site screening results and indel frequencies of human ANGPTL4s for gene manipulation.

DETAILED DESCRIPTION

Figure 1:
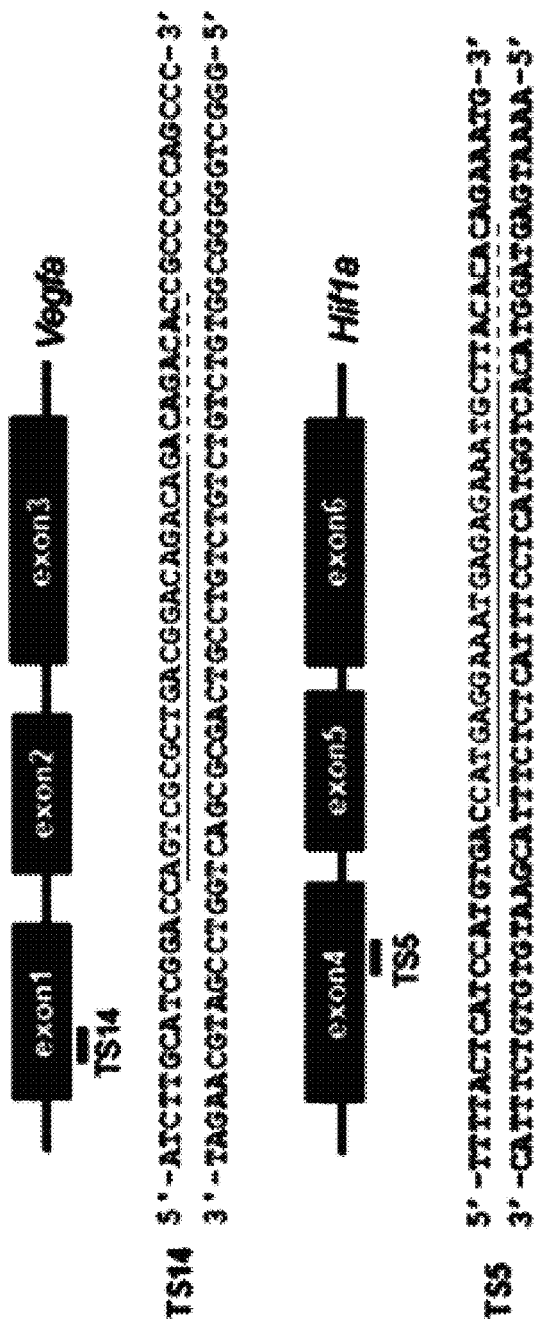
FIGS. 1, 2, 3, 4, 5, 6, and 7 show the reducing effect on a laser-induced choroidal neovascularization (CNV) area due to CjCas9 targeting Vegfa or Hif1a in mouse models with age-related macular degeneration (AMD)

Unless defined otherwise, all technical and scientific terms used herein have the same meaning as commonly understood by those of ordinary skill in the art to which the present invention belongs. Although methods and materials similar or identical to those described herein can be used in practice or testing of the present invention, suitable methods and materials are described below. All publications, patent applications, patents and other references mentioned herein are incorporated by reference in their entirety. In addition, materials, methods and examples are merely illustrative, and not intended to be limitive.

One aspect of the present invention relates to an artificially manipulated neovascularization system, which has a regulated neovascularization effect.

Specifically, the present invention relates to combination of various aspects capable of regulating neovascularization or improving or treating a neovascularization-associated disease by artificially manipulating a neovascularization-associated factor. The present invention includes a neovascularization-associated factor whose function is artificially modified, a method of manufacturing the same, a composition including the same, and a therapeutic use thereof.

Another aspect of the present invention relates to an additional regulating system with a third in vivo mechanism, concomitant with various functions of a specific factor (e.g., a gene known as a neovascularization-associated factor, etc.) whose function is artificially modified.

Specifically, targeting of a third in vivo function as well as a neovascularization function in which artificially manipulated specific factors are involved may lead to the regulation of corresponding mechanisms. The present invention includes a neovascularization-associated factor whose function is artificially modified, a method for manufacturing the same, a composition including the same, and therapeutic uses thereof for improving or treating a disease associated with the third function.

Neovascularization

An exemplary embodiment of the present invention relates to improvement and modification of a neovascularization-associated system.

The term "neovascularization" refers to a process of tissue vascularization, including generation, development and/or differentiation of new blood vessels. Here, neovascularization encompasses angiogenesis and vasculogenesis. Neovascularization may be closely related to various factors to promote or inhibit proliferation of vascular endothelial cells.

Neovascularization encompasses all mechanisms for extension from existing blood vessels, new generation of blood vessels from precursor cells, and/or an increase in diameter of an existing small blood vessel.

In addition, neovascularization encompasses all mechanisms associated with formation of new vessels, which is involved in vascular leakage or repair of damaged blood vessels.

The vascularization includes mechanisms concomitant with excessive and/or abnormal neovascularization in various severe disease states.

For example, in diseases such as cancer, macular degeneration, diabetic retinopathy, arthritis and psoriasis, excessive neovascularization occurs. In such a disease state, new blood vessels are provided to tissue with a disease, and normal tissue is damaged. In the case of cancer, new blood vessels allow tumor cells to enter into the circulation system and thus enable them to settle in another organ (tumor metastasis).

In one exemplary embodiment, the neovascularization may be ocular vascularization.

For example, the neovascularization may be found in eye diseases such as AMD, diabetic retinopathy and the like. Particularly, AMD is the most common cause of legal irreversible blindness in older people over the age of 65 in the US, Canada, England, Wales, Scotland and Australia, and about 10% to 15% of the patients show exudative (wet) diseases. The exudative AMD is characterized by neovascularization and disease-causing angiogenesis.

For example, ocular neovascularization may include choroidal neovascularization (CNV), corneal neovascularization and/or rubeosis iridis.

CNV is the vascularization in the choroid layer, and rapidly occurs in people having a defect in the Bruch's membrane, which is the innermost layer of the choroid. In addition, CNV is associated with an excessive amount of vascular endothelial growth factor (VEGF). CNV may cause excessive myopia, malignant myopia, or neovascular degenerative macular degeneration (e.g., wet macular degeneration).

Corneal neovascularization is the growth of new blood vessels from the pericorneal plexus in the periphery of the cornea into avascular corneal tissue due to oxygen deprivation, and may be mainly caused by congenital or inflammatory (e.g., rejection after corneal transplantation, grafted tissue or host diseases, atopic conjunctivitis, injections, ocular pemphigoid, Lyell's syndrome, and Stevens-Johnson syndrome), infectious (e.g., bacterial (*chlamydia*, syphilis, *Pseudomonas*), viral (herpes simplex virus and herpes zoster virus), fungal (*candida, aspergillus, fusarium*), parasistic (*Onchocerca volvulus*), degenerative, traumatic and iatrogenic (e.g., the wearing of contact lenses) diseases.

Rubeosis iridis is the vascularization on the surface of the iris, associated with diabetic retinopathy, and also known to be caused by central retinal vein occlusion, ocular ischemic syndrome, chronic retinal detachment, and the like.

In a certain embodiment, the neovascularization may be associated with survival, proliferation, persistency, cytotoxicity, and a cytokine-release function of vascular endothelial cells.

In a certain embodiment, neovascularization may be associated with an increase in the expression of an angiogenic cytokine.

In a certain embodiment, the neovascularization may be associated with functions of a receptor of vascular endothelial cells.

In a certain embodiment, the neovascularization may be associated with a migration ability of vascular endothelial cells.

In a certain embodiment, the neovascularization may be associated with an attachment ability of vascular endothelial cells.

Neovascularization-Associated Factor

One embodiment of the present invention relates to an artificially manipulated or modified neovascularization-associated factor.

The term "neovascularization-associated factor" includes all elements directly participating in or indirectly affecting vasculogenesis or angiogenesis. Here, the elements may include DNA, RNA, genes, peptides, polypeptides or proteins.

In an exemplary embodiment, the neovascularization-associated factor may include various substances which can have a non-natural, that is, artificially manipulated, neovascularization regulating function. For example, it may be a genetically manipulated or modified genes or proteins expressed in an immune cells.

The term "artificially manipulated" means an artificially modified state, which is not a naturally occurring state.

The term "genetically manipulated" means that a genetic modification is artificially introduced to biological or non-biological substances cited in the present invention, and may be, for example, genes and/or gene products (polypeptides, proteins, etc.) in which their genomes are artificially modified for a specific purpose.

As an exemplary example, the present invention provides a neovascularization-associated factor which is genetically manipulated or modified for a specific purpose.

Genes or proteins having the functions listed below may have multiple types of functions, not only one type of neovascularization-associated function. In addition, as needed, two or more neovascularization functions and factors may be provided.

The neovascularization-associated factor may promote or increase neovascularization.

The neovascularization-associated factor may suppress or inhibit neovascularization.

The neovascularization-associated factor may induce or activate a neovascularization environment.

The neovascularization-associated factor may induce a neovascularization-inhibited environment or inactivate a neovascularization environment.

The neovascularization-associated factor may regulate (promote, increase, suppress and/or inhibit etc.) neovascularization.

The neovascularization-associated factor may be utilized in improvement and treatment of a neovascularization-associated disease.

In an exemplary embodiment, the neovascularization-associated factor may be one or more selected from the group consisting of ABCA1, ACAT, ACC2, ADAMTS12, ADCY2, ADIPOQ, ADIPOR1, ADIPOR2, ADRB2, AGPAT5, AIP4, AKAP2, AKR1C2, AMPK, ANG2, ANGPT2, ANGPTL4, ANK1, ANXA1, APOA1, ARHGAP17, ATP10A, AUH, AUTOTAXIN, BAI3, BCAR1, BIN1, BMP3A, CA10, CAMK1D, CAMKK2, CD36, CD44, CDC42, CDH13, CHAT, CNTFR, COL4A2, CPT, CSHI1, CTNN, CUBN, CYP7B1, CYSLTR1, CYSLTR2, DGKB, DGKH, DGKZ, DHCR7, DHFR, DRD2, DRD5, EDG1, EDG2, EDG3, EDG4, EDG5, EDG6, EDG7, EDG8, EDNRA, EHHADH, ENPP6, EPAS1, ERBB4, ERK1, ERK2, ESRRG, ETFA, F2, FDPS, FGF2, FLNA, FLT4, FOXO1, FOXO3A, FTO, GABBR2, GATA3, GH1, GNA12, GNA13, GRK2, GRK5, GRM5, HAPLN1, HAS1, HAS2, HAS3, HCRTR2, HIF1A, HSD11B1, HYAL1, HYAL2, HYAL3, IL20RA, IL20RB, IL6ST, IL8, ITGA6, ITGB1, KDR, *LAMA*1, LDLR, LEPR, LEPTIN, LIFR, LIPL2, LKB1, LRP, LTBP2, MAT2B, ME1, MEGALIN, MERLIN, MET, MGST2, MMP2, MMP9, MTOR, MTR, NCK2, NEDD9, NFKB1, NFKBIB, NOS2A, NOS3, NR1I2, NR3C2, NRG1, NRP1, NRP2, OPRS1, OSBPL10, OSBPL3, OSTEOPONTIN, P2RY1, P2RY12, PAI1, PAI2, PAK1, PAK6, PALLD, PAP1, PAR1, PAXILLIN, PC, PCTP, PDE11A, PDE1A, PDE3A, PDE4D, PDE5, PDGFA, PDGFB, PDGFRA, PDGFRB, PI3K, PITPNC1, PKA, PKCD, PLA1A, PLA2, PLAT, PLAU, PLCB1, PLD1, PLD2, PLG, PLXDC2, PPARA, PPARG, PPARGC1B, PRKG1, PRL, PTGS2, PTN, PTPN11, PYK2, RAC1, RAS, RHEB, RHOA, ROCK1, ROCK2, RPS6KA1, RPS6KB2, SCARB1, SCHIP1, SGPP2, SLC25A21, SMAD3, SMAD4, SNCA, SORBS2, SPLA2, SPOCK1, SRD5A1, SREBF1, SREBF2, STAT3, TGFBR1, TGFBR2, TGFBR3, THBS1, THBS2, THEM2, THRB, TIAM1, TIMP2, TLL2, TSC1, TSC2, TSPO, VEGFA, VEGFR1, and YES1.

As an exemplary example of the present invention, the neovascularization-associated factor may be one or more selected from the group consisting of VEGFA, HIF1A, ANGPT2, EPAS1, and ANGPTL4.

In a certain embodiment, the neovascularization-associated factor may be VEGFA.

A vascular endothelial growth factor A (VEGFA) gene is a gene (full-length DNA, cDNA or mRNA) encoding a VEGFA protein also called MVCD1, VEGF or VPF. In one example, the VEGFA gene may be one or more selected from the group consisting of the following genes, but the present invention is not limited thereto: genes encoding human VEGFA (e.g., NCBI Accession No. NP_001020537.2 or NP_001020538.2), for example, VEGFA genes represented by NCBI Accession No. NM_001025366.2, NM_001025367.2, NM_003376, or NG_008732.1.

In a certain embodiment, the neovascularization-associated factor may be HIF1A.

A hypoxia-inducible factor 1-alpha (HIF-1-alpha; HIF1A) gene refers to a gene (full-length DNA, cDNA or mRNA) encoding a HIF1A protein also called HIF1, MOP1, PASD8 or bHLHe78. In an example, the HIF1A gene may be one or more selected from the group consisting of the following genes, but the present invention is not limited thereto: genes encoding human HIF1A (e.g., NCBI Accession No. NP_001230013.1 or NP_001521.1), for example, HIF1A genes represented by NCBI Accession No. NM_001243084.1, NM_001530.3, NM_181054.2, or NG_029606.1.

In a certain embodiment, the neovascularization-associated factor may be ANGPT2.

An angiopoietin-2 (ANGPT2) gene refers to a gene (full-length DNA, cDNA or mRNA) encoding an ANGPT2 protein also called AGPT2 or ANG2. In an example, the ANGPT2 gene may be one or more selected from the group consisting of the following genes, but the present invention is not limited thereto: genes encoding human ANGPT2 (e.g., NCBI Accession No. NP_001112359.1, NP_001112360.1 or NP_001138.1), for example, ANGPT2 genes represented by NCBI Accession No. NM_001118887.1, NM_001118888.1, NM_001147.2 or NG_029483.1.

In a certain embodiment, the neovascularization-associated factor may be EPAS1.

An endothelial PAS domain-containing protein 1 (EPAS1) gene refers to a gene (full-length DNA, cDNA or mRNA) encoding an EPAS1 protein also called ECYT4, HIF2A, HLF, MOP2, PASD2 or bHLHe73. In an example, the EPAS1 gene may be one or more selected from the group consisting of the following genes, but the present invention is not limited thereto: genes encoding human EPAS1 (e.g., NCBI Accession No. NP_001421.2, etc.), for example, EPAS1 genes represented by NCBI Accession No. NM_001430.4 or NG_016000.1.

In a certain embodiment, the neovascularization-associated factor may be ANGPTL4.

An angiopoietin-like 4 (ANGPTL4) gene refers to a gene (full-length DNA, cDNA or mRNA) encoding an ANGPTL4 protein also called ARP4, FIAF, HARP, HFARP, NL2, PGAR, TGQTL or UNQ171. In an example, the ANGPTL4 gene may be one or more selected from the group consisting of the following genes, but the present invention is not limited thereto: genes encoding human ANGPTL4 (e.g., NCBI Accession No. NP_001034756.1 or NP_647475.1), for example, ANGPTL4 genes represented by NCBI Accession No. NM_001039667.2, NM_139314.2, or NG_012169.1.

The neovascularization-associated factor may be derived from mammals including primates such as human, monkeys and the like, rodents such as rats, mice and the like, etc.

Information about the genes may be obtained from a known database such as GeneBank of the National Center for Biotechnology Information (NCBI).

In an exemplary embodiment of the present invention, the neovascularization-associated factor, for example, VEGFA, HIF1A, ANGPT2, EPAS1 or ANGPTL4, may be an artificially manipulated neovascularization-associated factor.

In a certain embodiment, the artificially manipulated neovascularization-associated factor may be genetically manipulated.

The gene manipulation or modification may be achieved by artificial insertion, deletion, substitution or inversion occurring in a partial or entire region of the genomic sequence of a wild type gene. In addition, the gene manipulation or modification may be achieved by fusion of manipulation or modification of two or more genes.

For example, the gene is inactivated by such gene manipulation or modification, such that a protein encoded from the gene may not be expressed in the form of a protein having an innate function.

For example, the gene may be further activated by such gene manipulation or modification, such that a protein encoded from the gene is to be expressed in the form of a protein having an improved function, compared to the innate function. In an example, when a function of the protein encoded by a specific gene is A, a function of a protein expressed by a manipulated gene may be totally different from A or may have an additional function (A+B) including A.

For example, a fusion of two or more proteins may be expressed using two or more genes having different or complementary functions due to such gene manipulation or modification.

For example, two or more proteins may be expressed separately or independently in cells by using two or more genes having different or complementary functions due to such gene manipulation or modification.

The manipulated neovascularization-associated factor may promote or increase neovascularization.

The manipulated neovascularization-associated factor may suppress or inhibit neovascularization.

The manipulated neovascularization-associated factor may induce or activate a neovascularization environment.

The manipulated neovascularization-associated factor may induce a neovascularization inhibiting environment or inactivate a neovascularization environment.

The manipulated neovascularization-associated factor may regulate (promote, increase, suppress and/or inhibit) neovascularization.

The manipulated neovascularization-associated factor may be utilized in improvement and treatment of a neovascularization-associated disease.

The manipulation includes all types of structural or functional modifications of the neovascularization-associated factor.

The structural modification of the neovascularization-associated factor includes all types of modifications, which are not the same as those of a wild type existing in a natural state.

For example, when the neovascularization-associated factor is DNA, RNA or a gene, the structural modification may be the loss of one or more nucleotides.

The structural modification may be the insertion of one or more nucleotides.

Here, the inserted nucleotides include all of a subject including a neovascularization-associated factor and nucleotides entering from the outside of the subject.

The structural modification may be the substitution of one or more nucleotides.

The structural modification may include the chemical modification of one or more nucleotides.

Here, the chemical modification includes all of the addition, removal and substitution of chemical functional groups.

As another example, when the neovascularization-associated factor is a peptide, a polypeptide or a protein, the structural modification may be the loss of one or more amino acids.

The structural modification may be the insertion of one or more amino acids.

Here, the inserted amino acids include all of a subject including a neovascularization-associated factor and amino acids entering from the outside of the subject.

The structural modification may be the substitution of one or more amino acids.

The structural modification may include the chemical modification of one or more amino acids.

Here, the chemical modification includes all of the addition, removal and substitution of chemical functional groups.

The structural modification may be the partial or entire attachment of a different peptide, polypeptide or protein.

Here, the different peptide, polypeptide or protein may be a neovascularization-associated factor, or a peptide, polypeptide or protein having a different function.

The functional modification of the neovascularization-associated factor may include all types having an improved or reduced function, compared to that of a wild type existing in a natural state, and having a third different function.

For example, when the neovascularization-associated factor is a peptide, polypeptide or protein, the functional modification may be a mutation of the neovascularization-associated factor.

Here, the mutation may be a mutation that enhances or suppresses a function of the neovascularization-associated factor.

The functional modification may have an additional function of the neovascularization-associated factor.

Here, the additional function may be the same or a different function. In addition, the neovascularization-associated factor having the additional function may be fused with a different peptide, polypeptide or protein.

The functional modification may be the enhancement in functionality due to increased expression of the neovascularization-associated factor.

The functional modification may be the degradation in functionality due to decreased expression of the neovascularization-associated factor.

In an exemplary embodiment, the manipulated neovascularization-associated factor may be induced by one or more of the following mutations:
- all or partial deletions of the neovascularization-associated factor, that is, a gene to be manipulated (hereinafter, referred to as a target gene), for example, deletion of 1 bp or longer nucleotides, for example, 1 to 30, 1 to 27, 1 to 25, 1 to 23, 1 to 20, 1 to 15, 1 to 10, 1 to 5, 1 to 3, or 1 nucleotide of the target gene,
- substitution of 1 bp or longer nucleotides, for example, 1 to 30, 1 to 27, 1 to 25, 1 to 23, 1 to 20, 1 to 15, 1 to 10, 1 to 5, 1 to 3, or 1 nucleotide of the target gene with a nucleotide different from a wild type, and
- insertion of one or more nucleotides, for example, 1 to 30, 1 to 27, 1 to 25, 1 to 23, 1 to 20, 1 to 15, 1 to 10, 1 to 5, 1 to 3, or 1 nucleotide (each independently selected from A, T, C and G) into a certain position of the target gene.

A part of the modified target gene ("target region") may be a continuous 1 bp or more, 3 bp or more, 5 bp or more, 7 bp or more, 10 bp or more, 12 bp or more, 15 bp or more, 17 bp or more, or 20 bp or more, for example, 1 bp to 30 bp, 3 bp to 30 bp, 5 bp to 30 bp, 7 bp to 30 bp, 10 bp to 30 bp, 12 bp to 30 bp, 15 bp to 30 bp, 17 bp to 30 bp, 20 bp to 30 bp, 1 bp to 27 bp, 3 bp to 27 bp, 5 bp to 27 bp, 7 bp to 27 bp, 10 bp to 27 bp, 12 bp to 27 bp, 15 bp to 27 bp, 17 bp to 27 bp, 20 bp to 27 bp, 1 bp to 25 bp, 3 bp to 25 bp, 5 bp to 25 bp, 7 bp to 25 bp, 10 bp to 25 bp, 12 bp to 25 bp, 15 bp to 25 bp, 17 bp to 25 bp, 20 bp to 25 bp, 1 bp to 23 bp, 3 bp to 23 bp, 5 bp to 23 bp, 7 bp to 23 bp, 10 bp to 23 bp, 12 bp to 23 bp, 15 bp to 23 bp, 17 bp to 23 bp, 20 bp to 23 bp, 1 bp to 20 bp, 3 bp to 20 bp, 5 bp to 20 bp, 7 bp to 20 bp, 10 bp to 20 bp, 12 bp to 20 bp, 15 bp to 20 bp, 17 bp to 20 bp, 21 bp to 25 bp, 18 bp to 22 bp, or 21 bp to 23 bp region of the base sequence of the gene.

Meanwhile, a different embodiment of the present invention relates to an additional system for regulating a third in vivo mechanism, concomitant with various functions of the above-described neovascularization-associated factors whose functions are artificially modified.

In one exemplary embodiment, VEGF may be involved in regulation of the third in vivo mechanism.

Since an increase in vascular permeability by VEGF may be a cause of edema, as well as tumor growth, artificially manipulated VEGF may increase a survival rate in various types of tumors (e.g., brain tumor, uterine cancer, vestibular schwannomas, etc.) or recover hearing loss, for example, by manipulation to inactivate VEGF. In addition, a decrease in vascular permeability by artificially manipulated VEGF may impart therapeutic effects on renal failure, arthritis, psoriasis, coronary disease, etc.

In addition, the artificially manipulated VEGF may impart a therapeutic effect on an autoimmune disease. For example, inflammation-inducing activity may be artificially regulated by VEGF, thereby imparting therapeutic effects on uveitis, rheumatoid arthritis, systemic lupus erythematosus, an inflammatory bowel disease, psoriasis, systemic sclerosis, multiple sclerosis, etc.

In addition, the artificially manipulated VEGF may impart a therapeutic effect on a mental disease. For example, a therapeutic effect on depression may be imparted by artificially regulating the expression of a neurotransmission-associated factor by VEGF.

In another embodiment, the artificially manipulated VEGF may be involved in the regulation of a third in vivo mechanism of HIF. The HIF may be HIF1 or HIF2.

The artificially manipulated HIF may regulate inflammation-inducing activity, thereby imparting therapeutic effects on uveitis, rheumatoid arthritis, systemic lupus erythematosus, an inflammatory bowel disease, psoriasis, systemic sclerosis, multiple sclerosis, etc.

In addition, the artificially manipulated HIF may provide a therapeutic effect on an autoimmune disease.

Likewise, the illustrative factors of the present invention which are artificially manipulated may regulate corresponding mechanisms by targeting the third in vivo function as well as the neovascularization function. One exemplary embodiment of the present invention includes such a neovascularization factor whose function is artificially modified and a method for manufacturing the same, a composition including the same, and uses of the factor and the composition for improving or treating a disease associated with a third function.

Neovascularization System
Neovascularization-Regulating System

In one aspect of the present invention, a neovascularization-regulating system for regulating neovascularization by artificially manipulating a neovascularization-associated factor is provided.

The term "neovascularization-regulating system" used herein includes all phenomena affecting the promotion, increase, suppression and/or inhibition of neovascularization by change of a function of an artificially manipulated neovascularization-associated factor, and also includes all substances, compositions, methods, and uses which are directly or indirectly involved in such a neovascularization-regulating system.

Each factor constituting such a neovascularization-regulating system is also generally called "neovascularization-regulating factor."

The system of the present invention includes a modified in vivo mechanism, associated with an artificially manipulated neovascularization-associated factor.

In a certain embodiment, the expression of hematopoietic stem cell surface antigens such as CD34, CD117, CD133, etc. and vascular endothelial cell antigens such as Flk-1/KDR, Tie-2, etc. may be regulated by the artificially manipulated neovascularization-associated factor.

In a certain embodiment, angiogenesis in which new vessels are formed by sprouting and the growth of cells constituting a blood vessel may be regulated.

In a certain embodiment, the activity of direct angiogenic factors (DAFs) directly stimulating endothelial cells may be regulated. The growth and/or migration of endothelial cells may be promoted or inhibited.

For example, the DAFs may include vascular endothelial growth factors (VEGFs), basic fibroblast growth factors (bFGFs), hepatocyte growth factors (HGFs), epidermal growth factors (EGFs), thymidine phosphorylase (PD-ECGF), placental growth factors (PlGFs), transforming growth factors (TGFs), proliferin, interleukin-8 of a cytokine, angiogenin (angiogenesis-inducing protein), fibrin, nicotinamide (vitamin B complex), angiopoietin (angiogenesis-promoting protein), platelet activating factors (PAFs), 12-hydroxy eicosatetraenoate (12-HETE; a toxic degradation product of arachidonic acid, which is an angiogenesis-promoting factor of epithelial cells), matrix metalloproteases (MMPs), sphingosine 1-phosphate (S1P), and leptin.

In a certain embodiment, two different intercellular signaling pathways operating in blood vessel cells, that is, PDGF and VEGF signaling pathways may be utilized.

In a certain embodiment, the activity of indirect angiogenic factors (IAFs) inducing angiogenesis by formation of DAFs may be regulated by stimulating vascular pericytes.

In a certain embodiment, vascular endothelial cells may be differentiated from endothelial progenitor cells (EPCs), and thus a mechanism of forming a primary vascular plexus may be regulated.

In a certain embodiment, the degradability of extracellular matrix components for the migration of endothelial cells may be regulated.

In a certain embodiment, a cell migration-associated signaling pathway may be regulated.

In a certain embodiment, the activity of VEGF receptors such as VEGFR-1 (flt-1; fms like-tyrosine kinase-1), VEGFR-2 (flk-1/KDR), and VEGFR-3, and a platelet derived growth factor (PDGF) receptor, or neuropilin-1 (NP-1) may be regulated.

In an exemplary embodiment, the neovascularization-regulating system includes a composition for manipulating a neovascularization-associated factor.

The composition for manipulation may be a composition capable of artificially manipulating a neovascularization-associated factor, and preferably, a composition for gene manipulation.

Hereinafter, the composition for gene manipulation will be described.

Composition for Manipulating Neovascularization-Associated Factor

Manipulation or modification of substances involved in the neovascularization-associated factor and the neovascularization system of the present invention is preferably accomplished by genetic manipulation.

In one aspect, composition and method for manipulating a gene by targeting a partial or entire non-coding or coding region of the neovascularization-associated factor may be provided.

In an exemplary embodiment, the composition and method may be used in manipulation or modification of one or more neovascularization regulating genes involved in the formation of a desired neovascularization system. The manipulation or modification may be performed by modification of nucleic acids constituting a gene. As a result of the manipulation, all of knockdown, knockout, and knockin are included.

In an exemplary embodiment, the manipulation may be performed by targeting a promoter region, or a transcription sequence, for example, an intron or exon sequence. A coding sequence, for example, a coding region, specifically, an initial coding region may be targeted for the modification of expression and knockout.

In an exemplary embodiment, the modification of nucleic acids may be substitution, deletion, and/or insertion of one or more nucleotides, for example, 1 to 30 bp, 1 to 27 bp, 1 to 25 bp, 1 to 23 bp, 1 to 20 bp, 1 to 15 bp, 1 to 10 bp, 1 to 5 bp, 1 to 3 bp, or 1 bp nucleotides.

In an exemplary embodiment, for the knockout of one or more neovascularization-associated genes, elimination of expression of one or more of the genes, or one or more knockouts of one or two alleles, the above-mentioned region may be targeted such that one or more neovascularization-associated genes contain a deletion or mutation.

In an exemplary embodiment, the knockdown of a gene may be used to decrease the expression of undesired alleles or transcriptomes.

In an exemplary embodiment, non-coding sequences of a promoter, an enhancer, an intron, a 3'UTR, and/or a polyadenylation signal may be targeted to be used in modifying a neovascularization-associated gene affecting a neovascularization function.

In an exemplary embodiment, the activity of a neovascularization-associated gene may be regulated, for example, activated or inactivated by the modification of nucleic acids of the gene.

In an exemplary embodiment, the modification of nucleic acids of the gene may catalyze cleavage of a single strand or double strands, that is, breaks of nucleic acid strands in a specific region of the target gene by a guide nucleic acid-editor protein complex, resulting in inactivation of the target gene.

In an exemplary embodiment, the nucleic acid strand breaks may be repaired through a mechanism such as homologous recombination or non-homologous end joining (NHEJ).

In this case, when the NHEJ mechanism takes place, a change in DNA sequence is induced at the cleavage site, resulting in inactivation of the gene. The repair by NHEJ may induce substitution, insertion or deletion of a short gene fragment, and may be used in the induction of a corresponding gene knockout.

In another aspect, the present invention provides a composition for manipulating a neovascularization-associated factor.

The composition for manipulation is a composition that is able to artificially manipulate a neovascularization-associated factor, and preferably, a composition for gene manipulation.

The composition may be employed in gene manipulation for one or more neovascularization-associated factors involved in formation of a desired neovascularization-regulating system.

The gene manipulation may be performed in consideration of a gene expression regulating process.

In an exemplary embodiment, it may be performed by selecting a suitable manipulation means for each stage of transcription, RNA processing, RNA transporting, RNA degradation, translation, and protein modification regulating stages.

In an exemplary embodiment, small RNA (sRNA) interferes with mRNA or reduces stability thereof using RNA interference (RNAi) or RNA silencing, and in some cases, breaks up mRNA to interrupt the delivery of protein synthesis information, resulting in regulation of the expression of genetic information.

The gene manipulation may be performed by modification of nucleic acids constituting a neovascularization-associated factor. As manipulation results, all of knockdown, knockout, and knockin are included.

In a certain embodiment, the modification of nucleic acids may be substitution, deletion, and/or insertion of one or more nucleotides, for example, 1 to 30 bp, 1 to 27 bp, 1 to 25 bp, 1 to 23 bp, 1 to 20 bp, 1 to 15 bp, 1 to 10 bp, 1 to 5 bp, 1 to 3 bp, or 1 bp nucleotides.

In a certain embodiment, for knockout of one or more neovascularization-associated factors, elimination of the expression of one or more factors, or one or more knockouts of one or two alleles, the gene may be manipulated such that one or more neovascularization-associated factors contain a deletion or mutation.

In a certain embodiment, knockdown of the neovascularization-associated factor may be used to decrease expression of undesired alleles or transcriptomes.

In a certain embodiment, the modification of nucleic acids may be insertion of one or more nucleic acid fragments or genes. Here, the nucleic acid fragment may be a nucleic acid sequence consisting of one or more nucleotides, and a length of the nucleic acid fragment may be 1 to 40 bp, 1 to 50 bp, 1 to 60 bp, 1 to 70 bp, 1 to 80 bp, 1 to 90 bp, 1 to 100 bp, 1 to 500 bp or 1 to 1000 bp. Here, the inserted gene may be one of the neovascularization-associated factors, or a gene having a different function.

In an exemplary embodiment, the modification of nucleic acids may employ a wild type or variant enzyme which is capable of catalyzing hydrolysis (cleavage) of bonds between nucleic acids in a DNA or RNA molecule, preferably, a DNA molecule. It may also employ a guide nucleic acid-editor protein complex.

For example, the gene may be manipulated using one or more nucleases selected from the group consisting of a meganuclease, a zinc finger nuclease, CRISPR/Cas9 (Cas9 protein), CRISPR-Cpf1 (Cpf1 protein) and a TALE-nuclease, thereby regulating the expression of genetic information.

In a certain embodiment, non-limitedly, the gene manipulation may be mediated by NHEJ or homology-directed repair (HDR) using a guide nucleic acid-editor protein complex, for example, a CRISPR/Cas system.

In this case, when the NHEJ mechanism takes place, a change in DNA sequence may be induced at a cleavage site, thereby inactivating the gene. Repair by NHEJ may induce substitution, insertion or deletion of a short gene fragment, and may be used in the induction of the knockout of a corresponding gene.

In another aspect, the present invention may provide the gene manipulation site.

In an exemplary embodiment, when the gene is modified by NHEJ-mediated modification, the gene manipulation site may be a site in the gene, triggering the decrease or elimination of expression of a neovascularization regulating gene product.

For example, the site may be in an initial coding region,
a promoter sequence,
an enhancer sequence,
a specific intron sequence, or
a specific exon sequence.

In an exemplary embodiment, the composition for manipulating a neovascularization-associated factor may target a neovascularization-associated factor affecting the regulation of neovascularization, such as a VEGFA gene, an HIF1A gene, an ANGPT2 gene, an EPAS1 gene, or an ANGPTL4 gene, as a manipulation subject.

Examples of target regions, that is, target sequences for regions in which gene manipulation occurs or which are recognized for gene manipulation are summarized in Table 1, Table 2, Table 3, Table 4 and Table 5.

The target sequence may target one or more genes.

The target sequence may simultaneously target two or more genes. Here, the two or more genes may be homologous genes or heterologous genes.

The gene may contain one or more target sequences.

The gene may be simultaneously targeted at two or more target sequences.

The gene may be changed in the site and number of gene manipulations according to the number of target sequences.

The gene manipulation may be designed in various forms depending on the number and positions of the target sequences.

The gene manipulation may simultaneously occur in two or more target sequences. Here, the two or more target sequences may be present in the homologous gene or heterologous gene.

The gene manipulation may be simultaneously performed with respect to the two or more genes. Here, the two or more genes may be homologous genes or heterologous genes.

Hereinafter, examples of target sequences which are able to be used in embodiments of the present invention are shown in the following tables:
Table 1 Target sequences of VEGFA gene
Table 2 Target sequences of HIF1A gene
Table 3 Target sequences of ANGPT2 gene
Table 4 Target sequences of EPAS1 gene
Table 5 Target sequences of ANGPTL4 gene

TABLE 1

| Gene | No. | Target sequence |
|---|---|---|
| VEGFA | 1 | GTAGAGCAGCAAGGCAAGGCTC (SEQ ID NO: 1) |
| VEGFA | 2 | CTTTCTGTCCTCAGTGGTCCCA (SEQ ID NO: 2) |
| VEGFA | 3 | GAGACCCGGTGGACATCTTCC (SEQ ID NO: 3) |
| VEGFA | 4 | TTCCAGGAGTACCCTGATGAGA (SEQ ID NO: 4) |
| VEGFA | 5 | TTGAAGATGTACTCGATCTCAT (SEQ ID NO: 5) |
| VEGFA | 6 | AGGGGCACACAGGATGGCTTGA (SEQ ID NO: 6) |
| VEGFA | 7 | AGCAGCCCCGCATCGCATCAG (SEQ ID NO: 7) |
| VEGFA | 8 | GCAGCAGCCCCGCATCGCATC (SEQ ID NO: 8) |
| VEGFA | 9 | GTGATGTTGGACTCCTCAGTGG (SEQ ID NO: 9) |
| VEGFA | 10 | TGGTGATGTTGGACTCCTCAGT (SEQ ID NO: 10) |
| VEGFA | 11 | CATGGTGATGTTGGACTCCTCA (SEQ ID NO: 11) |
| VEGFA | 12 | ATGCGGATCAAACCTCACCAAG (SEQ ID NO: 12) |
| VEGFA | 13 | CACATAGGAGAGATGAGCTTCC (SEQ ID NO: 13) |

TABLE 2

| Gene | No. | Target sequence |
|---|---|---|
| HIF1A | 1 | ACTCACCAGCATCCAGAAGTTT (SEQ ID NO: 14) |
| HIF1A | 2 | ATTTGGATATTGAAGATGACAT (SEQ ID NO: 15) |
| HIF1A | 3 | ATTTACATTTCTGATAATGTGA (SEQ ID NO: 16) |
| HIF1A | 4 | ATGTGTTTACAGTTTGAACTAA (SEQ ID NO: 17) |
| HIF1A | 5 | CTGTGTCCAGTTAGTTCAAACT (SEQ ID NO: 18) |
| HIF1A | 6 | ATGGTCACATGGATGAGTAAAA (SEQ ID NO: 19) |
| HIF1A | 7 | CATGAGGAAATGAGAGAAATGC (SEQ ID NO: 20) |
| HIF1A | 8 | CCCAGTGAGAAAAGGGAAAGAA (SEQ ID NO: 21) |
| HIF1A | 9 | TTGTGAAAAAGGGTAAAGAACA (SEQ ID NO: 22) |
| HIF1A | 10 | ATAGTTCTTCCTCGGCTAGTTA (SEQ ID NO: 23) |
| HIF1A | 11 | TCATAGTTCTTCCTCGGCTAGT (SEQ ID NO: 24) |

TABLE 2-continued

| Gene | No. | Target sequence | |
|---|---|---|---|
| HIF1A | 12 | TGTTCTTCATACACAGGTATTG | (SEQ ID NO: 25) |
| HIF1A | 13 | TACGTGAATGTGGCCTGTGCAG | (SEQ ID NO: 26) |
| HIF1A | 14 | CTGCACAGGCCACATTCACGTA | (SEQ ID NO: 27) |
| HIF1A | 15 | CTGAGGTTGGTTACTGTTGGTA | (SEQ ID NO: 28) |
| HIF1A | 16 | CAGGTCATAGGTGGTTTCTTAT | (SEQ ID NO: 29) |
| HIF1A | 17 | ACCAAGCAGGTCATAGGTGGTT | (SEQ ID NO: 30) |
| HIF1A | 18 | TTAGATAGCAAGACTTTCCTCA | (SEQ ID NO: 31) |

TABLE 3

| Gene | No. | Target sequence | |
|---|---|---|---|
| ANGPT2 | 1 | TCAGGTCCAGCATGGGTCCTGC | (SEQ ID NO: 32) |
| ANGPT2 | 2 | CGGCGCGTCCCTCTGCACAGCA | (SEQ ID NO: 33) |
| ANGPT2 | 3 | GCTGTGCAGAGGGACGCGCCGC | (SEQ ID NO: 34) |
| ANGPT2 | 4 | ATCGTATTCGAGCGGCGCGTCC | (SEQ ID NO: 35) |
| ANGPT2 | 5 | GATGTTCTCCAGCACTTGCAGC | (SEQ ID NO: 36) |
| ANGPT2 | 6 | AGTGCTGGAGAACATCATGGAA | (SEQ ID NO: 37) |
| ANGPT2 | 7 | ACAACATGAAGAAAGAAATGGT | (SEQ ID NO: 38) |
| ANGPT2 | 8 | AAATGGTAGAGATACAGCAGAA | (SEQ ID NO: 39) |
| ANGPT2 | 9 | TTCTATCATCACAGCCGTCTGG | (SEQ ID NO: 40) |
| ANGPT2 | 10 | AAGTTCAAGTCTCGTGGTCTGA | (SEQ ID NO: 41) |
| ANGPT2 | 11 | ACGAGACTTGAACTTCAGCTCT | (SEQ ID NO: 42) |
| ANGPT2 | 12 | AAGAAGGTGCTAGCTATGGAAG | (SEQ ID NO: 43) |
| ANGPT2 | 13 | GATGATGTGCTTGTCTTCCATA | (SEQ ID NO: 44) |

TABLE 4

| Gene | No. | Target sequence | |
|---|---|---|---|
| EPAS1 | 1 | AACACCTCCGTCTCCTTGCTCC | (SEQ ID NO: 45) |
| EPAS1 | 2 | GAAGCTGACCAGCAGATGGACA | (SEQ ID NO: 46) |
| EPAS1 | 3 | GCAATGAAACCCTCCAAGGCTT | (SEQ ID NO: 47) |
| EPAS1 | 4 | AAAACATCAGCAAGTTCATGGG | (SEQ ID NO: 48) |
| EPAS1 | 5 | GCAAGTTCATGGGACTTACACA | (SEQ ID NO: 49) |
| EPAS1 | 6 | GGTCGCAGGGATGAGTGAAGTC | (SEQ ID NO: 50) |
| EPAS1 | 7 | GCGGGACTTCTTCATGAGGATG | (SEQ ID NO: 51) |
| EPAS1 | 8 | GAAGTGCACGGTCACCAACAGA | (SEQ ID NO: 52) |
| EPAS1 | 9 | ACAGTACGGCCTCTGTTGGTGA | (SEQ ID NO: 53) |
| EPAS1 | 10 | TCCAGGTGGCTGACTTGAGGTT | (SEQ ID NO: 54) |
| EPAS1 | 11 | CAGGACAGCAGGGGCTCCTTGT | (SEQ ID NO: 55) |
| EPAS1 | 12 | TAGCCCCCATGCTTTGCGAGCA | (SEQ ID NO: 56) |

TABLE 5

| Gene | No. | Target sequence | |
|---|---|---|---|
| ANGPTL4 | 1 | GCATCAGGGCTGCCCCGGCCGT | (SEQ ID NO: 57) |
| ANGPTL4 | 2 | CACGGGTCCGCCCTGAGCGCTC | (SEQ ID NO: 58) |
| ANGPTL4 | 3 | GGACGCAAAGCGCGGCGACTTG | (SEQ ID NO: 59) |
| ANGPTL4 | 4 | TCCTGGGACGAGATGAATGTCC | (SEQ ID NO: 60) |
| ANGPTL4 | 5 | CTGCAGCTCGGCCAGGGCTGC | (SEQ ID NO: 61) |
| ANGPTL4 | 6 | CCAGGGGCTGCGCGAACACGCG | (SEQ ID NO: 62) |
| ANGPTL4 | 7 | CCCTCGGTTCCCTGACAGGCGG | (SEQ ID NO: 63) |
| ANGPTL4 | 8 | ACCCTGAGGTCCTTCACAGCCT | (SEQ ID NO: 64) |
| ANGPTL4 | 9 | TTCCACAAGGTGGCCCAGCAGC | (SEQ ID NO: 65) |
| ANGPTL4 | 10 | CAGCAGCAGCGGCACCTGGAGA | (SEQ ID NO: 66) |
| ANGPTL4 | 11 | TCCTAGTTTGGCCTCCTGGACC | (SEQ ID NO: 67) |
| ANGPTL4 | 12 | GACCCGGCTCACAATGTCAGCC | (SEQ ID NO: 68) |
| ANGPTL4 | 13 | GCTGTTGCGGTCCCCCGTGATG | (SEQ ID NO: 69) |
| ANGPTL4 | 14 | GGCGTTGCCATCCCAGTCCCGC | (SEQ ID NO: 70) |
| ANGPTL4 | 15 | AACGCCGAGTTGCTGCAGTTCT | (SEQ ID NO: 71) |
| ANGPTL4 | 16 | ATAGGCCGTGTCCTCGCCACCC | (SEQ ID NO: 72) |
| ANGPTL4 | 17 | GTTCTCCGTGCACCTGGGTGGC | (SEQ ID NO: 73) |
| ANGPTL4 | 18 | ACACGGCCTATAGCCTGCAGCT | (SEQ ID NO: 74) |
| ANGPTL4 | 19 | CCACCGTCCCACCCAGCGGCCT | (SEQ ID NO: 75) |
| ANGPTL4 | 20 | GTGATCCTGGTCCCAAGTGGAG | (SEQ ID NO: 76) |
| ANGPTL4 | 21 | GACCCCGGCAGGAGGCTGGTGG | (SEQ ID NO: 77) |
| ANGPTL4 | 22 | TGCAGCCATTCCAACCTCAACG | (SEQ ID NO: 78) |
| ANGPTL4 | 23 | TGCCGCTGCTGTGGGATGGAGC | (SEQ ID NO: 79) |

Composition for Manipulation-Gene Scissors System

The neovascularization-regulating system of the present invention may include a guide nucleic acid-editor protein complex as a composition for manipulating a neovascularization-associated factor.

Guide Nucleic Acid-Editor Protein Complex

The term "guide nucleic acid-editor protein complex" refers to a complex formed through the interaction between a guide nucleic acid and an editor protein, and the nucleic acid-protein complex includes a guide nucleic acid and an editor protein.

The term "guide nucleic acid" refers to a nucleic acid capable of recognizing a target nucleic acid, gene, chromosome or protein.

The guide nucleic acid may be present in the form of DNA, RNA or a DNA/RNA hybrid, and may have a nucleic acid sequence of 5 to 150 bases.

The guide nucleic acid may include one or more domains.

The domains may be, but are not limited to, a guide domain, a first complementary domain, a linker domain, a second complementary domain, a proximal domain, or a tail domain.

The guide nucleic acid may include two or more domains, which may be the same domain repeats, or different domains.

The guide nucleic acid may have one continuous nucleic acid sequence.

For example, the one continuous nucleic acid sequence may be (N)m, where N represents A, T, C or G, or A, U, C or G, and m is an integer of 1 to 150.

The guide nucleic acid may have two or more continuous nucleic acid sequences.

For example, the two or more continuous nucleic acid sequences may be (N)m and (N)o, where N represents A, T, C or G, or A, U, C or G, m and o are an integer of 1 to 150, and m and o may be the same as or different from each other.

The term "editor protein" refers to a peptide, polypeptide or protein which is able to directly bind to or interact with, without direct binding to, a nucleic acid.

The editor protein may be an enzyme.

The editor protein may be a fusion protein.

Here, the "fusion protein" refers to a protein that is produced by fusing an enzyme with an additional domain, peptide, polypeptide or protein.

The term "enzyme" refers to a protein that contains a domain capable of cleaving a nucleic acid, gene, chromosome or protein.

The additional domain, peptide, polypeptide or protein may be a functional domain, peptide, polypeptide or protein, which has a function the same as or different from the enzyme.

The fusion protein may include an additional domain, peptide, polypeptide or protein at one or more regions of the amino terminus (N-terminus) of the enzyme or the vicinity thereof; the carboxyl terminus (C-terminus) or the vicinity thereof; the middle part of the enzyme; and a combination thereof.

The fusion protein may include a functional domain, peptide, polypeptide or protein at one or more regions of the N-terminus of the enzyme or the vicinity thereof; the C-terminus or the vicinity thereof; the middle part of the enzyme; and a combination thereof.

The guide nucleic acid-editor protein complex may serve to modify a subject.

The subject may be a target nucleic acid, gene, chromosome or protein.

For example, the guide nucleic acid-editor protein complex may result in final regulation (e.g., inhibition, suppression, reduction, increase or promotion) of the expression of a protein of interest, removal of the protein, or expression of a new protein.

Here, the guide nucleic acid-editor protein complex may act at a DNA, RNA, gene or chromosome level.

The guide nucleic acid-editor protein complex may act in gene transcription and translation stages.

The guide nucleic acid-editor protein complex may act at a protein level.

1. Guide Nucleic Acids

The guide nucleic acid is a nucleic acid that is capable of recognizing a target nucleic acid, gene, chromosome or protein, and forms a guide nucleic acid-protein complex.

Here, the guide nucleic acid is configured to recognize or target a nucleic acid, gene, chromosome or protein targeted by the guide nucleic acid-protein complex.

The guide nucleic acid may be present in the form of DNA, RNA or a DNA/RNA mixture, and have a 5 to 150-nucleic acid sequence.

The guide nucleic acid may be present in a linear or circular shape.

The guide nucleic acid may be one continuous nucleic acid sequence.

For example, the one continuous nucleic acid sequence may be $(N)_m$, where N is A, T, C or G, or A, U, C or G, and m is an integer of 1 to 150.

The guide nucleic acid may be two or more continuous nucleic acid sequences.

For example, the two or more continuous nucleic acid sequences may be (N)m and (N)o, where N represents A, T, C or G, or A, U, C or G, m and o are an integer of 1 to 150, and may be the same as or different from each other.

The guide nucleic acid may include one or more domains.

Here, the domains may be, but are not limited to, a guide domain, a first complementary domain, a linker domain, a second complementary domain, a proximal domain, or a tail domain.

The guide nucleic acid may include two or more domains, which may be the same domain repeats, or different domains.

The domains will be described below.

i) Guide Domain

The term "guide domain" is a domain having a complementary guide sequence which is able to form a complementary bond with a target sequence on a target gene or nucleic acid, and serves to specifically interact with the target gene or nucleic acid.

The guide sequence is a nucleic acid sequence complementary to the target sequence on a target gene or nucleic acid, which has, for example, at least 50% or more, 55%, 60%, 65%, 70%, 75%, 80%, 85%, 90% or 95% complementarity or complete complementarity.

The guide domain may be a sequence of 5 to 50 bases.

In an example, the guide domain may be a sequence of 5 to 50, 10 to 50, 15 to 50, 20 to 50, 25 to 50, 30 to 50, 35 to 50, 40 to 50 or 45 to 50 bases.

In another example, the guide domain may be a sequence of 1 to 5, 5 to 10, 10 to 15, 15 to 20, 20 to 25, 25 to 30, 30 to 35, 35 to 40, 40 to 45, or 45 to 50 bases.

The guide domain may have a guide sequence.

The guide sequence may be a complementary base sequence which is able to form a complementary bond with the target sequence on the target gene or nucleic acid.

The guide sequence may be a nucleic acid sequence complementary to the target sequence on the target gene or nucleic acid, which has, for example, at least 70%, 75%, 80%, 85%, 90% or 95% or more complementarity or complete complementarity.

The guide sequence may be a 5 to 50-base sequence.

In an example, the guide domain may be a 5 to 50, 10 to 50, 15 to 50, 20 to 50, 25 to 50, 30 to 50, 35 to 50, 40 to 50, or 45 to 50-base sequence.

In another example, the guide sequence may be a 1 to 5, 5 to 10, 10 to 15, 15 to 20, 20 to 25, 25 to 30, 30 to 35, 35 to 40, 40 to 45, or 45 to 50-base sequence.

In addition, the guide domain may include a guide sequence and an additional base sequence.

The additional base sequence may be utilized to improve or degrade the function of the guide domain.

The additional base sequence may be utilized to improve or degrade the function of the guide sequence.

The additional base sequence may be a 1 to 35-base sequence.

In one example, the additional base sequence may be a 5 to 35, 10 to 35, 15 to 35, 20 to 35, 25 to 35 or 30 to 35-base sequence.

In another example, the additional base sequence may be a 1 to 5, 5 to 10, 10 to 15, 15 to 20, 20 to 25, 25 to 30 or 30 to 35-base sequence.

The additional base sequence may be located at the 5'end of the guide sequence.

The additional base sequence may be located at the 3'end of the guide sequence.

ii) First Complementary Domain

The term "first complementary domain" is a nucleic acid sequence including a nucleic acid sequence complementary to a second complementary domain, and has enough complementarity so as to form a double strand with the second complementary domain.

The first complementary domain may be a 5 to 35-base sequence.

In an example, the first complementary domain may be a 5 to 35, 10 to 35, 15 to 35, 20 to 35, 25 to 35, or 30 to 35-base sequence.

In another example, the first complementary domain may be a 1 to 5, 5 to 10, 10 to 15, 15 to 20, 20 to 25, 25 to 30 or 30 to 35-base sequence.

iii) Linker Domain

The term "linker domain" is a nucleic acid sequence connecting two or more domains, which are two or more identical or different domains. The linker domain may be connected with two or more domains by covalent bonding or non-covalent bonding, or may connect two or more domains by covalent bonding or non-covalent bonding.

The linker domain may be a 1 to 30-base sequence.

In one example, the linker domain may be a 1 to 5, 5 to 10, 10 to 15, 15 to 20, 20 to 25, or 25 to 30-base sequence.

In another example, the linker domain may be a 1 to 30, 5 to 30, 10 to 30, 15 to 30, 20 to 30, or 25 to 30-base sequence.

iv) Second Complementary Domain

The term "second complementary domain" is a nucleic acid sequence including a nucleic acid sequence complementary to the first complementary domain, and has enough complementarity so as to form a double strand with the first complementary domain.

The second complementary domain may have a base sequence complementary to the first complementary domain, and a base sequence having no complementarity to the first complementary domain, for example, a base sequence not forming a double strand with the first complementary domain, and may have a longer base sequence than the first complementary domain.

The second complementary domain may have a 5 to 35-base sequence.

In an example, the second complementary domain may be a 1 to 35, 5 to 35, 10 to 35, 15 to 35, 20 to 35, 25 to 35, or 30 to 35-base sequence.

In another example, the second complementary domain may be a 1 to 5, 5 to 10, 10 to 15, 15 to 20, 20 to 25, 25 to 30, or 30 to 35-base sequence.

v) Proximal Domain

The term "proximal domain" is a nucleic acid sequence located adjacent to the second complementary domain.

The proximal domain may have a complementary base sequence therein, and may be formed in a double strand due to a complementary base sequence.

The proximal domain may be a 1 to 20-base sequence.

In one example, the proximal domain may be a 1 to 20, 5 to 20, 10 to 20 or 15 to 20-base sequence.

In another example, the proximal domain may be a 1 to 5, 5 to 10, 10 to 15 or 15 to 20-base sequence.

vi) Tail Domain

The term "tail domain" is a nucleic acid sequence located at one or more ends of the both ends of the guide nucleic acid.

The tail domain may have a complementary base sequence therein, and may be formed in a double strand due to a complementary base sequence.

The tail domain may be a 1 to 50-base sequence.

In an example, the tail domain may be a 5 to 50, 10 to 50, 15 to 50, 20 to 50, 25 to 50, 30 to 50, 35 to 50, 40 to 50, or 45 to 50-base sequence.

In another example, the tail domain may be a 1 to 5, 5 to 10, 10 to 15, 15 to 20, 20 to 25, 25 to 30, 30 to 35, 35 to 40, 40 to 45, or 45 to 50-base sequence.

Meanwhile, a part or all of the nucleic acid sequences included in the domains, that is, the guide domain, the first complementary domain, the linker domain, the second complementary domain, the proximal domain and the tail domain may selectively or additionally include a chemical modification.

The chemical modification may be, but is not limited to, methylation, acetylation, phosphorylation, phosphorothioate linkage, a locked nucleic acid (LNA), 2'-O-methyl 3'phosphorothioate (MS) or 2'-O-methyl 3'thioPACE (MSP).

The guide nucleic acid includes one or more domains.

The guide nucleic acid may include a guide domain.

The guide nucleic acid may include a first complementary domain.

The guide nucleic acid may include a linker domain.

The guide nucleic acid may include a second complementary domain.

The guide nucleic acid may include a proximal domain.

The guide nucleic acid may include a tail domain.

Here, there may be 1, 2, 3, 4, 5, 6 or more domains.

The guide nucleic acid may include 1, 2, 3, 4, 5, 6 or more guide domains.

The guide nucleic acid may include 1, 2, 3, 4, 5, 6 or more first complementary domains.

The guide nucleic acid may include 1, 2, 3, 4, 5, 6 or more linker domains.

The guide nucleic acid may include 1, 2, 3, 4, 5, 6 or more second complementary domains.

The guide nucleic acid may include 1, 2, 3, 4, 5, 6 or more proximal domains.

The guide nucleic acid may include 1, 2, 3, 4, 5, 6 or more tail domains.

Here, in the guide nucleic acid, one type of domain may be duplicated.

The guide nucleic acid may include several domains with or without duplication.

The guide nucleic acid may include the same type of domain. Here, the same type of domain may have the same nucleic acid sequence or different nucleic acid sequences.

The guide nucleic acid may include two types of domains. Here, the two different types of domains may have different nucleic acid sequences or the same nucleic acid sequence.

The guide nucleic acid may include three types of domains. Here, the three different types of domains may have different nucleic acid sequences or the same nucleic acid sequence.

The guide nucleic acid may include four types of domains. Here, the four different types of domains may have different nucleic acid sequences, or the same nucleic acid sequence.

The guide nucleic acid may include five types of domains. Here, the five different types of domains may have different nucleic acid sequences, or the same nucleic acid sequence.

The guide nucleic acid may include six types of domains. Here, the six different types of domains may have different nucleic acid sequences, or the same nucleic acid sequence.

For example, the guide nucleic acid may consist of [guide domain]-[first complementary domain]-[linker domain]-[second complementary domain]-[linker domain]-[guide domain]-[first complementary domain]-[linker domain]-[second complementary domain]. Here, the two guide domains may include guide sequences for different or the same targets, the two first complementary domains and the two second complementary domains may have the same or different nucleic acid sequences. When the guide domains include guide sequences for different targets, the guide nucleic acids may specifically bind to two different targets, and here, the specific bindings may be performed simultaneously or sequentially. In addition, the linker domains may be cleaved by specific enzymes, and the guide nucleic acids may be divided into two or three parts in the presence of specific enzymes.

As a specific example of the guide nucleic acid of the present invention, gRNA will be described below.

gRNA

The term "gRNA" refers to a nucleic acid capable of specifically targeting a gRNA-CRISPR enzyme complex, that is, a CRISPR complex, with respect to a target gene or nucleic acid. In addition, the gRNA is a nucleic acid-specific RNA which may bind to a CRISPR enzyme and guide the CRISPR enzyme to the target gene or nucleic acid.

The gRNA may include multiple domains. Due to each domain, interactions may occur in a three-dimensional structure or active form of a gRNA strand, or between these strands.

The gRNA may be called single-stranded gRNA (single RNA molecule); or double-stranded gRNA (including more than one, generally, two discrete RNA molecules).

In one exemplary embodiment, the single-stranded gRNA may include a guide domain, that is, a domain including a guide sequence capable of forming a complementary bond with a target gene or nucleic acid; a first complementary domain; a linker domain; a second complementary domain, a domain having a sequence complementary to the first complementary domain sequence, thereby forming a double-stranded nucleic acid with the first complementary domain; a proximal domain; and optionally a tail domain in the 5' to 3' direction.

In another embodiment, the double-stranded gRNA may include a first strand which includes a guide domain, that is, a domain including a guide sequence capable of forming a complementary bond with a target gene or nucleic acid and a first complementary domain; and a second strand which includes a second complementary domain, a domain having a sequence complementary to the first complementary domain sequence, thereby forming a double-stranded nucleic acid with the first complementary domain, a proximal domain; and optionally a tail domain in the 5' to 3' direction.

Here, the first strand may be referred to as crRNA, and the second strand may be referred to as tracrRNA. The crRNA may include a guide domain and a first complementary domain, and the tracrRNA may include a second complementary domain, a proximal domain and optionally a tail domain.

In still another embodiment, the single-stranded gRNA may include a guide domain, that is, a domain including a guide sequence capable of forming a complementary bond with a target gene or nucleic acid; a first complementary domain; a second complementary domain, and a domain having a sequence complementary to the first complementary domain sequence, thereby forming a double-stranded nucleic acid with the first complementary domain in the 5' to 3' direction.

i) Guide Domain

The guide domain includes a complementary guide sequence capable of forming a complementary bond with a target sequence on a target gene or nucleic acid. The guide sequence may be a nucleic acid sequence having complementarity to the target sequence on the target gene or nucleic acid, for example, at least 70%, 75%, 80%, 85%, 90% or 95% or more complementarity or complete complementarity. The guide domain is considered to allow a gRNA-Cas complex, that is, a CRISPR complex to specifically interact with the target gene or nucleic acid.

The guide domain may be a 5 to 50-base sequence.

As an exemplary embodiment, the guide domain may be a 16, 17, 18, 19, 20, 21, 22, 23, 24 or 25-base sequence.

As an exemplary embodiment, the guide domain may include a 16, 17, 18, 19, 20, 21, 22, 23, 24 or 25-base sequence.

Here, the guide domain may include a guide sequence.

The guide sequence may be a complementary base sequence capable of forming a complementary bond with a target sequence on a target gene or nucleic acid.

The guide sequence may be a nucleic acid sequence complementary to the target sequence on the target gene or nucleic acid, which has, for example, at least 70%, 75%, 80%, 85%, 90% or 95% or more complementarity or complete complementarity.

In one exemplary embodiment, the guide sequence may be a nucleic acid sequence complementary to a target gene, that is, a target sequence of a neovascularization-associated factor such as a VEGFA gene, an HIF1A gene, an ANGPT2 gene, an EPAS1 gene or an ANGPTL4 gene, which has, for example, at least 70%, 75%, 80%, 85%, 90% or 95% or more complementarity or complete complementarity.

The guide sequence may be a 5 to 50-base sequence.

In an exemplary embodiment, the guide sequence may be a 16, 17, 18, 19, 20, 21, 22, 23, 24 or 25-base sequence.

In one exemplary embodiment, the guide sequence may include a 16, 17, 18, 19, 20, 21, 22, 23, 24 or 25-base sequence.

In one exemplary embodiment, the guide sequence may be a nucleic acid sequence complementary to a target sequence of the VEGFA gene, which is a 16, 17, 18, 19, 20, 21, 22, 23, 24 or 25-base sequence.

In one exemplary embodiment, the guide sequence may be a nucleic acid sequence complementary to a target sequence of the HIF1A gene, which is a 16, 17, 18, 19, 20, 21, 22, 23, 24 or 25-base sequence.

In one exemplary embodiment, the guide sequence may be a nucleic acid sequence complementary to a target sequence of the ANGPT2 gene, which is a 16, 17, 18, 19, 20, 21, 22, 23, 24 or 25-base sequence.

In one exemplary embodiment, the guide sequence may be a nucleic acid sequence complementary to a target sequence of the EPAS1 gene, which is a 16, 17, 18, 19, 20, 21, 22, 23, 24 or 25-base sequence.

In one exemplary embodiment, the guide sequence may be a nucleic acid sequence complementary to a target sequence of the ANGPTL4 gene, which is a 16, 17, 18, 19, 20, 21, 22, 23, 24 or 25-base sequence.

Here, target sequences of the target genes, that is, the neovascularization-associated factors such as the VEGFA gene, the HIF1A gene, the ANGPT2 gene, the EPAS1 gene, and the ANGPTL4 gene for the guide sequence are listed above in Table 1, Table 2, Table 3, Table 4 and Table 5, respectively, but the present invention is not limited thereto.

Here, the guide domain may include a guide sequence and an additional base sequence.

The additional base sequence may be a 1 to 35-base sequence.

In one exemplary embodiment, the additional base sequence may be a 1, 2, 3, 4, 5, 6, 7, 8, 9 or 10-base sequence.

For example, the additional base sequence may be a single base sequence, guanine (G), or a sequence of two bases, GG.

The additional base sequence may be located at the 5' end of the guide sequence.

The additional base sequence may be located at the 3' end of the guide sequence.

Selectively, a part or all of the base sequence of the guide domain may include a chemical modification. The chemical modification may be methylation, acetylation, phosphorylation, phosphorothioate linkage, a locked nucleic acid (LNA), 2'-O-methyl 3' phosphorothioate (MS) or 2'-O-methyl 3' thioPACE (MSP), but the present invention is not limited thereto.

ii) First Complementary Domain

The first complementary domain includes a nucleic acid sequence complementary to a second complementary domain, and has enough complementarity such that it is able to form a double strand with the second complementary domain.

Here, the first complementary domain may be a 5 to 35-base sequence. The first complementary domain may include a 5 to 35-base sequence.

In one exemplary embodiment, the first complementary domain may be a 5, 6, 7, 8, 9, 10, 11, 12, 13, 14, 15, 16, 17, 18, 19, 20, 21, 22, 23, 24, or 25-base sequence.

In another embodiment, the first complementary domain may include a 5, 6, 7, 8, 9, 10, 11, 12, 13, 14, 15, 16, 17, 18, 19, 20, 21, 22, 23, 24, or 25-base sequence.

The first complementary domain may have homology with a natural first complementary domain, or may be derived from a natural first complementary domain. In addition, the first complementary domain may have a difference in the base sequence of a first complementary domain depending on the species existing in nature, may be derived from a first complementary domain contained in the species existing in nature, or may have partial or complete homology with the first complementary domain contained in the species existing in nature.

In one exemplary embodiment, the first complementary domain may have partial, that is, at least 50% or more, or complete homology with a first complementary domain of *Streptococcus pyogenes*, *Campylobacter jejuni*, *Streptococcus thermophilus*, *Streptococcus aureus* or *Neisseria meningitides*, or a first complementary domain derived therefrom.

For example, when the first complementary domain is the first complementary domain of *Streptococcus pyogenes* or a first complementary domain derived therefrom, the first complementary domain may be 5'-GUUUUAGAGCUA-3' (SEQ ID NO: 1523) or a base sequence having partial, that is, at least 50% or more, or complete homology with 5'-GUUUUAGAGCUA-3' (SEQ ID NO: 1523). Here, the first complementary domain may further include (X)n, resulting in 5'-GUUUUAGAGCUA(X)n-3' (SEQ ID NO: 1530). The X may be selected from the group consisting of bases A, T, U and G, and the n may represent the number of bases, which is an integer of 5 to 15. Here, the (X)n may be n repeats of the same base, or a mixture of n bases of A, T, U and G.

In another embodiment, when the first complementary domain is the first complementary domain of *Campylobacter jejuni* or a first complementary domain derived therefrom, the first complementary domain may be 5'-GUUUUAGUCCCUUUUUAAAUUUCUU-3' (SEQ ID NO: 1524), or a base sequence having partial, that is, at least 50% or more, or complete homology with 5'-GUUUUAGUCCCUUUUUAAAUUUCUU-3' (SEQ ID NO: 1524). Here, the first complementary domain may further include (X)n, resulting in 5'-GUUUUAGUCCCUUUUUAAAUUUCUU(X)n-3' (SEQ ID NO: 1531). The X may be selected from the group consisting of bases A, T, U and G, and the n may represent the number of bases, which is an integer of 5 to 15. Here, the (X)n may represent n repeats of the same base, or a mixture of n bases of A, T, U and G.

In another embodiment, the first complementary domain may have partial, that is, at least 50% or more, or complete homology with a first complementary domain of Parcubacteria bacterium (GWC2011_GWC2_44_17), Lachnospiraceae bacterium (MC2017), *Butyrivibrio proteoclasticus*, *Peregrinibacteria bacterium* (GW2011_GWA_33_10), *Acidaminococcus* sp. (BV3L6), *Porphyromonas macacae*, Lachnospiraceae bacterium (ND2006), *Porphyromonas crevioricanis*, *Prevotella disiens*, *Moraxella bovoculi* (237), *Smithella* sp. (SC_KO8D17), *Leptospira inadai*, Lachnospiraceae bacterium (MA2020), *Francisella novicida* (U112), Candidatus Methanoplasma *termitum* or *Eubacterium eligens*, or a first complementary domain derived therefrom.

For example, when the first complementary domain is the first complementary domain of Parcubacteria bacterium or a first complementary domain derived therefrom, the first complementary domain may be 5'-UUUGUAGAU-3' (SEQ ID NO: 1525), or a base sequence having partial, that is, at least 50% or more homology with 5'-UUUGUAGAU-3' (SEQ ID NO: 1525). Here, the first complementary domain may further include (X)n, resulting in 5'-(X)nUUUGUAGAU-3' (SEQ ID NO: 1532). The X may be selected from the group consisting of bases A, T, U and G, and the n may represent the number of bases, which is an integer of 1 to 5. Here, the (X)n may represent n repeats of the same base, or a mixture of n bases of A, T, U and G.

Selectively, a part or all of the base sequence of the first complementary domain may have a chemical modification. The chemical modification may be methylation, acetylation, phosphorylation, phosphorothioate linkage, a locked nucleic acid (LNA), 2'-O-methyl 3' phosphorothioate (MS) or 2'-O-methyl 3' thioPACE (MSP), but the present invention is not limited thereto.

iii) Linker Domain

The linker domain is a nucleic acid sequence connecting two or more domains, and connects two or more identical or different domains. The linker domain may be connected with two or more domains, or may connect two or more domains by covalent or non-covalent bonding.

The linker domain may be a nucleic acid sequence connecting a first complementary domain with a second complementary domain to produce single-stranded gRNA.

The linker domain may be connected with the first complementary domain and the second complementary domain by covalent or non-covalent bonding.

The linker domain may connect the first complementary domain with the second complementary domain by covalent or non-covalent bonding The linker domain may be a 1 to 30-base sequence. The linker domain may include a 1 to 30-base sequence.

In an exemplary embodiment, the linker domain may be a 1 to 5, 5 to 10, 10 to 15, 15 to 20, 20 to 25 or 25 to 30-base sequence.

In an exemplary embodiment, the linker domain may include a 1 to 5, 5 to 10, 10 to 15, 15 to 20, 20 to 25, or 25 to 30-base sequence.

The linker domain is suitable to be used in a single-stranded gRNA molecule, and may be used to produce single-stranded gRNA by being connected with a first strand and a second strand of double-stranded gRNA or connecting the first strand with the second strand by covalent or non-covalent bonding. The linker domain may be used to produce single-stranded gRNA by being connected with crRNA and tracrRNA of double-stranded gRNA or connecting the crRNA with the tracrRNA by covalent or non-covalent bonding.

The linker domain may have homology with a natural sequence, for example, a partial sequence of tracrRNA, or may be derived therefrom.

Selectively, a part or all of the base sequence of the linker domain may have a chemical modification. The chemical modification may be methylation, acetylation, phosphorylation, phosphorothioate linkage, a locked nucleic acid (LNA), 2'-O-methyl 3' phosphorothioate (MS) or 2'-O-methyl 3' thioPACE (MSP), but the present invention is not limited thereto.

iv) Second Complementary Domain

The second complementary domain includes a nucleic acid sequence complementary to the first complementary domain, and has enough complementarity so as to form a double strand with the first complementary domain. The second complementary domain may include a base sequence complementary to the first complementary domain, and a base sequence having no complementarity with the first complementary domain, for example, a base sequence not forming a double strand with the first complementary domain, and may have a longer base sequence than the first complementary domain.

Here, the second complementary domain may be a 5 to 35-base sequence. The first complementary domain may include a 5 to 35-base sequence.

In an exemplary embodiment, the second complementary domain may be a 5, 6, 7, 8, 9, 10, 11, 12, 13, 14, 15, 16, 17, 18, 19, 20, 21, 22, 23, 24 or 25-base sequence.

In an exemplary embodiment, the second complementary domain may include a 5, 6, 7, 8, 9, 10, 11, 12, 13, 14, 15, 16, 17, 18, 19, 20, 21, 22, 23, 24 or 25-base sequence.

In addition, the second complementary domain may have homology with a natural second complementary domain, or may be derived from the natural second complementary domain. In addition, the second complementary domain may have a difference in base sequence of a second complementary domain according to a species existing in nature, and may be derived from a second complementary domain contained in the species existing in nature, or may have partial or complete homology with the second complementary domain contained in the species existing in nature.

In an exemplary embodiment, the second complementary domain may have partial, that is, at least 50% or more, or complete homology with a second complementary domain of *Streptococcus pyogenes, Campylobacter jejuni, Streptococcus thermophilus, Streptococcus aureus* or *Neisseria meningitides*, or a second complementary domain derived therefrom.

For example, when the second complementary domain is a second complementary domain of *Streptococcus pyogenes* or a second complementary domain derived therefrom, the second complementary domain may be 5'-UAGCAAGUUAAAAU-3' (SEQ ID NO: 1526), or a base sequence having partial, that is, at least 50% or more homology with 5'-UAGCAAGUUAAAAU-3' (SEQ ID NO: 1526) (a base sequence forming a double strand with the first complementary domain is underlined). Here, the second complementary domain may further include $(X)_n$ and/or $(X)_m$, resulting in 5'-$(X)_n$ UAGCAAGUUAAAAU$(X)_m$-3' (SEQ ID NO: 1533). The X may be selected from the group consisting of bases A, T, U and G, and each of the n and m may represent the number of bases, in which the n may be an integer of 1 to 15, and the m may be an integer of 1 to 6. Here, the $(X)_n$ may represent n repeats of the same base, or a mixture of n bases of A, T, U and G. In addition, $(X)_m$ may represent m repeats of the same base, or a mixture of m bases of A, T, U and G.

In another example, when the second complementary domain is the second complementary domain of *Campylobacter jejuni* or a second complementary domain derived therefrom, the second complementary domain may be 5'-AAGAAAUUUAAAAAGGGACUAAAAU-3' (SEQ ID NO: 1527), or a base sequence having partial, that is, at least 50% or more homology with 5'-AAGAAAUUUAAAAAGGGACUAAAAU-3' (SEQ ID NO: 1527) (a base sequence forming a double strand with the first complementary domain is underlined). Here, the second complementary domain may further include $(X)_n$ and/or $(X)_m$, resulting in 5'-$(X)_n$AAGAAAUUUAAAAAGGGACUAAAAU$(X)_m$-3' (SEQ ID NO: 1534). The X may be selected from the group consisting of bases A, T, U and G, and each of the n and m may represent the number of bases, in which the n may be an integer of 1 to 15, and the m may be an integer of 1 to 6. Here, $(X)_n$ may represent n repeats of the same base, or a mixture of n bases of A, T, U and G. In addition, $(X)_m$ may represent m repeats of the same base, or a mixture of m bases of A, T, U and G.

In another embodiment, the second complementary domain may have partial, that is, at least 50% or more, or complete homology with a first complementary domain of Parcubacteria bacterium (GWC2011_GWC2_44_17), Lachnospiraceae bacterium (MC2017), *Butyrivibrio proteoclasticus*, Peregrinibacteria bacterium (GW2011_GWA_33_10), *Acidaminococcus* sp. (BV3L6), *Porphyromonas macacae*, Lachnospiraceae bacterium (ND2006), *Porphyromonas crevioricanis*, *Prevotella disiens*, *Moraxella bovoculi* (237), *Smithella* sp. (SC_KO8D17), *Leptospira inadai*, Lachnospiraceae bacterium (MA2020), *Francisella novicida* (U112), Candidatus Methanoplasma *termitum* or *Eubacterium eligens*, or a second complementary domain derived therefrom.

For example, when the second complementary domain is a second complementary domain of Parcubacteria bacterium or a second complementary domain derived therefrom, the second complementary domain may be 5'-AAAUUUC-UACU-3' (SEQ ID NO: 1535), or a base sequence having partial, that is, at least 50% or more homology with 5'-AAAUUUCUACU-3' (SEQ ID NO: 1535) (a base sequence forming a double strand with the first complementary domain is underlined). Here, the second complementary domain may further include $(X)_n$ and/or $(X)_m$, resulting in 5'-(X)nAAAUUCUACU(X)m-3' (SEQ ID NO: 1563). The X may be selected from the group consisting of bases A, T, U and G, and each of the n and m may represent the number of bases, in which the n may be an integer of 1 to 10, and the m may be an integer of 1 to 6. Here, the (X)n may represent n repeats of the same base, or a mixture of n bases of A, T, U and G. In addition, the (X)m may represent m repeats of the same base, or a mixture of m bases of A, T, U and G.

Selectively, a part or all of the base sequence of the second complementary domain may have a chemical modification. The chemical modification may be methylation, acetylation, phosphorylation, phosphorothioate linkage, a locked nucleic acid (LNA), 2'-O-methyl 3'phosphorothioate (MS) or 2'-O-methyl 3'thioPACE (MSP), but the present invention is not limited thereto.

v) Proximal Domain

The proximal domain is a sequence of 1 to 20 bases located adjacent to the second complementary domain, and a domain located at the 3'end direction of the second complementary domain. Here, the proximal domain may be used to form a double strand between complementary base sequences therein.

In one exemplary embodiment, the proximal domain may be a 5, 6, 7, 8, 9, 10, 11, 12, 13, 14 or 15-base sequence.

In another embodiment, the proximal domain may include a 5, 6, 7, 8, 9, 10, 11, 12, 13, 14 or 15-base sequence.

In addition, the proximal domain may have homology with a natural proximal domain, or may be derived from the natural proximal domain. In addition, the proximal domain may have a difference in base sequence according to a species existing in nature, may be derived from a proximal domain contained in the species existing in nature, or may have partial or complete homology with the proximal domain contained in the species existing in nature.

In an exemplary embodiment, the proximal domain may have partial, that is, at least 50% or more, or complete homology with a proximal domain of *Streptococcus pyogenes, Campylobacter jejuni, Streptococcus thermophilus, Streptococcus aureus* or *Neisseria meningitides*, or a proximal domain derived therefrom.

For example, when the proximal domain is a proximal domain of *Streptococcus pyogenes* or a proximal domain derived therefrom, the proximal domain may be 5'-AAGGCUAGUCCG-3' (SEQ ID NO: 1557), or a base sequence having partial, that is, at least 50% or more homology with 5'-AAGGCUAGUCCG-3' (SEQ ID NO: 1557). Here, the proximal domain may further include (X)n, resulting in 5'-AAGGCUAGUCCG(X)n-3' (SEQ ID NO: 1558). The X may be selected from the group consisting of bases A, T, U and G, and the n may represent the number of bases, which is an integer of 1 to 15. Here, the (X)n may represent n repeats of the same base, or a mixture of n bases of A, T, U and G.

In yet another example, when the proximal domain is a proximal domain of *Campylobacter jejuni* or a proximal domain derived therefrom, the proximal domain may be 5'-AAAGAGUUUGC-3' (SEQ ID NO: 1559), or a base sequence having at least 50% or more homology with 5'-AAAGAGUUUGC-3' (SEQ ID NO: 1559). Here, the proximal domain may further include (X)n, resulting in 5'-AAAGAGUUUGC(X)n-3' (SEQ ID NO: 1560). The X may be selected from the group consisting of bases A, T, U and G, and the n may represent the number of bases, which is an integer of 1 to 40. Here, the (X)n may represent n repeats of the same base, or a mixture of n bases of A, T, U and G.

Selectively, a part or all of the base sequence of the proximal domain may have a chemical modification. The chemical modification may be methylation, acetylation, phosphorylation, phosphorothioate linkage, a locked nucleic acid (LNA), 2'-O-methyl 3'phosphorothioate (MS) or 2'-O-methyl 3'thioPACE (MSP), but the present invention is not limited thereto.

vi) Tail Domain

The tail domain is a domain which is able to be selectively added to the 3' end of single-stranded gRNA or double-stranded gRNA. The tail domain may be a 1 to 50-base sequence, or include a 1 to 50-base sequence. Here, the tail domain may be used to form a double strand between complementary base sequences therein.

In an exemplary embodiment, the tail domain may be a 1 to 5, 5 to 10, 10 to 15, 15 to 20, 20 to 25, 25 to 30, 30 to 35, 35 to 40, 40 to 45, or 45 to 50-base sequence.

In an exemplary embodiment, the tail domain may include a 1 to 5, 5 to 10, 10 to 15, 15 to 20, 20 to 25, 25 to 30, 30 to 35, 35 to 40, 40 to 45, or 45 to 50-base sequence.

In addition, the tail domain may have homology with a natural tail domain, or may be derived from the natural tail domain. In addition, the tail domain may have a difference in base sequence according to a species existing in nature, may be derived from a tail domain contained in a species existing in nature, or may have partial or complete homology with a tail domain contained in a species existing in nature.

In one exemplary embodiment, the tail domain may have partial, that is, at least 50% or more, or complete homology with a tail domain of *Streptococcus pyogenes, Campylobacter jejuni, Streptococcus thermophilus, Streptococcus aureus* or *Neisseria meningitides* or a tail domain derived therefrom.

For example, when the tail domain is a tail domain of *Streptococcus pyogenes* or a tail domain derived therefrom, the tail domain may be 5'-UUAUCAAC-UUGAAAAAGUGGCACCGAGUCGGUGC-3' (SEQ ID NO: 1551), or a base sequence having partial, that is, at least 50% or more homology with 5'-UUAUCAAC-UUGAAAAAGUGGCACCGAGUCGGUGC-3' (SEQ ID NO: 1551). Here, the tail domain may further include $(X)_n$, resulting in 5'-UUAUCAAC-UUGAAAAAGUGGCACCGAGUCGGUGC$(X)_n$-3' (SEQ ID NO: 1552). The X may be selected from the group consisting of bases A, T, U and G, and the n may represent the number of bases, which is an integer of 1 to 15. Here, the (X), may represent n repeats of the same base, or a mixture of n bases such as A, T, U and G.

In another example, when the tail domain is a tail domain of *Campylobacter jejuni* or a tail domain derived therefrom, the tail domain may be 5'-GGGACUCUGCGGGGUUA-CAAUCCCCUAAAACCGCUUUU-3' (SEQ ID NO: 1553), or a base sequence having partial, that is, at least 50% or more homology with 5'-GGGACUCUGCGGGGUUA-CAAUCCCCUAAAACCGCUUUU-3' (SEQ ID NO: 1553). Here, the tail domain may further include (X)n, resulting in 5'-GGGACUCUGCGGGGUUACAAUCCCC-UAAAACCGCUUUU(X)n-3' (SEQ ID NO: 1554). The X may be selected from the group consisting of bases A, T, U and G, and the n may represent the number of bases, which is an integer of 1 to 15. Here, the (X)n may represent n repeats of the same base, or a mixture of n bases of A, T, U and G.

In another embodiment, the tail domain may include a 1 to 10-base sequence at the 3' end involved in an in vitro or in vivo transcription method.

For example, when a T7 promoter is used in in vitro transcription of gRNA, the tail domain may be an arbitrary base sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil bases or alternative bases.

Selectively, a part or all of the base sequence of the tail domain may have a chemical modification. The chemical modification may be methylation, acetylation, phosphorylation, phosphorothioate linkage, a locked nucleic acid (LNA), 2'-O-methyl 3'phosphorothioate (MS) or 2'-O-methyl 3'thioPACE (MSP), but the present invention is not limited thereto.

The gRNA may include a plurality of domains as described above, and therefore, the length of the nucleic acid sequence may be regulated according to a domain contained in the gRNA, and interactions may occur in strands in a three-dimensional structure or active form of gRNA or between theses strands due to each domain.

The gRNA may be referred to as single-stranded gRNA (single RNA molecule); or double-stranded gRNA (including more than one, generally two discrete RNA molecules).

Double-Stranded gRNA

The double-stranded gRNA consists of a first strand and a second strand.

Here, the first strand may consist of 5'-[guide domain]-[first complementary domain]-3', and the second strand may consist of 5'-[second complementary domain]-[proximal domain]-3' or 5'-[second complementary domain]-[proximal domain]-[tail domain]-3'.

Here, the first strand may be referred to as crRNA, and the second strand may be referred to as tracrRNA.

First Strand

Guide Domain

In the first strand, the guide domain includes a complementary guide sequence which is able to form a complementary bond with a target sequence on a target gene or nucleic acid. The guide sequence is a nucleic acid sequence complementary to the target sequence on the target gene or nucleic acid, which has, for example, at least 70%, 75%, 80%, 85%, 90% or 95% or more complementarity or complete complementarity. The guide domain is considered to allow a gRNA-Cas complex, that is, a CRISPR complex to specifically interact with the target gene or nucleic acid.

Here, the guide domain may be a 5 to 50-base sequence, or includes a 5 to 50-base sequence. For example, the guide domain may be or include a 16, 17, 18, 19, 20, 21, 22, 23, 24 or 25-base sequence.

In addition, the guide domain may include a guide sequence.

Here, the guide sequence may be a complementary base sequence which is able to form a complementary bond with a target sequence on a target gene or nucleic acid, which has, for example, at least 70%, 75%, 80%, 85%, 90% or 95% or more complementarity or complete complementarity.

In an exemplary embodiment, the guide sequence may be a nucleic acid sequence complementary to a target gene, that is, a target sequence of a neovascularization-associated factor such as a VEGFA gene, an HIF1A gene, an ANGPT2 gene, an EPAS1 gene, or an ANGPTL4 gene, which has, for example, at least 70%, 75%, 80%, 85%, 90% or 95% or more complementarity or complete complementarity.

Here, the guide sequence may be a 5 to 50-base sequence or include a 5 to 50-base sequence. For example, the guide sequence may be or include a 16, 17, 18, 19, 20, 21, 22, 23, 24 or 25-base sequence.

In one exemplary embodiment, the guide sequence is a nucleic acid sequence complementary to a target sequence of the VEGFA gene. The guide sequence may be or include a 5 to 50-base sequence. For example, the guide sequence may be or include a 16, 17, 18, 19, 20, 21, 22, 23, 24 or 25-base sequence.

In one exemplary embodiment, the guide sequence may be a nucleic acid sequence complementary to a target sequence of the HIF1A gene. The guide sequence may be or include a 5 to 50-base sequence. For example, the guide sequence may be or include a 16, 17, 18, 19, 20, 21, 22, 23, 24 or 25-base sequence.

In one exemplary embodiment, the guide sequence may be a nucleic acid sequence complementary to a target sequence of the ANGPT2 gene. The guide sequence may be or include a 5 to 50-base sequence. For example, the guide sequence may be or include a 16, 17, 18, 19, 20, 21, 22, 23, 24 or 25-base sequence.

In one exemplary embodiment, the guide sequence is a nucleic acid sequence complementary to a target sequence of the EPAS1 gene. The guide sequence may be or include a 5 to 50-base sequence. For example, the guide sequence may be or include a 16, 17, 18, 19, 20, 21, 22, 23, 24 or 25-base sequence.

In one exemplary embodiment, the guide sequence is a nucleic acid sequence complementary to a target sequence of the ANGPTL4 gene. The guide sequence may be or include a 5 to 50-base sequence. For example, the guide sequence may be or include a 16, 17, 18, 19, 20, 21, 22, 23, 24 or 25-base sequence.

Here, for the guide sequence, target genes, that is, target sequences of neovascularization-associated factors such as a VEGFA gene, an HIF1A gene, an ANGPT2 gene, an EPAS1 gene, and an ANGPTL4 gene are listed above in Table 1, Table 2, Table 3, Table 4 and Table 5, but the present invention is not limited thereto.

Selectively, the guide domain may include a guide sequence and an additional base sequence.

Here, the additional base sequence may be a 1 to 35-base sequence. For example, the additional base sequence may be a 1, 2, 3, 4, 5, 6, 7, 8, 9 or 10-base sequence.

In one exemplary embodiment, the additional base sequence may include one base, guanine (G), or two bases, GG.

Here, the additional base sequence may be located at the 5' end of the guide domain, or at the 5' end of the guide sequence.

The additional base sequence may be located at the 3' end of the guide domain, or at the 3' end of the guide sequence.

First Complementary Domain

The first complementary domain includes a nucleic acid sequence complementary to a second complementary domain of the second strand, and is a domain having enough complementarity so as to form a double strand with the second complementary domain.

Here, the first complementary domain may be or include a 5 to 35-base sequence. For example, the first complementary domain may be or include a 5, 6, 7, 8, 9, 10, 11, 12, 13, 14, 15, 16, 17, 18, 19, 20, 21, 22, 23, 24 or 25-base sequence.

The first complementary domain may have homology with a natural first complementary domain, or may be derived from a natural first complementary domain. In addition, the first complementary domain may have a difference in base sequence according to a species existing in nature, may be derived from the first complementary domain contained in the species existing in nature, or may have partial or complete homology with the first complementary domain contained in the species existing in nature.

In one exemplary embodiment, the first complementary domain may have partial, that is, at least 50% or more, or complete homology with a first complementary domain of *Streptococcus pyogenes, Campylobacter jejuni, Streptococcus thermophilus, Streptococcus aureus* or *Neisseria meningitides*, or a first complementary domain derived therefrom.

Selectively, the first complementary domain may include an additional base sequence which does not undergo complementary bonding with the second complementary domain of the second strand.

Here, the additional base sequence may be a sequence of 1 to 15 bases. For example, the additional base sequence may be a sequence of 1 to 5, 5 to 10, or 10 to 15 bases.

Selectively, a part or all of the base sequence of the guide domain and/or first complementary domain may have a chemical modification. The chemical modification may be methylation, acetylation, phosphorylation, phosphorothioate linkage, a locked nucleic acid (LNA), 2'-O-methyl 3' phosphorothioate (MS) or 2'-O-methyl 3' thioPACE (MSP), but the present invention is not limited thereto.

Therefore, the first strand may consist of 5'-[guide domain]-[first complementary domain]-3' as described above.

In addition, the first strand may optionally include an additional base sequence.

In one example, the first strand may be 5'-(N$_{target}$)-(Q)$_m$-3'; or 5'-(X)$_a$-(N$_{target}$)-(X)$_b$-(Q)$_m$-(X)$_c$-3'.

Here, the Ntarget is a base sequence capable of forming a complementary bond with a target sequence on a target gene or nucleic acid, and a base sequence region which may be changed according to a target sequence on a target gene or nucleic acid.

In one exemplary embodiment, Ntarget may be a base sequence capable of forming a complementary bond with a target gene, that is, a target sequence of a neovascularization-associated factor such as a VEGFA gene, an HIF1A gene, an ANGPT2 gene, an EPAS1 gene or an ANGPTL4 gene.

Here, the (Q)m is a base sequence including the first complementary domain, which is able to form a complementary bond with the second complementary domain of the second strand. The (Q)m may be a sequence having partial or complete homology with the first complementary domain of a species existing in nature, and the base sequence of the first complementary domain may be changed according to the species of origin. The Q may be each independently selected from the group consisting of A, U, C and G, and the m may be the number of bases, which is an integer of 5 to 35.

For example, when the first complementary domain has partial or complete homology with a first complementary domain of *Streptococcus pyogenes* or a *Streptococcus pyogenes*-derived first complementary domain, the (Q)m may be 5'-GUUUUAGAGCUA-3' (SEQ ID NO: 1523), or a base sequence having at least 50% or more homology with 5'-GUUUUAGAGCUA-3' (SEQ ID NO: 1523).

In another example, when the first complementary domain has partial or complete homology with a first complementary domain of *Campylobacter jejuni* or a *Campylobacter jejuni*-derived first complementary domain, the (Q)m may be 5'-GUUUUAGUCCC-UUUUUAAAUUUCUU-3' (SEQ ID NO: 1524), or a base sequence having at least 50% or more homology with 5'-GUUUUAGUCCCUUUUUAAAUUUCUU-3' (SEQ ID NO: 1524).

In still another example, when the first complementary domain has partial or complete homology with a first complementary domain of *Streptococcus thermophilus* or a *Streptococcus thermophilus*-derived first complementary domain, the (Q)m may be 5'-GUUUUAGAGCUGUGUU-GUUUCG-3' (SEQ ID NO: 1555), or a base sequence having at least 50% or more homology with 5'-GUUUUA-GAGCUGUGUUGUUUCG-3' (SEQ ID NO: 1555).

In addition, each of the (X)a, (X)b and (X)c is selectively an additional base sequence, where the X may be each independently selected from the group consisting of A, U, C and G, and each of the a, b and c may be the number of bases, which is 0 or an integer of 1 to 20.

Second Strand

The second strand may consist of a second complementary domain and a proximal domain, and selectively include a tail domain.

Second Complementary Domain

In the second strand, the second complementary domain includes a nucleic acid sequence complementary to the first complementary domain of the first strand, and has enough complementarity so as to form a double strand with the first complementary domain. The second complementary domain may include a base sequence complementary to the first complementary domain and a base sequence not complementary to the first complementary domain, for example, a base sequence not forming a double strand with the first complementary domain, and may have a longer base sequence than the first complementary domain.

Here, the second complementary domain may be a 5 to 35-base sequence, or include a 5 to 35-base sequence. For example, the second complementary domain may be or include a 5, 6, 7, 8, 9, 10, 11, 12, 13, 14, 15, 16, 17, 18, 19, 20, 21, 22, 23, 24 or 25-base sequence, but the present invention is not limited thereto.

The second complementary domain may have homology with a natural second complementary domain, or may be derived from a natural second complementary domain. In addition, the second complementary domain may have a difference in base sequence thereof according to a species existing in nature, may be derived from a second complementary domain contained in the species existing in nature, or may have partial or complete homology with the second complementary domain contained in the species existing in nature.

In one exemplary embodiment, the second complementary domain may have partial, that is, at least 50% or more, or complete homology with a second complementary domain of *Streptococcus pyogenes, Campylobacter jejuni, Streptococcus thermophilus, Streptococcus aureus* or *Neisseria meningitides*, or a second complementary domain derived therefrom.

Selectively, the second complementary domain may further include an additional base sequence which does not undergo complementary bonding with the first complementary domain of the first strand.

Here, the additional base sequence may be a 1 to 25-base sequence. For example, the additional base sequence may be a 1 to 5, 5 to 10, 10 to 15, 15 to 20 or 20 to 25-base sequence.

Proximal Domain

In the second strand, the proximal domain is a sequence of 1 to 20 bases, and a domain located at the 3' end direction of the second complementary domain. For example, the proximal domain may be or include a sequence of 5, 6, 7, 8, 9, 10, 11, 12, 13, 14 or 15 bases.

Here, the proximal domain may have a double strand bond between complementary base sequences therein.

In addition, the proximal domain may have homology with a natural proximal domain, or may be derived from a natural proximal domain. In addition, the proximal domain may have a difference in base sequence according to a species existing in nature, may be derived from a proximal domain of a species existing in nature, or may have partial or complete homology with the proximal domain of a species existing in nature.

In one exemplary embodiment, the proximal domain may have partial, that is, at least 50% or more, or complete homology with a proximal domain of *Streptococcus pyogenes, Campylobacter jejuni, Streptococcus thermophilus, Streptococcus aureus* or *Neisseria meningitides*, or a proximal domain derived therefrom.

Tail Domain

Selectively, in the second strand, the tail domain may be a domain selectively added to the 3' end of the second strand, and the tail domain may be or include a 1 to 50-base sequence. For example, the tail domain may be or include a 1 to 5, 5 to 10, 10 to 15, 15 to 20, 20 to 25, 25 to 30, 30 to 35, 35 to 40, 40 to 45 or 45 to 50-base sequence.

Here, the tail domain may have a double strand bond between complementary base sequences therein.

In addition, the tail domain may have homology with a natural tail domain, or may be derived from a natural tail domain. In addition, the tail domain may have a difference in base sequence according to a species existing in nature, may be derived from a tail domain contained in the species existing in nature, or may have partial or complete homology with the tail domain contained in the species existing in nature.

In one exemplary embodiment, the tail domain may have partial, that is, at least 50% or more, or complete homology with a tail domain of *Streptococcus pyogenes, Campylobacter jejuni, Streptococcus thermophilus, Streptococcus aureus* or *Neisseria meningitides*, or a tail domain derived therefrom.

In another embodiment, the tail domain may include a sequence of 1 to 10 bases at the 3' end involved in an in vitro or in vivo transcription method.

For example, when a T7 promoter is used in in vitro transcription of gRNA, the tail domain may be an arbitrary base sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil bases or alternative bases.

Selectively, a part or all of each of the base sequence of the second complementary domain, the proximal domain and/or the tail domain may have a chemical modification. The chemical modification may be methylation, acetylation, phosphorylation, phosphorothioate linkage, a locked nucleic acid (LNA), 2'-O-methyl 3'phosphorothioate (MS) or 2'-O-methyl 3'thioPACE (MSP), but the present invention is not limited thereto.

Therefore, the second strand may consist of 5'-[second complementary domain]-[proximal domain]-3' or 5'-[second complementary domain]-[proximal domain]-[tail domain]-3' as described above.

In addition, the second strand may selectively include an additional base sequence.

In one exemplary embodiment, the second strand may be 5'-(Z)h-(P)k-3'; or 5'-(X)d-(Z)h-(X)e-(P)k-(X)f-3'.

In another embodiment, the second strand may be 5'-(Z)h-(P)k-(F)i-3'; or 5'-(X)d-(Z)h-(X)e-(P)k-(X)f-(F)i-3'.

Here, the (Z)h is a base sequence including a second complementary domain, which is able to form a complementary bond with the first complementary domain of the first strand. The (Z)h may be a sequence having partial or complete homology with the second complementary domain of a species existing in nature, and the base sequence of the second complementary domain may be modified according to the species of origin. The Z may be each independently selected from the group consisting of A, U, C and G, and the h may be the number of bases, which is an integer of 5 to 50.

For example, when the second complementary domain has partial or complete homology with a second complementary domain of *Streptococcus pyogenes* or a second complementary domain derived therefrom, the (Z)h may be 5'-UAGCAAGUUAAAAU-3' (SEQ ID NO: 1526), or a base sequence having at least 50% or more homology with 5'-UAGCAAGUUAAAAU-3' (SEQ ID NO: 1526).

In another example, when the second complementary domain has partial or complete homology with a second complementary domain of *Campylobacter jejuni* or a second complementary domain derived therefrom, the (Z)h may be 5'-AAGAAAUUUAAAAAGGGACUAAAAU-3' (SEQ ID NO: 1527), or a base sequence having at least 50% or more homology with 5'-AAGAAAUUUAAAAAGGGAC-UAAAAU-3' (SEQ ID NO: 1527).

In still another example, when the second complementary domain has partial or complete homology with a second complementary domain of *Streptococcus thermophilus* or a second complementary domain derived therefrom, the (Z)h may be 5'-CGAAACAACACAGCGAGUUAAAAU-3' (SEQ ID NO: 1556), or a base sequence having at least 50% or more homology with 5'-CGAAACAACACAGCGAGUUAAAAU-3' (SEQ ID NO: 1556).

The (P)k is a base sequence including a proximal domain, which may have partial or complete homology with a proximal domain of a species existing in nature, and the base sequence of the proximal domain may be modified according to the species of origin. The P may be each independently selected from the group consisting of A, U, C and G, and the k may be the number of bases, which is an integer of 1 to 20.

For example, when the proximal domain has partial or complete homology with a proximal domain of *Streptococcus pyogenes* or a proximal domain derived therefrom, the $(P)_k$ may be 5'-AAGGCUAGUCCG-3' (SEQ ID NO: 1557), or a base sequence having at least 50% or more homology with 5'-AAGGCUAGUCCG-3' (SEQ ID NO: 1557).

In another example, when the proximal domain has partial or complete homology with a proximal domain of *Campylobacter jejuni* or a proximal domain derived therefrom, the $(P)_k$ may be 5'-AAAGAGUUUGC-3' (SEQ ID NO: 1559), or a base sequence having at least 50% or more homology with 5'-AAAGAGUUUGC-3' (SEQ ID NO: 1559).

In still another example, when the proximal domain has partial or complete homology with a proximal domain of *Streptococcus thermophilus* or a proximal domain derived therefrom, the (P)k may be 5'-AAGGCUUAGUCCG-3' (SEQ ID NO: 1561), or a base sequence having at least 50% or more homology with 5'-AAGGCUUAGUCCG-3' (SEQ ID NO: 1561).

The (F)i may be a base sequence including a tail domain, and having partial or complete homology with a tail domain of a species existing in nature, and the base sequence of the tail domain may be modified according to the species of origin. The F may be each independently selected from the group consisting of A, U, C and G, and the i may be the number of bases, which is an integer of 1 to 50.

For example, when the tail domain has partial or complete homology with a tail domain of *Streptococcus pyogenes* or a tail domain derived therefrom, the (F)i may be 5'-UUAU-CAACUUGAAAAAGUGGCACCGAGUCGGUGC-3' (SEQ ID NO: 1551), or a base sequence having at least 50% or more homology with 5'-UUAUCAAC-UUGAAAAAGUGGCACCGAGUCGGUGC-3' (SEQ ID NO: 1551).

In another example, when the tail domain has partial or complete homology with a tail domain of *Campylobacter jejuni* or a tail domain derived therefrom, the (F)i may be 5'-GGGACUCUGCGGGGUUACAAUCCCC-UAAAACCGCUUUU-3' (SEQ ID NO: 1553), or a base sequence having at least 50% or more homology with 5'-GGGACUCUGCGGGGUUACAAUCCCC-UAAAACCGCUUUU-3' (SEQ ID NO: 1553).

In still another example, when the tail domain has partial or complete homology with a tail domain of *Streptococcus thermophilus* or a tail domain derived therefrom, the (F)i may be 5'-UACUCAACUUGAAAAG-GUGGCACCGAUUCGGUGUUUUU-3' (SEQ ID NO: 1562), or a base sequence having at least 50% or more homology with 5'-UACUCAACUUGAAAAG-GUGGCACCGAUUCGGUGUUUUU-3' (SEQ ID NO: 1562).

In addition, the (F)i may include a sequence of 1 to 10 bases at the 3' end involved in an in vitro or in vivo transcription method.

For example, when a T7 promoter is used in in vitro transcription of gRNA, the tail domain may be an arbitrary base sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil bases or alternative bases.

In addition, the (X)d, (X)e and (X)f may be base sequences selectively added, where the X may be each independently selected from the group consisting of A, U, C and G, and each of the d, e and f may be the number of bases, which is 0 or an integer of 1 to 20.

Single-Stranded gRNA

Single-stranded gRNA may be classified into two types.

i) Single-Stranded gRNA

First, there is single-stranded gRNA in which a first strand or a second strand of the double-stranded gRNA is linked by a linker domain, and here, the single-stranded gRNA consists of 5'-[first strand]-[linker domain]-[second strand]-3'.

Specifically, the single-stranded gRNA may consist of 5'-[guide domain]-[first complementary domain]-[linker domain]-[second complementary domain]-[proximal domain]-3' or 5'-[guide domain]-[first complementary domain]-[linker domain]-[second complementary domain]-[proximal domain]-[tail domain]-3'.

Each domain except the linker domain is the same as the description of each domain of the first and second strands of the double-stranded gRNA.

Linker Domain

In the single-stranded gRNA, the linker domain is a domain connecting a first strand and a second strand, and specifically, is a nucleic acid sequence which connects a first complementary domain with a second complementary domain to produce single-stranded gRNA. Here, the linker domain may be connected with the first complementary domain and the second complementary domain or connect the first complementary domain with the second complementary domain by covalent or non-covalent bonding.

The linker domain may be or include a 1 to 30-base sequence. For example, the linker domain may be or include a 1 to 5, 5 to 10, 10 to 15, 15 to 20, 20 to 25 or 25 to 30-base sequence.

The linker domain is suitable to be used in a single-stranded gRNA molecule, and may be connected with the first strand and the second strand of the double-stranded gRNA, or connect the first strand with the second strand by covalent or non-covalent bonding to be used in production of the single-stranded gRNA. The linker domain may be connected with crRNA and tracrRNA of the double-stranded gRNA, or connect crRNA with tracrRNA by covalent or non-covalent bonding to be used in production of the single-stranded gRNA.

The linker domain may have homology with a natural sequence, for example, a partial sequence of tracrRNA, or may be derived therefrom.

Selectively, a part or all of the base sequence of the linker domain may have a chemical modification. The chemical modification may be methylation, acetylation, phosphorylation, phosphorothioate linkage, a locked nucleic acid (LNA), 2'-O-methyl 3'phosphorothioate (MS) or 2'-O-methyl 3'thioPACE (MSP), but the present invention is not limited thereto.

Therefore, the single-stranded gRNA may consist of 5'-[guide domain]-[first complementary domain]-[linker domain]-[second complementary domain]-[proximal domain]-3' or 5'-[guide domain]-[first complementary domain]-[linker domain]-[second complementary domain]-[proximal domain]-[tail domain]-3' as described above.

In addition, the single-stranded gRNA may selectively include an additional base sequence.

In one exemplary embodiment, the single-stranded gRNA may be

5'-$(N_{target})$-$(Q)_m$-$(L)_j$-$(Z)_h$-$(P)_k$-3'; or
5'-$(N_{target})$-$(Q)_m$-$(L)_j$-$(Z)_h$-$(P)_k$-$(F)_i$-3'.

In another embodiment, the single-stranded gRNA may be

5'-$(X)_a$-$(N_{target})$-$(X)_b$-$(Q)_m$-$(X)_c$-$(L)_j$-$(X)_d$-$(Z)_h$-$(X)_e$-$(P)_k$-$(X)_f$-3'; or
5'-$(X)_a$-$(N_{target})$-$(X)_b$-$(Q)_m$-$(X)_c$-$(L)_j$-$(X)_d$-$(Z)_h$-$(X)_e$-$(P)_k$-$(X)_f$-$(F)_i$-3'.

Here, the $N_{target}$ is a base sequence capable of forming a complementary bond with a target sequence on a target gene or nucleic acid, and a base sequence region capable of being changed according to a target sequence on a target gene or nucleic acid.

In one exemplary embodiment, Ntarget is a base sequence capable of forming a complementary bond with a target gene, that is, a target sequence of a neovascularization-associated factor such as a VEGFA gene, an HIF1A gene, an ANGPT2 gene, an EPAS1 gene, or an ANGPTL4 gene.

The $(Q)m$ includes a base sequence including the first complementary domain, which is able to form a complementary bond with a second complementary domain. The $(Q)m$ may be a sequence having partial or complete homology with a first complementary domain of a species existing in nature, and the base sequence of the first complementary domain may be changed according to the species of origin. The Q may be each independently selected from the group consisting of A, U, C and G, and the m may be the number of bases, which is an integer of 5 to 35.

For example, when the first complementary domain has partial or complete homology with a first complementary domain of *Streptococcus pyogenes* or a first complementary domain derived therefrom, the (Q)m may be 5'-GUUUUA-GAGCUA-3' (SEQ ID NO: 1523), or a base sequence having at least 50% or more homology with 5'-GUUUUA-GAGCUA-3' (SEQ ID NO: 1523).

In another example, when the first complementary domain has partial or complete homology with a first complementary domain of *Campylobacter jejuni* or a first complementary domain derived therefrom, the (Q)m may be 5'-GUUUUAGUCCCUUUUUAAAUUUCUU-3' (SEQ ID NO: 1524), or a base sequence having at least 50% or more homology with 5'-GUUUUAGUCCC-UUUUUAAAUUUCUU-3' (SEQ ID NO: 1524).

In still another example, when the first complementary domain has partial or complete homology with a first complementary domain of *Streptococcus thermophilus* or a first complementary domain derived therefrom, the (Q)m may be 5'-GUUUUAGAGCUGUGUUGUUUCG-3' (SEQ ID NO: 1555), or a base sequence having at least 50% or more homology with 5'-GUUUUAGAGCUGUGUU-GUUUCG-3' (SEQ ID NO: 1555).

In addition, the (L)j is a base sequence including the linker domain, and connecting the first complementary domain with the second complementary domain, thereby producing single-stranded gRNA. Here, the L may be each independently selected from the group consisting of A, U, C and G, and the j may be the number of bases, which is an integer of 1 to 30.

The (Z)h is a base sequence including the second complementary domain, which is able to have a complementary bond with the first complementary domain. The (Z)h may be a sequence having partial or complete homology with the second complementary domain of a species existing in nature, and the base sequence of the second complementary domain may be changed according to the species of origin. The Z may be each independently selected from the group consisting of A, U, C and G, and the h is the number of bases, which may be an integer of 5 to 50.

For example, when the second complementary domain has partial or complete homology with a second complementary domain of *Streptococcus pyogenes* or a second complementary domain derived therefrom, the (Z)h may be 5'-UAGCAAGUUAAAAU-3' (SEQ ID NO: 1526), or a base sequence having at least 50% or more homology with 5'-UAGCAAGUUAAAAU-3' (SEQ ID NO: 1526).

In another example, when the second complementary domain has partial or complete homology with a second complementary domain of *Campylobacter jejuni* or a second complementary domain derived therefrom, the (Z)h may be 5'-AAGAAAUUUAAAAAGGGACUAAAAU-3' (SEQ ID NO: 1527), or a base sequence having at least 50% or more homology with 5'-AAGAAAUUUAAAAAGGGAC-UAAAAU-3' (SEQ ID NO: 1527).

In still another example, when the second complementary domain has partial or complete homology with a second complementary domain of *Streptococcus thermophilus* or a second complementary domain derived therefrom, the (Z)h may be 5'-CGAAACAACACAGCGAGUUAAAAU-3' (SEQ ID NO: 1556), or a base sequence having at least 50% or more homology with 5'-CGAAACAACACAGCGAGUUAAAAU-3' (SEQ ID NO: 1556).

The (P)k is a base sequence including a proximal domain, which may have partial or complete homology with a proximal domain of a species existing in nature, and the base sequence of the proximal domain may be modified according to the species of origin. The P may be each independently selected from the group consisting of A, U, C and G, and the k may be the number of bases, which is an integer of 1 to 20.

For example, when the proximal domain has partial or complete homology with a proximal domain of *Streptococcus pyogenes* or a proximal domain derived therefrom, the (P)k may be 5'-AAGGCUAGUCCG-3' (SEQ ID NO: 1557), or a base sequence having at least 50% or more homology with 5'-AAGGCUAGUCCG-3' (SEQ ID NO: 1557).

In another example, when the proximal domain has partial or complete homology with a proximal domain of *Campylobacter jejuni* or a proximal domain derived therefrom, the (P)k may be 5'-AAAGAGUUUGC-3' (SEQ ID NO: 1559), or a base sequence having at least 50% or more homology with 5'-AAAGAGUUUGC-3' (SEQ ID NO: 1559).

In still another example, when the proximal domain has partial or complete homology with a proximal domain of *Streptococcus thermophilus* or a proximal domain derived therefrom, the (P)k may be 5'-AAGGCUUAGUCCG-3' (SEQ ID NO: 1561), or a base sequence having at least 50% or more homology with 5'-AAGGCUUAGUCCG-3' (SEQ ID NO: 1561).

The (F)i may be a base sequence including a tail domain, and having partial or complete homology with a tail domain of a species existing in nature, and the base sequence of the tail domain may be modified according to the species of origin. The F may be each independently selected from the group consisting of A, U, C and G, and the i may be the number of bases, which is an integer of 1 to 50.

For example, when the tail domain has partial or complete homology with a tail domain of *Streptococcus pyogenes* or a tail domain derived therefrom, the (F)i may be 5'-UUAU-CAACUUGAAAAAGUGGCACCGAGUCGGUGC-3' (SEQ ID NO: 1551), or a base sequence having at least 50% or more homology with 5'-UUAUCAAC-UUGAAAAAGUGGCACCGAGUCGGUGC-3' (SEQ ID NO: 1551).

In another example, when the tail domain has partial or complete homology with a tail domain of *Campylobacter jejuni* or a tail domain derived therefrom, the (F)i may be 5'-GGGACUCUGCGGGGUUACAAUCCC-UAAAACCGCUUUU-3' (SEQ ID NO: 1553), or a base sequence having at least 50% or more homology with 5'-GGGACUCUGCGGGGUUACAAUCCC-UAAAACCGCUUUU-3' (SEQ ID NO: 1553).

In still another example, when the tail domain has partial or complete homology with a tail domain of *Streptococcus thermophilus* or a tail domain derived therefrom, the (F)i may be 5'-UACUCAACUUGAAAAG-GUGGCACCGAUUCGGUGUUUUU-3' (SEQ ID NO: 1562), or a base sequence having at least 50% or more homology with 5'-UACUCAACUUGAAAAG-GUGGCACCGAUUCGGUGUUUUU-3' (SEQ ID NO: 1562).

In addition, the (F)i may include a sequence of 1 to 10 bases at the 3' end involved in an in vitro or in vivo transcription method.

For example, when a T7 promoter is used in in vitro transcription of gRNA, the tail domain may be an arbitrary base sequence present at the 3' end of a DNA template. In addition, when a U6 promoter is used in in vivo transcription, the tail domain may be UUUUUU, when an H1 promoter is used in transcription, the tail domain may be UUUU, and when a pol-III promoter is used, the tail domain may include several uracil bases or alternative bases.

In addition, the (X)a, (X)b, (X)c, (X)d, (X)e and (X)f may be base sequences selectively added, where the X may be each independently selected from the group consisting of A, U, C and G, and each of the a, b, c, d, e and f may be the number of bases, which is 0 or an integer of 1 to 20.

ii) Single-Stranded gRNA

Second, the single-stranded gRNA may be single-stranded gRNA consisting of a guide domain, a first complementary domain and a second complementary domain, and here, the single-stranded gRNA may consist of: 5'-[second complementary domain]-[first complementary domain]-[guide domain]-3'; or 5'-[second complementary domain]-[linker domain]-[first complementary domain]-[guide domain]-3'.

Guide Domain

In the single-stranded gRNA, the guide domain includes a complementary guide sequence capable of forming a complementary bond with a target sequence on a target gene or nucleic acid. The guide sequence may be a nucleic acid sequence having complementarity to the target sequence on the target gene or nucleic acid, which has, for example, at least 70%, 75%, 80%, 85%, 90% or 95% or more complementarity or complete complementarity. The guide domain is considered to allow a gRNA-Cas complex, that is, a CRISPR complex to specifically interact with the target gene or nucleic acid.

Here, the guide domain may be or include a 5 to 50-base sequence. For example, the guide domain may be or include a 16, 17, 18, 19, 20, 21, 22, 23, 24 or 25-base sequence.

In addition, the guide domain may include a guide sequence.

Here, the guide sequence may be a complementary base sequence capable of forming a complementary bond with a target sequence on a target gene or nucleic acid, which has, for example, at least 70%, 75%, 80%, 85%, 90% or 95% or more complementarity or complete complementarity.

In one exemplary embodiment, the guide sequence may be a nucleic acid sequence complementary to a target gene, that is, a target sequence of a neovascularization-associated factor such as a VEGFA gene, an HIF1A gene, an ANGPT2 gene, an EPAS1 gene or an ANGPTL4 gene, which has, for example, at least 70%, 75%, 80%, 85%, 90% or 95% or more complementarity or complete complementarity.

Here, the guide sequence may be or include a 5 to 50-base sequence. For example, the guide sequence may be or include a 16, 17, 18, 19, 20, 21, 22, 23, 24 or 25-base sequence.

In one exemplary embodiment, the guide sequence may be a nucleic acid sequence complementary to a target sequence of the VEGFA gene. The guide sequence may be or include a 5 to 50-base sequence. For example, the guide sequence may be or include a 16, 17, 18, 19, 20, 21, 22, 23, 24 or 25-base sequence.

In one exemplary embodiment, the guide sequence may be a nucleic acid sequence complementary to a target sequence of the HIF1A gene. The guide sequence may be or include a 5 to 50-base sequence. For example, the guide sequence may be or include a 16, 17, 18, 19, 20, 21, 22, 23, 24 or 25-base sequence.

In one exemplary embodiment, the guide sequence may be a nucleic acid sequence complementary to a target sequence of the ANGPT2 gene. The guide sequence may be or include a 5 to 50-base sequence. For example, the guide sequence may be or include a 16, 17, 18, 19, 20, 21, 22, 23, 24 or 25-base sequence.

In one exemplary embodiment, the guide sequence may be a nucleic acid sequence complementary to a target sequence of the EPAS1 gene. The guide sequence may be or include a 5 to 50-base sequence. For example, the guide sequence may be or include a 16, 17, 18, 19, 20, 21, 22, 23, 24 or 25-base sequence.

In one exemplary embodiment, the guide sequence may be a nucleic acid sequence complementary to a target sequence of the ANGPTL4 gene. The guide sequence may be or include a 5 to 50-base sequence. For example, the guide sequence may be or include a 16, 17, 18, 19, 20, 21, 22, 23, 24 or 25-base sequence.

Here, target sequences of the target genes, that is, the neovascularization-associated factors such as the VEGFA gene, the HIF1A gene, the ANGPT2 gene, the EPAS1 gene, and the ANGPTL4 gene for the guide sequence are listed above in Table 1, Table 2, Table 3, Table 4 and Table 5, respectively, but the present invention is not limited thereto.

Selectively, the guide domain may include a guide sequence and an additional base sequence.

Here, the additional base sequence may be a 1 to 35-base sequence. For example, the additional base sequence may be a 1, 2, 3, 4, 5, 6, 7, 8, 9 or 10-base sequence.

In one exemplary embodiment, the additional base sequence may be a single base sequence, guanine (G), or a sequence of two bases, GG.

Here, the additional base sequence may be located at the 5' end of the guide domain, or at the 5' end of the guide sequence.

The additional base sequence may be located at the 3' end of the guide domain, or at the 3' end of the guide sequence.

First Complementary Domain

The first complementary domain is a domain including a nucleic acid sequence complementary to the second complementary domain, and having enough complementarity so as to form a double strand with the second complementary domain.

Here, the first complementary domain may be or include a 5 to 35-base sequence. For example, the first complementary domain may be or include a 5, 6, 7, 8, 9, 10, 11, 12, 13, 14, 15, 16, 17, 18, 19, 20, 21, 22, 23, 24 or 25-base sequence.

The first complementary domain may have homology with a natural first complementary domain, or may be derived from a natural first complementary domain. In addition, the first complementary domain may have a difference in the base sequence of a first complementary domain depending on the species existing in nature, may be derived from a first complementary domain contained in the species existing in nature, or may have partial or complete homology with the first complementary domain contained in the species existing in nature.

In one exemplary embodiment, the first complementary domain may have partial, that is, at least 50% or more, or complete homology with a first complementary domain of Parcubacteria bacterium (GWC2011_GWC2_44_17), Lachnospiraceae bacterium (MC2017), *Butyrivibrio proteoclasticus*, *Peregrinibacteria* bacterium (GW2011_GWA_33_10), *Acidaminococcus* sp. (BV3L6), *Porphyromonas macacae*, Lachnospiraceae bacterium (ND2006), *Porphyromonas crevioricanis, Prevotella disiens, Moraxella bovoculi* (237), *Smithella* sp. (SC_K08D17), *Leptospira inadai*, Lachnospiraceae bacterium (MA2020), *Francisella novicida* (U112), Candidatus Methanoplasma *termitum* or *Eubacterium eligens*, or a first complementary domain derived therefrom.

Selectively, the first complementary domain may include an additional base sequence which does not undergo complementary bonding with the second complementary domain.

Here, the additional base sequence may be a 1 to 15-base sequence. For example, the additional base sequence may be a 1 to 5, 5 to 10, or 10 to 15-base sequence.

Second Complementary Domain

The second complementary domain includes a nucleic acid sequence complementary to the first complementary domain, and has enough complementarity so as to form a double strand with the first complementary domain. The second complementary domain may include a base sequence complementary to the first complementary domain, and a base sequence having no complementarity with the first complementary domain, for example, a base sequence not forming a double strand with the first complementary domain, and may have a longer base sequence than the first complementary domain.

Here, the second complementary domain may be or include a 5 to 35-base sequence. For example, the second complementary domain may be a 5, 6, 7, 8, 9, 10, 11, 12, 13, 14, 15, 16, 17, 18, 19, 20, 21, 22, 23, 24 or 25-base sequence.

The second complementary domain may have homology with a natural second complementary domain, or may be derived from the natural second complementary domain. In addition, the second complementary domain may have a difference in base sequence of the second complementary domain according to a species existing in nature, and may be derived from second complementary domain contained in the species existing in nature, or may have partial or complete homology with the second complementary domain contained in the species existing in nature.

In one exemplary embodiment, the second complementary domain may have partial, that is, at least 50% or more, or complete homology with a second complementary domain of Parcubacteria bacterium (GWC2011_GWC2_44_17), Lachnospiraceae bacterium (MC2017), Butyrivibrio proteoclasticus, Peregrinibacteria bacterium (GW2011_GWA_33_10), Acidaminococcus sp. (BV3L6), Porphyromonas macacae, Lachnospiraceae bacterium (ND2006), Porphyromonas crevioricanis, Prevotella disiens, Moraxella bovoculi (237), Smithella sp. (SC_K08D17), Leptospira inadai, Lachnospiraceae bacterium (MA2020), Francisella novicida (U112), Candidatus Methanoplasma termitum or Eubacterium eligens, or a second complementary domain derived therefrom.

Selectively, the second complementary domain may include an additional base sequence which does not undergo complementary bonding with the first complementary domain.

Here, the additional base sequence may be a 1 to 15-base sequence. For example, the additional base sequence may be a 1 to 5, 5 to 10, or 10 to 15-base sequence.

Linker Domain

Selectively, the linker domain is a nucleic acid sequence connecting a first complementary domain with a second complementary domain to produce single-stranded gRNA. Here, the linker domain may be connected with the first complementary domain and the second complementary domain, or may connect the first and second complementary domains by covalent or non-covalent bonding.

The linker domain may be or include a 1 to 30-base sequence. For example, the linker domain may be or include a 1 to 5, 5 to 10, 10 to 15, 15 to 20, 20 to 25 or 25 to 30-base sequence.

Selectively, a part or all of the base sequence of the guide domain, the first complementary domain, the second complementary domain and the linker domain may have a chemical modification. The chemical modification may be methylation, acetylation, phosphorylation, phosphorothioate linkage, a locked nucleic acid (LNA), 2'-O-methyl 3'phosphorothioate (MS) or 2'-O-methyl 3'thioPACE (MSP), but the present invention is not limited thereto.

Therefore, the single-stranded gRNA may consist of 5'-[second complementary domain]-[first complementary domain]-[guide domain]-3' or 5'-[second complementary domain]-[linker domain]-[first complementary domain]-[guide domain]-3' as described above.

In addition, the single-stranded gRNA may selectively include an additional base sequence.

In one exemplary embodiment, the single-stranded gRNA may be 5'-$(Z)_h$-$(Q)_m$-$(N_{target})$-3'; or 5'-$(X)_a$-$(Z)_h$-$(X)_b$-$(Q)_m$-$(X)_c$-$(N_{target})$-3'. In another embodiment, the single-stranded gRNA may be 5'-$(Z)_h$-$(L)_j$-$(Q)_m$-$(N_{target})$-3'; or 5'-$(X)_a$-$(Z)_h$-$(L)_j$-$(Q)_m$-$(X)_c$-$(N_{target})$-3'.

Here, the $N_{target}$ is a base sequence capable of forming a complementary bond with a target sequence on a target gene or nucleic acid, and a base sequence region which may be changed according to a target sequence on a target gene or nucleic acid.

In one exemplary embodiment, Ntarget may be a base sequence capable of forming a complementary bond with a target gene, that is, a target sequence of a neovascularization-associated factor such as a VEGFA gene, an HIF1A gene, an ANGPT2 gene, an EPAS1 gene or an ANGPTL4 gene.

The $(Q)m$ is a base sequence including the first complementary domain, which is able to form a complementary bond with the second complementary domain of the second strand. The $(Q)m$ may be a sequence having partial or complete homology with the first complementary domain of a species existing in nature, and the base sequence of the first complementary domain may be changed according to the species of origin. The Q may be each independently selected from the group consisting of A, U, C and G, and the m may be the number of bases, which is an integer of 5 to 35.

For example, when the first complementary domain has partial or complete homology with a first complementary domain of Parcubacteria bacterium or a first complementary domain derived therefrom, the $(Q)m$ may be 5'-UUUGUA-GAU-3' (SEQ ID NO: 1525), or a base sequence having at least 50% or more homology with 5'-UUUGUAGAU-3' (SEQ ID NO: 1525).

The $(Z)h$ is a base sequence including a second complementary domain, which is able to form a complementary bond with the first complementary domain of the first strand. The $(Z)h$ may be a sequence having partial or complete homology with the second complementary domain of a species existing in nature, and the base sequence of the second complementary domain may be modified according to the species of origin. The Z may be each independently selected from the group consisting of A, U, C and G, and the h may be the number of bases, which is an integer of 5 to 50.

For example, when the second complementary domain has partial or complete homology with a second complementary domain of Parcubacteria bacterium or a Parcubacteria bacterium-derived second complementary domain, the $(Z)h$ may be 5'-AAAUUUCUACU-3' (SEQ ID NO: 1535), or a base sequence having at least 50% or more homology with 5'-AAAUUUCUACU-3' (SEQ ID NO: 1535).

In addition, the $(L)j$ is a base sequence including the linker domain, which connects the first complementary domain with the second complementary domain. Here, the L may be each independently selected from the group consisting of A, U, C and G, and the j may be the number of bases, which is an integer of 1 to 30.

In addition, each of the (X)a, (X)b and (X)c is selectively an additional base sequence, where the X may be each independently selected from the group consisting of A, U, C and G, and the a, b and c may be the number of bases, which is 0 or an integer of 1 to 20.

2. Editor Protein

An editor protein refers to a peptide, polypeptide or protein which is able to directly bind to or interact with, without direct binding to, a nucleic acid.

The nucleic acid may be a nucleic acid contained in a target nucleic acid, gene or chromosome.

The nucleic acid may be a guide nucleic acid.

The editor protein may be an enzyme.

The editor protein may be a fusion protein.

Here, the fusion protein refers to a protein produced by fusing an enzyme with an additional domain, peptide, polypeptide or protein.

The enzyme refers to a protein including a domain which is able to cleave a nucleic acid, gene, chromosome or protein.

The enzyme may be a nuclease, protease or restriction enzyme.

The additional domain, peptide, polypeptide or protein may be a functional domain, peptide, polypeptide or protein, which has a function the same as or different from the enzyme.

The fusion protein may include an additional domain, peptide, polypeptide or protein at one or more of an N-terminus of an enzyme or the proximity thereof; a C-terminus of the enzyme or the proximity thereof; the middle region of an enzyme; and a combination thereof.

The fusion protein may include a functional domain, peptide, polypeptide or protein at one or more of an N-terminus of an enzyme or the proximity thereof; a C-terminus of the enzyme or the proximity thereof; the middle region of an enzyme; and a combination thereof.

Here, the functional domain, peptide, polypeptide or protein may be a domain, peptide, polypeptide or protein having methylase activity, demethylase activity, transcription activation activity, transcription repression activity, transcription release factor activity, histone modification activity, RNA cleavage activity or nucleic acid binding activity, or a tag or reporter gene for isolation and purification of a protein (including a peptide), but the present invention is not limited thereto.

The functional domain, peptide, polypeptide or protein may be a deaminase.

The tag includes a histidine (His) tag, a V5 tag, a FLAG tag, an influenza hemagglutinin (HA) tag, a Myc tag, a VSV-G tag and a thioredoxin (Trx) tag, and the reporter gene includes glutathione-S-transferase (GST), horseradish peroxidase (HRP), chloramphenicol acetyltransferase (CAT) β-galactosidase, β-glucoronidase, luciferase, autofluorescent proteins including the green fluorescent protein (GFP), HcRed, DsRed, cyan fluorescent protein (CFP), yellow fluorescent protein (YFP) and blue fluorescent protein (BFP), but the present invention is not limited thereto.

In addition, the functional domain, peptide, polypeptide or protein may be a nuclear localization sequence or signal (NLS) or a nuclear export sequence or signal (NES).

The NLS may be NLS of SV40 virus large T-antigen with an amino acid sequence PKKKRKV; NLS derived from nucleoplasmin (e.g., nucleoplasmin bipartite NLS with a sequence KRPAATKKAGQAKKKK (SEQ ID NO: 1536)); c-myc NLS with an amino acid sequence PAAKRVKLD (SEQ ID NO: 1537) or RQRRNELKRSP (SEQ ID NO: 1538); hRNPA1 M9 NLS with a sequence NQSSNFGPMKGGNFGGRSSGPYGGGGQYFAK-PRNQGGY (SEQ ID NO: 1539); an importin-α-derived IBB domain sequence RMRIZFKNKGKDTAEL-RRRRVEVSVELRKAKKDEQILKRRNV (SEQ ID NO: 1540); myoma T protein sequences VSRKRPRP (SEQ ID NO: 1541) and PPKKARED (SEQ ID NO: 1542); human p53 sequence PQPKKKPL (SEQ ID NO: 1543); a mouse c-abl IV sequence SALIKKKKKMAP (SEQ ID NO: 1544); influenza virus NS1 sequences DRLRR (SEQ ID NO: 1550) and PKQKKRK (SEQ ID NO: 1545); a hepatitis virus-δ antigen sequence RKLKKKIKKL (SEQ ID NO: 1546); a mouse Mx1 protein sequence REKKKFLKRR (SEQ ID NO: 1547); a human poly(ADP-ribose) polymerase sequence KRKGDEVDGVDEVAKKKSKK (SEQ ID NO: 1548); or steroid hormone receptor (human) glucocorticoid sequence RKCLQAGMNLEARKTKK (SEQ ID NO: 1549), but the present invention is not limited thereto.

The editor protein may include a complete active enzyme.

Here, the "complete active enzyme" refers to an enzyme having the same function as a function of a wild-type enzyme, and for example, the wild-type enzyme cleaving the double strand of DNA has complete enzyme activity of entirely cleaving the double strand of DNA.

In addition, the complete active enzyme includes an enzyme having an improved function compared to the function of the wild-type enzyme, and for example, a specific modification or manipulation type of the wild-type enzyme cleaving the double strand of DNA has full enzyme activity which is improved compared to the wild-type enzyme, that is, activity of cleaving the double strand of DNA.

The editor protein may include an incomplete or partially active enzyme.

Here, the "incomplete or partially active enzyme" refers to an enzyme having some of the functions of the wild-type enzyme, and for example, a specific modification or manipulation type of the wild-type enzyme cleaving the double strand of DNA has incomplete or partial enzyme activity of cleaving a part of the double strand, that is, a single strand of DNA.

The editor protein may include an inactive enzyme.

Here, the "inactive enzyme" refers to an enzyme in which the function of a wild-type enzyme is completely inactivated. For example, a specific modification or manipulation type of the wild-type enzyme cleaving the double strand of DNA has inactivity so as not to completely cleave the DNA double strand.

The editor protein may be a natural enzyme or fusion protein.

The editor protein may be present in the form of a partially modified natural enzyme or fusion protein.

The editor protein may be an artificially produced enzyme or fusion protein, which does not exist in nature.

The editor protein may be present in the form of a partially modified artificial enzyme or fusion protein, which does not exist in nature.

Here, the modification may be substitution, removal, addition of amino acids contained in the editor protein, or a combination thereof.

In addition, the modification may be substitution, removal, addition of some bases in the base sequence encoding the editor protein, or a combination thereof.

As one exemplary embodiment of the editor protein of the present invention, a CRISPR enzyme will be described below.

CRISPR Enzyme

The term "CRISPR enzyme" is a main protein component of a CRISPR-Cas system, and forms a complex with gRNA, resulting in the CRISPR-Cas system.

The CRISPR enzyme is a nucleic acid or polypeptide (or a protein) having a sequence encoding the CRISPR enzyme, and representatively, a Type II CRISPR enzyme or Type V CRISPR enzyme is widely used.

The Type II CRISPR enzyme is Cas9, which may be derived from various microorganisms such as *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor bescii, Candidatus desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus* and *Acaryochloris marina*.

The term "Cas9" is an enzyme which binds to gRNA so as to cleave or modify a target sequence or position on a target gene or nucleic acid, and may consist of an HNH domain capable of cleaving a nucleic acid strand forming a complementary bond with gRNA, an RuvC domain capable of cleaving a nucleic acid strand forming a complementary bond with gRNA, an REC domain recognizing a target and a PI domain recognizing PAM. Hiroshi Nishimasu et al. (2014) Cell 156:935-949 may be referenced for specific structural characteristics of Cas9.

In addition, the Type V CRISPR enzyme may be Cpf1, which may be derived from *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Letospira, Desulfovibrio, Desulfonatronum, Opitutaceae, Tuberibacillus, Bacillus, Brevibacillus, Methylobacterium* or *Acidaminococcus*.

The Cpf1 may consist of an RuvC domain similar and corresponding to the RuvC domain of Cas9, an Nuc domain without the HNH domain of Cas9, an REC domain recognizing a target, a WED domain and a PI domain recognizing PAM. For specific structural characteristics of Cpf1, Takashi Yamano et al. (2016) Cell 165:949-962 may be referenced.

The CRISPR enzyme of the Cas9 or Cpf1 protein may be isolated from a microorganism existing in nature or non-naturally produced by a recombinant or synthetic method.

Type II CRISPR Enzyme

The crystal structure of the type II CRISPR enzyme was determined according to studies on two or more types of natural microbial type II CRISPR enzyme molecules (Jinek et al., Science, 343(6176):1247997, 2014) and studies on *Streptococcus pyogenes* Cas9 (SpCas9) complexed with gRNA (Nishimasu et al., Cell, 156:935-949, 2014; and Anders et al., Nature, 2014, doi: 10.1038/nature13579).

The type II CRISPR enzyme includes two lobes, that is, recognition (REC) and nuclease (NUC) lobes, and each lobe includes several domains.

The REC lobe includes an arginine-rich bridge helix (BH) domain, an REC1 domain and an REC2 domain.

Here, the BH domain is a long α-helix and arginine-rich region, and the REC1 and REC2 domains play an important role in recognizing a double strand formed in gRNA, for example, single-stranded gRNA, double-stranded gRNA or tracrRNA.

The NUC lobe includes an RuvC domain, an HNH domain and a PAM-interaction (PI) domain. Here, the RuvC domain encompasses RuvC-like domains, or the HNH domain is used to include HNH-like domains.

Here, the RuvC domain shares structural similarity with members of the microorganism family existing in nature having the type II CRISPR enzyme, and cleaves a single strand, for example, a non-complementary strand of a target gene or nucleic acid, that is, a strand not forming a complementary bond with gRNA. The RuvC domain is sometimes referred to as an RuvCI domain, RuvCII domain or RuvCIII domain in the art, and generally called an RuvC I, RuvCII or RuvCIII. For example, in the case of SpCas9, the RuvC domain is assembled from each of three divided RuvC domains (RuvC I, RuvCII and RuvCIII) located at the sequences of amino acids 1 to 59, 718 to 769 and 909 to 1098 of SpCas9, respectively.

The HNH domain shares structural similarity with the HNH endonuclease, and cleaves a single strand, for example, a complementary strand of a target nucleic acid molecule, that is, a strand forming a complementary bond with gRNA. The HNH domain is located between RuvC II and III motifs. For example, in the case of SpCas9, the HNH domain is located at amino acid sequence 775 to 908 of SpCas9.

The PI domain recognizes a specific base sequence in a target gene or nucleic acid, that is, a protospacer adjacent motif (PAM) or interacts with PAM. For example, in the case of SpCas9, the PI domain is located at the sequence of amino acids 1099 to 1368 of SpCas9.

Here, the PAM may vary according to the origin of the type II CRISPR enzyme. For example, when the CRISPR enzyme is SpCas9, PAM may be 5'-NGG-3', when the CRISPR enzyme is *Streptococcus thermophilus* Cas9 (StCas9), PAM may be 5'-NNAGAAW-3'(W=A or T), when the CRISPR enzyme is *Neisseria meningitides* Cas9 (NmCas9), PAM may be 5'-NNNNGATT-3', and when the CRISPR enzyme is *Campylobacter jejuni* Cas9 (CjCas9), PAM may be 5'-NNNVRYAC-3' (V=G or C or A, R=A or G, Y=C or T), where the N may be A, T, G or C; or A, U, G or C.

Type V CRISPR Enzyme

Type V CRISPR enzyme includes similar RuvC domains corresponding to the RuvC domains of the type II CRISPR enzyme, and may consist of an Nuc domain, instead of the HNH domain of the type II CRISPR enzyme, REC and WED domains, which recognize a target, and a PI domain recognizing PAM. For specific structural characteristics of the type V CRISPR enzyme, Takashi Yamano et al. (2016) Cell 165:949-962 may be referenced.

The type V CRISPR enzyme may interact with gRNA, thereby forming a gRNA-CRISPR enzyme complex, that is, a CRISPR complex, and may allow a guide sequence to approach a target sequence including a PAM sequence in cooperation with gRNA. Here, the ability of the type V CRISPR enzyme for interaction with a target gene or nucleic acid is dependent on the PAM sequence.

The PAM sequence is a sequence present in a target gene or nucleic acid, and may be recognized by the PI domain of the type V CRISPR enzyme. The PAM sequence may vary according to the origin of the type V CRISPR enzyme. That is, there are different PAM sequences which are able to be specifically recognized depending on a species.

In one example, the PAM sequence recognized by Cpf1 may be 5'-TTN-3' (N is A, T, C or G).

CRISPR Enzyme Activity

A CRISPR enzyme cleaves a double or single strand of a target gene or nucleic acid, and has nuclease activity causing breakage or deletion of the double or single strand. Generally, the wild-type type II CRISPR enzyme or type V CRISPR enzyme cleaves the double strand of the target gene or nucleic acid.

To manipulate or modify the above-described nuclease activity of the CRISPR enzyme, the CRISPR enzyme may be manipulated or modified, such a manipulated or modified CRISPR enzyme may be modified into an incompletely or partially active or inactive enzyme.

Incompletely or Partially Active Enzyme

A CRISPR enzyme modified to change enzyme activity, thereby exhibiting incomplete or partial activity is called a nickase.

The term "nickase" refers to a CRISPR enzyme manipulated or modified to cleave only one strand of the double strand of the target gene or nucleic acid, and the nickase has nuclease activity of cleaving a single strand, for example, a strand that is not complementary or complementary to gRNA of the target gene or nucleic acid. Therefore, to cleave the double strand, nuclease activity of the two nickases is needed.

For example, the nickase may have nuclease activity by the RuvC domain. That is, the nickase may include nuclease activity of the HNH domain, and to this end, the HNH domain may be manipulated or modified.

In one example, provided that the CRISPR enzyme is the type II CRISPR enzyme, when the residue 840 in the amino acid sequence of SpCas9 is mutated from histidine to alanine, the nuclease activity of the HNH domain is inactivated to be used as a nickase. Since the nickase produced thereby has nuclease activity of the RuvC domain, it is able to cleave a strand which does not form a complementary bond with a non-complementary strand of the target gene or nucleic acid, that is, gRNA.

In another exemplary embodiment, when the residue 559 in the amino acid sequence of CjCas9 is mutated from histidine to alanine, the nuclease activity of the HNH domain is inactivated to be used as a nickase. The nickase produced thereby has nuclease activity by the RuvC domain, and thus is able to cleave a non-complementary strand of the target gene or nucleic acid, that is, a strand that does not form a complementary bond with gRNA.

For example, the nickase may have nuclease activity by the HNH domain. That is, the nickase may include the nuclease activity of the RuvC domain, and to this end, the RuvC domain may be manipulated or modified.

In one example, provided that the CRISPR enzyme is the type II CRISPR enzyme, in one exemplary embodiment, when the residue 10 in the amino acid sequence of SpCas9 is mutated from aspartic acid to alanine, the nuclease activity of the RuvC domain is inactivated to be used as a nickase. The nickase produced thereby has the nuclease activity of the HNH domain, and thus is able to cleave a complementary strand of the target gene or nucleic acid, that is, a strand that forms a complementary bond with gRNA.

In another exemplary embodiment, when the residue 8 in the amino acid sequence of CjCas9 is mutated from aspartic acid to alanine, the nuclease activity of the RuvC domain is inactivated to be used as a nickase. The nickase produced thereby has the nuclease activity of the HNH domain, and thus is able to cleave a complementary strand of the target gene or nucleic acid, that is, a strand that forms a complementary bond with gRNA.

Inactive Enzyme

A CRISPR enzyme which is modified to make enzyme activity completely inactive is called an inactive CRISPR enzyme.

The term "inactive CRISPR enzyme" refers to a CRISPR enzyme which is modified not to completely cleave the double strand of the target gene or nucleic acid, and the inactive CRISPR enzyme has nuclease inactivity due to the mutation in the domain with nuclease activity of the wild-type CRISPR enzyme. The inactive CRISPR enzyme may be one in which the nuclease activities of the RuvC domain and the HNH domain are inactivated.

For example, the inactive CRISPR enzyme may be manipulated or modified in the RuvC domain and the HNH domain so as to inactive nuclease activity.

In one example, provided that the CRISPR enzyme is the type II CRISPR enzyme, in one exemplary embodiment, when the residues 10 and 840 in the amino acid sequence of SpCas9 are mutated from aspartic acid and histidine to alanine, respectively, nuclease activities by the RuvC domain and the HNH domain are inactivated, such that the double strand may not cleave completely the double strand of the target gene or nucleic acid.

In another exemplary embodiment, when the residues 8 and 559 in the amino acid sequence of CjCas9 are mutated from aspartic acid and histidine to alanine, the nuclease activities by the RuvC domain and the HNH domain are inactivated, such that the double strand may not cleave completely the double strand of the target gene or nucleic acid.

Other Activities

The CRISPR enzyme may have endonuclease activity, exonuclease activity or helicase activity, that is, an ability to anneal the helix structure of the double-stranded nucleic acid, in addition to the above-described nuclease activity.

In addition, the CRISPR enzyme may be modified to completely, incompletely, or partially activate the endonuclease activity, exonuclease activity or helicase activity.

Targeting of CRISPR Enzyme

The CRISPR enzyme may interact with gRNA, thereby forming a gRNA-CRISPR enzyme complex, that is, a CRISPR complex, and lead a guide sequence to approach a target sequence including a PAM sequence in cooperation with gRNA. Here, the ability of the CRISPR enzyme to interact with the target gene or nucleic acid is dependent on the PAM sequence.

The PAM sequence is a sequence present in the target gene or nucleic acid, which may be recognized by the PI domain of the CRISPR enzyme. The PAM sequence may vary depending on the origin of the CRISPR enzyme. That is, there are various PAM sequences which are able to be specifically recognized according to species.

In one example, provided that the CRISPR enzyme is the type II CRISPR enzyme,
  in the case of SpCas9, the PAM sequence may be 5'-NGG-3', 5'-NAG-3' and/or 5'-NGA-3', in the case of StCas9, the PAM sequence may be 5'-NGGNG-3' and/or 5'-NNAGAAW-3' (W=A or T), in the case of NmCas9, the PAM sequence may be 5'-NNNNGATT-3' and/or 5'-NNNGCTT-3', in the case of CjCas9, the PAM sequence may be 5'-NNNVRYAC-3' (V=G, C or A; R=A or G; Y=C or T), in the case of *Streptococcus mutans* Cas9 (SmCas9), the PAM sequence may be 5'-NGG-3' and/or 5'-NAAR-3' (R=A or G), and in the case of *Staphylococcus aureus* Cas9 (SaCas9), the PAM sequence may be 5'-NNGRR-3', 5'-NNGRRT-3' and/or 5'-NNGRRV-3' (R=A or G; V=G, C or A).

In another example, provided that the CRISPR enzyme is the type V CRISPR enzyme, in the case of Cpf1, the PAM sequence may be 5'-TTN-3'.

Here, the N may be A, T, G or C; or A, U, G or C.

The CRISPR enzyme capable of recognizing a specific PAM sequence may be manipulated or modified using the PAM sequence capable of being specifically recognized according to species. For example, the PI domain of SpCas9 may be replaced with the PI domain of CjCas9 so as to have the nuclease activity of SpCas9 and recognize a CjCas9-specific PAM sequence, thereby producing SpCas9 recognizing the CjCas9-specific PAM sequence. A specifically recognized PAM sequence may be changed by substitution or replacement of the PI domain.

CRISPR Enzyme Mutant

The CRISPR enzyme may be modified to improve or inhibit various characteristics such as nuclease activity, helicase activity, an ability to interact with gRNA, and an ability to approach the target gene or nucleic acid, for example, PAM recognizing ability of the CRISPR enzyme.

In addition, the CRISPR enzyme mutant may be a CRISPR enzyme which interacts with gRNA to form a gRNA-CRISPR enzyme complex, that is, a CRISPR complex, and is modified or manipulated to improve target specificity, when approaching or localized to the target gene or nucleic acid, such that only a double or single strand of the target gene or nucleic acid is cleaved without cleavage of a double or single strand of a non-target gene or nucleic acid which partially forms a complementary bond with gRNA and a non-target gene or nucleic acid which does not form a complementary bond therewith.

Here, an effect of cleaving the double or single strand of the non-target gene or nucleic acid partially forming a complementary bond with gRNA and the non-target gene or nucleic acid not forming a complementary bond therewith is referred to as an off-target effect, a position or base sequence of the non-target gene or nucleic acid partially forming a complementary bond with gRNA and the non-target gene or nucleic acid not forming a complementary bond therewith is referred to as an off-target. Here, there may be one or more off-targets. One the other hand, the cleavage effect of the double or single strand of the target gene or nucleic acid is referred to as an on-target effect, and a location or target sequence of the target gene or nucleic acid is referred to as an on-target.

The CRISPR enzyme mutant is modified in at least one of the amino acids of a naturally-occurring CRISPR enzyme, and may be modified, for example, improved or inhibited in one or more of the various characteristics such as nuclease activity, helicase activity, an ability to interact with gRNA, an ability to approach the target gene or nucleic acid and target specificity, compared to the unmodified CRISPR enzyme. Here, the modification may be substitution, removal, addition of an amino acid, or a mixture thereof.

In the CRISPR enzyme mutant, the modification may be a modification of one or two or more amino acids located in a region consisting of amino acids having positive charges, present in the naturally-occurring CRISPR enzyme.

For example, the modification may be a modification of one or two or more amino acids of the positively-charged amino acids such as lysine (K), arginine (R) and histidine (H), present in the naturally-occurring CRISPR enzyme.

The modification may be a modification of one or two or more amino acids located in a region composed of non-positively-charged amino acids present in the naturally-occurring CRISPR enzyme.

For example, the modification may be a modification of one or two or more amino acids of the non-positively-charged amino acids, that is, aspartic acid (D), glutamic acid (E), serine (S), threonine (T), asparagine (N), glutamine (Q), cysteine (C), proline (P), glycine (G), alanine (A), valine (V), isoleucine (I), leucine (L), methionine (M), phenylalanine (F), tyrosine (Y) and tryptophan (WV), present in the naturally-occurring CRISPR enzyme.

In another example, the modification may be a modification of one or two or more amino acids of non-charged amino acids, that is, serine (S), threonine (T), asparagine (N), glutamine (Q), cysteine (C), proline (P), glycine (G), alanine (A), valine (V), isoleucine (I), leucine (L), methionine (M), phenylalanine (F), tyrosine (Y) and tryptophan (WV), present in the naturally-occurring CRISPR enzyme.

In addition, the modification may be a modification of one or two or more of the amino acids having hydrophobic residues present in the naturally-occurring CRISPR enzyme.

For example, the modification may be a modification of one or two or more amino acids of glycine (G), alanine (A), valine (V), isoleucine (I), leucine (L), methionine (M), phenylalanine (F), tyrosine (Y) and tryptophan (WA), present in the naturally-occurring CRISPR enzyme.

The modification may be a modification of one or two or more of the amino acids having polar residues, present in the naturally-occurring CRISPR enzyme.

For example, the modification may be a modification of one or two or more amino acids of serine (S), threonine (T), asparagine (N), glutamine (Q), cysteine (C), proline (P), lysine (K), arginine (R), histidine (H), aspartic acid (D) and glutamic acid (E), present in the naturally-occurring CRISPR enzyme.

In addition, the modification may be a modification of one or two or more of the amino acids including lysine (K), arginine (R) and histidine (H), present in the naturally-occurring CRISPR enzyme.

For example, the modification may be a substitution of one or two or more of the amino acids including lysine (K), arginine (R) and histidine (H), present in the naturally-occurring CRISPR enzyme.

The modification may be a modification of one or two or more of the amino acids including aspartic acid (D) and glutamic acid (E), present in the naturally-occurring CRISPR enzyme.

For example, the modification may be a substitution of one or two or more of the amino acids including aspartic acid (D) and glutamic acid (E), present in the naturally-occurring CRISPR enzyme.

The modification may be a modification of one or two or more of the amino acids including serine (S), threonine (T), asparagine (N), glutamine (Q), cysteine (C), proline (P), glycine (G), alanine (A), valine (V), isoleucine (I), leucine (L), methionine (M), phenylalanine (F), tyrosine (Y) and tryptophan (WV), present in the naturally-occurring CRISPR enzyme.

For example, the modification may be a substitution of one or two or more of the amino acid including serine (S), threonine (T), asparagine (N), glutamine (Q), cysteine (C), proline (P), glycine (G), alanine (A), valine (V), isoleucine (I), leucine (L), methionine (M), phenylalanine (F), tyrosine (Y) and tryptophan (WV), present in the naturally-occurring CRISPR enzyme.

In addition, the modification may be a modification of one, two, three, four, five, six, seven or more of the amino acids present in the naturally-occurring CRISPR enzyme.

In addition, in the CRISPR enzyme mutant, the modification may be a modification of one or two or more of the amino acids present in the RuvC domain of the CRISPR enzyme. Here, the RuvC domain may be an RuvCI, RuvCII or RuvCIII domain.

The modification may be a modification of one or two or more of the amino acids present in the HNH domain of the CRISPR enzyme.

The modification may be a modification of one or two or more of the amino acids present in the REC domain of the CRISPR enzyme.

The modification may be one or two or more of the amino acids present in the PI domain of the CRISPR enzyme.

The modification may be a modification of two or more of the amino acids contained in at least two or more domains of the REC, RuvC, HNH and PI domains of the CRISPR enzyme.

In one example, the modification may be a modification of two or more of the amino acids contained in the REC and RuvC domains of the CRISPR enzyme.

In one exemplary embodiment, in the SpCas9 mutant, the modification may be a modification of at least two or more of the A203, H277, G366, F539, 1601, M763, D965 and F1038 amino acids contained in the REC and RuvC domains of SpCas9.

In another example, the modification may be a modification of two or more of the amino acids contained in the REC and HNH domains of the CRISPR enzyme.

In one exemplary embodiment, in the SpCas9 mutant, the modification may be a modification of at least two or more of the A203, H277, G366, F539, 1601 and K890 amino acids contained in the REC and HNH domains of SpCas9.

In one example, the modification may be a modification of two or more of the amino acids contained in the REC and PI domains of the CRISPR enzyme.

In one exemplary embodiment, in the SpCas9 mutant, the modification may be a modification of at least two or more of the A203, H277, G366, F539, 1601, T1102 and D1127 amino acids contained in the REC and PI domains of SpCas9.

In another example, the modification may be a modification of three or more of the amino acids contained in the REC, RuvC and HNH domains of the CRISPR enzyme.

In one exemplary embodiment, in the SpCas9 mutant, the modification may be a modification of at least three or more of the A203, H277, G366, F539, 1601, M763, K890, D965 and F1038 amino acids contained in the REC, RuvC and HNH domains of SpCas9.

In one example, the modification may be a modification of three or more of the amino acids contained in the REC, RuvC and PI domains contained in the CRISPR enzyme.

In one exemplary embodiment, in the SpCas9 mutant, the modification may be a modification of at least three or more of the A203, H277, G366, F539, 1601, M763, D965, F1038, T1102 and D1127 amino acids contained in the REC, RuvC and PI domains of SpCas9.

In another example, the modification may be a modification of three or more of the amino acids contained in the REC, HNH and PI domains of the CRISPR enzyme.

In one exemplary embodiment, in the SpCas9 mutant, the modification may be a modification of at least three or more of the A203, H277, G366, F539, 1601, K890, T1102 and D1127 amino acids contained in the REC, HNH and PI domains of SpCas9.

In one example, the modification may be a modification of three or more of the amino acids contained in the RuvC, HNH and PI domains of the CRISPR enzyme.

In one exemplary embodiment, in the SpCas9 mutant, the modification may be a modification of at least three or more of the M763, K890, D965, F1038, T1102 and D1127 amino acids contained in the RuvC, HNH and PI domains of SpCas9.

In another example, the modification may be a modification of four or more of the amino acids contained in the REC, RuvC, HNH and PI domains of the CRISPR enzyme.

In one exemplary embodiment, in the SpCas9 mutant, the modification may be a modification of at least four or more of the A203, H277, G366, F539, 1601, M763, K890, D965, F1038, T1102 and D1127 amino acids contained in the REC, RuvC, HNH and PI domains of SpCas9.

In addition, in the CRISPR enzyme mutant,
the modification may be a modification of one or two or more of the amino acids participating in the nuclease activity of the CRISPR enzyme.

For example, in the SpCas9 mutant, the modification may be a modification of one or two or more of the group consisting of the amino acids D10, E762, H840, N854, N863 and D986, or one or two or more of the group consisting of the amino acids corresponding to other Cas9 orthologs.

The modification may be a modification for partially inactivating the nuclease activity of the CRISPR enzyme, and such a CRISPR enzyme mutant may be a nickase.

Here, the modification may be a modification for inactivating the nuclease activity of the RuvC domain of the CRISPR enzyme, and such a CRISPR enzyme mutant may not cleave a non-complementary strand of a target gene or nucleic acid, that is, a strand which does not form a complementary bond with gRNA.

In one exemplary embodiment, in the case of SpCas9, when residue 10 of the amino acid sequence of SpCas9 is mutated from aspartic acid to alanine, that is, when mutated to D10A, the nuclease activity of the RuvC domain is inactivated, and thus the SpCas9 may be used as a nickase. The nickase produced thereby may not cleave a non-complementary strand of the target gene or nucleic acid, that is, a strand that does not form a complementary bond with gRNA.

In another exemplary embodiment, in the case of CjCas9, when residue 8 of the amino acid sequence of CjCas9 is mutated from aspartic acid to alanine, that is, when mutated to D8A, the nuclease activity of the RuvC domain is inactivated, and thus the CjCas9 may be used as a nickase. The nickase produced thereby may not cleave a non-complementary strand of the target gene or nucleic acid, that is, a strand that does not form a complementary bond with gRNA.

In addition, here, the modification may be a modification for inactivating the nuclease activity of the HNH domain of the CRISPR enzyme, and such a CRISPR enzyme mutant may not cleave a complementary strand of the target gene or nucleic acid, that is, a strand forming a complementary bond with gRNA.

In one exemplary embodiment, in the case of SpCas9, when residue 840 of the amino acid sequence of SpCas9 is mutated from histidine to alanine, that is, when mutated to H840A, the nuclease activity of the HNH domain is inactivated, and thus the SpCas9 may be used as a nickase. The nickase produced thereby may not cleave a complementary strand of the target gene or nucleic acid, that is, a strand that forms a complementary bond with gRNA.

In another exemplary embodiment, in the case of CjCas9, when residue 559 of the amino acid sequence of CjCas9 is mutated from histidine to alanine, that is, when mutated to H559A, the nuclease activity of the HNH domain is inactivated, and thus the CjCas9 may be used as a nickase. The nickase produced thereby may not cleave a complementary strand of the target gene or nucleic acid, that is, a strand that forms a complementary bond with gRNA.

In addition, the modification may be a modification for completely inactivating the nuclease activity of the CRISPR enzyme, and such a CRISPR enzyme mutant may be an inactive CRISPR enzyme.

Here, the modification may be a modification for inactivating the nuclease activities of the RuvC and HNH domains of the CRISPR enzyme, and such a CRISPR enzyme mutant may does not cleave a double strand of the target gene or nucleic acid.

In one exemplary embodiment, in the case of SpCas9, when the residues 10 and 840 in the amino acid sequence of SpCas9 are mutated from aspartic acid and histidine to alanine, that is, mutated to D10A and H840A, respectively, the nuclease activities of the RuvC domain and the HNH domain are inactivated, the double strand of the target gene or nucleic acid may not be completely cleaved.

In another exemplary embodiment, in the case of CjCas9, when residues 8 and 559 of the amino acid sequence of CjCas9 are mutated from aspartic acid and histidine to alanine, that is, mutated to D8A and H559A, respectively, the nuclease activities by the RuvC and HNH domains are inactivated, and thus the double strand of the target gene or nucleic acid may not be completely cleaved.

In addition, the CRISPR enzyme mutant may further include an optionally functional domain, in addition to the innate characteristics of the CRISPR enzyme, and such a CRISPR enzyme mutant may have an additional characteristic in addition to the innate characteristics.

Here, the functional domain may be a domain having methylase activity, demethylase activity, transcription activation activity, transcription repression activity, transcription release factor activity, histone modification activity, RNA cleavage activity or nucleic acid binding activity, or a tag or reporter gene for isolating and purifying a protein (including a peptide), but the present invention is not limited thereto.

The functional domain, peptide, polypeptide or protein may be a deaminase.

For example, an incomplete or partial CRISPR enzyme may additionally include a cytidine deaminase as a functional domain. In one exemplary embodiment, a cytidine deaminase, for example, apolipoprotein B editing complex 1 (APOBEC1) may be added to SpCas9 nickase, thereby producing a fusion protein. The [SpCas9 nickase]-[APOBEC1] formed thereby may be used in base repair or editing of C into T or U, or G into A.

The tag includes a histidine (His) tag, a V5 tag, a FLAG tag, an influenza hemagglutinin (HA) tag, a Myc tag, a VSV-G tag and a thioredoxin (Trx) tag, and the reporter gene includes glutathione-S-transferase (GST), horseradish peroxidase (HRP), chloramphenicol acetyltransferase (CAT) β-galactosidase, β-glucoronidase, luciferase, autofluorescent proteins including the green fluorescent protein (GFP), HcRed, DsRed, cyan fluorescent protein (CFP), yellow fluorescent protein (YFP) and blue fluorescent protein (BFP), but the present invention is not limited thereto.

In addition, the functional domain may be a nuclear localization sequence or signal (NLS) or a nuclear export sequence or signal (NES).

In one example, the CRISPR enzyme may include one or more NLSs. Here, one or more NLSs may be included at an N-terminus of an CRISPR enzyme or the proximity thereof; a C-terminus of the enzyme or the proximity thereof; or a combination thereof. The NLS may be an NLS sequence derived from the following NLSs, but the present invention is not limited thereto: NLS of a SV40 virus large T-antigen having the amino acid sequence PKKKRKV; NLS from nucleoplasmin (e.g., nucleoplasmin bipartite NLS having the sequence KRPAATKKAGQAKKKK (SEQ ID NO: 1536)); c-myc NLS having the amino acid sequence PAAKRVKLD (SEQ ID NO: 1537) or RQRRNELKRSP (SEQ ID NO: 1538); hRNPA1 M9 NLS having the sequence NQSSNFGPMKGGNFGGRSSGPYGGGGQYFAKPRNQGGY (SEQ ID NO: 1539); the sequence RMRIZFKNKGKDTAELRRRRVEVSVELRKAKKDEQILKRRNV (SEQ ID NO: 1540) of the IBB domain from importin-α; the sequences VSRKRPRP (SEQ ID NO: 1541) and PPKKARED (SEQ ID NO: 1542) of a myoma T protein; the sequence PQPKKKPL (SEQ ID NO: 1543) of human p53; the sequence SALIKKKKKMAP (SEQ ID NO: 1544) of mouse c-abl IV; the sequences DRLRR (SEQ ID NO: 1550) and PKQKKRK (SEQ ID NO: 1545) of influenza virus NS1; the sequence RKLKKKIKKL (SEQ ID NO: 1546) of a hepatitis delta virus antigen; the sequence REKKKFLKRR (SEQ ID NO: 1547) of a mouse Mx1 protein; the sequence KRKGDEVDGVDEVAKKKSKK (SEQ ID NO: 1548) of a human poly (ADP-ribose) polymerase; or the NLS sequence RKCLQAGMNLEARKTKK (SEQ ID NO: 1549), derived from a sequence of a steroid hormone receptor (human) glucocorticoid.

In addition, the CRISPR enzyme mutant may include a split-type CRISPR enzyme prepared by dividing the CRISPR enzyme into two or more parts. The term "split" refers to functional or structural division of a protein or random division of a protein into two or more parts.

Here, the split-type CRISPR enzyme may be a completely, incompletely or partially active enzyme or inactive enzyme.

For example, the SpCas9 may be divided into two parts between the residue 656, tyrosine, and the residue 657, threonine, thereby generating split SpCas9.

In addition, the split-type CRISPR enzyme may selectively include an additional domain, peptide, polypeptide or protein for reconstitution.

Here, the "reconstitution" refers to formation of the split-type CRISPR enzyme to be structurally the same or similar to the wild-type CRISPR enzyme.

The additional domain, peptide, polypeptide or protein for reconstitution may be FRB and FKBP dimerization domains; intein; ERT and VPR domains; or domains which form a heterodimer under specific conditions.

For example, the SpCas9 may be divided into two parts between the residue 713, serine, and the residue 714, glycine, thereby generating split SpCas9. The FRB domain may be connected to one of the two parts, and the FKBP domain may be connected to the other one. In the split SpCas9 produced thereby, the FRB domain and the FKBP domain may be formed in a dimer in an environment in which rapamycin is present, thereby producing a reconstituted CRISPR enzyme.

The CRISPR enzyme or CRISPR enzyme mutant described in the present invention may be a polypeptide, protein or nucleic acid having a sequence encoding the same, and may be codon-optimized for a subject to introduce the CRISPR enzyme or CRISPR enzyme mutant.

The term "codon optimization" refers to a process of modifying a nucleic acid sequence by maintaining a native amino acid sequence while replacing at least one codon of the native sequence with a codon more frequently or the most frequently used in host cells so as to improve expression in the host cells. A variety of species have a specific bias to a specific codon of a specific amino acid, and the codon bias (the difference in codon usage between organisms) is frequently correlated with efficiency of the translation of mRNA, which is considered to be dependent on the characteristic of a translated codon and availability of a specific tRNA molecule. The dominance of tRNA selected in cells generally reflects codons most frequently used in peptide synthesis. Therefore, a gene may be customized by optimal gene expression in a given organism based on codon optimization.

3. Target Sequence

The term "target sequence" is a base sequence present in a target gene or nucleic acid, and has complementarity to a guide sequence contained in a guide domain of a guide nucleic acid. The target sequence is a base sequence which may vary according to a target gene or nucleic acid, that is, a subject for gene manipulation or correction, which may be designed in various forms according to the target gene or nucleic acid.

The target sequence may form a complementary bond with the guide sequence contained in the guide domain of the guide nucleic acid, and a length of the target sequence may be the same as that of the guide sequence.

The target sequence may be a 5 to 50-base sequence.

In an embodiment, the target sequence may be a 16, 17, 18, 19, 20, 21, 22, 23, 24 or 25-base sequence.

The target sequence may be a nucleic acid sequence complementary to the guide sequence contained in the guide domain of the guide nucleic acid, which has, for example, at least 70%, 75%, 80%, 85%, 90% or 95% or more complementarity or complete complementarity.

In one example, the target sequence may be or include a 1 to 8-base sequence, which is not complementary to the guide sequence contained in the guide domain of the guide nucleic acid.

In addition, the target sequence may be a base sequence adjacent to a nucleic acid sequence that is able to be recognized by an editor protein.

In one example, the target sequence may be a continuous 5 to 50-base sequence adjacent to the 5' end and/or 3' end of the nucleic acid sequence that is able to be recognized by the editor protein.

In one exemplary embodiment, target sequences for a gRNA-CRISPR enzyme complex will be described below.

When the target gene or nucleic acid is targeted by the gRNA-CRISPR enzyme complex, the target sequence has complementarity to the guide sequence contained in the guide domain of gRNA. The target sequence is a base sequence which varies according to the target gene or nucleic acid, that is, a subject for gene manipulation or correction, which may be designed in various forms according to the target gene or nucleic acid.

In addition, the target sequence may be a base sequence adjacent to a PAM sequence which is able to be recognized by the CRISPR enzyme, that is, Cas9 or Cpf1.

In one example, the target sequence may be a continuous 5 to 50-base sequence adjacent to the 5' end and/or 3' end of the PAM sequence which is recognized by the CRISPR enzyme.

In one exemplary embodiment, when the CRISPR enzyme is SpCas9, the target sequence may be a continuous 16 to 25-base sequence adjacent to the 5' end and/or 3' end of a 5'-NGG-3', 5'-NAG-3' and/or 5'-NGA-3' (N=A, T, G or C; or A, U, G or C) sequence.

In another exemplary embodiment, when the CRISPR enzyme is StCas9, the target sequence may be a continuous 16 to 25-base sequence adjacent to the 5' end and/or 3' end of a 5'-NGGNG-3' and/or 5'-NNAGAAW-3' (W=A or T, and N=A, T, G or C; or A, U, G or C) sequence.

In still another exemplary embodiment, when the CRISPR enzyme is NmCas9, the target sequence may be a continuous 16 to 25-base sequence adjacent to the 5' end and/or 3' end of a 5'-NNNNGATT-3' and/or 5'-NNNGCTT-3' (N=A, T, G or C; or A, U, G or C) sequence.

In one exemplary embodiment, when the CRISPR enzyme is CjCas9, the target sequence may be a continuous 16 to 25-base sequence adjacent to the 5' end and/or 3' end of a 5'-NNNVRYAC-3' (V=G, C or A; R=A or G, Y=C or T, N=A, T, G or C; or A, U, G or C) sequence.

In another exemplary embodiment, when the CRISPR enzyme is SmCas9, the target sequence may be a continuous 16 to 25-base sequence adjacent to the 5' end and/or 3' end of a 5'-NGG-3' and/or 5'-NAAR-3'(R=A or G, N=A, T, G or C; or A, U, G or C) sequence.

In yet another exemplary embodiment, when the CRISPR enzyme is SaCas9, the target sequence may be a continuous 16 to 25-base sequence adjacent to the 5' end and/or 3' end of a 5'-NNGRR-3', 5'-NNGRRT-3' and/or 5'-NNGRRV-3' (R=A or G, V=G, C or A, N=A, T, G or C; or A, U, G or C) sequence.

In one exemplary embodiment, when the CRISPR enzyme is Cpf1, the target sequence may be a continuous 16 to 25-base sequence adjacent to the 5' end and/or 3' end of a 5'-TTN-3' (N=A, T, G or C; or A, U, G or C) sequence.

In one exemplary embodiment of the present invention, the target sequence may be a nucleic acid sequence contained in one or more genes selected from the group consisting of a VEGFA gene, an HIF1A gene, an ANGPT2 gene, an EPAS1 gene, and an ANGPTL4 gene.

The target sequence may be a nucleic acid sequence contained in the VEGFA gene.

The target sequence may be a nucleic acid sequence contained in the HIF1A gene.

The target sequence may be a nucleic acid sequence contained in the ANGPT2 gene.

The target sequence may be a nucleic acid sequence contained in the EPAS1 gene.

The target sequence may be a nucleic acid sequence contained in the ANGPTL4 gene.

Alternatively, the target sequence may be a partial nucleic acid sequence of one or more genes selected from the group consisting of a VEGFA gene, an HIF1A gene, an ANGPT2 gene, an EPAS1 gene, and an ANGPTL4 gene.

The target sequence may be a partial nucleic acid sequence of the VEGFA gene.

The target sequence may be a partial nucleic acid sequence of the HIF1A gene.

The target sequence may be a partial nucleic acid sequence of the ANGPT2 gene.

The target sequence may be a partial nucleic acid sequence of the EPAS1 gene.

The target sequence may be a partial nucleic acid sequence of the ANGPTL4 gene.

Alternatively, the target sequence may be a nucleic acid sequence of the coding or non-coding region or a mixture thereof of one or more genes selected from the group consisting of a VEGFA gene, an HIF1A gene, an ANGPT2 gene, an EPAS1 gene, and an ANGPTL4 gene.

The target sequence may be a nucleic acid sequence of the coding or non-coding region or a mixture thereof of the VEGFA gene.

The target sequence may be a nucleic acid sequence of the coding or non-coding region or a mixture thereof of the HIF1A gene.

The target sequence may be a nucleic acid sequence of the coding or non-coding region or a mixture thereof of the ANGPT2 gene.

The target sequence may be a nucleic acid sequence of the coding or non-coding region or a mixture thereof of the EPAS1 gene.

The target sequence may be a nucleic acid sequence of the coding or non-coding region or a mixture thereof of the ANGPTL4 gene.

Alternatively, the target sequence may be a nucleic acid sequence of the promoter, enhancer, 3'UTR or polyadenyl (polyA) region or a mixture thereof of one or more genes selected from the group consisting of a VEGFA gene, an HIF1A gene, an ANGPT2 gene, an EPAS1 gene, and an ANGPTL4 gene.

The target sequence may be a nucleic acid sequence of the promoter, enhancer, 3'UTR or polyadenyl (polyA) region or a mixture thereof of the VEGFA gene.

The target sequence may be a nucleic acid sequence of the promoter, enhancer, 3'UTR or polyadenyl (polyA) region or a mixture thereof of the HIF1A gene.

The target sequence may be a nucleic acid sequence of the promoter, enhancer, 3'UTR or polyadenyl (polyA) region or a mixture thereof of the ANGPT2 gene.

The target sequence may be a nucleic acid sequence of the promoter, enhancer, 3'UTR or polyadenyl (polyA) region or a mixture thereof of the EPAS1 gene.

The target sequence may be a nucleic acid sequence of the promoter, enhancer, 3'UTR or polyadenyl (polyA) region or a mixture thereof of the ANGPTL4 gene.

Alternatively, the target sequence may be a nucleic acid sequence of an exon, an intron or a mixture thereof of one or more genes selected from the group consisting of a VEGFA gene, an HIF1A gene, an ANGPT2 gene, an EPAS1 gene, and an ANGPTL4 gene.

The target sequence may be a nucleic acid sequence of an exon, an intron or a mixture thereof of the VEGFA gene.

The target sequence may be a nucleic acid sequence of an exon, an intron or a mixture thereof of the HIF1A gene.

The target sequence may be a nucleic acid sequence of an exon, an intron or a mixture thereof of the ANGPT2 gene.

The target sequence may be a nucleic acid sequence of an exon, an intron or a mixture thereof of the EPAS1 gene.

The target sequence may be a nucleic acid sequence of an exon, an intron or a mixture thereof of the ANGPTL4 gene.

Alternatively, The target sequence may be a nucleic acid sequence including or adjacent to a mutated region (e.g., a region different from a wild-type gene) of one or more genes selected from the group consisting of a VEGFA gene, an HIF1A gene, an ANGPT2 gene, an EPAS1 gene, and an ANGPTL4 gene.

The target sequence may be a nucleic acid sequence including or adjacent to a mutated region of the VEGFA gene.

The target sequence may be a nucleic acid sequence including or adjacent to a mutated region of the HIF1A gene.

The target sequence may be a nucleic acid sequence including or adjacent to a mutated region of the ANGPT2 gene.

The target sequence may be a nucleic acid sequence including or adjacent to a mutated region of the EPAS1 gene.

The target sequence may be a nucleic acid sequence including or adjacent to a mutated region of the ANGPTL4 gene.

Alternatively, the target sequence may be a continuous 5 to 50-nucleic acid sequence of one or more genes selected from the group consisting of a VEGFA gene, an HIF1A gene, an ANGPT2 gene, an EPAS1 gene, and an ANGPTL4 gene.

The target sequence may be a continuous 5 to 50-nucleic acid sequence of the VEGFA gene.

The target sequence may be a continuous 5 to 50-nucleic acid sequence of the HIF1A gene.

The target sequence may be a continuous 5 to 50-nucleic acid sequence of the ANGPT2 gene.

The target sequence may be a continuous 5 to 50-nucleic acid sequence of the EPAS1 gene.

The target sequence may be a continuous 5 to 50-nucleic acid sequence of the ANGPTL4 gene.

As one exemplary embodiment of the present invention, the above target sequences of the VEGFA gene, HIF1A gene, ANGPT2 gene, EPAS1 gene, and ANGPTL4 gene are summarized in Table 1, Table 2, Table 3, Table 4 and Table 5.

Neovascularization-Associated Factor-Manipulated Product

4. Guide Nucleic Acid-Editor Protein Complex and Use Thereof

A guide nucleic acid-editor protein complex may modify a target.

The target may be a target nucleic acid, gene, chromosome or protein.

For example, the guide nucleic acid-editor protein complex may be used to ultimately regulate (e.g., inhibit, suppress, reduce, increase or promote) the expression of a protein of interest, remove a protein, regulate (e.g., inhibit, suppress, reduce, increase or promote) protein activity, or express a new protein.

Here, the guide nucleic acid-editor protein complex may act at a DNA, RNA, gene or chromosomal level.

For example, the guide nucleic acid-editor protein complex may regulate (e.g., inhibit, suppress, reduce, increase or promote) the expression of a protein encoded by target DNA, remove a protein, regulate (e.g., inhibit, suppress, reduce, increase or promote) protein activity, or express a modified protein through manipulation or modification of the target DNA.

In another example, the guide nucleic acid-editor protein complex may regulate (e.g., inhibit, suppress, reduce, increase or promote) the expression of a protein encoded by target DNA, remove a protein, regulate (e.g., inhibit, suppress, reduce, increase or promote) protein activity, or express a modified protein through manipulation or modification of target RNA.

In one example, the guide nucleic acid-editor protein complex may regulate (e.g., inhibit, suppress, reduce, increase or promote) the expression of a protein encoded by target DNA, remove a protein, regulate (e.g., inhibit, suppress, reduce, increase or promote) protein activity, or express a modified protein through manipulation or modification of a target gene.

In another example, the guide nucleic acid-editor protein complex may regulate (e.g., inhibit, suppress, reduce, increase or promote) the expression of a protein encoded by target DNA, remove a protein, regulate (e.g., inhibit, suppress, reduce, increase or promote) protein activity, or express a modified protein through manipulation or modification of a target chromosome.

The guide nucleic acid-editor protein complex may act at gene transcription and translation stages.

In one example, the guide nucleic acid-editor protein complex may promote or suppress the transcription of a target gene, thereby regulating (e.g., inhibiting, suppressing, reducing, increasing or promoting) the expression of a protein encoded by the target gene.

In another example, the guide nucleic acid-editor protein complex may promote or suppress the translation of a target gene, thereby regulating (e.g., inhibiting, suppressing, reducing, increasing or promoting) the expression of a protein encoded by the target gene.

The guide nucleic acid-editor protein complex may act at a protein level.

In one example, the guide nucleic acid-editor protein complex may manipulate or modify a target protein, thereby removing the target protein or regulating (e.g., inhibiting, suppressing, reducing, increasing or promoting) protein activity.

In one exemplary embodiment, the present invention provides a guide nucleic acid-editor protein complex used to manipulate a neovascularization-associated factor, for example, a VEGFA gene, an HIF1A gene, an ANGPT2 gene, an EPAS1 gene, and/or an ANGPTL4 gene. Preferably, a gRNA-CRISPR enzyme complex is provided.

Particularly, the present invention may provide gRNA including a guide domain capable of forming a complementary bond with a target sequence from a gene, for example, isolated or non-natural gRNA and DNA encoding the same. The gRNA and the DNA sequence encoding the same may be designed to be able to complementarily bind to a target sequence listed in Table 1, Table 2, Table 3, Table 4 and Table 5.

In addition, a target region of the gRNA is designed to provide a third gene, which has a nucleic acid modification, for example, double or single strand breaks; or a specific function at a target site in a VEGFA gene, an HIF1A gene, an ANGPT2 gene, an EPAS1 gene, and/or an ANGPTL4 gene.

In addition, when two or more gRNAs are used to induce two or more cleaving events in a target gene, for example, a double or single strand break, the two or more cleaving events may occur due to the same or different Cas9 proteins.

The gRNA may target, for example, two or more of the VEGFA gene, the HIF1A gene, the ANGPT2 gene, the EPAS1 gene, and/or the ANGPTL4 gene, or two or more regions in each of the VEGFA gene, HIF1A gene, ANGPT2 gene, EPAS1 gene, and/or ANGPTL4 gene, and may independently induce the cleavage of a double strand and/or a single strand of the VEGFA gene, HIF1A gene, ANGPT2 gene, EPAS1 gene, and/or ANGPTL4 gene, or may induce the insertion of one foreign nucleotide into a cleavage site of the VEGFA gene, the HIF1A gene, the ANGPT2 gene, the EPAS1 gene, and/or the ANGPTL4 gene.

In addition, in another exemplary embodiment of the present invention, a nucleic acid constituting the guide nucleic acid-editor protein complex may include: (a) a sequence encoding a guide nucleic acid including a guide domain, which is complementary to a target sequence of the VEGFA gene, the HIF1A gene, the ANGPT2 gene, the EPAS1 gene, and/or the ANGPTL4 gene as described herein; and (b) a sequence encoding an editor protein.

Here, there may be two or more of the (a) according to a target region, and the (b) may employ the same or two or more editor proteins.

In an embodiment, the nucleic acid may be designed to target an enzymatically inactive editor protein or a fusion protein (e.g., a transcription repressor domain fusion) thereof to place it sufficiently adjacent to a knockdown target site in order to reduce, decrease or inhibit expression of the VEGFA gene, the HIF1A gene, the ANGPT2 gene, the EPAS1 gene, and/or the ANGPTL4 gene.

Besides, it should be obvious that the above-described structure, function, and all applications of the guide nucleic acid-editor protein complex will be utilized in manipulation of the VEGFA gene, the HIF1A gene, the ANGPT2 gene, the EPAS1 gene, and/or the ANGPTL4 gene.

Use of Guide Nucleic Acid-Editor Protein Complex

In an embodiment for the use of the guide nucleic acid-editor protein complex of the present invention, the manipulation or modification of target DNA, RNA, genes or chromosomes using the gRNA-CRISPR enzyme complex will be described below.

Gene Manipulation

A target gene or nucleic acid may be manipulated or corrected using the above-described gRNA-CRISPR enzyme complex, that is, the CRISPR complex. Here, the manipulation or correction of the target gene or nucleic acid includes all of the stages of i) cleaving or damaging the target gene or nucleic acid and ii) repairing the damaged target gene or nucleic acid.

i) Cleavage or Damage of Target Gene or Nucleic Acid i) The cleavage or damage of the target gene or nucleic acid may be cleavage or damage of the target gene or nucleic acid using the CRISPR complex, and particularly, cleavage or damage of a target sequence in the target gene or nucleic acid.

In one example, the cleavage or damage of the target gene or nucleic acid using the CRISPR complex may be complete cleavage or damage to the double strand of a target sequence.

In one exemplary embodiment, when wild-type SpCas9 is used, the double strand of a target sequence forming a complementary bond with gRNA may be completely cleaved.

In another exemplary embodiment, when SpCas9 nickase (D10A) and SpCas9 nickase (H840A) are used, a complementary single strand of a target sequence forming a complementary bond with gRNA may be cleaved by the SpCas9 nickase (D10A), and a non-complementary single strand of the target sequence forming a complementary bond with gRNA may be cleaved by the SpCas9 nickase (H840A), and the cleavages may take place sequentially or simultaneously.

In still another exemplary embodiment, when SpCas9 nickase (D10A) and SpCas9 nickase (H840A), and two gRNAs having different target sequences are used, a complementary single strand of a target sequence forming a complementary bond with the first gRNA may be cleaved by the SpCas9 nickase (D10A), a non-complementary single strand of a target sequence forming a complementary bond with the second gRNA may be cleaved by the SpCas9 nickase (H840A), and the cleavages may take place sequentially or simultaneously.

In another example, the cleavage or damage of a target gene or nucleic acid using the CRISPR complex may be cleavage or damage to only the single strand of a target sequence. Here, the single strand may be a complementary single strand of a target sequence forming a complementary bond with gRNA, or a non-complementary single strand of the target sequence forming a complementary bond with gRNA.

In one exemplary embodiment, when SpCas9 nickase (D10A) is used, a complementary single strand of a target sequence forming a complementary bond with gRNA may be cleaved by the SpCas9 nickase (D10A), but a non-complementary single strand of the target sequence forming a complementary bond with gRNA may not be cleaved.

In another exemplary embodiment, when SpCas9 nickase (H840A) is used, a complementary single strand of a target sequence forming a complementary bond with gRNA may be cleaved by the SpCas9 nickase (H840A), but a non-complementary single strand of the target sequence forming a complementary bond with gRNA may not be cleaved.

In yet another example, the cleavage or damage of a target gene or nucleic acid using the CRISPR complex may be partial removal of a nucleic acid fragment.

In one exemplary embodiment, when two gRNAs having different target sequences and wild-type SpCas9 are used, a double strand of a target sequence forming a complementary bond with the first gRNA may be cleaved, and a double strand of a target sequence forming a complementary bond with the second gRNA may be cleaved, resulting in the removal of nucleic acid fragments by the first and second gRNAs and SpCas9.

In another exemplary embodiment, when two gRNAs having different target sequences, wild-type SpCas9, SpCas9 nickase (D10A) and SpCas9 nickase (H840A) are used, a double strand of a target sequence forming a complementary bond with the first gRNA may be cleaved by the wild-type SpCas9, a complementary single strand of a target sequence forming a complementary bond with the second gRNA may be cleaved by the SpCas9 nickase (D10A), and a non-complementary single strand nay be cleaved by the SpCas9 nickase (H840A), resulting in the removal of nucleic acid fragments by the first and second gRNAs, the wild-type SpCas9, the SpCas9 nickase (D10A) and the SpCas9 nickase (H840A).

In still another exemplary embodiment, when two gRNAs having different target sequences, SpCas9 nickase (D10A) and SpCas9 nickase (H840A) are used, a complementary single strand of a target sequence forming a complementary bond with the first gRNA may be cleaved by the SpCas9 nickase (D10A), a non-complementary single strand may be cleaved by the SpCas9 nickase (H840A), a complementary double strand of a target sequence forming a complementary bond with the second gRNA may be cleaved by the SpCas9 nickase (D10A), and a non-complementary single strand may be cleaved by the SpCas9 nickase (H840A), resulting in the removal of nucleic acid fragments by the first and second gRNAs, the SpCas9 nickase (D10A) and the SpCas9 nickase (H840A).

In yet another exemplary embodiment, when three gRNAs having different target sequences, wild-type SpCas9, SpCas9 nickase (D10A) and SpCas9 nickase (H840A) are used, a double strand of a target sequence forming a complementary bond with the first gRNA may be cleaved by the wild-type SpCas9, a complementary single strand of a target sequence forming a complementary bond with the second gRNA may be cleaved by the SpCas9 nickase (D10A), and a non-complementary single strand of a target sequence forming a complementary bond with the third gRNA may be cleaved by the SpCas9 nickase (H840A), resulting in the removal of nucleic acid fragments by the first gRNA, the second gRNA, the third gRNA, the wild-type SpCas9, the SpCas9 nickase (D10A) and the SpCas9 nickase (H840A).

In yet another exemplary embodiment, when four gRNAs having different target sequences, SpCas9 nickase (D10A) and SpCas9 nickase (H840A) are used, a complementary single strand of a target sequence forming a complementary bond with the first gRNA may be cleaved by the SpCas9 nickase (D10A), a non-complementary single strand of a target sequence forming a complementary bond with the second gRNA may be cleaved by the SpCas9 nickase (H840A), a complementary single strand of a target sequence forming a complementary bond with the third gRNA may be cleaved by the SpCas9 nickase (D10A), and a non-complementary single strand of a target sequence forming a complementary bond with fourth gRNA may be cleaved by the SpCas9 nickase (H840A), resulting in the removal of nucleic acid fragments by the first gRNA, the second gRNA, the third gRNA, the fourth gRNA, the SpCas9 nickase (D10A) and the SpCas9 nickase (H840A).

ii) Repair or Restoration of Damaged Target Gene or Nucleic Acid

The target gene or nucleic acid cleaved or damaged by the CRISPR complex may be repaired or restored through NHEJ and homology-directed repairing (HDR).

Non-Homologous End Joining (NHEJ)

NHEJ is a method of restoration or repairing double strand breaks in DNA by joining both ends of a cleaved double or single strand together, and generally, when two compatible ends formed by breaking of the double strand (for example, cleavage) are frequently in contact with each other to completely join the two ends, the broken double strand is recovered. The NHEJ is a restoration method that is able to be used in the entire cell cycle, and usually occurs when there is no homologous genome to be used as a template in cells, like the G1 phase.

In the repair process of the damaged gene or nucleic acid using NHEJ, some insertions and/or deletions (indels) in the nucleic acid sequence occur in the NHEJ-repaired region, such insertions and/or deletions cause the leading frame to be shifted, resulting in frame-shifted transcriptome mRNA. As a result, innate functions are lost because of nonsense-mediated decay or the failure to synthesize normal proteins. In addition, while the leading frame is maintained, mutations in which insertion or deletion of a considerable amount of sequence may be caused to destroy the functionality of the proteins. The mutation is locus-dependent because mutations in a significant functional domain is probably less tolerated than mutations in a non-significant region of a protein.

While it is impossible to expect indel mutations produced by NHEJ in a natural state, a specific indel sequence is preferred in a given broken region, and can come from a small region of micro homology. Conventionally, the deletion length ranges from 1 bp to 50 bp, insertions tend to be shorter, and frequently include a short repeat sequence directly surrounding a broken region.

In addition, the NHEJ is a process causing a mutation, and when it is not necessary to produce a specific final sequence, may be used to delete a motif of the small sequence.

A specific knockout of a gene targeted by the CRISPR complex may be performed using such NHEJ. A double strand or two single strands of a target gene or nucleic acid may be cleaved using the CRISPR enzyme such as Cas9 or Cpf1, and the broken double strand or two single strands of the target gene or nucleic acid may have indels through the NHEJ, thereby inducing specific knockout of the target gene or nucleic acid. Here, the site of a target gene or nucleic acid cleaved by the CRISPR enzyme may be a non-coding or coding region, and in addition, the site of the target gene or nucleic acid restored by NHEJ may be a non-coding or coding region.

Homology Directed Repairing (HDR)

HDR is a correction method without an error, which uses a homologous sequence as a template to repair or restoration a damaged gene or nucleic acid, and generally, to repair or restoration broken DNA, that is, to restore innate information of cells, the broken DNA is repaired using information of a complementary base sequence which is not modified or information of a sister chromatid. The most common type of HDR is homologous recombination (HR). HDR is a repair or restoration method usually occurring in the S or G2/M phase of actively dividing cells.

To repair or restore damaged DNA using HDR, rather than using a complementary base sequence or sister chromatin of the cells, a DNA template artificially synthesized using information of a complementary base sequence or homologous base sequence, that is, a nucleic acid template including a complementary base sequence or homologous base sequence may be provided to the cells, thereby repairing the broken DNA. Here, when a nucleic acid sequence or nucleic acid fragment is further added to the nucleic acid template to repair the broken DNA, the nucleic acid sequence or nucleic acid fragment further added to the broken DNA may be subjected to knockin. The further added nucleic acid sequence or nucleic acid fragment may be a nucleic acid sequence or nucleic acid fragment for correcting the target gene or nucleic acid modified by a mutation to a normal gene or nucleic acid, or a gene or nucleic acid to be expressed in cells, but the present invention is not limited thereto.

In one example, a double or single strand of a target gene or nucleic acid may be cleaved using the CRISPR complex, a nucleic acid template including a base sequence complementary to a base sequence adjacent to the cleavage site may be provided to cells, and the cleaved base sequence of the target gene or nucleic acid may be repaired or restored through HDR.

Here, the nucleic acid template including the complementary base sequence may have broken DNA, that is, a cleaved double or single strand of a complementary base sequence, and further include a nucleic acid sequence or nucleic acid fragment to be inserted into the broken DNA. An additional nucleic acid sequence or nucleic acid fragment may be inserted into a cleaved site of the broken DNA, that is, the target gene or nucleic acid using the nucleic acid template including a nucleic acid sequence or nucleic acid fragment to be inserted into the complementary base sequence. Here, the nucleic acid sequence or nucleic acid fragment to be inserted and the additional nucleic acid sequence or nucleic acid fragment may be a nucleic acid sequence or nucleic acid fragment for correcting a target gene or nucleic acid modified by a mutation to a normal gene or nucleic acid or a gene or nucleic acid to be expressed in cells. The complementary base sequence may be a base sequence having complementary bonds with broken DNA, that is, right and left base sequences of the cleaved double or single strand of the target gene or nucleic acid. Alternatively, the complementary base sequence may be a base sequence having complementary bonds with broken DNA, that is, 3' and 5' ends of the cleaved double or single strand of the target gene or nucleic acid. The complementary base sequence may be a 15 to 3000-base sequence, a length or size of the complementary base sequence may be suitably designed according to a size of the nucleic acid template or the target gene. Here, as the nucleic acid template, a double- or single-stranded nucleic acid may be used, or it may be linear or circular, but the present invention is not limited thereto.

In another example, a double- or single-stranded target gene or nucleic acid is cleaved using the CRISPR complex, a nucleic acid template including a homologous base sequence with a base sequence adjacent to a cleavage site is provided to cells, and the cleaved base sequence of the target gene or nucleic acid may be repaired or restored by HDR.

Here, the nucleic acid template including the homologous base sequence may be broken DNA, that is, a cleaved double- or single-stranded homologous base sequence, and further include a nucleic acid sequence or nucleic acid fragment to be inserted into the broken DNA. An additional nucleic acid sequence or nucleic acid fragment may be inserted into broken DNA, that is, a cleaved site of a target gene or nucleic acid using the nucleic acid template including a homologous base sequence and a nucleic acid sequence or nucleic acid fragment to be inserted. Here, the nucleic acid sequence or nucleic acid fragment to be inserted and the additional nucleic acid sequence or nucleic acid fragment may be a nucleic acid sequence or nucleic acid fragment for correcting a target gene or nucleic acid modified by a mutation to a normal gene or nucleic acid or a gene or nucleic acid to be expressed in cells. The homologous base sequence may be broken DNA, that is, a base sequence having homology with cleaved double-stranded base sequence or right and left single-stranded base sequences of a target gene or nucleic acid. Alternatively, the complementary base sequence may be a base sequence having homology with broken DNA, that is, the 3' and 5' ends of a cleaved double or single strand of a target gene or nucleic acid. The homologous base sequence may be a 15 to 3000-base sequence, and a length or size of the homologous base sequence may be suitably designed according to a size of the nucleic acid template or a target gene or nucleic acid. Here, as the nucleic acid template, a double- or single-stranded nucleic acid may be used and may be linear or circular, but the present invention is not limited thereto.

Other than the NHEJ and HDR, there are methods of repairing or restoring broken DNA.

Single-Strand Annealing (SSA)

SSA is a method of repairing double strand breaks between two repeat sequences present in a target nucleic acid, and generally uses a repeat sequence of more than 30 bases. The repeat sequence is cleaved (to have sticky ends) to have a single strand with respect to a double strand of the target nucleic acid at each of the broken ends, and after the cleavage, a single-strand overhang containing the repeat sequence is coated with an RPA protein such that it is prevented from inappropriately annealing the repeat sequences to each other. RAD52 binds to each repeat sequence on the overhang, and a sequence capable of annealing a complementary repeat sequence is arranged. After annealing, a single-stranded flap of the overhang is cleaved, and synthesis of new DNA fills a certain gap to restore a DNA double strand. As a result of this repair, a DNA sequence between two repeats is deleted, and a deletion length may be dependent on various factors including the locations of the two repeats used herein, and a path or degree of the progress of cleavage.

SSA, similar to HDR, utilizes a complementary sequence, that is, a complementary repeat sequence, and in contrast, does not requires a nucleic acid template for modifying or correcting a target nucleic acid sequence.

Single-Strand Break Repair (SSBA)

Single strand breaks in a genome are repaired through a separate mechanism, SSBR, from the above-described repair mechanisms. In the case of single-strand DNA breaks, PARP1 and/or PARP2 recognizes the breaks and recruits a repair mechanism. PARP1 binding and activity with respect to the DNA breaks are temporary, and SSBR is promoted by promoting the stability of an SSBR protein complex in the damaged regions. The most important protein in the SSBR complex is XRCC1, which interacts with a protein promoting 3' and 5' end processing of DNA to stabilize the DNA. End processing is generally involved in repairing the damaged 3' end to a hydroxylated state, and/or the damaged 5' end to a phosphatic moiety, and after the ends are processed, DNA gap filling takes place. There are two methods for the DNA gap filling, that is, short patch repair and long patch repair, and the short patch repair involves insertion of a single base. After DNA gap filling, a DNA ligase promotes end joining.

Mismatch Repair (MMR)

MMR works on mismatched DNA bases. Each of an MSH2/6 or MSH2/3 complex has ATPase activity and thus plays an important role in recognizing a mismatch and initiating a repair, and the MSH2/6 primarily recognizes base-base mismatches and identifies one or two base mismatches, but the MSH2/3 primarily recognizes a larger mismatch.

Base Excision Repair (BER)

BER is a repair method which is active throughout the entire cell cycle, and used to remove a small non-helix-distorting base damaged region from the genome. In the damaged DNA, damaged bases are removed by cleaving an N-glycoside bond joining a base to the phosphate-deoxyribose backbone, and then the phosphodiester backbone is cleaved, thereby generating breaks in single-strand DNA. The broken single strand ends formed thereby were removed, a gap generated due to the removed single strand is filled with a new complementary base, and then an end of the newly-filled complementary base is ligated with the backbone by a DNA ligase, resulting in repair of the damaged DNA.

Nucleotide Excision Repair (NER)

NER is an excision mechanism important for removing large helix-distorting damage from DNA, and when the damage is recognized, a short single-strand DNA segment containing the damaged region is removed, resulting in a single strand gap of 22 to 30 bases. The generated gap is filled with a new complementary base, and an end of the newly filled complementary base is ligated with the backbone by a DNA ligase, resulting in the repair of the damaged DNA.

Gene Manipulation Effects

Manipulation or correction of a target gene or nucleic acid may largely lead to effects of knockout, knockdown, and knockin.

Knockout

The term "knockout" refers to inactivation of a target gene or nucleic acid, and the "inactivation of a target gene or nucleic acid" refers to a state in which transcription and/or translation of a target gene or nucleic acid does not occur. Transcription and translation of a gene causing a disease or a gene having an abnormal function may be inhibited through knockout, resulting in the prevention of protein expression.

For example, when a target gene or nucleic acid is edited or corrected using a gRNA-CRISPR enzyme complex, that is, a CRISPR complex, the target gene or nucleic acid may be cleaved using the CRISPR complex. The damaged target gene or nucleic acid may be repaired through NHEJ using the CRISPR complex. The damaged target gene or nucleic acid may have indels due to NHEJ, and thereby, specific knockout for the target gene or nucleic acid may be induced.

Knockdown

The term "knockdown" refers to a decrease in transcription and/or translation of a target gene or nucleic acid or the expression of a target protein. The onset of a disease may be prevented or a disease may be treated by regulating the overexpression of a gene or protein through the knockdown.

For example, when a target gene or nucleic acid is edited or corrected using a gRNA-CRISPR inactive enzyme-transcription inhibitory activity domain complex, that is, a CRISPR inactive complex including a transcription inhibitory activity domain, the CRISPR inactive complex may specifically bind to the target gene or nucleic acid, transcription of the target gene or nucleic acid may be inhibited by the transcription inhibitory activity domain included in the CRISPR inactive complex, thereby inducing knockdown in which expression of the corresponding gene or nucleic acid is inhibited.

Knockin

The term "knockin" refers to insertion of a specific nucleic acid or gene into a target gene or nucleic acid, and here, the "specific nucleic acid" refers to a gene or nucleic acid of interest to be inserted or expressed. A mutant gene triggering a disease may be utilized in disease treatment by correction to normal or insertion of a normal gene to induce expression of the normal gene through the knockin.

In addition, the knockin may further need a donor.

For example, when a target gene or nucleic acid is edited or corrected using a gRNA-CRISPR enzyme complex, that is, a CRISPR complex, the target gene or nucleic acid may be cleaved using the CRISPR complex. The target gene or nucleic acid damaged using the CRISPR complex may be repaired through HDR. Here, a specific nucleic acid may be inserted into the damaged gene or nucleic acid using a donor.

The term "donor" refers to a nucleic acid sequence that helps HDR-based repair of the damaged gene or nucleic acid, and here, the donor may include a specific nucleic acid.

The donor may be a double- or single-stranded nucleic acid.

The donor may be present in a linear or circular shape.

The donor may include a nucleic acid sequence having homology with a target gene or nucleic acid.

For example, the donor may include a nucleic acid sequence having homology with each of base sequences at a location into which a specific nucleic acid is to be inserted, for example, upstream (left) and downstream (right) of a damaged nucleic acid. Here, the specific nucleic acid to be inserted may be located between a nucleic acid sequence having homology with a base sequence downstream of the damaged nucleic acid and a nucleic acid sequence having homology with a base sequence upstream of the damaged nucleic acid. Here, the homologous nucleic acid sequence may have at least 50%, 55%, 60%, 65%, 70%, 75%, 80%, 85%, 90% or 95% or more homology or complete homology.

The donor may optionally include an additional nucleic acid sequence. Here, the additional nucleic acid sequence may serve to increase donor stability, knockin efficiency or HDR efficiency.

For example, the additional nucleic acid sequence may be an A, T-rich nucleic acid sequence, that is, an A-T rich domain. In addition, the additional nucleic acid sequence may be a scaffold/matrix attachment region (SMAR).

In one exemplary embodiment relating to a gene manipulation effect of the present invention, a manipulated target gene obtained using a gRNA-CRISPR enzyme complex, that is, a manipulated neovascularization-associated factor may have the following constitution.

In one exemplary embodiment, when the neovascularization-associated factor is a gene, the constitution of the artificially manipulated neovascularization-associated factor by the gRNA-CRISPR enzyme complex may include modification of one or more nucleic acids among a deletion or insertion of one or more nucleotides; a substitution with one or more nucleotides different from a wild-type gene; and an insertion of one or more foreign nucleotides in a continuous 1 bp to 50 bp, 1 bp to 40 bp or 1 bp to 30 bp, preferably, 3 bp to 25 bp region in the base sequence, which is located in a PAM sequence in a nucleic acid sequence constituting the neovascularization-associated factor or adjacent to a 5' end and/or 3' end thereof.

In addition, a chemical modification of one or more nucleotides may be included in the nucleic acid sequence constituting the neovascularization-associated factor.

Here, the "foreign nucleotide" is the concept including all exogenous, for example, heterologous or artificially-synthesized nucleotides, other than nucleotides innately included in the neovascularization-associated factor. The foreign nucleotide also includes a nucleotide with a size of several hundred, thousand or tens of thousands of bp to express a protein having a specific function, as well as a small oligonucleotide with a size of 50 bp or less. Such a foreign nucleotide may be a donor.

The chemical modification may include methylation, acetylation, phosphorylation, ubiquitination, ADP-ribosylation, myristylation, and glycosylation, for example, substitution of some functional groups contained in a nucleotide with any one of a hydrogen atom, a fluorine atom, an —O-alkyl group, an —O-acyl group, and an amino group, but the present invention is not limited thereto. In addition, to increase transferability of a nucleic acid molecule, the functional groups may also be substituted with any one of —Br, —Cl, —R, —R'OR, —SH, —SR, —N3 and —CN (R=alkyl, aryl, alkylene). In addition, the phosphate backbone of at least one nucleotide may be substituted with any one of an alkylphosphonate form, a phosphoroamidate form and a boranophosphate form. In addition, the chemical modification may be a substitution of at least one type of nucleotide contained in the nucleic acid molecule with any one of a locked nucleic acid (LNA), an unlocked nucleic acid (UNA), a morpholino, and a peptide nucleic acid (PNA), and the chemical modification may be bonding of the nucleic acid molecule with one or more selected from the group consisting of a lipid, a cell-penetrating peptide and a cell-target ligand.

To form a desired neovascularization regulating system, artificial modification using a gRNA-CRISPR enzyme complex may be applied to the nucleic acid constituting the neovascularization-associated factor.

A region including the nucleic acid modification of the neovascularization-associated factor may be a target region or target sequence.

Such a target sequence may be a target for the gRNA-CRISPR enzyme complex, and the target sequence may include or not include a PAM sequence recognized by the CRISPR enzyme. Such a target sequence may provide a critical standard in a gRNA designing stage to those of ordinary skill in the art.

Such nucleic acid modification includes the "cleavage" of a nucleic acid.

The term "cleavage" in a target region refers to breakage of a covalent backbone of polynucleotides. The cleavage includes enzymatic or chemical hydrolysis of a phosphodiester bond, but the present invention is not limited thereto, and also include various other methods. The cleavage is able to be performed on both of a single strand and a double strand, and the cleavage of a double strand may result from distinct single-strand cleavage. The double-strand cleavage may generate blunt ends or staggered ends.

When an inactivated CRISPR enzyme is used, it may induce a factor possessing a specific function to approach a certain region of the target region or neovascularization-associated factor without the cleavage process. Chemical modification of one or more nucleotides in the nucleic acid sequence of the neovascularization-associated factor may be included according to such a specific function.

In one example, various indels may occur due to target and non-target activities through the nucleic acid cleavage formed by the gRNA-CRISPR enzyme complex.

The term "indel" is the generic term for an insertion or deletion mutation occurring in-between some bases in a DNA base sequence. The indel may be introduced into a target sequence during repair by an HDR or NHEJ mechanism when the gRNA-CRISPR enzyme complex cleaves the nucleic acid (DNA or RNA) of the neovascularization-associated factor as described above.

The artificially manipulated neovascularization-associated factor of the present invention refers to modification of the nucleic acid sequence of an original gene by cleavage, indels, or insertion using a donor of such a nucleic acid, and contributes to a desired neovascularization regulating system, for example, exhibition of an effect of promoting or suppressing neovascularization.

For example, a specific protein may be expressed and its activity may be stimulated by the artificially manipulated neovascularization-associated factor.

A specific protein may be inactivated by the artificially manipulated neovascularization-associated factor.

In one example, a specific target region of each neovascularization-associated factor of the genome, for example, reverse regulatory genes such as a VEGFA gene, an HIF1A gene, an ANGPT2 gene, an EPAS1 gene, and/or an ANGPTL4 gene may be cleaved, resulting in knockdown or knockout of the gene.

In another example, targeted knockdown may be mediated using an enzymatically inactive CRISPR enzyme fused to a transcription repressor domain or chromatin-modified protein to change transcription, for example, to block, negatively regulate or decrease the transcription of a VEGFA gene, an HIF1A gene, an ANGPT2 gene, an EPAS1 gene, and/or an ANGPTL4 gene.

The neovascularization may be regulated by the artificially manipulated neovascularization-associated factor.

A neovascularization-associated disease may be improved or treated by the artificially manipulated neovascularization-associated factor.

In one exemplary embodiment of the present invention, the artificially manipulated neovascularization-associated factor may provide various artificially manipulated neovascularization-associated factors according to the constitutional characteristic of the gRNA-CRISPR enzyme complex (e.g., included in a target region of the neovascularization-associated factor or different in the adjacent major PAM sequence).

Hereinafter, while representative examples of CRISPR enzymes and a neovascularization-regulatory gene have been illustrated, they are merely specific examples, and thus the present invention is not limited thereto.

For example, when the CRISPR enzyme is a SpCas9 protein, the PAM sequence is 5'-NGG-3' (N is A, T, G, or C), and the cleaved base sequence region (target region) may be a continuous 1 bp to 25 bp, for example, 17 bp to 23 bp or 21 bp to 23 bp, region in the base sequence adjacent to the 5' end and/or 3' end of the 5'-NGG-3' sequence in a target gene.

The present invention may provide an artificially manipulated neovascularization-associated factor, for example, an artificially manipulated VEGFA gene, HIF1A gene, ANGPT2 gene, EPAS1 gene, and/or ANGPTL4 gene, which is prepared by
  a) deletion of one or more nucleotides of a continuous 1 bp to 25 bp, for example, 17 bp to 23 bp, region in the base sequence adjacent to the 5' end and/or 3' end of the 5'-NGG-3' (N is A, T, C or G) sequence,
  b) substitution of one or more nucleotides of a continuous 1 bp to 25 bp, for example, 17 bp to 23 bp, region in the base sequence adjacent to the 5' end and/or 3' end of the 5'-NGG-3' sequence with nucleotides different from those of the wild-type gene,
  c) insertion of one or more nucleotides into a continuous 1 bp to 25 bp, for example, 17 bp to 23 bp, region in the base sequence adjacent to the 5' end and/or 3' end of the 5'-NGG-3' sequence, or
  d) a combination of two or more selected from a) through c) in the nucleic acid sequence of the neovascularization-associated factor.

For example, when the CRISPR enzyme is a CjCas9 protein, the PAM sequence is 5'-NNNNRYAC-3' (each N is independently A, T, C or G, R is A or G, and Y is C or T), and the cleaved base sequence region (target region) may be a continuous 1 bp to 25 bp, for example, 17 bp to 23 bp or 21 bp to 23 bp, region in the base sequence adjacent to the 5' end and/or 3' end of the 5'-NNNNRYAC-3' sequence in a target gene.

The present invention may provide an artificially manipulated neovascularization-associated factor, for example, an artificially manipulated VEGFA gene, HIF1A gene, ANGPT2 gene, EPAS1 gene, and/or ANGPTL4 gene, which is prepared by
  a') deletion of one or more nucleotides of a continuous 1 bp to 25 bp, for example, 17 bp to 23 bp, region in the base sequence adjacent to the 5' end and/or 3' end of the 5'-NNNNRYAC-3' (each N is independently A, T, C or G, R is A or G, and Y is C or T),
  b') substitution of one or more nucleotides of a continuous 1 bp to 25 bp, for example, 17 bp to 23 bp, region in the base sequence adjacent to the 5' end and/or 3' end of the 5'-NNNNRYAC-3' sequence with nucleotides different from those of the wild-type gene,
  c') insertion of one or more nucleotides into a continuous 1 bp to 25 bp, for example, 17 bp to 23 bp, region in the base sequence adjacent to the 5' end and/or 3' end of the 5'-NNNNRYAC-3' sequence, or
  d') a combination of two or more selected from a') through c') in the nucleic acid sequence of the neovascularization-associated factor.

For example, when the CRISPR enzyme is a StCas9 protein, the PAM sequence is 5'-NNAGAAW-3' (each N is independently A, T, C or G, and W is A or T), and the cleaved base sequence region (target region) may be a continuous 1 bp to 25 bp, for example, 17 bp to 23 bp or 21 bp to 23 bp, region in the base sequence adjacent to the 5' end and/or 3' end of the 5'-NNAGAAW-3' sequence in a target gene.

The present invention may provide an artificially manipulated neovascularization-associated factor, for example, an artificially manipulated VEGFA gene, HIF1A gene, ANGPT2 gene, EPAS1 gene, and/or ANGPTL4 gene, which is prepared by
  a") deletion of one or more nucleotides of a continuous 1 bp to 25 bp, for example, 17 bp to 23 bp, region in the base sequence adjacent to the 5' end and/or 3' end of the 5'-NNAGAAW-3' sequence (each N is independently A, T, C or G, and W is A or T),
  b") substitution of one or more nucleotides of a continuous 1 bp to 25 bp, for example, 17 bp to 23 bp, region in the base sequence adjacent to the 5' end and/or 3' end of the 5'-NNAGAAW-3' sequence with nucleotides different from those of the wild-type gene,
  c") insertion of one or more nucleotides into a continuous 1 bp to 25 bp, for example, 17 bp to 23 bp, region in the base sequence adjacent to the 5' end and/or 3' end of the 5'-NNAGAAW-3' sequence, or
  d") a combination of two or more selected from a") through c") in the nucleic acid sequence of the neovascularization-associated factor.

For example, when the CRISPR enzyme is an NmCas9 protein, the PAM sequence is 5'-NNNNGATT-3'(each N is independently A, T, C or G), and the cleaved base sequence region (target region) may be a continuous 1 bp to 25 bp, for example, 17 bp to 23 bp or 21 bp to 23 bp, region in the base sequence adjacent to the 5' end and/or 3' end of the 5'-NNNNGATT-3' sequence in a target gene.

The present invention may provide an artificially manipulated neovascularization-associated factor, for example, an artificially manipulated VEGFA gene, HIF1A gene, ANGPT2 gene, EPAS1 gene, and/or ANGPTL4 gene, which is prepared by
  a'") deletion of one or more nucleotides of a continuous 1 bp to 25 bp, for example, 17 bp to 23 bp, region in the base sequence adjacent to the 5' end and/or the 3' end of the 5'-NNNNGATT-3' sequence (each N is independently A, T, C or G),
  b'") substitution of one or more nucleotides of a continuous 1 bp to 25 bp, for example, 17 bp to 23 bp, region in the base sequence adjacent to the 5' end and/or 3' end of the 5'-NNNNGATT-3' sequence with nucleotides different from those of the wild-type gene,
  c'") insertion of one or more nucleotides into a continuous 1 bp to 25 bp, for example, 17 bp to 23 bp, region in the base sequence adjacent to the 5'-NNNNGATT-3' sequence, or
  d'") a combination of two or more selected from a'") through c'") in the nucleic acid sequence of the neovascularization-associated factor.

For example, when the CRISPR enzyme is an SaCas9 protein, the PAM sequence is 5'-NNGRR(T)-3' (each N is independently A, T, C or G, R is A or G, and (T) is a randomly addable sequence), and the cleaved base sequence region (target region) may be a continuous 1 bp to 25 bp, for example, 17 bp to 23 bp or 21 bp to 23 bp, region in the base sequence adjacent to the 5' end and/or 3' end of the 5'-NNGRR(T)-3' sequence in a target gene.

The present invention may provide an artificially manipulated neovascularization-associated factor, for example, an artificially manipulated VEGFA gene, HIF1A gene, ANGPT2 gene, EPAS1 gene, and/or ANGPTL4 gene, which is prepared by a'''') deletion of one or more nucleotides of a continuous 1 bp to 25 bp, for example, 17 bp to 23 bp region, in the base sequence adjacent to the 5' end and/or the 3' end of the 5'-NNGRR(T)-3' sequence (each N is independently A, T, C or G, R is A or G, and (T) is a randomly addable sequence), b'''') substitution of one or more nucleotides of a continuous 1 bp to 25 bp, for example, 17 bp to 23 bp, region in the base sequence adjacent to the 5' end and/or 3' end of the 5'-NNGRR(T)-3' sequence with nucleotides different from those of the wild-type gene, c'''') insertion of one or more nucleotides into a continuous 1 bp to 25 bp, for example, 17 bp to 23 bp, region in the base sequence adjacent to the 5'-NNGRR(T)-3' sequence, or d'''') a combination of two or more selected from a'''') through c'''') in the nucleic acid sequence of the neovascularization-associated factor.

For example, when the CRISPR enzyme is a Cpf1 protein, the PAM sequence is 5'-TTN-3' (N is A, T, C or G), and the cleaved base sequence region (target region) may be a continuous 10 bp to 30 bp, for example, 15 bp to 26 bp, 17 bp to 30 bp or 17 bp to 26 bp, region in the base sequence adjacent to the 5' end or the 3' end of the 5'-TTN-3' sequence.

The Cpf1 protein may be derived from a microorganism such as Parcubacteria bacterium (GWC2011_GWC2_44_17), Lachnospiraceae bacterium (MC2017), *Butyrivibrio proteoclasticus, Peregrinibacteria* bacterium (GW2011_GWA_33_10), *Acidaminococcus* sp. (BV3L6), *Porphyromonas macacae*, Lachnospiraceae bacterium (ND2006), *Porphyromonas crevioricanis, Prevotella disiens, Moraxella bovoculi* (237), *Smithella* sp. (SC_KO8D17), *Leptospira inadai*, Lachnospiraceae bacterium (MA2020), *Francisella novicida* (U112), Candidatus Methanoplasma *termitum*, or *Eubacterium eligens*, for example, Parcubacteria bacterium (GWC2011_GWC2_44_17), *Peregrinibacteria* bacterium (GW2011_GWA_33_10), *Acidaminococcus* sp. (BV3L6), *Porphyromonas macacae*, Lachnospiraceae bacterium (ND2006), *Porphyromonas crevioricanis, Prevotella disiens, Moraxella bovoculi* (237), *Leptospira inadai*, Lachnospiraceae bacterium (MA2020), *Francisella novicida* (U112), Candidatus Methanoplasma *termitum*, or *Eubacterium eligens*, but the present invention is not limited thereto.

The present invention may provide an artificially manipulated neovascularization-associated factor, for example, an artificially manipulated VEGFA gene, HIF1A gene, ANGPT2 gene, EPAS1 gene, and/or ANGPTL4 gene, which is prepared by a''''') deletion of one or more nucleotides of a continuous 10 bp to 30 bp, for example, 15 bp to 26 bp, region in the base sequence adjacent to the 5' end and/or the 3' end of the 5'-TTN-3' sequence (N is A, T, C or G), b''''') substitution of one or more nucleotides of a continuous 10 bp to 30 bp, for example, 15 bp to 26 bp, region in the base sequence adjacent to the 5' end and/or 3' end of the 5'-TTN-3' sequence with nucleotides different from those of the wild-type gene, c''''') insertion of one or more nucleotides of a continuous 10 bp to 30 bp, for example, 15 bp to 26 bp, region in the base sequence adjacent to the 5' end and/or 3' end of the 5'-TTN-3' sequence, or d''''') a combination of two or more selected from a''''') through c''''') in the nucleic acid sequence of the neovascularization-associated factor.

In another exemplary embodiment, when the neovascularization-associated factor is a protein, the artificially manipulated protein includes all proteins involved in formation of new or modified blood vessels by a direct or indirect action of the gRNA-CRISPR enzyme complex.

For example, the artificially manipulated protein may be a protein expressed by a neovascularization-associated factor (gene) artificially manipulated by the gRNA-CRISPR enzyme complex or another protein increased or reduced by an influence by such protein activity, but the present invention is not limited thereto.

The artificially manipulated neovascularization-associated factor (protein) may have an amino acid composition and activity corresponding to the composition of the artificially manipulated neovascularization-associated factor (gene).

As an embodiment, an (i) artificially manipulated protein which is changed in expression characteristics may be provided.

For example, protein modification may have one or more characteristics:

a decrease or increase in expression level according to the deletion or insertion of one or more nucleotides in a continuous 1 bp to 50 bp, 1 bp to 40 bp, 1 bp to 30 bp, and preferably 3 bp to 25 bp region in the base sequence of the PAM sequence in the nucleic acid sequence of the neovascularization-associated factor or adjacent to the 5' end and/or the 3' end thereof;

a decrease or increase in expression level according to the substitution with one or more nucleotides different from those of a wild-type gene;

a decrease or increase in expression level, expression of a fusion protein or independent expression of a specific protein according to the insertion of one or more foreign nucleotides; and a decrease or increase in expression level of a third protein influenced by expression characteristics of the above-described proteins.

An (ii) artificially manipulated protein which is changed in structural characteristics may be provided.

For example, protein modification may have one or more characteristics:

a change in codons, amino acids and three-dimensional structure according to the deletion or insertion of one or more nucleotides in a continuous 1 bp to 50 bp, 1 bp to 40 bp, 1 bp to 30 bp, and preferably 3 bp to 25 bp region in the base sequence of the PAM sequence in the nucleic acid sequence of the neovascularization-associated factor or adjacent to the 5' end and/or the 3' end thereof;

a change in codons, amino acids, and three-dimensional structure thereby according to the substitution with one or more nucleotides different from a wild-type gene;

a change in codons, amino acids, and three-dimensional structure, or a fusion structure with a specific protein or independent structure from which a specific protein is separated according to the insertion of one or more foreign nucleotides; and a change in codons, amino acids, and three-dimensional structure of a third protein influenced by the above-described protein changed in structural characteristic.

An (iii) artificially manipulated protein changed in functional characteristics may be provided.

For example, protein modification may have one or more characteristics:

the activation or inactivation of a specific function or introduction of a new neovascularization function by protein modification caused by a deletion or insertion of one or more nucleotides in a continuous 1 bp to 50 bp, 1 bp to 40 bp, 1 bp to 30 bp, and preferably 3 bp to 25 bp region in the base sequence of the PAM sequence in the nucleic acid sequence of the neovascularization-associated factor or adjacent to the 5' end and/or the 3' end thereof;

the activation or inactivation of a specific function or introduction of a new function by protein modification caused by substitution with one or more nucleotides different from those of a wild-type gene;

the activation or inactivation of a specific function or introduction of a new function by protein modification caused by insertion of one or more foreign nucleotides, particularly, introduction of a third function to an existing function due to fusion or independent expression of a specific protein; and the change in the function of a third protein influenced by the above-described protein changed in functional characteristics.

In addition, a protein artificially manipulated by the chemical modification of one or more nucleotides in the nucleic acid sequence constituting the neovascularization-associated factor may be included.

For example, one or more of the expression, structural and functional characteristics of a protein caused by methylation, acetylation, phosphorylation, ubiquitination, ADP-ribosylation, myristylation and glycosylation may be changed.

For example, the third structure and function may be achieved by binding of a third protein into the nucleic acid sequence of the gene due to the chemical modification of nucleotides.

5. Other Additional Components

An additional component may be selectively added to increase the efficiency of a guide nucleic acid-editor protein complex or improve the repair efficiency of a damaged gene or nucleic acid.

The additional component may be selectively used to improve the efficiency of the guide nucleic acid-editor protein complex.

Activator

The additional component may be used as an activator to increase the cleavage efficiency of a target nucleic acid, gene or chromosome of the guide nucleic acid-editor protein complex.

The term "activator" refers to a nucleic acid serving to stabilize the bonding between the guide nucleic acid-editor protein complex and the target nucleic acid, gene or chromosome, or to allow the guide nucleic acid-editor protein complex to more easily approach the target nucleic acid, gene or chromosome.

The activator may be a double-stranded nucleic acid or single-stranded nucleic acid.

The activator may be linear or circular.

The activator may be divided into a "helper" that stabilizes the bonding between the guide nucleic acid-editor protein complex and the target nucleic acid, gene or chromosome, and an "escorter" that serves to allow the guide nucleic acid-editor protein complex to more easily approach the target nucleic acid, gene or chromosome.

The helper may increase the cleavage efficiency of the guide nucleic acid-editor protein complex with respect to the target nucleic acid, gene or chromosome.

For example, the helper includes a nucleic acid sequence having homology with the target nucleic acid, gene or chromosome. Therefore, when the guide nucleic acid-editor protein complex is bonded to the target nucleic acid, gene or chromosome, the homologous nucleic acid sequence included in the helper may form an additional complementary bond with the target nucleic acid, gene or chromosome to stabilize the bonding between the guide nucleic acid-editor protein complex and the target nucleic acid, gene or chromosome.

The escorter may increase the cleavage efficiency of the guide nucleic acid-editor protein complex with respect to the target nucleic acid, gene or chromosome.

For example, the escorter includes a nucleic acid sequence having homology with the target nucleic acid, gene or chromosome. Here, the homologous nucleic acid sequence included in the escorter may partly form a complementary bond with a guide nucleic acid of the guide nucleic acid-editor protein complex. Therefore, the escorter partly forming a complementary bond with the guide nucleic acid-editor protein complex may partly form a complementary bond with the target nucleic acid, gene or chromosome, and as a result, may allow the guide nucleic acid-editor protein complex to accurately approach the position of the target nucleic acid, gene or chromosome.

The homologous nucleic acid sequence may have at least 50%, 55%, 60%, 65%, 70%, 75%, 80%, 85%, 90% or 95% or more homology, or complete homology.

In addition, the additional component may be selectively used to improve the repair efficiency of the damaged gene or nucleic acid.

Assistor

The additional component may be used as an assistor to improve the repair efficiency of the damaged gene or nucleic acid.

The term "assistor" refers to a nucleic acid that serves to participate in a repair process or increase the repair efficiency of the damaged gene or nucleic acid, for example, the gene or nucleic acid cleaved by the guide nucleic acid-editor protein complex.

The assistor may be a double-stranded nucleic acid or single-stranded nucleic acid.

The assistor may be present in a linear or circular shape.

The assistor may be divided into an "NHEJ assistor" that participates in a repair process using NHEJ or improves repair efficiency and an "HDR assistor" that participates in a repair process using HDR or improves repair efficiency according to a repair method.

The NHEJ assistor may participate in a repair process or improve the repair efficiency of the damaged gene or nucleic acid using NHEJ.

For example, the NHEJ assistor may include a nucleic acid sequence having homology with a part of the damaged nucleic acid sequence. Here, the homologous nucleic acid sequence may include a nucleic acid sequence having homology with the nucleic acid sequence at one end (e.g., the 3' end) of the damaged nucleic acid sequence, and include a nucleic acid sequence having homology with the nucleic acid sequence at the other end (e.g., the 5' end) of the damaged nucleic acid sequence. In addition, a nucleic acid sequence having homology with each of the base sequences upstream and downstream of the damaged nucleic acid sequence may be included. The nucleic acid sequence having such homology may assist two parts of the damaged nucleic acid sequence to be placed in close proximity, thereby increasing the repair efficiency of the damaged nucleic acid by NHEJ.

The HDR assistor may participate in the repair process or improve repair efficiency of the damaged gene or nucleic acid using HDR.

For example, the HDR assistor may include a nucleic acid sequence having homology with a part of the damaged nucleic acid sequence. Here, the homologous nucleic acid sequence may include a nucleic acid sequence having homology with the nucleic acid sequence at one end (e.g., the 3' end) of the damaged nucleic acid sequence, and a nucleic acid sequence having homology with the nucleic acid sequence at the other end (e.g., the 5' end) of the damaged nucleic acid sequence. Alternatively, a nucleic acid sequence having homology with each of the base sequences upstream and downstream of the damaged nucleic acid sequence may be included. The nucleic acid sequence having such homology may serve as a template of the damaged nucleic acid sequence to increase the repair efficiency of the damaged nucleic acid by HDR.

In another example, the HDR assistor may include a nucleic acid sequence having homology with a part of the damaged nucleic acid sequence and a specific nucleic acid, for example, a nucleic acid or gene to be inserted. Here, the homologous nucleic acid sequence may include a nucleic acid sequence having homology with each of the base sequences upstream and downstream of the damaged nucleic acid sequence. The specific nucleic acid may be located between a nucleic acid sequence having homology with a base sequence downstream of the damaged nucleic acid and a nucleic acid sequence having homology with a base sequence upstream of the damaged nucleic acid. The nucleic acid sequence having such homology and specific nucleic acid may serve as a donor to insert a specific nucleic acid into the damaged nucleic acid, thereby increasing HDR efficiency for knockin.

The homologous nucleic acid sequence may have at least 50%, 55%, 60%, 65%, 70%, 75%, 80%, 85%, 90% or 95% or more homology or complete homology.

6. Subject

The term "subject" refers to an organism into which a guide nucleic acid, editor protein or guide nucleic acid-editor protein complex is introduced, an organism in which a guide nucleic acid, editor protein or guide nucleic acid-editor protein complex operates, or a specimen or sample obtained from the organism.

The subject may be an organism including a target nucleic acid, gene, chromosome or protein of the guide nucleic acid-editor protein complex.

The organism may be cells, tissue, a plant, an animal or a human.

The cells may be prokaryotic cells or eukaryotic cells.

The eukaryotic cells may be plant cells, animal cells or human cells, but the present invention is not limited thereto.

The tissue may be animal or human body tissue such as skin, liver, kidney, heart, lung, brain or muscle tissue.

The subject may be a specimen or sample including a target nucleic acid, gene, chromosome or protein of the guide nucleic acid-editor protein complex.

The specimen or sample may be obtained from an organism including a target nucleic acid, gene, chromosome or protein and may be saliva, blood, skin tissue, cancer cells or stem cells.

In the present invention, as a specific example, the subject may include a target gene or nucleic acid of the guide nucleic acid-editor protein complex.

Here, the target gene may be a neovascularization-associated factor, for example, a VEGFA gene, HIF1A gene, ANGPT2 gene, EPAS1 gene, and/or ANGPTL4 gene.

The target gene may be a wild type, or a modified form in the wild-type.

In one exemplary embodiment of the present invention, the subject may include a gene or nucleic acid manipulated by the guide nucleic acid-editor protein complex.

Here, the manipulated gene may be a neovascularization-associated factor, for example, a VEGFA gene, HIF1A gene, ANGPT2 gene, EPAS1 gene, and/or ANGPTL4 gene.

Here, the guide nucleic acid may target a neovascularization-associated factor, for example, a VEGFA gene, HIF1A gene, ANGPT2 gene, EPAS1 gene, and/or ANGPTL4 gene.

The guide nucleic acid may be a nucleic acid sequence complementary to a target sequence of the VEGFA gene, HIF1A gene, ANGPT2 gene, EPAS1 gene, and/or ANGPTL4 gene.

The guide nucleic acid may target one or more genes.

The guide nucleic acid may simultaneously target two or more genes. Here, the two or more genes may be homologous or heterologous genes.

The guide nucleic acid may target one or more target sequences.

The guide nucleic acid may be designed in various forms according to the number or locations of the target sequences.

In one exemplary embodiment of the present invention, the guide nucleic acid may be a nucleic acid sequence complementary to one or more target sequences of the sequences listed in Table 1, Table 2, Table 3, Table 4 and Table 5.

In a certain embodiment, for artificial manipulation of each gene, a guide nucleic acid sequence corresponding to any one of the target sequences of SEQ ID NOs: 1 to 79.

In a certain embodiment, for artificial manipulation of each gene, an editor protein that interacts with a guide nucleic acid sequence corresponding to, for example, forming a complex with any one of the target sequences of SEQ ID NOs: 1 to 1522, for example, SEQ ID NOs: 1 to 79, is provided.

In a certain embodiment, a nucleic acid modification product of each gene in which artificial manipulation occurs at a target sequence region of any one of SEQ ID NOs: 1 to 1522, for example, SEQ ID NOs: 1 to 79, and an expression product thereof are provided.

7. Delivery

The guide nucleic acid, editor protein or guide nucleic acid-editor protein complex may be delivered or introduced into a subject by various delivering methods and various forms.

The guide nucleic acid may be delivered or introduced into a subject in the form of DNA, RNA or a mixed form.

The editor protein may be delivered or introduced into a subject in the form of DNA, RNA, a DNA/RNA mixture, a peptide, a polypeptide, which encodes the editor protein, or a protein.

The guide nucleic acid-editor protein complex may be delivered or introduced into a target in the form of DNA, RNA or a mixture thereof, which encodes each component, that is, a guide nucleic acid or an editor protein.

The guide nucleic acid-editor protein complex may be delivered or introduced into a subject as a complex of a guide nucleic acid having a form of DNA, RNA or a mixture thereof and an editor protein having a form of a peptide, polypeptide or protein.

In addition, an additional component capable of increasing or inhibiting the efficiency of the guide nucleic acid-editor protein complex may be delivered or introduced into a subject by various delivering methods and in various forms.

The additional component may be delivered or introduced into a subject in the form of DNA, RNA, a DNA/RNA mixture, a peptide, a polypeptide or a protein.

i) Delivery in Form of DNA, RNA or Mixture Thereof

The form of DNA, RNA or a mixture thereof, which encodes the guide nucleic acid and/or editor protein may be delivered or introduced into a subject by a method known in the art.

Or, the form of DNA, RNA or a mixture thereof, which encodes the guide nucleic acid and/or editor protein may be delivered or introduced into a subject by a vector, a non-vector or a combination thereof.

The vector may be a viral or non-viral vector (e.g., a plasmid).

The non-vector may be naked DNA, a DNA complex or mRNA.

Vector-Based Introduction

The nucleic acid sequence encoding the guide nucleic acid and/or editor protein may be delivered or introduced into a subject by a vector.

The vector may include a nucleic acid sequence encoding a guide nucleic acid and/or editor protein.

For example, the vector may simultaneously include nucleic acid sequences, which encode the guide nucleic acid and the editor protein, respectively.

For example, the vector may include the nucleic acid sequence encoding the guide nucleic acid.

As an example, domains included in the guide nucleic acid may be contained all in one vector, or may be divided and then contained in different vectors.

For example, the vector may include the nucleic acid sequence encoding the editor protein.

In one example, in the case of the editor protein, the nucleic acid sequence encoding the editor protein may be contained in one vector, or may be divided and then contained in several vectors.

The vector may include one or more regulatory/control components.

Here, the regulatory/control components may include a promoter, an enhancer, an intron, a polyadenylation signal, a Kozak consensus sequence, an internal ribosome entry site (IRES), a splice acceptor and/or a 2A sequence.

The promoter may be a promoter recognized by RNA polymerase II.

The promoter may be a promoter recognized by RNA polymerase III.

The promoter may be an inducible promoter.

The promoter may be a subject-specific promoter.

The promoter may be a viral or non-viral promoter.

The promoter may use a suitable promoter according to a control region (that is, a nucleic acid sequence encoding a guide nucleic acid or editor protein).

For example, a promoter useful for the guide nucleic acid may be a H1, EF-1a, tRNA or U6 promoter. For example, a promoter useful for the editor protein may be a CMV, EF-1a, EFS, MSCV, PGK or CAG promoter.

The vector may be a viral vector or recombinant viral vector.

The virus may be a DNA virus or an RNA virus.

Here, the DNA virus may be a double-stranded DNA (dsDNA) virus or single-stranded DNA (ssDNA) virus.

Here, the RNA virus may be a single-stranded RNA (ssRNA) virus.

The virus may be a retrovirus, a lentivirus, an adenovirus, adeno-associated virus (AAV), vaccinia virus, a poxvirus or a herpes simplex virus, but the present invention is not limited thereto.

Generally, the virus may infect a host (e.g., cells), thereby introducing a nucleic acid encoding the genetic information of the virus into the host or inserting a nucleic acid encoding the genetic information into the host genome. The guide nucleic acid and/or editor protein may be introduced into a subject using a virus having such a characteristic. The guide nucleic acid and/or editor protein introduced using the virus may be temporarily expressed in the subject (e.g., cells). Alternatively, the guide nucleic acid and/or editor protein introduced using the virus may be continuously expressed in a subject (e.g., cells) for a long time (e.g., 1, 2 or 3 weeks, 1, 2, 3, 6 or 9 months, 1 or 2 years, or permanently).

The packaging capability of the virus may vary from at least 2 kb to 50 kb according to the type of virus. Depending on such a packaging capability, a viral vector including a guide nucleic acid or an editor protein or a viral vector including both of a guide nucleic acid and an editor protein may be designed. Alternatively, a viral vector including a guide nucleic acid, an editor protein and additional components may be designed.

In one example, a nucleic acid sequence encoding a guide nucleic acid and/or editor protein may be delivered or introduced by a recombinant lentivirus.

In another example, a nucleic acid sequence encoding a guide nucleic acid and/or editor protein may be delivered or introduced by a recombinant adenovirus.

In still another example, a nucleic acid sequence encoding a guide nucleic acid and/or editor protein may be delivered or introduced by recombinant AAV.

In yet another example, a nucleic acid sequence encoding a guide nucleic acid and/or editor protein may be delivered or introduced by a hybrid virus, for example, one or more hybrids of the virus listed herein.

Non-Vector-Based Introduction

A nucleic acid sequence encoding a guide nucleic acid and/or editor protein may be delivered or introduced into a subject using a non-vector.

The non-vector may include a nucleic acid sequence encoding a guide nucleic acid and/or editor protein.

The non-vector may be naked DNA, a DNA complex, mRNA, or a mixture thereof.

The non-vector may be delivered or introduced into a subject by electroporation, particle bombardment, sonoporation, magnetofection, transient cell compression or squeezing (e.g., described in the literature [Lee, et al, (2012) Nano Lett., 12, 6322-6327]), lipid-mediated transfection, a dendrimer, nanoparticles, calcium phosphate, silica, a silicate (Ormosil), or a combination thereof.

As an example, the delivery through electroporation may be performed by mixing cells and a nucleic acid sequence encoding a guide nucleic acid and/or editor protein in a cartridge, chamber or cuvette, and applying electrical stimuli with a predetermined duration and amplitude to the cells.

In another example, the non-vector may be delivered using nanoparticles. The nanoparticles may be inorganic nanoparticles (e.g., magnetic nanoparticles, silica, etc.) or organic nanoparticles (e.g., a polyethylene glycol (PEG)-coated lipid, etc.). The outer surface of the nanoparticles may be conjugated with a positively-charged polymer which is attachable (e.g., polyethyleneimine, polylysine, polyserine, etc.).

In a certain embodiment, the non-vector may be delivered using a lipid shell.

In a certain embodiment, the non-vector may be delivered using an exosome. The exosome is an endogenous nano-vesicle for transferring a protein and RNA, which can deliver RNA to the brain and another target organ.

In a certain embodiment, the non-vector may be delivered using a liposome. The liposome is a spherical vesicle structure which is composed of single or multiple lamellar lipid bilayers surrounding internal aqueous compartments and an external, lipophilic phospholipid bilayer which is relatively non-transparent. While the liposome may be made from several different types of lipids; phospholipids are most generally used to produce the liposome as a drug carrier.

Other additives may be included.

ii) Delivery in Form of Peptide, Polypeptide or Protein

An editor protein in the form of a peptide, polypeptide or protein may be delivered or introduced into a subject by a method known in the art The peptide, polypeptide or protein form may be delivered or introduced into a subject by electroporation, micro-injection, transient cell compression or squeezing (e.g., described in the literature [Lee, et al, (2012) Nano Lett., 12, 6322-6327]), lipid-mediated transfection, nanoparticles, a liposome, peptide-mediated delivery or a combination thereof.

The peptide, polypeptide or protein may be delivered with a nucleic acid sequence encoding a guide nucleic acid.

In one example, the transfer through electroporation may be performed by mixing cells into which the editor protein will be introduced with or without a guide nucleic acid in a cartridge, chamber or cuvette, and applying electrical stimuli with a predetermined duration and amplitude to the cells.

iii) Delivery in Form of Nucleic Acid-Protein Mixture

The guide nucleic acid and the editor protein may be delivered or introduced into a subject in the form of a guide nucleic acid-editor protein complex.

For example, the guide nucleic acid may be DNA, RNA or a mixture thereof. The editor protein may be a peptide, polypeptide or protein.

In one example, the guide nucleic acid and the editor protein may be delivered or introduced into a subject in the form of a guide nucleic acid-editor protein complex containing an RNA-type guide nucleic acid and a protein-type editor protein, that is, a ribonucleoprotein (RNP).

In the present invention, as an embodiment of a method for delivering the guide nucleic acid and/or editor protein into a subject, the delivery of gRNA, a CRISPR enzyme or a gRNA-CRISPR enzyme complex will be described below.

In an embodiment of the present invention, a nucleic acid sequence encoding the gRNA and/or CRISPR enzyme will be delivered or introduced into a subject using a vector.

The vector may include the nucleic acid sequence encoding the gRNA and/or CRISPR enzyme.

For example, the vector may simultaneously include the nucleic acid sequences encoding the gRNA and the CRISPR enzyme.

For example, the vector may include the nucleic acid sequence encoding the gRNA.

In one example, domains contained in the gRNA may be contained in one vector, or may be divided and then contained in different vectors.

For example, the vector may include the nucleic acid sequence encoding the CRISPR enzyme.

In one example, in the case of the CRISPR enzyme, the nucleic acid sequence encoding the CRISPR enzyme may be contained in one vector, or may be divided and then contained in several vectors.

The vector may include one or more regulatory/control components.

Here, the regulatory/control components may include a promoter, an enhancer, an intron, a polyadenylation signal, a Kozak consensus sequence, an internal ribosome entry site (IRES), a splice acceptor and/or a 2A sequence.

The promoter may be a promoter recognized by RNA polymerase II.

The promoter may be a promoter recognized by RNA polymerase Ill.

The promoter may be an inducible promoter.

The promoter may be a subject-specific promoter.

The promoter may be a viral or non-viral promoter.

The promoter may use a suitable promoter according to a control region (that is, a nucleic acid sequence encoding the gRNA and/or CRISPR enzyme).

For example, a promoter useful for the gRNA may be a H1, EF-1a, tRNA or U6 promoter. For example, a promoter useful for the CRISPR enzyme may be a CMV, EF-1a, EFS, MSCV, PGK or CAG promoter.

The vector may be a viral vector or recombinant viral vector.

The virus may be a DNA virus or an RNA virus.

Here, the DNA virus may be a double-stranded DNA (dsDNA) virus or single-stranded DNA (ssDNA) virus.

Here, the RNA virus may be a single-stranded RNA (ssRNA) virus.

The virus may be a retrovirus, a lentivirus, an adenovirus, adeno-associated virus (AAV), vaccinia virus, a poxvirus or a herpes simplex virus, but the present invention is not limited thereto.

Generally, the virus may infect a host (e.g., cells), thereby introducing a nucleic acid encoding the genetic information of the virus into the host or inserting a nucleic acid encoding the genetic information into the host genome. The gRNA and/or CRISPR enzyme may be introduced into a subject using a virus having such a characteristic. The gRNA and/or CRISPR enzyme introduced using the virus may be temporarily expressed in the subject (e.g., cells). Alternatively, the gRNA and/or CRISPR enzyme introduced using the virus may be continuously expressed in a subject (e.g., cells) for a long time (e.g., 1, 2 or 3 weeks, 1, 2, 3, 6 or 9 months, 1 or 2 years, or permanently).

The packaging capability of the virus may vary from at least 2 kb to 50 kb according to the type of virus. Depending on such a packaging capability, a viral vector only including gRNA or a CRISPR enzyme or a viral vector including both of gRNA and a CRISPR enzyme may be designed. Alternatively, a viral vector including gRNA, a CRISPR enzyme and additional components may be designed.

In one example, a nucleic acid sequence encoding gRNA and/or a CRISPR enzyme may be delivered or introduced by a recombinant lentivirus.

In another example, a nucleic acid sequence encoding gRNA and/or a CRISPR enzyme may be delivered or introduced by a recombinant adenovirus.

In still another example, a nucleic acid sequence encoding gRNA and/or a CRISPR enzyme may be delivered or introduced by recombinant AAV.

In yet another example, a nucleic acid sequence encoding gRNA and/or a CRISPR enzyme may be delivered or introduced by one or more hybrids of hybrid viruses, for example, the viruses described herein.

In one exemplary embodiment of the present invention, the gRNA-CRISPR enzyme complex may be delivered or introduced into a subject.

For example, the gRNA may be present in the form of DNA, RNA or a mixture thereof. The CRISPR enzyme may be present in the form of a peptide, polypeptide or protein.

In one example, the gRNA and CRISPR enzyme may be delivered or introduced into a subject in the form of a gRNA-CRISPR enzyme complex including RNA-type gRNA and a protein-type CRISPR, that is, a ribonucleoprotein (RNP).

The gRNA-CRISPR enzyme complex may be delivered or introduced into a subject by electroporation, microinjection, transient cell compression or squeezing (e.g., described in the literature [Lee, et al, (2012) Nano Lett., 12, 6322-6327]), lipid-mediated transfection, nanoparticles, a liposome, peptide-mediated delivery or a combination thereof.

8. Transformant

The term "transformant" refers to an organism into which a guide nucleic acid, editor protein or guide nucleic acid-editor protein complex is introduced, an organism in which a guide nucleic acid, editor protein or guide nucleic acid-editor protein complex is expressed, or a specimen or sample obtained from the organism.

The transformant may be an organism into which a guide nucleic acid, editor protein or guide nucleic acid-editor protein complex is introduced in the form of DNA, RNA or a mixture thereof.

For example, the transformant may be an organism into which a vector including a nucleic acid sequence encoding a guide nucleic acid and/or editor protein is introduced. Here, the vector may be a non-viral vector, viral vector or recombinant viral vector.

In another example, the transformant may be an organism into which a nucleic acid sequence encoding a guide nucleic acid and/or editor protein is introduced in a non-vector form. Here, the non-vector may be naked DNA, a DNA complex, mRNA or a mixture thereof.

The transformant may be an organism into which a guide nucleic acid, editor protein or guide nucleic acid-editor protein complex is introduced in the form of a peptide, polypeptide or protein.

The transformant may be an organism into which a guide nucleic acid, editor protein or guide nucleic acid-editor protein complex is introduced in the form of DNA, RNA, a peptide, a polypeptide, a protein or a mixture thereof.

For example, the transformant may be an organism into which a guide nucleic acid-editor protein complex including an RNA-type guide nucleic acid and a protein-type editor protein is introduced.

The transformant may be an organism including a target nucleic acid, gene, chromosome or protein of the guide nucleic acid-editor protein complex.

The organism may be cells, tissue, a plant, an animal or a human.

The cells may be prokaryotic cells or eukaryotic cells.

The eukaryotic cells may be plant cells, animal cells, or human cells, but the present invention is not limited thereto.

The tissue may be an animal or human body tissue such as skin, liver, kidney, heart, lung, brain, or muscle tissue.

The transformant may be an organism in(to) to which a guide nucleic acid, editor protein or guide nucleic acid-editor protein complex is introduced or expressed, or a specimen or sample obtained from the organism.

The specimen or sample may be saliva, blood, skin tissue, cancer cells or stem cells.

Use

One exemplary embodiment of the present invention relates to a use of treating a neovascularization-associated disease using a method of administering a composition for artificially manipulating a neovascularization-associated factor or an artificially manipulated neovascularization-associated factor to a subject.

Targets for the treatment may be mammals including primates such as a human or a monkey, rodents such as a mouse or a rat, etc.

Diseases to be Treated

In an embodiment, diseases to be treated may be neovascularization-associated diseases.

The term "neovascularization-associated diseases" refer to all states including excessive and/or abnormal neovascularization. The neovascularization-associated diseases refer to disorders characterized by vascularization which is not changed or regulated, except tumorigenesis or neoplastic transformation, that is, cancer. The neovascularization-associated diseases include an ocular neovascularization disease.

Neovascular diseases include neovascularization-dependent cancer, for example, solid tumors, hematomas such as leukemia and tumor metastasis; benign tumors such as hemangiomas, acoustic neuromas, neurofibroma, trachomas and pyogenic granulomas; rheumatoid arthritis; psoriasis; ocular neovascularization diseases such as diabetic retinopathy, retinopathy of prematurity, macular degenerations including dry age-related macular degeneration and wet age-related macular degeneration, corneal graft rejection, neovascular glaucoma, retrolental fibroplasia, rubeosis; Osler-Webber Syndrome; myocardial neovascularization blindness; plaque neovascularization; telangiectasia; hemophiliac joint; angiofibromas; and wound granulation, but the present invention is not limited thereto.

In a certain embodiment, the neovascularization-associated diseases may be one or more diseases selected from the group consisting of rheumatoid arthritis, psoriasis, Osler-Webber Syndrome, myocardial neovascularization blindness, plaque neovascularization, telangiectasia, hemophiliac joint, angiofibromas, and wound granulation.

In an embodiment, the neovascularization-associated disease may be a disease including excessive and/or abnormal neovascularization.

In an embodiment, the neovascularization-associated disease may be neovascularization-dependent cancer.

Here, the neovascularization-dependent cancer includes solid tumors, hematologic tumors such as leukemia and tumor metastasis.

The neovascularization-dependent cancer may be, for example, solid tumors, hematologic tumors such as leukemia and tumor metastasis; benign tumors such as hemangiomas, acoustic neuromas, neurofibromas, trachomas and pyogenic granulomas.

In a certain embodiment, the neovascularization-associated disease may be a benign tumor.

The benign tumor may include hemangiomas, acoustic neuromas, trachomas and pyogenic granulomas.

In a certain embodiment, the neovascularization-associated disease may be an ocular neovascularization disease.

The term "ocular neovascularization disease" refers to all ocular diseases including excessive and/or abnormal neovascularization. The ocular neovascularization disease includes a disorder characterized by vascularization that is not changed or regulated in the eyes.

As an example, the ocular neovascularization diseases may include: ischemic retinopathy, optic papillary neovascularization, iris neovascularization, retinal neovascularization, choroidal neovascularization, corneal neovascularization, vitreous neovascularization, glaucoma, panus, pterygiums, macular edemas, diabetic retinopathy, proliferative diabetic retinopathy, diabetic macular edemas, vascular retinopathy, retinal degeneration, uveitis, inflammatory diseases of the retina, and proliferative vitreoretinopathy.

In one exemplary embodiment, the ocular neovascularization disease may be diabetic retinopathy or macular degeneration.

Diabetic Retinopathy

Diabetic retinopathy is a diabetic complication occurring in approximately 40 to 45% of the patients diagnosed with any one of Type 1 diabetes or Type 2 diabetes.

Diabetic retinopathy usually affects both eyes, and generally progresses in four stages. The first stage, that is, mild nonproliferative retinopathy is characterized by ocular microaneurysms. Small scaled swelling occurs in a retinal capillary tube and a small vessel. In the second stage, that is, moderate nonproliferative retinopathy, a blood vessel provided to the retina starts to be blocked. In the third stage, that is, severe nonproliferative retinopathy, the occlusion leads to a decrease in blood supply to the retina, and the retina sends a neovascularization signal to the eye in order to provide blood supply to the retina. In the fourth stage, that is, proliferative retinopathy, which is the most advanced stage, angiogenesis occurs, but the new blood vessel is abnormal, weak, and grows on the surface of a vitreous gel contained in the retina and the eyes.

The diabetic retinopathy includes insulin-dependent diabetes, insulin-independent diabetes, retinal detachment, diabetic retinopathy, and vitreous hemorrhage.

Macular Degeneration

The macular degeneration refers to a disease in which visual impairment is caused by macular degeneration, and is also called age-related macular degeneration (AMD).

The AMD includes early, intermediate and advanced AMD, and also includes all of dry AMD, for example, geographic atrophy, and wet AMD which is also known as neovascular or exudative AMD.

Dry macular degeneration is a prevalent type accounting for approximately 90% of the AMDs when a lesion such as a druse (the state in which waste is accumulated in the macula) or retinal pigment epithelial atrophy is generated in the retina. Wet macular degeneration is characterized by production of choroidal neovascularization under the retina.

Dry macular degeneration includes macular degeneration caused by a missense mutation in an immunoregulatory complement factor H (CFH) gene.

In another exemplary embodiment, a use of a system for regulating an additional, third in vivo mechanism, accompanied with various functions of specific factors artificially modified in function (e.g., a gene known as a neovascularization-associated factor, etc.) may be provided.

For example, the specific factors artificially modified in function may be one or more genes of a VEGFA gene, an HIF1A gene, an ANGPT2 gene, an EPAS1 gene and an ANGPTL4 gene.

The third mechanism may be an in vivo mechanism in which the genes are involved, other than neovascularization.

Pharmaceutical Composition

One exemplary embodiment of the present invention relates to a composition to be used in treatment of a disease using an artificially manipulated neovascularization-associated factor.

The composition may include an artificially manipulated neovascularization-associated factor or a manipulation composition capable of artificially manipulating the neovascularization-associated factor. The composition may be referred to as a therapeutic composition or pharmaceutical composition.

In an exemplary embodiment, the composition may include an artificially manipulated neovascularization-associated factor, that is, a gene and/or protein.

In an exemplary embodiment, the composition may include a manipulation composition capable of artificially manipulating a neovascularization-associated factor.

The manipulation composition may include a guide nucleic acid-editor protein complex.

The manipulation composition may include a guide nucleic acid and/or editor protein.

The manipulation composition may include a nucleic acid encoding the guide nucleic acid and/or editor protein.

The manipulation composition may include a virus comprising a nucleic acid encoding the guide nucleic acid and/or editor protein.

In another exemplary embodiment, the composition may further include an additional element.

The additional element may include a suitable carrier for delivery into the body of a subject.

In one exemplary embodiment, the composition may include an expression product of a neovascularization-associated factor manipulated in a sufficient amount to suppress an angiovascular disorder.

The "sufficient amount to suppress an angiovascular disorder" refers to an effective amount necessary to treat or prevent an angiovascular disorder or a symptom thereof.

In one exemplary embodiment, the following therapeutic compositions will be provided:

a composition for treating an angiovascular disorder, which includes a guide nucleic acid capable of forming a complementary bond with each of one or more target sequences in nucleic acid sequences of one or more genes selected from the group consisting of a VEGFA gene, an HIF1A gene, an ANGPT2 gene, an EPAS1 gene and an ANGPTL4 gene, or a nucleic acid sequence encoding the same, and an editor protein or a nucleic acid sequence encoding the same;

a composition for treating an angiovascular disorder, which includes a guide nucleic acid capable of forming a complementary bond with each of the target sequences of SEQ ID NOs: 1 to 1522, for example, SEQ ID NOs: 1 to 79, of nucleic acid sequences of one or more genes selected from the group consisting of a VEGFA gene, an HIF1A gene, an ANGPT2 gene, an EPAS1 gene and an ANGPTL4 gene, or a nucleic acid sequence encoding the same, and an editor protein or a nucleic acid sequence encoding the same; and a composition for treating an angiovascular disorder, which includes a complex formed of a guide nucleic acid capable of forming a complementary bond with each of the target sequences of SEQ ID NOs: 1 to 1522, for example, SEQ ID NOs: 1 to 79, of nucleic acid sequences of one or more genes selected from the group consisting of a VEGFA gene, an HIF1A gene, an ANGPT2 gene, an EPAS1 gene and an ANGPTL4 gene or a nucleic acid sequence encoding the same; and an editor protein.

Here, the guide nucleic acid or nucleic acid sequence encoding the same; and a nucleic acid sequence encoding the editor protein may be present in the form of one or more vectors. The guide nucleic acid or nucleic acid sequence encoding the same; and a nucleic acid sequence encoding the editor protein may be present in the form of homologous or heterologous vectors.

Treatment Method

In another exemplary embodiment of the present invention, a method for treating a disease in a patient, which includes producing the above-described composition and administering an effective amount of the composition to a patient requiring the same, is provided.

Gene Manipulating Treatment

A treatment method for regulating neovascularization by manipulating a gene of a living organism may be used. Such a treatment method may be achieved by directly injecting a composition for manipulating a gene to manipulate the gene of a living organism into the organism.

The composition for gene manipulation may include a guide nucleic acid-editor protein complex.

The composition for gene manipulation may be injected into a specific location of the body.

Here, the specific location of the body may be tissue in which neovascularization excessively and/or abnormally occurs, or a location close thereto. For example, the specific location of the body may be, for example, the eyeball.

Subjects for administration of the composition may be mammals including primates such as a human or a monkey, rodents such as a mouse or a rat, etc.

The composition may be administered by any convenient method such as injection, transfusion, implantation or transplantation. The composition may be administered subcutaneously, intradermally, intraocularly, intravitreally, intratumorally, intranodally, intramedullarily, intramuscularly, intravenously, intralymphatically, or intraperitoneally.

A dose (pharmaceutically effective amount to obtain a predetermined, desired effect) of the composition may be selected from all integers in the value ranges of 104-109 cells, for example, 105 to 106 cells/kg (body weight), per kg of the subject of administration, but the present invention is not limited thereto. The composition may be suitably prescribed in consideration of the age, health condition and body weight of the subject of administration, the types of treatments simultaneously received, if they were, frequency of the co-treatments, and characteristics of a desired effect.

In one aspect, the present invention provides a method for modifying a target polynucleotide in prokaryotic cells, which may be achieved in vivo, ex vivo, or in vitro.

In some embodiments, the method may include sampling cells or a cell population from a human or non-human animal, and modifying the cell or cells. Culturing may occur at any step ex vivo. The cell or cells may also be reintroduced into a non-human animal or plant. The reintroduced cells are most preferably stem cells.

In still another exemplary embodiment, the present invention may provide a method for artificially manipulating cells, which includes: introducing (a) a guide nucleic acid capable of forming a complementary bond with the target sequences of SEQ ID NOs: 1 to 1522, for example, SEQ ID NOs: 1 to 79, of nucleic acid sequences of one or more genes selected from the group consisting of a VEGFA gene, an HIF1A gene, an ANGPT2 gene, an EPAS1 gene and an ANGPTL4 gene or a nucleic acid sequence encoding the same; and (b) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Streptococcus aureus*-derived Cas9 protein, a *Neisseria meningitidis*-derived Cas9 protein, and a Cpf1 protein, or a nucleic acid sequence encoding the same to cells.

The guide nucleic acid and the editor protein may be present in one or more vectors in the form of a nucleic acid sequence, or in a complex of a combination of the guide nucleic acid and the editor protein.

The introduction step may be carried out in vivo or ex vivo.

A technique of the above-described "7. Delivery" section may be referenced before the introduction step.

For example, the introduction stage may be achieved by one or more methods selected from electroporation, liposomes, plasmids, viral vectors, nanoparticles, and a protein translocation domain (PTD) fusion protein method.

For example, the viral vector may be one or more selected from the group consisting of a retrovirus, a lentivirus, an adenovirus, adeno-associated virus (AAV), vaccinia virus, a poxvirus and a herpes simplex virus.

When a neovascularization-associated factor is artificially manipulated using the method and composition of some embodiments of the present invention, it is possible to regulate, for example, inhibit, suppress, stimulate and/or increase neovascularization, and therefore an effect of suppressing or improving excessive and/or abnormal neovascularization may be obtained.

Additional Uses

In a certain embodiment, the present invention may provide a kit for preparing a composition for treating AMD or diabetic retinopathy.

The kit may be prepared by a conventional preparation method known in the art.

The kit may further include a detectable label. The term "detectable label" refers to an atom or molecule for specifically detecting a molecule containing a label among the same type of molecules without a label. The detectable label may be attached to an antibody specifically binding to a protein or a fragment thereof, an interaction protein, a ligand, nanoparticles, or an aptamer. The detectable label may include a radionuclide, a fluorophore, and an enzyme.

In a certain embodiment, the present invention may provide a method for screening a material capable of regulating the expression level of one or more genes of an artificially manipulated VEGFA gene, HIF1A gene, ANGPT2 gene, EPAS1 gene and ANGPTL4 gene.

In a certain embodiment, the present invention may provide a method for providing information on the sequence of a target site which is able to be artificially manipulated in a subject by analyzing the sequences of one or more genes selected from the group consisting of a VEGFA gene, an HIF1A gene, an ANGPT2 gene, an EPAS1 gene and an ANGPTL4 gene.

In addition, a method for constructing a library using the information provided by such a method.

Here, a known database may be used.

In specific embodiments, an animal or cells which can be used for research using the method of the present invention may be provided.

An animal or cells which includes chromosome editing in one or more nucleic acid sequences associated with a disease may be prepared using the above-described method. Such a nucleic acid sequence may be a reference sequence which may encode a disease-associated protein sequence or may be associated with a disease.

In one exemplary embodiment, an effect of mutation and occurrence and/or progression of a disease may be studied in an animal or cells using measurements conventionally used in disease research with the animal or cells prepared by the method of the present invention. Alternatively, a pharmaceutical effect of an active compound in a disease using such an animal or cells may be studied.

In another exemplary embodiment, the effect of the strategy of a possible gene therapy may be evaluated using the animal or cells prepared by the method of the present invention. That is, the development and/or progression of a corresponding disease may be suppressed or reduced by modifying a chromosome sequence encoding a disease-associated protein. Particularly, this method includes forming a modified protein by editing a chromosome sequence encoding a disease-associated protein, resulting in the achievement of a modified response of the animal or cells. Therefore, in some embodiments, a genetically-modified animal may be compared with an animal vulnerable to the development of a corresponding disease, thereby evaluating the effect of a gene therapy process.

Such uses may include a disease model, a pharmacological model, a developmental model, a cell function model, and a humanized model. For example, a neovascularization-associated disease model, a pharmacological model, a developmental model, a cell function model, and a humanized model may be included.

An artificially manipulated neovascularization-associated factor and a neovascularization system artificially modified in function thereby can be effectively used to treat a neovascularization-associated disease, for example, a neovascularization-associated ocular disease (eye disease). The efficiency of a neovascularization system may be improved by regulating various in vivo mechanisms in which various neovascularization-associated factors are involved.

Hereinafter, the present invention will be described in further detail with reference to examples.

The examples are merely provided to describe the present invention in further detail, and it might be obvious to those of ordinary skill in the art that the scope of the present invention is not limited to the following examples.

Experimental Methods

1. Design of sgRNA

CRISPR/Cas9 target regions of human VEGFA gene (NCBI Accession No. NM_001025366.2), HIF1A gene (NCBI Accession No. NM_001243084.1), ANGPT2 gene (NCBI Accession No. NM_001118887.1), EPAS1 gene (NCBI Accession No. NM_001430.4) and ANGPTL4 gene (NCBI Accession No. NM_001039667.2) were selected using CRISPR RGEN Tools (Institute for Basic Science, Korea). The target regions of the genes may be different according to the type of CRISPR enzyme. Target sequences of the genes for CjCas9 are summarized in Tables 1 to 5 and Tables 6 to 9 listed above, and target sequences of the genes for SpCas9 are summarized in Tables 10 to 14.

TABLE 6

Target sequences of VEGFA gene

| Gene | No. | Target sequence |
|---|---|---|
| VEGFA | 1 | AAATCCCGGTATAAGTCCTGGA (SEQ ID NO: 80) |
| VEGFA | 2 | GCACCAACGTACACGCTCCAGG (SEQ ID NO: 81) |
| VEGFA | 3 | CATTAGACAGCAGCGGGCACCA (SEQ ID NO: 82) |
| VEGFA | 4 | GGCATTAGACAGCAGCGGGCAC (SEQ ID NO: 83) |
| VEGFA | 5 | GGCTCCAGGGCATTAGACAGCA (SEQ ID NO: 84) |
| VEGFA | 6 | GCTCAGAGCGGAGAAAGCATTT (SEQ ID NO: 85) |
| VEGFA | 7 | GGAACATTTACACGTCTGCGGA (SEQ ID NO: 86) |
| VEGFA | 8 | GCAGACGTGTAAATGTTCCTGC (SEQ ID NO: 87) |

TABLE 6-continued

Target sequences of VEGFA gene

| Gene | No. | Target sequence |
|---|---|---|
| VEGFA | 9 | GAGTCTGTGTTTTTGCAGGAAC (SEQ ID NO: 88) |
| VEGFA | 10 | GGCGAGGCAGCTTGAGTTAAAC (SEQ ID NO: 89) |

TABLE 7

Target sequences of HIF1A gene

| Gene | No. | Target sequence |
|---|---|---|
| HIF1A | 1 | ACTAAAGGACAAGTCACCACAG (SEQ ID NO: 90) |
| HIF1A | 2 | TATCCACCTCTTTTGGCAAGCA (SEQ ID NO: 91) |
| HIF1A | 3 | TGAAACTCAAGCAACTGTCATA (SEQ ID NO: 92) |
| HIF1A | 4 | CTCACAACGTAATTCACACATA (SEQ ID NO: 93) |
| HIF1A | 5 | TACTTACCTCACAACGTAATTC (SEQ ID NO: 94) |
| HIF1A | 6 | AACTTACTTACCTCACAACGTA (SEQ ID NO: 95) |
| HIF1A | 7 | TCTTGTTTTGACAGTGGTATTA (SEQ ID NO: 96) |
| HIF1A | 8 | GGGAGAAAATCAAGTCGTGCTG (SEQ ID NO: 97) |
| HIF1A | 9 | TATCTGAAGATTCAACCGGTTT (SEQ ID NO: 98) |
| HIF1A | 10 | GCTATTCACCAAAGTTGAATCA (SEQ ID NO: 99) |
| HIF1A | 11 | AACTTTGCTGGCCCCAGCCGCT (SEQ ID NO: 100) |
| HIF1A | 12 | AAACTGATGACCAGCAACTTGA (SEQ ID NO: 101) |
| HIF1A | 13 | GGGGAGCATTACATCATTATAT (SEQ ID NO: 102) |
| HIF1A | 14 | AGCCACTTCGAAGTAGTGCTGA (SEQ ID NO: 103) |
| HIF1A | 15 | CAACTTCTTGATTGAGTGCAGG (SEQ ID NO: 104) |
| HIF1A | 16 | TTACCATGCCCCAGATTCAGGA (SEQ ID NO: 105) |
| HIF1A | 17 | TCAGACACCTAGTCCTTCCGAT (SEQ ID NO: 106) |
| HIF1A | 18 | ATTGGTAGAAAAACTTTTTGCT (SEQ ID NO: 107) |
| HIF1A | 19 | AACTCATGTATTTGCTGTTTTA (SEQ ID NO: 108) |
| HIF1A | 20 | AAGCCCTGAAAGCGCAAGTCCT (SEQ ID NO: 109) |
| HIF1A | 21 | CAGTTACAGTATTCCAGCAGAC (SEQ ID NO: 110) |
| HIF1A | 22 | AGGTTCTTGTATTTGAGTCTGC (SEQ ID NO: 111) |
| HIF1A | 23 | ATGCAATCAATATTTTAATGTC (SEQ ID NO: 112) |
| HIF1A | 24 | TGATTGCATCTCCATCTCCTAC (SEQ ID NO: 113) |
| HIF1A | 25 | TAGTGCCACATCATCACCATAT (SEQ ID NO: 114) |
| HIF1A | 26 | GAGTATCTCTATATGGTGATGA (SEQ ID NO: 115) |
| HIF1A | 27 | ATACCTTTGACTCAAAGCGACA (SEQ ID NO: 116) |
| HIF1A | 28 | TTCCTGAGGAAGAACTAAATCC (SEQ ID NO: 117) |
| HIF1A | 29 | TCTGTTCACTAGATTTGCATCC (SEQ ID NO: 118) |
| HIF1A | 30 | GAATGGAGCAAAAGACAATTAT (SEQ ID NO: 119) |
| HIF1A | 31 | GTTATGATTGTGAAGTTAATGC (SEQ ID NO: 120) |

TABLE 8

Target sequences of EPAS1 gene

| Gene | No. | Target sequence |
|---|---|---|
| EPAS1 | 1 | AACACCTCCGTCTCCTTGCTCC (SEQ ID NO: 121) |
| EPAS1 | 2 | TGGAGGCCTTGTCCAGATGGGA (SEQ ID NO: 122) |
| EPAS1 | 3 | TGCGACTGGCAATCAGCTTCCT (SEQ ID NO: 123) |
| EPAS1 | 4 | CGACTGGCAATCAGCTTCCTGC (SEQ ID NO: 124) |
| EPAS1 | 5 | GAAGCTGACCAGCAGATGGACA (SEQ ID NO: 125) |
| EPAS1 | 6 | GCAATGAAACCCTCCAAGGCTT (SEQ ID NO: 126) |
| EPAS1 | 7 | AAAACATCAGCAAGTTCATGGG (SEQ ID NO: 127) |
| EPAS1 | 8 | GCAAGTTCATGGGACTTACACA (SEQ ID NO: 128) |
| EPAS1 | 9 | GGTCGCAGGGATGAGTGAAGTC (SEQ ID NO: 129) |
| EPAS1 | 10 | GCGGGACTTCTTCATGAGGATG (SEQ ID NO: 130) |
| EPAS1 | 11 | GAAGTGCACGGTCACCAACAGA (SEQ ID NO: 131) |
| EPAS1 | 12 | ACAGTACGGCCTCTGTTGGTGA (SEQ ID NO: 132) |
| EPAS1 | 13 | TCCAGGTGGCTGACTTGAGGTT (SEQ ID NO: 133) |
| EPAS1 | 14 | TCCACGCCTGTCTCAGGTCTTG (SEQ ID NO: 134) |
| EPAS1 | 15 | CAGGACAGCAGGGGCTCCTTGT (SEQ ID NO: 135) |
| EPAS1 | 16 | CTCATCATCATGTGTGAACCAA (SEQ ID NO: 136) |
| EPAS1 | 17 | ATGTGGGATGGGTGCTGGATTG (SEQ ID NO: 137) |
| EPAS1 | 18 | GCCACTTACTACCTGACCCTTG (SEQ ID NO: 138) |
| EPAS1 | 19 | TGGCCACTTACTACCTGACCCT (SEQ ID NO: 139) |
| EPAS1 | 20 | ACCAAGGGTCAGGTAGTAAGTG (SEQ ID NO: 140) |
| EPAS1 | 21 | TAGCCCCCATGCTTTGCGAGCA (SEQ ID NO: 141) |
| EPAS1 | 22 | GATGACCGTCCCCTGGGTCTCC (SEQ ID NO: 142) |
| EPAS1 | 23 | CTCAGGACGTAGTTGACACACA (SEQ ID NO: 143) |
| EPAS1 | 24 | CATGCTTACCTCAGGACGTAGT (SEQ ID NO: 144) |
| EPAS1 | 25 | CACATGCTTACCTCAGGACGTA (SEQ ID NO: 145) |
| EPAS1 | 26 | CAGGGATTCAGTCTGGTCCATG (SEQ ID NO: 146) |
| EPAS1 | 27 | GGTGAATAGGAAGTTACTCTTC (SEQ ID NO: 147) |
| EPAS1 | 28 | ATGGGCCACGGAGTTGAGGAGC (SEQ ID NO: 148) |
| EPAS1 | 29 | CTAGCCCAATAGCCCTGAAGAC (SEQ ID NO: 149) |
| EPAS1 | 30 | AGTGATTGAGAAGCTCTTCGCC (SEQ ID NO: 150) |
| EPAS1 | 31 | GGACACAGAGGCCAAGGACCAA (SEQ ID NO: 151) |
| EPAS1 | 32 | CCTGATCTCCACAGCCATCTAC (SEQ ID NO: 152) |
| EPAS1 | 33 | CGGATTTCAATGAGCTGGACTT (SEQ ID NO: 153) |
| EPAS1 | 34 | TCAATGAGCTGGACTTGGAGAC (SEQ ID NO: 154) |
| EPAS1 | 35 | GCGGAGAACCCACAGTCCACCC (SEQ ID NO: 155) |
| EPAS1 | 36 | CCAGTGGCTGGAAGATGTTTGT (SEQ ID NO: 156) |
| EPAS1 | 37 | TTCCAGCCACTGGCCCCTGTAG (SEQ ID NO: 157) |
| EPAS1 | 38 | CTGGAGAGCAAGAAGACAGAGC (SEQ ID NO: 158) |

TABLE 8-continued

Target sequences of EPAS1 gene

| Gene | No. | Target sequence |
|---|---|---|
| EPAS1 | 39 | GAGAGAGGGGTGCTGGCCTGGC (SEQ ID NO: 159) |
| EPAS1 | 40 | CCTGCCACCGTGCTGTGGCCAG (SEQ ID NO: 160) |
| EPAS1 | 41 | TCTCTCTTCCATGGGGGGCAGA (SEQ ID NO: 161) |
| EPAS1 | 42 | CACAAAGTGGGCCGTCGGGGAT (SEQ ID NO: 162) |
| EPAS1 | 43 | GGAGAGGGCTACCATGGCCGGA (SEQ ID NO: 163) |
| EPAS1 | 44 | CTCAGGTCCTGGAAGGCTTGCT (SEQ ID NO: 164) |
| EPAS1 | 45 | CTCCCAGGGGGACCCACCTGGT (SEQ ID NO: 165) |
| EPAS1 | 46 | TGCCGGACAAGCCACTGAGCGC (SEQ ID NO: 166) |
| EPAS1 | 47 | TTCCCCCCACAGTGCTACGCCA (SEQ ID NO: 167) |
| EPAS1 | 48 | CTGTAGTCCTGGTACTGGGTGG (SEQ ID NO: 168) |
| EPAS1 | 49 | TGGGCTGACGACAGGCTGTAGT (SEQ ID NO: 169) |
| EPAS1 | 50 | TCCTTGCAGGAGCGTGGAGCTT (SEQ ID NO: 170) |

TABLE 9

Target sequences of ANGPT2 gene

| Gene | No. | Target sequence |
|---|---|---|
| ANGPT2 | 1 | GACTGTGCTGAAGTATTCAAAT (SEQ ID NO: 171) |
| ANGPT2 | 2 | CTGTGCTGAAGTATTCAAATCA (SEQ ID NO: 172) |
| ANGPT2 | 3 | TGGTGTGTCCTGATTTGAATAC (SEQ ID NO: 173) |
| ANGPT2 | 4 | GCCATTCGTGGTGTGTCCTGAT (SEQ ID NO: 174) |
| ANGPT2 | 5 | ATCAGGACACACCACGAATGGC (SEQ ID NO: 175) |
| ANGPT2 | 6 | CTAATCAGCAACGCTATGTGCT (SEQ ID NO: 176) |
| ANGPT2 | 7 | AATCAGCAACGCTATGTGCTTA (SEQ ID NO: 177) |
| ANGPT2 | 8 | TTCCCAGTCTTTAAGGTGTATT (SEQ ID NO: 178) |
| ANGPT2 | 9 | TCTTCACTTGAGAGATAGAAAT (SEQ ID NO: 179) |
| ANGPT2 | 10 | CATCAGCCAACCAGGAAATGAT (SEQ ID NO: 180) |
| ANGPT2 | 11 | CTGTTAGCATTTGTGAACATTT (SEQ ID NO: 181) |
| ANGPT2 | 12 | TGTGGTCCTTCCAACTTGAACG (SEQ ID NO: 182) |
| ANGPT2 | 13 | CGGAATGTACTATCCACAGAGG (SEQ ID NO: 183) |
| ANGPT2 | 14 | TTATTTGTGTTCTGCCTCTGTG (SEQ ID NO: 184) |
| ANGPT2 | 15 | ACAAATAAGTTCAACGGCATTA (SEQ ID NO: 185) |
| ANGPT2 | 16 | AGCGAATAGCCTGAGCCTTTCC (SEQ ID NO: 186) |

TABLE 10

Target sequences of VEGFA gene for SpCas9

| Gene | No. | Target sequence |
|---|---|---|
| VEGFA-Sp1 | 1 | CAGCTGACCAGTCGCGCTGA (SEQ ID NO: 187) |
| VEGFA-Sp2 | 2 | GTGGTAGCTGGGGCTGGGGG (SEQ ID NO: 188) |
| VEGFA-Sp3 | 3 | GAGGTGGTAGCTGGGGCTGG (SEQ ID NO: 189) |
| VEGFA-Sp4 | 4 | GGAGGTGGTAGCTGGGGCTG (SEQ ID NO: 190) |
| VEGFA-Sp5 | 5 | AGGAGGTGGTAGCTGGGGCT (SEQ ID NO: 191) |
| VEGFA-Sp6 | 6 | GAGGAGGTGGTAGCTGGGGC (SEQ ID NO: 192) |
| VEGFA-Sp7 | 7 | CGGGGAGGAGGTGGTAGCTG (SEQ ID NO: 193) |
| VEGFA-Sp8 | 8 | CCCAGCTACCACCTCCTCCC (SEQ ID NO: 194) |
| VEGFA-Sp9 | 9 | CCGGGGAGGAGGTGGTAGCT (SEQ ID NO: 195) |
| VEGFA-Sp10 | 10 | GCCGGGGAGGAGGTGGTAGC (SEQ ID NO: 196) |
| VEGFA-Sp11 | 11 | GCTACCACCTCCTCCCCGGC (SEQ ID NO: 197) |
| VEGFA-Sp12 | 12 | ACCACCTCCTCCCCGGCCGG (SEQ ID NO: 198) |
| VEGFA-Sp13 | 13 | GCCGCCGGCCGGGGAGGAGG (SEQ ID NO: 199) |
| VEGFA-Sp14 | 14 | ACCTCCTCCCCGGCCGGCGG (SEQ ID NO: 200) |
| VEGFA-Sp15 | 15 | TCCGCCGCCGGCCGGGGAGG (SEQ ID NO: 201) |
| VEGFA-Sp16 | 16 | CTGTCCGCCGCCGGCCGGGG (SEQ ID NO: 202) |
| VEGFA-Sp17 | 17 | CCCCGGCCGGCGGCGGACAG (SEQ ID NO: 203) |
| VEGFA-Sp18 | 18 | CCACTGTCCGCCGCCGGCCG (SEQ ID NO: 204) |
| VEGFA-Sp19 | 19 | TCCACTGTCCGCCGCCGGCC (SEQ ID NO: 205) |
| VEGFA-Sp20 | 20 | GTCCACTGTCCGCCGCCGGC (SEQ ID NO: 206) |
| VEGFA-Sp21 | 21 | CCGGCGGCGGACAGTGGACG (SEQ ID NO: 207) |
| VEGFA-Sp22 | 22 | CCGCGTCCACTGTCCGCCGC (SEQ ID NO: 208) |
| VEGFA-Sp23 | 23 | GCGGCGGACAGTGGACGCGG (SEQ ID NO: 209) |
| VEGFA-Sp24 | 24 | GTGGACGCGGCGGCGAGCCG (SEQ ID NO: 210) |
| VEGFA-Sp25 | 25 | TGGACGCGGCGGCGAGCCGC (SEQ ID NO: 211) |
| VEGFA-Sp26 | 26 | CGCGGCGGCGAGCCGCGGGC (SEQ ID NO: 212) |
| VEGFA-Sp27 | 27 | GCGGCGGCGAGCCGCGGGCA (SEQ ID NO: 213) |
| VEGFA-Sp28 | 28 | CGGCGGCGAGCCGCGGGCAG (SEQ ID NO: 214) |
| VEGFA-Sp29 | 29 | GGCGAGCCGCGGGCAGGGGC (SEQ ID NO: 215) |
| VEGFA-Sp30 | 30 | CGGGCTCCGGCCCCTGCCCG (SEQ ID NO: 216) |
| VEGFA-Sp31 | 31 | CAGGGGCCGGAGCCCGCGCC (SEQ ID NO: 217) |
| VEGFA-Sp32 | 32 | GGGCCGGAGCCCGCGCCCGG (SEQ ID NO: 218) |
| VEGFA-Sp33 | 33 | CCGGAGCCCGCGCCCGGAGG (SEQ ID NO: 219) |
| VEGFA-Sp34 | 34 | CCGCCTCCGGGCGCGGGCTC (SEQ ID NO: 220) |
| VEGFA-Sp35 | 35 | CGGAGCCCGCGCCCGGAGGC (SEQ ID NO: 221) |
| VEGFA-Sp36 | 36 | GGAGCCCGCGCCCGGAGGCG (SEQ ID NO: 222) |
| VEGFA-Sp37 | 37 | GCCCGCGCCCGGAGGCGGGG (SEQ ID NO: 223) |
| VEGFA-Sp38 | 38 | TCCACCCCGCCTCCGGGCGC (SEQ ID NO: 224) |

TABLE 10-continued

Target sequences of VEGFA gene for SpCas9

| Gene | No. | Target sequence |
|---|---|---|
| VEGFA-Sp39 | 39 | CTCCACCCCGCCTCCGGGCG (SEQ ID NO: 225) |
| VEGFA-Sp40 | 40 | CGCGCCCGGAGGCGGGGTGG (SEQ ID NO: 226) |
| VEGFA-Sp41 | 41 | GCGCCCGGAGGCGGGGTGGA (SEQ ID NO: 227) |
| VEGFA-Sp42 | 42 | CGCCCGGAGGCGGGGTGGAG (SEQ ID NO: 228) |
| VEGFA-Sp43 | 43 | GCCCGGAGGCGGGGTGGAGG (SEQ ID NO: 229) |
| VEGFA-Sp44 | 44 | ACCCCCTCCACCCCGCCTCC (SEQ ID NO: 230) |
| VEGFA-Sp45 | 45 | GACCCCCTCCACCCCGCCTC (SEQ ID NO: 331) |
| VEGFA-Sp46 | 46 | GGAGGCGGGGTGGAGGGGGT (SEQ ID NO: 232) |
| VEGFA-Sp47 | 47 | GAGGCGGGGTGGAGGGGGTC (SEQ ID NO: 233) |
| VEGFA-Sp48 | 48 | AGGCGGGGTGGAGGGGGTCG (SEQ ID NO: 234) |
| VEGFA-Sp49 | 49 | GTGGAGGGGGTCGGGGCTCG (SEQ ID NO: 235) |
| VEGFA-Sp50 | 50 | GAAACTTTTCGTCCAACTTC (SEQ ID NO: 236) |
| VEGFA-Sp51 | 51 | AAACTTTTCGTCCAACTTCT (SEQ ID NO: 237) |
| VEGFA-Sp52 | 52 | AGCGAGAACAGCCCAGAAGT (SEQ ID NO: 238) |
| VEGFA-Sp53 | 53 | CTTCTGGGCTGTTCTCGCTT (SEQ ID NO: 239) |
| VEGFA-Sp54 | 54 | CTGGGCTGTTCTCGCTTCGG (SEQ ID NO: 240) |
| VEGFA-Sp55 | 55 | TTCTCGCTTCGGAGGAGCCG (SEQ ID NO: 241) |
| VEGFA-Sp56 | 56 | CGGAGGAGCCGTGGTCCGCG (SEQ ID NO: 242) |
| VEGFA-Sp57 | 57 | GGAGGAGCCGTGGTCCGCGC (SEQ ID NO: 243) |
| VEGFA-Sp58 | 58 | GAGGAGCCGTGGTCCGCGCG (SEQ ID NO: 244) |
| VEGFA-Sp59 | 59 | AGGAGCCGTGGTCCGCGCGG (SEQ ID NO: 245) |
| VEGFA-Sp60 | 60 | GGCTTCCCCGCGCGGACCA (SEQ ID NO: 246) |
| VEGFA-Sp61 | 61 | TCGGCTCGGCTTCCCCCGCG (SEQ ID NO: 247) |
| VEGFA-Sp62 | 62 | GCGGGGGAAGCCGAGCCGAG (SEQ ID NO: 248) |
| VEGFA-Sp63 | 63 | TCTCGCGGCTCCGCTCGGCT (SEQ ID NO: 249) |
| VEGFA-Sp64 | 64 | GCACTTCTCGCGGCTCCGCT (SEQ ID NO: 250) |
| VEGFA-Sp65 | 65 | AGCCGCGAGAAGTGCTAGCT (SEQ ID NO: 251) |
| VEGFA-Sp66 | 66 | GCCGCGAGAAGTGCTAGCTC (SEQ ID NO: 252) |
| VEGFA-Sp67 | 67 | GCCCGAGCTAGCACTTCTCG (SEQ ID NO: 253) |
| VEGFA-Sp68 | 68 | CGAGAAGTGCTAGCTCGGGC (SEQ ID NO: 254) |
| VEGFA-Sp69 | 69 | GAGAAGTGCTAGCTCGGGCC (SEQ ID NO: 255) |
| VEGFA-Sp70 | 70 | AAGTGCTAGCTCGGGCCGGG (SEQ ID NO: 256) |
| VEGFA-Sp71 | 71 | GGGCCGGGAGGAGCCGCAGC (SEQ ID NO: 257) |
| VEGFA-Sp72 | 72 | CCGGGAGGAGCCGCAGCCGG (SEQ ID NO: 258) |
| VEGFA-Sp73 | 73 | CCTCCGGCTGCGGCTCCTCC (SEQ ID NO: 259) |
| VEGFA-Sp74 | 74 | GGAGGAGCCGCAGCCGGAGG (SEQ ID NO: 260) |
| VEGFA-Sp75 | 75 | GAGGAGCCGCAGCCGGAGGA (SEQ ID NO: 261) |
| VEGFA-Sp76 | 76 | AGGAGCCGCAGCCGGAGGAG (SEQ ID NO: 262) |

TABLE 10-continued

Target sequences of VEGFA gene for SpCas9

| Gene | No. | Target sequence |
|---|---|---|
| VEGFA-Sp77 | 77 | GGAGCCGCAGCCGGAGGAGG (SEQ ID NO: 263) |
| VEGFA-Sp78 | 78 | GCCGCAGCCGGAGGAGGGGG (SEQ ID NO: 264) |
| VEGFA-Sp79 | 79 | TCCTCCCCTCCTCCGGCTG (SEQ ID NO: 265) |
| VEGFA-Sp80 | 80 | GCAGCCGGAGGAGGGGGAGG (SEQ ID NO: 266) |
| VEGFA-Sp81 | 81 | TCTTCCTCCTCCCCCTCCTC (SEQ ID NO: 267) |
| VEGFA-Sp82 | 82 | GAAGAGAAGGAAGAGGAGAG (SEQ ID NO: 268) |
| VEGFA-Sp83 | 83 | AAGAGAAGGAAGAGGAGAGG (SEQ ID NO: 269) |
| VEGFA-Sp84 | 84 | AAGAGGAGAGGGGCCGCAG (SEQ ID NO: 270) |
| VEGFA-Sp85 | 85 | AGGGGGCCGCAGTGGCGACT (SEQ ID NO: 271) |
| VEGFA-Sp86 | 86 | CGAGCGCCGAGTCGCCACTG (SEQ ID NO: 272) |
| VEGFA-Sp87 | 87 | CGCAGTGGCGACTCGGCGCT (SEQ ID NO: 273) |
| VEGFA-Sp88 | 88 | GCGACTCGGCGCTCGGAAGC (SEQ ID NO: 274) |
| VEGFA-Sp89 | 89 | CGACTCGGCGCTCGGAAGCC (SEQ ID NO: 275) |
| VEGFA-Sp90 | 90 | GCGCTCGGAAGCCGGGCTCA (SEQ ID NO: 276) |
| VEGFA-Sp91 | 91 | TCGGAAGCCGGGCTCATGGA (SEQ ID NO: 277) |
| VEGFA-Sp92 | 92 | CGGAAGCCGGGCTCATGGAC (SEQ ID NO: 278) |
| VEGFA-Sp93 | 93 | GCCGGGCTCATGGACGGGTG (SEQ ID NO: 279) |
| VEGFA-Sp94 | 94 | GCCTCACCCGTCCATGAGCC (SEQ ID NO: 280) |
| VEGFA-Sp95 | 95 | GGGCTCATGGACGGGTGAGG (SEQ ID NO: 281) |
| VEGFA-Sp96 | 96 | CTCATGGACGGGTGAGGCGG (SEQ ID NO: 282) |
| VEGFA-Sp97 | 97 | TCCAGCCGCGCGCGCTCCCC (SEQ ID NO: 283) |
| VEGFA-Sp98 | 98 | GCCTGGGGAGCGCGCGCGGC (SEQ ID NO: 284) |
| VEGFA-Sp99 | 99 | CAGGGCCTGGGGAGCGCGCG (SEQ ID NO: 285) |
| VEGFA-Sp100 | 100 | CGCGCGCGCTCCCCAGGCCC (SEQ ID NO: 286) |
| VEGFA-Sp101 | 101 | GCGCTCCCCAGGCCCTGGCC (SEQ ID NO: 287) |
| VEGFA-Sp102 | 102 | CGCTCCCCAGGCCCTGGCCC (SEQ ID NO: 288) |
| VEGFA-Sp103 | 103 | GAGGCCCGGGCCAGGGCCTG (SEQ ID NO: 289) |
| VEGFA-Sp104 | 104 | CGAGGCCCGGGCCAGGGCCT (SEQ ID NO: 290) |
| VEGFA-Sp105 | 105 | CCAGGCCCTGGCCCGGGCCT (SEQ ID NO: 291) |
| VEGFA-Sp106 | 106 | CCGAGGCCCGGGCCAGGGCC (SEQ ID NO: 292) |
| VEGFA-Sp107 | 107 | CAGGCCCTGGCCCGGGCCTC (SEQ ID NO: 293) |
| VEGFA-Sp108 | 108 | CCCTGGCCCGGGCCTCGGGC (SEQ ID NO: 294) |
| VEGFA-Sp109 | 109 | CCGGCCCGAGGCCCGGGCCA (SEQ ID NO: 295) |
| VEGFA-Sp110 | 110 | CCTGGCCCGGGCCTCGGGCC (SEQ ID NO: 296) |
| VEGFA-Sp111 | 111 | CCCGGCCCGAGGCCCGGGCC (SEQ ID NO: 297) |
| VEGFA-Sp112 | 112 | CTGGCCCGGGCCTCGGGCCG (SEQ ID NO: 298) |
| VEGFA-Sp113 | 113 | GCCCGGGCCTCGGGCCGGGG (SEQ ID NO: 299) |
| VEGFA-Sp114 | 114 | TCCTCCCCGGCCCGAGGCCC (SEQ ID NO: 300) |

TABLE 10-continued

Target sequences of VEGFA gene for SpCas9

| Gene | No. | Target sequence |
|---|---|---|
| VEGFA-Sp115 | 115 | TTCCTCCCCGGCCCGAGGCC (SEQ ID NO: 301) |
| VEGFA-Sp116 | 116 | TACTCTTCCTCCCCGGCCCG (SEQ ID NO: 302) |
| VEGFA-Sp117 | 117 | GGCGAGCTACTCTTCCTCCC (SEQ ID NO: 303) |
| VEGFA-Sp118 | 118 | GGAGGAAGAGTAGCTCGCCG (SEQ ID NO: 304) |
| VEGFA-Sp119 | 119 | AGTAGCTCGCCGAGGCGCCG (SEQ ID NO: 305) |
| VEGFA-Sp120 | 120 | CGCCGAGGCGCCGAGGAGAG (SEQ ID NO: 306) |
| VEGFA-Sp121 | 121 | GCCGAGGCGCCGAGGAGAGC (SEQ ID NO: 307) |
| VEGFA-Sp122 | 122 | GCCCGCTCTCCTCGGCGCCT (SEQ ID NO: 308) |
| VEGFA-Sp123 | 123 | GTGGGGCGGCCCGCTCTCCT (SEQ ID NO: 309) |
| VEGFA-Sp124 | 124 | GGCCGCCCCACAGCCCGAGC (SEQ ID NO: 310) |
| VEGFA-Sp125 | 125 | CTCCGGCTCGGGCTGTGGGG (SEQ ID NO: 311) |
| VEGFA-Sp126 | 126 | CCCCACAGCCCGAGCCGGAG (SEQ ID NO: 312) |
| VEGFA-Sp127 | 127 | CCTCTCCGGCTCGGGCTGTG (SEQ ID NO: 313) |
| VEGFA-Sp128 | 128 | CCCACAGCCCGAGCCGGAGA (SEQ ID NO: 314) |
| VEGFA-Sp129 | 129 | CCCTCTCCGGCTCGGGCTGT (SEQ ID NO: 315) |
| VEGFA-Sp130 | 130 | TCCCTCTCCGGCTCGGGCTG (SEQ ID NO: 316) |
| VEGFA-Sp131 | 131 | TCGCGCTCCCTCTCCGGCTC (SEQ ID NO: 317) |
| VEGFA-Sp132 | 132 | CTCGCGCTCCCTCTCCGGCT (SEQ ID NO: 318) |
| VEGFA-Sp133 | 133 | CGCGGCTCGCGCTCCCTCTC (SEQ ID NO: 319) |
| VEGFA-Sp134 | 134 | AGAGGGAGCGCGAGCCGCGC (SEQ ID NO: 320) |
| VEGFA-Sp135 | 135 | CGAGCCGCGCCGGCCCCGGT (SEQ ID NO: 321) |
| VEGFA-Sp136 | 136 | GAGCCGCGCCGGCCCCGGTC (SEQ ID NO: 322) |
| VEGFA-Sp137 | 137 | AGGCCCGACCGGGGCCGGCG (SEQ ID NO: 323) |
| VEGFA-Sp138 | 138 | TTCGGAGGCCCGACCGGGGC (SEQ ID NO: 324) |
| VEGFA-Sp139 | 139 | TGGTTTCGGAGGCCCGACCG (SEQ ID NO: 325) |
| VEGFA-Sp140 | 140 | ATGGTTTCGGAGGCCCGACC (SEQ ID NO: 326) |
| VEGFA-Sp141 | 141 | CATGGTTTCGGAGGCCCGAC (SEQ ID NO: 327) |
| VEGFA-Sp142 | 142 | CAGAAAGTTCATGGTTTCGG (SEQ ID NO: 328) |
| VEGFA-Sp143 | 143 | CAGCAGAAAGTTCATGGTTT (SEQ ID NO: 329) |
| VEGFA-Sp144 | 144 | CCATGAACTTTCTGCTGTCT (SEQ ID NO: 330) |
| VEGFA-Sp145 | 145 | CCAAGACAGCAGAAAGTTCA (SEQ ID NO: 331) |
| VEGFA-Sp146 | 146 | CATGAACTTTCTGCTGTCTT (SEQ ID NO: 332) |
| VEGFA-Sp147 | 147 | TTCTGCTGTCTTGGGTGCAT (SEQ ID NO: 333) |
| VEGFA-Sp148 | 148 | GGAGGTAGAGCAGCAAGGCA (SEQ ID NO: 334) |
| VEGFA-Sp149 | 149 | ATGGTGGAGGTAGAGCAGCA (SEQ ID NO: 335) |
| VEGFA-Sp150 | 150 | GCTCTACCTCCACCATGCCA (SEQ ID NO: 336) |
| VEGFA-Sp151 | 151 | CGCTTACCTTGGCATGGTGG (SEQ ID NO: 337) |
| VEGFA-Sp152 | 152 | GACCGCTTACCTTGGCATGG (SEQ ID NO: 338) |

TABLE 10-continued

Target sequences of VEGFA gene for SpCas9

| Gene | No. | Target sequence |
|---|---|---|
| VEGFA-Sp153 | 153 | CACGACCGCTTACCTTGGCA (SEQ ID NO: 339) |
| VEGFA-Sp154 | 154 | TTTCTGTCCTCAGTGGTCCC (SEQ ID NO: 340) |
| VEGFA-Sp155 | 155 | GGTGCAGCCTGGGACCACTG (SEQ ID NO: 341) |
| VEGFA-Sp156 | 156 | GTGGTCCCAGGCTGCACCCA (SEQ ID NO: 342) |
| VEGFA-Sp157 | 157 | TTCTGCCATGGGTGCAGCCT (SEQ ID NO: 343) |
| VEGFA-Sp158 | 158 | CTTCTGCCATGGGTGCAGCC (SEQ ID NO: 344) |
| VEGFA-Sp159 | 159 | CAGGCTGCACCCATGGCAGA (SEQ ID NO: 345) |
| VEGFA-Sp160 | 160 | GCTGCACCCATGGCAGAAGG (SEQ ID NO: 346) |
| VEGFA-Sp161 | 161 | GCACCCATGGCAGAAGGAGG (SEQ ID NO: 347) |
| VEGFA-Sp162 | 162 | CACCCATGGCAGAAGGAGGA (SEQ ID NO: 348) |
| VEGFA-Sp163 | 163 | TGCCCTCCTCCTTCTGCCAT (SEQ ID NO: 349) |
| VEGFA-Sp164 | 164 | CTGCCCTCCTCCTTCTGCCA (SEQ ID NO: 350) |
| VEGFA-Sp165 | 165 | GGAGGGCAGAATCATCACGA (SEQ ID NO: 351) |
| VEGFA-Sp166 | 166 | TCATGCAGTGGTGAAGTTCA (SEQ ID NO: 352) |
| VEGFA-Sp167 | 167 | CTGCCATCCAATCGAGACCC (SEQ ID NO: 353) |
| VEGFA-Sp168 | 168 | CCATCCAATCGAGACCCTGG (SEQ ID NO: 354) |
| VEGFA-Sp169 | 169 | CCACCAGGGTCTCGATTGGA (SEQ ID NO: 355) |
| VEGFA-Sp170 | 170 | ATGTCCACCAGGGTCTCGAT (SEQ ID NO: 356) |
| VEGFA-Sp171 | 171 | GACCCTGGTGGACATCTTCC (SEQ ID NO: 357) |
| VEGFA-Sp172 | 172 | CTCCTGGAAGATGTCCACCA (SEQ ID NO: 358) |
| VEGFA-Sp173 | 173 | ACTCCTGGAAGATGTCCACC (SEQ ID NO: 359) |
| VEGFA-Sp174 | 174 | CGATCTCATCAGGGTACTCC (SEQ ID NO: 360) |
| VEGFA-Sp175 | 175 | AGATGTACTCGATCTCATCA (SEQ ID NO: 361) |
| VEGFA-Sp176 | 176 | AAGATGTACTCGATCTCATC (SEQ ID NO: 362) |
| VEGFA-Sp177 | 177 | CGCATCAGGGGCACACAGGA (SEQ ID NO: 363) |
| VEGFA-Sp178 | 178 | GCATCGCATCAGGGGCACAC (SEQ ID NO: 364) |
| VEGFA-Sp179 | 179 | TGTGTGCCCCTGATGCGATG (SEQ ID NO: 365) |
| VEGFA-Sp180 | 180 | GTGTGCCCCTGATGCGATGC (SEQ ID NO: 366) |
| VEGFA-Sp181 | 181 | TGTGCCCCTGATGCGATGCG (SEQ ID NO: 367) |
| VEGFA-Sp182 | 182 | GTGCCCCTGATGCGATGCGG (SEQ ID NO: 368) |
| VEGFA-Sp183 | 183 | CAGCCCCGCATCGCATCAG (SEQ ID NO: 369) |
| VEGFA-Sp184 | 184 | GCAGCCCCGCATCGCATCA (SEQ ID NO: 370) |
| VEGFA-Sp185 | 185 | AGCAGCCCCGCATCGCATC (SEQ ID NO: 371) |
| VEGFA-Sp186 | 186 | CGGGGGCTGCTGCAATGACG (SEQ ID NO: 372) |
| VEGFA-Sp187 | 187 | GGGGGCTGCTGCAATGACGA (SEQ ID NO: 373) |
| VEGFA-Sp188 | 188 | CTGCTGCAATGACGAGGGCC (SEQ ID NO: 374) |
| VEGFA-Sp189 | 189 | CCTGGAGTGTGTGCCCACTG (SEQ ID NO: 375) |
| VEGFA-Sp190 | 190 | CCTCAGTGGGCACACACTCC (SEQ ID NO: 376) |

TABLE 10-continued

Target sequences of VEGFA gene for SpCas9

| Gene | No. | Target sequence |
|---|---|---|
| VEGFA-Sp191 | 191 | GTGATGTTGGACTCCTCAGT (SEQ ID NO: 377) |
| VEGFA-Sp192 | 192 | GGTGATGTTGGACTCCTCAG (SEQ ID NO: 378) |
| VEGFA-Sp193 | 193 | GGAGTCCAACATCACCATGC (SEQ ID NO: 379) |
| VEGFA-Sp194 | 194 | GTCCAACATCACCATGCAGG (SEQ ID NO: 380) |
| VEGFA-Sp195 | 195 | TCCAACATCACCATGCAGGT (SEQ ID NO: 381) |
| VEGFA-Sp196 | 196 | GCCCACCTGCATGGTGATGT (SEQ ID NO: 382) |
| VEGFA-Sp197 | 197 | CCCAAAGATGCCCACCTGCA (SEQ ID NO: 383) |
| VEGFA-Sp198 | 198 | TCCTTCCTTTCCAGATTATG (SEQ ID NO: 384) |
| VEGFA-Sp199 | 199 | GAGGTTTGATCCGCATAATC (SEQ ID NO: 385) |
| VEGFA-Sp200 | 200 | ATGCGGATCAAACCTCACCA (SEQ ID NO: 386) |
| VEGFA-Sp201 | 201 | CCTCACCAAGGCCAGCACAT (SEQ ID NO: 387) |
| VEGFA-Sp202 | 202 | CCTATGTGCTGGCCTTGGTG (SEQ ID NO: 388) |
| VEGFA-Sp203 | 203 | TCTCTCCTATGTGCTGGCCT (SEQ ID NO: 389) |
| VEGFA-Sp204 | 204 | AGCTCATCTCTCCTATGTGC (SEQ ID NO: 390) |
| VEGFA-Sp205 | 205 | ATTCACATTTGTTGTGCTGT (SEQ ID NO: 391) |
| VEGFA-Sp206 | 206 | AGCACAACAAATGTGAATGC (SEQ ID NO: 392) |
| VEGFA-Sp207 | 207 | AACAAATGTGAATGCAGGTG (SEQ ID NO: 393) |
| VEGFA-Sp208 | 208 | TGTCTTGCTCTATCTTTCTT (SEQ ID NO: 394) |
| VEGFA-Sp209 | 209 | TTTTCCAGAAAATCAGTTCG (SEQ ID NO: 395) |
| VEGFA-Sp210 | 210 | CTTTCCTCGAACTGATTTTC (SEQ ID NO: 396) |
| VEGFA-Sp211 | 211 | CAGAAAATCAGTTCGAGGAA (SEQ ID NO: 397) |
| VEGFA-Sp212 | 212 | AGAAAATCAGTTCGAGGAAA (SEQ ID NO: 398) |
| VEGFA-Sp213 | 213 | ATCAGTTCGAGGAAAGGGAA (SEQ ID NO: 399) |
| VEGFA-Sp214 | 214 | TCAGTTCGAGGAAAGGGAAA (SEQ ID NO: 400) |
| VEGFA-Sp215 | 215 | CAGTTCGAGGAAAGGGAAAG (SEQ ID NO: 401) |
| VEGFA-Sp216 | 216 | AACGAAAGCGCAAGAAATCC (SEQ ID NO: 402) |
| VEGFA-Sp217 | 217 | AGAAATCCCGGTATAAGTCC (SEQ ID NO: 403) |
| VEGFA-Sp218 | 218 | CACGCTCCAGGACTTATACC (SEQ ID NO: 404) |
| VEGFA-Sp219 | 219 | ACACGCTCCAGGACTTATAC (SEQ ID NO: 405) |
| VEGFA-Sp220 | 220 | AAGTCCTGGAGCGTGTACGT (SEQ ID NO: 406) |
| VEGFA-Sp221 | 221 | GGCACCAACGTACACGCTCC (SEQ ID NO: 407) |
| VEGFA-Sp222 | 222 | CCCGCTGCTGTCTAATGCCC (SEQ ID NO: 408) |
| VEGFA-Sp223 | 223 | CCAGGGCATTAGACAGCAGC (SEQ ID NO: 409) |
| VEGFA-Sp224 | 224 | TCCAGGGCATTAGACAGCAG (SEQ ID NO: 410) |
| VEGFA-Sp225 | 225 | CTAATGCCCTGGAGCCTCCC (SEQ ID NO: 411) |
| VEGFA-Sp226 | 226 | TGGGGGCCAGGGAGGCTCCA (SEQ ID NO: 412) |
| VEGFA-Sp227 | 227 | CTGGGGGCCAGGGAGGCTCC (SEQ ID NO: 413) |
| VEGFA-Sp228 | 228 | GGTTGTACTGGGGGCCAGGG (SEQ ID NO: 414) |

TABLE 10-continued

Target sequences of VEGFA gene for SpCas9

| Gene | No. | Target sequence |
|---|---|---|
| VEGFA-Sp229 | 229 | GGAGGTTGTACTGGGGCCA (SEQ ID NO: 415) |
| VEGFA-Sp230 | 230 | CGGAGGTTGTACTGGGGCC (SEQ ID NO: 416) |
| VEGFA-Sp231 | 231 | GCAGGCGGAGGTTGTACTGG (SEQ ID NO: 417) |
| VEGFA-Sp232 | 232 | TTGCCTTTTTGCAGTCCCTG (SEQ ID NO: 418) |
| VEGFA-Sp233 | 233 | TGCCTTTTTGCAGTCCCTGT (SEQ ID NO: 419) |
| VEGFA-Sp234 | 234 | CGCTCTGAGCAAGGCCCACA (SEQ ID NO: 420) |
| VEGFA-Sp235 | 235 | CCTGTGGGCCTTGCTCAGAG (SEQ ID NO: 421) |
| VEGFA-Sp236 | 236 | CCGCTCTGAGCAAGGCCCAC (SEQ ID NO: 422) |
| VEGFA-Sp237 | 237 | TGCTTTCTCCGCTCTGAGCA (SEQ ID NO: 423) |
| VEGFA-Sp238 | 238 | CAGGAACATTTACACGTCTG (SEQ ID NO: 424) |
| VEGFA-Sp239 | 239 | ACGCGAGTCTGTGTTTTTGC (SEQ ID NO: 425) |
| VEGFA-Sp240 | 240 | AAACACAGACTCGCGTTGCA (SEQ ID NO: 426) |
| VEGFA-Sp241 | 241 | CAGACTCGCGTTGCAAGGCG (SEQ ID NO: 427) |
| VEGFA-Sp242 | 242 | AGTTAAACGAACGTACTTGC (SEQ ID NO: 428) |
| VEGFA-Sp243 | 243 | AAACGAACGTACTTGCAGGT (SEQ ID NO: 429) |
| VEGFA-Sp244 | 244 | CCCTCAGATGTGACAAGCCG (SEQ ID NO: 430) |
| VEGFA-Sp245 | 245 | GCCTCGGCTTGTCACATCTG (SEQ ID NO: 431) |
| VEGFA-Sp246 | 246 | TCAGATGTGACAAGCCGAGG (SEQ ID NO: 432) |
| VEGFA-Sp247 | 247 | ACAAGCCGAGGCGGTGAGCC (SEQ ID NO: 433) |
| VEGFA-Sp248 | 248 | GCCGAGGCGGTGAGCCGGGC (SEQ ID NO: 434) |
| VEGFA-Sp249 | 249 | TCCTGCCCGGCTCACCGCCT (SEQ ID NO: 435) |

TABLE 11

Target sequences of HIF1A gene for SpCas9

| Gene | No. | Target sequence |
|---|---|---|
| HIF1A-Sp1 | 1 | TTTAAATGAGCTCCCAATGT (SEQ ID NO: 436) |
| HIF1A-Sp2 | 2 | GAGCTCCCAATGTCGGAGTT (SEQ ID NO: 437) |
| HIF1A-Sp3 | 3 | GTTTTCCAAACTCCGACATT (SEQ ID NO: 438) |
| HIF1A-Sp4 | 4 | TGTTTTCCAAACTCCGACAT (SEQ ID NO: 439) |
| HIF1A-Sp5 | 5 | AAATTTGTCTTTTTAAAAGA (SEQ ID NO: 440) |
| HIF1A-Sp6 | 6 | GTCTTTTTAAAAGAAGGTCT (SEQ ID NO: 441) |
| HIF1A-Sp7 | 7 | AAACTCAAAACCTGAAGAAT (SEQ ID NO: 442) |
| HIF1A-Sp8 | 8 | CTGATTTCTTCCAATTCTTC (SEQ ID NO: 443) |
| HIF1A-Sp9 | 9 | GAAGAAATCAGAATAGAAAA (SEQ ID NO: 444) |
| HIF1A-Sp10 | 10 | AAGAAATCAGAATAGAAAAT (SEQ ID NO: 445) |
| HIF1A-Sp11 | 11 | ATCAGAATAGAAAATGGGTA (SEQ ID NO: 446) |
| HIF1A-Sp12 | 12 | CTCGAGATGCAGCCAGATCT (SEQ ID NO: 447) |
| HIF1A-Sp13 | 13 | TTCTTTACTTCGCCGAGATC (SEQ ID NO: 448) |
| HIF1A-Sp14 | 14 | GAACTCACATTATGTGGAAG (SEQ ID NO: 449) |
| HIF1A-Sp15 | 15 | AGATGCGAACTCACATTATG (SEQ ID NO: 450) |
| HIF1A-Sp16 | 16 | TGTGAGTTCGCATCTTGATA (SEQ ID NO: 451) |
| HIF1A-Sp17 | 17 | TTGATAAGGCCTCTGTGATG (SEQ ID NO: 452) |
| HIF1A-Sp18 | 18 | GATGGTAAGCCTCATCACAG (SEQ ID NO: 453) |
| HIF1A-Sp19 | 19 | CCATCAGCTATTTGCGTGTG (SEQ ID NO: 454) |
| HIF1A-Sp20 | 20 | CCTCACACGCAAATAGCTGA (SEQ ID NO: 455) |

TABLE 11-continued

Target sequences of HIF1A gene for SpCas9

| Gene | No. | Target sequence |
|---|---|---|
| HIF1A-Sp21 | 21 | TTTGCGTGTGAGGAAACTTC (SEQ ID NO: 456) |
| HIF1A-Sp22 | 22 | GTGAGGAAACTTCTGGATGC (SEQ ID NO: 457) |
| HIF1A-Sp23 | 23 | TGTGCCCTTTTTAGGTGATT (SEQ ID NO: 458) |
| HIF1A-Sp24 | 24 | TTGCTTTTATTTGAAAGCCT (SEQ ID NO: 459) |
| HIF1A-Sp25 | 25 | TTTTATTTGAAAGCCTTGGA (SEQ ID NO: 460) |
| HIF1A-Sp26 | 26 | AGCCTTGGATGGTTTTGTTA (SEQ ID NO: 461) |
| HIF1A-Sp27 | 27 | AACCATAACAAAACCATCCA (SEQ ID NO: 462) |
| HIF1A-Sp28 | 28 | GTTATGGTTCTCACAGATGA (SEQ ID NO: 463) |
| HIF1A-Sp29 | 29 | TGATAATGTGAACAAATACA (SEQ ID NO: 464) |
| HIF1A-Sp30 | 30 | GATAATGTGAACAAATACAT (SEQ ID NO: 465) |
| HIF1A-Sp31 | 31 | CAAATACATGGGATTAACTC (SEQ ID NO: 466) |
| HIF1A-Sp32 | 32 | TGTTTACAGTTTGAACTAAC (SEQ ID NO: 467) |
| HIF1A-Sp33 | 33 | TACTCATCCATGTGACCATG (SEQ ID NO: 468) |
| HIF1A-Sp34 | 34 | CTCATTTCCTCATGGTCACA (SEQ ID NO: 469) |
| HIF1A-Sp35 | 35 | GCATTTCTCTCATTTCCTCA (SEQ ID NO: 470) |
| HIF1A-Sp36 | 36 | GAAATGCTTACACACAGAAA (SEQ ID NO: 471) |
| HIF1A-Sp37 | 37 | TTCATTAGGCCTTGTGAAAA (SEQ ID NO: 472) |
| HIF1A-Sp38 | 38 | TCATTAGGCCTTGTGAAAAA (SEQ ID NO: 473) |
| HIF1A-Sp39 | 39 | GTTCTTTACCCTTTTTCACA (SEQ ID NO: 474) |
| HIF1A-Sp40 | 40 | AAGTGTACCCTAACTAGCCG (SEQ ID NO: 475) |
| HIF1A-Sp41 | 41 | AGTTCTTCCTCGGCTAGTTA (SEQ ID NO: 476) |
| HIF1A-Sp42 | 42 | TAGTTCTTCCTCGGCTAGTT (SEQ ID NO: 477) |
| HIF1A-Sp43 | 43 | TTATGTTCATAGTTCTTCCT (SEQ ID NO: 478) |
| HIF1A-Sp44 | 44 | TGAACATAAAGTCTGCAACA (SEQ ID NO: 479) |
| HIF1A-Sp45 | 45 | CATAAAGTCTGCAACATGGA (SEQ ID NO: 480) |
| HIF1A-Sp46 | 46 | ACACAGGTATTGCACTGCAC (SEQ ID NO: 481) |
| HIF1A-Sp47 | 47 | TGGTATCATATACGTGAATG (SEQ ID NO: 482) |
| HIF1A-Sp48 | 48 | ACACTGAGGTTGGTTACTGT (SEQ ID NO: 483) |
| HIF1A-Sp49 | 49 | AACAGTAACCAACCTCAGTG (SEQ ID NO: 484) |
| HIF1A-Sp50 | 50 | ACAGTAACCAACCTCAGTGT (SEQ ID NO: 485) |
| HIF1A-Sp51 | 51 | TCTTATACCCACACTGAGGT (SEQ ID NO: 486) |
| HIF1A-Sp52 | 52 | GGTTTCTTATACCCACACTG (SEQ ID NO: 487) |
| HIF1A-Sp53 | 53 | GAAACCACCTATGACCTGCT (SEQ ID NO: 488) |
| HIF1A-Sp54 | 54 | AGCACCAAGCAGGTCATAGG (SEQ ID NO: 489) |
| HIF1A-Sp55 | 55 | ATCAGCACCAAGCAGGTCAT (SEQ ID NO: 490) |
| HIF1A-Sp56 | 56 | TTCACAAATCAGCACCAAGC (SEQ ID NO: 491) |
| HIF1A-Sp57 | 57 | ATATTTGATGGGTGAGGAAT (SEQ ID NO: 492) |
| HIF1A-Sp58 | 58 | AATATTTGATGGGTGAGGAA (SEQ ID NO: 493) |
| HIF1A-Sp59 | 59 | ATTTCAATATTTGATGGGTG (SEQ ID NO: 494) |
| HIF1A-Sp60 | 60 | AAGGAATTTCAATATTTGAT (SEQ ID NO: 495) |
| HIF1A-Sp61 | 61 | AAAGGAATTTCAATATTTGA (SEQ ID NO: 496) |
| HIF1A-Sp62 | 62 | AGGAAAGTCTTGCTATCTAA (SEQ ID NO: 497) |
| HIF1A-Sp63 | 63 | TTTCCTCAGTCGACACAGCC (SEQ ID NO: 498) |
| HIF1A-Sp64 | 64 | TATCCAGGCTGTGTCGACTG (SEQ ID NO: 499) |
| HIF1A-Sp65 | 65 | AATAAGAAAATTTCATATCC (SEQ ID NO: 500) |
| HIF1A-Sp66 | 66 | AATTTCTTATTGTGATGAA (SEQ ID NO: 501) |
| HIF1A-Sp67 | 67 | TAACAGAATTACCGAATTGA (SEQ ID NO: 502) |
| HIF1A-Sp68 | 68 | AACAGAATTACCGAATTGAT (SEQ ID NO: 503) |
| HIF1A-Sp69 | 69 | TGGCTCATATCCCATCAATT (SEQ ID NO: 504) |
| HIF1A-Sp70 | 70 | TATGAGCCAGAAGAACTTTT (SEQ ID NO: 505) |

TABLE 11-continued

Target sequences of HIF1A gene for SpCas9

| Gene | No. | Target sequence |
|---|---|---|
| HIF1A-Sp71 | 71 | GAGCGGCCTAAAAGTTCTTC (SEQ ID NO: 506) |
| HIF1A-Sp72 | 72 | GATAATATTCATAAATTGAG (SEQ ID NO: 507) |
| HIF1A-Sp73 | 73 | TTATGAATATTATCATGCTT (SEQ ID NO: 508) |
| HIF1A-Sp74 | 74 | CTTACTATCATGATGAGTTT (SEQ ID NO: 509) |
| HIF1A-Sp75 | 75 | TCCCCCCTAGTGTTTACTAA (SEQ ID NO: 510) |
| HIF1A-Sp76 | 76 | TTGTCCTTTAGTAAACACTA (SEQ ID NO: 511) |
| HIF1A-Sp77 | 77 | CTTGTCCTTTAGTAAACACT (SEQ ID NO: 512) |
| HIF1A-Sp78 | 78 | ACTAAAGGACAAGTCACCAC (SEQ ID NO: 513) |
| HIF1A-Sp79 | 79 | AAGTCACCACAGGACAGTAC (SEQ ID NO: 514) |
| HIF1A-Sp80 | 80 | AAGCATCCTGTACTGTCCTG (SEQ ID NO: 515) |
| HIF1A-Sp81 | 81 | TACAGGATGCTTGCCAAAAG (SEQ ID NO: 516) |
| HIF1A-Sp82 | 82 | AGGATGCTTGCCAAAAGAGG (SEQ ID NO: 517) |
| HIF1A-Sp83 | 83 | CCAAAAGAGGTGGATATGTC (SEQ ID NO: 518) |
| HIF1A-Sp84 | 84 | CCAGACATATCCACCTCTTT (SEQ ID NO: 519) |
| HIF1A-Sp85 | 85 | CAAAAGAGGTGGATATGTCT (SEQ ID NO: 520) |
| HIF1A-Sp86 | 86 | GCACTGTGGTTGAGAATTCT (SEQ ID NO: 521) |
| HIF1A-Sp87 | 87 | TTCACACATACAATGCACTG (SEQ ID NO: 522) |
| HIF1A-Sp88 | 88 | TATGTGTGAATTACGTTGTG (SEQ ID NO: 523) |
| HIF1A-Sp89 | 89 | GACACATTCTGTTTGTTGAA (SEQ ID NO: 524) |
| HIF1A-Sp90 | 90 | GGACACATTCTGTTTGTTGA (SEQ ID NO: 525) |
| HIF1A-Sp91 | 91 | AACAGAATGTGTCCTTAAAC (SEQ ID NO: 526) |
| HIF1A-Sp92 | 92 | CTGAAGATTCAACCGGTTTA (SEQ ID NO: 527) |
| HIF1A-Sp93 | 93 | TTCATATCTGAAGATTCAAC (SEQ ID NO: 528) |
| HIF1A-Sp94 | 94 | TGTATCTTCTGATTCAACTT (SEQ ID NO: 529) |
| HIF1A-Sp95 | 95 | CCTCTTTGACAAACTTAAGA (SEQ ID NO: 530) |
| HIF1A-Sp96 | 96 | CCTTCTTAAGTTTGTCAAAG (SEQ ID NO: 531) |
| HIF1A-Sp97 | 97 | ACCTGATGCTTTAACTTTGC (SEQ ID NO: 532) |
| HIF1A-Sp98 | 98 | GCCAGCAAAGTTAAAGCATC (SEQ ID NO: 533) |
| HIF1A-Sp99 | 99 | ACTTTGCTGGCCCCAGCCGC (SEQ ID NO: 534) |
| HIF1A-Sp100 | 100 | GATTGTGTCTCCAGCGGCTG (SEQ ID NO: 535) |
| HIF1A-Sp101 | 101 | TGATTGTGTCTCCAGCGGCT (SEQ ID NO: 536) |
| HIF1A-Sp102 | 102 | ATGATTGTGTCTCCAGCGGC (SEQ ID NO: 537) |
| HIF1A-Sp103 | 103 | AGATATGATTGTGTCTCCAG (SEQ ID NO: 538) |
| HIF1A-Sp104 | 104 | ACAATCATATCTTTAGATTT (SEQ ID NO: 539) |
| HIF1A-Sp105 | 105 | TCTTTAGATTTTGGCAGCAA (SEQ ID NO: 540) |
| HIF1A-Sp106 | 106 | GTCATCAGTTTCTGTGTCTG (SEQ ID NO: 541) |
| HIF1A-Sp107 | 107 | AACTGATGACCAGCAACTTG (SEQ ID NO: 542) |
| HIF1A-Sp108 | 108 | ATGGTACTTCCTCAAGTTGC (SEQ ID NO: 543) |
| HIF1A-Sp109 | 109 | AGCATTACATCATTATATAA (SEQ ID NO: 544) |
| HIF1A-Sp110 | 110 | GTAATTTTCGTTGGGTGAG (SEQ ID NO: 545) |
| HIF1A-Sp111 | 111 | TGTAATTTTCGTTGGGTGA (SEQ ID NO: 546) |
| HIF1A-Sp112 | 112 | CTGTAATTTTCGTTGGGTG (SEQ ID NO: 547) |
| HIF1A-Sp113 | 113 | ATATTCTGTAATTTTTCGTT (SEQ ID NO: 548) |
| HIF1A-Sp114 | 114 | TATATTCTGTAATTTTTCGT (SEQ ID NO: 549) |
| HIF1A-Sp115 | 115 | AAAATTACAGAATATAAATT (SEQ ID NO: 550) |
| HIF1A-Sp116 | 116 | GGCGTTTCAGCGGTGGGTAA (SEQ ID NO: 551) |
| HIF1A-Sp117 | 117 | GGCTTTGGCGTTTCAGCGGT (SEQ ID NO: 552) |
| HIF1A-Sp118 | 118 | TGGCTTTGGCGTTTCAGCGG (SEQ ID NO: 553) |
| HIF1A-Sp119 | 119 | AAGTGGCTTTGGCGTTTCAG (SEQ ID NO: 554) |

TABLE 11-continued

Target sequences of HIF1A gene for SpCas9

| Gene | No. | Target sequence |
|---|---|---|
| HIF1A-Sp120 | 120 | GCACTACTTCGAAGTGGCTT (SEQ ID NO: 555) |
| HIF1A-Sp121 | 121 | GGGTCAGCACTACTTCGAAG (SEQ ID NO: 556) |
| HIF1A-Sp122 | 122 | CAACTTCTTGATTGAGTGCA (SEQ ID NO: 557) |
| HIF1A-Sp123 | 123 | GCAACTTCTTGATTGAGTGC (SEQ ID NO: 558) |
| HIF1A-Sp124 | 124 | AGAACCAAATCCAGAGTCAC (SEQ ID NO: 559) |
| HIF1A-Sp125 | 125 | AGTTCCAGTGACTCTGGATT (SEQ ID NO: 560) |
| HIF1A-Sp126 | 126 | AAAGAAAGTTCCAGTGACTC (SEQ ID NO: 561) |
| HIF1A-Sp127 | 127 | TTTTACCATGCCCCAGATTC (SEQ ID NO: 562) |
| HIF1A-Sp128 | 128 | CTGATCCTGAATCTGGGGCA (SEQ ID NO: 563) |
| HIF1A-Sp129 | 129 | GGTGTCTGATCCTGAATCTG (SEQ ID NO: 564) |
| HIF1A-Sp130 | 130 | AGGTGTCTGATCCTGAATCT (SEQ ID NO: 565) |
| HIF1A-Sp131 | 131 | TAGGTGTCTGATCCTGAATC (SEQ ID NO: 566) |
| HIF1A-Sp132 | 132 | CAGACACCTAGTCCTTCCGA (SEQ ID NO: 567) |
| HIF1A-Sp133 | 133 | GTGCTTCCATCGGAAGGACT (SEQ ID NO: 568) |
| HIF1A-Sp134 | 134 | TGTCTAGTCGTTCCATCGGA (SEQ ID NO: 569) |
| HIF1A-Sp135 | 135 | ACTTTGTCTAGTGCTTCCAT (SEQ ID NO: 570) |
| HIF1A-Sp136 | 136 | CACTAGACAAAGTTCACCTG (SEQ ID NO: 571) |
| HIF1A-Sp137 | 137 | AGACAAAGTTCACCTGAGGT (SEQ ID NO: 572) |
| HIF1A-Sp138 | 138 | TATATCATGACACCTACCTC (SEQ ID NO: 573) |
| HIF1A-Sp139 | 139 | CAATATTCACTGGGACTATT (SEQ ID NO: 574) |
| HIF1A-Sp140 | 140 | ACATAAAAACAATATTCACT (SEQ ID NO: 575) |
| HIF1A-Sp141 | 141 | CACATAAAAACAATATTCAC (SEQ ID NO: 576) |
| HIF1A-Sp142 | 142 | CAGTGAATATTGTTTTTATG (SEQ ID NO: 577) |
| HIF1A-Sp143 | 143 | TTTTTATGTGGATAGTGATA (SEQ ID NO: 578) |
| HIF1A-Sp144 | 144 | TATGGTCAATGAATTCAAGT (SEQ ID NO: 579) |
| HIF1A-Sp145 | 145 | CAATGAATTCAAGTTGGAAT (SEQ ID NO: 580) |
| HIF1A-Sp146 | 146 | AAAGAACCCATTTTCTACTC (SEQ ID NO: 581) |
| HIF1A-Sp147 | 147 | CATATACCTGAGTAGAAAAT (SEQ ID NO: 582) |
| HIF1A-Sp148 | 148 | TCATATACCTGAGTAGAAAA (SEQ ID NO: 583) |
| HIF1A-Sp149 | 149 | AAAGGACACAGATTTAGACT (SEQ ID NO: 584) |
| HIF1A-Sp150 | 150 | GTTAGCTCCCTATATCCCAA (SEQ ID NO: 585) |
| HIF1A-Sp151 | 151 | TCATCATCCATTGGGATATA (SEQ ID NO: 586) |
| HIF1A-Sp152 | 152 | GTCATCATCCATTGGGATAT (SEQ ID NO: 587) |
| HIF1A-Sp153 | 153 | ACTGGAAGTCATCATCCATT (SEQ ID NO: 588) |
| HIF1A-Sp154 | 154 | AACTGGAAGTCATCATCCAT (SEQ ID NO: 589) |
| HIF1A-Sp155 | 155 | ACTGATCGAAGGAACGTAAC (SEQ ID NO: 590) |
| HIF1A-Sp156 | 156 | TAATGGTGACAACTGATCGA (SEQ ID NO: 591) |
| HIF1A-Sp157 | 157 | CTTGCGGAACTGCTTTCTAA (SEQ ID NO: 592) |
| HIF1A-Sp158 | 158 | ACTTGCGCTTTCAGGGCTTG (SEQ ID NO: 593) |
| HIF1A-Sp159 | 159 | TTTGAGGACTTGCGCTTTCA (SEQ ID NO: 594) |
| HIF1A-Sp160 | 160 | CTTTGAGGACTTGCGCTTTC (SEQ ID NO: 595) |
| HIF1A-Sp161 | 161 | AATACTGTAACTGTGCTTTG (SEQ ID NO: 596) |
| HIF1A-Sp162 | 162 | GTTCTTGTATTTGAGTCTGC (SEQ ID NO: 597) |
| HIF1A-Sp163 | 163 | GTAGTGGTGGCATTAGCAGT (SEQ ID NO: 598) |
| HIF1A-Sp164 | 164 | AGTGGTGGCAGTGGTAGTGG (SEQ ID NO: 599) |
| HIF1A-Sp165 | 165 | ATCAGTGGTGGCAGTGGTAG (SEQ ID NO: 600) |
| HIF1A-Sp166 | 166 | TAATTCATCAGTGGTGGCAG (SEQ ID NO: 601) |
| HIF1A-Sp167 | 167 | TGTTTTTAATTCATCAGTGG (SEQ ID NO: 602) |
| HIF1A-Sp168 | 168 | CACTGTTTTTAATTCATCAG (SEQ ID NO: 603) |

TABLE 11-continued

Target sequences of HIF1A gene for SpCas9

| Gene | No. | Target sequence |
|---|---|---|
| HIF1A-Sp169 | 169 | AACAGTGACAAAAGACCGTA (SEQ ID NO: 604) |
| HIF1A-Sp170 | 170 | ATATTTTAATGTCTTCCATA (SEQ ID NO: 605) |
| HIF1A-Sp171 | 171 | TTATGTATGTGGGTAGGAGA (SEQ ID NO: 606) |
| HIF1A-Sp172 | 172 | GTTTCTTTATGTATGTGGGT (SEQ ID NO: 607) |
| HIF1A-Sp173 | 173 | AGTAGTTTCTTTATGTATGT (SEQ ID NO: 608) |
| HIF1A-Sp174 | 174 | TAGTAGTTTCTTTATGTATG (SEQ ID NO: 609) |
| HIF1A-Sp175 | 175 | ATCTCTATATGGTGATGATG (SEQ ID NO: 610) |
| HIF1A-Sp176 | 176 | CGACTTTGAGTATCTCTATA (SEQ ID NO: 611) |
| HIF1A-Sp177 | 177 | CATATAGAGATACTCAAAGT (SEQ ID NO: 612) |
| HIF1A-Sp178 | 178 | ACAGCCTCACCAAACAGAGC (SEQ ID NO: 613) |
| HIF1A-Sp179 | 179 | TTTTCCTGCTCTGTTTGGTG (SEQ ID NO: 614) |
| HIF1A-Sp180 | 180 | TCACCAAACAGAGCAGGAAA (SEQ ID NO: 615) |
| HIF1A-Sp181 | 181 | ACTCCTTTTCCTGCTCTGTT (SEQ ID NO: 616) |
| HIF1A-Sp182 | 182 | GATAACACGTTAGGGCTTCT (SEQ ID NO: 617) |
| HIF1A-Sp183 | 183 | AAGCGACAGATAACACGTTA (SEQ ID NO: 618) |
| HIF1A-Sp184 | 184 | AAAGCGACAGATAACACGTT (SEQ ID NO: 619) |
| HIF1A-Sp185 | 185 | TATCTGTCGCTTTGAGTCAA (SEQ ID NO: 620) |
| HIF1A-Sp186 | 186 | TTTCAGAACTACAGTTCCTG (SEQ ID NO: 621) |
| HIF1A-Sp187 | 187 | TTTGGATTTAGTTCTTCCTC (SEQ ID NO: 622) |
| HIF1A-Sp188 | 188 | TTCTGCAAAGCTAGTATCTT (SEQ ID NO: 623) |
| HIF1A-Sp189 | 189 | TGCTCAGAGAAAGCGAAAAA (SEQ ID NO: 624) |
| HIF1A-Sp190 | 190 | AAGCGAAAAATGGAACATGA (SEQ ID NO: 625) |
| HIF1A-Sp191 | 191 | GTAGTAGCTGCATGATCGTC (SEQ ID NO: 626) |
| HIF1A-Sp192 | 192 | CAGCTACTACATCACTTTCT (SEQ ID NO: 627) |
| HIF1A-Sp193 | 193 | CTTTCTTGGAAACGTGTAAA (SEQ ID NO: 628) |
| HIF1A-Sp194 | 194 | ACAATTATTTTAATACCCTC (SEQ ID NO: 629) |
| HIF1A-Sp195 | 195 | AAAAGAATAAACTAACCAGA (SEQ ID NO: 630) |
| HIF1A-Sp196 | 196 | AAAAAGAATAAACTAACCAG (SEQ ID NO: 631) |
| HIF1A-Sp197 | 197 | AGATTTAGCATGTAGACTGC (SEQ ID NO: 632) |
| HIF1A-Sp198 | 198 | GATTTAGCATGTAGACTGCT (SEQ ID NO: 633) |
| HIF1A-Sp199 | 199 | ATTTAGCATGTAGACTGCTG (SEQ ID NO: 634) |
| HIF1A-Sp200 | 200 | TAGACTGCTGGGGCAATCAA (SEQ ID NO: 635) |
| HIF1A-Sp201 | 201 | GGGCAATCAATGGATGAAAG (SEQ ID NO: 636) |
| HIF1A-Sp202 | 202 | CAATCATAACTGGTCAGCTG (SEQ ID NO: 637) |
| HIF1A-Sp203 | 203 | ATTAACTTCACAATCATAAC (SEQ ID NO: 638) |
| HIF1A-Sp204 | 204 | GAAGTTAATGCTCCTATACA (SEQ ID NO: 639) |
| HIF1A-Sp205 | 205 | AGGTTTCTGCTGCCTTGTAT (SEQ ID NO: 640) |
| HIF1A-Sp206 | 206 | AGGCAGCAGAAACCTACTGC (SEQ ID NO: 641) |
| HIF1A-Sp207 | 207 | GGCAGCAGAAACCTACTGCA (SEQ ID NO: 642) |
| HIF1A-Sp208 | 208 | GTAATTCTTCACCCTGCAGT (SEQ ID NO: 643) |
| HIF1A-Sp209 | 209 | TGAAGAATTACTCAGAGCTT (SEQ ID NO: 644) |

TABLE 12

Target sequences of EPAS1-gene for SpCas9

| Gene | No. | Target sequence |
|---|---|---|
| EPAS1-Sp1 | 1 | AGCGACAATGACAGCTGACA (SEQ ID NO: 645) |
| EPAS1-Sp2 | 2 | CAGCTGACAAGGAGAAGAAA (SEQ ID NO: 646) |
| EPAS1-Sp3 | 3 | TTCTCCACTTAGGAGTAGCT (SEQ ID NO: 647) |

TABLE 12-continued

Target sequences of EPAS1-gene for SpCas9

| Gene | No. | Target sequence |
| --- | --- | --- |
| EPAS1-Sp4 | 4 | CACTTAGGAGTAGCTCGGAG (SEQ ID NO: 648) |
| EPAS1-Sp5 | 5 | TTAGGAGTAGCTCGGAGAGG (SEQ ID NO: 649) |
| EPAS1-Sp6 | 6 | GAGTAGCTCGGAGAGGAGGA (SEQ ID NO: 650) |
| EPAS1-Sp7 | 7 | AGAGGAGGAAGGAGAAGTCC (SEQ ID NO: 651) |
| EPAS1-Sp8 | 8 | GAGGAGGAAGGAGAAGTCCC (SEQ ID NO: 652) |
| EPAS1-Sp9 | 9 | AGAAGTCCCGGGATGCTGCG (SEQ ID NO: 653) |
| EPAS1-Sp10 | 10 | CCCGGGATGCTGCGCGGTGC (SEQ ID NO: 654) |
| EPAS1-Sp11 | 11 | CCGGCACCGCGCAGCATCCC (SEQ ID NO: 655) |
| EPAS1-Sp12 | 12 | GCCGGCACCGCGCAGCATCC (SEQ ID NO: 656) |
| EPAS1-Sp13 | 13 | GGGATGCTGCGCGGTGCCGG (SEQ ID NO: 657) |
| EPAS1-Sp14 | 14 | TGCGCGGTGCCGGCGGAGCA (SEQ ID NO: 658) |
| EPAS1-Sp15 | 15 | GTGCCGGCGGAGCAAGGAGA (SEQ ID NO: 659) |
| EPAS1-Sp16 | 16 | CCGGCGGAGCAAGGAGACGG (SEQ ID NO: 660) |
| EPAS1-Sp17 | 17 | CCTCCGTCTCCTTGCTCCGC (SEQ ID NO: 661) |
| EPAS1-Sp18 | 18 | GACGGAGGTGTTCTATGAGC (SEQ ID NO: 662) |
| EPAS1-Sp19 | 19 | GTGGGGCAGAGGCAGCTCAT (SEQ ID NO: 663) |
| EPAS1-Sp20 | 20 | TGTGGGGCAGAGGCAGCTCA (SEQ ID NO: 664) |
| EPAS1-Sp21 | 21 | GAGCTCACACTGTGGGGCAG (SEQ ID NO: 665) |
| EPAS1-Sp22 | 22 | AGATGGGAGCTCACACTGTG (SEQ ID NO: 666) |
| EPAS1-Sp23 | 23 | CAGATGGGAGCTCACACTGT (SEQ ID NO: 667) |
| EPAS1-Sp24 | 24 | CCACAGTGTGAGCTCCCATC (SEQ ID NO: 668) |
| EPAS1-Sp25 | 25 | CCAGATGGGAGCTCACACTG (SEQ ID NO: 669) |
| EPAS1-Sp26 | 26 | TGTGAGCTCCCATCTGGACA (SEQ ID NO: 670) |
| EPAS1-Sp27 | 27 | GATGGAGGCCTTGTCCAGAT (SEQ ID NO: 671) |
| EPAS1-Sp28 | 28 | TGATGGAGGCCTTGTCCAGA (SEQ ID NO: 672) |
| EPAS1-Sp29 | 29 | CAAGGCCTCCATCATGCGAC (SEQ ID NO: 673) |
| EPAS1-Sp30 | 30 | GATTGCCAGTCGCATGATGG (SEQ ID NO: 674) |
| EPAS1-Sp31 | 31 | GCTGATTGCCAGTCGCATGA (SEQ ID NO: 675) |
| EPAS1-Sp32 | 32 | AGAGGAGCTTGTGTGTTCGC (SEQ ID NO: 676) |
| EPAS1-Sp33 | 33 | ACACACAAGCTCCTCTCCTC (SEQ ID NO: 677) |
| EPAS1-Sp34 | 34 | CAAGCTCCTCTCCTCAGGTA (SEQ ID NO: 678) |
| EPAS1-Sp35 | 35 | TGCTGGCCTTACCTGAGGAG (SEQ ID NO: 679) |
| EPAS1-Sp36 | 36 | GAGCCTGCTGGCCTTACCTG (SEQ ID NO: 680) |
| EPAS1-Sp37 | 37 | GACTCGTTTTCAGAGCAAAC (SEQ ID NO: 681) |
| EPAS1-Sp38 | 38 | CTGCTGGTCAGCTTCGGCTT (SEQ ID NO: 682) |
| EPAS1-Sp39 | 39 | AGCCGAAGCTGACCAGCAGA (SEQ ID NO: 683) |
| EPAS1-Sp40 | 40 | GTCCATCTGCTGGTCAGCTT (SEQ ID NO: 684) |
| EPAS1-Sp41 | 41 | GGTACAAGTTGTCCATCTGC (SEQ ID NO: 685) |

TABLE 12-continued

Target sequences of EPAS1-gene for SpCas9

| Gene | No. | Target sequence |
|---|---|---|
| EPAS1-Sp42 | 42 | CAACTTGTACCTGAAAGCCT (SEQ ID NO: 686) |
| EPAS1-Sp43 | 43 | CITGTACCTGAAAGCCTTGG (SEQ ID NO: 687) |
| EPAS1-Sp44 | 44 | TTGTACCTGAAAGCCTTGGA (SEQ ID NO: 688) |
| EPAS1-Sp45 | 45 | TGAAACCCTCCAAGGCTTTC (SEQ ID NO: 689) |
| EPAS1-Sp46 | 46 | CACGGCAATGAAACCCTCCA (SEQ ID NO: 690) |
| EPAS1-Sp47 | 47 | CTTGGAGGGTTTCATTGCCG (SEQ ID NO: 691) |
| EPAS1-Sp48 | 48 | ATTGCCGTGGTGACCCAAGA (SEQ ID NO: 692) |
| EPAS1-Sp49 | 49 | GTCGCCATCTTGGGTCACCA (SEQ ID NO: 693) |
| EPAS1-Sp50 | 50 | AAAGATCATGTCGCCATCTT (SEQ ID NO: 694) |
| EPAS1-Sp51 | 51 | GAAAGATCATGTCGCCATCT (SEQ ID NO: 695) |
| EPAS1-Sp52 | 52 | AGAAAACATCAGCAAGTICA (SEQ ID NO: 696) |
| EPAS1-Sp53 | 53 | GAAAACATCAGCAAGTTCAT (SEQ ID NO: 697) |
| EPAS1-Sp54 | 54 | CAAGTTCATGGGACTTACAC (SEQ ID NO: 698) |
| EPAS1-Sp55 | 55 | TTGAAACAGGTGGAGCTAAC (SEQ ID NO: 699) |
| EPAS1-Sp56 | 56 | CACTCATCCCTGCGACCATG (SEQ ID NO: 700) |
| EPAS1-Sp57 | 57 | CGAATCTCCTCATGGTCGCA (SEQ ID NO: 701) |
| EPAS1-Sp58 | 58 | ACGAATCTCCTCATGGTCGC (SEQ ID NO: 702) |
| EPAS1-Sp59 | 59 | GGTTCTCACGAATCTCCTCA (SEQ ID NO: 703) |
| EPAS1-Sp60 | 60 | GAGAACCTGAGTCTCAAAAA (SEQ ID NO: 704) |
| EPAS1-Sp61 | 61 | GGATACCATTTTTGAGACTC (SEQ ID NO: 705) |
| EPAS1-Sp62 | 62 | ATCCTTCCACATCCAGGCTC (SEQ ID NO: 706) |
| EPAS1-Sp63 | 63 | CCACATCCAGGCTCTGGITT (SEQ ID NO: 707) |
| EPAS1-Sp64 | 64 | CACATCCAGGCTCTGGTTTT (SEQ ID NO: 708) |
| EPAS1-Sp65 | 65 | TTTTTCCCAAAACCAGAGCC (SEQ ID NO: 709) |
| EPAS1-Sp66 | 66 | GCAAAGACATGTCCACAGAG (SEQ ID NO: 710) |
| EPAS1-Sp67 | 67 | CAAAGACATGTCCACAGAGC (SEQ ID NO: 711) |
| EPAS1-Sp68 | 68 | CATGAAGAAGTCCCGCTCTG (SEQ ID NO: 712) |
| EPAS1-Sp69 | 69 | CAGAGCGGGACTTCTTCATG (SEQ ID NO: 713) |
| EPAS1-Sp70 | 70 | CTTCATGAGGATGAAGTGCA (SEQ ID NO: 714) |
| EPAS1-Sp71 | 71 | AAGTGCACGGTCACCAACAG (SEQ ID NO: 715) |
| EPAS1-Sp72 | 72 | GTTGACAGTACGGCCTCTGT (SEQ ID NO: 716) |
| EPAS1-Sp73 | 73 | CTGACTTGAGGTTGACAGTA (SEQ ID NO: 717) |
| EPAS1-Sp74 | 74 | TCAACCTCAAGTCAGCCACC (SEQ ID NO: 718) |
| EPAS1-Sp75 | 75 | CCTCAAGTCAGCCACCTGGA (SEQ ID NO: 719) |
| EPAS1-Sp76 | 76 | CCTTCCAGGTGGCTGACTTG (SEQ ID NO: 720) |
| EPAS1-Sp77 | 77 | AAGTCAGCCACCTGGAAGGT (SEQ ID NO: 721) |
| EPAS1-Sp78 | 78 | AGTCAGCCACCTGGAAGGTA (SEQ ID NO: 722) |
| EPAS1-Sp79 | 79 | ATGTTGCCCTACCTTCCAGG (SEQ ID NO: 723) |

TABLE 12-continued

Target sequences of EPAS1-gene for SpCas9

| Gene | No. | Target sequence |
|---|---|---|
| EPAS1-Sp80 | 80 | CTGATGTTGCCCTACCTTCC (SEQ ID NO: 724) |
| EPAS1-Sp81 | 81 | GTCTCAGGTCTTGCACTGCA (SEQ ID NO: 725) |
| EPAS1-Sp82 | 82 | TCTCAGGTCTTGCACTGCAC (SEQ ID NO: 726) |
| EPAS1-Sp83 | 83 | GGTCTTGCACTGCACGGGCC (SEQ ID NO: 727) |
| EPAS1-Sp84 | 84 | AGTTGTTGTAGACTTTCACC (SEQ ID NO: 728) |
| EPAS1-Sp85 | 85 | CACACAGACTATTGTGAGGA (SEQ ID NO: 729) |
| EPAS1-Sp86 | 86 | CCTCCTCACAATAGTCTGTG (SEQ ID NO: 730) |
| EPAS1-Sp87 | 87 | CCACACAGACTATTGTGAGG (SEQ ID NO: 731) |
| EPAS1-Sp88 | 88 | TAGCCACACAGACTATTGTG (SEQ ID NO: 732) |
| EPAS1-Sp89 | 89 | CAATAGTCTGTGTGGCTACA (SEQ ID NO: 733) |
| EPAS1-Sp90 | 90 | ATGATGAGGCAGGACAGCAG (SEQ ID NO: 734) |
| EPAS1-Sp91 | 91 | GATGATGAGGCAGGACAGCA (SEQ ID NO: 735) |
| EPAS1-Sp92 | 92 | TGATGATGAGGCAGGACAGC (SEQ ID NO: 736) |
| EPAS1-Sp93 | 93 | TTCACACATGATGATGAGGC (SEQ ID NO: 737) |
| EPAS1-Sp94 | 94 | TTGGTTCACACATGATGATG (SEQ ID NO: 738) |
| EPAS1-Sp95 | 95 | ATGTGGGATGGGTGCTGGAT (SEQ ID NO: 739) |
| EPAS1-Sp96 | 96 | AATCCAGCACCCATCCCACA (SEQ ID NO: 740) |
| EPAS1-Sp97 | 97 | TGTCCATGTGGGATGGGTGC (SEQ ID NO: 741) |
| EPAS1-Sp98 | 98 | GGGGGATGTCCATGTGGGAT (SEQ ID NO: 742) |
| EPAS1-Sp99 | 99 | AGGGGGATGTCCATGTGGGA (SEQ ID NO: 743) |
| EPAS1-Sp100 | 100 | ATCCCACATGGACATCCCCC (SEQ ID NO: 744) |
| EPAS1-Sp101 | 101 | ATCCAGGGGGATGTCCATGT (SEQ ID NO: 745) |
| EPAS1-Sp102 | 102 | TATCCAGGGGGATGTCCATG (SEQ ID NO: 746) |
| EPAS1-Sp103 | 103 | GGAAGGTCTTGCTATCCAGG (SEQ ID NO: 747) |
| EPAS1-Sp104 | 104 | AGGAAGGTCTTGCTATCCAG (SEQ ID NO: 748) |
| EPAS1-Sp105 | 105 | CAGGAAGGTCTTGCTATCCA (SEQ ID NO: 749) |
| EPAS1-Sp106 | 106 | TCAGGAAGGTCTTGCTATCC (SEQ ID NO: 750) |
| EPAS1-Sp107 | 107 | CATGCTGTGGCGGCTCAGGA (SEQ ID NO: 751) |
| EPAS1-Sp108 | 108 | CTTCCTGAGCCGCCACAGCA (SEQ ID NO: 752) |
| EPAS1-Sp109 | 109 | TGTCCATGCTGTGGCGGCTC (SEQ ID NO: 753) |
| EPAS1-Sp110 | 110 | ACTTCATGTCCATGCTGTGG (SEQ ID NO: 754) |
| EPAS1-Sp111 | 111 | TGAACTTCATGTCCATGCTG (SEQ ID NO: 755) |
| EPAS1-Sp112 | 112 | AGTTCACCTACTGTGATGAC (SEQ ID NO: 756) |
| EPAS1-Sp113 | 113 | CACCTACTGTGATGACAGGT (SEQ ID NO: 757) |
| EPAS1-Sp114 | 114 | ACCTACTGTGATGACAGGTA (SEQ ID NO: 758) |
| EPAS1-Sp115 | 115 | CCCCTACCTGTCATCACAGT (SEQ ID NO: 759) |
| EPAS1-Sp116 | 116 | CTCAGAATCACAGAACTGAT (SEQ ID NO: 760) |
| EPAS1-Sp117 | 117 | ACTGATTGGTTACCACCCTG (SEQ ID NO: 761) |

TABLE 12-continued

Target sequences of EPAS1-gene for SpCas9

| Gene | No. | Target sequence |
|---|---|---|
| EPAS1-Sp118 | 118 | TACCACCCTGAGGAGCTGCT (SEQ ID NO: 762) |
| EPAS1-Sp119 | 119 | GGCCAAGCAGCTCCTCAGGG (SEQ ID NO: 763) |
| EPAS1-Sp120 | 120 | AGCGGCCAAGCAGCTCCTCA (SEQ ID NO: 764) |
| EPAS1-Sp121 | 121 | GAGCGGCCAAGCAGCTCCTC (SEQ ID NO: 765) |
| EPAS1-Sp122 | 122 | GGTAGAATTCATAGGCTGAG (SEQ ID NO: 766) |
| EPAS1-Sp123 | 123 | TAGCGCATGGTAGAATTCAT (SEQ ID NO: 767) |
| EPAS1-Sp124 | 124 | TGTTCTCGGAGTCTAGCGCA (SEQ ID NO: 768) |
| EPAS1-Sp125 | 125 | GTGACTCTTGGTCATGTTCT (SEQ ID NO: 769) |
| EPAS1-Sp126 | 126 | CTCACAGTTCTGGTGACTCT (SEQ ID NO: 770) |
| EPAS1-Sp127 | 127 | ACTCCTGGAACTCACAGTTC (SEQ ID NO: 771) |
| EPAS1-Sp128 | 128 | TCCTCCCCTAGTGTGCACCA (SEQ ID NO: 772) |
| EPAS1-Sp129 | 129 | CCTCCCCTAGTGTGCACCAA (SEQ ID NO: 773) |
| EPAS1-Sp130 | 130 | CTGACCCTTGGTGCACACTA (SEQ ID NO: 774) |
| EPAS1-Sp131 | 131 | CCTAGTGTGCACCAAGGGTC (SEQ ID NO: 775) |
| EPAS1-Sp132 | 132 | CCTGACCCTTGGTGCACACT (SEQ ID NO: 776) |
| EPAS1-Sp133 | 133 | ACCAAGGGTCAGGTAGTAAG (SEQ ID NO: 777) |
| EPAS1-Sp134 | 134 | GCCACTTACTACCTGACCCT (SEQ ID NO: 778) |
| EPAS1-Sp135 | 135 | AGGTAGTAAGTGGCCAGTAC (SEQ ID NO: 779) |
| EPAS1-Sp136 | 136 | GCTTTGCGAGCATCCGGTAC (SEQ ID NO: 780) |
| EPAS1-Sp137 | 137 | TACCGGATGCTCGCAAAGCA (SEQ ID NO: 781) |
| EPAS1-Sp138 | 138 | ACCGGATGCTCGCAAAGCAT (SEQ ID NO: 782) |
| EPAS1-Sp139 | 139 | CCGGATGCTCGCAAAGCATG (SEQ ID NO: 783) |
| EPAS1-Sp140 | 140 | CCCCATGCTTTGCGAGCATC (SEQ ID NO: 784) |
| EPAS1-Sp141 | 141 | CGGATGCTCGCAAAGCATGG (SEQ ID NO: 785) |
| EPAS1-Sp142 | 142 | CAAAGCATGGGGGCTACGTG (SEQ ID NO: 786) |
| EPAS1-Sp143 | 143 | GCATGGGGGCTACGTGTGGC (SEQ ID NO: 787) |
| EPAS1-Sp144 | 144 | CTACGTGTGGCTGGAGACCC (SEQ ID NO: 788) |
| EPAS1-Sp145 | 145 | TACGTGTGGCTGGAGACCCA (SEQ ID NO: 789) |
| EPAS1-Sp146 | 146 | ACGTGTGGCTGGAGACCCAG (SEQ ID NO: 790) |
| EPAS1-Sp147 | 147 | GTGGCTGGAGACCCAGGGGA (SEQ ID NO: 791) |
| EPAS1-Sp148 | 148 | GTTGTAGATGACCGTCCCCT (SEQ ID NO: 792) |
| EPAS1-Sp149 | 149 | GGTTGTAGATGACCGTCCCC (SEQ ID NO: 793) |
| EPAS1-Sp150 | 150 | ACTGGGGCTGCAGGTTGCGA (SEQ ID NO: 794) |
| EPAS1-Sp151 | 151 | CACTGGGGCTGCAGGTTGCG (SEQ ID NO: 795) |
| EPAS1-Sp152 | 152 | ACATGATGCACTGGGGCTGC (SEQ ID NO: 796) |
| EPAS1-Sp153 | 153 | TTGACACACATGATGCACTG (SEQ ID NO: 797) |
| EPAS1-Sp154 | 154 | GTTGACACACATGATGCACT (SEQ ID NO: 798) |
| EPAS1-Sp155 | 155 | AGTTGACACACATGATGCAC (SEQ ID NO: 799) |

TABLE 12-continued

Target sequences of EPAS1-gene for SpCas9

| Gene | No. | Target sequence |
|---|---|---|
| EPAS1-Sp156 | 156 | TGTGTGTCAACTACGTCCTG (SEQ ID NO: 800) |
| EPAS1-Sp157 | 157 | AGCCCTCACATGCTTACCTC (SEQ ID NO: 801) |
| EPAS1-Sp158 | 158 | TGAGATTGAGAAGAATGACG (SEQ ID NO: 802) |
| EPAS1-Sp159 | 159 | GAATGACGTGGTGTTCTCCA (SEQ ID NO: 803) |
| EPAS1-Sp160 | 160 | CAGGGATTCAGTCTGGTCCA (SEQ ID NO: 804) |
| EPAS1-Sp161 | 161 | GCTTGAACAGGGATTCAGTC (SEQ ID NO: 805) |
| EPAS1-Sp162 | 162 | CATCAGGTGGGGCTTGAACA (SEQ ID NO: 806) |
| EPAS1-Sp163 | 163 | CCTGTTCAAGCCCCACCTGA (SEQ ID NO: 807) |
| EPAS1-Sp164 | 164 | CCATCAGGTGGGGCTTGAAC (SEQ ID NO: 808) |
| EPAS1-Sp165 | 165 | CTGTTCATGGCCATCAGGTG (SEQ ID NO: 809) |
| EPAS1-Sp166 | 166 | GCTGTTCATGGCCATCAGGT (SEQ ID NO: 810) |
| EPAS1-Sp167 | 167 | TGCTGTTCATGGCCATCAGG (SEQ ID NO: 811) |
| EPAS1-Sp168 | 168 | AGATGCTGTTCATGGCCATC (SEQ ID NO: 812) |
| EPAS1-Sp169 | 169 | GCTATCAAAGATGCTGTTCA (SEQ ID NO: 813) |
| EPAS1-Sp170 | 170 | AACAGCATCTTTGATAGCAG (SEQ ID NO: 814) |
| EPAS1-Sp171 | 171 | CATCTTTGATAGCAGTGGCA (SEQ ID NO: 815) |
| EPAS1-Sp172 | 172 | ATCTTIGATAGCAGTGGCAA (SEQ ID NO: 816) |
| EPAS1-Sp173 | 173 | TCTTTGATAGCAGTGGCAAG (SEQ ID NO: 817) |
| EPAS1-Sp174 | 174 | CTTTGATAGCAGTGGCAAGG (SEQ ID NO: 818) |
| EPAS1-Sp175 | 175 | CTTCCTATTCACCAAGCTAA (SEQ ID NO: 819) |
| EPAS1-Sp176 | 176 | CCTATTCACCAAGCTAAAGG (SEQ ID NO: 820) |
| EPAS1-Sp177 | 177 | CCTCCTTTAGCTTGGTGAAT (SEQ ID NO: 821) |
| EPAS1-Sp178 | 178 | CTCGGGCTCCTCCTTTAGCT (SEQ ID NO: 822) |
| EPAS1-Sp179 | 179 | CAAGCTAAAGGAGGAGCCCG (SEQ ID NO: 823) |
| EPAS1-Sp180 | 180 | AAAGGAGGAGCCCGAGGAGC (SEQ ID NO: 824) |
| EPAS1-Sp181 | 181 | GCCCGAGGAGCTGGCCCAGC (SEQ ID NO: 825) |
| EPAS1-Sp182 | 182 | GCCAGCTGGGCCAGCTCCTC (SEQ ID NO: 826) |
| EPAS1-Sp183 | 183 | AGCCAGCTGGGCCAGCTCCT (SEQ ID NO: 827) |
| EPAS1-Sp184 | 184 | GCCCAGCTGGCTCCCACCCC (SEQ ID NO: 828) |
| EPAS1-Sp185 | 185 | TCCTGGGGTGGGAGCCAGCT (SEQ ID NO: 829) |
| EPAS1-Sp186 | 186 | CTCCTGGGGTGGGAGCCACC (SEQ ID NO: 830) |
| EPAS1-Sp187 | 187 | ATGATGGCGTCTCCTGGGGT (SEQ ID NO: 831) |
| EPAS1-Sp188 | 188 | GATGATGGCGTCTCCTGGGG (SEQ ID NO: 832) |
| EPAS1-Sp189 | 189 | AGAGATGATGGCGTCTCCTG (SEQ ID NO: 833) |
| EPAS1-Sp190 | 190 | GAGAGATGATGGCGTCTCCT (SEQ ID NO: 834) |
| EPAS1-Sp191 | 191 | AGAGAGATGATGGCGTCTCC (SEQ ID NO: 835) |
| EPAS1-Sp192 | 192 | AGGAGACGCCATCATCTCTC (SEQ ID NO: 836) |
| EPAS1-Sp193 | 193 | GCCATCATCTCTCTGGATTT (SEQ ID NO: 837) |

TABLE 12-continued

Target sequences of EPAS1-gene for SpCas9

| Gene | No. | Target sequence |
|---|---|---|
| EPAS1-Sp194 | 194 | ACCGAAATCCAGAGAGATGA (SEQ ID NO: 838) |
| EPAS1-Sp195 | 195 | ATCATCTCTCTGGATTTCGG (SEQ ID NO: 839) |
| EPAS1-Sp196 | 196 | TCATCTCTCTGGATTTCGGT (SEQ ID NO: 840) |
| EPAS1-Sp197 | 197 | CTCGAAGTTCTGATTCCCTG (SEQ ID NO: 841) |
| EPAS1-Sp198 | 198 | CACAGGGAATCAGAACTTCG (SEQ ID NO: 842) |
| EPAS1-Sp199 | 199 | TTCGAGGAGTCCTCAGCCTA (SEQ ID NO: 843) |
| EPAS1-Sp200 | 200 | GGAGTCCTCAGCCTATGGCA (SEQ ID NO: 844) |
| EPAS1-Sp201 | 201 | GATGGCCTTGCCATAGGCTG (SEQ ID NO: 845) |
| EPAS1-Sp202 | 202 | GGGCAGGATGGCCTTGCCAT (SEQ ID NO: 846) |
| EPAS1-Sp203 | 203 | TGGCTGGCTCGGGGGCAGGA (SEQ ID NO: 847) |
| EPAS1-Sp204 | 204 | TCCTGCCCCCGAGCCAGCCA (SEQ ID NO: 848) |
| EPAS1-Sp205 | 205 | CCTGCCCCCGAGCCAGCCAT (SEQ ID NO: 849) |
| EPAS1-Sp206 | 206 | CCCATGGCTGGCTCGGGGGC (SEQ ID NO: 850) |
| EPAS1-Sp207 | 207 | GTGGCCCATGGCTGGCTCGG (SEQ ID NO: 851) |
| EPAS1-Sp208 | 208 | CGTGGCCCATGGCTGGCTCG (SEQ ID NO: 852) |
| EPAS1-Sp209 | 209 | CCCGAGCCAGCCATGGGCCA (SEQ ID NO: 853) |
| EPAS1-Sp210 | 210 | CCGTGGCCCATGGCTGGCTC (SEQ ID NO: 854) |
| EPAS1-Sp211 | 211 | TCCGTGGCCCATGGCTGGCT (SEQ ID NO: 855) |
| EPAS1-Sp212 | 212 | TCAACTCCGTGGCCCATGGC (SEQ ID NO: 856) |
| EPAS1-Sp213 | 213 | AGCCATGGGCCACGGAGTTG (SEQ ID NO: 857) |
| EPAS1-Sp214 | 214 | CTCCTCAACTCCGTGGCCCA (SEQ ID NO: 858) |
| EPAS1-Sp215 | 215 | GCTGTGGCTCCTCAACTCCG (SEQ ID NO: 859) |
| EPAS1-Sp216 | 216 | GAGCCACAGCACCCAGAGCG (SEQ ID NO: 860) |
| EPAS1-Sp217 | 217 | CAGCCTCGCTCTGGGTGCTG (SEQ ID NO: 861) |
| EPAS1-Sp218 | 218 | CACAGCACCCAGAGCGAGGC (SEQ ID NO: 862) |
| EPAS1-Sp219 | 219 | ACAGCACCCAGAGCGAGGCT (SEQ ID NO: 863) |
| EPAS1-Sp220 | 220 | CAGGCTCCCAGCCTCGCTCT (SEQ ID NO: 864) |
| EPAS1-Sp221 | 221 | GCAGGCTCCCAGCCTCGCTC (SEQ ID NO: 865) |
| EPAS1-Sp222 | 222 | GGGGCACGGTGAAGGCAGGC (SEQ ID NO: 866) |
| EPAS1-Sp223 | 223 | GCCTGCCTTCACCGTGCCCC (SEQ ID NO: 867) |
| EPAS1-Sp224 | 224 | GCCTGGGGCACGGTGAAGGC (SEQ ID NO: 868) |
| EPAS1-Sp225 | 225 | AGCTGCCTGGGGCACGGTGA (SEQ ID NO: 869) |
| EPAS1-Sp226 | 226 | CGGGGCAGCTGCCTGGGGCA (SEQ ID NO: 870) |
| EPAS1-Sp227 | 227 | CGTGCCCCAGGCAGCTGCCC (SEQ ID NO: 871) |
| EPAS1-Sp228 | 228 | GTGCCCCAGGCAGCTGCCCC (SEQ ID NO: 872) |
| EPAS1-Sp229 | 229 | CTGCCCGGGGCAGCTGCCTG (SEQ ID NO: 873) |
| EPAS1-Sp230 | 230 | GCTGCCCGGGGCAGCTGCCT (SEQ ID NO: 874) |
| EPAS1-Sp231 | 231 | TGCTGCCCGGGGCAGCTGCC (SEQ ID NO: 875) |

TABLE 12-continued

Target sequences of EPAS1-gene for SpCas9

| Gene | No. | Target sequence |
|------|-----|-----------------|
| EPAS1-Sp232 | 232 | ACTGGGGGTGGTGCTGCCCG (SEQ ID NO: 876) |
| EPAS1-Sp233 | 233 | CACTGGGGGTGGTGCTGCCC (SEQ ID NO: 877) |
| EPAS1-Sp234 | 234 | GCACTGGGGGTGGTGCTGCC (SEQ ID NO: 878) |
| EPAS1-Sp235 | 235 | GCTGCTGGTGGCACTGGGGG (SEQ ID NO: 879) |
| EPAS1-Sp236 | 236 | GCTGCTGCTGGTGGCACTGG (SEQ ID NO: 880) |
| EPAS1-Sp237 | 237 | TGCTGCTGCTGGTGGCACTG (SEQ ID NO: 881) |
| EPAS1-Sp238 | 238 | CTGCTGCTGCTGGTGGCACT (SEQ ID NO: 882) |
| EPAS1-Sp239 | 239 | GCTGCTGCTGCTGGTGGCAC (SEQ ID NO: 883) |
| EPAS1-Sp240 | 240 | GCAGCTGCTGCTGCTGCTGG (SEQ ID NO: 884) |
| EPAS1-Sp241 | 241 | CAGCAGCAGCAGCTGCTCCA (SEQ ID NO: 885) |
| EPAS1-Sp242 | 242 | TCTTCAGGGCTATTGGGCTA (SEQ ID NO: 886) |
| EPAS1-Sp243 | 243 | GTCTTCAGGGCTATTGGGCT (SEQ ID NO: 887) |
| EPAS1-Sp244 | 244 | TAATAGTCTTCAGGGCTATT (SEQ ID NO: 888) |
| EPAS1-Sp245 | 245 | GTAATAGTCTTCAGGGCTAT (SEQ ID NO: 889) |
| EPAS1-Sp246 | 246 | AAGATGTGTAATAGTCTTCA (SEQ ID NO: 890) |
| EPAS1-Sp247 | 247 | AAAGATGTGTAATAGTCTTC (SEQ ID NO: 891) |
| EPAS1-Sp248 | 248 | TGAAGACTATTACACATCTT (SEQ ID NO: 892) |
| EPAS1-Sp249 | 249 | TCTCAATCACTTCAATCTTC (SEQ ID NO: 893) |
| EPAS1-Sp250 | 250 | GATTGAGAAGCTCTTCGCCA (SEQ ID NO: 894) |
| EPAS1-Sp251 | 251 | GCTCTTCGCCATGGACACAG (SEQ ID NO: 895) |
| EPAS1-Sp252 | 252 | CGCCATGGACACAGAGGCCA (SEQ ID NO: 896) |
| EPAS1-Sp253 | 253 | GTCCTTGGCCTCTGTGTCCA (SEQ ID NO: 897) |
| EPAS1-Sp254 | 254 | CTGGGTACTGCATTGGTCCT (SEQ ID NO: 898) |
| EPAS1-Sp255 | 255 | CAAGGACCAATGCAGTACCC (SEQ ID NO: 899) |
| EPAS1-Sp256 | 256 | CATCTACCTGGGTACTGCAT (SEQ ID NO: 900) |
| EPAS1-Sp257 | 257 | AGCTCATTGAAATCCGTCTG (SEQ ID NO: 901) |
| EPAS1-Sp258 | 258 | TCAGACGGATTTCAATGAGC (SEQ ID NO: 902) |
| EPAS1-Sp259 | 259 | GGATTTCAATGAGCIGGACT (SEQ ID NO: 903) |
| EPAS1-Sp260 | 260 | TGAGCTGGACTTGGAGACAC (SEQ ID NO: 904) |
| EPAS1-Sp261 | 261 | ACTGGCACCCTATATCCCCA (SEQ ID NO: 905) |
| EPAS1-Sp262 | 262 | GCACCCTATATCCCCATGGA (SEQ ID NO: 906) |
| EPAS1-Sp263 | 263 | CACCCTATATCCCCATGGAC (SEQ ID NO: 907) |
| EPAS1-Sp264 | 264 | ACCCTATATCCCCATGGACG (SEQ ID NO: 908) |
| EPAS1-Sp265 | 265 | TCCCCGTCCATGGGATATA (SEQ ID NO: 909) |
| EPAS1-Sp266 | 266 | TTCCCCGTCCATGGGGATAT (SEQ ID NO: 910) |
| EPAS1-Sp267 | 267 | GGAAGTCTTCCCCGTCCATG (SEQ ID NO: 911) |
| EPAS1-Sp268 | 268 | TGGAAGTCTTCCCCGTCCAT (SEQ ID NO: 912) |
| EPAS1-Sp269 | 269 | CTGGAAGTCTTCCCCGTCCA (SEQ ID NO: 913) |

TABLE 12-continued

Target sequences of EPAS1-gene for SpCas9

| Gene | No. | Target sequence |
|---|---|---|
| EPAS1-Sp270 | 270 | CGGGGCAGATGGGGCTTAGC (SEQ ID NO: 914) |
| EPAS1-Sp271 | 271 | GCTAAGCCCCATCTGCCCCG (SEQ ID NO: 915) |
| EPAS1-Sp272 | 272 | GCCCCATCTGCCCCGAGGAG (SEQ ID NO: 916) |
| EPAS1-Sp273 | 273 | GCCGCTCCTCGGGGCAGATG (SEQ ID NO: 917) |
| EPAS1-Sp274 | 274 | AGCCGCTCCTCGGGGCAGAT (SEQ ID NO: 918) |
| EPAS1-Sp275 | 275 | GAGCCGCTCCTCGGGGCAGA (SEQ ID NO: 919) |
| EPAS1-Sp276 | 276 | CTGCCCCGAGGAGCGGCTCT (SEQ ID NO: 920) |
| EPAS1-Sp277 | 277 | CCCCGAGGAGCGGCTCTTGG (SEQ ID NO: 921) |
| EPAS1-Sp278 | 278 | CCGCCAAGAGCCGCTCCTCG (SEQ ID NO: 922) |
| EPAS1-Sp279 | 279 | TCCGCCAAGAGCCGCTCCTC (SEQ ID NO: 923) |
| EPAS1-Sp280 | 280 | CTCCGCCAAGAGCCGCTCCT (SEQ ID NO: 924) |
| EPAS1-Sp281 | 281 | AGTGCTGGGGGTGGACTGT (SEQ ID NO: 925) |
| EPAS1-Sp282 | 282 | CAGTGCTGGGGGTGGACTG (SEQ ID NO: 926) |
| EPAS1-Sp283 | 283 | ACTGAAGCAGTGCTGGGGGG (SEQ ID NO: 927) |
| EPAS1-Sp284 | 284 | GGCACTGAAGCAGTGCTGGG (SEQ ID NO: 928) |
| EPAS1-Sp285 | 285 | TGGCACTGAAGCAGTGCTGG (SEQ ID NO: 929) |
| EPAS1-Sp286 | 286 | ATGGCACTGAAGCAGTGCTG (SEQ ID NO: 930) |
| EPAS1-Sp287 | 287 | CATGGCACTGAAGCAGTGCT (SEQ ID NO: 931) |
| EPAS1-Sp288 | 288 | TCATGGCACTGAAGCAGTGC (SEQ ID NO: 932) |
| EPAS1-Sp289 | 289 | TGGCTGGAAGATGTTTGTCA (SEQ ID NO: 933) |
| EPAS1-Sp290 | 290 | GACAAACATCTTCCAGCCAC (SEQ ID NO: 934) |
| EPAS1-Sp291 | 291 | GGGCTACAGGGGCCAGTGGC (SEQ ID NO: 935) |
| EPAS1-Sp292 | 292 | TGCGGGCTACAGGGGCCAG (SEQ ID NO: 936) |
| EPAS1-Sp293 | 293 | GGGACTGTGCGGGCTACAG (SEQ ID NO: 937) |
| EPAS1-Sp294 | 294 | AGGGACTGTGCGGGCTACA (SEQ ID NO: 938) |
| EPAS1-Sp295 | 295 | AAGGGACTGTGCGGGCTAC (SEQ ID NO: 939) |
| EPAS1-Sp296 | 296 | CAGGAGGAAGGGACTGTGCG (SEQ ID NO: 940) |
| EPAS1-Sp297 | 297 | CCCGCACAGTCCCTTCCTCC (SEQ ID NO: 941) |
| EPAS1-Sp298 | 298 | CCAGGAGGAAGGGACTGTGC (SEQ ID NO: 942) |
| EPAS1-Sp299 | 299 | TCCAGGAGGAAGGGACTGTG (SEQ ID NO: 943) |
| EPAS1-Sp300 | 300 | TGAAACTTGTCCAGGAGGAA (SEQ ID NO: 944) |
| EPAS1-Sp301 | 301 | CTGAAACTTGTCCAGGAGGA (SEQ ID NO: 945) |
| EPAS1-Sp302 | 302 | GCTGCTGAAACTTGTCCAGG (SEQ ID NO: 946) |
| EPAS1-Sp303 | 303 | GCTGCTGCTGAAACTTGTCC (SEQ ID NO: 947) |
| EPAS1-Sp304 | 304 | GGACAAGTTTCAGCAGCAGC (SEQ ID NO: 948) |
| EPAS1-Sp305 | 305 | AGAAGACAGAGCCCGAGCAC (SEQ ID NO: 949) |
| EPAS1-Sp306 | 306 | GÅGGACATGGGCCGGTGCTC (SEQ ID NO: 950) |
| EPAS1-Sp307 | 307 | GGAGGACATGGGCCGGTGCT (SEQ ID NO: 951) |

TABLE 12-continued

Target sequences of EPAS1-gene for SpCas9

| Gene | No. | Target sequence |
|---|---|---|
| EPAS1-Sp308 | 308 | AGAAGATGGAGGACATGGGC (SEQ ID NO: 952) |
| EPAS1-Sp309 | 309 | TCAAAGAAGATGGAGGACAT (SEQ ID NO: 953) |
| EPAS1-Sp310 | 310 | ATCAAAGAAGATGGAGGACA (SEQ ID NO: 954) |
| EPAS1-Sp311 | 311 | TCCTCCATCTTCTTTGATGC (SEQ ID NO: 955) |
| EPAS1-Sp312 | 312 | TCCGGCATCAAAGAAGATGG (SEQ ID NO: 956) |
| EPAS1-Sp313 | 313 | GCTTCCGGCATCAAAGAAGA (SEQ ID NO: 957) |
| EPAS1-Sp314 | 314 | TGGCAGGGATGCTTTGCTTC (SEQ ID NO: 958) |
| EPAS1-Sp315 | 315 | GCATCCCTGCCACCGTGCTG (SEQ ID NO: 959) |
| EPAS1-Sp316 | 316 | CTGGCCACAGCACGGTGGCA (SEQ ID NO: 960) |
| EPAS1-Sp317 | 317 | CCTGCCACCGTGCTGTGGCC (SEQ ID NO: 961) |
| EPAS1-Sp318 | 318 | CCTGGCCACAGCACGGTGGC (SEQ ID NO: 962) |
| EPAS1-Sp319 | 319 | CTGGCCTGGCCACAGCACGG (SEQ ID NO: 963) |
| EPAS1-Sp320 | 320 | GTGCTGGCCTGGCCACAGCA (SEQ ID NO: 964) |
| EPAS1-Sp321 | 321 | AAGAGAGAGGGGTGCTGGCC (SEQ ID NO: 965) |
| EPAS1-Sp322 | 322 | CATGGAAGAGAGAGGGGTGC (SEQ ID NO: 966) |
| EPAS1-Sp323 | 323 | CAGCACCCCTCTCTCTTCCA (SEQ ID NO: 967) |
| EPAS1-Sp324 | 324 | AGCACCCCTCTCTCTTCCAT (SEQ ID NO: 968) |
| EPAS1-Sp325 | 325 | GCACCCCTCTCTCTTCCATG (SEQ ID NO: 969) |
| EPAS1-Sp326 | 326 | CACCCCTCTCTCTTCCATGG (SEQ ID NO: 970) |
| EPAS1-Sp327 | 327 | ACCCCTCTCTCTTCCATGGG (SEQ ID NO: 971) |
| EPAS1-Sp328 | 328 | GCCCCCCATGGAAGAGAGAG (SEQ ID NO: 972) |
| EPAS1-Sp329 | 329 | TGCCCCCCATGGAAGAGAGA (SEQ ID NO: 973) |
| EPAS1-Sp330 | 330 | CTGCCCCCCATGGAAGAGAG (SEQ ID NO: 974) |
| EPAS1-Sp331 | 331 | GGTATTGGATCTGCCCCCCA (SEQ ID NO: 975) |
| EPAS1-Sp332 | 332 | GGGGCAGATCCAATACCCAG (SEQ ID NO: 976) |
| EPAS1-Sp333 | 333 | ATCTGGGGCCACTGGGTAT (SEQ ID NO: 977) |
| EPAS1-Sp334 | 334 | TGGTGGATCTGGGGGCCACT (SEQ ID NO: 978) |
| EPAS1-Sp335 | 335 | ATGGTGGATCTGGGGGCCAC (SEQ ID NO: 979) |
| EPAS1-Sp336 | 336 | AAATGTAATGGTGGATCTGG (SEQ ID NO: 980) |
| EPAS1-Sp337 | 337 | AAAATGTAATGGTGGATCTG (SEQ ID NO: 981) |
| EPAS1-Sp338 | 338 | CAAAATGTAATGGTGGATCT (SEQ ID NO: 982) |
| EPAS1-Sp339 | 339 | CCAGATCCACCATTACATTT (SEQ ID NO: 983) |
| EPAS1-Sp340 | 340 | CCAAAATGTAATGGTGGATC (SEQ ID NO: 984) |
| EPAS1-Sp341 | 341 | CAGATCCACCATTACATTTT (SEQ ID NO: 985) |
| EPAS1-Sp342 | 342 | GTGGGCCCAAAATGTAATGG (SEQ ID NO: 986) |
| EPAS1-Sp343 | 343 | TTTGTGGGCCCAAAATGTAA (SEQ ID NO: 987) |
| EPAS1-Sp344 | 344 | TACATTTTGGGCCCACAAAG (SEQ ID NO: 988) |
| EPAS1-Sp345 | 345 | ACATTTTGGGCCCACAAAGT (SEQ ID NO: 989) |

TABLE 12-continued

Target sequences of EPAS1-gene for SpCas9

| Gene | No. | Target sequence |
|---|---|---|
| EPAS1-Sp346 | 346 | GGGCCCACAAAGTGGGCCGT (SEQ ID NO: 990) |
| EPAS1-Sp347 | 347 | GGCCCACAAAGTGGGCCGTC (SEQ ID NO: 991) |
| EPAS1-Sp348 | 348 | GCCCACAAAGTGGGCCGTCG (SEQ ID NO: 992) |
| EPAS1-Sp349 | 349 | TCCCCGACGGCCCACTTTGT (SEQ ID NO: 993) |
| EPAS1-Sp350 | 350 | ATCCCCGACGGCCCACTTTG (SEQ ID NO: 994) |
| EPAS1-Sp351 | 351 | CTCTGTGCGCTGATCCCCGA (SEQ ID NO: 995) |
| EPAS1-Sp352 | 352 | GGATCAGCGCACAGAGTTCT (SEQ ID NO: 996) |
| EPAS1-Sp353 | 353 | GATCAGCGCACAGAGTTCTT (SEQ ID NO: 997) |
| EPAS1-Sp354 | 354 | GTTCTTGGGAGCAGCGCCGT (SEQ ID NO: 998) |
| EPAS1-Sp355 | 355 | TTCTTGGGAGCAGCGCCGTT (SEQ ID NO: 999) |
| EPAS1-Sp356 | 356 | TCTTGGGAGCAGCGCCGTTG (SEQ ID NO: 1000) |
| EPAS1-Sp357 | 357 | GGAGAGACAGGGGGCCCCAA (SEQ ID NO: 1001) |
| EPAS1-Sp358 | 358 | ACATGGGGTGGAGAGACAGG (SEQ ID NO: 1002) |
| EPAS1-Sp359 | 359 | GACATGGGGTGGAGAGACAG (SEQ ID NO: 1003) |
| EPAS1-Sp360 | 360 | AGACATGGGGTGGAGAGACA (SEQ ID NO: 1004) |
| EPAS1-Sp361 | 361 | GAGACATGGGGTGGAGAGAC (SEQ ID NO: 1005) |
| EPAS1-Sp362 | 362 | TTGAAGGTGGAGACATGGGG (SEQ ID NO: 1006) |
| EPAS1-Sp363 | 363 | GTCTTGAAGGTGGAGACATG (SEQ ID NO: 1007) |
| EPAS1-Sp364 | 364 | TGTCTTGAAGGTGGAGACAT (SEQ ID NO: 1008) |
| EPAS1-Sp365 | 365 | TTGTCTTGAAGGTGGAGACA (SEQ ID NO: 1009) |
| EPAS1-Sp366 | 366 | ATGTCTCCACCITCAAGACA (SEQ ID NO: 1010) |
| EPAS1-Sp367 | 367 | TGCCACTTACCTTGTCTTGA (SEQ ID NO: 1011) |
| EPAS1-Sp368 | 368 | CGGGCTTGGCAGGTCTGCAA (SEQ ID NO: 1012) |
| EPAS1-Sp369 | 369 | GGGCTTGGCAGGTCTGCAAA (SEQ ID NO: 1013) |
| EPAS1-Sp370 | 370 | GGCAGGTCTGCAAAGGGTTT (SEQ ID NO: 1014) |
| EPAS1-Sp371 | 371 | GCAGGTCTGCAAAGGGTTTT (SEQ ID NO: 1015) |
| EPAS1-Sp372 | 372 | CAGGTCTGCAAAGGGTTTTG (SEQ ID NO: 1016) |
| EPAS1-Sp373 | 373 | GCAAAGGGTTTTGGGGCTCG (SEQ ID NO: 1017) |
| EPAS1-Sp374 | 374 | AGGCCCAGACGTGCTGAGTC (SEQ ID NO: 1018) |
| EPAS1-Sp375 | 375 | TGGCCGGACTCAGCACGTCT (SEQ ID NO: 1019) |
| EPAS1-Sp376 | 376 | ATGGCCGGACTCAGCACGTC (SEQ ID NO: 1020) |
| EPAS1-Sp377 | 377 | AGACGTGCTGAGTCCGGCCA (SEQ ID NO: 1021) |
| EPAS1-Sp378 | 378 | TTGGAGAGGGCTACCATGGC (SEQ ID NO: 1022) |
| EPAS1-Sp379 | 379 | CTTGTTGGAGAGGGCTACCA (SEQ ID NO: 1023) |
| EPAS1-Sp380 | 380 | CAGCTTCAGCTTGTIGGAGA (SEQ ID NO: 1024) |
| EPAS1-Sp381 | 381 | TCAGCTTCAGCTTGTTGGAG (SEQ ID NO: 1025) |
| EPAS1-Sp382 | 382 | TCGCTTCAGCTTCAGCTTGT (SEQ ID NO: 1026) |
| EPAS1-Sp383 | 383 | GCTGAAGCTGAAGCGACAGC (SEQ ID NO: 1027) |

TABLE 12-continued

Target sequences of EPAS1-gene for SpCas9

| Gene | No. | Target sequence |
|---|---|---|
| EPAS1-Sp384 | 384 | GTATGAAGAGCAAGCCTTCC (SEQ ID NO: 1028) |
| EPAS1-Sp385 | 385 | CAAGCCTTCCAGGACCTGAG (SEQ ID NO: 1029) |
| EPAS1-Sp386 | 386 | AAGCCTTCCAGGACCTGAGC (SEQ ID NO: 1030) |
| EPAS1-Sp387 | 387 | AGCCTTCCAGGACCTGAGCG (SEQ ID NO: 1031) |
| EPAS1-Sp388 | 388 | CACCCCGCTCAGGTCCTGGA (SEQ ID NO: 1032) |
| EPAS1-Sp389 | 389 | GACTCACCCCGCTCAGGTCC (SEQ ID NO: 1033) |
| EPAS1-Sp390 | 390 | GGGGATGACTCACCCCGCTC (SEQ ID NO: 1034) |
| EPAS1-Sp391 | 391 | TACTCCCAGGGGGACCCACC (SEQ ID NO: 1035) |
| EPAS1-Sp392 | 392 | TCCCAGGGGGACCCACCTGG (SEQ ID NO: 1036) |
| EPAS1-Sp393 | 393 | GCCACCAGGTGGGTCCCCCT (SEQ ID NO: 1037) |
| EPAS1-Sp394 | 394 | TGCCACCAGGTGGGTCCCCC (SEQ ID NO: 1038) |
| EPAS1-Sp395 | 395 | GTGAGGTGCTGCCACCAGGT (SEQ ID NO: 1039) |
| EPAS1-Sp360 | 360 | AGACATGGGGTGGAGAGACA (SEQ ID NO: 1004) |
| EPAS1-Sp361 | 361 | GAGACATGGGGTGGAGAGAC (SEQ ID NO: 1005) |
| EPAS1-Sp362 | 362 | TTGAAGGTGGAGACATGGGG (SEQ ID NO: 1006) |
| EPAS1-Sp363 | 363 | GTCTTGAAGGTGGAGACATG (SEQ ID NO: 1007) |
| EPAS1-Sp364 | 364 | TGTCTTGAAGGTGGAGACAT (SEQ ID NO: 1008) |
| EPAS1-Sp365 | 365 | TTGTCTTGAAGGTGGAGACA (SEQ ID NO: 1009) |
| EPAS1-Sp366 | 366 | ATGTCTCCACCITCAAGACA (SEQ ID NO: 1010) |
| EPAS1-Sp367 | 367 | TGCCACTTACCTTGTCTTGA (SEQ ID NO: 1011) |
| EPAS1-Sp368 | 368 | CGGGCTTGGCAGGTCTGCAA (SEQ ID NO: 1012) |
| EPAS1-Sp369 | 369 | GGGCTTGGCAGGTCTGCAAA (SEQ ID NO: 1013) |
| EPAS1-Sp370 | 370 | GGCAGGTCTGCAAAGGGTTT (SEQ ID NO: 1014) |
| EPAS1-Sp371 | 371 | GCAGGTCTGCAAAGGGTTTT (SEQ ID NO: 1015) |
| EPAS1-Sp372 | 372 | CAGGTCTGCAAAGGGTTTTG (SEQ ID NO: 1016) |
| EPAS1-Sp373 | 373 | GCAAAGGGTTTTGGGGCTCG (SEQ ID NO: 1017) |
| EPAS1-Sp374 | 374 | AGGCCCAGACGTGCTGAGTC (SEQ ID NO: 1018) |
| EPAS1-Sp375 | 375 | TGGCCGGACTCAGCACGTCT (SEQ ID NO: 1019) |
| EPAS1-Sp376 | 376 | ATGGCCGGACTCAGCACGTC (SEQ ID NO: 1020) |
| EPAS1-Sp377 | 377 | AGACGTGCTGAGTCCGGCCA (SEQ ID NO: 1021) |
| EPAS1-Sp378 | 378 | TTGGAGAGGGCTACCATGGC (SEQ ID NO: 1022) |
| EPAS1-Sp379 | 379 | CTTGTTGGAGAGGGCTACCA (SEQ ID NO: 1023) |
| EPAS1-Sp380 | 380 | CAGCTTCAGCTTGTIGGAGA (SEQ ID NO: 1024) |
| EPAS1-Sp381 | 381 | TCAGCTTCAGCTTGTTGGAG (SEQ ID NO: 1025) |
| EPAS1-Sp382 | 382 | TCGCTTCAGCTTCAGCTTGT (SEQ ID NO: 1026) |
| EPAS1-Sp383 | 383 | GCTGAAGCTGAAGCGACAGC (SEQ ID NO: 1027) |
| EPAS1-Sp384 | 384 | GTATGAAGAGCAAGCCTTCC (SEQ ID NO: 1028) |
| EPAS1-Sp385 | 385 | CAAGCCTTCCAGGACCTGAG (SEQ ID NO: 1029) |

TABLE 12-continued

Target sequences of EPAS1-gene for SpCas9

| Gene | No. | Target sequence |
|---|---|---|
| EPAS1-Sp386 | 386 | AAGCCTTCCAGGACCTGAGC (SEQ ID NO: 1030) |
| EPAS1-Sp387 | 387 | AGCCTTCCAGGACCTGAGCG (SEQ ID NO: 1031) |
| EPAS1-Sp388 | 388 | CACCCCGCTCAGGTCCTGGA (SEQ ID NO: 1032) |
| EPAS1-Sp389 | 389 | GACTCACCCCGCTCAGGTCC (SEQ ID NO: 1033) |
| EPAS1-Sp390 | 390 | GGGGATGACTCACCCCGCTC (SEQ ID NO: 1034) |
| EPAS1-Sp391 | 391 | TACTCCCAGGGGACCCACC (SEQ ID NO: 1035) |
| EPAS1-Sp392 | 392 | TCCCAGGGGACCCACCTGG (SEQ ID NO: 1036) |
| EPAS1-Sp393 | 393 | GCCACCAGGTGGGTCCCCCT (SEQ ID NO: 1037) |
| EPAS1-Sp394 | 394 | TGCCACCAGGTGGGTCCCCC (SEQ ID NO: 1038) |
| EPAS1-Sp395 | 395 | GTGAGGTGCTGCCACCAGGT (SEQ ID NO: 1039) |
| EPAS1-Sp396 | 396 | TGTGAGGTGCTGCCACCAGG (SEQ ID NO: 1040) |
| EPAS1-Sp397 | 397 | AAATGTGAGGTGCTGCCACC (SEQ ID NO: 1041) |
| EPAS1-Sp398 | 398 | GCAGCACCTCACATTTGATG (SEQ ID NO: 1042) |
| EPAS1-Sp399 | 399 | CCTCACATTTGATGTGGAAA (SEQ ID NO: 1043) |
| EPAS1-Sp400 | 400 | CCGTTTCCACATCAAATGTG (SEQ ID NO: 1044) |
| EPAS1-Sp401 | 401 | GGAAACGGATGAAGAACCTC (SEQ ID NO: 1045) |
| EPAS1-Sp402 | 402 | GAAACGGATGAAGAACCTCA (SEQ ID NO: 1046) |
| EPAS1-Sp403 | 403 | AAACGGATGAAGAACCTCAG (SEQ ID NO: 1047) |
| EPAS1-Sp404 | 404 | CGGATGAAGAACCTCAGGGG (SEQ ID NO: 1048) |
| EPAS1-Sp405 | 405 | GGATGAAGAACCTCAGGGGT (SEQ ID NO: 1049) |
| EPAS1-Sp406 | 406 | AAGGGCAGCTCCCACCCCTG (SEQ ID NO: 1050) |
| EPAS1-Sp407 | 407 | TGGGAGCTGCCCTTTGATGC (SEQ ID NO: 1051) |
| EPAS1-Sp408 | 408 | GTGGCTTGTCCGGCATCAAA (SEQ ID NO: 1052) |
| EPAS1-Sp409 | 409 | AGTGGCTTGTCCGGCATCAA (SEQ ID NO: 1053) |
| EPAS1-Sp410 | 410 | TTTGCGCTCAGTGGCTTGTC (SEQ ID NO: 1054) |
| EPAS1-Sp411 | 411 | TTGGGTACATTTGCGCTCAG (SEQ ID NO: 1055) |
| EPAS1-Sp412 | 412 | CTGAGCGCAAATGTACCCAA (SEQ ID NO: 1056) |
| EPAS1-Sp413 | 413 | TGTGGCCGCTGCTCACCATT (SEQ ID NO: 1057) |
| EPAS1-Sp414 | 414 | CTGTGGCCGCTGCTCACCAT (SEQ ID NO: 1058) |
| EPAS1-Sp415 | 415 | AGTTCACCCAAAACCCCATG (SEQ ID NO: 1059) |
| EPAS1-Sp416 | 416 | GTTCACCCAAAACCCCATGA (SEQ ID NO: 1060) |
| EPAS1-Sp417 | 417 | TTCACCCAAAACCCCATGAG (SEQ ID NO: 1061) |
| EPAS1-Sp418 | 418 | CAGGCCCCTCATGGGGTTTT (SEQ ID NO: 1062) |
| EPAS1-Sp419 | 419 | CCAAAACCCCATGAGGGGCC (SEQ ID NO: 1063) |
| EPAS1-Sp420 | 420 | CCAGGCCCCTCATGGGGTTT (SEQ ID NO: 1064) |
| EPAS1-Sp421 | 421 | CAAAACCCCATGAGGGGCCT (SEQ ID NO: 1065) |
| EPAS1-Sp422 | 422 | GATGGCCCAGGCCCCTCATG (SEQ ID NO: 1066) |
| EPAS1-Sp423 | 423 | GGATGGCCCAGGCCCCTCAT (SEQ ID NO: 1067) |

TABLE 12-continued

Target sequences of EPAS1-gene for SpCas9

| Gene | No. | Target sequence |
|---|---|---|
| EPAS1-Sp424 | 424 | GGGATGGCCCAGGCCCCTCA (SEQ ID NO: 1068) |
| EPAS1-Sp425 | 425 | GATGTCTCAGGGGATGGCCC (SEQ ID NO: 1069) |
| EPAS1-Sp426 | 426 | GCGGCAGATGTCTCAGGGGA (SEQ ID NO: 1070) |
| EPAS1-Sp427 | 427 | GGCAGCGGCAGATGTCTCAG (SEQ ID NO: 1071) |
| EPAS1-Sp428 | 428 | TGGCAGCGGCAGATGTCTCA (SEQ ID NO: 1072) |
| EPAS1-Sp429 | 429 | GTGGCAGCGGCAGATGTCTC (SEQ ID NO: 1073) |
| EPAS1-Sp430 | 430 | GCAGATGGAGGCTGTGGCAG (SEQ ID NO: 1074) |
| EPAS1-Sp431 | 431 | CTGATGGCAGATGGAGGCTG (SEQ ID NO: 1075 |
| EPAS1-Sp432 | 432 | CCTCCATCTGCCATCAGTCC (SEQ ID NO: 1076) |
| EPAS1-Sp433 | 433 | CCGGGACTGATGGCAGATGG (SEQ ID NO: 1077) |
| EPAS1-Sp434 | 434 | CTCCATCTGCCATCAGTCCC (SEQ ID NO: 1078) |
| EPAS1-Sp435 | 435 | TCCATCTGCCATCAGTCCCG (SEQ ID NO: 1079) |
| EPAS1-Sp436 | 436 | TCCCCGGGACTGATGGCAGA (SEQ ID NO: 1080) |
| EPAS1-Sp437 | 437 | GCTGTTCTCCCCGGGACTGA (SEQ ID NO: 1081) |
| EPAS1-Sp438 | 438 | CTGCTCTTGCTGTTCTCCCC (SEQ ID NO: 1082) |
| EPAS1-Sp439 | 439 | CCGGGGAGAACAGCAAGAGC (SEQ ID NO: 1083) |
| EPAS1-Sp440 | 440 | CCTGCTCTTGCTGTTCTCCC (SEQ ID NO: 1084) |
| EPAS1-Sp441 | 441 | GGGTGGCGTAGCACTGTGGG (SEQ ID NO: 1085) |
| EPAS1-Sp442 | 442 | TGGGTGGCGTAGCACTGTGG (SEQ ID NO: 1086) |
| EPAS1-Sp443 | 443 | CTGGGTGGCGTAGCACTGTG (SEQ ID NO: 1087) |
| EPAS1-Sp444 | 444 | ACTGGGTGGCGTAGCACTGT (SEQ ID NO: 1088) |
| EPAS1-Sp445 | 445 | TACTGGGTGGCGTAGCACTG (SEQ ID NO: 1089) |
| EPAS1-Sp446 | 446 | GTGCTACGCCACCCAGTACC (SEQ ID NO: 1090) |
| EPAS1-Sp447 | 447 | GCTGTAGTCCTGGTACTGGG (SEQ ID NO: 1091) |
| EPAS1-Sp448 | 448 | CAGGCTGTAGTCCTGGTACT (SEQ ID NO: 1092) |
| EPAS1-Sp449 | 449 | ACAGGCTGTAGTCCTGGTAC (SEQ ID NO: 1093) |
| EPAS1-Sp450 | 450 | CTGACGACAGGCTGTAGTCC (SEQ ID NO: 1094) |
| EPAS1-Sp451 | 451 | CAGCCTGTCGTCAGCCCACA (SEQ ID NO: 1095) |
| EPAS1-Sp452 | 452 | ACACCTTGTGGGCTGACGAC (SEQ ID NO: 1096) |
| EPAS1-Sp453 | 453 | TCGTCAGCCCACAAGGTGTC (SEQ ID NO: 1097) |
| EPAS1-Sp454 | 454 | TCAGCCCACAAGGTGTCAGG (SEQ ID NO: 1098) |
| EPAS1-Sp455 | 455 | CAGCCCACAAGGTGTCAGGT (SEQ ID NO: 1099) |
| EPAS1-Sp456 | 456 | ACACCCACCTGACACCTTGT (SEQ ID NO: 1100) |
| EPAS1-Sp457 | 457 | CACACCCACCTGACACCTTG (SEQ ID NO: 1101) |
| EPAS1-Sp458 | 458 | ACCAACCCTTCTTTCAGGCA (SEQ ID NO: 1102) |
| EPAS1-Sp459 | 459 | TTCTTTCAGGCATGGCAAGC (SEQ ID NO: 1103) |
| EPAS1-Sp460 | 460 | GGCATGGCAAGCCGGCTGCT (SEQ ID NO: 1104) |
| EPAS1-Sp461 | 461 | GCATGGCAAGCCGGCTGCTC (SEQ ID NO: 1105) |

TABLE 12-continued

Target sequences of EPAS1-gene for SpCas9

| Gene | No. | Target sequence |
|---|---|---|
| EPAS1-Sp462 | 462 | CAAATGAGGGCCCGAGCAGC (SEQ ID NO: 1106) |
| EPAS1-Sp463 | 463 | AGCAGGTAGGACTCAAATGA (SEQ ID NO: 1107) |
| EPAS1-Sp464 | 464 | CAGCAGGTAGGACTCAAATG (SEQ ID NO: 1108) |
| EPAS1-Sp465 | 465 | GGTCAGTTCGGGCAGCAGGT (SEQ ID NO: 1109) |
| EPAS1-Sp466 | 466 | ATCTGGTCAGTTCGGGCAGC (SEQ ID NO: 1110) |
| EPAS1-Sp467 | 467 | CAGTCATATCTGGTCAGTTC (SEQ ID NO: 1111) |
| EPAS1-Sp468 | 468 | ACAGTCATATCTGGTCAGTT (SEQ ID NO: 1112) |
| EPAS1-Sp469 | 469 | ACTGACCAGATATGACTGTG (SEQ ID NO: 1113) |
| EPAS1-Sp470 | 470 | GTTCACCTCACAGTCATATC (SEQ ID NO: 1114) |
| EPAS1-Sp471 | 471 | TGAGGTGAACGTGCCCGTGC (SEQ ID NO: 1115) |
| EPAS1-Sp472 | 472 | GAGGTGAACGTGCCCGTGCT (SEQ ID NO: 1116) |
| EPAS1-Sp473 | 473 | AGCGTGGAGCTTCCCAGCAC (SEQ ID NO: 1117) |
| EPAS1-Sp474 | 474 | GAGCGTGGAGCTTCCCAGCA (SEQ ID NO: 1118) |
| EPAS1-Sp475 | 475 | GGAAGCTCCACGCTCCTGCA (SEQ ID NO: 1119) |
| EPAS1-Sp476 | 476 | AGCTCCACGCTCCTGCAAGG (SEQ ID NO: 1120) |
| EPAS1-Sp477 | 477 | GCTCCACGCTCCTGCAAGGA (SEQ ID NO: 1121) |
| EPAS1-Sp478 | 478 | CTCCACGCTCCTGCAAGGAG (SEQ ID NO: 1122) |
| EPAS1-Sp479 | 479 | GTCCCCTCCTTGCAGGAGCG (SEQ ID NO: 1123) |
| EPAS1-Sp480 | 480 | TGAGGAGGTCCCCTCCTTGC (SEQ ID NO: 1124) |
| EPAS1-Sp481 | 481 | AGGGGACCTCCTCAGAGCCC (SEQ ID NO: 1125) |
| EPAS1-Sp482 | 482 | CCTCCTCAGAGCCCTGGACC (SEQ ID NO: 1126) |
| EPAS1-Sp483 | 483 | CCTGGTCCAGGGCTCTGAGG (SEQ ID NO: 1127) |
| EPAS1-Sp484 | 484 | TGGCCTGGTCCAGGGCTCTG (SEQ ID NO: 1128) |
| EPAS1-Sp485 | 485 | GGCTCAGGTGGCCTGGTCCA (SEQ ID NO: 1129) |
| EPAS1-Sp486 | 486 | TGGCTCAGGTGGCCTGGTCC (SEQ ID NO: 1130) |
| EPAS1-Sp487 | 487 | TGGACCAGGCCACCTGAGCC (SEQ ID NO: 1131) |
| EPAS1-Sp488 | 488 | AAGGCCTGGCTCAGGTGGCC (SEQ ID NO: 1132) |
| EPAS1-Sp489 | 489 | GGTAGAAGGCCTGGCTCAGG (SEQ ID NO: 1133) |

TABLE 13

Target sequences of ANGPT2 gene for SpCas9

| Gene | No. | Target sequence |
|---|---|---|
| ANGPT2-Sp1 | 1 | TCTGAGCTGTGATCTTGTCT (SEQ ID NO: 1134) |
| ANGPT2-Sp2 | 2 | CCGCAGCCTATAACAACTTT (SEQ ID NO: 1135) |
| ANGPT2-Sp3 | 3 | CCGAAAGTTGTTATAGGCTG (SEQ ID NO: 1136) |
| ANGPT2-Sp4 | 4 | GCTCTTCCGAAAGTTGTTAT (SEQ ID NO: 1137) |
| ANGPT2-Sp5 | 5 | TAACAACTTTCGGAAGAGCA (SEQ ID NO: 1138) |

TABLE 13-continued

Target sequences of ANGPT2 gene for SpCas9

| Gene | No. | Target sequence |
|---|---|---|
| ANGPT2-Sp6 | 6 | CGGAAGAGCATGGACAGCAT (SEQ ID NO: 1139) |
| ANGPT2-Sp7 | 7 | CATAGGAAAGAAGCAATATC (SEQ ID NO: 1140) |
| ANGPT2-Sp8 | 8 | AAGCAATATCAGGTCCAGCA (SEQ ID NO: 1141) |
| ANGPT2-Sp9 | 9 | AGCAATATCAGGTCCAGCAT (SEQ ID NO: 1142) |
| ANGPT2-Sp10 | 10 | TGTAGCTGCAGGACCCATGC (SEQ ID NO: 1143) |
| ANGPT2-Sp11 | 11 | CAGGAGGAAAGTGTAGCTGC (SEQ ID NO: 1144) |
| ANGPT2-Sp12 | 12 | CACTTTCCTCCTGCCAGAGA (SEQ ID NO: 1145) |
| ANGPT2-Sp13 | 13 | AGTIGTCCATCTCTGGCAGG (SEQ ID NO: 1146) |
| ANGPT2-Sp14 | 14 | GGCAGTTGTCCATCTCTGGC (SEQ ID NO: 1147) |
| ANGPT2-Sp15 | 15 | GAGCGGCAGTTGTCCATCTC (SEQ ID NO: 1148) |
| ANGPT2-Sp16 | 16 | CGTAGGGGCTGGAGGAAGAG (SEQ ID NO: 1149) |
| ANGPT2-Sp17 | 17 | ATTGGACACGTAGGGGCTGG (SEQ ID NO: 1150) |
| ANGPT2-Sp18 | 18 | AGCATTGGACACGTAGGGGC (SEQ ID NO: 1151) |
| ANGPT2-Sp19 | 19 | GCACAGCATTGGACACGTAG (SEQ ID NO: 1152) |
| ANGPT2-Sp20 | 20 | TGCACAGCATTGGACACGTA (SEQ ID NO: 1153) |
| ANGPT2-Sp21 | 21 | CTGCACAGCATTGGACACGT (SEQ ID NO: 1154) |
| ANGPT2-Sp22 | 22 | ACGTGTCCAATGCTGTGCAG (SEQ ID NO: 1155) |
| ANGPT2-Sp23 | 23 | CGTGTCCAATGCTGTGCAGA (SEQ ID NO: 1156) |
| ANGPT2-Sp24 | 24 | CGCGTCCCTCTGCACAGCAT (SEQ ID NO: 1157) |
| ANGPT2-Sp25 | 25 | GCCGCTCGAATACGATGACT (SEQ ID NO: 1158) |
| ANGPT2-Sp26 | 26 | ACCGAGTCATCGTATTCGAG (SEQ ID NO: 1159) |
| ANGPT2-Sp27 | 27 | AATACGATGACTCGGTGCAG (SEQ ID NO: 1160) |
| ANGPT2-Sp28 | 28 | GGTGCAGAGGCTGCAAGTGC (SEQ ID NO: 1161) |
| ANGPT2-Sp29 | 29 | GCAAGTGCTGGAGAACATCA (SEQ ID NO: 1162) |
| ANGPT2-Sp30 | 30 | TCATGGAAAACAACACTCAG (SEQ ID NO: 1163) |
| ANGPT2-Sp31 | 31 | CAACACTCAGTGGCTAATGA (SEQ ID NO: 1164) |
| ANGPT2-Sp32 | 32 | ACTCAGTGGCTAATGAAGGT (SEQ ID NO: 1165) |
| ANGPT2-Sp33 | 33 | CTAGCTTGAGAATTATATCC (SEQ ID NO: 1166) |
| ANGPT2-Sp34 | 34 | TTTCTTTCTTCATGTIGTCC (SEQ ID NO: 1167) |
| ANGPT2-Sp35 | 35 | GGACAACATGAAGAAAGAAA (SEQ ID NO: 1168) |
| ANGPT2-Sp36 | 36 | GAATGCAGTACAGAACCAGA (SEQ ID NO: 1169) |
| ANGPT2-Sp37 | 37 | TTTCTATCATCACAGCCGTC (SEQ ID NO: 1170) |
| ANGPT2-Sp38 | 38 | ACGGCTGTGATGATAGAAAT (SEQ ID NO: 1171) |
| ANGPT2-Sp39 | 39 | CGGCTGTGATGATAGAAATA (SEQ ID NO: 1172) |
| ANGPT2-Sp40 | 40 | AAACCTGTTGAACCAAACAG (SEQ ID NO: 1173) |
| ANGPT2-Sp41 | 41 | GCTCCGCTGTTTGGTTCAAC (SEQ ID NO: 1174) |
| ANGPT2-Sp42 | 42 | ACCAAACAGCGGAGCAAACG (SEQ ID NO: 1175) |
| ANGPT2-Sp43 | 43 | TCCGCGTTTGCTCCGCTGTT (SEQ ID NO: 1176) |

TABLE 13-continued

Target sequences of ANGPT2 gene for SpCas9

| Gene | No. | Target sequence |
|---|---|---|
| ANGPT2-Sp44 | 44 | AACGCGGAAGTTAACTGATG (SEQ ID NO: 1177) |
| ANGPT2-Sp45 | 45 | CTAGCTTGAGAATTATATCC (SEQ ID NO: 1178) |
| ANGPT2-Sp46 | 46 | TTTCTTTCTTCATGITGTCC (SEQ ID NO: 1179) |
| ANGPT2-Sp47 | 47 | GGACAACATGAAGAAAGAAA (SEQ ID NO: 1180) |
| ANGPT2-Sp48 | 48 | GAATGCAGTACAGAACCAGA (SEQ ID NO: 1181) |
| ANGPT2-Sp49 | 49 | TTTCTATCATCACAGCCGTC (SEQ ID NO: 1182) |
| ANGPT2-Sp50 | 50 | ACGGCTGTGATGATAGAAAT (SEQ ID NO: 1183) |
| ANGPT2-Sp51 | 51 | CGGCTGTGATGATAGAAATA (SEQ ID NO: 1184) |
| ANGPT2-Sp52 | 52 | AAACCTGTTGAACCAAACAG (SEQ ID NO: 1185) |
| ANGPT2-Sp53 | 53 | GCTCCGCTGTTTGGTTCAAC (SEQ ID NO: 1186) |
| ANGPT2-Sp54 | 54 | ACCAAACAGCGGAGCAAACG (SEQ ID NO: 1187) |
| ANGPT2-Sp55 | 55 | TCCGCGTTTGCTCCGCTGTT (SEQ ID NO: 1188) |
| ANGPT2-Sp56 | 56 | AACGCGGAAGTTAACTGATG (SEQ ID NO: 1189) |
| ANGPT2-Sp57 | 57 | TACAAGTTTCCTAGAAAAGA (SEQ ID NO: 1190) |
| ANGPT2-Sp58 | 58 | TAGCTAGCACCTTCTTTTCT (SEQ ID NO: 1191) |
| ANGPT2-Sp59 | 59 | AGAAAAGAAGGTGCTAGCTA (SEQ ID NO: 1192) |
| ANGPT2-Sp60 | 60 | CTTCTTTTATTGACTGTAGT (SEQ ID NO: 1193) |
| ANGPT2-Sp61 | 61 | AGAAGAGAAAGATCAGCTAC (SEQ ID NO: 1194) |
| ANGPT2-Sp62 | 62 | TTCAATGATGGAATTTTGCT (SEQ ID NO: 1195) |
| ANGPT2-Sp63 | 63 | TTTTTCTAGTTCTTCAATGA (SEQ ID NO: 1196) |
| ANGPT2-Sp64 | 64 | AAAAAAAATAGIGACTGCCA (SEQ ID NO: 1197) |
| ANGPT2-Sp65 | 65 | AAGAACTGAATTATTCACCG (SEQ ID NO: 1198) |
| ANGPT2-Sp66 | 66 | GAAGCAGCAACATGATCTCA (SEQ ID NO: 1199) |
| ANGPT2-Sp67 | 67 | TGTAAACTTACAGTTTGATG (SEQ ID NO: 1200) |
| ANGPT2-Sp68 | 68 | CTATTTTTAAAAGCAGCTA (SEQ ID NO: 1201) |
| ANGPT2-Sp69 | 69 | GTTCTTCTTTAGCAACAGTG (SEQ ID NO: 1202) |
| ANGPT2-Sp70 | 70 | TGTTCTTCTTTAGCAACAGT (SEQ ID NO: 1203) |
| ANGPT2-Sp71 | 71 | TTGTTCTTCTTTAGCAACAG (SEQ ID NO: 1204) |
| ANGPT2-Sp72 | 72 | TGTGCTGAAGTATTCAAATC (SEQ ID NO: 1205) |
| ANGPT2-Sp73 | 73 | AAATCAGGACACACCACGAA (SEQ ID NO: 1206) |
| ANGPT2-Sp74 | 74 | TAACGTGTAGATGCCATTCG (SEQ ID NO: 1207) |
| ANGPT2-Sp75 | 75 | TGATCTCTTCTGTAGAATTA (SEQ ID NO: 1208) |
| ANGPT2-Sp76 | 76 | TTGATCTETTCTGTAGAATT (SEQ ID NO: 1209) |
| ANGPT2-Sp77 | 77 | TAATTCTACAGAAGAGATCA (SEQ ID NO: 1210) |
| ANGPT2-Sp78 | 78 | CTACAGAAGAGATCAAGGTG (SEQ ID NO: 1211) |
| ANGPT2-Sp79 | 79 | TTTGCAGGCCTACTGTGACA (SEQ ID NO: 1212) |
| ANGPT2-Sp80 | 80 | GCCTACTGTGACATGGAAGC (SEQ ID NO: 1213) |
| ANGPT2-Sp81 | 81 | TCCAGCTTCCATGTCACAGT (SEQ ID NO: 1214) |

TABLE 13-continued

Target sequences of ANGPT2 gene for SpCas9

| Gene | No. | Target sequence |
|---|---|---|
| ANGPT2-Sp82 | 82 | TACTGIGACATGGAAGCTGG (SEQ ID NO: 1215) |
| ANGPT2-Sp83 | 83 | TGTGACATGGAAGCTGGAGG (SEQ ID NO: 1216) |
| ANGPT2-Sp84 | 84 | GACATGGAAGCTGGAGGAGG (SEQ ID NO: 1217) |
| ANGPT2-Sp85 | 85 | ACATGGAAGCTGGAGGAGGC (SEQ ID NO: 1218) |
| ANGPT2-Sp86 | 86 | TGGAAGCTGGAGGAGGGGGG (SEQ ID NO: 1219) |
| ANGPT2-Sp87 | 87 | GACAATTATTCAGCGACGTG (SEQ ID NO: 1220) |
| ANGPT2-Sp88 | 88 | ATTATTCAGCGACGTGAGGA (SEQ ID NO: 1221) |
| ANGPT2-Sp89 | 89 | ATGGCAGCGTTGATTTTCAG (SEQ ID NO: 1222) |
| ANGPT2-Sp90 | 90 | GCGTTGATTTTCAGAGGACT (SEQ ID NO: 1223) |
| ANGPT2-Sp91 | 91 | GACTTGGAAAGAATATAAAG (SEQ ID NO: 1224) |
| ANGPT2-Sp92 | 92 | GGAAAGAATATAAAGTGGTA (SEQ ID NO: 1225) |
| ANGPT2-Sp93 | 93 | CAGGGATTTGGTAACCCTTC (SEQ ID NO: 1226) |
| ANGPT2-Sp94 | 94 | GTAACCCTTCAGGAGAATAT (SEQ ID NO: 1227) |
| ANGPT2-Sp95 | 95 | CCCTTCAGGAGAATATTGGC (SEQ ID NO: 1228) |
| ANGPT2-Sp96 | 96 | CCAGCCAATATTCTCCTGAA (SEQ ID NO: 1229) |
| ANGPT2-Sp97 | 97 | CCTTCAGGAGAATATTGGCT (SEQ ID NO: 1230) |
| ANGPT2-Sp98 | 98 | CCCAGCCAATATTCTCCTGA (SEQ ID NO: 1231) |
| ANGPT2-Sp99 | 99 | TTAAAATACACCTTAAAGAC (SEQ ID NO: 1232) |
| ANGPT2-Sp100 | 100 | TAAAATACACCTTAAAGACT (SEQ ID NO: 1233) |
| ANGPT2-Sp101 | 101 | ATACACCTTAAAGACTGGGA (SEQ ID NO: 1234) |
| ANGPT2-Sp102 | 102 | TACACCTTAAAGACTGGGAA (SEQ ID NO: 1235) |
| ANGPT2-Sp103 | 103 | CATTCCCTTCCCAGTCTTTA (SEQ ID NO: 1236) |
| ANGPT2-Sp104 | 104 | TAAAGACTGGGAAGGGAATG (SEQ ID NO: 1237) |
| ANGPT2-Sp105 | 105 | CAAGTGAAGAACTCAATTAT (SEQ ID NO: 1238) |
| ANGPT2-Sp106 | 106 | GCTTACAGGATTCACCTTAA (SEQ ID NO: 1239) |
| ANGPT2-Sp107 | 107 | ATTCACCTTAAAGGACTTAC (SEQ ID NO: 1240) |
| ANGPT2-Sp108 | 108 | ITCACCITAAAGGACTTACA (SEQ ID NO: 1241) |
| ANGPT2-Sp109 | 109 | CTGTCCCTGTAAGTCCTTTA (SEQ ID NO: 1242) |
| ANGPT2-Sp110 | 110 | AAAGGACTTACAGGGACAGC (SEQ ID NO: 1243) |
| ANGPT2-Sp111 | 111 | GCTGATGCTGCTTATTTTGC (SEQ ID NO: 1244) |
| ANGPT2-Sp112 | 112 | ATAAGCAGCATCAGCCAACC (SEQ ID NO: 1245) |
| ANGPT2-Sp113 | 113 | TGCTAAAATCATTTCCTGGT (SEQ ID NO: 1246) |
| ANGPT2-Sp114 | 114 | TTTGTGCTAAAATCATTTCC (SEQ ID NO: 1247) |
| ANGPT2-Sp115 | 115 | AGGAAATGATTTTAGCACAA (SEQ ID NO: 1248) |
| ANGPT2-Sp116 | 116 | AATGATTTTAGCACAAAGGA (SEQ ID NO: 1249) |
| ANGPT2-Sp117 | 117 | AAATGTTCACAAATGCTAAC (SEQ ID NO: 1250) |
| ANGPT2-Sp118 | 118 | TGTTCACAAATGCTAACAGG (SEQ ID NO: 1251) |
| ANGPT2-Sp119 | 119 | CACAAATGCTAACAGGAGGT (SEQ ID NO: 1252) |

TABLE 13-continued

Target sequences of ANGPT2 gene for SpCas9

| Gene | No. | Target sequence |
| --- | --- | --- |
| ANGPT2-Sp120 | 120 | ACAAATGCTAACAGGAGGTA (SEQ ID NO: 1253) |
| ANGPT2-Sp121 | 121 | GGCTGGTGGTTTGATGCATG (SEQ ID NO: 1254) |
| ANGPT2-Sp122 | 122 | TGTGGTCCTTCCAACTTGAA (SEQ ID NO: 1255) |
| ANGPT2-Sp123 | 123 | TACATTCCGTTCAAGTTGGA (SEQ ID NO: 1256) |
| ANGPT2-Sp124 | 124 | ATAGTACATTCCGTTCAAGT (SEQ ID NO: 1257) |
| ANGPT2-Sp125 | 125 | ACGGAATGTACTATCCACAG (SEQ ID NO: 1258) |
| ANGPT2-Sp126 | 126 | TTATTTGTGTTCTGCCTCTG (SEQ ID NO: 1259) |
| ANGPT2-Sp127 | 127 | CAGAACACAAATAAGTTCAA (SEQ ID NO: 1260) |
| ANGPT2-Sp128 | 128 | ATAAGTTCAACGGCATTAAA (SEQ ID NO: 1261) |
| ANGPT2-Sp129 | 129 | ACGGCATTAAATGGTACTAC (SEQ ID NO: 1262) |
| ANGPT2-Sp130 | 130 | ATTAAATGGTACTACTGGAA (SEQ ID NO: 1263) |
| ANGPT2-Sp131 | 131 | TGGTACTACTGGAAAGGCTC (SEQ ID NO: 1264) |
| ANGPT2-Sp132 | 132 | AGGCTCAGGCTATTCGCTCA (SEQ ID NO: 1265) |
| ANGPT2-Sp133 | 133 | TGGTCGGATCATCATGGTTG (SEQ ID NO: 1266) |
| ANGPT2-Sp134 | 134 | ATCTGCTGGTCGGATCATCA (SEQ ID NO: 1267) |
| ANGPT2-Sp135 | 135 | ATGTTTAGAAATCTGCTGGT (SEQ ID NO: 1268) |
| ANGPT2-Sp136 | 136 | TGGGATGTTTAGAAATCTGC (SEQ ID NO: 1269) |

TABLE 14

Target sequences of ANGPTL4-gene for SpCas9

| Gene | No. | Target sequence |
| --- | --- | --- |
| ANGPTL4-Sp1 | 1 | AGGCTACCTAAGAGGATGAG (SEQ ID NO: 1270) |
| ANGPTL4-Sp2 | 2 | GAGGATGAGCGGTGCTCCGA (SEQ ID NO: 1271) |
| ANGPTL4-Sp3 | 3 | ATGAGCGGTGCTCCGACGGC (SEQ ID NO: 1272) |
| ANGPTL4-Sp4 | 4 | TGAGCGGTGCTCCGACGGCC (SEQ ID NO: 1273) |
| ANGPTL4 Sp5 | 5 | GAGCGGTGCTCCGACGGCCG (SEQ ID NO: 1274) |
| ANGPTL4-Sp6 | 6 | ATCAGGGCTGCCCCGGCCGT (SEQ ID NO: 1275) |
| ANGPTL4-Sp7 | 7 | GCAGAGCATCAGGGCTGCCC (SEQ ID NO: 1276) |
| ANGPTL4-Sp8 | 8 | GGTGGCGGCGCAGAGCATCA (SEQ ID NO: 1277) |
| ANGPTL4-Sp9 | 9 | CGGTGGCGGCGCAGAGCATC (SEQ ID NO: 1278) |
| ANGPTL4-Sp10 | 10 | GCTCAGTAGCACGGCGGTGG (SEQ ID NO: 1279) |
| ANGPTL4-Sp11 | 11 | AGCGCTCAGTAGCACGGCGG (SEQ ID NO: 1280) |
| ANGPTL4-Sp12 | 12 | CTGAGCGCTCAGTAGCACGG (SEQ ID NO: 1281) |
| ANGPTL4-Sp13 | 13 | CGCCGTGCTACTGAGCGCTC (SEQ ID NO: 1282) |
| ANGPTL4-Sp14 | 14 | GCCGTGCTACTGAGCGCTCA (SEQ ID NO: 1283) |
| ANGPTL4-Sp15 | 15 | GCCCTGAGCGCTCAGTAGCA (SEQ ID NO: 1284) |
| ANGPTL4-Sp16 | 16 | GIGCTACTGAGCGCTCAGGG (SEQ ID NO: 1285) |
| ANGPTL4 Sp17 | 17 | CGCGGCGACTTGGACTGCAC (SEQ ID NO: 1286) |

TABLE 14-continued

Target sequences of ANGPTL4-gene for SpCas9

| Gene | No. | Target sequence |
|---|---|---|
| ANGPTL4-Sp18 | 18 | GCGCGGCGACTTGGACTGCA (SEQ ID NO: 1287) |
| ANGPTL4-Sp19 | 19 | GGACGCAAAGCGCGGCGACT (SEQ ID NO: 1288) |
| ANGPTL4-Sp20 | 20 | AGTCGCCGCGCTTTGCGTCC (SEQ ID NO: 1289) |
| ANGPTL4-Sp21 | 21 | GTCGCCGCGCTTTGCGTCCT (SEQ ID NO: 1290) |
| ANGPTL4-Sp22 | 22 | TCGTCCCAGGACGCAAAGCG (SEQ ID NO: 1291) |
| ANGPTL4-Sp23 | 23 | CAGGACATTCATCTCGTCCC (SEQ ID NO: 1292) |
| ANGPTL4-Sp24 | 24 | CTGGGACGAGATGAATGTCC (SEQ ID NO: 1293) |
| ANGPTL4-Sp25 | 25 | GAGATGAATGTCCTGGCGCA (SEQ ID NO: 1294) |
| ANGPTL4-Sp26 | 26 | GCTGCAGGAGTCCGTGCGCC (SEQ ID NO: 1295) |
| ANGPTL4-Sp27 | 27 | GCGCACGGACTCCTGCAGCT (SEQ ID NO: 1296) |
| ANGPTL4-Sp28 | 28 | CGGACTCCTGCAGCTCGGCC (SEQ ID NO: 1297) |
| ANGPTL4-Sp29 | 29 | GGACTCCTGCAGCTCGGCCA (SEQ ID NO: 1298) |
| ANGPTL4-Sp30 | 30 | GACTCCTGCAGCTCGGCCAG (SEQ ID NO: 1299) |
| ANGPTL4-Sp31 | 31 | GCAGCCCTGGCCGAGCTGC (SEQ ID NO: 1300) |
| ANGPTL4 Sp32 | 32 | CCAGGGGCTGCGCGAACACG (SEQ ID NO: 1301) |
| ANGPTL4-Sp33 | 33 | CCGCGTGTTCGCGCAGCCCC (SEQ ID NO: 1302) |
| ANGPTL4-Sp34 | 34 | CAGCGCGCTCAGCTGACTGC (SEQ ID NO: 1303) |
| ANGPTL4-Sp35 | 35 | CCGCAGTCAGCTGAGCGCGC (SEQ ID NO: 1304) |
| ANGPTL4-Sp36 | 36 | CCAGCGCGCTCAGCTGACTG (SEQ ID NO: 1305) |
| ANGPTL4-Sp37 | 37 | GTCAGCTGAGCGCGCTGGAG (SEQ ID NO: 1306) |
| ANGPTL4 Sp38 | 38 | GAGCGGCGCCTGAGCGCGTG (SEQ ID NO: 1307) |
| ANGPTL4-Sp39 | 39 | AGCGGCGCCTGAGCGCGTGC (SEQ ID NO: 1308) |
| ANGPTL4-Sp40 | 40 | AGGCGGACCCGCACGCGCTC (SEQ ID NO: 1309) |
| ANGPTL4-Sp41 | 41 | CGCGTGCGGGTCCGCCTGTC (SEQ ID NO: 1310) |
| ANGPTL4-Sp42 | 42 | GCGTGCGGGTCCGCCTGTCA (SEQ ID NO: 1311) |
| ANGPTL4-Sp43 | 43 | GTCCGCCTGTCAGGGAACCG (SEQ ID NO: 1312) |
| ANGPTL4-Sp44 | 44 | TCCGCCTGTCAGGGAACCGA (SEQ ID NO: 1313) |
| ANGPTL4-Sp45 | 45 | CCGCCTGTCAGGGAACCGAG (SEQ ID NO: 1314) |
| ANGPTL4-Sp46 | 46 | CCCCTCGGTTCCCTGACAGG (SEQ ID NO: 1315) |
| ANGPTL4-Sp47 | 47 | GGACCCCTCGGTTCCCTGAC (SEQ ID NO: 1316) |
| ANGPTL4-Sp48 | 48 | CGGGAGGTCGGTGGACCCCT (SEQ ID NO: 1317) |
| ANGPTL4 Sp49 | 49 | AGGGGCTAACGGGAGGTCGG (SEQ ID NO: 1318) |
| ANGPTL4-Sp50 | 50 | CTCAGGGGCTAACGGGAGGT (SEQ ID NO: 1319) |
| ANGPTL4-Sp51 | 51 | GGCTCTCAGGGGCTAACGGG (SEQ ID NO: 1320) |
| ANGPTL4-Sp52 | 52 | TCCCGTTAGCCCCTGAGAGC (SEQ ID NO: 1321) |
| ANGPTL4-Sp53 | 53 | CCCGTTAGCCCCTGAGAGCC (SEQ ID NO: 1322) |
| ANGPTL4-Sp54 | 54 | CCCGGCTCTCAGGGGCTAAC (SEQ ID NO: 1323) |
| ANGPTL4-Sp55 | 55 | ACCCGGCTCTCAGGGGCTAA (SEQ ID NO: 1324) |

TABLE 14-continued

Target sequences of ANGPTL4-gene for SpCas9

| Gene | No. | Target sequence |
|---|---|---|
| ANGPTL4-Sp56 | 56 | GTTAGCCCCTGAGAGCCGGG (SEQ ID NO: 1325) |
| ANGPTL4-Sp57 | 57 | AGGGTCCACCCGGCTCTCAG (SEQ ID NO: 1326) |
| ANGPTL4-Sp58 | 58 | CAGGGTCCACCCGGCTCTCA (SEQ ID NO: 1327) |
| ANGPTL4-Sp59 | 59 | TCAGGGTCCACCCGGCTCTC (SEQ ID NO: 1328) |
| ANGPTL4-Sp60 | 60 | TGAGAGCCGGGTGGACCCTG (SEQ ID NO: 1329) |
| ANGPTL4-Sp61 | 61 | GAAGGACCTCAGGGTCCACC (SEQ ID NO: 1330) |
| ANGPTL4-Sp62 | 62 | GCAGGCTGTGAAGGACCTCA (SEQ ID NO: 1331) |
| ANGPTL4-Sp63 | 63 | TGCAGGCTGTGAAGGACCTC (SEQ ID NO: 1332) |
| ANGPTL4-Sp64 | 64 | TGAGGTCCTTCACAGCCTGC (SEQ ID NO: 1333) |
| ANGPTL4-Sp65 | 65 | CACGTACCTGCAGGCTGTGA (SEQ ID NO: 1334) |
| ANGPTL4-Sp66 | 66 | CCCTGGGGACACGTACCTGC (SEQ ID NO: 1335) |
| ANGPTL4-Sp67 | 67 | CCCTCCCCAGACACAACTCA (SEQ ID NO: 1336) |
| ANGPTL4 Sp68 | 68 | TGAGCCTTGAGTIGTGTCTG (SEQ ID NO: 1337) |
| ANGPTL4-Sp69 | 69 | CTGAGCCTTGAGTTGTGTCT (SEQ ID NO: 1338) |
| ANGPTL4-Sp70 | 70 | TCTGAGCCTTGAGTIGTGTC (SEQ ID NO: 1339) |
| ANGPTL4-Sp71 | 71 | AACTCAAGGCTCAGAACAGC (SEQ ID NO: 1340) |
| ANGPTL4-Sp72 | 72 | GATCCAGCAACTCTTCCACA (SEQ ID NO: 1341) |
| ANGPTL4-Sp73 | 73 | CCAGCAACTCTTCCACAAGG (SEQ ID NO: 1342) |
| ANGPTL4-Sp74 | 74 | CCACCTTGTGGAAGAGTTGC (SEQ ID NO: 1343) |
| ANGPTL4-Sp75 | 75 | GCTGCTGCTGGGCCACCTTG (SEQ ID NO: 1344) |
| ANGPTL4 Sp76 | 76 | ACAAGGTGGCCCAGCAGCAG (SEQ ID NO: 1345) |
| ANGPTL4-Sp77 | 77 | GGCCCAGCAGCAGCGGCACC (SEQ ID NO: 1346) |
| ANGPTL4-Sp78 | 78 | CTCCAGGTGCCGCTGCTGCT (SEQ ID NO: 1347) |
| ANGPTL4-Sp79 | 79 | TCTCCAGGTGCCGCTGCTGC (SEQ ID NO: 1348) |
| ANGPTL4-Sp80 | 80 | TTCGCAGGTGCTGCTTCTCC (SEQ ID NO: 1349) |
| ANGPTL4-Sp81 | 81 | TTTGCAGATGCTGAATTCGC (SEQ ID NO: 1350) |
| ANGPTL4-Sp82 | 82 | AATTCAGCATCTGCAAAGCC (SEQ ID NO: 1351) |
| ANGPTL4-Sp83 | 83 | CCCTTGATCCTAGGGTTACC (SEQ ID NO: 1352) |
| ANGPTL4-Sp84 | 84 | CCCATCCTAGTTTGGCCTCC (SEQ ID NO: 1353) |
| ANGPTL4 Sp85 | 85 | GTGGTCCAGGAGGCCAAACT (SEQ ID NO: 1354) |
| ANGPTL4-Sp86 | 86 | CTAGGTGCTTGTGGTCCAGG (SEQ ID NO: 1355) |
| ANGPTL4-Sp87 | 87 | GGTCTAGGTGCTTGTGGTCC (SEQ ID NO: 1356) |
| ANGPTL4-Sp88 | 88 | CCACAAGCACCTAGACCATG (SEQ ID NO: 1357) |
| ANGPTL4-Sp89 | 89 | CCTCATGGTCTAGGTGCTTG (SEQ ID NO: 1358) |
| ANGPTL4-Sp90 | 90 | CAAGCACCTAGACCATGAGG (SEQ ID NO: 1359) |
| ANGPTL4-Sp91 | 91 | GCTTGGCCACCTCATGGTCT (SEQ ID NO: 1360) |
| ANGPTL4-Sp92 | 92 | GGGCAGGCTTGGCCACCTCA (SEQ ID NO: 1361) |
| ANGPTL4-Sp93 | 93 | CCAAGCCTGCCCGAAGAAAG (SEQ ID NO: 1362) |

TABLE 14-continued

Target sequences of ANGPTL4-gene for SpCas9

| Gene | No. | Target sequence |
|---|---|---|
| ANGPTL4-Sp94 | 94 | CCTCTTTCTTCGGGCAGGCT (SEQ ID NO: 1363) |
| ANGPTL4-Sp95 | 95 | GGCAGCCTCTTTCTTCGGGC (SEQ ID NO: 1364) |
| ANGPTL4-Sp96 | 96 | CTCGGGCAGCCTCTTTCTTC (SEQ ID NO: 1365) |
| ANGPTL4-Sp97 | 97 | TCTCGGGCAGCCTCTTTCTT (SEQ ID NO: 1366) |
| ANGPTL4-Sp98 | 98 | AAGAAAGAGGCTGCCCGAGA (SEQ ID NO: 1367) |
| ANGPTL4-Sp99 | 99 | TCAACTGGCTGGGCCATCTC (SEQ ID NO: 1368) |
| ANGPTL4-Sp100 | 100 | GTCAACTGGCTGGGCCATCT (SEQ ID NO: 1369) |
| ANGPTL4.Sp101 | 101 | GATGGCCCAGCCAGTTGACC (SEQ ID NO: 1370) |
| ANGPTL4-Sp102 | 102 | GTGAGCCGGGTCAACTGGCT (SEQ ID NO: 1371) |
| ANGPTL4-Sp103 | 103 | TGTGAGCCGGGTCAACTGGC (SEQ ID NO: 1372) |
| ANGPTL4-Sp104 | 104 | ACATTGTGAGCCGGGTCAAC (SEQ ID NO: 1373) |
| ANGPTL4-Sp105 | 105 | GGCGGCTGACATTGTGAGCC (SEQ ID NO: 1374) |
| ANGPTL4-Sp106 | 106 | AGGCGGCTGACATTGTGAGC (SEQ ID NO: 1375) |
| ANGPTL4-Sp107 | 107 | GCAGACACTCACGGTGCAGG (SEQ ID NO: 1376) |
| ANGPTL4-Sp108 | 108 | GGGGCAGACACTCACGGTGC (SEQ ID NO: 1377) |
| ANGPTL4-Sp109 | 109 | ATCTCCCTTCAGGGCTGCCC (SEQ ID NO: 1378) |
| ANGPTL4-Sp110 | 110 | TCTCCCTTCAGGGCTGCCCA (SEQ ID NO: 1379) |
| ANGPTL4-Sp111 | 111 | AGGGCTGCCCAGGGATTGCC (SEQ ID NO: 1380) |
| ANGPTL4-Sp112 | 112 | AACAGCTCCTGGCAATCCCT (SEQ ID NO: 1381) |
| ANGPTL4-Sp113 | 113 | GAACAGCTCCTGGCAATCCC (SEQ ID NO: 1382) |
| ANGPTL4-Sp114 | 114 | GGATTGCCAGGAGCTGTTCC (SEQ ID NO: 1383) |
| ANGPTL4-Sp115 | 115 | TGCCAGGAGCTGTTCCAGGT (SEQ ID NO: 1384) |
| ANGPTL4-Sp116 | 116 | CCAGGAGCTGTTCCAGGTTG (SEQ ID NO: 1385) |
| ANGPTL4-Sp117 | 117 | CCCCAACCTGGAACAGCTCC (SEQ ID NO: 1386) |
| ANGPTL4-Sp118 | 118 | AGCTGTTCCAGGTTGGGGAG (SEQ ID NO: 1387) |
| ANGPTL4-Sp119 | 119 | CACTCTGCCTCTCCCCAACC (SEQ ID NO: 1388) |
| ANGPTL4-Sp120 | 120 | CAGGTTGGGGAGAGGCAGAG (SEQ ID NO: 1389) |
| ANGPTL4 Sp121 | 121 | ACTATTIGAAATCCAGCCTC (SEQ ID NO: 1390) |
| ANGPTLA-Sp122 | 122 | CTATTTGAAATCCAGCCTCA (SEQ ID NO: 1391) |
| ANGPTL4 Sp123 | 123 | TATTTGAAATCCAGCCTCAG (SEQ ID NO: 1392) |
| ANGPTL4-Sp124 | 124 | ATGGCGGAGACCCCTGAGGC (SEQ ID NO: 1393) |
| ANGPTL4-5p125 | 125 | AAAAATGGCGGAGACCCCTG (SEQ ID NO: 1394) |
| ANGPTL4-Sp126 | 126 | TCAGGGGTCTCCGCCATTTT (SEQ ID NO: 1395) |
| ANGPTL4-Sp127 | 127 | TTGCAGTTCACCAAAAATGG (SEQ ID NO: 1396) |
| ANGPTL4-Sp128 | 128 | ATCTTGCAGTTCACCAAAAA (SEQ ID NO: 1397) |
| ANGPTL4-Sp129 | 129 | GTGAACTGCAAGATGACCTC (SEQ ID NO: 1398) |
| ANGPTL4-Sp130 | 130 | ACTGCAAGATGACCTCAGGT (SEQ ID NO: 1399) |
| ANGPTL4-Sp131 | 131 | CTGCAAGATGACCTCAGGTA (SEQ ID NO: 1400) |

TABLE 14-continued

Target sequences of ANGPTL4-gene for SpCas9

| Gene | No. | Target sequence |
|---|---|---|
| ANGPTL4-Sp132 | 132 | GGACTAACACACCCTACCTG (SEQ ID NO: 1401) |
| ANGPTL4-Sp133 | 133 | GTACCTTTCTGGGCAGATGG (SEQ ID NO: 1402) |
| ANGPTL4 Sp134 | 134 | CTTTCTGGGCAGATGGAGGC (SEQ ID NO: 1403) |
| ANGPTL4-Sp135 | 135 | GAGGCTGGACAGTAATTCAG (SEQ ID NO: 1404) |
| ANGPTL4-Sp136 | 136 | GTAATTCAGAGGCGCCACGA (SEQ ID NO: 1405) |
| ANGPTL4-Sp137 | 137 | GAGGCGCCACGATGGCTCAG (SEQ ID NO: 1406) |
| ANGPTL4-Sp138 | 138 | TGAAGTCCACTGAGCCATCG (SEQ ID NO: 1407) |
| ANGPTL4-Sp139 | 139 | ATGGCTCAGTGGACTTCAAC (SEQ ID NO: 1408) |
| ANGPTL4-Sp140 | 140 | CAGTGGACTTCAACCGGCCC (SEQ ID NO: 1409) |
| ANGPTLA-Sp141 | 141 | AGTGGACTTCAACCGGCCCT (SEQ ID NO: 1410) |
| ANGPTL4-Sp142 | 142 | CCGGCCCTGGGAAGCCTACA (SEQ ID NO: 1411) |
| ANGPTL4-Sp143 | 143 | CCTTGTAGGCTTCCCAGGGC (SEQ ID NO: 1412) |
| ANGPTL4-Sp144 | 144 | GCCCTGGGAAGCCTACAAGG (SEQ ID NO: 1413) |
| ANGPTL4-Sp145 | 145 | CCCTGGGAAGCCTACAAGGC (SEQ ID NO: 1414) |
| ANGPTL4-Sp146 | 146 | CCCGCCTTGTAGGCTTCCCA (SEQ ID NO: 1415) |
| ANGPTL4-Sp147 | 147 | CCTGGGAAGCCTACAAGGCG (SEQ ID NO: 1416) |
| ANGPTL4-Sp148 | 148 | CCCCGCCTTGTAGGCTTCCC (SEQ ID NO: 1417) |
| ANGPTL4-Sp149 | 149 | GAAGCCTACAAGGCGGGGTT SEQ ID NO: 1418) |
| ANGPTL4-Sp150 | 150 | AAGCCTACAAGGCGGGGTTT (SEQ ID NO: 1419) |
| ANGPTL4-Sp151 | 151 | AGCCTACAAGGCGGGGTTTG (SEQ ID NO: 1420) |
| ANGPTL4-Sp152 | 152 | ATCCCCAAACCCCGCCTTGT (SEQ ID NO: 1421) |
| ANGPTL4-Sp153 | 153 | GCGGGGTTTGGGGATCCCCA (SEQ ID NO: 1422) |
| ANGPTL4-Sp154 | 154 | GGTTTGGGGATCCCCACGGT (SEQ ID NO: 1423) |
| ANGPTL4-Sp155 | 155 | CACTAGAAACACCTACCGTG (SEQ ID NO: 1424) |
| ANGPTL4-Sp156 | 156 | CCACTAGAAACACCTACCGT (SEQ ID NO: 1425) |
| ANGPTL4-Sp157 | 157 | CTCCCACTCCAGGCGAGTTC (SEQ ID NO: 1426) |
| ANGPTL4-Sp158 | 158 | CACTCCAGGCGAGTTCTGGC (SEQ ID NO: 1427) |
| ANGPTL4-Sp159 | 159 | ACTCCAGGCGAGTTCTGGCT (SEQ ID NO: 1428) |
| ANGPTL4-Sp160 | 160 | AGACCCAGCCAGAACTCGCC (SEQ ID NO: 1429) |
| ANGPTL4-Sp161 | 161 | AGGCGAGTTCTGGCTGGGTC (SEQ ID NO: 1430) |
| ANGPTL4-Sp162 | 162 | GTTCTGGCTGGGTCTGGAGA (SEQ ID NO: 1431) |
| ANGATL4-Sp163 | 163 | GGAGAAGGTGCATAGCATCA (SEQ ID NO: 1432) |
| ANGPTL4-Sp164 | 164 | GAGAAGGTGCATAGCATCAC (SEQ ID NO: 1433) |
| ANGPTL4-Sp165 | 165 | AGAAGGTGCATAGCATCACG (SEQ ID NO: 1434) |
| ANGPTL4-Sp166 | 166 | GAAGGTGCATAGCATCACGG (SEQ ID NO: 1435) |
| ANGPTL4-Sp167 | 167 | GGGGGACCGCAACAGCCGCC (SEQ ID NO: 1436) |
| ANGPTL4-Sp168 | 168 | GCACGGCCAGGCGGCTGTTG (SEQ ID NO: 1437) |
| ANGPTL4-Sp169 | 169 | GCCGCCTGGCCGTGCAGCTG (SEQ ID NO: 1438) |

TABLE 14-continued

Target sequences of ANGPTL4-gene for SpCas9

| Gene | No. | Target sequence |
|---|---|---|
| ANGPTL4-Sp170 | 170 | CCGCCTGGCCGTGCAGCTGC (SEQ ID NO: 1439) |
| ANGPTL4-Sp171 | 171 | CCCGCAGCTGCACGGCCAGG (SEQ ID NO: 1440) |
| ANGPTL4-Sp172 | 172 | AGTCCCGCAGCTGCACGGCC (SEQ ID NO: 1441) |
| ANGPTL4-Sp173 | 173 | TGGCCGTGCAGCTGCGGGAC (SEQ ID NO: 1442) |
| ANGPTL4-Sp174 | 174 | GGCCGTGCAGCTGCGGGACT (SEQ ID NO: 1443) |
| ANGPTL4-Sp175 | 175 | ATCCCAGTCCCGCAGCTGCA (SEQ ID NO: 1444) |
| ANGPTL4-Sp176 | 176 | GTGCAGCTGCGGGACTGGGA (SEQ ID NO: 1445) |
| ANGPTL4-Sp177 | 177 | CACGGAGAACTGCAGCAACT (SEQ ID NO: 1446) |
| ANGPTL4-Sp178 | 178 | GCTGCAGTTCTCCGTGCACC (SEQ ID NO: 1447) |
| ANGPTL4-Sp179 | 179 | CTGCAGTTCTCCGTGCACCT (SEQ ID NO: 1448) |
| ANGPTL4-Sp180 | 180 | CAGTTCTCCGTGCACCTGGG (SEQ ID NO: 1449) |
| ANGPTL4-Sp181 | 181 | CTCCGTGCACCTGGGTGGCG (SEQ ID NO: 1450) |
| ANGPTL4-Sp182 | 182 | GTCCTCGCCACCCAGGTGCA (SEQ ID NO: 1451) |
| ANGPTL4-Sp183 | 183 | GCACCTGGGTGGCGAGGACA (SEQ ID NO: 1452) |
| ANGPTL4-Sp184 | 184 | AGGCCGTGTCCTCGCCACCC (SEQ ID NO: 1453) |
| ANGPTL4-Sp185 | 185 | TGCAGTGAGCTGCAGGCTAT (SEQ ID NO: 1454) |
| ANGPTL4-Sp186 | 186 | CCTGCAGCTCACTGCACCCG (SEQ ID NO: 1455) |
| ANGPTL4-Sp187 | 187 | CCACGGGTGCAGTGAGCTGC (SEQ ID NO: 1456) |
| ANGPTL4-Sp188 | 188 | CAGCTCACTGCACCCGTGGC (SEQ ID NO: 1457) |
| ANGPTL4-Sp189 | 189 | TGCACCCGTGGCCGGCCAGC (SEQ ID NO: 1458) |
| ANGPTL4-Sp190 | 190 | GCACCCGTGGCCGGCCAGCT (SEQ ID NO: 1459) |
| ANGPTL4-Sp191 | 191 | GCGCCCAGCTGGCCGGCCAC (SEQ ID NO: 1460) |
| ANGPTL4-Sp192 | 192 | GGCGCCCAGCTGGCCGGCCA (SEQ ID NO: 1461) |
| ANGPTL4-Sp193 | 193 | GGTGGTGGCGCCCAGCTGGC (SEQ ID NO: 1462) |
| ANGPTL4-Sp194 | 194 | GGACGGTGGTGGCGCCCAGC (SEQ ID NO: 1463) |
| ANGPTL4-Sp195 | 195 | GCCACCACCGTCCCACCCAG (SEQ ID NO: 1464) |
| ANGPTL4-Sp196 | 196 | GCCGCTGGGTGGGACGGTGG (SEQ ID NO: 1465) |
| ANGPTL4-Sp197 | 197 | GAGGCCGCTGGGTGGGACGG (SEQ ID NO: 1466) |
| ANGPTL4-Sp198 | 198 | GGAGAGGCCGCTGGGTGGGA (SEQ ID NO: 1467) |
| ANGPTL4-Sp199 | 199 | GTACGGAGAGGCCGCTGGGT (SEQ ID NO: 1468) |
| ANGPTL4-Sp200 | 200 | GGTACGGAGAGGCCGCTGGG (SEQ ID NO: 1469) |
| ANGPTL4-Sp201 | 201 | AAGGGTACGGAGAGGCCGCT (SEQ ID NO: 1470) |
| ANGPTL4-Sp202 | 202 | GAAGGGTACGGAGAGGCCGC (SEQ 10 NO: 1471) |
| ANGPTL4-Sp203 | 203 | AAGTGGAGAAGGGTACGGAG (SEQ ID NO: 1472) |
| ANGPTL4-Sp204 | 204 | TCTCCGTACCCTTCTCCACT (SEQ ID NO: 1473) |
| ANGPTL4-Sp205 | 205 | CTCCGTACCCTTCTCCACTT (SEQ ID NO: 1474) |
| ANGPTL4-Sp206 | 206 | GTCCCAAGTGGAGAAGGGTA (SEQ ID NO: 1475) |
| ANGPTL4-Sp207 | 207 | ACCCTTCTCCACTTGGGACC (SEQ ID NO: 1476) |

TABLE 14-continued

Target sequences of ANGPTL4-gene for SpCas9

| Gene | No. | Target sequence |
|---|---|---|
| ANGPTL4-Sp208 | 208 | TCCTGGTCCCAAGTGGAGAA (SEQ ID NO: 1477) |
| ANGPTL4-Sp209 | 209 | ATCCTGGTCCCAAGTGGAGA (SEQ ID NO: 1478) |
| ANGPTL4-Sp210 | 210 | GTCGTGATCCTGGTCCCAAG (SEQ ID NO: 1479) |
| ANGPTL4-Sp211 | 211 | ACCAGGATCACGACCTCCGC (SEQ ID NO: 1480) |
| ANGPTL4-Sp212 | 212 | CCAGGATCACGACCTCCGCA (SEQ ID NO: 1481) |
| ANGPTL4-Sp213 | 213 | CCCTGCGGAGGTCGTGATCC (SEQ ID NO: 1482) |
| ANGPTL4-Sp214 | 214 | CGCAGTTCTTGTCCCTGCGG (SEQ ID NO: 1483) |
| ANGPTL4-Sp215 | 215 | TGGCGCAGTTCTTGTCCCTG (SEQ ID NO: 1484) |
| ANGPTL4-Sp216 | 216 | AACTGCGCCAAGAGCCTCTC (SEQ ID NO: 1485) |
| ANGPTL4-Sp217 | 217 | CTGCTCACCAGAGAGGCTCT (SEQ ID NO: 1486) |
| ANGPTL4-Sp218 | 218 | GCAGGGCCTGCTCACCAGAG (SEQ ID NO: 1487) |
| ANGPTL4-Sp219 | 219 | CCCTGACCCCGGCAGGAGGC (SEQ ID NO: 1488) |
| ANGPTL4-Sp220 | 220 | TGACCCCGGCAGGAGGCTGG (SEQ ID NO: 1489) |
| ANGPTL4-Sp221 | 221 | CCGGCAGGAGGCTGGTGGTT (SEQ ID NO: 1490) |
| ANGPTL4-Sp222 | 222 | GTTGAGGTTGGAATGGCTGC (SEQ ID NO: 1491) |
| ANGPTL4-Sp223 | 223 | TGCAGCCATTCCAACCTCAA (SEQ ID NO: 1492) |
| ANGPTL4-Sp224 | 224 | ACTGGCCGTTGAGGTTGGAA (SEQ ID NO: 1493) |
| ANGPTL4-Sp225 | 225 | GAAGTACTGGCCGTTGAGGT (SEQ ID NO: 1494) |
| ANGPTL4-Sp226 | 226 | AGCGGAAGTACTGGCCGTTG (SEQ ID NO: 1495) |
| ANGPTL4-Sp227 | 227 | GTGGGATGGAGCGGAAGTAC (SEQ ID NO: 1496) |
| ANGPTL4-Sp228 | 228 | TCCGCTCCATCCCACAGCAG (SEQ ID NO: 1497) |
| ANGPTL4-Sp229 | 229 | GCCGCTGCTGTGGGATGGAG (SEQ ID NO: 1498) |
| ANGPTL4-Sp230 | 230 | CTTCTGCCGCTGCTGTGGGA (SEQ ID NO: 1499) |
| ANGPTL4-Sp231 | 231 | TAAGCTTCTGCCGCTGCTGT (SEQ ID NO: 1500) |
| ANGPTL4-Sp232 | 232 | TTAAGCTTCTGCCGCTGCTG (SEQ ID NO: 1501) |
| ANGPTL4-Sp233 | 233 | GCAGCGGCAGAAGCTTAAGA (SEQ ID NO: 1502) |
| ANGPTL4-Sp234 | 234 | CAGCGGCAGAAGCTTAAGAA (SEQ ID NO: 1503) |
| ANGPTL4-Sp235 | 235 | AGCTTAAGAAGGGAATCTTC (SEQ ID NO: 1504) |
| ANGPTL4-Sp236 | 236 | AGGGAATCTTCTGGAAGACC (SEQ ID NO: 1505) |
| ANGPTL4-Sp237 | 237 | GAATCTTCTGGAAGACCTGG (SEQ ID NO: 1506) |
| ANGPTL4-Sp238 | 238 | AATCTTCTGGAAGACCTGGC (SEQ ID NO: 1507) |
| ANGPTL4-Sp239 | 239 | ATCTTCTGGAAGACCTGGCG (SEQ ID NO: 1508) |
| ANGPTL4-Sp240 | 240 | CGGGTAGTAGCGGCCCCGCC (SEQ ID NO: 1509) |
| ANGPTL4-Sp241 | 241 | GGGCCGCTACTACCCGCTGC (SEQ ID NO: 1510) |
| ANGPTL4-Sp242 | 242 | TGGCCTGCAGCGGGTAGTAG (SEQ ID NO: 1511) |
| ANGPTL4-Sp243 | 243 | ACATGGTGGTGGCCTGCAGC (SEQ ID NO: 1512) |
| ANGPTL4-Sp244 | 244 | AACATGGTGGTGGCCTGCAG (SEQ ID NO: 1513) |
| ANGPTL4-Sp245 | 245 | GGGCTGGATCAACATGGTGG (SEQ ID NO: 1514) |

TABLE 14-continued

Target sequences of ANGPTL4-gene for SpCas9

| Gene | No. | Target sequence |
|---|---|---|
| ANGPTL4-Sp246 | 246 | CATGGGCTGGATCAACATGG (SEQ ID NO: 1515) |
| ANGPTL4-Sp247 | 247 | CACCATGTTGATCCAGCCCA (SEQ ID NO: 1516) |
| ANGPTL4-Sp248 | 248 | TGCCATGGGCTGGATCAACA (SEQ ID NO: 1517) |
| ANGPTL4-Sp249 | 249 | GATCCAGCCCATGGCAGCAG (SEQ ID NO: 1518) |
| ANGPTL4-Sp250 | 250 | CTGCCTCTGCTGCCATGGGC (SEQ ID NO: 1519) |
| ANGPTL4-Sp251 | 251 | GAGGCTGCCTCTGCTGCCAT (SEQ ID NO: 1520) |
| ANGPTL4-Sp252 | 252 | GGAGGCTGCCTCTGCTGCCA (SEQ ID NO: 1521) |
| ANGPTL4-Sp253 | 253 | GGCCCAGCCAGGACGCTAGG (SEQ ID NO: 1522) |

2. Construction of CjCas9 and sgRNA Plasmids

A sequence encoding human codon-optimized CjCas9 (derived from *Campylobacter jejuni* subsp. *jejuni* NCTC 11168) was synthesized to have a nuclear localization signal (NLS) and an HA epitope at the C-terminus (GeneArt™ Gene Synthesis, Thermo Fisher Scientific), and the synthesized nucleic acid sequence was replicated using a p3s plasmid described in previous research (Cho, S. W., Kim, S., Kim, J. M. & Kim, J. S. Targeted genome engineering in human cells with the Cas9 RNA-guided endonuclease. Nature Biotechnology 31, 230-232 (2013)).

A tracrRNA (transactivating crRNA) sequence and a pre-crRNA (precursor CRISPR RNA) sequence were connected using a GAAA or TGAA linker, thereby producing sgRNA. The sgRNA regulated transcription with an U6 promoter.

3. PAM Characterization Using Cell-Based Reporter Analysis

An AAVS1 target site (AAVS1-TS1) having a variable PAM sequence (5'-NNNNXCAC-3', 5'-NNNNAXAC-3', 5'-NNNNACXC-3', and 5'-NNNNACAX-3') including a random sequence at the X site was synthesized (Macrogen, Inc.), and the synthesized nucleic acid sequence may be replicated using a surrogate reporter plasmid encoding RFP and GFP.

To determine a suitable PAM sequence, the constructed reporter plasmid (100 ng), and plasmids encoding CjCas9 (225 ng) and sgRNA (675 ng) were co-transfected into HEK293 cells ($1 \times 10^5$) using lipofectamine 2000 (Invitrogen). Two days after the transfection, a fractionation of the GFP and RFP-positive cells was measured by flow cytometry (BD Accuri™ C6, BD).

4. Cell Culture and Mutation Analysis

HEK293 (ATCC, CRL-1573) cells and mouse NIH 3T3 (ATCC, CRL-1658) cells were cultured in a Dulbecco's modified Eagle's medium (DMEM) supplemented with 100 units/mL penicillin, 100 mg/mL streptomycin, and 10% fetal bovine serum (FBS).

A sgRNA plasmid (750 ng) and a CjCas9 plasmid (250 ng) were transfected into cells ($0.5 \sim 1 \times 10^5$) using lipofectamine 2000 (Invitrogen). 48 hours after the transfection, genome DNA was separated using a DNeasy blood & tissue kit (Qiagen), and an on-target or off-target site was amplified for targeted deep sequencing. Deep sequencing libraries were generated by PCR. TruSeq HT Dual Index primers were used to label respective samples. Mixed libraries were subjected to paired-end sequencing (LAS, Inc.), and indel frequencies were calculated.

5. Construction of AAV Vectors Encoding CjCas9 and sgRNA Sequences

An AAV inverted terminal repeat (ITR)-based vector plasmid containing an sgRNA sequence and a CjCas9 gene having NLS and HA tags at the C-terminus was constructed. sgRNA transcription was induced by an U6 promoter, and CjCas9 expression was regulated by an EFS promoter in C2C12 myoblasts, or by a Spc512 promoter in the TA muscle of C57BL/6 mice.

For retinal delivery, an AAV vector encoding the U6 promoter-induced sgRNA and CjCas9 under the control of the EFS promoter, specific to the Vegfa gene and Hif1a gene, was constructed, wherein CjCas9 had eGFP linked to the C-terminus using a self-cleaved T2A peptide.

6. Production, Purification and Characterization of AAV Vector

To produce the AAV vector, a pseudotype of AAVDJ or AAV9 capsids was used. The HEK293T cells were transfected with pAAV-ITR-CjCas9-sgRNA, pAAVED2/9, and a helper plasmid. The HEK293T cells were cultured in a 2% FBS-containing DMEM. Recombinant AAV vector stocks were produced using PEI coprecipitation by mixing polyplus-transfection (PEIpro), triple-transfection and the plasmid in a molar ratio of 1:1:1 in the HEK293T cells. After 72 hours of culturing, the cells were lysed, and particles were isolated and purified with iodixanol (Sigma-Aldrich) by step-gradient ultracentrifugation. The number of vector genomes was quantified through quantitative PCR.

7. AAV Transduction in Mouse Myoblasts

Mouse myoblasts were infected with various viral amounts of AAVDJ-CjCas9 (multiplicity of infection (MOI): 1, 5, 10, 50, and 100 (determined by quantitative PCR)), and cultured in 2% FBS-containing DMEM. For the target deep sequencing, cells were obtained at different points of time. MOI 1 is considered as infection by one virus particle among a total of 100 virus particles determined by quantitative PCR.

8. Animals

Management, use and treatment of all animals used in this research were performed under the guidance provided by the Seoul National University Animal Care and Use Committee, ophthalmology and security research, and the strict agreement according to the ARVO statement on animal use in veterinary medicine. In this research, specific male pathogen free (SPF)-6-week old C57BL/6J mice were used. The mice were maintained in a 12-hour light/dark cycle.

Diabetic model mice were induced by injecting streptozotocin (STZ, Sigma-Aldrich, St. Louis, MO, USA) intraperitonially once. As a control, a citrate buffer was injected. 4 days after the STZ injection, when a blood glucose level of the mouse was 300 mg/dl or more, diabetes was considered to be induced.

9. Injection of AAV into Vitreous Body

A mixture of tiletamine and zolazepam in a ratio of 1:1 (2.25 mg/kg (body weight) each), and 0.7 mg/kg (body weight) of xylazine hydrochloride was injected into a vitreous body of a 6-week old mouse for anesthetization. 2 µl (2×10¹⁰ viral genome) of AAV9-CjCas9 was injected into the vitreous body using a Nanofil syringe (World Precision Instruments Inc.) having a 33 G blunt needle under a surgical microscope (Leica Microsystems Ltd.).

In the case of diabetic mouse models, the mice were injected with STZ to induce diabetes, anesthetized after 1 or 7 weeks, and 2 µl of the mixture containing 0.8×10⁸ vg/µl of CjCas9:Vegfa or 1.5×10⁹ vg/µl of Rosa26 was injected in the vitreous body.

10. Immunofluorescence Staining and Imaging of Retinal Tissue 42 days after the injection, the sample was fixed with formalin and embedded in paraffin (n=4). A sample obtained by cross-section of the sample-embedded paraffin was immunostained with an anti-HA antibody (Roche, 3F10, 1:1000), an anti-opsin antibody (Millipore, AB5405, 1:1000), and an Alexa Fluor 488 or 594 antibody (Thermo Fisher Scientific, 1:500). An opsin-positive site was detected in RPE cells expressing HA-tagged CjCas9 using Image J software (1.47v, NIH). The distribution of CjCas9 and eGFP was visualized on RPE flat-mounts using a confocal microscope (LSM 710, Carl Zeiss).

11. Extraction of Genome DNA

To extract DNA from RPE and the retina, after obtaining images of RPE and the retina flat-mounts, the tissue samples were washed with PBS. RPE cells were separated from the choroid/sclera by vortexing for 30 seconds in a lysis buffer (NucleoSpin Tissue, Macherey-Nagel). Genome DNA was analyzed to identify complete isolation of the RPE cells from remaining choroid/sclera tissue. The genome DNA was analyzed by target deep sequencing.

12. Mouse Vegfa ELISA 42 days after the injection, a total RPE mixture was isolated from neural retina tissue, and two kinds of tissue were frozen for subsequent analysis. The sample tissue was lysed in 120 µl of a cell lysis buffer (CST #9803), and the amount of a Vegfa protein was measured using a mouse VEGF Quantikine ELISA kit (MMV00, R&D Systems).

13. Laser-Induced CNV Model

After anesthetization of a mouse, eye drops containing 0.5% phenylephrine and 0.5% tropicamide were injected to dilate a pupil. Laser photocoagulation was performed using an indirect head set delivery system (Iridex) and a laser system (Ilooda). Parameters of the laser are a wavelength of 532 nm, a spot size of 200 µm, a power of 800 mW and exposure time of 70 ms. A laser burn was induced in the proximity of the optical nerve three to four times. Burns in which bubbles are generated without bleeding of the vitreous body were only used for the research. After 7 days, an eyeball was fixed with 4% paraformaldehyde at room temperature for one hour. An RPE mixture (RPE/choroid/sclera) was immunostained overnight at 4° C. using isolectin-B4 (Thermo Fisher Scientific, cat. no. 121413, 1:100) and an anti-GFP antibody (Abcam, ab6556, 1:100). The RPE mixture was flat-mounted, and visualized using a fluorescent microscope (Eclipse 90i, Nikon) or a confocal microscope (LSM 710, Carl Zeiss) at a 100× magnification. A CNV site was detected using Image J software (1.47v, NIH). An average of three to four CNV sites per eyeball was analyzed. Each group consists of 17 to 18 eyeballs.

14. Quantitative and Qualitative Analyses for Rupturing of Retinal Vessels

To detect vascular leakage, STZ-induced diabetic mouse models were used. 200 µl of an Evans blue dye (20 mg/ml) dissolved in PBS was intravenously injected into an anesthetized mouse. Two hours after perfusion, an eyeball was extracted to be fixed with 4% paraformaldehyde for 1 hour. The retina was excised in 2×PBS and flat-mounted, and images of the retina were obtained at 40× and 100× magnifications using a fluorescent microscope (Eclipse 90i, Nikon).

To quantitatively analyze the vascular leakage, representative four sites of the vascular leakage in the mid-peripheral retina (0.5 µm×0.5 µm) of each mouse were selected. The mid-peripheral retina was designated as the middle ⅓ of the retina from the optic nerve head to the ciliary body, images were modulated according to color threshold values based on the automatic isodata algorithm using the Image J software (1.47v, NIH), and regions of interest containing the Evans blue dye were marked in red. Afterward, the regions marked in red were detected. The data were normalized with data of control mice, and represented as vascular leakage (%).

15. Data Analysis

To previously determine a sample size in vitro or in vivo, a statistical method was not used. For statistical analysis, one-way ANOVA and Tukey post-hoc tests were used.

Example 1. Confirmation of CjCas9 Expression Through AAV in Mouse Retinal Tissue Since CjCas9 consisting of 984 amino acids has a considerably smaller size (2.95 kbp) than SpCas9, both CjCas9 gene and sgRNA are able to be packaged in one AAV vector. Therefore, in this example, to confirm the possibility of gene manipulation using CjCas9 as a method for treating AMD, CjCas9-expressing AAV was used.

Figure 2:
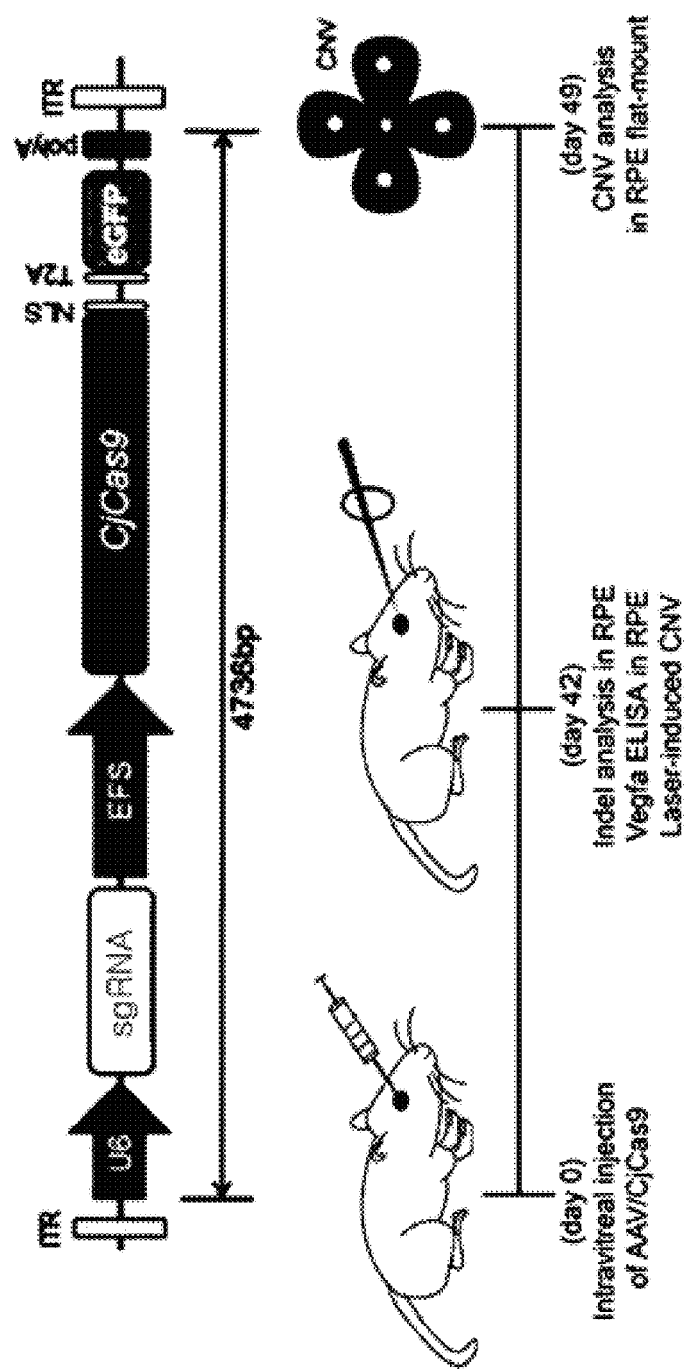
Figure 4:
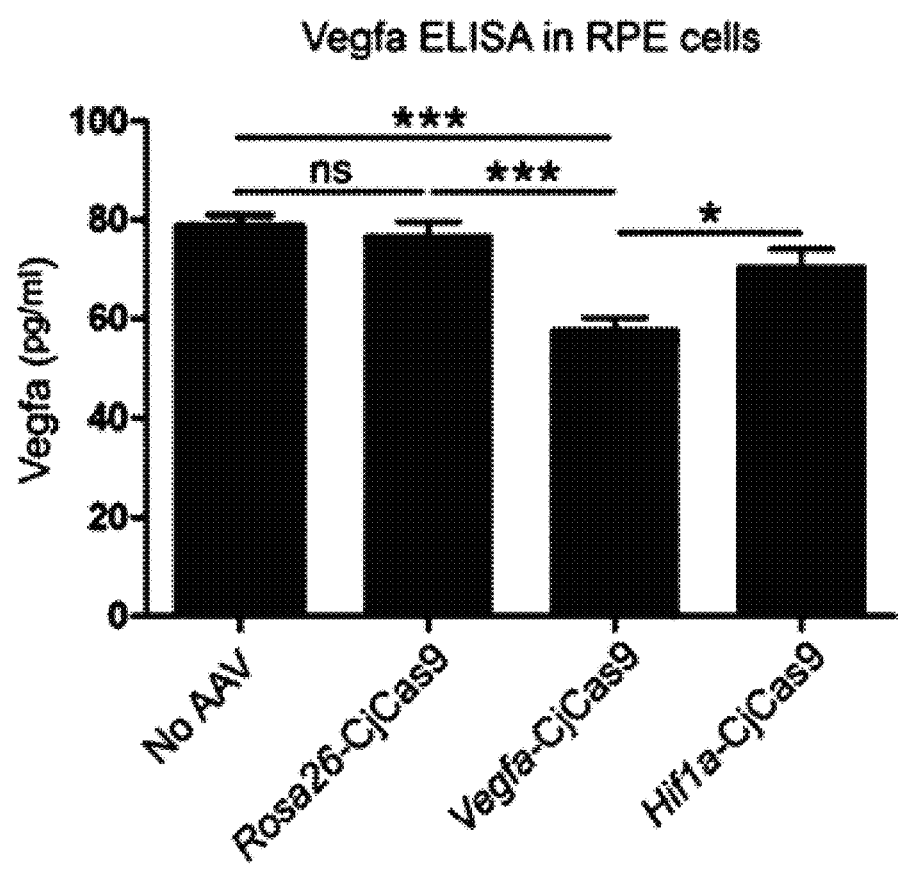

To confirm the expression of CjCas9 through AAV in tissue such as the retina in a mouse, under the control of U6 promoter-induced sgRNA and an EFS promoter specific to a choroidal neovascularization (CNV)-associated Vegfa gene and an Hif1a gene, a CjCas9-coding AAV9 vector was constructed, and here, CjCas9 was linked to eGFP at the C-terminus using a self-cleaved T2A peptide (FIGS. 1 and 2). The constructed virus was injected into an eyeball through injection into the vitreous body, and after 6 weeks, CjCas9 expression in the eyeball was confirmed, an indel frequency was measured using target deep sequencing, and the amount of Vegfa protein was measured through ELISA (FIG. 4).

Figure 8:
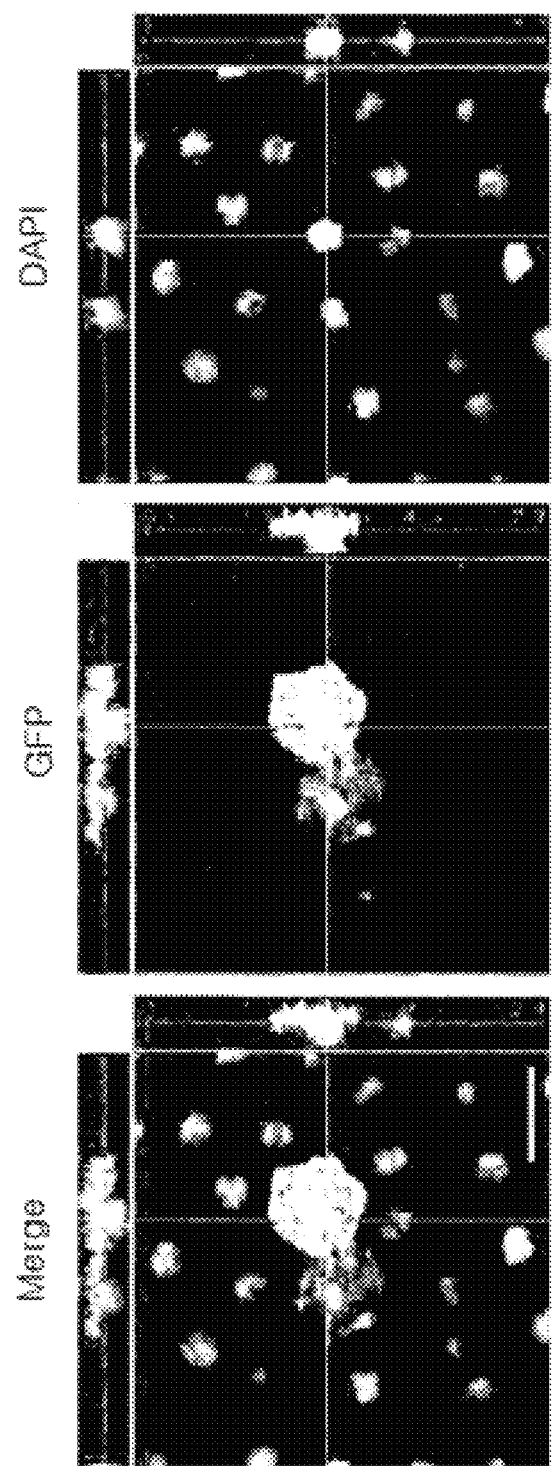
FIG. 8 shows images of in vivo expression of eGFP with CjCas9 in mouse RPE cells (n=6, anti-GFP antibody (green) and DAPI (blue), Scale bar=20 µm).

The expression of the CjCas9-linked eGFP was confirmed in retinal pigment epithelial (RPE) cells (FIG. 8).

Figure 3:
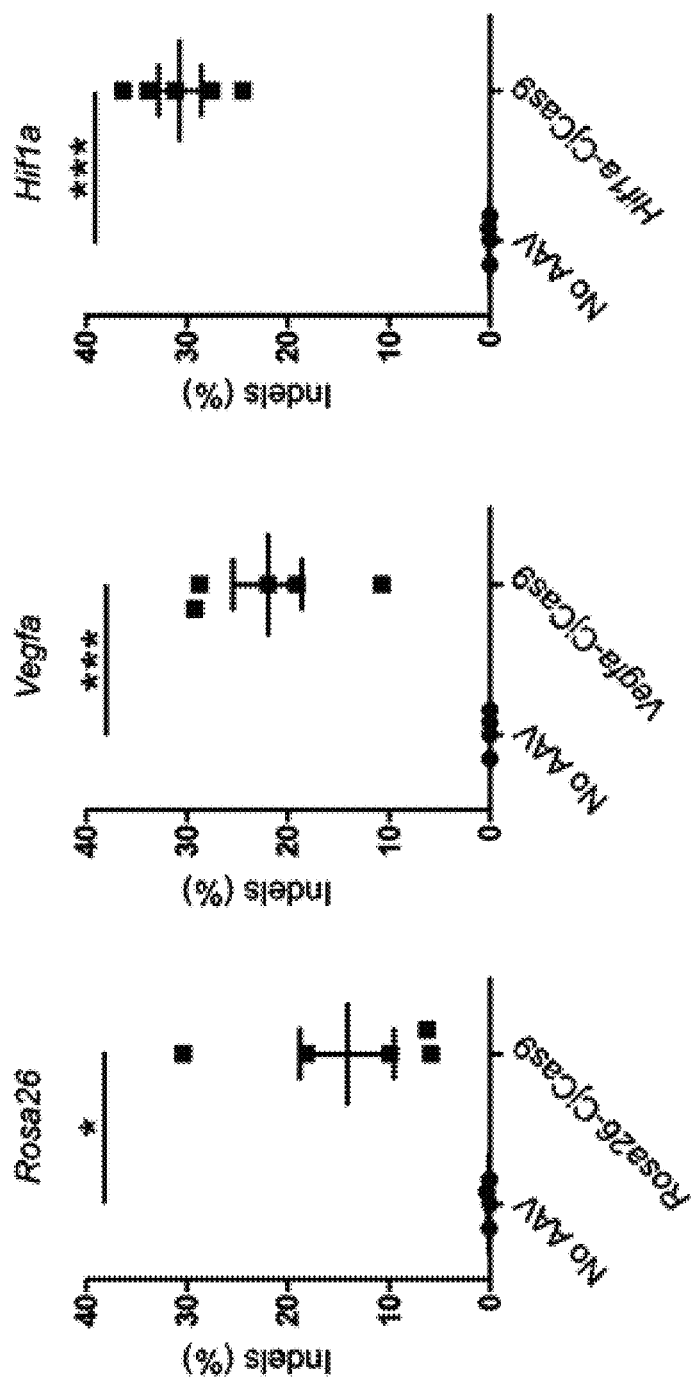
Figure 5:
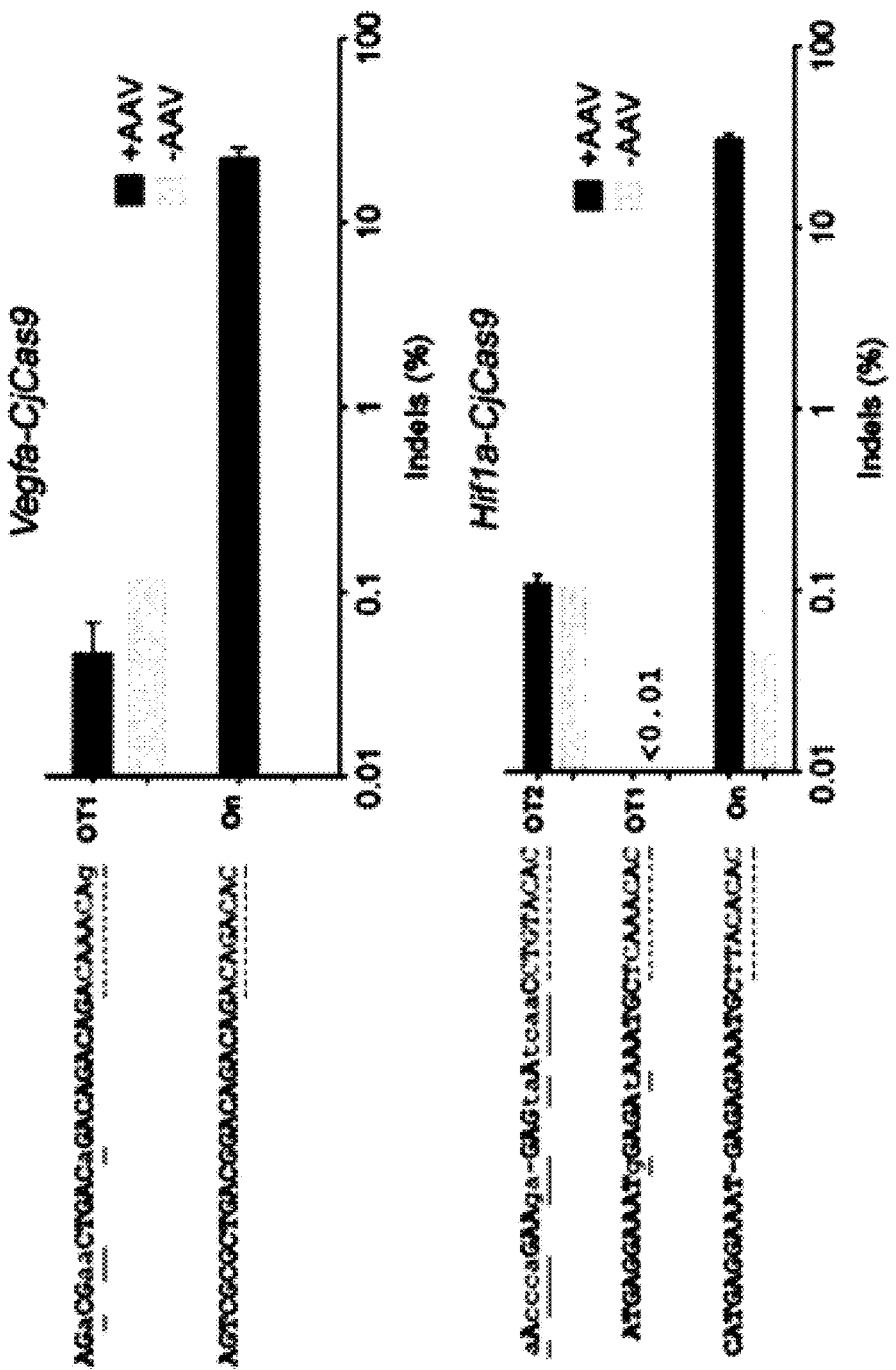

In addition, indels induced by CjCas9 were observed at Rosa26, Vegfa, and Hif1a target sites of the RPE cells, indel frequencies of 14±5%, 22±3%, and 31±2% were confirmed, respectively (FIG. 3). In addition, noticeable off-target indels were not induced by Vegfa- or Hif1a-specific sgRNA in the cells (FIG. 5).

As expected, the expression level of the Vegfa protein was decreased in AAV-treated RPE cells encoding Vegfa-specific CjCas9 (AAV-CjCas9: Vegfa), but was not when Hif1a- or Rosa26-specific CjCas9 (AAV-CjCas9: Hif1a or Rosa26)-coding AAV was treated (FIG. 4). Particularly, since a Hif1a protein is degraded under a normoxia condition, the expression level of the protein was not able to be measured.

Figure 6:
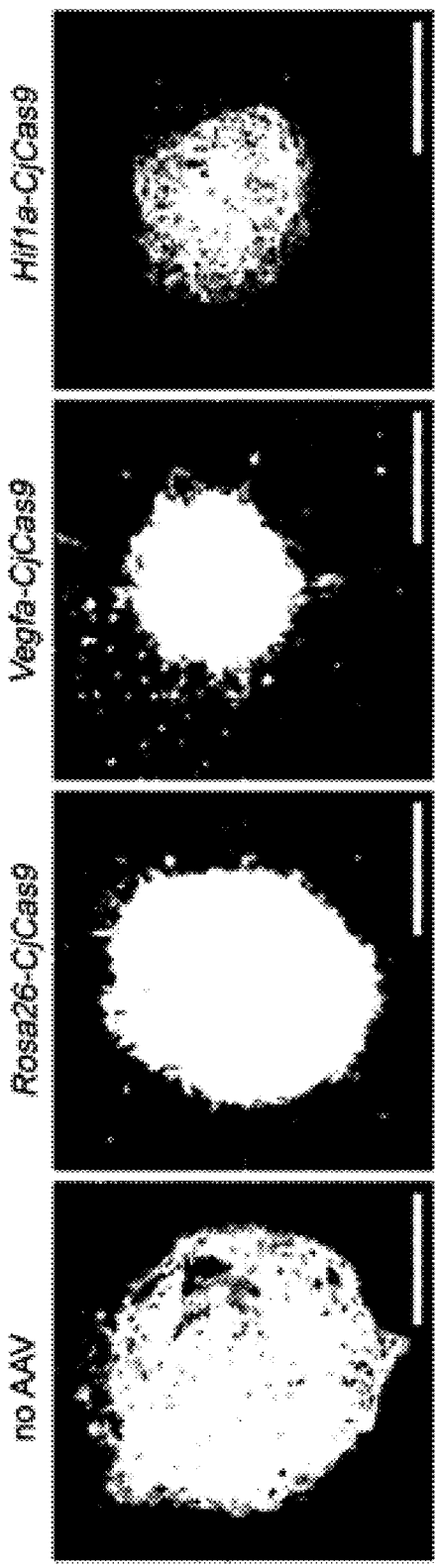
Figure 7:
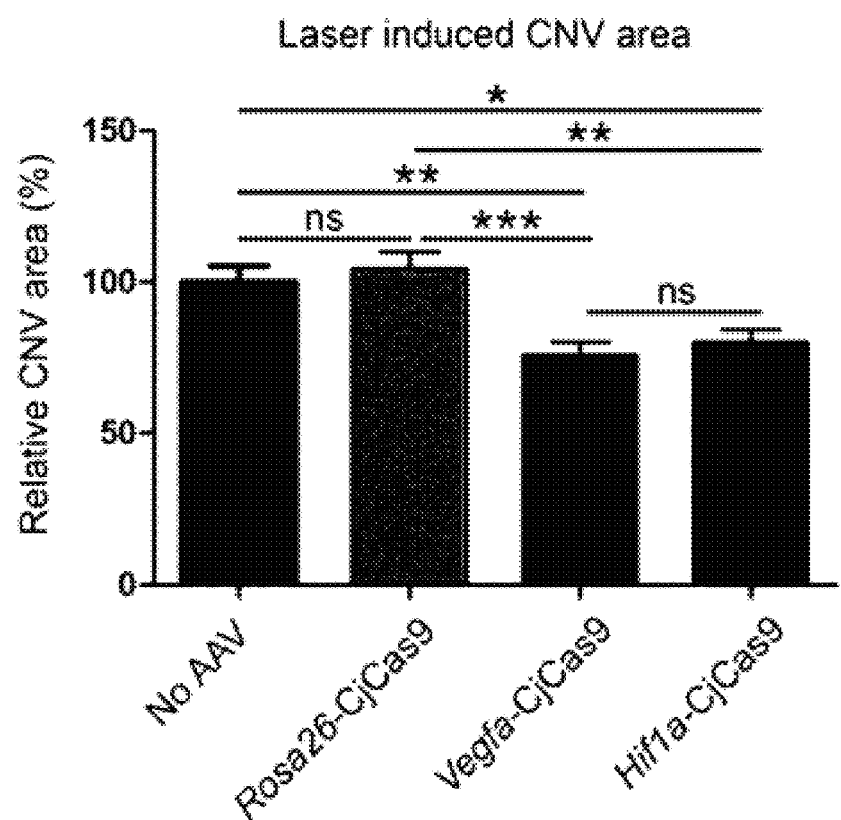

Example 2. Effect of Vegfa- or Hif1a-Specific AAV-CjCas9 Using CNV-Induced Mouse To induce CNV, an eyeball was injected with AAV, and after 6 weeks, subjected to laser treatment, followed by detecting the CNV sites one week after the laser treatment (FIG. 6). When AAV-CjCas9: Vegfa and AAV-CjCas9: Hif1a were injected onto respective eyeballs, it was confirmed that, compared with an AAV-free negative control, CNV sites were decreased 24±4% and 20±4%, respectively (FIGS. 6 and 7). In the case of another negative control, that is, Rosa26-specific CjCas9, no therapeutic effect was confirmed, either.

Example 3. Effect of AAV-CjCas9 for AMD Treatment

Figure 9:
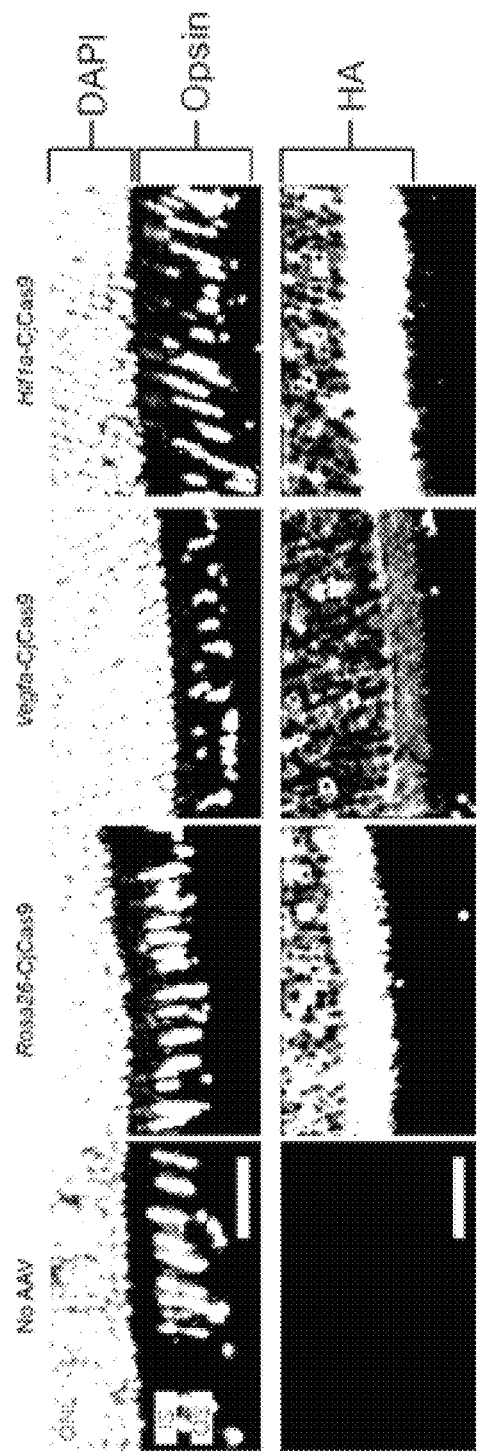
FIGS. 9 and 10 show opsin-positive areas in the retinas of AAV/CjCas9-injected mice.
Figure 10:
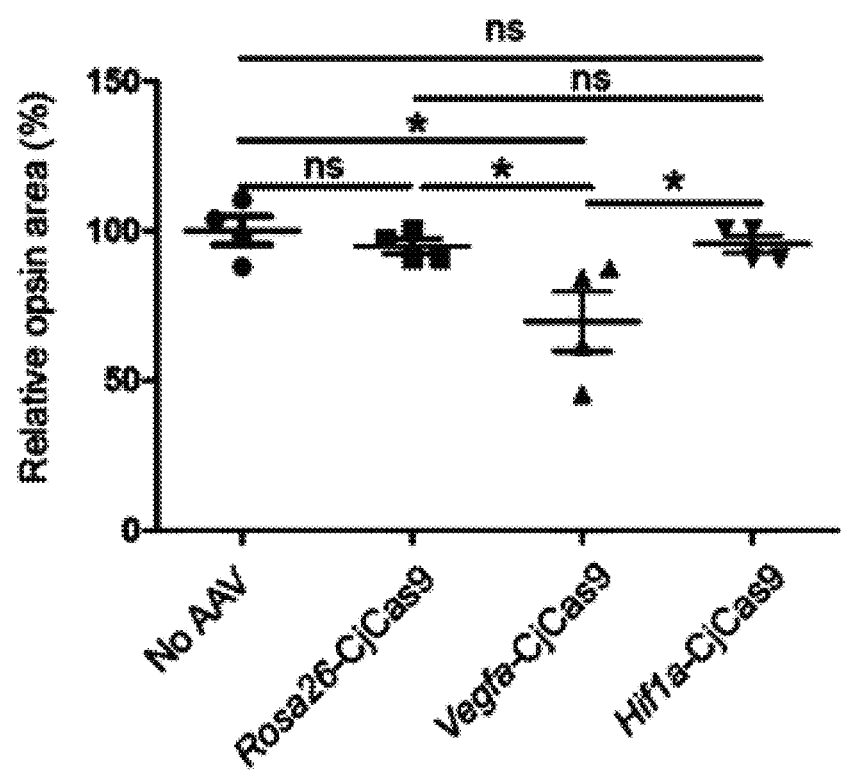

Since cone dysfunction is caused by conditional knockout of a Vegfa gene in the mouse RPE cells, the cause of side effects by the AAV-induced gene knockout in the RPE cells was investigated. To this end, the size of a cone function-related opsin-positive site in the retina was measured. As a result, the Vegfa-specific CjCas9 was decreased in size by approximately 30±10% the AAV-free control (FIGS. 9 and 10). However, as expected, the Hif1a- or Rosa26-specific CjCas9 did not induce cone dysfunction. Such a result may suggest that Hif1a inactivation for treatment of AMD inhibits neovascularization and does not cause cone dysfunction. HIF1A is a hypoxia-inducible transcription factor, and serves to activate VEGFA transcription. Unlike VEGFA, which is a primary therapeutic target for AMD treatment and a secretory protein, HIF1A may not be considered as a drug target, and generally, a transcription factor such as HIF1A may not be directly targeted by an antibody or aptamer, or small molecules. In this research, as the Hif1a gene was effectively inactivated in the RPE cells using CjCas9 targeting the Hif1a gene on the eyeball of a mouse, it was confirmed that the CNV sites were reduced in the AMD mouse models (FIGS. 9 and 10).

Example 4. Effect of AAV-CjCas9 for Treatment of Retinal Disease

Figure 11:
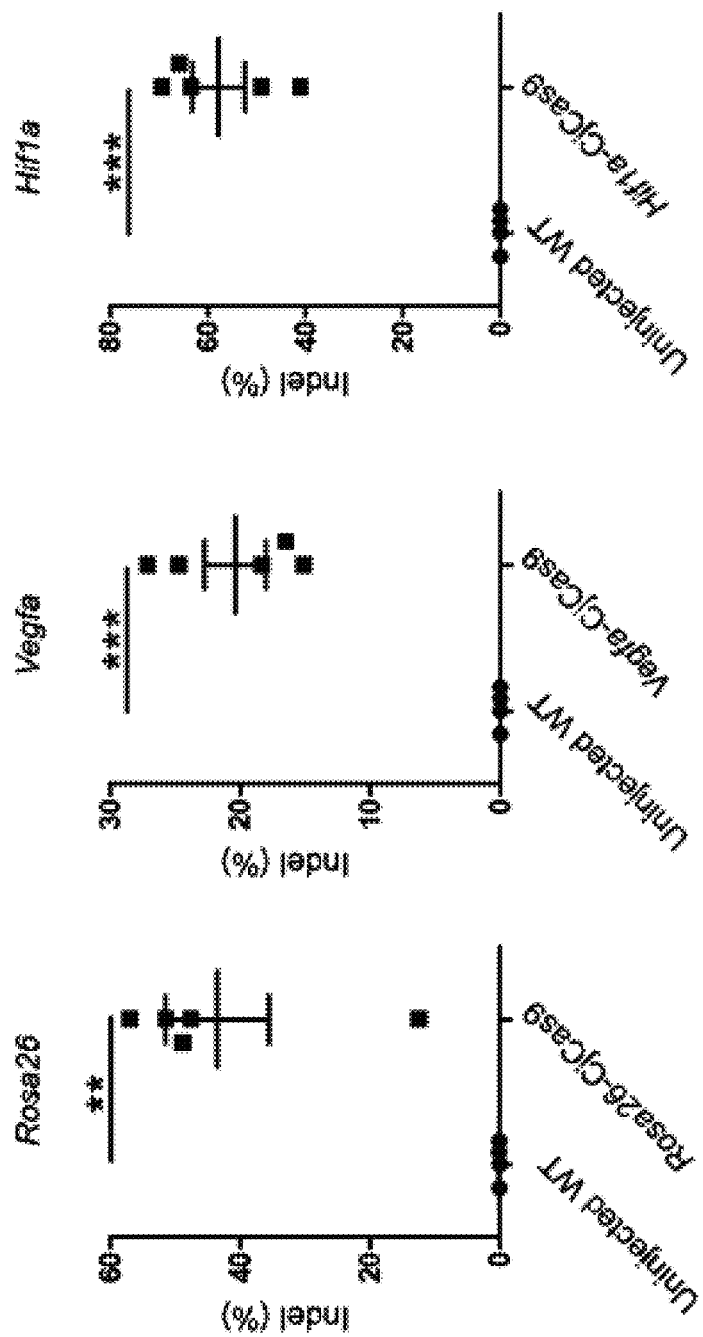
FIGS. 11 and 12 show reduced expression of VEGF due to CjCas9 targeting Vegfa or Hif1a in retinal tissue.
Figure 12:
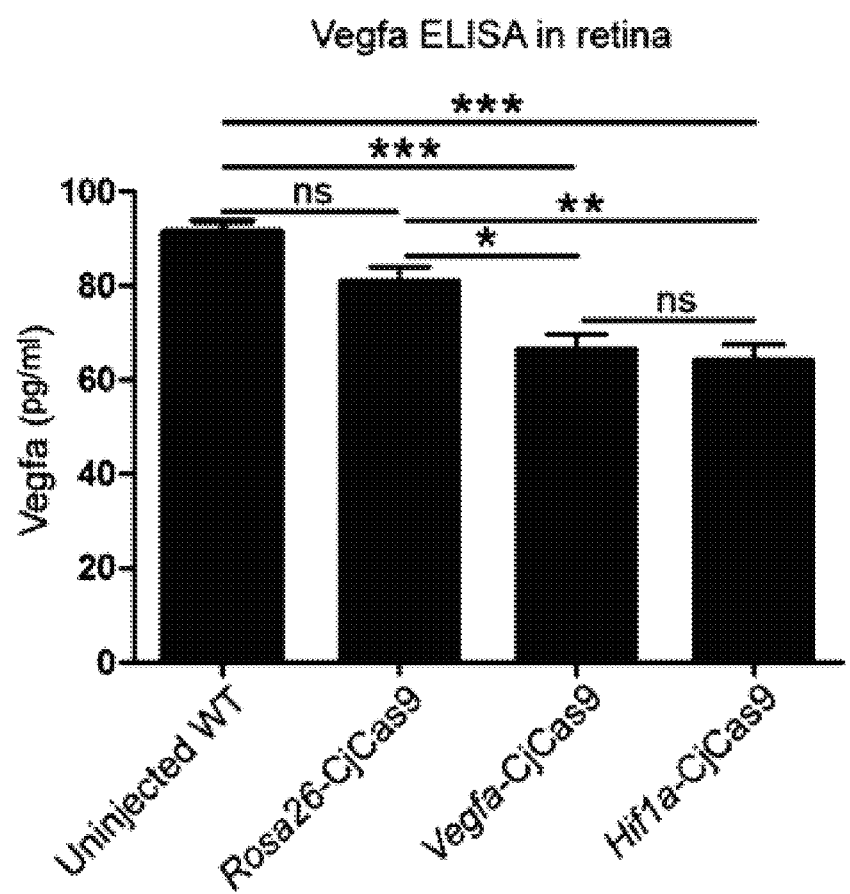

For extended application to retinal diseases such as diabetic retinopathy (DR), retinopathy of prematurity, etc., the constructed virus was injected into the eyeball through injection into the vitreous body, and 6 weeks later, the in vivo genome editing effect caused by the indel frequency in retinal tissue was observed by target deep sequencing, followed by confirming an expression level of the Vegfa protein through ELISA (FIG. 2). In the retinal tissue, the indels induced by CjCas9 were observed at the Rosa26, Vegfa, and Hif1a target sites in the retinal cells, indel frequencies of 44±8%, 20±2%, and 58±5% were confirmed, respectively (FIG. 11). As expected, an expression level of the Vegfa protein was decreased in retinal cells when treated with AAV encoding Vegfa- or Hif1a-specific CjCas9 (AAV-CjCas9: Vegfa or Hif1a), but did not when AAV encoding Rosa26-specific CjCas9 (AAV-CjCas9: Rosa26) was treated (FIG. 12).

Example 5. Effect of AAV-CjCas9 for Treatment of Diabetic Retinopathy

Figure 13:
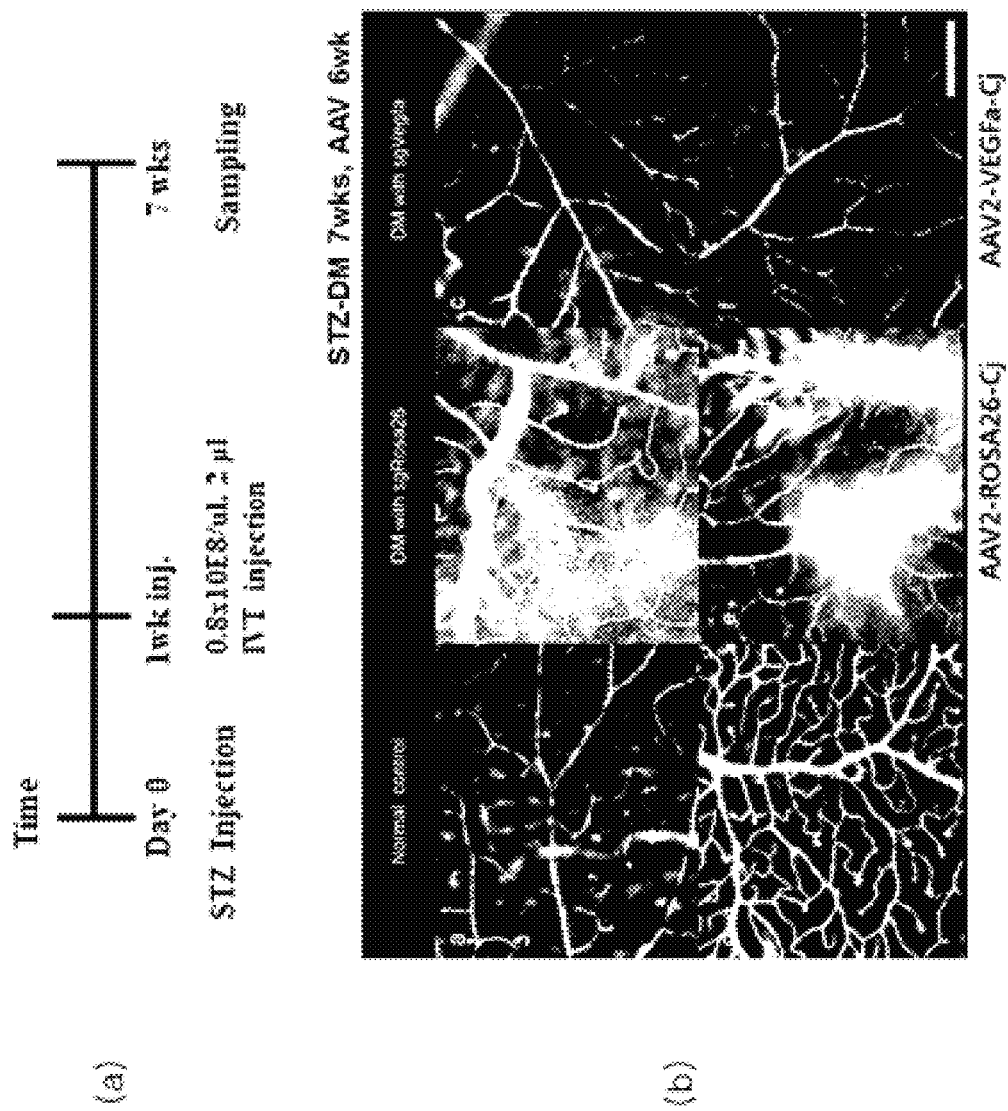
FIG. 13 shows the reducing effect of CjCas9 targeting Vegfa on vascular leakage and blood leakage in retinas of diabetic retinopathy mouse models, (a) an in vivo test schedule, (b) images of reduced effects on vascular leakage and blood leakage in mouse retinas injected with AAV2-CjCa9 targeting Vegfa.
Figure 14:
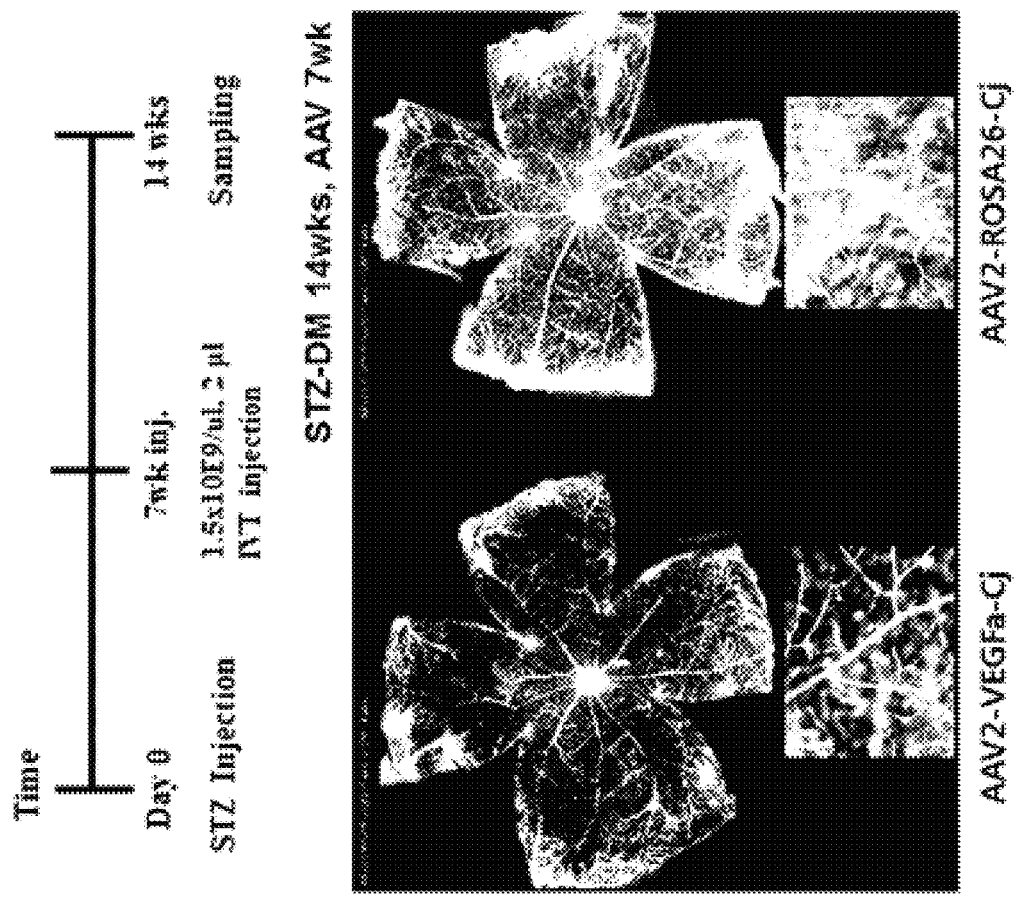
FIGS. 14 and 15 show the reducing effect of CjCas9 targeting Vegfa on vascular leakage and blood leakage in retinas of diabetic retinopathy mouse models.
Figure 15:
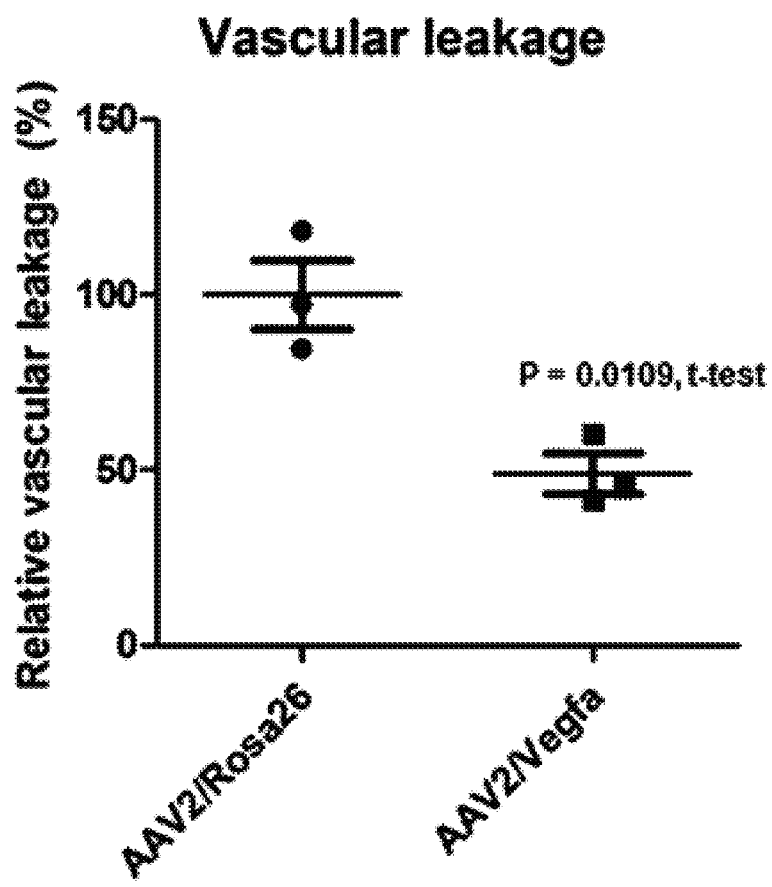

Diabetic retinopathy is characterized by the symptoms of vascular leakage and blood leakage. Therefore, in this example, the vascular leakage or blood leakage symptom was confirmed using diabetes-induced mice using STZ, and an improvement or treatment effect caused by CjCas9 was confirmed. As a result, it was confirmed that the blood leakage caused by vascular leakage and rupturing was decreased in the Vegfa-specific CjCas9 (AAV-CjCas9: Vegfa)-injected retina. Compared with Rosa26-specific CjCas9 (AAV-CjCas9: Rosa26)-injected mice, vascular leakage and blood leakage in Vegfa-specific CjCas9 (AAV-CjCas9: Vegfa)-injected mice were decreased and thus recovered to a level similar as in normal mice of the same age. Such a result was similarly shown in both of an experiment in which STZ was injected, AAV-CjCas9 was injected after 7 weeks and observation was performed after 6 weeks (FIG. 13), and an experiment in which STZ was injected, AAV-CjCas9 was injected after 14 weeks and observation was performed after 7 weeks (FIGS. 14 and 15). According to the above results, it was confirmed that Vegfa-specific CjCas9 (AAV-CjCas9: Vegfa) has an effect of reducing vascular leakage and blood leakage, and thus it can be expected that the Vegfa-specific CjCas9 (AAV-CjCas9: Vegfa) can effectively treat diabetic retinopathy.

Example 6. Screening of Target Site of Human Neovascularization-Associated Factor To extend the application of the previously-described example, in addition to human VEGFA (FIG. 16) and human HIF1A (FIG. 17), human ANGPT2 (FIG. 19), human EPAS1 (FIG. 20) and human ANGPTL4 (FIG. 21) were selected as potential targets of genome editing for AMD and DR treatments to screen the target site of each gene capable of being effectively edited in human cells using a CjCas9 system. Particularly, the CjCas9 target site of the mouse Hif1a gene was completely conserved in a human or a different mammal (FIG. 18). Additionally, the high editing efficiency of the conserved target site was observed in human cells (FIG. 17, sgRNA #7). Therefore, it is expected that AAV for Hif1a suggested in this research or a mutant thereof is able to be used in treatment of a future human patient.

INDUSTRIAL APPLICABILITY

An artificially manipulated neovascularization-associated factor and a neovascularization system artificially modified in function thereby can be effectively used in treatment of an angiogenic disease, for example, an angiogenesis-associated ocular disease.

Efficiency of the neovascularization system can be improved by regulating characteristics such as survival, proliferation, persistency, cytotoxicity, and cytokine-release of various neovascularization-associated factors.

Original Claims

1. An artificially manipulated neovascularization-associated factor, which is selected from the group consisting of a VEGFA gene, an HIF1A gene, an ANGPT2 gene, an EPAS1 gene and an ANGPTL4 gene, which has a modification in a nucleic acid sequence.
2. The artificially manipulated neovascularization-associated factor of paragraph 1, wherein the modification in the nucleic acid sequence is artificially caused by a guide nucleic acid-editor protein complex.

3. The artificially manipulated neovascularization-associated factor of paragraph 1, wherein the neovascularization-associated factor is one or more selected from the group consisting of a VEGFA gene, an HIF1A gene, an ANGPT2 gene, an EPAS1 gene and an ANGPTL4 gene.

4. The artificially manipulated neovascularization-associated factor of paragraph 1, wherein the gene is a neovascularization-associated factor artificially manipulated by a guide nucleic acid-editor protein complex, wherein the neovascularization-associated factor artificially manipulated includes one or more modifications of nucleic acids which is at least one of a deletion or insertion of one or more nucleotides, a substitution with one or more nucleotides different from a wild-type gene, and an insertion of one or more foreign nucleotide, in a proto-spacer-adjacent motif (PAM) sequence in a nucleic acid sequence constituting the neovascularization-associated factor or in a continuous 1 bp to 50 bp the base sequence region adjacent to the 5' end and/or 3' end thereof, or a chemical modification of one or more nucleotides in a nucleic acid sequence constituting the neovascularization-associated factor.

5. The artificially manipulated neovascularization-associated factor of paragraph 1, wherein the modification of nucleic acids occurs in a promoter region of the gene.

6. The artificially manipulated neovascularization-associated factor of paragraph 1, wherein the modification of nucleic acids occurs in an exon region of the gene.

7. The artificially manipulated neovascularization-associated factor of paragraph 1, wherein the modification of nucleic acids occurs in an intron region of the gene.

8. The artificially manipulated neovascularization-associated factor of paragraph 1, wherein the modification of nucleic acids occurs in an enhancer region of the gene.

9. The artificially manipulated neovascularization-associated factor of paragraph 4, wherein the PAM sequence is, one or more of the following sequences (described in the 5' to 3' direction): NGG (N is A, T, C or G); NNNNRYAC (each N is independently A, T, C or G, R is A or G, and Y is C or T); NNAGAAW (each N is independently A, T, C or G, and W is A or T); NNNNGATT (each N is independently A, T, C or G); NNGRR(T) (each N is independently A, T, C or G, R is A or G); and TTN (N is A, T, C or G).

10. The artificially manipulated neovascularization-associated factor of paragraph 2, wherein the editor protein includes one or more selected from the group consisting of a *Streptococcus pyogenes*-derived Cas9 protein, a *Campylobacter jejuni*-derived Cas9 protein, a *Streptococcus thermophilus*-derived Cas9 protein, a *Streptococcus aureus*-derived Cas9 protein, a *Neisseria meningitidis*-derived Cas9 protein, and a Cpf1 protein.

11. A guide nucleic acid, which is capable of forming complementary bonds with respect to the target sequences of SEQ ID NOs: 1 to 79 in the nucleic acid sequences of one or more genes selected from the group consisting of a VEGFA gene, an HIF1A gene, an ANGPT2 gene, an EPAS1 gene and an ANGPTL4 gene, respectively.

12. The guide nucleic acid of paragraph 11, which includes one or more guide nucleic acids selected from the group consisting of: guide nucleic acids capable of forming complementary bonds with respect to the target sequences of SEQ ID NOs: 3, 4, 7, 9, 10 and 11 in the nucleic acid sequence of the VEGFA gene, respectively; guide nucleic acids capable of forming complementary bonds with respect to the target sequences of SEQ ID NOs: 14, 18, 19, 20, 26, 29 and 31 in the nucleic acid sequence of the HIF1A gene, respectively; guide nucleic acids capable of forming complementary bonds with respect to the target sequences of SEQ ID NOs: 33, 34, 37, 38, 39 and 43 in the nucleic acid sequence of the ANGPT2 gene, respectively; guide nucleic acids capable of forming complementary bonds with respect to the target sequences of SEQ ID NOs: 47, 48, 49, 50, 53, 54 and 55 in the nucleic acid sequence of the EPAS1 gene, respectively; and guide nucleic acids capable of forming complementary bonds with respect to the target sequences of SEQ ID NOs: 64, 66, 67, 73, 76 and 79 in the nucleic acid sequence of the ANGPTL4 gene, respectively.

13. The guide nucleic acid of paragraph 11, wherein the guide nucleic acid is nucleotide molecule of 18 to 23 bp.

14. A composition for gene manipulation, comprising: a guide nucleic acid capable of forming a complementary bond with respect to the target sequences of SEQ ID NOs: 1 to 79 in nucleic acid sequences of one or more genes selected from the group consisting of a VEGFA gene, an HIF1A gene, an ANGPT2 gene, an EPAS1 gene and an ANGPTL4 gene, respectively, or a nucleic acid sequence encoding the same; and an editor protein or a nucleic acid sequence encoding the same.

15. The composition for gene manipulation of paragraph 14, wherein the editor protein includes one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Streptococcus aureus*-derived Cas9 protein, a *Neisseria meningitidis*-derived Cas9 protein, and a Cpf1 protein.

16. The composition for gene manipulation of paragraph 14, wherein the gene manipulation includes one or more modifications of nucleic acids which is at least one of a deletion or insertion of one or more nucleotides, a substitution with one or more nucleotides different from a wild-type gene, and an insertion of one or more foreign nucleotide, in a proto-spacer-adjacent motif (PAM) sequence in a nucleic acid sequence constituting the neovascularization-associated factor or in a continuous 1 bp to 50 bp the base sequence region adjacent to the 5' end and/or 3' end thereof, or a chemical modification of one or more nucleotides in a nucleic acid sequence constituting the neovascularization-associated factor.

17. The composition for gene manipulation of paragraph 16, wherein the PAM sequence includes one or more of the following sequences (described in the 5' to 3' direction): NGG (N is A, T, C or G); NNNNRYAC (each N is independently A, T, C or G, R is A or G, and Y is C or T); NNAGAAW (each N is independently A, T, C or G, and W is A or T); NNNNGATT (each N is independently A, T, C or G); NNGRR(T) (each N is independently A, T, C or G, R is A or G); and TTN (N is A, T, C or G).

18. The composition for gene manipulation of paragraph 14, wherein the composition for gene manipulation is formed in a viral vector system.

19. The composition for gene manipulation of paragraph 18, wherein the viral vector includes one or more selected from a retrovirus, a lentivirus, an adenovirus, adeno-associated virus (AAV), vaccinia virus, a poxvirus and a herpes simplex virus.
20. A method for providing information on a sequence of an artificially manipulatable target site in a subject by analyzing sequences of one or more genes selected from the group consisting of a VEGFA gene, an HIF1A gene, an ANGPT2 gene, an EPAS1 gene and an ANGPTL4 gene.
21. A method for constructing a library using the information provided by the method of claim 20.
22. A kit for gene manipulation, comprising: (a) a guide nucleic acid capable of forming complementary bonds with respect to each of the target sequences of SEQ ID NOs: 1 to 79, in the nucleic acid sequences of one or more genes selected from the group consisting of a VEGFA gene, an HIF1A gene, an ANGPT2 gene, an EPAS1 gene and an ANGPTL4 gene, respectively, or a nucleic acid sequence encoding the same; and (b) an editor protein including one or more proteins selected from the group consisting of a *Streptococcus pyogenes*-derived Cas9 protein, a *Campylobacter jejuni*-derived Cas9 protein, a *Streptococcus thermophilus*-derived Cas9 protein, a *Streptococcus aureus*-derived Cas9 protein, a *Neisseria meningitidis*-derived Cas9 protein, and a Cpf1 protein, respectively, or a nucleic acid sequence encoding the same.
23. A composition for treating an angiovascular disorder, comprising: a guide nucleic acid capable of forming complementary bonds with respect to each of one or more target sequences in the nucleic acid sequences of one or more genes selected from the group consisting of a VEGFA gene, an HIF1A gene, an ANGPT2 gene, an EPAS1 gene and an ANGPTL4 gene, respectively, or a nucleic acid sequence encoding the same; and an editor protein or a nucleic acid sequence encoding the same.
24. The composition for treating of paragraph 23, wherein the target sequence includes one or more of target sequences of SEQ ID NOs: 1 to 79.
25. The composition for treating of paragraph 23, wherein the editor protein is a *Campylobacter jejuni*-derived Cas9 protein.
26. The composition for treating of paragraph 23, wherein the angiovascular disorder is ischemic retinopathy or retinopathy of prematurity.

SEQUENCE LISTING

```
<160> NUMBER OF SEQ ID NOS: 1578

<210> SEQ ID NO 1
<211> LENGTH: 22
<212> TYPE: DNA
<213> ORGANISM: homo sapiens

<400> SEQUENCE: 1
gtagagcagc aaggcaaggc tc                                          22

<210> SEQ ID NO 2
<211> LENGTH: 22
<212> TYPE: DNA
<213> ORGANISM: homo sapiens

<400> SEQUENCE: 2
ctttctgtcc tcagtggtcc ca                                          22

<210> SEQ ID NO 3
<211> LENGTH: 22
<212> TYPE: DNA
<213> ORGANISM: homo sapiens

<400> SEQUENCE: 3
gagaccctgg tggacatctt cc                                          22

<210> SEQ ID NO 4
<211> LENGTH: 22
<212> TYPE: DNA
<213> ORGANISM: homo sapiens

<400> SEQUENCE: 4
ttccaggagt accctgatga ga                                          22

<210> SEQ ID NO 5
<211> LENGTH: 22
<212> TYPE: DNA
<213> ORGANISM: homo sapiens
```

```
<400> SEQUENCE: 5
ttgaagatgt actcgatctc at                                          22

<210> SEQ ID NO 6
<211> LENGTH: 22
<212> TYPE: DNA
<213> ORGANISM: homo sapiens

<400> SEQUENCE: 6
aggggcacac aggatggctt ga                                          22

<210> SEQ ID NO 7
<211> LENGTH: 22
<212> TYPE: DNA
<213> ORGANISM: homo sapiens

<400> SEQUENCE: 7
agcagccccc gcatcgcatc ag                                          22

<210> SEQ ID NO 8
<211> LENGTH: 22
<212> TYPE: DNA
<213> ORGANISM: homo sapiens

<400> SEQUENCE: 8
gcagcagccc ccgcatcgca tc                                          22

<210> SEQ ID NO 9
<211> LENGTH: 22
<212> TYPE: DNA
<213> ORGANISM: homo sapiens

<400> SEQUENCE: 9
gtgatgttgg actcctcagt gg                                          22

<210> SEQ ID NO 10
<211> LENGTH: 22
<212> TYPE: DNA
<213> ORGANISM: homo sapiens

<400> SEQUENCE: 10
tggtgatgtt ggactcctca gt                                          22

<210> SEQ ID NO 11
<211> LENGTH: 22
<212> TYPE: DNA
<213> ORGANISM: homo sapiens

<400> SEQUENCE: 11
catggtgatg ttggactcct ca                                          22

<210> SEQ ID NO 12
<211> LENGTH: 22
<212> TYPE: DNA
<213> ORGANISM: homo sapiens

<400> SEQUENCE: 12
atgcggatca aacctcacca ag                                          22

<210> SEQ ID NO 13
<211> LENGTH: 22
<212> TYPE: DNA
<213> ORGANISM: homo sapiens
```

```
<400> SEQUENCE: 13
cacataggag agatgagctt cc                                              22

<210> SEQ ID NO 14
<211> LENGTH: 22
<212> TYPE: DNA
<213> ORGANISM: homo sapiens

<400> SEQUENCE: 14
actcaccagc atccagaagt tt                                              22

<210> SEQ ID NO 15
<211> LENGTH: 22
<212> TYPE: DNA
<213> ORGANISM: homo sapiens

<400> SEQUENCE: 15
atttggatat tgaagatgac at                                              22

<210> SEQ ID NO 16
<211> LENGTH: 22
<212> TYPE: DNA
<213> ORGANISM: homo sapiens

<400> SEQUENCE: 16
atttacattt ctgataatgt ga                                              22

<210> SEQ ID NO 17
<211> LENGTH: 22
<212> TYPE: DNA
<213> ORGANISM: homo sapiens

<400> SEQUENCE: 17
atgtgtttac agtttgaact aa                                              22

<210> SEQ ID NO 18
<211> LENGTH: 22
<212> TYPE: DNA
<213> ORGANISM: homo sapiens

<400> SEQUENCE: 18
ctgtgtccag ttagttcaaa ct                                              22

<210> SEQ ID NO 19
<211> LENGTH: 22
<212> TYPE: DNA
<213> ORGANISM: homo sapiens

<400> SEQUENCE: 19
atggtcacat ggatgagtaa aa                                              22

<210> SEQ ID NO 20
<211> LENGTH: 22
<212> TYPE: DNA
<213> ORGANISM: homo sapiens

<400> SEQUENCE: 20
catgaggaaa tgagagaaat gc                                              22

<210> SEQ ID NO 21
<211> LENGTH: 22
<212> TYPE: DNA
```

```
<213> ORGANISM: homo sapiens

<400> SEQUENCE: 21
cccagtgaga aagggaaag aa                                    22

<210> SEQ ID NO 22
<211> LENGTH: 22
<212> TYPE: DNA
<213> ORGANISM: homo sapiens

<400> SEQUENCE: 22
ttgtgaaaaa gggtaaagaa ca                                   22

<210> SEQ ID NO 23
<211> LENGTH: 22
<212> TYPE: DNA
<213> ORGANISM: homo sapiens

<400> SEQUENCE: 23
atagttcttc ctcggctagt ta                                   22

<210> SEQ ID NO 24
<211> LENGTH: 22
<212> TYPE: DNA
<213> ORGANISM: homo sapiens

<400> SEQUENCE: 24
tcatagttct tcctcggcta gt                                   22

<210> SEQ ID NO 25
<211> LENGTH: 22
<212> TYPE: DNA
<213> ORGANISM: homo sapiens

<400> SEQUENCE: 25
tgttcttcat acacaggtat tg                                   22

<210> SEQ ID NO 26
<211> LENGTH: 22
<212> TYPE: DNA
<213> ORGANISM: homo sapiens

<400> SEQUENCE: 26
tacgtgaatg tggcctgtgc ag                                   22

<210> SEQ ID NO 27
<211> LENGTH: 22
<212> TYPE: DNA
<213> ORGANISM: homo sapiens

<400> SEQUENCE: 27
ctgcacaggc cacattcacg ta                                   22

<210> SEQ ID NO 28
<211> LENGTH: 22
<212> TYPE: DNA
<213> ORGANISM: homo sapiens

<400> SEQUENCE: 28
ctgaggttgg ttactgttgg ta                                   22

<210> SEQ ID NO 29
<211> LENGTH: 22
```

```
<212> TYPE: DNA
<213> ORGANISM: homo sapiens

<400> SEQUENCE: 29
caggtcatag gtggtttctt at                                              22

<210> SEQ ID NO 30
<211> LENGTH: 22
<212> TYPE: DNA
<213> ORGANISM: homo sapiens

<400> SEQUENCE: 30
accaagcagg tcataggtgg tt                                              22

<210> SEQ ID NO 31
<211> LENGTH: 22
<212> TYPE: DNA
<213> ORGANISM: homo sapiens

<400> SEQUENCE: 31
ttagatagca agactttcct ca                                              22

<210> SEQ ID NO 32
<211> LENGTH: 22
<212> TYPE: DNA
<213> ORGANISM: homo sapiens

<400> SEQUENCE: 32
tcaggtccag catgggtcct gc                                              22

<210> SEQ ID NO 33
<211> LENGTH: 22
<212> TYPE: DNA
<213> ORGANISM: homo sapiens

<400> SEQUENCE: 33
cggcgcgtcc ctctgcacag ca                                              22

<210> SEQ ID NO 34
<211> LENGTH: 22
<212> TYPE: DNA
<213> ORGANISM: homo sapiens

<400> SEQUENCE: 34
gctgtgcaga gggacgcgcc gc                                              22

<210> SEQ ID NO 35
<211> LENGTH: 22
<212> TYPE: DNA
<213> ORGANISM: homo sapiens

<400> SEQUENCE: 35
atcgtattcg agcggcgcgt cc                                              22

<210> SEQ ID NO 36
<211> LENGTH: 22
<212> TYPE: DNA
<213> ORGANISM: homo sapiens

<400> SEQUENCE: 36
gatgttctcc agcacttgca gc                                              22

<210> SEQ ID NO 37
```

-continued

```
<211> LENGTH: 22
<212> TYPE: DNA
<213> ORGANISM: homo sapiens

<400> SEQUENCE: 37
agtgctggag aacatcatgg aa                                              22

<210> SEQ ID NO 38
<211> LENGTH: 22
<212> TYPE: DNA
<213> ORGANISM: homo sapiens

<400> SEQUENCE: 38
acaacatgaa gaaagaaatg gt                                              22

<210> SEQ ID NO 39
<211> LENGTH: 22
<212> TYPE: DNA
<213> ORGANISM: homo sapiens

<400> SEQUENCE: 39
aaatggtaga gatacagcag aa                                              22

<210> SEQ ID NO 40
<211> LENGTH: 22
<212> TYPE: DNA
<213> ORGANISM: homo sapiens

<400> SEQUENCE: 40
ttctatcatc acagccgtct gg                                              22

<210> SEQ ID NO 41
<211> LENGTH: 22
<212> TYPE: DNA
<213> ORGANISM: homo sapiens

<400> SEQUENCE: 41
aagttcaagt ctcgtggtct ga                                              22

<210> SEQ ID NO 42
<211> LENGTH: 22
<212> TYPE: DNA
<213> ORGANISM: homo sapiens

<400> SEQUENCE: 42
acgagacttg aacttcagct ct                                              22

<210> SEQ ID NO 43
<211> LENGTH: 22
<212> TYPE: DNA
<213> ORGANISM: homo sapiens

<400> SEQUENCE: 43
aagaaggtgc tagctatgga ag                                              22

<210> SEQ ID NO 44
<211> LENGTH: 22
<212> TYPE: DNA
<213> ORGANISM: homo sapiens

<400> SEQUENCE: 44
gatgatgtgc ttgtcttcca ta                                              22
```

```
<210> SEQ ID NO 45
<211> LENGTH: 22
<212> TYPE: DNA
<213> ORGANISM: homo sapiens

<400> SEQUENCE: 45
aacacctccg tctccttgct cc                                              22

<210> SEQ ID NO 46
<211> LENGTH: 22
<212> TYPE: DNA
<213> ORGANISM: homo sapiens

<400> SEQUENCE: 46
gaagctgacc agcagatgga ca                                              22

<210> SEQ ID NO 47
<211> LENGTH: 22
<212> TYPE: DNA
<213> ORGANISM: homo sapiens

<400> SEQUENCE: 47
gcaatgaaac cctccaaggc tt                                              22

<210> SEQ ID NO 48
<211> LENGTH: 22
<212> TYPE: DNA
<213> ORGANISM: homo sapiens

<400> SEQUENCE: 48
aaaacatcag caagttcatg gg                                              22

<210> SEQ ID NO 49
<211> LENGTH: 22
<212> TYPE: DNA
<213> ORGANISM: homo sapiens

<400> SEQUENCE: 49
gcaagttcat gggacttaca ca                                              22

<210> SEQ ID NO 50
<211> LENGTH: 22
<212> TYPE: DNA
<213> ORGANISM: homo sapiens

<400> SEQUENCE: 50
ggtcgcaggg atgagtgaag tc                                              22

<210> SEQ ID NO 51
<211> LENGTH: 22
<212> TYPE: DNA
<213> ORGANISM: homo sapiens

<400> SEQUENCE: 51
gcgggacttc ttcatgagga tg                                              22

<210> SEQ ID NO 52
<211> LENGTH: 22
<212> TYPE: DNA
<213> ORGANISM: homo sapiens

<400> SEQUENCE: 52
gaagtgcacg gtcaccaaca ga                                              22
```

```
<210> SEQ ID NO 53
<211> LENGTH: 22
<212> TYPE: DNA
<213> ORGANISM: homo sapiens

<400> SEQUENCE: 53
acagtacggc tctgttggt ga                                                 22

<210> SEQ ID NO 54
<211> LENGTH: 22
<212> TYPE: DNA
<213> ORGANISM: homo sapiens

<400> SEQUENCE: 54
tccaggtggc tgacttgagg tt                                                22

<210> SEQ ID NO 55
<211> LENGTH: 22
<212> TYPE: DNA
<213> ORGANISM: homo sapiens

<400> SEQUENCE: 55
caggacagca ggggctcctt gt                                                22

<210> SEQ ID NO 56
<211> LENGTH: 22
<212> TYPE: DNA
<213> ORGANISM: homo sapiens

<400> SEQUENCE: 56
tagcccccat gctttgcgag ca                                                22

<210> SEQ ID NO 57
<211> LENGTH: 22
<212> TYPE: DNA
<213> ORGANISM: homo sapiens

<400> SEQUENCE: 57
gcatcagggc tgccccggcc gt                                                22

<210> SEQ ID NO 58
<211> LENGTH: 22
<212> TYPE: DNA
<213> ORGANISM: homo sapiens

<400> SEQUENCE: 58
gcatcagggc tgccccggcc gt                                                22

<210> SEQ ID NO 59
<211> LENGTH: 22
<212> TYPE: DNA
<213> ORGANISM: homo sapiens

<400> SEQUENCE: 59
ggacgcaaag cgcggcgact tg                                                22

<210> SEQ ID NO 60
<211> LENGTH: 22
<212> TYPE: DNA
<213> ORGANISM: homo sapiens

<400> SEQUENCE: 60
tcctgggacg agatgaatgt cc                                                22
```

<210> SEQ ID NO 61
<211> LENGTH: 22
<212> TYPE: DNA
<213> ORGANISM: homo sapiens

<400> SEQUENCE: 61
ctgcagctcg gccaggggct gc    22

<210> SEQ ID NO 62
<211> LENGTH: 22
<212> TYPE: DNA
<213> ORGANISM: homo sapiens

<400> SEQUENCE: 62
ccaggggctg cgcgaacacg cg    22

<210> SEQ ID NO 63
<211> LENGTH: 22
<212> TYPE: DNA
<213> ORGANISM: homo sapiens

<400> SEQUENCE: 63
ccctcggttc cctgacaggc gg    22

<210> SEQ ID NO 64
<211> LENGTH: 22
<212> TYPE: DNA
<213> ORGANISM: homo sapiens

<400> SEQUENCE: 64
accctgaggt ccttcacagc ct    22

<210> SEQ ID NO 65
<211> LENGTH: 22
<212> TYPE: DNA
<213> ORGANISM: homo sapiens

<400> SEQUENCE: 65
ttccacaagg tggcccagca gc    22

<210> SEQ ID NO 66
<211> LENGTH: 22
<212> TYPE: DNA
<213> ORGANISM: homo sapiens

<400> SEQUENCE: 66
cagcagcagc ggcacctgga ga    22

<210> SEQ ID NO 67
<211> LENGTH: 22
<212> TYPE: DNA
<213> ORGANISM: homo sapiens

<400> SEQUENCE: 67
tcctagtttg gcctcctgga cc    22

<210> SEQ ID NO 68
<211> LENGTH: 22
<212> TYPE: DNA
<213> ORGANISM: homo sapiens

<400> SEQUENCE: 68

```
gacccggctc acaatgtcag cc                                              22

<210> SEQ ID NO 69
<211> LENGTH: 22
<212> TYPE: DNA
<213> ORGANISM: homo sapiens

<400> SEQUENCE: 69
gctgttgcgg tcccccgtga tg                                              22

<210> SEQ ID NO 70
<211> LENGTH: 22
<212> TYPE: DNA
<213> ORGANISM: homo sapiens

<400> SEQUENCE: 70
ggcgttgcca tcccagtccc gc                                              22

<210> SEQ ID NO 71
<211> LENGTH: 22
<212> TYPE: DNA
<213> ORGANISM: homo sapiens

<400> SEQUENCE: 71
aacgccgagt tgctgcagtt ct                                              22

<210> SEQ ID NO 72
<211> LENGTH: 22
<212> TYPE: DNA
<213> ORGANISM: homo sapiens

<400> SEQUENCE: 72
ataggccgtg tcctcgccac cc                                              22

<210> SEQ ID NO 73
<211> LENGTH: 22
<212> TYPE: DNA
<213> ORGANISM: homo sapiens

<400> SEQUENCE: 73
gttctccgtg cacctgggtg gc                                              22

<210> SEQ ID NO 74
<211> LENGTH: 22
<212> TYPE: DNA
<213> ORGANISM: homo sapiens

<400> SEQUENCE: 74
acacggccta tagcctgcag ct                                              22

<210> SEQ ID NO 75
<211> LENGTH: 22
<212> TYPE: DNA
<213> ORGANISM: homo sapiens

<400> SEQUENCE: 75
ccaccgtccc acccagcggc ct                                              22

<210> SEQ ID NO 76
<211> LENGTH: 22
<212> TYPE: DNA
<213> ORGANISM: homo sapiens

<400> SEQUENCE: 76
```

| | |
|---|---|
| gtgatcctgg tcccaagtgg ag | 22 |

<210> SEQ ID NO 77
<211> LENGTH: 22
<212> TYPE: DNA
<213> ORGANISM: homo sapiens

<400> SEQUENCE: 77

| | |
|---|---|
| gaccccggca ggaggctggt gg | 22 |

<210> SEQ ID NO 78
<211> LENGTH: 22
<212> TYPE: DNA
<213> ORGANISM: homo sapiens

<400> SEQUENCE: 78

| | |
|---|---|
| tgcagccatt ccaacctcaa cg | 22 |

<210> SEQ ID NO 79
<211> LENGTH: 22
<212> TYPE: DNA
<213> ORGANISM: homo sapiens

<400> SEQUENCE: 79

| | |
|---|---|
| tgccgctgct gtgggatgga gc | 22 |

<210> SEQ ID NO 80
<211> LENGTH: 22
<212> TYPE: DNA
<213> ORGANISM: homo sapiens

<400> SEQUENCE: 80

| | |
|---|---|
| aaatcccggt ataagtcctg ga | 22 |

<210> SEQ ID NO 81
<211> LENGTH: 22
<212> TYPE: DNA
<213> ORGANISM: homo sapiens

<400> SEQUENCE: 81

| | |
|---|---|
| gcaccaacgt acacgctcca gg | 22 |

<210> SEQ ID NO 82
<211> LENGTH: 22
<212> TYPE: DNA
<213> ORGANISM: homo sapiens

<400> SEQUENCE: 82

| | |
|---|---|
| cattagacag cagcgggcac ca | 22 |

<210> SEQ ID NO 83
<211> LENGTH: 22
<212> TYPE: DNA
<213> ORGANISM: homo sapiens

<400> SEQUENCE: 83

| | |
|---|---|
| ggcattagac agcagcgggc ac | 22 |

<210> SEQ ID NO 84
<211> LENGTH: 22
<212> TYPE: DNA
<213> ORGANISM: homo sapiens

```
<400> SEQUENCE: 84
ggctccaggg cattagacag ca                                        22

<210> SEQ ID NO 85
<211> LENGTH: 22
<212> TYPE: DNA
<213> ORGANISM: homo sapiens

<400> SEQUENCE: 85
gctcagagcg gagaaagcat tt                                        22

<210> SEQ ID NO 86
<211> LENGTH: 22
<212> TYPE: DNA
<213> ORGANISM: homo sapiens

<400> SEQUENCE: 86
ggaacattta cacgtctgcg ga                                        22

<210> SEQ ID NO 87
<211> LENGTH: 22
<212> TYPE: DNA
<213> ORGANISM: homo sapiens

<400> SEQUENCE: 87
gcagacgtgt aaatgttcct gc                                        22

<210> SEQ ID NO 88
<211> LENGTH: 22
<212> TYPE: DNA
<213> ORGANISM: homo sapiens

<400> SEQUENCE: 88
gagtctgtgt ttttgcagga ac                                        22

<210> SEQ ID NO 89
<211> LENGTH: 22
<212> TYPE: DNA
<213> ORGANISM: homo sapiens

<400> SEQUENCE: 89
gcaccaacgt acacgctcca gg                                        22

<210> SEQ ID NO 90
<211> LENGTH: 22
<212> TYPE: DNA
<213> ORGANISM: homo sapiens

<400> SEQUENCE: 90
actaaaggac aagtcaccac ag                                        22

<210> SEQ ID NO 91
<211> LENGTH: 22
<212> TYPE: DNA
<213> ORGANISM: homo sapiens

<400> SEQUENCE: 91
tatccacctc ttttggcaag ca                                        22

<210> SEQ ID NO 92
<211> LENGTH: 22
<212> TYPE: DNA
```

```
<400> SEQUENCE: 92
tgaaactcaa gcaactgtca ta                                          22

<210> SEQ ID NO 93
<211> LENGTH: 22
<212> TYPE: DNA
<213> ORGANISM: homo sapiens

<400> SEQUENCE: 93
ctcacaacgt aattcacaca ta                                          22

<210> SEQ ID NO 94
<211> LENGTH: 22
<212> TYPE: DNA
<213> ORGANISM: homo sapiens

<400> SEQUENCE: 94
tacttacctc acaacgtaat tc                                          22

<210> SEQ ID NO 95
<211> LENGTH: 22
<212> TYPE: DNA
<213> ORGANISM: homo sapiens

<400> SEQUENCE: 95
aacttactta cctcacaacg ta                                          22

<210> SEQ ID NO 96
<211> LENGTH: 22
<212> TYPE: DNA
<213> ORGANISM: homo sapiens

<400> SEQUENCE: 96
tcttgttttg acagtggtat ta                                          22

<210> SEQ ID NO 97
<211> LENGTH: 22
<212> TYPE: DNA
<213> ORGANISM: homo sapiens

<400> SEQUENCE: 97
gggagaaaat caagtcgtgc tg                                          22

<210> SEQ ID NO 98
<211> LENGTH: 22
<212> TYPE: DNA
<213> ORGANISM: homo sapiens

<400> SEQUENCE: 98
tatctgaaga ttcaaccggt tt                                          22

<210> SEQ ID NO 99
<211> LENGTH: 22
<212> TYPE: DNA
<213> ORGANISM: homo sapiens

<400> SEQUENCE: 99
gctattcacc aaagttgaat ca                                          22

<210> SEQ ID NO 100
<211> LENGTH: 22
<212> TYPE: DNA
```

-continued

<213> ORGANISM: homo sapiens

<400> SEQUENCE: 100
aactttgctg gccccagccg ct                                    22

<210> SEQ ID NO 101
<211> LENGTH: 22
<212> TYPE: DNA
<213> ORGANISM: homo sapiens

<400> SEQUENCE: 101
aaactgatga ccagcaactt ga                                    22

<210> SEQ ID NO 102
<211> LENGTH: 22
<212> TYPE: DNA
<213> ORGANISM: homo sapiens

<400> SEQUENCE: 102
ggggagcatt acatcattat at                                    22

<210> SEQ ID NO 103
<211> LENGTH: 22
<212> TYPE: DNA
<213> ORGANISM: homo sapiens

<400> SEQUENCE: 103
agccacttcg aagtagtgct ga                                    22

<210> SEQ ID NO 104
<211> LENGTH: 22
<212> TYPE: DNA
<213> ORGANISM: homo sapiens

<400> SEQUENCE: 104
caacttcttg attgagtgca gg                                    22

<210> SEQ ID NO 105
<211> LENGTH: 22
<212> TYPE: DNA
<213> ORGANISM: homo sapiens

<400> SEQUENCE: 105
ttaccatgcc ccagattcag ga                                    22

<210> SEQ ID NO 106
<211> LENGTH: 22
<212> TYPE: DNA
<213> ORGANISM: homo sapiens

<400> SEQUENCE: 106
tcagacacct agtccttccg at                                    22

<210> SEQ ID NO 107
<211> LENGTH: 22
<212> TYPE: DNA
<213> ORGANISM: homo sapiens

<400> SEQUENCE: 107
attggtagaa aaactttttg ct                                    22

<210> SEQ ID NO 108
<211> LENGTH: 22

```
<212> TYPE: DNA
<213> ORGANISM: homo sapiens

<400> SEQUENCE: 108
aactcatgta tttgctgttt ta                                          22

<210> SEQ ID NO 109
<211> LENGTH: 22
<212> TYPE: DNA
<213> ORGANISM: homo sapiens

<400> SEQUENCE: 109
aagccctgaa agcgcaagtc ct                                          22

<210> SEQ ID NO 110
<211> LENGTH: 22
<212> TYPE: DNA
<213> ORGANISM: homo sapiens

<400> SEQUENCE: 110
cagttacagt attccagcag ac                                          22

<210> SEQ ID NO 111
<211> LENGTH: 22
<212> TYPE: DNA
<213> ORGANISM: homo sapiens

<400> SEQUENCE: 111
aggttcttgt atttgagtct gc                                          22

<210> SEQ ID NO 112
<211> LENGTH: 22
<212> TYPE: DNA
<213> ORGANISM: homo sapiens

<400> SEQUENCE: 112
atgcaatcaa tattttaatg tc                                          22

<210> SEQ ID NO 113
<211> LENGTH: 22
<212> TYPE: DNA
<213> ORGANISM: homo sapiens

<400> SEQUENCE: 113
tgattgcatc tccatctcct ac                                          22

<210> SEQ ID NO 114
<211> LENGTH: 22
<212> TYPE: DNA
<213> ORGANISM: homo sapiens

<400> SEQUENCE: 114
tagtgccaca tcatcaccat at                                          22

<210> SEQ ID NO 115
<211> LENGTH: 22
<212> TYPE: DNA
<213> ORGANISM: homo sapiens

<400> SEQUENCE: 115
gagtatctct atatggtgat ga                                          22

<210> SEQ ID NO 116
```

```
<211> LENGTH: 22
<212> TYPE: DNA
<213> ORGANISM: homo sapiens

<400> SEQUENCE: 116
atacctttga ctcaaagcga ca                                              22

<210> SEQ ID NO 117
<211> LENGTH: 22
<212> TYPE: DNA
<213> ORGANISM: homo sapiens

<400> SEQUENCE: 117
ttcctgagga agaactaaat cc                                              22

<210> SEQ ID NO 118
<211> LENGTH: 22
<212> TYPE: DNA
<213> ORGANISM: homo sapiens

<400> SEQUENCE: 118
tctgttcact agatttgcat cc                                              22

<210> SEQ ID NO 119
<211> LENGTH: 22
<212> TYPE: DNA
<213> ORGANISM: homo sapiens

<400> SEQUENCE: 119
gaatggagca aaagacaatt at                                              22

<210> SEQ ID NO 120
<211> LENGTH: 22
<212> TYPE: DNA
<213> ORGANISM: homo sapiens

<400> SEQUENCE: 120
gttatgattg tgaagttaat gc                                              22

<210> SEQ ID NO 121
<211> LENGTH: 22
<212> TYPE: DNA
<213> ORGANISM: homo sapiens

<400> SEQUENCE: 121
aacacctccg tctccttgct cc                                              22

<210> SEQ ID NO 122
<211> LENGTH: 22
<212> TYPE: DNA
<213> ORGANISM: homo sapiens

<400> SEQUENCE: 122
tggaggcctt gtccagatgg ga                                              22

<210> SEQ ID NO 123
<211> LENGTH: 22
<212> TYPE: DNA
<213> ORGANISM: homo sapiens

<400> SEQUENCE: 123
tgcgactggc aatcagcttc ct                                              22
```

```
<210> SEQ ID NO 124
<211> LENGTH: 22
<212> TYPE: DNA
<213> ORGANISM: homo sapiens

<400> SEQUENCE: 124
cgactggcaa tcagcttcct gc                                              22

<210> SEQ ID NO 125
<211> LENGTH: 22
<212> TYPE: DNA
<213> ORGANISM: homo sapiens

<400> SEQUENCE: 125
gaagctgacc agcagatgga ca                                              22

<210> SEQ ID NO 126
<211> LENGTH: 22
<212> TYPE: DNA
<213> ORGANISM: homo sapiens

<400> SEQUENCE: 126
gcaatgaaac cctccaaggc tt                                              22

<210> SEQ ID NO 127
<211> LENGTH: 22
<212> TYPE: DNA
<213> ORGANISM: homo sapiens

<400> SEQUENCE: 127
aaaacatcag caagttcatg gg                                              22

<210> SEQ ID NO 128
<211> LENGTH: 22
<212> TYPE: DNA
<213> ORGANISM: homo sapiens

<400> SEQUENCE: 128
gcaagttcat gggacttaca ca                                              22

<210> SEQ ID NO 129
<211> LENGTH: 22
<212> TYPE: DNA
<213> ORGANISM: homo sapiens

<400> SEQUENCE: 129
ggtcgcaggg atgagtgaag tc                                              22

<210> SEQ ID NO 130
<211> LENGTH: 22
<212> TYPE: DNA
<213> ORGANISM: homo sapiens

<400> SEQUENCE: 130
gcgggacttc ttcatgagga tg                                              22

<210> SEQ ID NO 131
<211> LENGTH: 22
<212> TYPE: DNA
<213> ORGANISM: homo sapiens

<400> SEQUENCE: 131
gaagtgcacg gtcaccaaca ga                                              22
```

```
<210> SEQ ID NO 132
<211> LENGTH: 22
<212> TYPE: DNA
<213> ORGANISM: homo sapiens

<400> SEQUENCE: 132
acagtacggc ctctgttggt ga                                              22

<210> SEQ ID NO 133
<211> LENGTH: 22
<212> TYPE: DNA
<213> ORGANISM: homo sapiens

<400> SEQUENCE: 133
tccaggtggc tgacttgagg tt                                              22

<210> SEQ ID NO 134
<211> LENGTH: 22
<212> TYPE: DNA
<213> ORGANISM: homo sapiens

<400> SEQUENCE: 134
tccacgcctg tctcaggtct tg                                              22

<210> SEQ ID NO 135
<211> LENGTH: 22
<212> TYPE: DNA
<213> ORGANISM: homo sapiens

<400> SEQUENCE: 135
caggacagca ggggctcctt gt                                              22

<210> SEQ ID NO 136
<211> LENGTH: 22
<212> TYPE: DNA
<213> ORGANISM: homo sapiens

<400> SEQUENCE: 136
ctcatcatca tgtgtgaacc aa                                              22

<210> SEQ ID NO 137
<211> LENGTH: 22
<212> TYPE: DNA
<213> ORGANISM: homo sapiens

<400> SEQUENCE: 137
atgtgggatg ggtgctggat tg                                              22

<210> SEQ ID NO 138
<211> LENGTH: 22
<212> TYPE: DNA
<213> ORGANISM: homo sapiens

<400> SEQUENCE: 138
gccacttact acctgaccct tg                                              22

<210> SEQ ID NO 139
<211> LENGTH: 22
<212> TYPE: DNA
<213> ORGANISM: homo sapiens

<400> SEQUENCE: 139
tggccactta ctacctgacc ct                                              22
```

```
<210> SEQ ID NO 140
<211> LENGTH: 22
<212> TYPE: DNA
<213> ORGANISM: homo sapiens

<400> SEQUENCE: 140
accaagggtc aggtagtaag tg                                              22

<210> SEQ ID NO 141
<211> LENGTH: 22
<212> TYPE: DNA
<213> ORGANISM: homo sapiens

<400> SEQUENCE: 141
tagcccccat gctttgcgag ca                                              22

<210> SEQ ID NO 142
<211> LENGTH: 22
<212> TYPE: DNA
<213> ORGANISM: homo sapiens

<400> SEQUENCE: 142
gatgaccgtc ccctgggtct cc                                              22

<210> SEQ ID NO 143
<211> LENGTH: 22
<212> TYPE: DNA
<213> ORGANISM: homo sapiens

<400> SEQUENCE: 143
ctcaggacgt agttgacaca ca                                              22

<210> SEQ ID NO 144
<211> LENGTH: 22
<212> TYPE: DNA
<213> ORGANISM: homo sapiens

<400> SEQUENCE: 144
catgcttacc tcaggacgta gt                                              22

<210> SEQ ID NO 145
<211> LENGTH: 22
<212> TYPE: DNA
<213> ORGANISM: homo sapiens

<400> SEQUENCE: 145
cacatgctta cctcaggacg ta                                              22

<210> SEQ ID NO 146
<211> LENGTH: 22
<212> TYPE: DNA
<213> ORGANISM: homo sapiens

<400> SEQUENCE: 146
cagggattca gtctggtcca tg                                              22

<210> SEQ ID NO 147
<211> LENGTH: 22
<212> TYPE: DNA
<213> ORGANISM: homo sapiens

<400> SEQUENCE: 147
```

```
ggtgaatagg aagttactct tc                                              22

<210> SEQ ID NO 148
<211> LENGTH: 22
<212> TYPE: DNA
<213> ORGANISM: homo sapiens

<400> SEQUENCE: 148
atgggccacg gagttgagga gc                                              22

<210> SEQ ID NO 149
<211> LENGTH: 22
<212> TYPE: DNA
<213> ORGANISM: homo sapiens

<400> SEQUENCE: 149
ctagcccaat agccctgaag ac                                              22

<210> SEQ ID NO 150
<211> LENGTH: 22
<212> TYPE: DNA
<213> ORGANISM: homo sapiens

<400> SEQUENCE: 150
agtgattgag aagctcttcg cc                                              22

<210> SEQ ID NO 151
<211> LENGTH: 22
<212> TYPE: DNA
<213> ORGANISM: homo sapiens

<400> SEQUENCE: 151
ggacacagag gccaaggacc aa                                              22

<210> SEQ ID NO 152
<211> LENGTH: 22
<212> TYPE: DNA
<213> ORGANISM: homo sapiens

<400> SEQUENCE: 152
cctgatctcc acagccatct ac                                              22

<210> SEQ ID NO 153
<211> LENGTH: 22
<212> TYPE: DNA
<213> ORGANISM: homo sapiens

<400> SEQUENCE: 153
cggatttcaa tgagctggac tt                                              22

<210> SEQ ID NO 154
<211> LENGTH: 22
<212> TYPE: DNA
<213> ORGANISM: homo sapiens

<400> SEQUENCE: 154
tcaatgagct ggacttggag ac                                              22

<210> SEQ ID NO 155
<211> LENGTH: 22
<212> TYPE: DNA
<213> ORGANISM: homo sapiens

<400> SEQUENCE: 155
```

```
gcggagaacc cacagtccac cc                                              22
```

<210> SEQ ID NO 156
<211> LENGTH: 22
<212> TYPE: DNA
<213> ORGANISM: homo sapiens

<400> SEQUENCE: 156

```
ccagtggctg gaagatgttt gt                                              22
```

<210> SEQ ID NO 157
<211> LENGTH: 22
<212> TYPE: DNA
<213> ORGANISM: homo sapiens

<400> SEQUENCE: 157

```
ttccagccac tggcccctgt ag                                              22
```

<210> SEQ ID NO 158
<211> LENGTH: 22
<212> TYPE: DNA
<213> ORGANISM: homo sapiens

<400> SEQUENCE: 158

```
ctggagagca agaagacaga gc                                              22
```

<210> SEQ ID NO 159
<211> LENGTH: 22
<212> TYPE: DNA
<213> ORGANISM: homo sapiens

<400> SEQUENCE: 159

```
gagagagggg tgctggcctg gc                                              22
```

<210> SEQ ID NO 160
<211> LENGTH: 22
<212> TYPE: DNA
<213> ORGANISM: homo sapiens

<400> SEQUENCE: 160

```
cctgccaccg tgctgtggcc ag                                              22
```

<210> SEQ ID NO 161
<211> LENGTH: 22
<212> TYPE: DNA
<213> ORGANISM: homo sapiens

<400> SEQUENCE: 161

```
tctctcttcc atgggggca ga                                               22
```

<210> SEQ ID NO 162
<211> LENGTH: 22
<212> TYPE: DNA
<213> ORGANISM: homo sapiens

<400> SEQUENCE: 162

```
cacaaagtgg gccgtcgggg at                                              22
```

<210> SEQ ID NO 163
<211> LENGTH: 22
<212> TYPE: DNA
<213> ORGANISM: homo sapiens

<400> SEQUENCE: 163
ggagagggct accatggccg ga                                              22

<210> SEQ ID NO 164
<211> LENGTH: 22
<212> TYPE: DNA
<213> ORGANISM: homo sapiens

<400> SEQUENCE: 164
ctcaggtcct ggaaggcttg ct                                              22

<210> SEQ ID NO 165
<211> LENGTH: 22
<212> TYPE: DNA
<213> ORGANISM: homo sapiens

<400> SEQUENCE: 165
ctcccagggg gacccacctg gt                                              22

<210> SEQ ID NO 166
<211> LENGTH: 22
<212> TYPE: DNA
<213> ORGANISM: homo sapiens

<400> SEQUENCE: 166
tgccggacaa gccactgagc gc                                              22

<210> SEQ ID NO 167
<211> LENGTH: 22
<212> TYPE: DNA
<213> ORGANISM: homo sapiens

<400> SEQUENCE: 167
ttccccccac agtgctacgc ca                                              22

<210> SEQ ID NO 168
<211> LENGTH: 22
<212> TYPE: DNA
<213> ORGANISM: homo sapiens

<400> SEQUENCE: 168
ctgtagtcct ggtactgggt gg                                              22

<210> SEQ ID NO 169
<211> LENGTH: 22
<212> TYPE: DNA
<213> ORGANISM: homo sapiens

<400> SEQUENCE: 169
tgggctgacg acaggctgta gt                                              22

<210> SEQ ID NO 170
<211> LENGTH: 22
<212> TYPE: DNA
<213> ORGANISM: homo sapiens

<400> SEQUENCE: 170
tccttgcagg agcgtggagc tt                                              22

<210> SEQ ID NO 171
<211> LENGTH: 22
<212> TYPE: DNA
<213> ORGANISM: homo sapiens -continued

```
<400> SEQUENCE: 171
gactgtgctg aagtattcaa at                                            22

<210> SEQ ID NO 172
<211> LENGTH: 22
<212> TYPE: DNA
<213> ORGANISM: homo sapiens

<400> SEQUENCE: 172
ctgtgctgaa gtattcaaat ca                                            22

<210> SEQ ID NO 173
<211> LENGTH: 22
<212> TYPE: DNA
<213> ORGANISM: homo sapiens

<400> SEQUENCE: 173
tggtgtgtcc tgatttgaat ac                                            22

<210> SEQ ID NO 174
<211> LENGTH: 22
<212> TYPE: DNA
<213> ORGANISM: homo sapiens

<400> SEQUENCE: 174
gccattcgtg gtgtgtcctg at                                            22

<210> SEQ ID NO 175
<211> LENGTH: 22
<212> TYPE: DNA
<213> ORGANISM: homo sapiens

<400> SEQUENCE: 175
atcaggacac accacgaatg gc                                            22

<210> SEQ ID NO 176
<211> LENGTH: 22
<212> TYPE: DNA
<213> ORGANISM: homo sapiens

<400> SEQUENCE: 176
ctaatcagca acgctatgtg ct                                            22

<210> SEQ ID NO 177
<211> LENGTH: 22
<212> TYPE: DNA
<213> ORGANISM: homo sapiens

<400> SEQUENCE: 177
aatcagcaac gctatgtgct ta                                            22

<210> SEQ ID NO 178
<211> LENGTH: 22
<212> TYPE: DNA
<213> ORGANISM: homo sapiens

<400> SEQUENCE: 178
ttcccagtct ttaaggtgta tt                                            22

<210> SEQ ID NO 179
<211> LENGTH: 22
<212> TYPE: DNA
```

```
<213> ORGANISM: homo sapiens

<400> SEQUENCE: 179
tcttcacttg agagatagaa at                                              22

<210> SEQ ID NO 180
<211> LENGTH: 22
<212> TYPE: DNA
<213> ORGANISM: homo sapiens

<400> SEQUENCE: 180
catcagccaa ccaggaaatg at                                              22

<210> SEQ ID NO 181
<211> LENGTH: 22
<212> TYPE: DNA
<213> ORGANISM: homo sapiens

<400> SEQUENCE: 181
ctgttagcat ttgtgaacat tt                                              22

<210> SEQ ID NO 182
<211> LENGTH: 22
<212> TYPE: DNA
<213> ORGANISM: homo sapiens

<400> SEQUENCE: 182
tgtggtcctt ccaacttgaa cg                                              22

<210> SEQ ID NO 183
<211> LENGTH: 22
<212> TYPE: DNA
<213> ORGANISM: homo sapiens

<400> SEQUENCE: 183
cggaatgtac tatccacaga gg                                              22

<210> SEQ ID NO 184
<211> LENGTH: 22
<212> TYPE: DNA
<213> ORGANISM: homo sapiens

<400> SEQUENCE: 184
ttatttgtgt tctgcctctg tg                                              22

<210> SEQ ID NO 185
<211> LENGTH: 22
<212> TYPE: DNA
<213> ORGANISM: homo sapiens

<400> SEQUENCE: 185
acaaataagt tcaacggcat ta                                              22

<210> SEQ ID NO 186
<211> LENGTH: 22
<212> TYPE: DNA
<213> ORGANISM: homo sapiens

<400> SEQUENCE: 186
agcgaatagc ctgagccttt cc                                              22

<210> SEQ ID NO 187
<211> LENGTH: 20
```

```
<212> TYPE: DNA
<213> ORGANISM: homo sapiens

<400> SEQUENCE: 187
cagctgacca gtcgcgctga                                               20

<210> SEQ ID NO 188
<211> LENGTH: 20
<212> TYPE: DNA
<213> ORGANISM: homo sapiens

<400> SEQUENCE: 188
gtggtagctg gggctggggg                                               20

<210> SEQ ID NO 189
<211> LENGTH: 20
<212> TYPE: DNA
<213> ORGANISM: homo sapiens

<400> SEQUENCE: 189
gaggtggtag ctggggctgg                                               20

<210> SEQ ID NO 190
<211> LENGTH: 20
<212> TYPE: DNA
<213> ORGANISM: homo sapiens

<400> SEQUENCE: 190
ggaggtggta gctggggctg                                               20

<210> SEQ ID NO 191
<211> LENGTH: 20
<212> TYPE: DNA
<213> ORGANISM: homo sapiens

<400> SEQUENCE: 191
aggaggtggt agctggggct                                               20

<210> SEQ ID NO 192
<211> LENGTH: 20
<212> TYPE: DNA
<213> ORGANISM: homo sapiens

<400> SEQUENCE: 192
gaggaggtgg tagctggggc                                               20

<210> SEQ ID NO 193
<211> LENGTH: 20
<212> TYPE: DNA
<213> ORGANISM: homo sapiens

<400> SEQUENCE: 193
cggggaggag gtggtagctg                                               20

<210> SEQ ID NO 194
<211> LENGTH: 20
<212> TYPE: DNA
<213> ORGANISM: homo sapiens

<400> SEQUENCE: 194
cccagctacc acctcctccc                                               20

<210> SEQ ID NO 195
```

```
<211> LENGTH: 20
<212> TYPE: DNA
<213> ORGANISM: homo sapiens

<400> SEQUENCE: 195
ccggggagga ggtggtagct                                              20

<210> SEQ ID NO 196
<211> LENGTH: 20
<212> TYPE: DNA
<213> ORGANISM: homo sapiens

<400> SEQUENCE: 196
gccggggagg aggtggtagc                                              20

<210> SEQ ID NO 197
<211> LENGTH: 20
<212> TYPE: DNA
<213> ORGANISM: homo sapiens

<400> SEQUENCE: 197
gctaccacct cctccccggc                                              20

<210> SEQ ID NO 198
<211> LENGTH: 20
<212> TYPE: DNA
<213> ORGANISM: homo sapiens

<400> SEQUENCE: 198
accacctcct ccccggccgg                                              20

<210> SEQ ID NO 199
<211> LENGTH: 20
<212> TYPE: DNA
<213> ORGANISM: homo sapiens

<400> SEQUENCE: 199
gccgccggcc ggggaggagg                                              20

<210> SEQ ID NO 200
<211> LENGTH: 20
<212> TYPE: DNA
<213> ORGANISM: homo sapiens

<400> SEQUENCE: 200
acctcctccc cggccggcgg                                              20

<210> SEQ ID NO 201
<211> LENGTH: 20
<212> TYPE: DNA
<213> ORGANISM: homo sapiens

<400> SEQUENCE: 201
tccgccgccg gccggggagg                                              20

<210> SEQ ID NO 202
<211> LENGTH: 20
<212> TYPE: DNA
<213> ORGANISM: homo sapiens

<400> SEQUENCE: 202
ctgtccgccg ccggccgggg                                              20
```

```
<210> SEQ ID NO 203
<211> LENGTH: 20
<212> TYPE: DNA
<213> ORGANISM: homo sapiens

<400> SEQUENCE: 203
ccccggccgg cggcggacag                                               20

<210> SEQ ID NO 204
<211> LENGTH: 20
<212> TYPE: DNA
<213> ORGANISM: homo sapiens

<400> SEQUENCE: 204
ccactgtccg ccgccggccg                                               20

<210> SEQ ID NO 205
<211> LENGTH: 20
<212> TYPE: DNA
<213> ORGANISM: homo sapiens

<400> SEQUENCE: 205
tccactgtcc gccgccggcc                                               20

<210> SEQ ID NO 206
<211> LENGTH: 20
<212> TYPE: DNA
<213> ORGANISM: homo sapiens

<400> SEQUENCE: 206
gtccactgtc cgccgccggc                                               20

<210> SEQ ID NO 207
<211> LENGTH: 20
<212> TYPE: DNA
<213> ORGANISM: homo sapiens

<400> SEQUENCE: 207
ccggcggcgg acagtggacg                                               20

<210> SEQ ID NO 208
<211> LENGTH: 20
<212> TYPE: DNA
<213> ORGANISM: homo sapiens

<400> SEQUENCE: 208
ccgcgtccac tgtccgccgc                                               20

<210> SEQ ID NO 209
<211> LENGTH: 20
<212> TYPE: DNA
<213> ORGANISM: homo sapiens

<400> SEQUENCE: 209
gcggcggaca gtggacgcgg                                               20

<210> SEQ ID NO 210
<211> LENGTH: 20
<212> TYPE: DNA
<213> ORGANISM: homo sapiens

<400> SEQUENCE: 210
gtggacgcgg cggcgagccg                                               20
```

```
<210> SEQ ID NO 211
<211> LENGTH: 20
<212> TYPE: DNA
<213> ORGANISM: homo sapiens

<400> SEQUENCE: 211
tggacgcggc ggcgagccgc                                          20

<210> SEQ ID NO 212
<211> LENGTH: 20
<212> TYPE: DNA
<213> ORGANISM: homo sapiens

<400> SEQUENCE: 212
cgcggcggcg agccgcgggc                                          20

<210> SEQ ID NO 213
<211> LENGTH: 20
<212> TYPE: DNA
<213> ORGANISM: homo sapiens

<400> SEQUENCE: 213
gcggcggcga gccgcgggca                                          20

<210> SEQ ID NO 214
<211> LENGTH: 20
<212> TYPE: DNA
<213> ORGANISM: homo sapiens

<400> SEQUENCE: 214
cggcggcgag ccgcgggcag                                          20

<210> SEQ ID NO 215
<211> LENGTH: 20
<212> TYPE: DNA
<213> ORGANISM: homo sapiens

<400> SEQUENCE: 215
ggcgagccgc gggcaggggc                                          20

<210> SEQ ID NO 216
<211> LENGTH: 20
<212> TYPE: DNA
<213> ORGANISM: homo sapiens

<400> SEQUENCE: 216
cgggctccgg ccctgcccg                                           20

<210> SEQ ID NO 217
<211> LENGTH: 20
<212> TYPE: DNA
<213> ORGANISM: homo sapiens

<400> SEQUENCE: 217
caggggccgg agcccgcgcc                                          20

<210> SEQ ID NO 218
<211> LENGTH: 20
<212> TYPE: DNA
<213> ORGANISM: homo sapiens

<400> SEQUENCE: 218
gggccggagc ccgcgcccgg                                          20
```

<210> SEQ ID NO 219
<211> LENGTH: 20
<212> TYPE: DNA
<213> ORGANISM: homo sapiens

<400> SEQUENCE: 219
ccggagcccg cgcccggagg                                              20

<210> SEQ ID NO 220
<211> LENGTH: 20
<212> TYPE: DNA
<213> ORGANISM: homo sapiens

<400> SEQUENCE: 220
ccgcctccgg gcgcgggctc                                              20

<210> SEQ ID NO 221
<211> LENGTH: 20
<212> TYPE: DNA
<213> ORGANISM: homo sapiens

<400> SEQUENCE: 221
cggagcccgc gcccggaggc                                              20

<210> SEQ ID NO 222
<211> LENGTH: 20
<212> TYPE: DNA
<213> ORGANISM: homo sapiens

<400> SEQUENCE: 222
ggagcccgcg cccggaggcg                                              20

<210> SEQ ID NO 223
<211> LENGTH: 20
<212> TYPE: DNA
<213> ORGANISM: homo sapiens

<400> SEQUENCE: 223
gcccgcgccc ggaggcgggg                                              20

<210> SEQ ID NO 224
<211> LENGTH: 20
<212> TYPE: DNA
<213> ORGANISM: homo sapiens

<400> SEQUENCE: 224
tccaccccgc ctccgggcgc                                              20

<210> SEQ ID NO 225
<211> LENGTH: 20
<212> TYPE: DNA
<213> ORGANISM: homo sapiens

<400> SEQUENCE: 225
ctccaccccg cctccgggcg                                              20

<210> SEQ ID NO 226
<211> LENGTH: 20
<212> TYPE: DNA
<213> ORGANISM: homo sapiens

<400> SEQUENCE: 226
cgcgcccgga ggcggggtgg                                                   20

<210> SEQ ID NO 227
<211> LENGTH: 20
<212> TYPE: DNA
<213> ORGANISM: homo sapiens

<400> SEQUENCE: 227
gcgcccggag gcggggtgga                                                   20

<210> SEQ ID NO 228
<211> LENGTH: 20
<212> TYPE: DNA
<213> ORGANISM: homo sapiens

<400> SEQUENCE: 228
cgcccggagg cggggtggag                                                   20

<210> SEQ ID NO 229
<211> LENGTH: 20
<212> TYPE: DNA
<213> ORGANISM: homo sapiens

<400> SEQUENCE: 229
gcccggaggc ggggtggagg                                                   20

<210> SEQ ID NO 230
<211> LENGTH: 20
<212> TYPE: DNA
<213> ORGANISM: homo sapiens

<400> SEQUENCE: 230
accccctcca ccccgcctcc                                                   20

<210> SEQ ID NO 231
<211> LENGTH: 20
<212> TYPE: DNA
<213> ORGANISM: homo sapiens

<400> SEQUENCE: 231
gaccccctcc accccgcctc                                                   20

<210> SEQ ID NO 232
<211> LENGTH: 20
<212> TYPE: DNA
<213> ORGANISM: homo sapiens

<400> SEQUENCE: 232
ggaggcgggg tggaggggt                                                    20

<210> SEQ ID NO 233
<211> LENGTH: 20
<212> TYPE: DNA
<213> ORGANISM: homo sapiens

<400> SEQUENCE: 233
gaggcggggt ggaggggtc                                                    20

<210> SEQ ID NO 234
<211> LENGTH: 20
<212> TYPE: DNA
<213> ORGANISM: homo sapiens

<400> SEQUENCE: 234 aggcgggtg gagggggtcg    20

<210> SEQ ID NO 235
<211> LENGTH: 20
<212> TYPE: DNA
<213> ORGANISM: homo sapiens

<400> SEQUENCE: 235 gtggagggg tcggggctcg    20

<210> SEQ ID NO 236
<211> LENGTH: 20
<212> TYPE: DNA
<213> ORGANISM: homo sapiens

<400> SEQUENCE: 236 gaaactttc gtccaacttc    20

<210> SEQ ID NO 237
<211> LENGTH: 20
<212> TYPE: DNA
<213> ORGANISM: homo sapiens

<400> SEQUENCE: 237 aaactttcg tccaacttct    20

<210> SEQ ID NO 238
<211> LENGTH: 20
<212> TYPE: DNA
<213> ORGANISM: homo sapiens

<400> SEQUENCE: 238
agcgagaaca gcccagaagt    20

<210> SEQ ID NO 239
<211> LENGTH: 20
<212> TYPE: DNA
<213> ORGANISM: homo sapiens

<400> SEQUENCE: 239
cttctgggct gttctcgctt    20

<210> SEQ ID NO 240
<211> LENGTH: 20
<212> TYPE: DNA
<213> ORGANISM: homo sapiens

<400> SEQUENCE: 240
ctgggctgtt ctcgcttcgg    20

<210> SEQ ID NO 241
<211> LENGTH: 20
<212> TYPE: DNA
<213> ORGANISM: homo sapiens

<400> SEQUENCE: 241
ttctcgcttc ggaggagccg    20

<210> SEQ ID NO 242
<211> LENGTH: 20
<212> TYPE: DNA
<213> ORGANISM: homo sapiens

```
<400> SEQUENCE: 242
cggaggagcc gtggtccgcg                                              20

<210> SEQ ID NO 243
<211> LENGTH: 20
<212> TYPE: DNA
<213> ORGANISM: homo sapiens

<400> SEQUENCE: 243
ggaggagccg tggtccgcgc                                              20

<210> SEQ ID NO 244
<211> LENGTH: 20
<212> TYPE: DNA
<213> ORGANISM: homo sapiens

<400> SEQUENCE: 244
gaggagccgt ggtccgcgcg                                              20

<210> SEQ ID NO 245
<211> LENGTH: 20
<212> TYPE: DNA
<213> ORGANISM: homo sapiens

<400> SEQUENCE: 245
aggagccgtg gtccgcgcgg                                              20

<210> SEQ ID NO 246
<211> LENGTH: 20
<212> TYPE: DNA
<213> ORGANISM: homo sapiens

<400> SEQUENCE: 246
ggcttccccc gcgcggacca                                              20

<210> SEQ ID NO 247
<211> LENGTH: 20
<212> TYPE: DNA
<213> ORGANISM: homo sapiens

<400> SEQUENCE: 247
tcggctcggc ttcccccgcg                                              20

<210> SEQ ID NO 248
<211> LENGTH: 20
<212> TYPE: DNA
<213> ORGANISM: homo sapiens

<400> SEQUENCE: 248
gcgggggaag ccgagccgag                                              20

<210> SEQ ID NO 249
<211> LENGTH: 20
<212> TYPE: DNA
<213> ORGANISM: homo sapiens

<400> SEQUENCE: 249
tctcgcggct ccgctcggct                                              20

<210> SEQ ID NO 250
<211> LENGTH: 20
<212> TYPE: DNA
<213> ORGANISM: homo sapiens
```

```
<400> SEQUENCE: 250
gcacttctcg cggctccgct                                              20

<210> SEQ ID NO 251
<211> LENGTH: 20
<212> TYPE: DNA
<213> ORGANISM: homo sapiens

<400> SEQUENCE: 251
agccgcgaga agtgctagct                                              20

<210> SEQ ID NO 252
<211> LENGTH: 20
<212> TYPE: DNA
<213> ORGANISM: homo sapiens

<400> SEQUENCE: 252
gccgcgagaa gtgctagctc                                              20

<210> SEQ ID NO 253
<211> LENGTH: 20
<212> TYPE: DNA
<213> ORGANISM: homo sapiens

<400> SEQUENCE: 253
gcccgagcta gcacttctcg                                              20

<210> SEQ ID NO 254
<211> LENGTH: 20
<212> TYPE: DNA
<213> ORGANISM: homo sapiens

<400> SEQUENCE: 254
cgagaagtgc tagctcgggc                                              20

<210> SEQ ID NO 255
<211> LENGTH: 20
<212> TYPE: DNA
<213> ORGANISM: homo sapiens

<400> SEQUENCE: 255
gagaagtgct agctcgggcc                                              20

<210> SEQ ID NO 256
<211> LENGTH: 20
<212> TYPE: DNA
<213> ORGANISM: homo sapiens

<400> SEQUENCE: 256
aagtgctagc tcgggccggg                                              20

<210> SEQ ID NO 257
<211> LENGTH: 20
<212> TYPE: DNA
<213> ORGANISM: homo sapiens

<400> SEQUENCE: 257
gggccgggag gagccgcagc                                              20

<210> SEQ ID NO 258
<211> LENGTH: 20
<212> TYPE: DNA
```

<213> ORGANISM: homo sapiens

<400> SEQUENCE: 258
ccgggaggag ccgcagccgg                                        20

<210> SEQ ID NO 259
<211> LENGTH: 20
<212> TYPE: DNA
<213> ORGANISM: homo sapiens

<400> SEQUENCE: 259
cctccggctg cggctcctcc                                        20

<210> SEQ ID NO 260
<211> LENGTH: 20
<212> TYPE: DNA
<213> ORGANISM: homo sapiens

<400> SEQUENCE: 260
ggaggagccg cagccggagg                                        20

<210> SEQ ID NO 261
<211> LENGTH: 20
<212> TYPE: DNA
<213> ORGANISM: homo sapiens

<400> SEQUENCE: 261
gaggagccgc agccggagga                                        20

<210> SEQ ID NO 262
<211> LENGTH: 20
<212> TYPE: DNA
<213> ORGANISM: homo sapiens

<400> SEQUENCE: 262
aggagccgca gccggaggag                                        20

<210> SEQ ID NO 263
<211> LENGTH: 20
<212> TYPE: DNA
<213> ORGANISM: homo sapiens

<400> SEQUENCE: 263
ggagccgcag ccggaggagg                                        20

<210> SEQ ID NO 264
<211> LENGTH: 20
<212> TYPE: DNA
<213> ORGANISM: homo sapiens

<400> SEQUENCE: 264
gccgcagccg gaggaggggg                                        20

<210> SEQ ID NO 265
<211> LENGTH: 20
<212> TYPE: DNA
<213> ORGANISM: homo sapiens

<400> SEQUENCE: 265 tcctcccccct cctccggctg                                       20

<210> SEQ ID NO 266
<211> LENGTH: 20

```
<212> TYPE: DNA
<213> ORGANISM: homo sapiens

<400> SEQUENCE: 266
gcagccggag gagggggagg                                               20

<210> SEQ ID NO 267
<211> LENGTH: 20
<212> TYPE: DNA
<213> ORGANISM: homo sapiens

<400> SEQUENCE: 267
tcttcctcct ccccctcctc                                               20

<210> SEQ ID NO 268
<211> LENGTH: 20
<212> TYPE: DNA
<213> ORGANISM: homo sapiens

<400> SEQUENCE: 268
gaagagaagg aagaggagag                                               20

<210> SEQ ID NO 269
<211> LENGTH: 20
<212> TYPE: DNA
<213> ORGANISM: homo sapiens

<400> SEQUENCE: 269
aagagaagga agaggagagg                                               20

<210> SEQ ID NO 270
<211> LENGTH: 20
<212> TYPE: DNA
<213> ORGANISM: homo sapiens

<400> SEQUENCE: 270
aagaggagag ggggccgcag                                               20

<210> SEQ ID NO 271
<211> LENGTH: 20
<212> TYPE: DNA
<213> ORGANISM: homo sapiens

<400> SEQUENCE: 271 aggggggccgc agtggcgact                                              20

<210> SEQ ID NO 272
<211> LENGTH: 20
<212> TYPE: DNA
<213> ORGANISM: homo sapiens

<400> SEQUENCE: 272
cgagcgccga gtcgccactg                                               20

<210> SEQ ID NO 273
<211> LENGTH: 20
<212> TYPE: DNA
<213> ORGANISM: homo sapiens

<400> SEQUENCE: 273
cgcagtggcg actcggcgct                                               20

<210> SEQ ID NO 274
```

```
<211> LENGTH: 20
<212> TYPE: DNA
<213> ORGANISM: homo sapiens

<400> SEQUENCE: 274
gcgactcggc gctcggaagc                                               20

<210> SEQ ID NO 275
<211> LENGTH: 20
<212> TYPE: DNA
<213> ORGANISM: homo sapiens

<400> SEQUENCE: 275
cgactcggcg ctcggaagcc                                               20

<210> SEQ ID NO 276
<211> LENGTH: 20
<212> TYPE: DNA
<213> ORGANISM: homo sapiens

<400> SEQUENCE: 276
gcgctcggaa gccgggctca                                               20

<210> SEQ ID NO 277
<211> LENGTH: 20
<212> TYPE: DNA
<213> ORGANISM: homo sapiens

<400> SEQUENCE: 277
tcggaagccg ggctcatgga                                               20

<210> SEQ ID NO 278
<211> LENGTH: 20
<212> TYPE: DNA
<213> ORGANISM: homo sapiens

<400> SEQUENCE: 278
cggaagccgg gctcatggac                                               20

<210> SEQ ID NO 279
<211> LENGTH: 20
<212> TYPE: DNA
<213> ORGANISM: homo sapiens

<400> SEQUENCE: 279
gccgggctca tggacgggtg                                               20

<210> SEQ ID NO 280
<211> LENGTH: 20
<212> TYPE: DNA
<213> ORGANISM: homo sapiens

<400> SEQUENCE: 280
gcctcacccg tccatgagcc                                               20

<210> SEQ ID NO 281
<211> LENGTH: 20
<212> TYPE: DNA
<213> ORGANISM: homo sapiens

<400> SEQUENCE: 281
gggctcatgg acgggtgagg                                               20
```

```
<210> SEQ ID NO 282
<211> LENGTH: 20
<212> TYPE: DNA
<213> ORGANISM: homo sapiens

<400> SEQUENCE: 282
ctcatggacg ggtgaggcgg                                                    20

<210> SEQ ID NO 283
<211> LENGTH: 20
<212> TYPE: DNA
<213> ORGANISM: homo sapiens

<400> SEQUENCE: 283
tccagccgcg cgcgctcccc                                                    20

<210> SEQ ID NO 284
<211> LENGTH: 20
<212> TYPE: DNA
<213> ORGANISM: homo sapiens

<400> SEQUENCE: 284
gcctggggag cgcgcgcggc                                                    20

<210> SEQ ID NO 285
<211> LENGTH: 20
<212> TYPE: DNA
<213> ORGANISM: homo sapiens

<400> SEQUENCE: 285
cagggcctgg ggagcgcgcg                                                    20

<210> SEQ ID NO 286
<211> LENGTH: 20
<212> TYPE: DNA
<213> ORGANISM: homo sapiens

<400> SEQUENCE: 286
cgcgcgcgct ccccaggccc                                                    20

<210> SEQ ID NO 287
<211> LENGTH: 20
<212> TYPE: DNA
<213> ORGANISM: homo sapiens

<400> SEQUENCE: 287
gcgctcccca ggccctggcc                                                    20

<210> SEQ ID NO 288
<211> LENGTH: 20
<212> TYPE: DNA
<213> ORGANISM: homo sapiens

<400> SEQUENCE: 288
cgctccccag gccctggccc                                                    20

<210> SEQ ID NO 289
<211> LENGTH: 20
<212> TYPE: DNA
<213> ORGANISM: homo sapiens

<400> SEQUENCE: 289
gaggcccggg ccagggcctg                                                    20
```

```
<210> SEQ ID NO 290
<211> LENGTH: 20
<212> TYPE: DNA
<213> ORGANISM: homo sapiens

<400> SEQUENCE: 290
cgaggcccgg gccagggcct                                              20

<210> SEQ ID NO 291
<211> LENGTH: 20
<212> TYPE: DNA
<213> ORGANISM: homo sapiens

<400> SEQUENCE: 291
ccaggccctg gcccgggcct                                              20

<210> SEQ ID NO 292
<211> LENGTH: 20
<212> TYPE: DNA
<213> ORGANISM: homo sapiens

<400> SEQUENCE: 292
ccgaggcccg ggccagggcc                                              20

<210> SEQ ID NO 293
<211> LENGTH: 20
<212> TYPE: DNA
<213> ORGANISM: homo sapiens

<400> SEQUENCE: 293
caggccctgg cccgggcctc                                              20

<210> SEQ ID NO 294
<211> LENGTH: 20
<212> TYPE: DNA
<213> ORGANISM: homo sapiens

<400> SEQUENCE: 294
ccctggcccg ggcctcgggc                                              20

<210> SEQ ID NO 295
<211> LENGTH: 20
<212> TYPE: DNA
<213> ORGANISM: homo sapiens

<400> SEQUENCE: 295
ccggcccgag gcccgggcca                                              20

<210> SEQ ID NO 296
<211> LENGTH: 20
<212> TYPE: DNA
<213> ORGANISM: homo sapiens

<400> SEQUENCE: 296
cctggcccgg gcctcgggcc                                              20

<210> SEQ ID NO 297
<211> LENGTH: 20
<212> TYPE: DNA
<213> ORGANISM: homo sapiens

<400> SEQUENCE: 297
cccggcccga ggcccgggcc                                              20
```

<210> SEQ ID NO 298
<211> LENGTH: 20
<212> TYPE: DNA
<213> ORGANISM: homo sapiens

<400> SEQUENCE: 298
ctggcccggg cctcgggccg					20

<210> SEQ ID NO 299
<211> LENGTH: 20
<212> TYPE: DNA
<213> ORGANISM: homo sapiens

<400> SEQUENCE: 299
gcccgggcct cgggccgggg					20

<210> SEQ ID NO 300
<211> LENGTH: 20
<212> TYPE: DNA
<213> ORGANISM: homo sapiens

<400> SEQUENCE: 300
tcctccccgg cccgaggccc					20

<210> SEQ ID NO 301
<211> LENGTH: 20
<212> TYPE: DNA
<213> ORGANISM: homo sapiens

<400> SEQUENCE: 301
ttcctccccg gcccgaggcc					20

<210> SEQ ID NO 302
<211> LENGTH: 20
<212> TYPE: DNA
<213> ORGANISM: homo sapiens

<400> SEQUENCE: 302
tactcttcct ccccggcccg					20

<210> SEQ ID NO 303
<211> LENGTH: 20
<212> TYPE: DNA
<213> ORGANISM: homo sapiens

<400> SEQUENCE: 303
ggcgagctac tcttcctccc					20

<210> SEQ ID NO 304
<211> LENGTH: 20
<212> TYPE: DNA
<213> ORGANISM: homo sapiens

<400> SEQUENCE: 304
ggaggaagag tagctcgccg					20

<210> SEQ ID NO 305
<211> LENGTH: 20
<212> TYPE: DNA
<213> ORGANISM: homo sapiens

<400> SEQUENCE: 305
agtagctcgc cgaggcgccg                                           20

<210> SEQ ID NO 306
<211> LENGTH: 20
<212> TYPE: DNA
<213> ORGANISM: homo sapiens

<400> SEQUENCE: 306
cgccgaggcg ccgaggagag                                           20

<210> SEQ ID NO 307
<211> LENGTH: 20
<212> TYPE: DNA
<213> ORGANISM: homo sapiens

<400> SEQUENCE: 307
gccgaggcgc cgaggagagc                                           20

<210> SEQ ID NO 308
<211> LENGTH: 20
<212> TYPE: DNA
<213> ORGANISM: homo sapiens

<400> SEQUENCE: 308
gcccgctctc ctcggcgcct                                           20

<210> SEQ ID NO 309
<211> LENGTH: 20
<212> TYPE: DNA
<213> ORGANISM: homo sapiens

<400> SEQUENCE: 309
gtggggcggc ccgctctcct                                           20

<210> SEQ ID NO 310
<211> LENGTH: 20
<212> TYPE: DNA
<213> ORGANISM: homo sapiens

<400> SEQUENCE: 310
ggccgcccca cagcccgagc                                           20

<210> SEQ ID NO 311
<211> LENGTH: 20
<212> TYPE: DNA
<213> ORGANISM: homo sapiens

<400> SEQUENCE: 311
ctccggctcg ggctgtgggg                                           20

<210> SEQ ID NO 312
<211> LENGTH: 20
<212> TYPE: DNA
<213> ORGANISM: homo sapiens

<400> SEQUENCE: 312
ccccacagcc cgagccggag                                           20

<210> SEQ ID NO 313
<211> LENGTH: 20
<212> TYPE: DNA
<213> ORGANISM: homo sapiens

<400> SEQUENCE: 313

```
cctctccggc tcgggctgtg                                              20
```

<210> SEQ ID NO 314
<211> LENGTH: 20
<212> TYPE: DNA
<213> ORGANISM: homo sapiens

<400> SEQUENCE: 314

```
cccacagccc gagccggaga                                              20
```

<210> SEQ ID NO 315
<211> LENGTH: 20
<212> TYPE: DNA
<213> ORGANISM: homo sapiens

<400> SEQUENCE: 315

```
ccctctccgg ctcgggctgt                                              20
```

<210> SEQ ID NO 316
<211> LENGTH: 20
<212> TYPE: DNA
<213> ORGANISM: homo sapiens

<400> SEQUENCE: 316

```
tccctctccg gctcgggctg                                              20
```

<210> SEQ ID NO 317
<211> LENGTH: 20
<212> TYPE: DNA
<213> ORGANISM: homo sapiens

<400> SEQUENCE: 317

```
tcgcgctccc tctccggctc                                              20
```

<210> SEQ ID NO 318
<211> LENGTH: 20
<212> TYPE: DNA
<213> ORGANISM: homo sapiens

<400> SEQUENCE: 318

```
ctcgcgctcc ctctccggct                                              20
```

<210> SEQ ID NO 319
<211> LENGTH: 20
<212> TYPE: DNA
<213> ORGANISM: homo sapiens

<400> SEQUENCE: 319

```
cgcggctcgc gctccctctc                                              20
```

<210> SEQ ID NO 320
<211> LENGTH: 20
<212> TYPE: DNA
<213> ORGANISM: homo sapiens

<400> SEQUENCE: 320

```
agagggagcg cgagccgcgc                                              20
```

<210> SEQ ID NO 321
<211> LENGTH: 20
<212> TYPE: DNA
<213> ORGANISM: homo sapiens

```
<400> SEQUENCE: 321
cgagccgcgc cggccccggt                                                      20

<210> SEQ ID NO 322
<211> LENGTH: 20
<212> TYPE: DNA
<213> ORGANISM: homo sapiens

<400> SEQUENCE: 322
gagccgcgcc ggccccggtc                                                      20

<210> SEQ ID NO 323
<211> LENGTH: 20
<212> TYPE: DNA
<213> ORGANISM: homo sapiens

<400> SEQUENCE: 323
aggcccgacc ggggccggcg                                                      20

<210> SEQ ID NO 324
<211> LENGTH: 20
<212> TYPE: DNA
<213> ORGANISM: homo sapiens

<400> SEQUENCE: 324
ttcggaggcc cgaccggggc                                                      20

<210> SEQ ID NO 325
<211> LENGTH: 20
<212> TYPE: DNA
<213> ORGANISM: homo sapiens

<400> SEQUENCE: 325
tggtttcgga ggcccgaccg                                                      20

<210> SEQ ID NO 326
<211> LENGTH: 20
<212> TYPE: DNA
<213> ORGANISM: homo sapiens

<400> SEQUENCE: 326
atggtttcgg aggcccgacc                                                      20

<210> SEQ ID NO 327
<211> LENGTH: 20
<212> TYPE: DNA
<213> ORGANISM: homo sapiens

<400> SEQUENCE: 327
catggtttcg gaggcccgac                                                      20

<210> SEQ ID NO 328
<211> LENGTH: 20
<212> TYPE: DNA
<213> ORGANISM: homo sapiens

<400> SEQUENCE: 328
cagaaagttc atggtttcgg                                                      20

<210> SEQ ID NO 329
<211> LENGTH: 20
<212> TYPE: DNA
<213> ORGANISM: homo sapiens
```

```
<400> SEQUENCE: 329
cagcagaaag ttcatggttt                                              20

<210> SEQ ID NO 330
<211> LENGTH: 20
<212> TYPE: DNA
<213> ORGANISM: homo sapiens

<400> SEQUENCE: 330
ccatgaactt tctgctgtct                                              20

<210> SEQ ID NO 331
<211> LENGTH: 20
<212> TYPE: DNA
<213> ORGANISM: homo sapiens

<400> SEQUENCE: 331
ccaagacagc agaaagttca                                              20

<210> SEQ ID NO 332
<211> LENGTH: 20
<212> TYPE: DNA
<213> ORGANISM: homo sapiens

<400> SEQUENCE: 332
catgaacttt ctgctgtctt                                              20

<210> SEQ ID NO 333
<211> LENGTH: 20
<212> TYPE: DNA
<213> ORGANISM: homo sapiens

<400> SEQUENCE: 333
ttctgctgtc ttgggtgcat                                              20

<210> SEQ ID NO 334
<211> LENGTH: 20
<212> TYPE: DNA
<213> ORGANISM: homo sapiens

<400> SEQUENCE: 334
ggaggtagag cagcaaggca                                              20

<210> SEQ ID NO 335
<211> LENGTH: 20
<212> TYPE: DNA
<213> ORGANISM: homo sapiens

<400> SEQUENCE: 335
atggtggagg tagagcagca                                              20

<210> SEQ ID NO 336
<211> LENGTH: 20
<212> TYPE: DNA
<213> ORGANISM: homo sapiens

<400> SEQUENCE: 336
gctctacctc caccatgcca                                              20

<210> SEQ ID NO 337
<211> LENGTH: 20
<212> TYPE: DNA
```

<213> ORGANISM: homo sapiens

<400> SEQUENCE: 337
cgcttacctt ggcatggtgg                                           20

<210> SEQ ID NO 338
<211> LENGTH: 20
<212> TYPE: DNA
<213> ORGANISM: homo sapiens

<400> SEQUENCE: 338
gaccgcttac cttggcatgg                                           20

<210> SEQ ID NO 339
<211> LENGTH: 20
<212> TYPE: DNA
<213> ORGANISM: homo sapiens

<400> SEQUENCE: 339
cacgaccgct taccttggca                                           20

<210> SEQ ID NO 340
<211> LENGTH: 20
<212> TYPE: DNA
<213> ORGANISM: homo sapiens

<400> SEQUENCE: 340
tttctgtcct cagtggtccc                                           20

<210> SEQ ID NO 341
<211> LENGTH: 20
<212> TYPE: DNA
<213> ORGANISM: homo sapiens

<400> SEQUENCE: 341
ggtgcagcct gggaccactg                                           20

<210> SEQ ID NO 342
<211> LENGTH: 20
<212> TYPE: DNA
<213> ORGANISM: homo sapiens

<400> SEQUENCE: 342
gtggtcccag gctgcaccca                                           20

<210> SEQ ID NO 343
<211> LENGTH: 20
<212> TYPE: DNA
<213> ORGANISM: homo sapiens

<400> SEQUENCE: 343
ttctgccatg ggtgcagcct                                           20

<210> SEQ ID NO 344
<211> LENGTH: 20
<212> TYPE: DNA
<213> ORGANISM: homo sapiens

<400> SEQUENCE: 344
cttctgccat gggtgcagcc                                           20

<210> SEQ ID NO 345
<211> LENGTH: 20

```
<212> TYPE: DNA
<213> ORGANISM: homo sapiens

<400> SEQUENCE: 345
caggctgcac ccatggcaga                                              20

<210> SEQ ID NO 346
<211> LENGTH: 20
<212> TYPE: DNA
<213> ORGANISM: homo sapiens

<400> SEQUENCE: 346
gctgcaccca tggcagaagg                                              20

<210> SEQ ID NO 347
<211> LENGTH: 20
<212> TYPE: DNA
<213> ORGANISM: homo sapiens

<400> SEQUENCE: 347
gcacccatgg cagaaggagg                                              20

<210> SEQ ID NO 348
<211> LENGTH: 20
<212> TYPE: DNA
<213> ORGANISM: homo sapiens

<400> SEQUENCE: 348
cacccatggc agaaggagga                                              20

<210> SEQ ID NO 349
<211> LENGTH: 20
<212> TYPE: DNA
<213> ORGANISM: homo sapiens

<400> SEQUENCE: 349
tgccctcctc cttctgccat                                              20

<210> SEQ ID NO 350
<211> LENGTH: 20
<212> TYPE: DNA
<213> ORGANISM: homo sapiens

<400> SEQUENCE: 350
ctgccctcct ccttctgcca                                              20

<210> SEQ ID NO 351
<211> LENGTH: 20
<212> TYPE: DNA
<213> ORGANISM: homo sapiens

<400> SEQUENCE: 351
ggagggcaga atcatcacga                                              20

<210> SEQ ID NO 352
<211> LENGTH: 20
<212> TYPE: DNA
<213> ORGANISM: homo sapiens

<400> SEQUENCE: 352
tcatgcagtg gtgaagttca                                              20

<210> SEQ ID NO 353
```

```
<211> LENGTH: 20
<212> TYPE: DNA
<213> ORGANISM: homo sapiens

<400> SEQUENCE: 353
ctgccatcca atcgagaccc                                               20

<210> SEQ ID NO 354
<211> LENGTH: 20
<212> TYPE: DNA
<213> ORGANISM: homo sapiens

<400> SEQUENCE: 354
ccatccaatc gagaccctgg                                               20

<210> SEQ ID NO 355
<211> LENGTH: 20
<212> TYPE: DNA
<213> ORGANISM: homo sapiens

<400> SEQUENCE: 355
ccaccagggt ctcgattgga                                               20

<210> SEQ ID NO 356
<211> LENGTH: 20
<212> TYPE: DNA
<213> ORGANISM: homo sapiens

<400> SEQUENCE: 356
atgtccacca gggtctcgat                                               20

<210> SEQ ID NO 357
<211> LENGTH: 20
<212> TYPE: DNA
<213> ORGANISM: homo sapiens

<400> SEQUENCE: 357
gaccctggtg gacatcttcc                                               20

<210> SEQ ID NO 358
<211> LENGTH: 20
<212> TYPE: DNA
<213> ORGANISM: homo sapiens

<400> SEQUENCE: 358
ctcctggaag atgtccacca                                               20

<210> SEQ ID NO 359
<211> LENGTH: 20
<212> TYPE: DNA
<213> ORGANISM: homo sapiens

<400> SEQUENCE: 359
actcctggaa gatgtccacc                                               20

<210> SEQ ID NO 360
<211> LENGTH: 20
<212> TYPE: DNA
<213> ORGANISM: homo sapiens

<400> SEQUENCE: 360
cgatctcatc agggtactcc                                               20
```

```
<210> SEQ ID NO 361
<211> LENGTH: 20
<212> TYPE: DNA
<213> ORGANISM: homo sapiens

<400> SEQUENCE: 361
agatgtactc gatctcatca                                              20

<210> SEQ ID NO 362
<211> LENGTH: 20
<212> TYPE: DNA
<213> ORGANISM: homo sapiens

<400> SEQUENCE: 362
aagatgtact cgatctcatc                                              20

<210> SEQ ID NO 363
<211> LENGTH: 20
<212> TYPE: DNA
<213> ORGANISM: homo sapiens

<400> SEQUENCE: 363
cgcatcaggg gcacacagga                                              20

<210> SEQ ID NO 364
<211> LENGTH: 20
<212> TYPE: DNA
<213> ORGANISM: homo sapiens

<400> SEQUENCE: 364
gcatcgcatc aggggcacac                                              20

<210> SEQ ID NO 365
<211> LENGTH: 20
<212> TYPE: DNA
<213> ORGANISM: homo sapiens

<400> SEQUENCE: 365
tgtgtgcccc tgatgcgatg                                              20

<210> SEQ ID NO 366
<211> LENGTH: 20
<212> TYPE: DNA
<213> ORGANISM: homo sapiens

<400> SEQUENCE: 366
gtgtgcccct gatgcgatgc                                              20

<210> SEQ ID NO 367
<211> LENGTH: 20
<212> TYPE: DNA
<213> ORGANISM: homo sapiens

<400> SEQUENCE: 367
tgtgcccctg atgcgatgcg                                              20

<210> SEQ ID NO 368
<211> LENGTH: 20
<212> TYPE: DNA
<213> ORGANISM: homo sapiens

<400> SEQUENCE: 368
gtgcccctga tgcgatgcgg                                              20
```

```
<210> SEQ ID NO 369
<211> LENGTH: 20
<212> TYPE: DNA
<213> ORGANISM: homo sapiens

<400> SEQUENCE: 369
cagcccccgc atcgcatcag                                                    20

<210> SEQ ID NO 370
<211> LENGTH: 20
<212> TYPE: DNA
<213> ORGANISM: homo sapiens

<400> SEQUENCE: 370
gcagcccccg catcgcatca                                                    20

<210> SEQ ID NO 371
<211> LENGTH: 20
<212> TYPE: DNA
<213> ORGANISM: homo sapiens

<400> SEQUENCE: 371
agcagccccc gcatcgcatc                                                    20

<210> SEQ ID NO 372
<211> LENGTH: 20
<212> TYPE: DNA
<213> ORGANISM: homo sapiens

<400> SEQUENCE: 372
cgggggctgc tgcaatgacg                                                    20

<210> SEQ ID NO 373
<211> LENGTH: 20
<212> TYPE: DNA
<213> ORGANISM: homo sapiens

<400> SEQUENCE: 373
gggggctgct gcaatgacga                                                    20

<210> SEQ ID NO 374
<211> LENGTH: 20
<212> TYPE: DNA
<213> ORGANISM: homo sapiens

<400> SEQUENCE: 374
ctgctgcaat gacgagggcc                                                    20

<210> SEQ ID NO 375
<211> LENGTH: 20
<212> TYPE: DNA
<213> ORGANISM: homo sapiens

<400> SEQUENCE: 375
cctggagtgt gtgcccactg                                                    20

<210> SEQ ID NO 376
<211> LENGTH: 20
<212> TYPE: DNA
<213> ORGANISM: homo sapiens

<400> SEQUENCE: 376
cctcagtggg cacacactcc                                                    20
```

<210> SEQ ID NO 377
<211> LENGTH: 20
<212> TYPE: DNA
<213> ORGANISM: homo sapiens

<400> SEQUENCE: 377
gtgatgttgg actcctcagt                                         20

<210> SEQ ID NO 378
<211> LENGTH: 20
<212> TYPE: DNA
<213> ORGANISM: homo sapiens

<400> SEQUENCE: 378
ggtgatgttg gactcctcag                                         20

<210> SEQ ID NO 379
<211> LENGTH: 20
<212> TYPE: DNA
<213> ORGANISM: homo sapiens

<400> SEQUENCE: 379
ggagtccaac atcaccatgc                                         20

<210> SEQ ID NO 380
<211> LENGTH: 20
<212> TYPE: DNA
<213> ORGANISM: homo sapiens

<400> SEQUENCE: 380
gtccaacatc accatgcagg                                         20

<210> SEQ ID NO 381
<211> LENGTH: 20
<212> TYPE: DNA
<213> ORGANISM: homo sapiens

<400> SEQUENCE: 381
tccaacatca ccatgcaggt                                         20

<210> SEQ ID NO 382
<211> LENGTH: 20
<212> TYPE: DNA
<213> ORGANISM: homo sapiens

<400> SEQUENCE: 382
gcccacctgc atggtgatgt                                         20

<210> SEQ ID NO 383
<211> LENGTH: 20
<212> TYPE: DNA
<213> ORGANISM: homo sapiens

<400> SEQUENCE: 383
cccaaagatg cccacctgca                                         20

<210> SEQ ID NO 384
<211> LENGTH: 20
<212> TYPE: DNA
<213> ORGANISM: homo sapiens

<400> SEQUENCE: 384

| | |
|---|---|
| tccttcctttccagattatg | 20 |

<210> SEQ ID NO 385
<211> LENGTH: 20
<212> TYPE: DNA
<213> ORGANISM: homo sapiens

<400> SEQUENCE: 385

| | |
|---|---|
| gaggtttgatccgcataatc | 20 |

<210> SEQ ID NO 386
<211> LENGTH: 20
<212> TYPE: DNA
<213> ORGANISM: homo sapiens

<400> SEQUENCE: 386

| | |
|---|---|
| atgcggatcaaacctcacca | 20 |

<210> SEQ ID NO 387
<211> LENGTH: 20
<212> TYPE: DNA
<213> ORGANISM: homo sapiens

<400> SEQUENCE: 387

| | |
|---|---|
| cctcaccaaggccagcacat | 20 |

<210> SEQ ID NO 388
<211> LENGTH: 20
<212> TYPE: DNA
<213> ORGANISM: homo sapiens

<400> SEQUENCE: 388

| | |
|---|---|
| cctatgtgctggccttggtg | 20 |

<210> SEQ ID NO 389
<211> LENGTH: 20
<212> TYPE: DNA
<213> ORGANISM: homo sapiens

<400> SEQUENCE: 389

| | |
|---|---|
| tctctcctatgtgctggcct | 20 |

<210> SEQ ID NO 390
<211> LENGTH: 20
<212> TYPE: DNA
<213> ORGANISM: homo sapiens

<400> SEQUENCE: 390

| | |
|---|---|
| agctcatctctcctatgtgc | 20 |

<210> SEQ ID NO 391
<211> LENGTH: 20
<212> TYPE: DNA
<213> ORGANISM: homo sapiens

<400> SEQUENCE: 391

| | |
|---|---|
| attcacatttgttgtgctgt | 20 |

<210> SEQ ID NO 392
<211> LENGTH: 20
<212> TYPE: DNA
<213> ORGANISM: homo sapiens

<400> SEQUENCE: 392

```
agcacaacaa atgtgaatgc                                               20

<210> SEQ ID NO 393
<211> LENGTH: 20
<212> TYPE: DNA
<213> ORGANISM: homo sapiens

<400> SEQUENCE: 393
aacaaatgtg aatgcaggtg                                               20

<210> SEQ ID NO 394
<211> LENGTH: 20
<212> TYPE: DNA
<213> ORGANISM: homo sapiens

<400> SEQUENCE: 394
tgtcttgctc tatctttctt                                               20

<210> SEQ ID NO 395
<211> LENGTH: 20
<212> TYPE: DNA
<213> ORGANISM: homo sapiens

<400> SEQUENCE: 395
ttttccagaa aatcagttcg                                               20

<210> SEQ ID NO 396
<211> LENGTH: 20
<212> TYPE: DNA
<213> ORGANISM: homo sapiens

<400> SEQUENCE: 396
cttccctcga actgattttc                                               20

<210> SEQ ID NO 397
<211> LENGTH: 20
<212> TYPE: DNA
<213> ORGANISM: homo sapiens

<400> SEQUENCE: 397
cagaaaatca gttcgaggaa                                               20

<210> SEQ ID NO 398
<211> LENGTH: 20
<212> TYPE: DNA
<213> ORGANISM: homo sapiens

<400> SEQUENCE: 398
agaaaatcag ttcgaggaaa                                               20

<210> SEQ ID NO 399
<211> LENGTH: 20
<212> TYPE: DNA
<213> ORGANISM: homo sapiens

<400> SEQUENCE: 399
atcagttcga ggaaagggaa                                               20

<210> SEQ ID NO 400
<211> LENGTH: 20
<212> TYPE: DNA
<213> ORGANISM: homo sapiens
```

```
<400> SEQUENCE: 400
tcagttcgag gaaagggaaa                                              20

<210> SEQ ID NO 401
<211> LENGTH: 20
<212> TYPE: DNA
<213> ORGANISM: homo sapiens

<400> SEQUENCE: 401
cagttcgagg aaagggaaag                                              20

<210> SEQ ID NO 402
<211> LENGTH: 20
<212> TYPE: DNA
<213> ORGANISM: homo sapiens

<400> SEQUENCE: 402
aacgaaagcg caagaaatcc                                              20

<210> SEQ ID NO 403
<211> LENGTH: 20
<212> TYPE: DNA
<213> ORGANISM: homo sapiens

<400> SEQUENCE: 403
agaaatcccg gtataagtcc                                              20

<210> SEQ ID NO 404
<211> LENGTH: 20
<212> TYPE: DNA
<213> ORGANISM: homo sapiens

<400> SEQUENCE: 404
cacgctccag gacttatacc                                              20

<210> SEQ ID NO 405
<211> LENGTH: 20
<212> TYPE: DNA
<213> ORGANISM: homo sapiens

<400> SEQUENCE: 405
acacgctcca ggacttatac                                              20

<210> SEQ ID NO 406
<211> LENGTH: 20
<212> TYPE: DNA
<213> ORGANISM: homo sapiens

<400> SEQUENCE: 406
aagtcctgga gcgtgtacgt                                              20

<210> SEQ ID NO 407
<211> LENGTH: 20
<212> TYPE: DNA
<213> ORGANISM: homo sapiens

<400> SEQUENCE: 407
ggcaccaacg tacacgctcc                                              20

<210> SEQ ID NO 408
<211> LENGTH: 20
<212> TYPE: DNA
<213> ORGANISM: homo sapiens
```

```
<400> SEQUENCE: 408
cccgctgctg tctaatgccc                                          20

<210> SEQ ID NO 409
<211> LENGTH: 20
<212> TYPE: DNA
<213> ORGANISM: homo sapiens

<400> SEQUENCE: 409
ccagggcatt agacagcagc                                          20

<210> SEQ ID NO 410
<211> LENGTH: 20
<212> TYPE: DNA
<213> ORGANISM: homo sapiens

<400> SEQUENCE: 410
tccagggcat tagacagcag                                          20

<210> SEQ ID NO 411
<211> LENGTH: 20
<212> TYPE: DNA
<213> ORGANISM: homo sapiens

<400> SEQUENCE: 411
ctaatgccct ggagcctccc                                          20

<210> SEQ ID NO 412
<211> LENGTH: 20
<212> TYPE: DNA
<213> ORGANISM: homo sapiens

<400> SEQUENCE: 412
tgggggccag ggaggctcca                                          20

<210> SEQ ID NO 413
<211> LENGTH: 20
<212> TYPE: DNA
<213> ORGANISM: homo sapiens

<400> SEQUENCE: 413
ctgggggcca gggaggctcc                                          20

<210> SEQ ID NO 414
<211> LENGTH: 20
<212> TYPE: DNA
<213> ORGANISM: homo sapiens

<400> SEQUENCE: 414
ggttgtactg ggggccaggg                                          20

<210> SEQ ID NO 415
<211> LENGTH: 20
<212> TYPE: DNA
<213> ORGANISM: homo sapiens

<400> SEQUENCE: 415
ggaggttgta ctgggggcca                                          20

<210> SEQ ID NO 416
<211> LENGTH: 20
<212> TYPE: DNA
```

```
<213> ORGANISM: homo sapiens

<400> SEQUENCE: 416
cggaggttgt actgggggcc                                               20

<210> SEQ ID NO 417
<211> LENGTH: 20
<212> TYPE: DNA
<213> ORGANISM: homo sapiens

<400> SEQUENCE: 417
gcaggcggag gttgtactgg                                               20

<210> SEQ ID NO 418
<211> LENGTH: 20
<212> TYPE: DNA
<213> ORGANISM: homo sapiens

<400> SEQUENCE: 418
ttgccttttt gcagtccctg                                               20

<210> SEQ ID NO 419
<211> LENGTH: 20
<212> TYPE: DNA
<213> ORGANISM: homo sapiens

<400> SEQUENCE: 419 tgccttttg cagtccctgt                                                20

<210> SEQ ID NO 420
<211> LENGTH: 20
<212> TYPE: DNA
<213> ORGANISM: homo sapiens

<400> SEQUENCE: 420
cgctctgagc aaggcccaca                                               20

<210> SEQ ID NO 421
<211> LENGTH: 20
<212> TYPE: DNA
<213> ORGANISM: homo sapiens

<400> SEQUENCE: 421
cctgtgggcc ttgctcagag                                               20

<210> SEQ ID NO 422
<211> LENGTH: 20
<212> TYPE: DNA
<213> ORGANISM: homo sapiens

<400> SEQUENCE: 422
ccgctctgag caaggcccac                                               20

<210> SEQ ID NO 423
<211> LENGTH: 20
<212> TYPE: DNA
<213> ORGANISM: homo sapiens

<400> SEQUENCE: 423
tgctttctcc gctctgagca                                               20

<210> SEQ ID NO 424
<211> LENGTH: 20
```

```
<212> TYPE: DNA
<213> ORGANISM: homo sapiens

<400> SEQUENCE: 424
caggaacatt tacacgtctg                                           20

<210> SEQ ID NO 425
<211> LENGTH: 20
<212> TYPE: DNA
<213> ORGANISM: homo sapiens

<400> SEQUENCE: 425
acgcgagtct gtgtttttgc                                           20

<210> SEQ ID NO 426
<211> LENGTH: 20
<212> TYPE: DNA
<213> ORGANISM: homo sapiens

<400> SEQUENCE: 426
aaacacagac tcgcgttgca                                           20

<210> SEQ ID NO 427
<211> LENGTH: 20
<212> TYPE: DNA
<213> ORGANISM: homo sapiens

<400> SEQUENCE: 427
cagactcgcg ttgcaaggcg                                           20

<210> SEQ ID NO 428
<211> LENGTH: 20
<212> TYPE: DNA
<213> ORGANISM: homo sapiens

<400> SEQUENCE: 428
agttaaacga acgtacttgc                                           20

<210> SEQ ID NO 429
<211> LENGTH: 20
<212> TYPE: DNA
<213> ORGANISM: homo sapiens

<400> SEQUENCE: 429
aaacgaacgt acttgcaggt                                           20

<210> SEQ ID NO 430
<211> LENGTH: 20
<212> TYPE: DNA
<213> ORGANISM: homo sapiens

<400> SEQUENCE: 430
ccctcagatg tgacaagccg                                           20

<210> SEQ ID NO 431
<211> LENGTH: 20
<212> TYPE: DNA
<213> ORGANISM: homo sapiens

<400> SEQUENCE: 431
gcctcggctt gtcacatctg                                           20

<210> SEQ ID NO 432
```

```
<211> LENGTH: 20
<212> TYPE: DNA
<213> ORGANISM: homo sapiens

<400> SEQUENCE: 432
tcagatgtga caagccgagg                                               20

<210> SEQ ID NO 433
<211> LENGTH: 20
<212> TYPE: DNA
<213> ORGANISM: homo sapiens

<400> SEQUENCE: 433
acaagccgag gcggtgagcc                                               20

<210> SEQ ID NO 434
<211> LENGTH: 20
<212> TYPE: DNA
<213> ORGANISM: homo sapiens

<400> SEQUENCE: 434
gccgaggcgg tgagccgggc                                               20

<210> SEQ ID NO 435
<211> LENGTH: 20
<212> TYPE: DNA
<213> ORGANISM: homo sapiens

<400> SEQUENCE: 435
tcctgcccgg ctcaccgcct                                               20

<210> SEQ ID NO 436
<211> LENGTH: 20
<212> TYPE: DNA
<213> ORGANISM: homo sapiens

<400> SEQUENCE: 436
tttaaatgag ctcccaatgt                                               20

<210> SEQ ID NO 437
<211> LENGTH: 20
<212> TYPE: DNA
<213> ORGANISM: homo sapiens

<400> SEQUENCE: 437
gagctcccaa tgtcggagtt                                               20

<210> SEQ ID NO 438
<211> LENGTH: 20
<212> TYPE: DNA
<213> ORGANISM: homo sapiens

<400> SEQUENCE: 438
gttttccaaa ctccgacatt                                               20

<210> SEQ ID NO 439
<211> LENGTH: 20
<212> TYPE: DNA
<213> ORGANISM: homo sapiens

<400> SEQUENCE: 439
tgttttccaa actccgacat                                               20
```

-continued

```
<210> SEQ ID NO 440
<211> LENGTH: 20
<212> TYPE: DNA
<213> ORGANISM: homo sapiens

<400> SEQUENCE: 440
aaatttgtct ttttaaaaga                                              20

<210> SEQ ID NO 441
<211> LENGTH: 20
<212> TYPE: DNA
<213> ORGANISM: homo sapiens

<400> SEQUENCE: 441
gtctttttaa aagaaggtct                                              20

<210> SEQ ID NO 442
<211> LENGTH: 20
<212> TYPE: DNA
<213> ORGANISM: homo sapiens

<400> SEQUENCE: 442
aaactcaaaa cctgaagaat                                              20

<210> SEQ ID NO 443
<211> LENGTH: 20
<212> TYPE: DNA
<213> ORGANISM: homo sapiens

<400> SEQUENCE: 443
ctgatttctt ccaattcttc                                              20

<210> SEQ ID NO 444
<211> LENGTH: 20
<212> TYPE: DNA
<213> ORGANISM: homo sapiens

<400> SEQUENCE: 444
gaagaaatca gaatagaaaa                                              20

<210> SEQ ID NO 445
<211> LENGTH: 20
<212> TYPE: DNA
<213> ORGANISM: homo sapiens

<400> SEQUENCE: 445
aagaaatcag aatagaaaat                                              20

<210> SEQ ID NO 446
<211> LENGTH: 20
<212> TYPE: DNA
<213> ORGANISM: homo sapiens

<400> SEQUENCE: 446
atcagaatag aaaatgggta                                              20

<210> SEQ ID NO 447
<211> LENGTH: 20
<212> TYPE: DNA
<213> ORGANISM: homo sapiens

<400> SEQUENCE: 447
ctcgagatgc agccagatct                                              20
```

```
<210> SEQ ID NO 448
<211> LENGTH: 20
<212> TYPE: DNA
<213> ORGANISM: homo sapiens

<400> SEQUENCE: 448
ttctttactt cgccgagatc                                               20

<210> SEQ ID NO 449
<211> LENGTH: 20
<212> TYPE: DNA
<213> ORGANISM: homo sapiens

<400> SEQUENCE: 449
gaactcacat tatgtggaag                                               20

<210> SEQ ID NO 450
<211> LENGTH: 20
<212> TYPE: DNA
<213> ORGANISM: homo sapiens

<400> SEQUENCE: 450
agatgcgaac tcacattatg                                               20

<210> SEQ ID NO 451
<211> LENGTH: 20
<212> TYPE: DNA
<213> ORGANISM: homo sapiens

<400> SEQUENCE: 451
tgtgagttcg catcttgata                                               20

<210> SEQ ID NO 452
<211> LENGTH: 20
<212> TYPE: DNA
<213> ORGANISM: homo sapiens

<400> SEQUENCE: 452
ttgataaggc ctctgtgatg                                               20

<210> SEQ ID NO 453
<211> LENGTH: 20
<212> TYPE: DNA
<213> ORGANISM: homo sapiens

<400> SEQUENCE: 453
gatggtaagc ctcatcacag                                               20

<210> SEQ ID NO 454
<211> LENGTH: 20
<212> TYPE: DNA
<213> ORGANISM: homo sapiens

<400> SEQUENCE: 454
ccatcagcta tttgcgtgtg                                               20

<210> SEQ ID NO 455
<211> LENGTH: 20
<212> TYPE: DNA
<213> ORGANISM: homo sapiens

<400> SEQUENCE: 455
cctcacacgc aaatagctga                                               20
```

<210> SEQ ID NO 456
<211> LENGTH: 20
<212> TYPE: DNA
<213> ORGANISM: homo sapiens

<400> SEQUENCE: 456
tttgcgtgtg aggaaacttc                                          20

<210> SEQ ID NO 457
<211> LENGTH: 20
<212> TYPE: DNA
<213> ORGANISM: homo sapiens

<400> SEQUENCE: 457
gtgaggaaac ttctggatgc                                          20

<210> SEQ ID NO 458
<211> LENGTH: 20
<212> TYPE: DNA
<213> ORGANISM: homo sapiens

<400> SEQUENCE: 458
tgtgcccttt ttaggtgatt                                          20

<210> SEQ ID NO 459
<211> LENGTH: 20
<212> TYPE: DNA
<213> ORGANISM: homo sapiens

<400> SEQUENCE: 459
ttgcttttat ttgaaagcct                                          20

<210> SEQ ID NO 460
<211> LENGTH: 20
<212> TYPE: DNA
<213> ORGANISM: homo sapiens

<400> SEQUENCE: 460
ttttatttga aagccttgga                                          20

<210> SEQ ID NO 461
<211> LENGTH: 20
<212> TYPE: DNA
<213> ORGANISM: homo sapiens

<400> SEQUENCE: 461
agccttggat ggttttgtta                                          20

<210> SEQ ID NO 462
<211> LENGTH: 20
<212> TYPE: DNA
<213> ORGANISM: homo sapiens

<400> SEQUENCE: 462
aaccataaca aaaccatcca                                          20

<210> SEQ ID NO 463
<211> LENGTH: 20
<212> TYPE: DNA
<213> ORGANISM: homo sapiens

<400> SEQUENCE: 463
gttatggttc tcacagatga                                              20

<210> SEQ ID NO 464
<211> LENGTH: 20
<212> TYPE: DNA
<213> ORGANISM: homo sapiens

<400> SEQUENCE: 464
tgataatgtg aacaaataca                                              20

<210> SEQ ID NO 465
<211> LENGTH: 20
<212> TYPE: DNA
<213> ORGANISM: homo sapiens

<400> SEQUENCE: 465
gataatgtga acaaatacat                                              20

<210> SEQ ID NO 466
<211> LENGTH: 20
<212> TYPE: DNA
<213> ORGANISM: homo sapiens

<400> SEQUENCE: 466
caaatacatg ggattaactc                                              20

<210> SEQ ID NO 467
<211> LENGTH: 20
<212> TYPE: DNA
<213> ORGANISM: homo sapiens

<400> SEQUENCE: 467
tgtttacagt ttgaactaac                                              20

<210> SEQ ID NO 468
<211> LENGTH: 20
<212> TYPE: DNA
<213> ORGANISM: homo sapiens

<400> SEQUENCE: 468
tactcatcca tgtgaccatg                                              20

<210> SEQ ID NO 469
<211> LENGTH: 20
<212> TYPE: DNA
<213> ORGANISM: homo sapiens

<400> SEQUENCE: 469
ctcatttcct catggtcaca                                              20

<210> SEQ ID NO 470
<211> LENGTH: 20
<212> TYPE: DNA
<213> ORGANISM: homo sapiens

<400> SEQUENCE: 470
gcatttctct catttcctca                                              20

<210> SEQ ID NO 471
<211> LENGTH: 20
<212> TYPE: DNA
<213> ORGANISM: homo sapiens

<400> SEQUENCE: 471

| | |
|---|---|
| gaaatgctta cacacagaaa | 20 |

<210> SEQ ID NO 472
<211> LENGTH: 20
<212> TYPE: DNA
<213> ORGANISM: homo sapiens

<400> SEQUENCE: 472

| | |
|---|---|
| ttcattaggc cttgtgaaaa | 20 |

<210> SEQ ID NO 473
<211> LENGTH: 20
<212> TYPE: DNA
<213> ORGANISM: homo sapiens

<400> SEQUENCE: 473

| | |
|---|---|
| tcattaggcc ttgtgaaaaa | 20 |

<210> SEQ ID NO 474
<211> LENGTH: 20
<212> TYPE: DNA
<213> ORGANISM: homo sapiens

<400> SEQUENCE: 474

| | |
|---|---|
| gttctttacc cttttcaca | 20 |

<210> SEQ ID NO 475
<211> LENGTH: 20
<212> TYPE: DNA
<213> ORGANISM: homo sapiens

<400> SEQUENCE: 475

| | |
|---|---|
| aagtgtaccc taactagccg | 20 |

<210> SEQ ID NO 476
<211> LENGTH: 20
<212> TYPE: DNA
<213> ORGANISM: homo sapiens

<400> SEQUENCE: 476

| | |
|---|---|
| agttcttcct cggctagtta | 20 |

<210> SEQ ID NO 477
<211> LENGTH: 20
<212> TYPE: DNA
<213> ORGANISM: homo sapiens

<400> SEQUENCE: 477

| | |
|---|---|
| tagttcttcc tcggctagtt | 20 |

<210> SEQ ID NO 478
<211> LENGTH: 20
<212> TYPE: DNA
<213> ORGANISM: homo sapiens

<400> SEQUENCE: 478

| | |
|---|---|
| ttatgttcat agttcttcct | 20 |

<210> SEQ ID NO 479
<211> LENGTH: 20
<212> TYPE: DNA
<213> ORGANISM: homo sapiens -continued

```
<400> SEQUENCE: 479
tgaacataaa gtctgcaaca                                              20

<210> SEQ ID NO 480
<211> LENGTH: 20
<212> TYPE: DNA
<213> ORGANISM: homo sapiens

<400> SEQUENCE: 480
cataaagtct gcaacatgga                                              20

<210> SEQ ID NO 481
<211> LENGTH: 20
<212> TYPE: DNA
<213> ORGANISM: homo sapiens

<400> SEQUENCE: 481
acacaggtat tgcactgcac                                              20

<210> SEQ ID NO 482
<211> LENGTH: 20
<212> TYPE: DNA
<213> ORGANISM: homo sapiens

<400> SEQUENCE: 482
tggtatcata tacgtgaatg                                              20

<210> SEQ ID NO 483
<211> LENGTH: 20
<212> TYPE: DNA
<213> ORGANISM: homo sapiens

<400> SEQUENCE: 483
acactgaggt tggttactgt                                              20

<210> SEQ ID NO 484
<211> LENGTH: 20
<212> TYPE: DNA
<213> ORGANISM: homo sapiens

<400> SEQUENCE: 484
aacagtaacc aacctcagtg                                              20

<210> SEQ ID NO 485
<211> LENGTH: 20
<212> TYPE: DNA
<213> ORGANISM: homo sapiens

<400> SEQUENCE: 485
acagtaacca acctcagtgt                                              20

<210> SEQ ID NO 486
<211> LENGTH: 20
<212> TYPE: DNA
<213> ORGANISM: homo sapiens

<400> SEQUENCE: 486
tcttataccc acactgaggt                                              20

<210> SEQ ID NO 487
<211> LENGTH: 20
<212> TYPE: DNA
<213> ORGANISM: homo sapiens
```

```
<400> SEQUENCE: 487
ggtttcttat acccacactg                                              20

<210> SEQ ID NO 488
<211> LENGTH: 20
<212> TYPE: DNA
<213> ORGANISM: homo sapiens

<400> SEQUENCE: 488
gaaaccacct atgacctgct                                              20

<210> SEQ ID NO 489
<211> LENGTH: 20
<212> TYPE: DNA
<213> ORGANISM: homo sapiens

<400> SEQUENCE: 489
agcaccaagc aggtcatagg                                              20

<210> SEQ ID NO 490
<211> LENGTH: 20
<212> TYPE: DNA
<213> ORGANISM: homo sapiens

<400> SEQUENCE: 490
atcagcacca agcaggtcat                                              20

<210> SEQ ID NO 491
<211> LENGTH: 20
<212> TYPE: DNA
<213> ORGANISM: homo sapiens

<400> SEQUENCE: 491
ttcacaaatc agcaccaagc                                              20

<210> SEQ ID NO 492
<211> LENGTH: 20
<212> TYPE: DNA
<213> ORGANISM: homo sapiens

<400> SEQUENCE: 492
atatttgatg ggtgaggaat                                              20

<210> SEQ ID NO 493
<211> LENGTH: 20
<212> TYPE: DNA
<213> ORGANISM: homo sapiens

<400> SEQUENCE: 493
aatatttgat gggtgaggaa                                              20

<210> SEQ ID NO 494
<211> LENGTH: 20
<212> TYPE: DNA
<213> ORGANISM: homo sapiens

<400> SEQUENCE: 494
atttcaatat tgatgggtg                                               20

<210> SEQ ID NO 495
<211> LENGTH: 20
<212> TYPE: DNA
```

```
<213> ORGANISM: homo sapiens

<400> SEQUENCE: 495
aaggaatttc aatatttgat                                               20

<210> SEQ ID NO 496
<211> LENGTH: 20
<212> TYPE: DNA
<213> ORGANISM: homo sapiens

<400> SEQUENCE: 496
aaaggaattt caatatttga                                               20

<210> SEQ ID NO 497
<211> LENGTH: 20
<212> TYPE: DNA
<213> ORGANISM: homo sapiens

<400> SEQUENCE: 497
aggaaagtct tgctatctaa                                               20

<210> SEQ ID NO 498
<211> LENGTH: 20
<212> TYPE: DNA
<213> ORGANISM: homo sapiens

<400> SEQUENCE: 498
tttcctcagt cgacacagcc                                               20

<210> SEQ ID NO 499
<211> LENGTH: 20
<212> TYPE: DNA
<213> ORGANISM: homo sapiens

<400> SEQUENCE: 499
tatccaggct gtgtcgactg                                               20

<210> SEQ ID NO 500
<211> LENGTH: 20
<212> TYPE: DNA
<213> ORGANISM: homo sapiens

<400> SEQUENCE: 500
aataagaaaa tttcatatcc                                               20

<210> SEQ ID NO 501
<211> LENGTH: 20
<212> TYPE: DNA
<213> ORGANISM: homo sapiens

<400> SEQUENCE: 501
aattttctta ttgtgatgaa                                               20

<210> SEQ ID NO 502
<211> LENGTH: 20
<212> TYPE: DNA
<213> ORGANISM: homo sapiens

<400> SEQUENCE: 502
taacagaatt accgaattga                                               20

<210> SEQ ID NO 503
<211> LENGTH: 20
```

```
<212> TYPE: DNA
<213> ORGANISM: homo sapiens

<400> SEQUENCE: 503
aacagaatta ccgaattgat                                             20

<210> SEQ ID NO 504
<211> LENGTH: 20
<212> TYPE: DNA
<213> ORGANISM: homo sapiens

<400> SEQUENCE: 504
tggctcatat cccatcaatt                                             20

<210> SEQ ID NO 505
<211> LENGTH: 20
<212> TYPE: DNA
<213> ORGANISM: homo sapiens

<400> SEQUENCE: 505
tatgagccag aagaactttt                                             20

<210> SEQ ID NO 506
<211> LENGTH: 20
<212> TYPE: DNA
<213> ORGANISM: homo sapiens

<400> SEQUENCE: 506
gagcggccta aaagttcttc                                             20

<210> SEQ ID NO 507
<211> LENGTH: 20
<212> TYPE: DNA
<213> ORGANISM: homo sapiens

<400> SEQUENCE: 507
gataatattc ataaattgag                                             20

<210> SEQ ID NO 508
<211> LENGTH: 20
<212> TYPE: DNA
<213> ORGANISM: homo sapiens

<400> SEQUENCE: 508
ttatgaatat tatcatgctt                                             20

<210> SEQ ID NO 509
<211> LENGTH: 20
<212> TYPE: DNA
<213> ORGANISM: homo sapiens

<400> SEQUENCE: 509
cttactatca tgatgagttt                                             20

<210> SEQ ID NO 510
<211> LENGTH: 20
<212> TYPE: DNA
<213> ORGANISM: homo sapiens

<400> SEQUENCE: 510
tcccccctag tgtttactaa                                             20

<210> SEQ ID NO 511
```

```
<211> LENGTH: 20
<212> TYPE: DNA
<213> ORGANISM: homo sapiens

<400> SEQUENCE: 511 ttgtcccttta gtaaacacta                                              20

<210> SEQ ID NO 512
<211> LENGTH: 20
<212> TYPE: DNA
<213> ORGANISM: homo sapiens

<400> SEQUENCE: 512
cttgtccttt agtaaacact                                               20

<210> SEQ ID NO 513
<211> LENGTH: 20
<212> TYPE: DNA
<213> ORGANISM: homo sapiens

<400> SEQUENCE: 513
actaaaggac aagtcaccac                                               20

<210> SEQ ID NO 514
<211> LENGTH: 20
<212> TYPE: DNA
<213> ORGANISM: homo sapiens

<400> SEQUENCE: 514
aagtcaccac aggacagtac                                               20

<210> SEQ ID NO 515
<211> LENGTH: 20
<212> TYPE: DNA
<213> ORGANISM: homo sapiens

<400> SEQUENCE: 515
aagcatcctg tactgtcctg                                               20

<210> SEQ ID NO 516
<211> LENGTH: 20
<212> TYPE: DNA
<213> ORGANISM: homo sapiens

<400> SEQUENCE: 516
tacaggatgc ttgccaaaag                                               20

<210> SEQ ID NO 517
<211> LENGTH: 20
<212> TYPE: DNA
<213> ORGANISM: homo sapiens

<400> SEQUENCE: 517
aggatgcttg ccaaaagagg                                               20

<210> SEQ ID NO 518
<211> LENGTH: 20
<212> TYPE: DNA
<213> ORGANISM: homo sapiens

<400> SEQUENCE: 518
ccaaaagagg tggatatgtc                                               20
```

```
<210> SEQ ID NO 519
<211> LENGTH: 20
<212> TYPE: DNA
<213> ORGANISM: homo sapiens

<400> SEQUENCE: 519
ccagacatat ccacctcttt                                               20

<210> SEQ ID NO 520
<211> LENGTH: 20
<212> TYPE: DNA
<213> ORGANISM: homo sapiens

<400> SEQUENCE: 520
caaaagaggt ggatatgtct                                               20

<210> SEQ ID NO 521
<211> LENGTH: 20
<212> TYPE: DNA
<213> ORGANISM: homo sapiens

<400> SEQUENCE: 521
gcactgtggt tgagaattct                                               20

<210> SEQ ID NO 522
<211> LENGTH: 20
<212> TYPE: DNA
<213> ORGANISM: homo sapiens

<400> SEQUENCE: 522
ttcacacata caatgcactg                                               20

<210> SEQ ID NO 523
<211> LENGTH: 20
<212> TYPE: DNA
<213> ORGANISM: homo sapiens

<400> SEQUENCE: 523
tatgtgtgaa ttacgttgtg                                               20

<210> SEQ ID NO 524
<211> LENGTH: 20
<212> TYPE: DNA
<213> ORGANISM: homo sapiens

<400> SEQUENCE: 524
gacacattct gtttgttgaa                                               20

<210> SEQ ID NO 525
<211> LENGTH: 20
<212> TYPE: DNA
<213> ORGANISM: homo sapiens

<400> SEQUENCE: 525
ggacacattc tgtttgttga                                               20

<210> SEQ ID NO 526
<211> LENGTH: 20
<212> TYPE: DNA
<213> ORGANISM: homo sapiens

<400> SEQUENCE: 526
aacagaatgt gtccttaaac                                               20
```

```
<210> SEQ ID NO 527
<211> LENGTH: 20
<212> TYPE: DNA
<213> ORGANISM: homo sapiens

<400> SEQUENCE: 527
ctgaagattc aaccggttta                                               20

<210> SEQ ID NO 528
<211> LENGTH: 20
<212> TYPE: DNA
<213> ORGANISM: homo sapiens

<400> SEQUENCE: 528
ttcatatctg aagattcaac                                               20

<210> SEQ ID NO 529
<211> LENGTH: 20
<212> TYPE: DNA
<213> ORGANISM: homo sapiens

<400> SEQUENCE: 529
tgtatcttct gattcaactt                                               20

<210> SEQ ID NO 530
<211> LENGTH: 20
<212> TYPE: DNA
<213> ORGANISM: homo sapiens

<400> SEQUENCE: 530
cctctttgac aaacttaaga                                               20

<210> SEQ ID NO 531
<211> LENGTH: 20
<212> TYPE: DNA
<213> ORGANISM: homo sapiens

<400> SEQUENCE: 531
ccttcttaag tttgtcaaag                                               20

<210> SEQ ID NO 532
<211> LENGTH: 20
<212> TYPE: DNA
<213> ORGANISM: homo sapiens

<400> SEQUENCE: 532
acctgatgct ttaactttgc                                               20

<210> SEQ ID NO 533
<211> LENGTH: 20
<212> TYPE: DNA
<213> ORGANISM: homo sapiens

<400> SEQUENCE: 533
gccagcaaag ttaaagcatc                                               20

<210> SEQ ID NO 534
<211> LENGTH: 20
<212> TYPE: DNA
<213> ORGANISM: homo sapiens

<400> SEQUENCE: 534
actttgctgg ccccagccgc                                               20
```

<210> SEQ ID NO 535
<211> LENGTH: 20
<212> TYPE: DNA
<213> ORGANISM: homo sapiens

<400> SEQUENCE: 535
gattgtgtct ccagcggctg                                          20

<210> SEQ ID NO 536
<211> LENGTH: 20
<212> TYPE: DNA
<213> ORGANISM: homo sapiens

<400> SEQUENCE: 536
tgattgtgtc tccagcggct                                          20

<210> SEQ ID NO 537
<211> LENGTH: 20
<212> TYPE: DNA
<213> ORGANISM: homo sapiens

<400> SEQUENCE: 537
atgattgtgt ctccagcggc                                          20

<210> SEQ ID NO 538
<211> LENGTH: 20
<212> TYPE: DNA
<213> ORGANISM: homo sapiens

<400> SEQUENCE: 538
agatatgatt gtgtctccag                                          20

<210> SEQ ID NO 539
<211> LENGTH: 20
<212> TYPE: DNA
<213> ORGANISM: homo sapiens

<400> SEQUENCE: 539
acaatcatat ctttagattt                                          20

<210> SEQ ID NO 540
<211> LENGTH: 20
<212> TYPE: DNA
<213> ORGANISM: homo sapiens

<400> SEQUENCE: 540
tctttagatt ttggcagcaa                                          20

<210> SEQ ID NO 541
<211> LENGTH: 20
<212> TYPE: DNA
<213> ORGANISM: homo sapiens

<400> SEQUENCE: 541
gtcatcagtt tctgtgtctg                                          20

<210> SEQ ID NO 542
<211> LENGTH: 20
<212> TYPE: DNA
<213> ORGANISM: homo sapiens

<400> SEQUENCE: 542

```
aactgatgac cagcaacttg                                               20

<210> SEQ ID NO 543
<211> LENGTH: 20
<212> TYPE: DNA
<213> ORGANISM: homo sapiens

<400> SEQUENCE: 543
atggtacttc ctcaagttgc                                               20

<210> SEQ ID NO 544
<211> LENGTH: 20
<212> TYPE: DNA
<213> ORGANISM: homo sapiens

<400> SEQUENCE: 544
agcattacat cattatataa                                               20

<210> SEQ ID NO 545
<211> LENGTH: 20
<212> TYPE: DNA
<213> ORGANISM: homo sapiens

<400> SEQUENCE: 545 gtaattttc gttgggtgag                                                20

<210> SEQ ID NO 546
<211> LENGTH: 20
<212> TYPE: DNA
<213> ORGANISM: homo sapiens

<400> SEQUENCE: 546 tgtaatttt cgttgggtga                                                20

<210> SEQ ID NO 547
<211> LENGTH: 20
<212> TYPE: DNA
<213> ORGANISM: homo sapiens

<400> SEQUENCE: 547 ctgtaattt tcgttgggtg                                                20

<210> SEQ ID NO 548
<211> LENGTH: 20
<212> TYPE: DNA
<213> ORGANISM: homo sapiens

<400> SEQUENCE: 548
atattctgta atttttcgtt                                               20

<210> SEQ ID NO 549
<211> LENGTH: 20
<212> TYPE: DNA
<213> ORGANISM: homo sapiens

<400> SEQUENCE: 549
tatattctgt aatttttcgt                                               20

<210> SEQ ID NO 550
<211> LENGTH: 20
<212> TYPE: DNA
<213> ORGANISM: homo sapiens

<400> SEQUENCE: 550
```
aaaattacag aatataaatt                                                    20

<210> SEQ ID NO 551
<211> LENGTH: 20
<212> TYPE: DNA
<213> ORGANISM: homo sapiens

<400> SEQUENCE: 551
ggcgtttcag cggtgggtaa                                                    20

<210> SEQ ID NO 552
<211> LENGTH: 20
<212> TYPE: DNA
<213> ORGANISM: homo sapiens

<400> SEQUENCE: 552
ggctttggcg tttcagcggt                                                    20

<210> SEQ ID NO 553
<211> LENGTH: 20
<212> TYPE: DNA
<213> ORGANISM: homo sapiens

<400> SEQUENCE: 553
tggctttggc gtttcagcgg                                                    20

<210> SEQ ID NO 554
<211> LENGTH: 20
<212> TYPE: DNA
<213> ORGANISM: homo sapiens

<400> SEQUENCE: 554
aagtggcttt ggcgtttcag                                                    20

<210> SEQ ID NO 555
<211> LENGTH: 20
<212> TYPE: DNA
<213> ORGANISM: homo sapiens

<400> SEQUENCE: 555
gcactacttc gaagtggctt                                                    20

<210> SEQ ID NO 556
<211> LENGTH: 20
<212> TYPE: DNA
<213> ORGANISM: homo sapiens

<400> SEQUENCE: 556
gggtcagcac tacttcgaag                                                    20

<210> SEQ ID NO 557
<211> LENGTH: 20
<212> TYPE: DNA
<213> ORGANISM: homo sapiens

<400> SEQUENCE: 557
caacttcttg attgagtgca                                                    20

<210> SEQ ID NO 558
<211> LENGTH: 20
<212> TYPE: DNA
<213> ORGANISM: homo sapiens

```
<400> SEQUENCE: 558
gcaacttctt gattgagtgc                                              20

<210> SEQ ID NO 559
<211> LENGTH: 20
<212> TYPE: DNA
<213> ORGANISM: homo sapiens

<400> SEQUENCE: 559
agaaccaaat ccagagtcac                                              20

<210> SEQ ID NO 560
<211> LENGTH: 20
<212> TYPE: DNA
<213> ORGANISM: homo sapiens

<400> SEQUENCE: 560
agttccagtg actctggatt                                              20

<210> SEQ ID NO 561
<211> LENGTH: 20
<212> TYPE: DNA
<213> ORGANISM: homo sapiens

<400> SEQUENCE: 561
aaagaaagtt ccagtgactc                                              20

<210> SEQ ID NO 562
<211> LENGTH: 20
<212> TYPE: DNA
<213> ORGANISM: homo sapiens

<400> SEQUENCE: 562
ttttaccatg ccccagattc                                              20

<210> SEQ ID NO 563
<211> LENGTH: 20
<212> TYPE: DNA
<213> ORGANISM: homo sapiens

<400> SEQUENCE: 563
ctgatcctga atctggggca                                              20

<210> SEQ ID NO 564
<211> LENGTH: 20
<212> TYPE: DNA
<213> ORGANISM: homo sapiens

<400> SEQUENCE: 564
ggtgtctgat cctgaatctg                                              20

<210> SEQ ID NO 565
<211> LENGTH: 20
<212> TYPE: DNA
<213> ORGANISM: homo sapiens

<400> SEQUENCE: 565
aggtgtctga tcctgaatct                                              20

<210> SEQ ID NO 566
<211> LENGTH: 20
<212> TYPE: DNA
<213> ORGANISM: homo sapiens
```

```
<400> SEQUENCE: 566
taggtgtctg atcctgaatc                                           20

<210> SEQ ID NO 567
<211> LENGTH: 20
<212> TYPE: DNA
<213> ORGANISM: homo sapiens

<400> SEQUENCE: 567
cagacaccta gtccttccga                                           20

<210> SEQ ID NO 568
<211> LENGTH: 20
<212> TYPE: DNA
<213> ORGANISM: homo sapiens

<400> SEQUENCE: 568
gtgcttccat cggaaggact                                           20

<210> SEQ ID NO 569
<211> LENGTH: 20
<212> TYPE: DNA
<213> ORGANISM: homo sapiens

<400> SEQUENCE: 569
tgtctagtgc ttccatcgga                                           20

<210> SEQ ID NO 570
<211> LENGTH: 20
<212> TYPE: DNA
<213> ORGANISM: homo sapiens

<400> SEQUENCE: 570
actttgtcta gtgcttccat                                           20

<210> SEQ ID NO 571
<211> LENGTH: 20
<212> TYPE: DNA
<213> ORGANISM: homo sapiens

<400> SEQUENCE: 571
cactagacaa agttcacctg                                           20

<210> SEQ ID NO 572
<211> LENGTH: 20
<212> TYPE: DNA
<213> ORGANISM: homo sapiens

<400> SEQUENCE: 572
agacaaagtt cacctgaggt                                           20

<210> SEQ ID NO 573
<211> LENGTH: 20
<212> TYPE: DNA
<213> ORGANISM: homo sapiens

<400> SEQUENCE: 573
tatatcatga cacctacctc                                           20

<210> SEQ ID NO 574
<211> LENGTH: 20
<212> TYPE: DNA
```

```
<213> ORGANISM: homo sapiens

<400> SEQUENCE: 574
caatattcac tgggactatt                                           20

<210> SEQ ID NO 575
<211> LENGTH: 20
<212> TYPE: DNA
<213> ORGANISM: homo sapiens

<400> SEQUENCE: 575
acataaaaac aatattcact                                           20

<210> SEQ ID NO 576
<211> LENGTH: 20
<212> TYPE: DNA
<213> ORGANISM: homo sapiens

<400> SEQUENCE: 576
cacataaaaa caatattcac                                           20

<210> SEQ ID NO 577
<211> LENGTH: 20
<212> TYPE: DNA
<213> ORGANISM: homo sapiens

<400> SEQUENCE: 577
cagtgaatat tgttttatg                                            20

<210> SEQ ID NO 578
<211> LENGTH: 20
<212> TYPE: DNA
<213> ORGANISM: homo sapiens

<400> SEQUENCE: 578
tttttatgtg gatagtgata                                           20

<210> SEQ ID NO 579
<211> LENGTH: 20
<212> TYPE: DNA
<213> ORGANISM: homo sapiens

<400> SEQUENCE: 579
tatggtcaat gaattcaagt                                           20

<210> SEQ ID NO 580
<211> LENGTH: 20
<212> TYPE: DNA
<213> ORGANISM: homo sapiens

<400> SEQUENCE: 580
caatgaattc aagttggaat                                           20

<210> SEQ ID NO 581
<211> LENGTH: 20
<212> TYPE: DNA
<213> ORGANISM: homo sapiens

<400> SEQUENCE: 581
aaagaaccca ttttctactc                                           20

<210> SEQ ID NO 582
<211> LENGTH: 20
```

```
<212> TYPE: DNA
<213> ORGANISM: homo sapiens

<400> SEQUENCE: 582
catatacctg agtagaaaat                                          20

<210> SEQ ID NO 583
<211> LENGTH: 20
<212> TYPE: DNA
<213> ORGANISM: homo sapiens

<400> SEQUENCE: 583
tcatatacct gagtagaaaa                                          20

<210> SEQ ID NO 584
<211> LENGTH: 20
<212> TYPE: DNA
<213> ORGANISM: homo sapiens

<400> SEQUENCE: 584
aaaggacaca gatttagact                                          20

<210> SEQ ID NO 585
<211> LENGTH: 20
<212> TYPE: DNA
<213> ORGANISM: homo sapiens

<400> SEQUENCE: 585
gttagctccc tatatcccaa                                          20

<210> SEQ ID NO 586
<211> LENGTH: 20
<212> TYPE: DNA
<213> ORGANISM: homo sapiens

<400> SEQUENCE: 586
tcatcatcca ttgggatata                                          20

<210> SEQ ID NO 587
<211> LENGTH: 20
<212> TYPE: DNA
<213> ORGANISM: homo sapiens

<400> SEQUENCE: 587
gtcatcatcc attgggatat                                          20

<210> SEQ ID NO 588
<211> LENGTH: 20
<212> TYPE: DNA
<213> ORGANISM: homo sapiens

<400> SEQUENCE: 588
actggaagtc atcatccatt                                          20

<210> SEQ ID NO 589
<211> LENGTH: 20
<212> TYPE: DNA
<213> ORGANISM: homo sapiens

<400> SEQUENCE: 589
aactggaagt catcatccat                                          20

<210> SEQ ID NO 590
```

```
<211> LENGTH: 20
<212> TYPE: DNA
<213> ORGANISM: homo sapiens

<400> SEQUENCE: 590
actgatcgaa ggaacgtaac                                        20

<210> SEQ ID NO 591
<211> LENGTH: 20
<212> TYPE: DNA
<213> ORGANISM: homo sapiens

<400> SEQUENCE: 591
taatggtgac aactgatcga                                        20

<210> SEQ ID NO 592
<211> LENGTH: 20
<212> TYPE: DNA
<213> ORGANISM: homo sapiens

<400> SEQUENCE: 592
cttgcggaac tgctttctaa                                        20

<210> SEQ ID NO 593
<211> LENGTH: 20
<212> TYPE: DNA
<213> ORGANISM: homo sapiens

<400> SEQUENCE: 593
acttgcgctt tcagggcttg                                        20

<210> SEQ ID NO 594
<211> LENGTH: 20
<212> TYPE: DNA
<213> ORGANISM: homo sapiens

<400> SEQUENCE: 594
tttgaggact tgcgctttca                                        20

<210> SEQ ID NO 595
<211> LENGTH: 20
<212> TYPE: DNA
<213> ORGANISM: homo sapiens

<400> SEQUENCE: 595
ctttgaggac ttgcgctttc                                        20

<210> SEQ ID NO 596
<211> LENGTH: 20
<212> TYPE: DNA
<213> ORGANISM: homo sapiens

<400> SEQUENCE: 596
aatactgtaa ctgtgctttg                                        20

<210> SEQ ID NO 597
<211> LENGTH: 20
<212> TYPE: DNA
<213> ORGANISM: homo sapiens

<400> SEQUENCE: 597
gttcttgtat ttgagtctgc                                        20
```

-continued

```
<210> SEQ ID NO 598
<211> LENGTH: 20
<212> TYPE: DNA
<213> ORGANISM: homo sapiens

<400> SEQUENCE: 598
gtagtggtgg cattagcagt                                              20

<210> SEQ ID NO 599
<211> LENGTH: 20
<212> TYPE: DNA
<213> ORGANISM: homo sapiens

<400> SEQUENCE: 599
agtggtggca gtggtagtgg                                              20

<210> SEQ ID NO 600
<211> LENGTH: 20
<212> TYPE: DNA
<213> ORGANISM: homo sapiens

<400> SEQUENCE: 600
atcagtggtg gcagtggtag                                              20

<210> SEQ ID NO 601
<211> LENGTH: 20
<212> TYPE: DNA
<213> ORGANISM: homo sapiens

<400> SEQUENCE: 601
taattcatca gtggtggcag                                              20

<210> SEQ ID NO 602
<211> LENGTH: 20
<212> TYPE: DNA
<213> ORGANISM: homo sapiens

<400> SEQUENCE: 602
tgtttttaat tcatcagtgg                                              20

<210> SEQ ID NO 603
<211> LENGTH: 20
<212> TYPE: DNA
<213> ORGANISM: homo sapiens

<400> SEQUENCE: 603
cactgttttt aattcatcag                                              20

<210> SEQ ID NO 604
<211> LENGTH: 20
<212> TYPE: DNA
<213> ORGANISM: homo sapiens

<400> SEQUENCE: 604
aacagtgaca aaagaccgta                                              20

<210> SEQ ID NO 605
<211> LENGTH: 20
<212> TYPE: DNA
<213> ORGANISM: homo sapiens

<400> SEQUENCE: 605
atattttaat gtcttccata                                              20
```

```
<210> SEQ ID NO 606
<211> LENGTH: 20
<212> TYPE: DNA
<213> ORGANISM: homo sapiens

<400> SEQUENCE: 606
ttatgtatgt gggtaggaga                                              20

<210> SEQ ID NO 607
<211> LENGTH: 20
<212> TYPE: DNA
<213> ORGANISM: homo sapiens

<400> SEQUENCE: 607
gtttctttat gtatgtgggt                                              20

<210> SEQ ID NO 608
<211> LENGTH: 20
<212> TYPE: DNA
<213> ORGANISM: homo sapiens

<400> SEQUENCE: 608
agtagtttct ttatgtatgt                                              20

<210> SEQ ID NO 609
<211> LENGTH: 20
<212> TYPE: DNA
<213> ORGANISM: homo sapiens

<400> SEQUENCE: 609
tagtagtttc tttatgtatg                                              20

<210> SEQ ID NO 610
<211> LENGTH: 20
<212> TYPE: DNA
<213> ORGANISM: homo sapiens

<400> SEQUENCE: 610
atctctatat ggtgatgatg                                              20

<210> SEQ ID NO 611
<211> LENGTH: 20
<212> TYPE: DNA
<213> ORGANISM: homo sapiens

<400> SEQUENCE: 611
cgactttgag tatctctata                                              20

<210> SEQ ID NO 612
<211> LENGTH: 20
<212> TYPE: DNA
<213> ORGANISM: homo sapiens

<400> SEQUENCE: 612
catatagaga tactcaaagt                                              20

<210> SEQ ID NO 613
<211> LENGTH: 20
<212> TYPE: DNA
<213> ORGANISM: homo sapiens

<400> SEQUENCE: 613
acagcctcac caaacagagc                                              20
```

```
<210> SEQ ID NO 614
<211> LENGTH: 20
<212> TYPE: DNA
<213> ORGANISM: homo sapiens

<400> SEQUENCE: 614
ttttcctgct ctgtttggtg                                                    20

<210> SEQ ID NO 615
<211> LENGTH: 20
<212> TYPE: DNA
<213> ORGANISM: homo sapiens

<400> SEQUENCE: 615
tcaccaaaca gagcaggaaa                                                    20

<210> SEQ ID NO 616
<211> LENGTH: 20
<212> TYPE: DNA
<213> ORGANISM: homo sapiens

<400> SEQUENCE: 616
actccttttc ctgctctgtt                                                    20

<210> SEQ ID NO 617
<211> LENGTH: 20
<212> TYPE: DNA
<213> ORGANISM: homo sapiens

<400> SEQUENCE: 617
gataacacgt tagggcttct                                                    20

<210> SEQ ID NO 618
<211> LENGTH: 20
<212> TYPE: DNA
<213> ORGANISM: homo sapiens

<400> SEQUENCE: 618
aagcgacaga taacacgtta                                                    20

<210> SEQ ID NO 619
<211> LENGTH: 20
<212> TYPE: DNA
<213> ORGANISM: homo sapiens

<400> SEQUENCE: 619
aaagcgacag ataacacgtt                                                    20

<210> SEQ ID NO 620
<211> LENGTH: 20
<212> TYPE: DNA
<213> ORGANISM: homo sapiens

<400> SEQUENCE: 620
tatctgtcgc tttgagtcaa                                                    20

<210> SEQ ID NO 621
<211> LENGTH: 20
<212> TYPE: DNA
<213> ORGANISM: homo sapiens

<400> SEQUENCE: 621
```
tttcagaact acagttcctg                                           20

<210> SEQ ID NO 622
<211> LENGTH: 20
<212> TYPE: DNA
<213> ORGANISM: homo sapiens

<400> SEQUENCE: 622
tttggattta gttcttcctc                                           20

<210> SEQ ID NO 623
<211> LENGTH: 20
<212> TYPE: DNA
<213> ORGANISM: homo sapiens

<400> SEQUENCE: 623
ttctgcaaag ctagtatctt                                           20

<210> SEQ ID NO 624
<211> LENGTH: 20
<212> TYPE: DNA
<213> ORGANISM: homo sapiens

<400> SEQUENCE: 624
tgctcagaga aagcgaaaaa                                           20

<210> SEQ ID NO 625
<211> LENGTH: 20
<212> TYPE: DNA
<213> ORGANISM: homo sapiens

<400> SEQUENCE: 625
aagcgaaaaa tggaacatga                                           20

<210> SEQ ID NO 626
<211> LENGTH: 20
<212> TYPE: DNA
<213> ORGANISM: homo sapiens

<400> SEQUENCE: 626
gtagtagctg catgatcgtc                                           20

<210> SEQ ID NO 627
<211> LENGTH: 20
<212> TYPE: DNA
<213> ORGANISM: homo sapiens

<400> SEQUENCE: 627
cagctactac atcactttct                                           20

<210> SEQ ID NO 628
<211> LENGTH: 20
<212> TYPE: DNA
<213> ORGANISM: homo sapiens

<400> SEQUENCE: 628
ctttcttgga aacgtgtaaa                                           20

<210> SEQ ID NO 629
<211> LENGTH: 20
<212> TYPE: DNA
<213> ORGANISM: homo sapiens

<400> SEQUENCE: 629
acaattattt taatacccctc                                    20

<210> SEQ ID NO 630
<211> LENGTH: 20
<212> TYPE: DNA
<213> ORGANISM: homo sapiens

<400> SEQUENCE: 630
aaaagaataa actaaccaga                                     20

<210> SEQ ID NO 631
<211> LENGTH: 20
<212> TYPE: DNA
<213> ORGANISM: homo sapiens

<400> SEQUENCE: 631
aaaaagaata aactaaccag                                     20

<210> SEQ ID NO 632
<211> LENGTH: 20
<212> TYPE: DNA
<213> ORGANISM: homo sapiens

<400> SEQUENCE: 632
agatttagca tgtagactgc                                     20

<210> SEQ ID NO 633
<211> LENGTH: 20
<212> TYPE: DNA
<213> ORGANISM: homo sapiens

<400> SEQUENCE: 633
gatttagcat gtagactgct                                     20

<210> SEQ ID NO 634
<211> LENGTH: 20
<212> TYPE: DNA
<213> ORGANISM: homo sapiens

<400> SEQUENCE: 634
atttagcatg tagactgctg                                     20

<210> SEQ ID NO 635
<211> LENGTH: 20
<212> TYPE: DNA
<213> ORGANISM: homo sapiens

<400> SEQUENCE: 635
tagactgctg gggcaatcaa                                     20

<210> SEQ ID NO 636
<211> LENGTH: 20
<212> TYPE: DNA
<213> ORGANISM: homo sapiens

<400> SEQUENCE: 636
gggcaatcaa tggatgaaag                                     20

<210> SEQ ID NO 637
<211> LENGTH: 20
<212> TYPE: DNA
<213> ORGANISM: homo sapiens -continued

<400> SEQUENCE: 637
caatcataac tggtcagctg                                              20

<210> SEQ ID NO 638
<211> LENGTH: 20
<212> TYPE: DNA
<213> ORGANISM: homo sapiens

<400> SEQUENCE: 638
attaacttca caatcataac                                              20

<210> SEQ ID NO 639
<211> LENGTH: 20
<212> TYPE: DNA
<213> ORGANISM: homo sapiens

<400> SEQUENCE: 639
gaagttaatg ctcctataca                                              20

<210> SEQ ID NO 640
<211> LENGTH: 20
<212> TYPE: DNA
<213> ORGANISM: homo sapiens

<400> SEQUENCE: 640
aggtttctgc tgccttgtat                                              20

<210> SEQ ID NO 641
<211> LENGTH: 20
<212> TYPE: DNA
<213> ORGANISM: homo sapiens

<400> SEQUENCE: 641
aggcagcaga aacctactgc                                              20

<210> SEQ ID NO 642
<211> LENGTH: 20
<212> TYPE: DNA
<213> ORGANISM: homo sapiens

<400> SEQUENCE: 642
ggcagcagaa acctactgca                                              20

<210> SEQ ID NO 643
<211> LENGTH: 20
<212> TYPE: DNA
<213> ORGANISM: homo sapiens

<400> SEQUENCE: 643
gtaattcttc accctgcagt                                              20

<210> SEQ ID NO 644
<211> LENGTH: 20
<212> TYPE: DNA
<213> ORGANISM: homo sapiens

<400> SEQUENCE: 644
tgaagaatta ctcagagctt                                              20

<210> SEQ ID NO 645
<211> LENGTH: 20
<212> TYPE: DNA
<213> ORGANISM: homo sapiens

```
<400> SEQUENCE: 645
agcgacaatg acagctgaca                                              20

<210> SEQ ID NO 646
<211> LENGTH: 20
<212> TYPE: DNA
<213> ORGANISM: homo sapiens

<400> SEQUENCE: 646
cagctgacaa ggagaagaaa                                              20

<210> SEQ ID NO 647
<211> LENGTH: 20
<212> TYPE: DNA
<213> ORGANISM: homo sapiens

<400> SEQUENCE: 647
ttctccactt aggagtagct                                              20

<210> SEQ ID NO 648
<211> LENGTH: 20
<212> TYPE: DNA
<213> ORGANISM: homo sapiens

<400> SEQUENCE: 648
cacttaggag tagctcggag                                              20

<210> SEQ ID NO 649
<211> LENGTH: 20
<212> TYPE: DNA
<213> ORGANISM: homo sapiens

<400> SEQUENCE: 649
ttaggagtag ctcggagagg                                              20

<210> SEQ ID NO 650
<211> LENGTH: 20
<212> TYPE: DNA
<213> ORGANISM: homo sapiens

<400> SEQUENCE: 650
gagtagctcg gagaggagga                                              20

<210> SEQ ID NO 651
<211> LENGTH: 20
<212> TYPE: DNA
<213> ORGANISM: homo sapiens

<400> SEQUENCE: 651
agaggaggaa ggagaagtcc                                              20

<210> SEQ ID NO 652
<211> LENGTH: 20
<212> TYPE: DNA
<213> ORGANISM: homo sapiens

<400> SEQUENCE: 652
gaggaggaag gagaagtccc                                              20

<210> SEQ ID NO 653
<211> LENGTH: 20
<212> TYPE: DNA
```

```
<213> ORGANISM: homo sapiens

<400> SEQUENCE: 653
agaagtcccg ggatgctgcg                                          20

<210> SEQ ID NO 654
<211> LENGTH: 20
<212> TYPE: DNA
<213> ORGANISM: homo sapiens

<400> SEQUENCE: 654
cccgggatgc tgcgcggtgc                                          20

<210> SEQ ID NO 655
<211> LENGTH: 20
<212> TYPE: DNA
<213> ORGANISM: homo sapiens

<400> SEQUENCE: 655
ccggcaccgc gcagcatccc                                          20

<210> SEQ ID NO 656
<211> LENGTH: 20
<212> TYPE: DNA
<213> ORGANISM: homo sapiens

<400> SEQUENCE: 656
gccggcaccg cgcagcatcc                                          20

<210> SEQ ID NO 657
<211> LENGTH: 20
<212> TYPE: DNA
<213> ORGANISM: homo sapiens

<400> SEQUENCE: 657
gggatgctgc gcggtgccgg                                          20

<210> SEQ ID NO 658
<211> LENGTH: 20
<212> TYPE: DNA
<213> ORGANISM: homo sapiens

<400> SEQUENCE: 658
tgcgcggtgc cggcggagca                                          20

<210> SEQ ID NO 659
<211> LENGTH: 20
<212> TYPE: DNA
<213> ORGANISM: homo sapiens

<400> SEQUENCE: 659
gtgccggcgg agcaaggaga                                          20

<210> SEQ ID NO 660
<211> LENGTH: 20
<212> TYPE: DNA
<213> ORGANISM: homo sapiens

<400> SEQUENCE: 660
ccggcggagc aaggagacgg                                          20

<210> SEQ ID NO 661
<211> LENGTH: 20
```

<212> TYPE: DNA
<213> ORGANISM: homo sapiens

<400> SEQUENCE: 661
cctccgtctc cttgctccgc                    20

<210> SEQ ID NO 662
<211> LENGTH: 20
<212> TYPE: DNA
<213> ORGANISM: homo sapiens

<400> SEQUENCE: 662
gacggaggtg ttctatgagc                    20

<210> SEQ ID NO 663
<211> LENGTH: 20
<212> TYPE: DNA
<213> ORGANISM: homo sapiens

<400> SEQUENCE: 663
gtggggcaga ggcagctcat                    20

<210> SEQ ID NO 664
<211> LENGTH: 20
<212> TYPE: DNA
<213> ORGANISM: homo sapiens

<400> SEQUENCE: 664
tgtggggcag aggcagctca                    20

<210> SEQ ID NO 665
<211> LENGTH: 20
<212> TYPE: DNA
<213> ORGANISM: homo sapiens

<400> SEQUENCE: 665
gagctcacac tgtggggcag                    20

<210> SEQ ID NO 666
<211> LENGTH: 20
<212> TYPE: DNA
<213> ORGANISM: homo sapiens

<400> SEQUENCE: 666
agatgggagc tcacactgtg                    20

<210> SEQ ID NO 667
<211> LENGTH: 20
<212> TYPE: DNA
<213> ORGANISM: homo sapiens

<400> SEQUENCE: 667
cagatgggag ctcacactgt                    20

<210> SEQ ID NO 668
<211> LENGTH: 20
<212> TYPE: DNA
<213> ORGANISM: homo sapiens

<400> SEQUENCE: 668
ccacagtgtg agctcccatc                    20

<210> SEQ ID NO 669

```
<211> LENGTH: 20
<212> TYPE: DNA
<213> ORGANISM: homo sapiens

<400> SEQUENCE: 669
ccagatggga gctcacactg                                               20

<210> SEQ ID NO 670
<211> LENGTH: 20
<212> TYPE: DNA
<213> ORGANISM: homo sapiens

<400> SEQUENCE: 670
tgtgagctcc catctggaca                                               20

<210> SEQ ID NO 671
<211> LENGTH: 20
<212> TYPE: DNA
<213> ORGANISM: homo sapiens

<400> SEQUENCE: 671
gatggaggcc ttgtccagat                                               20

<210> SEQ ID NO 672
<211> LENGTH: 20
<212> TYPE: DNA
<213> ORGANISM: homo sapiens

<400> SEQUENCE: 672
tgatggaggc cttgtccaga                                               20

<210> SEQ ID NO 673
<211> LENGTH: 20
<212> TYPE: DNA
<213> ORGANISM: homo sapiens

<400> SEQUENCE: 673
caaggcctcc atcatgcgac                                               20

<210> SEQ ID NO 674
<211> LENGTH: 20
<212> TYPE: DNA
<213> ORGANISM: homo sapiens

<400> SEQUENCE: 674
gattgccagt cgcatgatgg                                               20

<210> SEQ ID NO 675
<211> LENGTH: 20
<212> TYPE: DNA
<213> ORGANISM: homo sapiens

<400> SEQUENCE: 675
gctgattgcc agtcgcatga                                               20

<210> SEQ ID NO 676
<211> LENGTH: 20
<212> TYPE: DNA
<213> ORGANISM: homo sapiens

<400> SEQUENCE: 676
agaggagctt gtgtgttcgc                                               20
```

```
<210> SEQ ID NO 677
<211> LENGTH: 20
<212> TYPE: DNA
<213> ORGANISM: homo sapiens

<400> SEQUENCE: 677
acacacaagc tcctctcctc                                              20

<210> SEQ ID NO 678
<211> LENGTH: 20
<212> TYPE: DNA
<213> ORGANISM: homo sapiens

<400> SEQUENCE: 678
caagctcctc tcctcaggta                                              20

<210> SEQ ID NO 679
<211> LENGTH: 20
<212> TYPE: DNA
<213> ORGANISM: homo sapiens

<400> SEQUENCE: 679
tgctggcctt acctgaggag                                              20

<210> SEQ ID NO 680
<211> LENGTH: 20
<212> TYPE: DNA
<213> ORGANISM: homo sapiens

<400> SEQUENCE: 680
gagcctgctg gccttacctg                                              20

<210> SEQ ID NO 681
<211> LENGTH: 20
<212> TYPE: DNA
<213> ORGANISM: homo sapiens

<400> SEQUENCE: 681
gactcgtttt cagagcaaac                                              20

<210> SEQ ID NO 682
<211> LENGTH: 20
<212> TYPE: DNA
<213> ORGANISM: homo sapiens

<400> SEQUENCE: 682
ctgctggtca gcttcggctt                                              20

<210> SEQ ID NO 683
<211> LENGTH: 20
<212> TYPE: DNA
<213> ORGANISM: homo sapiens

<400> SEQUENCE: 683
agccgaagct gaccagcaga                                              20

<210> SEQ ID NO 684
<211> LENGTH: 20
<212> TYPE: DNA
<213> ORGANISM: homo sapiens

<400> SEQUENCE: 684
gtccatctgc tggtcagctt                                              20
```

```
<210> SEQ ID NO 685
<211> LENGTH: 20
<212> TYPE: DNA
<213> ORGANISM: homo sapiens

<400> SEQUENCE: 685
ggtacaagtt gtccatctgc                                              20

<210> SEQ ID NO 686
<211> LENGTH: 20
<212> TYPE: DNA
<213> ORGANISM: homo sapiens

<400> SEQUENCE: 686
caacttgtac ctgaaagcct                                              20

<210> SEQ ID NO 687
<211> LENGTH: 20
<212> TYPE: DNA
<213> ORGANISM: homo sapiens

<400> SEQUENCE: 687
cttgtacctg aaagccttgg                                              20

<210> SEQ ID NO 688
<211> LENGTH: 20
<212> TYPE: DNA
<213> ORGANISM: homo sapiens

<400> SEQUENCE: 688
ttgtacctga aagccttgga                                              20

<210> SEQ ID NO 689
<211> LENGTH: 20
<212> TYPE: DNA
<213> ORGANISM: homo sapiens

<400> SEQUENCE: 689
tgaaaccctc caaggctttc                                              20

<210> SEQ ID NO 690
<211> LENGTH: 20
<212> TYPE: DNA
<213> ORGANISM: homo sapiens

<400> SEQUENCE: 690
cacggcaatg aaaccctcca                                              20

<210> SEQ ID NO 691
<211> LENGTH: 20
<212> TYPE: DNA
<213> ORGANISM: homo sapiens

<400> SEQUENCE: 691
cttggagggt ttcattgccg                                              20

<210> SEQ ID NO 692
<211> LENGTH: 20
<212> TYPE: DNA
<213> ORGANISM: homo sapiens

<400> SEQUENCE: 692
attgccgtgg tgacccaaga                                              20
```

<210> SEQ ID NO 693
<211> LENGTH: 20
<212> TYPE: DNA
<213> ORGANISM: homo sapiens

<400> SEQUENCE: 693
gtcgccatct tgggtcacca                                              20

<210> SEQ ID NO 694
<211> LENGTH: 20
<212> TYPE: DNA
<213> ORGANISM: homo sapiens

<400> SEQUENCE: 694
aaagatcatg tcgccatctt                                              20

<210> SEQ ID NO 695
<211> LENGTH: 20
<212> TYPE: DNA
<213> ORGANISM: homo sapiens

<400> SEQUENCE: 695
gaaagatcat gtcgccatct                                              20

<210> SEQ ID NO 696
<211> LENGTH: 20
<212> TYPE: DNA
<213> ORGANISM: homo sapiens

<400> SEQUENCE: 696
agaaaacatc agcaagttca                                              20

<210> SEQ ID NO 697
<211> LENGTH: 20
<212> TYPE: DNA
<213> ORGANISM: homo sapiens

<400> SEQUENCE: 697
gaaaacatca gcaagttcat                                              20

<210> SEQ ID NO 698
<211> LENGTH: 20
<212> TYPE: DNA
<213> ORGANISM: homo sapiens

<400> SEQUENCE: 698
caagttcatg ggacttacac                                              20

<210> SEQ ID NO 699
<211> LENGTH: 20
<212> TYPE: DNA
<213> ORGANISM: homo sapiens

<400> SEQUENCE: 699
ttgaaacagg tggagctaac                                              20

<210> SEQ ID NO 700
<211> LENGTH: 20
<212> TYPE: DNA
<213> ORGANISM: homo sapiens

<400> SEQUENCE: 700

```
cactcatccc tgcgaccatg                                               20

<210> SEQ ID NO 701
<211> LENGTH: 20
<212> TYPE: DNA
<213> ORGANISM: homo sapiens

<400> SEQUENCE: 701
cgaatctcct catggtcgca                                               20

<210> SEQ ID NO 702
<211> LENGTH: 20
<212> TYPE: DNA
<213> ORGANISM: homo sapiens

<400> SEQUENCE: 702
acgaatctcc tcatggtcgc                                               20

<210> SEQ ID NO 703
<211> LENGTH: 20
<212> TYPE: DNA
<213> ORGANISM: homo sapiens

<400> SEQUENCE: 703
ggttctcacg aatctcctca                                               20

<210> SEQ ID NO 704
<211> LENGTH: 20
<212> TYPE: DNA
<213> ORGANISM: homo sapiens

<400> SEQUENCE: 704
gagaacctga gtctcaaaaa                                               20

<210> SEQ ID NO 705
<211> LENGTH: 20
<212> TYPE: DNA
<213> ORGANISM: homo sapiens

<400> SEQUENCE: 705
ggataccatt tttgagactc                                               20

<210> SEQ ID NO 706
<211> LENGTH: 20
<212> TYPE: DNA
<213> ORGANISM: homo sapiens

<400> SEQUENCE: 706
atccttccac atccaggctc                                               20

<210> SEQ ID NO 707
<211> LENGTH: 20
<212> TYPE: DNA
<213> ORGANISM: homo sapiens

<400> SEQUENCE: 707
ccacatccag gctctggttt                                               20

<210> SEQ ID NO 708
<211> LENGTH: 20
<212> TYPE: DNA
<213> ORGANISM: homo sapiens

<400> SEQUENCE: 708
```

```
cacatccagg ctctggtttt                                              20

<210> SEQ ID NO 709
<211> LENGTH: 20
<212> TYPE: DNA
<213> ORGANISM: homo sapiens

<400> SEQUENCE: 709
tttttcccaa aaccagagcc                                              20

<210> SEQ ID NO 710
<211> LENGTH: 20
<212> TYPE: DNA
<213> ORGANISM: homo sapiens

<400> SEQUENCE: 710
gcaaagacat gtccacagag                                              20

<210> SEQ ID NO 711
<211> LENGTH: 20
<212> TYPE: DNA
<213> ORGANISM: homo sapiens

<400> SEQUENCE: 711
caaagacatg tccacagagc                                              20

<210> SEQ ID NO 712
<211> LENGTH: 20
<212> TYPE: DNA
<213> ORGANISM: homo sapiens

<400> SEQUENCE: 712
catgaagaag tcccgctctg                                              20

<210> SEQ ID NO 713
<211> LENGTH: 20
<212> TYPE: DNA
<213> ORGANISM: homo sapiens

<400> SEQUENCE: 713
cagagcggga cttcttcatg                                              20

<210> SEQ ID NO 714
<211> LENGTH: 20
<212> TYPE: DNA
<213> ORGANISM: homo sapiens

<400> SEQUENCE: 714
cttcatgagg atgaagtgca                                              20

<210> SEQ ID NO 715
<211> LENGTH: 20
<212> TYPE: DNA
<213> ORGANISM: homo sapiens

<400> SEQUENCE: 715
aagtgcacgg tcaccaacag                                              20

<210> SEQ ID NO 716
<211> LENGTH: 20
<212> TYPE: DNA
<213> ORGANISM: homo sapiens
```

```
<400> SEQUENCE: 716
gttgacagta cggcctctgt                                            20

<210> SEQ ID NO 717
<211> LENGTH: 20
<212> TYPE: DNA
<213> ORGANISM: homo sapiens

<400> SEQUENCE: 717
ctgacttgag gttgacagta                                            20

<210> SEQ ID NO 718
<211> LENGTH: 20
<212> TYPE: DNA
<213> ORGANISM: homo sapiens

<400> SEQUENCE: 718
tcaacctcaa gtcagccacc                                            20

<210> SEQ ID NO 719
<211> LENGTH: 20
<212> TYPE: DNA
<213> ORGANISM: homo sapiens

<400> SEQUENCE: 719
cctcaagtca gccacctgga                                            20

<210> SEQ ID NO 720
<211> LENGTH: 20
<212> TYPE: DNA
<213> ORGANISM: homo sapiens

<400> SEQUENCE: 720
ccttccaggt ggctgacttg                                            20

<210> SEQ ID NO 721
<211> LENGTH: 20
<212> TYPE: DNA
<213> ORGANISM: homo sapiens

<400> SEQUENCE: 721
aagtcagcca cctggaaggt                                            20

<210> SEQ ID NO 722
<211> LENGTH: 20
<212> TYPE: DNA
<213> ORGANISM: homo sapiens

<400> SEQUENCE: 722
agtcagccac ctggaaggta                                            20

<210> SEQ ID NO 723
<211> LENGTH: 20
<212> TYPE: DNA
<213> ORGANISM: homo sapiens

<400> SEQUENCE: 723
atgttgccct accttccagg                                            20

<210> SEQ ID NO 724
<211> LENGTH: 20
<212> TYPE: DNA
<213> ORGANISM: homo sapiens
```

```
-continued

<400> SEQUENCE: 724
ctgatgttgc cctaccttcc                                              20

<210> SEQ ID NO 725
<211> LENGTH: 20
<212> TYPE: DNA
<213> ORGANISM: homo sapiens

<400> SEQUENCE: 725
gtctcaggtc ttgcactgca                                              20

<210> SEQ ID NO 726
<211> LENGTH: 20
<212> TYPE: DNA
<213> ORGANISM: homo sapiens

<400> SEQUENCE: 726
tctcaggtct tgcactgcac                                              20

<210> SEQ ID NO 727
<211> LENGTH: 20
<212> TYPE: DNA
<213> ORGANISM: homo sapiens

<400> SEQUENCE: 727
ggtcttgcac tgcacgggcc                                              20

<210> SEQ ID NO 728
<211> LENGTH: 20
<212> TYPE: DNA
<213> ORGANISM: homo sapiens

<400> SEQUENCE: 728
agttgttgta gactttcacc                                              20

<210> SEQ ID NO 729
<211> LENGTH: 20
<212> TYPE: DNA
<213> ORGANISM: homo sapiens

<400> SEQUENCE: 729
cacacagact attgtgagga                                              20

<210> SEQ ID NO 730
<211> LENGTH: 20
<212> TYPE: DNA
<213> ORGANISM: homo sapiens

<400> SEQUENCE: 730
cctcctcaca atagtctgtg                                              20

<210> SEQ ID NO 731
<211> LENGTH: 20
<212> TYPE: DNA
<213> ORGANISM: homo sapiens

<400> SEQUENCE: 731
ccacacagac tattgtgagg                                              20

<210> SEQ ID NO 732
<211> LENGTH: 20
<212> TYPE: DNA
```

-continued

<213> ORGANISM: homo sapiens

<400> SEQUENCE: 732
tagccacaca gactattgtg                                           20

<210> SEQ ID NO 733
<211> LENGTH: 20
<212> TYPE: DNA
<213> ORGANISM: homo sapiens

<400> SEQUENCE: 733
caatagtctg tgtggctaca                                           20

<210> SEQ ID NO 734
<211> LENGTH: 20
<212> TYPE: DNA
<213> ORGANISM: homo sapiens

<400> SEQUENCE: 734
atgatgaggc aggacagcag                                           20

<210> SEQ ID NO 735
<211> LENGTH: 20
<212> TYPE: DNA
<213> ORGANISM: homo sapiens

<400> SEQUENCE: 735
gatgatgagg caggacagca                                           20

<210> SEQ ID NO 736
<211> LENGTH: 20
<212> TYPE: DNA
<213> ORGANISM: homo sapiens

<400> SEQUENCE: 736
tgatgatgag gcaggacagc                                           20

<210> SEQ ID NO 737
<211> LENGTH: 20
<212> TYPE: DNA
<213> ORGANISM: homo sapiens

<400> SEQUENCE: 737
ttcacacatg atgatgaggc                                           20

<210> SEQ ID NO 738
<211> LENGTH: 20
<212> TYPE: DNA
<213> ORGANISM: homo sapiens

<400> SEQUENCE: 738
ttggttcaca catgatgatg                                           20

<210> SEQ ID NO 739
<211> LENGTH: 20
<212> TYPE: DNA
<213> ORGANISM: homo sapiens

<400> SEQUENCE: 739
atgtgggatg ggtgctggat                                           20

<210> SEQ ID NO 740
<211> LENGTH: 20

```
<212> TYPE: DNA
<213> ORGANISM: homo sapiens

<400> SEQUENCE: 740
aatccagcac ccatcccaca                                                 20

<210> SEQ ID NO 741
<211> LENGTH: 20
<212> TYPE: DNA
<213> ORGANISM: homo sapiens

<400> SEQUENCE: 741
tgtccatgtg ggatgggtgc                                                 20

<210> SEQ ID NO 742
<211> LENGTH: 20
<212> TYPE: DNA
<213> ORGANISM: homo sapiens

<400> SEQUENCE: 742
gggggatgtc catgtgggat                                                 20

<210> SEQ ID NO 743
<211> LENGTH: 20
<212> TYPE: DNA
<213> ORGANISM: homo sapiens

<400> SEQUENCE: 743
agggggatgt ccatgtggga                                                 20

<210> SEQ ID NO 744
<211> LENGTH: 20
<212> TYPE: DNA
<213> ORGANISM: homo sapiens

<400> SEQUENCE: 744
atcccacatg gacatccccc                                                 20

<210> SEQ ID NO 745
<211> LENGTH: 20
<212> TYPE: DNA
<213> ORGANISM: homo sapiens

<400> SEQUENCE: 745
atccaggggg atgtccatgt                                                 20

<210> SEQ ID NO 746
<211> LENGTH: 20
<212> TYPE: DNA
<213> ORGANISM: homo sapiens

<400> SEQUENCE: 746
tatccagggg gatgtccatg                                                 20

<210> SEQ ID NO 747
<211> LENGTH: 20
<212> TYPE: DNA
<213> ORGANISM: homo sapiens

<400> SEQUENCE: 747
ggaaggtctt gctatccagg                                                 20

<210> SEQ ID NO 748
```

```
<211> LENGTH: 20
<212> TYPE: DNA
<213> ORGANISM: homo sapiens

<400> SEQUENCE: 748
aggaaggtct tgctatccag                                               20

<210> SEQ ID NO 749
<211> LENGTH: 20
<212> TYPE: DNA
<213> ORGANISM: homo sapiens

<400> SEQUENCE: 749
caggaaggtc ttgctatcca                                               20

<210> SEQ ID NO 750
<211> LENGTH: 20
<212> TYPE: DNA
<213> ORGANISM: homo sapiens

<400> SEQUENCE: 750
tcaggaaggt cttgctatcc                                               20

<210> SEQ ID NO 751
<211> LENGTH: 20
<212> TYPE: DNA
<213> ORGANISM: homo sapiens

<400> SEQUENCE: 751
catgctgtgg cggctcagga                                               20

<210> SEQ ID NO 752
<211> LENGTH: 20
<212> TYPE: DNA
<213> ORGANISM: homo sapiens

<400> SEQUENCE: 752
cttcctgagc cgccacagca                                               20

<210> SEQ ID NO 753
<211> LENGTH: 20
<212> TYPE: DNA
<213> ORGANISM: homo sapiens

<400> SEQUENCE: 753
tgtccatgct gtggcggctc                                               20

<210> SEQ ID NO 754
<211> LENGTH: 20
<212> TYPE: DNA
<213> ORGANISM: homo sapiens

<400> SEQUENCE: 754
acttcatgtc catgctgtgg                                               20

<210> SEQ ID NO 755
<211> LENGTH: 20
<212> TYPE: DNA
<213> ORGANISM: homo sapiens

<400> SEQUENCE: 755
tgaacttcat gtccatgctg                                               20
```

```
<210> SEQ ID NO 756
<211> LENGTH: 20
<212> TYPE: DNA
<213> ORGANISM: homo sapiens

<400> SEQUENCE: 756
agttcaccta ctgtgatgac                                              20

<210> SEQ ID NO 757
<211> LENGTH: 20
<212> TYPE: DNA
<213> ORGANISM: homo sapiens

<400> SEQUENCE: 757
cacctactgt gatgacaggt                                              20

<210> SEQ ID NO 758
<211> LENGTH: 20
<212> TYPE: DNA
<213> ORGANISM: homo sapiens

<400> SEQUENCE: 758
acctactgtg atgacaggta                                              20

<210> SEQ ID NO 759
<211> LENGTH: 20
<212> TYPE: DNA
<213> ORGANISM: homo sapiens

<400> SEQUENCE: 759
cccctacctg tcatcacagt                                              20

<210> SEQ ID NO 760
<211> LENGTH: 20
<212> TYPE: DNA
<213> ORGANISM: homo sapiens

<400> SEQUENCE: 760
ctcagaatca cagaactgat                                              20

<210> SEQ ID NO 761
<211> LENGTH: 20
<212> TYPE: DNA
<213> ORGANISM: homo sapiens

<400> SEQUENCE: 761
actgattggt taccaccctg                                              20

<210> SEQ ID NO 762
<211> LENGTH: 20
<212> TYPE: DNA
<213> ORGANISM: homo sapiens

<400> SEQUENCE: 762
taccaccctg aggagctgct                                              20

<210> SEQ ID NO 763
<211> LENGTH: 20
<212> TYPE: DNA
<213> ORGANISM: homo sapiens

<400> SEQUENCE: 763
ggccaagcag ctcctcaggg                                              20
```

```
<210> SEQ ID NO 764
<211> LENGTH: 20
<212> TYPE: DNA
<213> ORGANISM: homo sapiens

<400> SEQUENCE: 764
agcggccaag cagctcctca                                               20

<210> SEQ ID NO 765
<211> LENGTH: 20
<212> TYPE: DNA
<213> ORGANISM: homo sapiens

<400> SEQUENCE: 765
gagcggccaa gcagctcctc                                               20

<210> SEQ ID NO 766
<211> LENGTH: 20
<212> TYPE: DNA
<213> ORGANISM: homo sapiens

<400> SEQUENCE: 766
ggtagaattc ataggctgag                                               20

<210> SEQ ID NO 767
<211> LENGTH: 20
<212> TYPE: DNA
<213> ORGANISM: homo sapiens

<400> SEQUENCE: 767
tagcgcatgg tagaattcat                                               20

<210> SEQ ID NO 768
<211> LENGTH: 20
<212> TYPE: DNA
<213> ORGANISM: homo sapiens

<400> SEQUENCE: 768
tgttctcgga gtctagcgca                                               20

<210> SEQ ID NO 769
<211> LENGTH: 20
<212> TYPE: DNA
<213> ORGANISM: homo sapiens

<400> SEQUENCE: 769
gtgactcttg gtcatgttct                                               20

<210> SEQ ID NO 770
<211> LENGTH: 20
<212> TYPE: DNA
<213> ORGANISM: homo sapiens

<400> SEQUENCE: 770
ctcacagttc tggtgactct                                               20

<210> SEQ ID NO 771
<211> LENGTH: 20
<212> TYPE: DNA
<213> ORGANISM: homo sapiens

<400> SEQUENCE: 771
actcctggaa ctcacagttc                                               20
```

<210> SEQ ID NO 772
<211> LENGTH: 20
<212> TYPE: DNA
<213> ORGANISM: homo sapiens

<400> SEQUENCE: 772 tcctcccta gtgtgcacca                                         20

<210> SEQ ID NO 773
<211> LENGTH: 20
<212> TYPE: DNA
<213> ORGANISM: homo sapiens

<400> SEQUENCE: 773
cctcccctag tgtgcaccaa                                        20

<210> SEQ ID NO 774
<211> LENGTH: 20
<212> TYPE: DNA
<213> ORGANISM: homo sapiens

<400> SEQUENCE: 774
ctgacccttg gtgcacacta                                        20

<210> SEQ ID NO 775
<211> LENGTH: 20
<212> TYPE: DNA
<213> ORGANISM: homo sapiens

<400> SEQUENCE: 775
cctagtgtgc accaagggtc                                        20

<210> SEQ ID NO 776
<211> LENGTH: 20
<212> TYPE: DNA
<213> ORGANISM: homo sapiens

<400> SEQUENCE: 776
cctgaccctt ggtgcacact                                        20

<210> SEQ ID NO 777
<211> LENGTH: 20
<212> TYPE: DNA
<213> ORGANISM: homo sapiens

<400> SEQUENCE: 777
accaagggtc aggtagtaag                                        20

<210> SEQ ID NO 778
<211> LENGTH: 20
<212> TYPE: DNA
<213> ORGANISM: homo sapiens

<400> SEQUENCE: 778
gccacttact acctgaccct                                        20

<210> SEQ ID NO 779
<211> LENGTH: 20
<212> TYPE: DNA
<213> ORGANISM: homo sapiens

<400> SEQUENCE: 779
aggtagtaag tggccagtac                                          20

<210> SEQ ID NO 780
<211> LENGTH: 20
<212> TYPE: DNA
<213> ORGANISM: homo sapiens

<400> SEQUENCE: 780
gctttgcgag catccggtac                                          20

<210> SEQ ID NO 781
<211> LENGTH: 20
<212> TYPE: DNA
<213> ORGANISM: homo sapiens

<400> SEQUENCE: 781
taccggatgc tcgcaaagca                                          20

<210> SEQ ID NO 782
<211> LENGTH: 20
<212> TYPE: DNA
<213> ORGANISM: homo sapiens

<400> SEQUENCE: 782
accggatgct cgcaaagcat                                          20

<210> SEQ ID NO 783
<211> LENGTH: 20
<212> TYPE: DNA
<213> ORGANISM: homo sapiens

<400> SEQUENCE: 783
ccggatgctc gcaaagcatg                                          20

<210> SEQ ID NO 784
<211> LENGTH: 20
<212> TYPE: DNA
<213> ORGANISM: homo sapiens

<400> SEQUENCE: 784
ccccatgctt tgcgagcatc                                          20

<210> SEQ ID NO 785
<211> LENGTH: 20
<212> TYPE: DNA
<213> ORGANISM: homo sapiens

<400> SEQUENCE: 785
cggatgctcg caaagcatgg                                          20

<210> SEQ ID NO 786
<211> LENGTH: 20
<212> TYPE: DNA
<213> ORGANISM: homo sapiens

<400> SEQUENCE: 786
caaagcatgg gggctacgtg                                          20

<210> SEQ ID NO 787
<211> LENGTH: 20
<212> TYPE: DNA
<213> ORGANISM: homo sapiens

<400> SEQUENCE: 787

| | |
|---|---|
| gcatggggc tacgtgtggc | 20 |

<210> SEQ ID NO 788
<211> LENGTH: 20
<212> TYPE: DNA
<213> ORGANISM: homo sapiens

<400> SEQUENCE: 788

| | |
|---|---|
| ctacgtgtgg ctggagaccc | 20 |

<210> SEQ ID NO 789
<211> LENGTH: 20
<212> TYPE: DNA
<213> ORGANISM: homo sapiens

<400> SEQUENCE: 789

| | |
|---|---|
| tacgtgtggc tggagaccca | 20 |

<210> SEQ ID NO 790
<211> LENGTH: 20
<212> TYPE: DNA
<213> ORGANISM: homo sapiens

<400> SEQUENCE: 790

| | |
|---|---|
| acgtgtggct ggagacccag | 20 |

<210> SEQ ID NO 791
<211> LENGTH: 20
<212> TYPE: DNA
<213> ORGANISM: homo sapiens

<400> SEQUENCE: 791

| | |
|---|---|
| gtggctggag acccagggga | 20 |

<210> SEQ ID NO 792
<211> LENGTH: 20
<212> TYPE: DNA
<213> ORGANISM: homo sapiens

<400> SEQUENCE: 792

| | |
|---|---|
| gttgtagatg accgtcccct | 20 |

<210> SEQ ID NO 793
<211> LENGTH: 20
<212> TYPE: DNA
<213> ORGANISM: homo sapiens

<400> SEQUENCE: 793

| | |
|---|---|
| ggttgtagat gaccgtcccc | 20 |

<210> SEQ ID NO 794
<211> LENGTH: 20
<212> TYPE: DNA
<213> ORGANISM: homo sapiens

<400> SEQUENCE: 794

| | |
|---|---|
| actggggctg caggttgcga | 20 |

<210> SEQ ID NO 795
<211> LENGTH: 20
<212> TYPE: DNA
<213> ORGANISM: homo sapiens

<400> SEQUENCE: 795
cactggggct gcaggttgcg    20

<210> SEQ ID NO 796
<211> LENGTH: 20
<212> TYPE: DNA
<213> ORGANISM: homo sapiens

<400> SEQUENCE: 796
acatgatgca ctggggctgc    20

<210> SEQ ID NO 797
<211> LENGTH: 20
<212> TYPE: DNA
<213> ORGANISM: homo sapiens

<400> SEQUENCE: 797
ttgacacaca tgatgcactg    20

<210> SEQ ID NO 798
<211> LENGTH: 20
<212> TYPE: DNA
<213> ORGANISM: homo sapiens

<400> SEQUENCE: 798
gttgacacac atgatgcact    20

<210> SEQ ID NO 799
<211> LENGTH: 20
<212> TYPE: DNA
<213> ORGANISM: homo sapiens

<400> SEQUENCE: 799
agttgacaca catgatgcac    20

<210> SEQ ID NO 800
<211> LENGTH: 20
<212> TYPE: DNA
<213> ORGANISM: homo sapiens

<400> SEQUENCE: 800
tgtgtgtcaa ctacgtcctg    20

<210> SEQ ID NO 801
<211> LENGTH: 20
<212> TYPE: DNA
<213> ORGANISM: homo sapiens

<400> SEQUENCE: 801
agccctcaca tgcttacctc    20

<210> SEQ ID NO 802
<211> LENGTH: 20
<212> TYPE: DNA
<213> ORGANISM: homo sapiens

<400> SEQUENCE: 802
tgagattgag aagaatgacg    20

<210> SEQ ID NO 803
<211> LENGTH: 20
<212> TYPE: DNA
<213> ORGANISM: homo sapiens

```
<400> SEQUENCE: 803
gaatgacgtg gtgttctcca                                              20

<210> SEQ ID NO 804
<211> LENGTH: 20
<212> TYPE: DNA
<213> ORGANISM: homo sapiens

<400> SEQUENCE: 804
cagggattca gtctggtcca                                              20

<210> SEQ ID NO 805
<211> LENGTH: 20
<212> TYPE: DNA
<213> ORGANISM: homo sapiens

<400> SEQUENCE: 805
gcttgaacag ggattcagtc                                              20

<210> SEQ ID NO 806
<211> LENGTH: 20
<212> TYPE: DNA
<213> ORGANISM: homo sapiens

<400> SEQUENCE: 806
catcaggtgg ggcttgaaca                                              20

<210> SEQ ID NO 807
<211> LENGTH: 20
<212> TYPE: DNA
<213> ORGANISM: homo sapiens

<400> SEQUENCE: 807
cctgttcaag ccccacctga                                              20

<210> SEQ ID NO 808
<211> LENGTH: 20
<212> TYPE: DNA
<213> ORGANISM: homo sapiens

<400> SEQUENCE: 808
ccatcaggtg gggcttgaac                                              20

<210> SEQ ID NO 809
<211> LENGTH: 20
<212> TYPE: DNA
<213> ORGANISM: homo sapiens

<400> SEQUENCE: 809
ctgttcatgg ccatcaggtg                                              20

<210> SEQ ID NO 810
<211> LENGTH: 20
<212> TYPE: DNA
<213> ORGANISM: homo sapiens

<400> SEQUENCE: 810
gctgttcatg gccatcaggt                                              20

<210> SEQ ID NO 811
<211> LENGTH: 20
<212> TYPE: DNA
```

```
<213> ORGANISM: homo sapiens

<400> SEQUENCE: 811
tgctgttcat ggccatcagg                                           20

<210> SEQ ID NO 812
<211> LENGTH: 20
<212> TYPE: DNA
<213> ORGANISM: homo sapiens

<400> SEQUENCE: 812
agatgctgtt catggccatc                                           20

<210> SEQ ID NO 813
<211> LENGTH: 20
<212> TYPE: DNA
<213> ORGANISM: homo sapiens

<400> SEQUENCE: 813
gctatcaaag atgctgttca                                           20

<210> SEQ ID NO 814
<211> LENGTH: 20
<212> TYPE: DNA
<213> ORGANISM: homo sapiens

<400> SEQUENCE: 814
aacagcatct ttgatagcag                                           20

<210> SEQ ID NO 815
<211> LENGTH: 20
<212> TYPE: DNA
<213> ORGANISM: homo sapiens

<400> SEQUENCE: 815
catctttgat agcagtggca                                           20

<210> SEQ ID NO 816
<211> LENGTH: 20
<212> TYPE: DNA
<213> ORGANISM: homo sapiens

<400> SEQUENCE: 816
atctttgata gcagtggcaa                                           20

<210> SEQ ID NO 817
<211> LENGTH: 20
<212> TYPE: DNA
<213> ORGANISM: homo sapiens

<400> SEQUENCE: 817
tctttgatag cagtggcaag                                           20

<210> SEQ ID NO 818
<211> LENGTH: 20
<212> TYPE: DNA
<213> ORGANISM: homo sapiens

<400> SEQUENCE: 818
ctttgatagc agtggcaagg                                           20

<210> SEQ ID NO 819
<211> LENGTH: 20
```

```
<212> TYPE: DNA
<213> ORGANISM: homo sapiens

<400> SEQUENCE: 819
cttcctattc accaagctaa                                         20

<210> SEQ ID NO 820
<211> LENGTH: 20
<212> TYPE: DNA
<213> ORGANISM: homo sapiens

<400> SEQUENCE: 820
cctattcacc aagctaaagg                                         20

<210> SEQ ID NO 821
<211> LENGTH: 20
<212> TYPE: DNA
<213> ORGANISM: homo sapiens

<400> SEQUENCE: 821
cctcctttag cttggtgaat                                         20

<210> SEQ ID NO 822
<211> LENGTH: 20
<212> TYPE: DNA
<213> ORGANISM: homo sapiens

<400> SEQUENCE: 822
ctcgggctcc tcctttagct                                         20

<210> SEQ ID NO 823
<211> LENGTH: 20
<212> TYPE: DNA
<213> ORGANISM: homo sapiens

<400> SEQUENCE: 823
caagctaaag gaggagcccg                                         20

<210> SEQ ID NO 824
<211> LENGTH: 20
<212> TYPE: DNA
<213> ORGANISM: homo sapiens

<400> SEQUENCE: 824
aaaggaggag cccgaggagc                                         20

<210> SEQ ID NO 825
<211> LENGTH: 20
<212> TYPE: DNA
<213> ORGANISM: homo sapiens

<400> SEQUENCE: 825
gcccgaggag ctggcccagc                                         20

<210> SEQ ID NO 826
<211> LENGTH: 20
<212> TYPE: DNA
<213> ORGANISM: homo sapiens

<400> SEQUENCE: 826
gccagctggg ccagctcctc                                         20

<210> SEQ ID NO 827
```

```
<211> LENGTH: 20
<212> TYPE: DNA
<213> ORGANISM: homo sapiens

<400> SEQUENCE: 827
agccagctgg gccagctcct                                               20

<210> SEQ ID NO 828
<211> LENGTH: 20
<212> TYPE: DNA
<213> ORGANISM: homo sapiens

<400> SEQUENCE: 828
gcccagctgg ctcccacccc                                               20

<210> SEQ ID NO 829
<211> LENGTH: 20
<212> TYPE: DNA
<213> ORGANISM: homo sapiens

<400> SEQUENCE: 829
tcctggggtg ggagccagct                                               20

<210> SEQ ID NO 830
<211> LENGTH: 20
<212> TYPE: DNA
<213> ORGANISM: homo sapiens

<400> SEQUENCE: 830
ctcctggggt gggagccagc                                               20

<210> SEQ ID NO 831
<211> LENGTH: 20
<212> TYPE: DNA
<213> ORGANISM: homo sapiens

<400> SEQUENCE: 831
atgatggcgt ctcctggggt                                               20

<210> SEQ ID NO 832
<211> LENGTH: 20
<212> TYPE: DNA
<213> ORGANISM: homo sapiens

<400> SEQUENCE: 832
gatgatggcg tctcctgggg                                               20

<210> SEQ ID NO 833
<211> LENGTH: 20
<212> TYPE: DNA
<213> ORGANISM: homo sapiens

<400> SEQUENCE: 833
agagatgatg gcgtctcctg                                               20

<210> SEQ ID NO 834
<211> LENGTH: 20
<212> TYPE: DNA
<213> ORGANISM: homo sapiens

<400> SEQUENCE: 834
gagagatgat ggcgtctcct                                               20
```

```
<210> SEQ ID NO 835
<211> LENGTH: 20
<212> TYPE: DNA
<213> ORGANISM: homo sapiens

<400> SEQUENCE: 835
agagagatga tggcgtctcc                                              20

<210> SEQ ID NO 836
<211> LENGTH: 20
<212> TYPE: DNA
<213> ORGANISM: homo sapiens

<400> SEQUENCE: 836
aggagacgcc atcatctctc                                              20

<210> SEQ ID NO 837
<211> LENGTH: 20
<212> TYPE: DNA
<213> ORGANISM: homo sapiens

<400> SEQUENCE: 837
gccatcatct ctctggattt                                              20

<210> SEQ ID NO 838
<211> LENGTH: 20
<212> TYPE: DNA
<213> ORGANISM: homo sapiens

<400> SEQUENCE: 838
accgaaatcc agagagatga                                              20

<210> SEQ ID NO 839
<211> LENGTH: 20
<212> TYPE: DNA
<213> ORGANISM: homo sapiens

<400> SEQUENCE: 839
atcatctctc tggatttcgg                                              20

<210> SEQ ID NO 840
<211> LENGTH: 20
<212> TYPE: DNA
<213> ORGANISM: homo sapiens

<400> SEQUENCE: 840
tcatctctct ggatttcggt                                              20

<210> SEQ ID NO 841
<211> LENGTH: 20
<212> TYPE: DNA
<213> ORGANISM: homo sapiens

<400> SEQUENCE: 841
ctcgaagttc tgattccctg                                              20

<210> SEQ ID NO 842
<211> LENGTH: 20
<212> TYPE: DNA
<213> ORGANISM: homo sapiens

<400> SEQUENCE: 842
cacagggaat cagaacttcg                                              20
```

```
<210> SEQ ID NO 843
<211> LENGTH: 20
<212> TYPE: DNA
<213> ORGANISM: homo sapiens

<400> SEQUENCE: 843
ttcgaggagt cctcagccta                                            20

<210> SEQ ID NO 844
<211> LENGTH: 20
<212> TYPE: DNA
<213> ORGANISM: homo sapiens

<400> SEQUENCE: 844
ggagtcctca gcctatggca                                            20

<210> SEQ ID NO 845
<211> LENGTH: 20
<212> TYPE: DNA
<213> ORGANISM: homo sapiens

<400> SEQUENCE: 845
gatggccttg ccataggctg                                            20

<210> SEQ ID NO 846
<211> LENGTH: 20
<212> TYPE: DNA
<213> ORGANISM: homo sapiens

<400> SEQUENCE: 846
gggcaggatg gccttgccat                                            20

<210> SEQ ID NO 847
<211> LENGTH: 20
<212> TYPE: DNA
<213> ORGANISM: homo sapiens

<400> SEQUENCE: 847
tggctggctc gggggcagga                                            20

<210> SEQ ID NO 848
<211> LENGTH: 20
<212> TYPE: DNA
<213> ORGANISM: homo sapiens

<400> SEQUENCE: 848
tcctgccccc gagccagcca                                            20

<210> SEQ ID NO 849
<211> LENGTH: 20
<212> TYPE: DNA
<213> ORGANISM: homo sapiens

<400> SEQUENCE: 849 cctgccccccg agccagccat                                           20

<210> SEQ ID NO 850
<211> LENGTH: 20
<212> TYPE: DNA
<213> ORGANISM: homo sapiens

<400> SEQUENCE: 850
cccatggctg gctcggggggc                                           20
```

<210> SEQ ID NO 851
<211> LENGTH: 20
<212> TYPE: DNA
<213> ORGANISM: homo sapiens

<400> SEQUENCE: 851
gtggcccatg gctggctcgg                                               20

<210> SEQ ID NO 852
<211> LENGTH: 20
<212> TYPE: DNA
<213> ORGANISM: homo sapiens

<400> SEQUENCE: 852
cgtggcccat ggctggctcg                                               20

<210> SEQ ID NO 853
<211> LENGTH: 20
<212> TYPE: DNA
<213> ORGANISM: homo sapiens

<400> SEQUENCE: 853
cccgagccag ccatgggcca                                               20

<210> SEQ ID NO 854
<211> LENGTH: 20
<212> TYPE: DNA
<213> ORGANISM: homo sapiens

<400> SEQUENCE: 854
ccgtggccca tggctggctc                                               20

<210> SEQ ID NO 855
<211> LENGTH: 20
<212> TYPE: DNA
<213> ORGANISM: homo sapiens

<400> SEQUENCE: 855
tccgtggccc atggctggct                                               20

<210> SEQ ID NO 856
<211> LENGTH: 20
<212> TYPE: DNA
<213> ORGANISM: homo sapiens

<400> SEQUENCE: 856
tcaactccgt ggcccatggc                                               20

<210> SEQ ID NO 857
<211> LENGTH: 20
<212> TYPE: DNA
<213> ORGANISM: homo sapiens

<400> SEQUENCE: 857
agccatgggc cacggagttg                                               20

<210> SEQ ID NO 858
<211> LENGTH: 20
<212> TYPE: DNA
<213> ORGANISM: homo sapiens

<400> SEQUENCE: 858
ctcctcaact ccgtggccca                     20

<210> SEQ ID NO 859
<211> LENGTH: 20
<212> TYPE: DNA
<213> ORGANISM: homo sapiens

<400> SEQUENCE: 859
gctgtggctc ctcaactccg                     20

<210> SEQ ID NO 860
<211> LENGTH: 20
<212> TYPE: DNA
<213> ORGANISM: homo sapiens

<400> SEQUENCE: 860
gagccacagc acccagagcg                     20

<210> SEQ ID NO 861
<211> LENGTH: 20
<212> TYPE: DNA
<213> ORGANISM: homo sapiens

<400> SEQUENCE: 861
cagcctcgct ctgggtgctg                     20

<210> SEQ ID NO 862
<211> LENGTH: 20
<212> TYPE: DNA
<213> ORGANISM: homo sapiens

<400> SEQUENCE: 862
cacagcaccc agagcgaggc                     20

<210> SEQ ID NO 863
<211> LENGTH: 20
<212> TYPE: DNA
<213> ORGANISM: homo sapiens

<400> SEQUENCE: 863
acagcaccca gagcgaggct                     20

<210> SEQ ID NO 864
<211> LENGTH: 20
<212> TYPE: DNA
<213> ORGANISM: homo sapiens

<400> SEQUENCE: 864
caggctccca gcctcgctct                     20

<210> SEQ ID NO 865
<211> LENGTH: 20
<212> TYPE: DNA
<213> ORGANISM: homo sapiens

<400> SEQUENCE: 865
gcaggctccc agcctcgctc                     20

<210> SEQ ID NO 866
<211> LENGTH: 20
<212> TYPE: DNA
<213> ORGANISM: homo sapiens

<400> SEQUENCE: 866

```
ggggcacggt gaaggcaggc                                          20

<210> SEQ ID NO 867
<211> LENGTH: 20
<212> TYPE: DNA
<213> ORGANISM: homo sapiens

<400> SEQUENCE: 867
gcctgccttc accgtgcccc                                          20

<210> SEQ ID NO 868
<211> LENGTH: 20
<212> TYPE: DNA
<213> ORGANISM: homo sapiens

<400> SEQUENCE: 868
gcctggggca cggtgaaggc                                          20

<210> SEQ ID NO 869
<211> LENGTH: 20
<212> TYPE: DNA
<213> ORGANISM: homo sapiens

<400> SEQUENCE: 869
agctgcctgg ggcacggtga                                          20

<210> SEQ ID NO 870
<211> LENGTH: 20
<212> TYPE: DNA
<213> ORGANISM: homo sapiens

<400> SEQUENCE: 870
cggggcagct gcctggggca                                          20

<210> SEQ ID NO 871
<211> LENGTH: 20
<212> TYPE: DNA
<213> ORGANISM: homo sapiens

<400> SEQUENCE: 871
cgtgccccag gcagctgccc                                          20

<210> SEQ ID NO 872
<211> LENGTH: 20
<212> TYPE: DNA
<213> ORGANISM: homo sapiens

<400> SEQUENCE: 872
gtgccccagg cagctgcccc                                          20

<210> SEQ ID NO 873
<211> LENGTH: 20
<212> TYPE: DNA
<213> ORGANISM: homo sapiens

<400> SEQUENCE: 873
ctgcccgggg cagctgcctg                                          20

<210> SEQ ID NO 874
<211> LENGTH: 20
<212> TYPE: DNA
<213> ORGANISM: homo sapiens
```

-continued

```
<400> SEQUENCE: 874
gctgcccggg gcagctgcct                                              20

<210> SEQ ID NO 875
<211> LENGTH: 20
<212> TYPE: DNA
<213> ORGANISM: homo sapiens

<400> SEQUENCE: 875
tgctgcccgg ggcagctgcc                                              20

<210> SEQ ID NO 876
<211> LENGTH: 20
<212> TYPE: DNA
<213> ORGANISM: homo sapiens

<400> SEQUENCE: 876 actggggtg gtgctgcccg                                               20

<210> SEQ ID NO 877
<211> LENGTH: 20
<212> TYPE: DNA
<213> ORGANISM: homo sapiens

<400> SEQUENCE: 877 cactggggt ggtgctgccc                                               20

<210> SEQ ID NO 878
<211> LENGTH: 20
<212> TYPE: DNA
<213> ORGANISM: homo sapiens

<400> SEQUENCE: 878 gcactgggg tggtgctgcc                                               20

<210> SEQ ID NO 879
<211> LENGTH: 20
<212> TYPE: DNA
<213> ORGANISM: homo sapiens

<400> SEQUENCE: 879
gctgctggtg gcactggggg                                              20

<210> SEQ ID NO 880
<211> LENGTH: 20
<212> TYPE: DNA
<213> ORGANISM: homo sapiens

<400> SEQUENCE: 880
gctgctgctg gtggcactgg                                              20

<210> SEQ ID NO 881
<211> LENGTH: 20
<212> TYPE: DNA
<213> ORGANISM: homo sapiens

<400> SEQUENCE: 881
tgctgctgct ggtggcactg                                              20

<210> SEQ ID NO 882
<211> LENGTH: 20
<212> TYPE: DNA
<213> ORGANISM: homo sapiens
```

```
<400> SEQUENCE: 882
ctgctgctgc tggtggcact                                          20

<210> SEQ ID NO 883
<211> LENGTH: 20
<212> TYPE: DNA
<213> ORGANISM: homo sapiens

<400> SEQUENCE: 883
gctgctgctg ctggtggcac                                          20

<210> SEQ ID NO 884
<211> LENGTH: 20
<212> TYPE: DNA
<213> ORGANISM: homo sapiens

<400> SEQUENCE: 884
gcagctgctg ctgctgctgg                                          20

<210> SEQ ID NO 885
<211> LENGTH: 20
<212> TYPE: DNA
<213> ORGANISM: homo sapiens

<400> SEQUENCE: 885
cagcagcagc agctgctcca                                          20

<210> SEQ ID NO 886
<211> LENGTH: 20
<212> TYPE: DNA
<213> ORGANISM: homo sapiens

<400> SEQUENCE: 886
tcttcagggc tattgggcta                                          20

<210> SEQ ID NO 887
<211> LENGTH: 20
<212> TYPE: DNA
<213> ORGANISM: homo sapiens

<400> SEQUENCE: 887
gtcttcaggg ctattgggct                                          20

<210> SEQ ID NO 888
<211> LENGTH: 20
<212> TYPE: DNA
<213> ORGANISM: homo sapiens

<400> SEQUENCE: 888
taatagtctt cagggctatt                                          20

<210> SEQ ID NO 889
<211> LENGTH: 20
<212> TYPE: DNA
<213> ORGANISM: homo sapiens

<400> SEQUENCE: 889
gtaatagtct tcagggctat                                          20

<210> SEQ ID NO 890
<211> LENGTH: 20
<212> TYPE: DNA
```

```
<213> ORGANISM: homo sapiens

<400> SEQUENCE: 890
aagatgtgta atagtcttca                                          20

<210> SEQ ID NO 891
<211> LENGTH: 20
<212> TYPE: DNA
<213> ORGANISM: homo sapiens

<400> SEQUENCE: 891
aaagatgtgt aatagtcttc                                          20

<210> SEQ ID NO 892
<211> LENGTH: 20
<212> TYPE: DNA
<213> ORGANISM: homo sapiens

<400> SEQUENCE: 892
tgaagactat tacacatctt                                          20

<210> SEQ ID NO 893
<211> LENGTH: 20
<212> TYPE: DNA
<213> ORGANISM: homo sapiens

<400> SEQUENCE: 893
tctcaatcac ttcaatcttc                                          20

<210> SEQ ID NO 894
<211> LENGTH: 20
<212> TYPE: DNA
<213> ORGANISM: homo sapiens

<400> SEQUENCE: 894
gattgagaag ctcttcgcca                                          20

<210> SEQ ID NO 895
<211> LENGTH: 20
<212> TYPE: DNA
<213> ORGANISM: homo sapiens

<400> SEQUENCE: 895
gctcttcgcc atggacacag                                          20

<210> SEQ ID NO 896
<211> LENGTH: 20
<212> TYPE: DNA
<213> ORGANISM: homo sapiens

<400> SEQUENCE: 896
cgccatggac acagaggcca                                          20

<210> SEQ ID NO 897
<211> LENGTH: 20
<212> TYPE: DNA
<213> ORGANISM: homo sapiens

<400> SEQUENCE: 897
gtccttggcc tctgtgtcca                                          20

<210> SEQ ID NO 898
<211> LENGTH: 20
```

```
<212> TYPE: DNA
<213> ORGANISM: homo sapiens

<400> SEQUENCE: 898
ctgggtactg cattggtcct                                           20

<210> SEQ ID NO 899
<211> LENGTH: 20
<212> TYPE: DNA
<213> ORGANISM: homo sapiens

<400> SEQUENCE: 899
caaggaccaa tgcagtaccc                                           20

<210> SEQ ID NO 900
<211> LENGTH: 20
<212> TYPE: DNA
<213> ORGANISM: homo sapiens

<400> SEQUENCE: 900
catctacctg ggtactgcat                                           20

<210> SEQ ID NO 901
<211> LENGTH: 20
<212> TYPE: DNA
<213> ORGANISM: homo sapiens

<400> SEQUENCE: 901
agctcattga aatccgtctg                                           20

<210> SEQ ID NO 902
<211> LENGTH: 20
<212> TYPE: DNA
<213> ORGANISM: homo sapiens

<400> SEQUENCE: 902
tcagacggat ttcaatgagc                                           20

<210> SEQ ID NO 903
<211> LENGTH: 20
<212> TYPE: DNA
<213> ORGANISM: homo sapiens

<400> SEQUENCE: 903
ggatttcaat gagctggact                                           20

<210> SEQ ID NO 904
<211> LENGTH: 20
<212> TYPE: DNA
<213> ORGANISM: homo sapiens

<400> SEQUENCE: 904
tgagctggac ttggagacac                                           20

<210> SEQ ID NO 905
<211> LENGTH: 20
<212> TYPE: DNA
<213> ORGANISM: homo sapiens

<400> SEQUENCE: 905
actggcaccc tatatcccca                                           20

<210> SEQ ID NO 906
```

```
<211> LENGTH: 20
<212> TYPE: DNA
<213> ORGANISM: homo sapiens

<400> SEQUENCE: 906
gcaccctata tccccatgga                                                   20

<210> SEQ ID NO 907
<211> LENGTH: 20
<212> TYPE: DNA
<213> ORGANISM: homo sapiens

<400> SEQUENCE: 907
caccctatat ccccatggac                                                   20

<210> SEQ ID NO 908
<211> LENGTH: 20
<212> TYPE: DNA
<213> ORGANISM: homo sapiens

<400> SEQUENCE: 908
accctatatc cccatggacg                                                   20

<210> SEQ ID NO 909
<211> LENGTH: 20
<212> TYPE: DNA
<213> ORGANISM: homo sapiens

<400> SEQUENCE: 909
tccccgtcca tggggatata                                                   20

<210> SEQ ID NO 910
<211> LENGTH: 20
<212> TYPE: DNA
<213> ORGANISM: homo sapiens

<400> SEQUENCE: 910
ttccccgtcc atggggatat                                                   20

<210> SEQ ID NO 911
<211> LENGTH: 20
<212> TYPE: DNA
<213> ORGANISM: homo sapiens

<400> SEQUENCE: 911
ggaagtcttc cccgtccatg                                                   20

<210> SEQ ID NO 912
<211> LENGTH: 20
<212> TYPE: DNA
<213> ORGANISM: homo sapiens

<400> SEQUENCE: 912
tggaagtctt ccccgtccat                                                   20

<210> SEQ ID NO 913
<211> LENGTH: 20
<212> TYPE: DNA
<213> ORGANISM: homo sapiens

<400> SEQUENCE: 913
ctggaagtct tccccgtcca                                                   20
```

```
<210> SEQ ID NO 914
<211> LENGTH: 20
<212> TYPE: DNA
<213> ORGANISM: homo sapiens

<400> SEQUENCE: 914
cggggcagat ggggcttagc                                              20

<210> SEQ ID NO 915
<211> LENGTH: 20
<212> TYPE: DNA
<213> ORGANISM: homo sapiens

<400> SEQUENCE: 915
gctaagcccc atctgccccg                                              20

<210> SEQ ID NO 916
<211> LENGTH: 20
<212> TYPE: DNA
<213> ORGANISM: homo sapiens

<400> SEQUENCE: 916
gccccatctg ccccgaggag                                              20

<210> SEQ ID NO 917
<211> LENGTH: 20
<212> TYPE: DNA
<213> ORGANISM: homo sapiens

<400> SEQUENCE: 917
gccgctcctc ggggcagatg                                              20

<210> SEQ ID NO 918
<211> LENGTH: 20
<212> TYPE: DNA
<213> ORGANISM: homo sapiens

<400> SEQUENCE: 918
agccgctcct cggggcagat                                              20

<210> SEQ ID NO 919
<211> LENGTH: 20
<212> TYPE: DNA
<213> ORGANISM: homo sapiens

<400> SEQUENCE: 919
gagccgctcc tcggggcaga                                              20

<210> SEQ ID NO 920
<211> LENGTH: 20
<212> TYPE: DNA
<213> ORGANISM: homo sapiens

<400> SEQUENCE: 920
ctgccccgag gagcggctct                                              20

<210> SEQ ID NO 921
<211> LENGTH: 20
<212> TYPE: DNA
<213> ORGANISM: homo sapiens

<400> SEQUENCE: 921
ccccgaggag cggctcttgg                                              20
```

<210> SEQ ID NO 922
<211> LENGTH: 20
<212> TYPE: DNA
<213> ORGANISM: homo sapiens

<400> SEQUENCE: 922
ccgccaagag ccgctcctcg                                               20

<210> SEQ ID NO 923
<211> LENGTH: 20
<212> TYPE: DNA
<213> ORGANISM: homo sapiens

<400> SEQUENCE: 923
tccgccaaga gccgctcctc                                               20

<210> SEQ ID NO 924
<211> LENGTH: 20
<212> TYPE: DNA
<213> ORGANISM: homo sapiens

<400> SEQUENCE: 924
ctccgccaag agccgctcct                                               20

<210> SEQ ID NO 925
<211> LENGTH: 20
<212> TYPE: DNA
<213> ORGANISM: homo sapiens

<400> SEQUENCE: 925
agtgctgggg ggtggactgt                                               20

<210> SEQ ID NO 926
<211> LENGTH: 20
<212> TYPE: DNA
<213> ORGANISM: homo sapiens

<400> SEQUENCE: 926
cagtgctggg gggtggactg                                               20

<210> SEQ ID NO 927
<211> LENGTH: 20
<212> TYPE: DNA
<213> ORGANISM: homo sapiens

<400> SEQUENCE: 927
actgaagcag tgctgggggg                                               20

<210> SEQ ID NO 928
<211> LENGTH: 20
<212> TYPE: DNA
<213> ORGANISM: homo sapiens

<400> SEQUENCE: 928
ggcactgaag cagtgctggg                                               20

<210> SEQ ID NO 929
<211> LENGTH: 20
<212> TYPE: DNA
<213> ORGANISM: homo sapiens

<400> SEQUENCE: 929
tggcactgaa gcagtgctgg                                               20

<210> SEQ ID NO 930
<211> LENGTH: 20
<212> TYPE: DNA
<213> ORGANISM: homo sapiens

<400> SEQUENCE: 930
atggcactga agcagtgctg                                               20

<210> SEQ ID NO 931
<211> LENGTH: 20
<212> TYPE: DNA
<213> ORGANISM: homo sapiens

<400> SEQUENCE: 931
catggcactg aagcagtgct                                               20

<210> SEQ ID NO 932
<211> LENGTH: 20
<212> TYPE: DNA
<213> ORGANISM: homo sapiens

<400> SEQUENCE: 932
tcatggcact gaagcagtgc                                               20

<210> SEQ ID NO 933
<211> LENGTH: 20
<212> TYPE: DNA
<213> ORGANISM: homo sapiens

<400> SEQUENCE: 933
tggctggaag atgtttgtca                                               20

<210> SEQ ID NO 934
<211> LENGTH: 20
<212> TYPE: DNA
<213> ORGANISM: homo sapiens

<400> SEQUENCE: 934
gacaaacatc ttccagccac                                               20

<210> SEQ ID NO 935
<211> LENGTH: 20
<212> TYPE: DNA
<213> ORGANISM: homo sapiens

<400> SEQUENCE: 935
gggctacagg ggccagtggc                                               20

<210> SEQ ID NO 936
<211> LENGTH: 20
<212> TYPE: DNA
<213> ORGANISM: homo sapiens

<400> SEQUENCE: 936
tgcggggcta caggggccag                                               20

<210> SEQ ID NO 937
<211> LENGTH: 20
<212> TYPE: DNA
<213> ORGANISM: homo sapiens

<400> SEQUENCE: 937
gggactgtgc ggggctacag                                              20

<210> SEQ ID NO 938
<211> LENGTH: 20
<212> TYPE: DNA
<213> ORGANISM: homo sapiens

<400> SEQUENCE: 938
agggactgtg cggggctaca                                              20

<210> SEQ ID NO 939
<211> LENGTH: 20
<212> TYPE: DNA
<213> ORGANISM: homo sapiens

<400> SEQUENCE: 939
aagggactgt gcggggctac                                              20

<210> SEQ ID NO 940
<211> LENGTH: 20
<212> TYPE: DNA
<213> ORGANISM: homo sapiens

<400> SEQUENCE: 940
caggaggaag ggactgtgcg                                              20

<210> SEQ ID NO 941
<211> LENGTH: 20
<212> TYPE: DNA
<213> ORGANISM: homo sapiens

<400> SEQUENCE: 941
cccgcacagt cccttcctcc                                              20

<210> SEQ ID NO 942
<211> LENGTH: 20
<212> TYPE: DNA
<213> ORGANISM: homo sapiens

<400> SEQUENCE: 942
ccaggaggaa gggactgtgc                                              20

<210> SEQ ID NO 943
<211> LENGTH: 20
<212> TYPE: DNA
<213> ORGANISM: homo sapiens

<400> SEQUENCE: 943
tccaggagga agggactgtg                                              20

<210> SEQ ID NO 944
<211> LENGTH: 20
<212> TYPE: DNA
<213> ORGANISM: homo sapiens

<400> SEQUENCE: 944
tgaaacttgt ccaggaggaa                                              20

<210> SEQ ID NO 945
<211> LENGTH: 20
<212> TYPE: DNA
<213> ORGANISM: homo sapiens

<400> SEQUENCE: 945
ctgaaacttg tccaggagga                                               20

<210> SEQ ID NO 946
<211> LENGTH: 20
<212> TYPE: DNA
<213> ORGANISM: homo sapiens

<400> SEQUENCE: 946
gctgctgaaa cttgtccagg                                               20

<210> SEQ ID NO 947
<211> LENGTH: 20
<212> TYPE: DNA
<213> ORGANISM: homo sapiens

<400> SEQUENCE: 947
gctgctgctg aaacttgtcc                                               20

<210> SEQ ID NO 948
<211> LENGTH: 20
<212> TYPE: DNA
<213> ORGANISM: homo sapiens

<400> SEQUENCE: 948
ggacaagttt cagcagcagc                                               20

<210> SEQ ID NO 949
<211> LENGTH: 20
<212> TYPE: DNA
<213> ORGANISM: homo sapiens

<400> SEQUENCE: 949
agaagacaga gcccgagcac                                               20

<210> SEQ ID NO 950
<211> LENGTH: 20
<212> TYPE: DNA
<213> ORGANISM: homo sapiens

<400> SEQUENCE: 950
gaggacatgg gccggtgctc                                               20

<210> SEQ ID NO 951
<211> LENGTH: 20
<212> TYPE: DNA
<213> ORGANISM: homo sapiens

<400> SEQUENCE: 951
ggaggacatg ggccggtgct                                               20

<210> SEQ ID NO 952
<211> LENGTH: 20
<212> TYPE: DNA
<213> ORGANISM: homo sapiens

<400> SEQUENCE: 952
agaagatgga ggacatgggc                                               20

<210> SEQ ID NO 953
<211> LENGTH: 20
<212> TYPE: DNA
<213> ORGANISM: homo sapiens

<400> SEQUENCE: 953
tcaaagaaga tggaggacat						20

<210> SEQ ID NO 954
<211> LENGTH: 20
<212> TYPE: DNA
<213> ORGANISM: homo sapiens

<400> SEQUENCE: 954
atcaaagaag atggaggaca						20

<210> SEQ ID NO 955
<211> LENGTH: 20
<212> TYPE: DNA
<213> ORGANISM: homo sapiens

<400> SEQUENCE: 955
tcctccatct tctttgatgc						20

<210> SEQ ID NO 956
<211> LENGTH: 20
<212> TYPE: DNA
<213> ORGANISM: homo sapiens

<400> SEQUENCE: 956
tccggcatca aagaagatgg						20

<210> SEQ ID NO 957
<211> LENGTH: 20
<212> TYPE: DNA
<213> ORGANISM: homo sapiens

<400> SEQUENCE: 957
gcttccggca tcaaagaaga						20

<210> SEQ ID NO 958
<211> LENGTH: 20
<212> TYPE: DNA
<213> ORGANISM: homo sapiens

<400> SEQUENCE: 958
tggcagggat gctttgcttc						20

<210> SEQ ID NO 959
<211> LENGTH: 20
<212> TYPE: DNA
<213> ORGANISM: homo sapiens

<400> SEQUENCE: 959
gcatccctgc caccgtgctg						20

<210> SEQ ID NO 960
<211> LENGTH: 20
<212> TYPE: DNA
<213> ORGANISM: homo sapiens

<400> SEQUENCE: 960
ctggccacag cacggtggca						20

<210> SEQ ID NO 961
<211> LENGTH: 20
<212> TYPE: DNA
<213> ORGANISM: homo sapiens

```
<400> SEQUENCE: 961
cctgccaccg tgctgtggcc                                              20

<210> SEQ ID NO 962
<211> LENGTH: 20
<212> TYPE: DNA
<213> ORGANISM: homo sapiens

<400> SEQUENCE: 962
cctggccaca gcacggtggc                                              20

<210> SEQ ID NO 963
<211> LENGTH: 20
<212> TYPE: DNA
<213> ORGANISM: homo sapiens

<400> SEQUENCE: 963
ctggcctggc cacagcacgg                                              20

<210> SEQ ID NO 964
<211> LENGTH: 20
<212> TYPE: DNA
<213> ORGANISM: homo sapiens

<400> SEQUENCE: 964
gtgctggcct ggccacagca                                              20

<210> SEQ ID NO 965
<211> LENGTH: 20
<212> TYPE: DNA
<213> ORGANISM: homo sapiens

<400> SEQUENCE: 965
aagagagagg ggtgctggcc                                              20

<210> SEQ ID NO 966
<211> LENGTH: 20
<212> TYPE: DNA
<213> ORGANISM: homo sapiens

<400> SEQUENCE: 966
catggaagag agagggggtgc                                             20

<210> SEQ ID NO 967
<211> LENGTH: 20
<212> TYPE: DNA
<213> ORGANISM: homo sapiens

<400> SEQUENCE: 967
cagcacccct ctctcttcca                                              20

<210> SEQ ID NO 968
<211> LENGTH: 20
<212> TYPE: DNA
<213> ORGANISM: homo sapiens

<400> SEQUENCE: 968
agcacccctc tctcttccat                                              20

<210> SEQ ID NO 969
<211> LENGTH: 20
<212> TYPE: DNA
```

<213> ORGANISM: homo sapiens

<400> SEQUENCE: 969
gcacccctct ctcttccatg                                              20

<210> SEQ ID NO 970
<211> LENGTH: 20
<212> TYPE: DNA
<213> ORGANISM: homo sapiens

<400> SEQUENCE: 970
cacccctctc tcttccatgg                                              20

<210> SEQ ID NO 971
<211> LENGTH: 20
<212> TYPE: DNA
<213> ORGANISM: homo sapiens

<400> SEQUENCE: 971
acccctctct cttccatggg                                              20

<210> SEQ ID NO 972
<211> LENGTH: 20
<212> TYPE: DNA
<213> ORGANISM: homo sapiens

<400> SEQUENCE: 972 gcccccccatg gaagagagag                                             20

<210> SEQ ID NO 973
<211> LENGTH: 20
<212> TYPE: DNA
<213> ORGANISM: homo sapiens

<400> SEQUENCE: 973 tgcccccat ggaagagaga                                               20

<210> SEQ ID NO 974
<211> LENGTH: 20
<212> TYPE: DNA
<213> ORGANISM: homo sapiens

<400> SEQUENCE: 974 ctgccccca tggaagagag                                               20

<210> SEQ ID NO 975
<211> LENGTH: 20
<212> TYPE: DNA
<213> ORGANISM: homo sapiens

<400> SEQUENCE: 975
ggtattggat ctgccccca                                               20

<210> SEQ ID NO 976
<211> LENGTH: 20
<212> TYPE: DNA
<213> ORGANISM: homo sapiens

<400> SEQUENCE: 976
ggggcagatc caatacccag                                              20

<210> SEQ ID NO 977
<211> LENGTH: 20

```
<212> TYPE: DNA
<213> ORGANISM: homo sapiens

<400> SEQUENCE: 977
atctgggggc cactgggtat                                              20

<210> SEQ ID NO 978
<211> LENGTH: 20
<212> TYPE: DNA
<213> ORGANISM: homo sapiens

<400> SEQUENCE: 978
tggtggatct gggggccact                                              20

<210> SEQ ID NO 979
<211> LENGTH: 20
<212> TYPE: DNA
<213> ORGANISM: homo sapiens

<400> SEQUENCE: 979
atggtggatc tgggggccac                                              20

<210> SEQ ID NO 980
<211> LENGTH: 20
<212> TYPE: DNA
<213> ORGANISM: homo sapiens

<400> SEQUENCE: 980
aaatgtaatg gtggatctgg                                              20

<210> SEQ ID NO 981
<211> LENGTH: 20
<212> TYPE: DNA
<213> ORGANISM: homo sapiens

<400> SEQUENCE: 981
aaaatgtaat ggtggatctg                                              20

<210> SEQ ID NO 982
<211> LENGTH: 20
<212> TYPE: DNA
<213> ORGANISM: homo sapiens

<400> SEQUENCE: 982
caaaatgtaa tggtggatct                                              20

<210> SEQ ID NO 983
<211> LENGTH: 20
<212> TYPE: DNA
<213> ORGANISM: homo sapiens

<400> SEQUENCE: 983
ccagatccac cattacattt                                              20

<210> SEQ ID NO 984
<211> LENGTH: 20
<212> TYPE: DNA
<213> ORGANISM: homo sapiens

<400> SEQUENCE: 984
ccaaaatgta atggtggatc                                              20

<210> SEQ ID NO 985
```

```
<211> LENGTH: 20
<212> TYPE: DNA
<213> ORGANISM: homo sapiens

<400> SEQUENCE: 985
cagatccacc attacatttt                                               20

<210> SEQ ID NO 986
<211> LENGTH: 20
<212> TYPE: DNA
<213> ORGANISM: homo sapiens

<400> SEQUENCE: 986
gtgggcccaa aatgtaatgg                                               20

<210> SEQ ID NO 987
<211> LENGTH: 20
<212> TYPE: DNA
<213> ORGANISM: homo sapiens

<400> SEQUENCE: 987
tttgtgggcc caaaatgtaa                                               20

<210> SEQ ID NO 988
<211> LENGTH: 20
<212> TYPE: DNA
<213> ORGANISM: homo sapiens

<400> SEQUENCE: 988
tacattttgg gcccacaaag                                               20

<210> SEQ ID NO 989
<211> LENGTH: 20
<212> TYPE: DNA
<213> ORGANISM: homo sapiens

<400> SEQUENCE: 989
acattttggg cccacaaagt                                               20

<210> SEQ ID NO 990
<211> LENGTH: 20
<212> TYPE: DNA
<213> ORGANISM: homo sapiens

<400> SEQUENCE: 990
gggcccacaa agtgggccgt                                               20

<210> SEQ ID NO 991
<211> LENGTH: 20
<212> TYPE: DNA
<213> ORGANISM: homo sapiens

<400> SEQUENCE: 991
ggcccacaaa gtgggccgtc                                               20

<210> SEQ ID NO 992
<211> LENGTH: 20
<212> TYPE: DNA
<213> ORGANISM: homo sapiens

<400> SEQUENCE: 992
gcccacaaag tgggccgtcg                                               20
```

```
<210> SEQ ID NO 993
<211> LENGTH: 20
<212> TYPE: DNA
<213> ORGANISM: homo sapiens

<400> SEQUENCE: 993
tccccgacgg cccactttgt                                              20

<210> SEQ ID NO 994
<211> LENGTH: 20
<212> TYPE: DNA
<213> ORGANISM: homo sapiens

<400> SEQUENCE: 994
atccccgacg gcccactttg                                              20

<210> SEQ ID NO 995
<211> LENGTH: 20
<212> TYPE: DNA
<213> ORGANISM: homo sapiens

<400> SEQUENCE: 995
ctctgtgcgc tgatccccga                                              20

<210> SEQ ID NO 996
<211> LENGTH: 20
<212> TYPE: DNA
<213> ORGANISM: homo sapiens

<400> SEQUENCE: 996
ggatcagcgc acagagttct                                              20

<210> SEQ ID NO 997
<211> LENGTH: 20
<212> TYPE: DNA
<213> ORGANISM: homo sapiens

<400> SEQUENCE: 997
gatcagcgca cagagttctt                                              20

<210> SEQ ID NO 998
<211> LENGTH: 20
<212> TYPE: DNA
<213> ORGANISM: homo sapiens

<400> SEQUENCE: 998
gttcttggga gcagcgccgt                                              20

<210> SEQ ID NO 999
<211> LENGTH: 20
<212> TYPE: DNA
<213> ORGANISM: homo sapiens

<400> SEQUENCE: 999
ttcttgggag cagcgccgtt                                              20

<210> SEQ ID NO 1000
<211> LENGTH: 20
<212> TYPE: DNA
<213> ORGANISM: homo sapiens

<400> SEQUENCE: 1000
tcttgggagc agcgccgttg                                              20
```

```
<210> SEQ ID NO 1001
<211> LENGTH: 20
<212> TYPE: DNA
<213> ORGANISM: homo sapiens

<400> SEQUENCE: 1001
ggagagacag ggggcccaa                                                    20

<210> SEQ ID NO 1002
<211> LENGTH: 20
<212> TYPE: DNA
<213> ORGANISM: homo sapiens

<400> SEQUENCE: 1002
acatggggtg gagagacagg                                                   20

<210> SEQ ID NO 1003
<211> LENGTH: 20
<212> TYPE: DNA
<213> ORGANISM: homo sapiens

<400> SEQUENCE: 1003
gacatggggt ggagagacag                                                   20

<210> SEQ ID NO 1004
<211> LENGTH: 20
<212> TYPE: DNA
<213> ORGANISM: homo sapiens

<400> SEQUENCE: 1004
agacatgggg tggagagaca                                                   20

<210> SEQ ID NO 1005
<211> LENGTH: 20
<212> TYPE: DNA
<213> ORGANISM: homo sapiens

<400> SEQUENCE: 1005
gagacatggg gtggagagac                                                   20

<210> SEQ ID NO 1006
<211> LENGTH: 20
<212> TYPE: DNA
<213> ORGANISM: homo sapiens

<400> SEQUENCE: 1006
ttgaaggtgg agacatgggg                                                   20

<210> SEQ ID NO 1007
<211> LENGTH: 20
<212> TYPE: DNA
<213> ORGANISM: homo sapiens

<400> SEQUENCE: 1007
gtcttgaagg tggagacatg                                                   20

<210> SEQ ID NO 1008
<211> LENGTH: 20
<212> TYPE: DNA
<213> ORGANISM: homo sapiens

<400> SEQUENCE: 1008
tgtcttgaag gtggagacat                                                   20
```

<210> SEQ ID NO 1009
<211> LENGTH: 20
<212> TYPE: DNA
<213> ORGANISM: homo sapiens

<400> SEQUENCE: 1009
ttgtcttgaa ggtggagaca                                          20

<210> SEQ ID NO 1010
<211> LENGTH: 20
<212> TYPE: DNA
<213> ORGANISM: homo sapiens

<400> SEQUENCE: 1010
atgtctccac cttcaagaca                                          20

<210> SEQ ID NO 1011
<211> LENGTH: 20
<212> TYPE: DNA
<213> ORGANISM: homo sapiens

<400> SEQUENCE: 1011
tgccacttac cttgtcttga                                          20

<210> SEQ ID NO 1012
<211> LENGTH: 20
<212> TYPE: DNA
<213> ORGANISM: homo sapiens

<400> SEQUENCE: 1012
cgggcttggc aggtctgcaa                                          20

<210> SEQ ID NO 1013
<211> LENGTH: 20
<212> TYPE: DNA
<213> ORGANISM: homo sapiens

<400> SEQUENCE: 1013
gggcttggca ggtctgcaaa                                          20

<210> SEQ ID NO 1014
<211> LENGTH: 20
<212> TYPE: DNA
<213> ORGANISM: homo sapiens

<400> SEQUENCE: 1014
ggcaggtctg caaagggttt                                          20

<210> SEQ ID NO 1015
<211> LENGTH: 20
<212> TYPE: DNA
<213> ORGANISM: homo sapiens

<400> SEQUENCE: 1015
gcaggtctgc aaagggtttt                                          20

<210> SEQ ID NO 1016
<211> LENGTH: 20
<212> TYPE: DNA
<213> ORGANISM: homo sapiens

<400> SEQUENCE: 1016
caggtctgca aagggttttg                                      20

<210> SEQ ID NO 1017
<211> LENGTH: 20
<212> TYPE: DNA
<213> ORGANISM: homo sapiens

<400> SEQUENCE: 1017
gcaaagggtt ttggggctcg                                      20

<210> SEQ ID NO 1018
<211> LENGTH: 20
<212> TYPE: DNA
<213> ORGANISM: homo sapiens

<400> SEQUENCE: 1018
aggcccagac gtgctgagtc                                      20

<210> SEQ ID NO 1019
<211> LENGTH: 20
<212> TYPE: DNA
<213> ORGANISM: homo sapiens

<400> SEQUENCE: 1019
tggccggact cagcacgtct                                      20

<210> SEQ ID NO 1020
<211> LENGTH: 20
<212> TYPE: DNA
<213> ORGANISM: homo sapiens

<400> SEQUENCE: 1020
atggccggac tcagcacgtc                                      20

<210> SEQ ID NO 1021
<211> LENGTH: 20
<212> TYPE: DNA
<213> ORGANISM: homo sapiens

<400> SEQUENCE: 1021
agacgtgctg agtccggcca                                      20

<210> SEQ ID NO 1022
<211> LENGTH: 20
<212> TYPE: DNA
<213> ORGANISM: homo sapiens

<400> SEQUENCE: 1022
ttggagaggg ctaccatggc                                      20

<210> SEQ ID NO 1023
<211> LENGTH: 20
<212> TYPE: DNA
<213> ORGANISM: homo sapiens

<400> SEQUENCE: 1023
cttgttggag agggctacca                                      20

<210> SEQ ID NO 1024
<211> LENGTH: 20
<212> TYPE: DNA
<213> ORGANISM: homo sapiens

<400> SEQUENCE: 1024
cagcttcagc ttgttggaga                                                    20

<210> SEQ ID NO 1025
<211> LENGTH: 20
<212> TYPE: DNA
<213> ORGANISM: homo sapiens

<400> SEQUENCE: 1025
tcagcttcag cttgttggag                                                    20

<210> SEQ ID NO 1026
<211> LENGTH: 20
<212> TYPE: DNA
<213> ORGANISM: homo sapiens

<400> SEQUENCE: 1026
tcgcttcagc ttcagcttgt                                                    20

<210> SEQ ID NO 1027
<211> LENGTH: 20
<212> TYPE: DNA
<213> ORGANISM: homo sapiens

<400> SEQUENCE: 1027
gctgaagctg aagcgacagc                                                    20

<210> SEQ ID NO 1028
<211> LENGTH: 20
<212> TYPE: DNA
<213> ORGANISM: homo sapiens

<400> SEQUENCE: 1028
gtatgaagag caagccttcc                                                    20

<210> SEQ ID NO 1029
<211> LENGTH: 20
<212> TYPE: DNA
<213> ORGANISM: homo sapiens

<400> SEQUENCE: 1029
caagccttcc aggacctgag                                                    20

<210> SEQ ID NO 1030
<211> LENGTH: 20
<212> TYPE: DNA
<213> ORGANISM: homo sapiens

<400> SEQUENCE: 1030
aagccttcca ggacctgagc                                                    20

<210> SEQ ID NO 1031
<211> LENGTH: 20
<212> TYPE: DNA
<213> ORGANISM: homo sapiens

<400> SEQUENCE: 1031
agccttccag gacctgagcg                                                    20

<210> SEQ ID NO 1032
<211> LENGTH: 20
<212> TYPE: DNA
<213> ORGANISM: homo sapiens

```
<400> SEQUENCE: 1032
caccccgctc aggtcctgga                                              20

<210> SEQ ID NO 1033
<211> LENGTH: 20
<212> TYPE: DNA
<213> ORGANISM: homo sapiens

<400> SEQUENCE: 1033
gactcacccc gctcaggtcc                                              20

<210> SEQ ID NO 1034
<211> LENGTH: 20
<212> TYPE: DNA
<213> ORGANISM: homo sapiens

<400> SEQUENCE: 1034
ggggatgact caccccgctc                                              20

<210> SEQ ID NO 1035
<211> LENGTH: 20
<212> TYPE: DNA
<213> ORGANISM: homo sapiens

<400> SEQUENCE: 1035
tactcccagg gggacccacc                                              20

<210> SEQ ID NO 1036
<211> LENGTH: 20
<212> TYPE: DNA
<213> ORGANISM: homo sapiens

<400> SEQUENCE: 1036
tcccaggggg acccacctgg                                              20

<210> SEQ ID NO 1037
<211> LENGTH: 20
<212> TYPE: DNA
<213> ORGANISM: homo sapiens

<400> SEQUENCE: 1037
gccaccaggt gggtccccct                                              20

<210> SEQ ID NO 1038
<211> LENGTH: 20
<212> TYPE: DNA
<213> ORGANISM: homo sapiens

<400> SEQUENCE: 1038
tgccaccagg tgggtccccc                                              20

<210> SEQ ID NO 1039
<211> LENGTH: 20
<212> TYPE: DNA
<213> ORGANISM: homo sapiens

<400> SEQUENCE: 1039
gtgaggtgct gccaccaggt                                              20

<210> SEQ ID NO 1040
<211> LENGTH: 20
<212> TYPE: DNA
<213> ORGANISM: homo sapiens
```

```
<400> SEQUENCE: 1040
tgtgaggtgc tgccaccagg                                                 20

<210> SEQ ID NO 1041
<211> LENGTH: 20
<212> TYPE: DNA
<213> ORGANISM: homo sapiens

<400> SEQUENCE: 1041
aaatgtgagg tgctgccacc                                                 20

<210> SEQ ID NO 1042
<211> LENGTH: 20
<212> TYPE: DNA
<213> ORGANISM: homo sapiens

<400> SEQUENCE: 1042
gcagcacctc acatttgatg                                                 20

<210> SEQ ID NO 1043
<211> LENGTH: 20
<212> TYPE: DNA
<213> ORGANISM: homo sapiens

<400> SEQUENCE: 1043
cctcacattt gatgtggaaa                                                 20

<210> SEQ ID NO 1044
<211> LENGTH: 20
<212> TYPE: DNA
<213> ORGANISM: homo sapiens

<400> SEQUENCE: 1044
ccgtttccac atcaaatgtg                                                 20

<210> SEQ ID NO 1045
<211> LENGTH: 20
<212> TYPE: DNA
<213> ORGANISM: homo sapiens

<400> SEQUENCE: 1045
ggaaacggat gaagaacctc                                                 20

<210> SEQ ID NO 1046
<211> LENGTH: 20
<212> TYPE: DNA
<213> ORGANISM: homo sapiens

<400> SEQUENCE: 1046
gaaacggatg aagaacctca                                                 20

<210> SEQ ID NO 1047
<211> LENGTH: 20
<212> TYPE: DNA
<213> ORGANISM: homo sapiens

<400> SEQUENCE: 1047
aaacggatga agaacctcag                                                 20

<210> SEQ ID NO 1048
<211> LENGTH: 20
<212> TYPE: DNA
```

```
<213> ORGANISM: homo sapiens

<400> SEQUENCE: 1048
cggatgaaga acctcagggg                                               20

<210> SEQ ID NO 1049
<211> LENGTH: 20
<212> TYPE: DNA
<213> ORGANISM: homo sapiens

<400> SEQUENCE: 1049
ggatgaagaa cctcaggggt                                               20

<210> SEQ ID NO 1050
<211> LENGTH: 20
<212> TYPE: DNA
<213> ORGANISM: homo sapiens

<400> SEQUENCE: 1050
aagggcagct cccacccctg                                               20

<210> SEQ ID NO 1051
<211> LENGTH: 20
<212> TYPE: DNA
<213> ORGANISM: homo sapiens

<400> SEQUENCE: 1051
tgggagctgc cctttgatgc                                               20

<210> SEQ ID NO 1052
<211> LENGTH: 20
<212> TYPE: DNA
<213> ORGANISM: homo sapiens

<400> SEQUENCE: 1052
gtggcttgtc cggcatcaaa                                               20

<210> SEQ ID NO 1053
<211> LENGTH: 20
<212> TYPE: DNA
<213> ORGANISM: homo sapiens

<400> SEQUENCE: 1053
agtggcttgt ccggcatcaa                                               20

<210> SEQ ID NO 1054
<211> LENGTH: 20
<212> TYPE: DNA
<213> ORGANISM: homo sapiens

<400> SEQUENCE: 1054
tttgcgctca gtggcttgtc                                               20

<210> SEQ ID NO 1055
<211> LENGTH: 20
<212> TYPE: DNA
<213> ORGANISM: homo sapiens

<400> SEQUENCE: 1055
ttgggtacat ttgcgctcag                                               20

<210> SEQ ID NO 1056
<211> LENGTH: 20
```

```
<212> TYPE: DNA
<213> ORGANISM: homo sapiens

<400> SEQUENCE: 1056
ctgagcgcaa atgtacccaa                                              20

<210> SEQ ID NO 1057
<211> LENGTH: 20
<212> TYPE: DNA
<213> ORGANISM: homo sapiens

<400> SEQUENCE: 1057
tgtggccgct gctcaccatt                                              20

<210> SEQ ID NO 1058
<211> LENGTH: 20
<212> TYPE: DNA
<213> ORGANISM: homo sapiens

<400> SEQUENCE: 1058
ctgtggccgc tgctcaccat                                              20

<210> SEQ ID NO 1059
<211> LENGTH: 20
<212> TYPE: DNA
<213> ORGANISM: homo sapiens

<400> SEQUENCE: 1059
agttcaccca aaaccccatg                                              20

<210> SEQ ID NO 1060
<211> LENGTH: 20
<212> TYPE: DNA
<213> ORGANISM: homo sapiens

<400> SEQUENCE: 1060
gttcacccaa aaccccatga                                              20

<210> SEQ ID NO 1061
<211> LENGTH: 20
<212> TYPE: DNA
<213> ORGANISM: homo sapiens

<400> SEQUENCE: 1061
ttcacccaaa accccatgag                                              20

<210> SEQ ID NO 1062
<211> LENGTH: 20
<212> TYPE: DNA
<213> ORGANISM: homo sapiens

<400> SEQUENCE: 1062
caggcccctc atgggttttt                                              20

<210> SEQ ID NO 1063
<211> LENGTH: 20
<212> TYPE: DNA
<213> ORGANISM: homo sapiens

<400> SEQUENCE: 1063
ccaaaacccc atgaggggcc                                              20

<210> SEQ ID NO 1064
```

```
<211> LENGTH: 20
<212> TYPE: DNA
<213> ORGANISM: homo sapiens

<400> SEQUENCE: 1064
ccaggcccct catggggttt                                        20

<210> SEQ ID NO 1065
<211> LENGTH: 20
<212> TYPE: DNA
<213> ORGANISM: homo sapiens

<400> SEQUENCE: 1065
caaaacccca tgagggcct                                         20

<210> SEQ ID NO 1066
<211> LENGTH: 20
<212> TYPE: DNA
<213> ORGANISM: homo sapiens

<400> SEQUENCE: 1066
gatggcccag gcccctcatg                                        20

<210> SEQ ID NO 1067
<211> LENGTH: 20
<212> TYPE: DNA
<213> ORGANISM: homo sapiens

<400> SEQUENCE: 1067
ggatggccca ggcccctcat                                        20

<210> SEQ ID NO 1068
<211> LENGTH: 20
<212> TYPE: DNA
<213> ORGANISM: homo sapiens

<400> SEQUENCE: 1068
gggatggccc aggcccctca                                        20

<210> SEQ ID NO 1069
<211> LENGTH: 20
<212> TYPE: DNA
<213> ORGANISM: homo sapiens

<400> SEQUENCE: 1069
gatgtctcag gggatggccc                                        20

<210> SEQ ID NO 1070
<211> LENGTH: 20
<212> TYPE: DNA
<213> ORGANISM: homo sapiens

<400> SEQUENCE: 1070
gcggcagatg tctcagggga                                        20

<210> SEQ ID NO 1071
<211> LENGTH: 20
<212> TYPE: DNA
<213> ORGANISM: homo sapiens

<400> SEQUENCE: 1071
ggcagcggca gatgtctcag                                        20
```

```
<210> SEQ ID NO 1072
<211> LENGTH: 20
<212> TYPE: DNA
<213> ORGANISM: homo sapiens

<400> SEQUENCE: 1072
tggcagcggc agatgtctca                                          20

<210> SEQ ID NO 1073
<211> LENGTH: 20
<212> TYPE: DNA
<213> ORGANISM: homo sapiens

<400> SEQUENCE: 1073
gtggcagcgg cagatgtctc                                          20

<210> SEQ ID NO 1074
<211> LENGTH: 20
<212> TYPE: DNA
<213> ORGANISM: homo sapiens

<400> SEQUENCE: 1074
gcagatggag gctgtggcag                                          20

<210> SEQ ID NO 1075
<211> LENGTH: 20
<212> TYPE: DNA
<213> ORGANISM: homo sapiens

<400> SEQUENCE: 1075
ctgatggcag atggaggctg                                          20

<210> SEQ ID NO 1076
<211> LENGTH: 20
<212> TYPE: DNA
<213> ORGANISM: homo sapiens

<400> SEQUENCE: 1076
cctccatctg ccatcagtcc                                          20

<210> SEQ ID NO 1077
<211> LENGTH: 20
<212> TYPE: DNA
<213> ORGANISM: homo sapiens

<400> SEQUENCE: 1077
ccgggactga tggcagatgg                                          20

<210> SEQ ID NO 1078
<211> LENGTH: 20
<212> TYPE: DNA
<213> ORGANISM: homo sapiens

<400> SEQUENCE: 1078
ctccatctgc catcagtccc                                          20

<210> SEQ ID NO 1079
<211> LENGTH: 20
<212> TYPE: DNA
<213> ORGANISM: homo sapiens

<400> SEQUENCE: 1079
tccatctgcc atcagtcccg                                          20
```

```
<210> SEQ ID NO 1080
<211> LENGTH: 20
<212> TYPE: DNA
<213> ORGANISM: homo sapiens

<400> SEQUENCE: 1080
tccccgggac tgatggcaga                                              20

<210> SEQ ID NO 1081
<211> LENGTH: 20
<212> TYPE: DNA
<213> ORGANISM: homo sapiens

<400> SEQUENCE: 1081
gctgttctcc ccgggactga                                              20

<210> SEQ ID NO 1082
<211> LENGTH: 20
<212> TYPE: DNA
<213> ORGANISM: homo sapiens

<400> SEQUENCE: 1082
ctgctcttgc tgttctcccc                                              20

<210> SEQ ID NO 1083
<211> LENGTH: 20
<212> TYPE: DNA
<213> ORGANISM: homo sapiens

<400> SEQUENCE: 1083
ccggggagaa cagcaagagc                                              20

<210> SEQ ID NO 1084
<211> LENGTH: 20
<212> TYPE: DNA
<213> ORGANISM: homo sapiens

<400> SEQUENCE: 1084
cctgctcttg ctgttctccc                                              20

<210> SEQ ID NO 1085
<211> LENGTH: 20
<212> TYPE: DNA
<213> ORGANISM: homo sapiens

<400> SEQUENCE: 1085
gggtggcgta gcactgtggg                                              20

<210> SEQ ID NO 1086
<211> LENGTH: 20
<212> TYPE: DNA
<213> ORGANISM: homo sapiens

<400> SEQUENCE: 1086
tgggtggcgt agcactgtgg                                              20

<210> SEQ ID NO 1087
<211> LENGTH: 20
<212> TYPE: DNA
<213> ORGANISM: homo sapiens

<400> SEQUENCE: 1087
ctgggtggcg tagcactgtg                                              20
```

<210> SEQ ID NO 1088
<211> LENGTH: 20
<212> TYPE: DNA
<213> ORGANISM: homo sapiens

<400> SEQUENCE: 1088
actgggtggc gtagcactgt                                               20

<210> SEQ ID NO 1089
<211> LENGTH: 20
<212> TYPE: DNA
<213> ORGANISM: homo sapiens

<400> SEQUENCE: 1089
tactgggtgg cgtagcactg                                               20

<210> SEQ ID NO 1090
<211> LENGTH: 20
<212> TYPE: DNA
<213> ORGANISM: homo sapiens

<400> SEQUENCE: 1090
gtgctacgcc acccagtacc                                               20

<210> SEQ ID NO 1091
<211> LENGTH: 20
<212> TYPE: DNA
<213> ORGANISM: homo sapiens

<400> SEQUENCE: 1091
gctgtagtcc tggtactggg                                               20

<210> SEQ ID NO 1092
<211> LENGTH: 20
<212> TYPE: DNA
<213> ORGANISM: homo sapiens

<400> SEQUENCE: 1092
caggctgtag tcctggtact                                               20

<210> SEQ ID NO 1093
<211> LENGTH: 20
<212> TYPE: DNA
<213> ORGANISM: homo sapiens

<400> SEQUENCE: 1093
acaggctgta gtcctggtac                                               20

<210> SEQ ID NO 1094
<211> LENGTH: 20
<212> TYPE: DNA
<213> ORGANISM: homo sapiens

<400> SEQUENCE: 1094
ctgacgacag gctgtagtcc                                               20

<210> SEQ ID NO 1095
<211> LENGTH: 20
<212> TYPE: DNA
<213> ORGANISM: homo sapiens

<400> SEQUENCE: 1095

-continued cagcctgtcg tcagcccaca                                                20

<210> SEQ ID NO 1096
<211> LENGTH: 20
<212> TYPE: DNA
<213> ORGANISM: homo sapiens

<400> SEQUENCE: 1096
acaccttgtg ggctgacgac                                                20

<210> SEQ ID NO 1097
<211> LENGTH: 20
<212> TYPE: DNA
<213> ORGANISM: homo sapiens

<400> SEQUENCE: 1097
tcgtcagccc acaaggtgtc                                                20

<210> SEQ ID NO 1098
<211> LENGTH: 20
<212> TYPE: DNA
<213> ORGANISM: homo sapiens

<400> SEQUENCE: 1098
tcagcccaca aggtgtcagg                                                20

<210> SEQ ID NO 1099
<211> LENGTH: 20
<212> TYPE: DNA
<213> ORGANISM: homo sapiens

<400> SEQUENCE: 1099
cagcccacaa ggtgtcaggt                                                20

<210> SEQ ID NO 1100
<211> LENGTH: 20
<212> TYPE: DNA
<213> ORGANISM: homo sapiens

<400> SEQUENCE: 1100
acacccacct gacaccttgt                                                20

<210> SEQ ID NO 1101
<211> LENGTH: 20
<212> TYPE: DNA
<213> ORGANISM: homo sapiens

<400> SEQUENCE: 1101
cacacccacc tgacaccttg                                                20

<210> SEQ ID NO 1102
<211> LENGTH: 20
<212> TYPE: DNA
<213> ORGANISM: homo sapiens

<400> SEQUENCE: 1102
accaaccctt ctttcaggca                                                20

<210> SEQ ID NO 1103
<211> LENGTH: 20
<212> TYPE: DNA
<213> ORGANISM: homo sapiens

<400> SEQUENCE: 1103
ttctttcagg catggcaagc     20

<210> SEQ ID NO 1104
<211> LENGTH: 20
<212> TYPE: DNA
<213> ORGANISM: homo sapiens

<400> SEQUENCE: 1104
ggcatggcaa gccggctgct     20

<210> SEQ ID NO 1105
<211> LENGTH: 20
<212> TYPE: DNA
<213> ORGANISM: homo sapiens

<400> SEQUENCE: 1105
gcatggcaag ccggctgctc     20

<210> SEQ ID NO 1106
<211> LENGTH: 20
<212> TYPE: DNA
<213> ORGANISM: homo sapiens

<400> SEQUENCE: 1106
caaatgaggg cccgagcagc     20

<210> SEQ ID NO 1107
<211> LENGTH: 20
<212> TYPE: DNA
<213> ORGANISM: homo sapiens

<400> SEQUENCE: 1107
agcaggtagg actcaaatga     20

<210> SEQ ID NO 1108
<211> LENGTH: 20
<212> TYPE: DNA
<213> ORGANISM: homo sapiens

<400> SEQUENCE: 1108
cagcaggtag gactcaaatg     20

<210> SEQ ID NO 1109
<211> LENGTH: 20
<212> TYPE: DNA
<213> ORGANISM: homo sapiens

<400> SEQUENCE: 1109
ggtcagttcg ggcagcaggt     20

<210> SEQ ID NO 1110
<211> LENGTH: 20
<212> TYPE: DNA
<213> ORGANISM: homo sapiens

<400> SEQUENCE: 1110
atctggtcag ttcgggcagc     20

<210> SEQ ID NO 1111
<211> LENGTH: 20
<212> TYPE: DNA
<213> ORGANISM: homo sapiens -continued

```
<400> SEQUENCE: 1111
cagtcatatc tggtcagttc                                               20

<210> SEQ ID NO 1112
<211> LENGTH: 20
<212> TYPE: DNA
<213> ORGANISM: homo sapiens

<400> SEQUENCE: 1112
acagtcatat ctggtcagtt                                               20

<210> SEQ ID NO 1113
<211> LENGTH: 20
<212> TYPE: DNA
<213> ORGANISM: homo sapiens

<400> SEQUENCE: 1113
actgaccaga tatgactgtg                                               20

<210> SEQ ID NO 1114
<211> LENGTH: 20
<212> TYPE: DNA
<213> ORGANISM: homo sapiens

<400> SEQUENCE: 1114
gttcacctca cagtcatatc                                               20

<210> SEQ ID NO 1115
<211> LENGTH: 20
<212> TYPE: DNA
<213> ORGANISM: homo sapiens

<400> SEQUENCE: 1115
tgaggtgaac gtgcccgtgc                                               20

<210> SEQ ID NO 1116
<211> LENGTH: 20
<212> TYPE: DNA
<213> ORGANISM: homo sapiens

<400> SEQUENCE: 1116
gaggtgaacg tgcccgtgct                                               20

<210> SEQ ID NO 1117
<211> LENGTH: 20
<212> TYPE: DNA
<213> ORGANISM: homo sapiens

<400> SEQUENCE: 1117
agcgtggagc ttcccagcac                                               20

<210> SEQ ID NO 1118
<211> LENGTH: 20
<212> TYPE: DNA
<213> ORGANISM: homo sapiens

<400> SEQUENCE: 1118
gagcgtggag cttcccagca                                               20

<210> SEQ ID NO 1119
<211> LENGTH: 20
<212> TYPE: DNA
<213> ORGANISM: homo sapiens
```

<400> SEQUENCE: 1119
ggaagctcca cgctcctgca                                        20

<210> SEQ ID NO 1120
<211> LENGTH: 20
<212> TYPE: DNA
<213> ORGANISM: homo sapiens

<400> SEQUENCE: 1120
agctccacgc tcctgcaagg                                        20

<210> SEQ ID NO 1121
<211> LENGTH: 20
<212> TYPE: DNA
<213> ORGANISM: homo sapiens

<400> SEQUENCE: 1121
gctccacgct cctgcaagga                                        20

<210> SEQ ID NO 1122
<211> LENGTH: 20
<212> TYPE: DNA
<213> ORGANISM: homo sapiens

<400> SEQUENCE: 1122
ctccacgctc ctgcaaggag                                        20

<210> SEQ ID NO 1123
<211> LENGTH: 20
<212> TYPE: DNA
<213> ORGANISM: homo sapiens

<400> SEQUENCE: 1123 gtccctcct tgcaggagcg                                         20

<210> SEQ ID NO 1124
<211> LENGTH: 20
<212> TYPE: DNA
<213> ORGANISM: homo sapiens

<400> SEQUENCE: 1124
tgaggaggtc ccctccttgc                                        20

<210> SEQ ID NO 1125
<211> LENGTH: 20
<212> TYPE: DNA
<213> ORGANISM: homo sapiens

<400> SEQUENCE: 1125
aggggacctc ctcagagccc                                        20

<210> SEQ ID NO 1126
<211> LENGTH: 20
<212> TYPE: DNA
<213> ORGANISM: homo sapiens

<400> SEQUENCE: 1126
cctcctcaga gccctggacc                                        20

<210> SEQ ID NO 1127
<211> LENGTH: 20
<212> TYPE: DNA

<213> ORGANISM: homo sapiens

<400> SEQUENCE: 1127
cctggtccag ggctctgagg                                               20

<210> SEQ ID NO 1128
<211> LENGTH: 20
<212> TYPE: DNA
<213> ORGANISM: homo sapiens

<400> SEQUENCE: 1128
tggcctggtc cagggctctg                                               20

<210> SEQ ID NO 1129
<211> LENGTH: 20
<212> TYPE: DNA
<213> ORGANISM: homo sapiens

<400> SEQUENCE: 1129
ggctcaggtg gcctggtcca                                               20

<210> SEQ ID NO 1130
<211> LENGTH: 20
<212> TYPE: DNA
<213> ORGANISM: homo sapiens

<400> SEQUENCE: 1130
tggctcaggt ggcctggtcc                                               20

<210> SEQ ID NO 1131
<211> LENGTH: 20
<212> TYPE: DNA
<213> ORGANISM: homo sapiens

<400> SEQUENCE: 1131
tggaccaggc cacctgagcc                                               20

<210> SEQ ID NO 1132
<211> LENGTH: 20
<212> TYPE: DNA
<213> ORGANISM: homo sapiens

<400> SEQUENCE: 1132
aaggcctggc tcaggtggcc                                               20

<210> SEQ ID NO 1133
<211> LENGTH: 20
<212> TYPE: DNA
<213> ORGANISM: homo sapiens

<400> SEQUENCE: 1133
ggtagaaggc ctggctcagg                                               20

<210> SEQ ID NO 1134
<211> LENGTH: 20
<212> TYPE: DNA
<213> ORGANISM: homo sapiens

<400> SEQUENCE: 1134
tctgagctgt gatcttgtct                                               20

<210> SEQ ID NO 1135
<211> LENGTH: 20

```
<212> TYPE: DNA
<213> ORGANISM: homo sapiens

<400> SEQUENCE: 1135
ccgcagccta taacaacttt                                              20

<210> SEQ ID NO 1136
<211> LENGTH: 20
<212> TYPE: DNA
<213> ORGANISM: homo sapiens

<400> SEQUENCE: 1136
ccgaaagttg ttataggctg                                              20

<210> SEQ ID NO 1137
<211> LENGTH: 20
<212> TYPE: DNA
<213> ORGANISM: homo sapiens

<400> SEQUENCE: 1137
gctcttccga aagttgttat                                              20

<210> SEQ ID NO 1138
<211> LENGTH: 20
<212> TYPE: DNA
<213> ORGANISM: homo sapiens

<400> SEQUENCE: 1138
taacaacttt cggaagagca                                              20

<210> SEQ ID NO 1139
<211> LENGTH: 20
<212> TYPE: DNA
<213> ORGANISM: homo sapiens

<400> SEQUENCE: 1139
cggaagagca tggacagcat                                              20

<210> SEQ ID NO 1140
<211> LENGTH: 20
<212> TYPE: DNA
<213> ORGANISM: homo sapiens

<400> SEQUENCE: 1140
cataggaaag aagcaatatc                                              20

<210> SEQ ID NO 1141
<211> LENGTH: 20
<212> TYPE: DNA
<213> ORGANISM: homo sapiens

<400> SEQUENCE: 1141
aagcaatatc aggtccagca                                              20

<210> SEQ ID NO 1142
<211> LENGTH: 20
<212> TYPE: DNA
<213> ORGANISM: homo sapiens

<400> SEQUENCE: 1142
agcaatatca ggtccagcat                                              20

<210> SEQ ID NO 1143
```

```
<211> LENGTH: 20
<212> TYPE: DNA
<213> ORGANISM: homo sapiens

<400> SEQUENCE: 1143
tgtagctgca ggacccatgc                                              20

<210> SEQ ID NO 1144
<211> LENGTH: 20
<212> TYPE: DNA
<213> ORGANISM: homo sapiens

<400> SEQUENCE: 1144
caggaggaaa gtgtagctgc                                              20

<210> SEQ ID NO 1145
<211> LENGTH: 20
<212> TYPE: DNA
<213> ORGANISM: homo sapiens

<400> SEQUENCE: 1145
cactttcctc ctgccagaga                                              20

<210> SEQ ID NO 1146
<211> LENGTH: 20
<212> TYPE: DNA
<213> ORGANISM: homo sapiens

<400> SEQUENCE: 1146
agttgtccat ctctggcagg                                              20

<210> SEQ ID NO 1147
<211> LENGTH: 20
<212> TYPE: DNA
<213> ORGANISM: homo sapiens

<400> SEQUENCE: 1147
ggcagttgtc catctctggc                                              20

<210> SEQ ID NO 1148
<211> LENGTH: 20
<212> TYPE: DNA
<213> ORGANISM: homo sapiens

<400> SEQUENCE: 1148
gagcggcagt tgtccatctc                                              20

<210> SEQ ID NO 1149
<211> LENGTH: 20
<212> TYPE: DNA
<213> ORGANISM: homo sapiens

<400> SEQUENCE: 1149 cgtagggget ggaggaagag                                              20

<210> SEQ ID NO 1150
<211> LENGTH: 20
<212> TYPE: DNA
<213> ORGANISM: homo sapiens

<400> SEQUENCE: 1150
attggacacg tagggctgg                                               20
```

```
<210> SEQ ID NO 1151
<211> LENGTH: 20
<212> TYPE: DNA
<213> ORGANISM: homo sapiens

<400> SEQUENCE: 1151
agcattggac acgtaggggc                                               20

<210> SEQ ID NO 1152
<211> LENGTH: 20
<212> TYPE: DNA
<213> ORGANISM: homo sapiens

<400> SEQUENCE: 1152
gcacagcatt ggacacgtag                                               20

<210> SEQ ID NO 1153
<211> LENGTH: 20
<212> TYPE: DNA
<213> ORGANISM: homo sapiens

<400> SEQUENCE: 1153
tgcacagcat tggacacgta                                               20

<210> SEQ ID NO 1154
<211> LENGTH: 20
<212> TYPE: DNA
<213> ORGANISM: homo sapiens

<400> SEQUENCE: 1154
ctgcacagca ttggacacgt                                               20

<210> SEQ ID NO 1155
<211> LENGTH: 20
<212> TYPE: DNA
<213> ORGANISM: homo sapiens

<400> SEQUENCE: 1155
acgtgtccaa tgctgtgcag                                               20

<210> SEQ ID NO 1156
<211> LENGTH: 20
<212> TYPE: DNA
<213> ORGANISM: homo sapiens

<400> SEQUENCE: 1156
cgtgtccaat gctgtgcaga                                               20

<210> SEQ ID NO 1157
<211> LENGTH: 20
<212> TYPE: DNA
<213> ORGANISM: homo sapiens

<400> SEQUENCE: 1157
cgcgtccctc tgcacagcat                                               20

<210> SEQ ID NO 1158
<211> LENGTH: 20
<212> TYPE: DNA
<213> ORGANISM: homo sapiens

<400> SEQUENCE: 1158
gccgctcgaa tacgatgact                                               20
```

```
<210> SEQ ID NO 1159
<211> LENGTH: 20
<212> TYPE: DNA
<213> ORGANISM: homo sapiens

<400> SEQUENCE: 1159
accgagtcat cgtattcgag                                               20

<210> SEQ ID NO 1160
<211> LENGTH: 20
<212> TYPE: DNA
<213> ORGANISM: homo sapiens

<400> SEQUENCE: 1160
aatacgatga ctcggtgcag                                               20

<210> SEQ ID NO 1161
<211> LENGTH: 20
<212> TYPE: DNA
<213> ORGANISM: homo sapiens

<400> SEQUENCE: 1161
ggtgcagagg ctgcaagtgc                                               20

<210> SEQ ID NO 1162
<211> LENGTH: 20
<212> TYPE: DNA
<213> ORGANISM: homo sapiens

<400> SEQUENCE: 1162
gcaagtgctg gagaacatca                                               20

<210> SEQ ID NO 1163
<211> LENGTH: 20
<212> TYPE: DNA
<213> ORGANISM: homo sapiens

<400> SEQUENCE: 1163
tcatggaaaa caacactcag                                               20

<210> SEQ ID NO 1164
<211> LENGTH: 20
<212> TYPE: DNA
<213> ORGANISM: homo sapiens

<400> SEQUENCE: 1164
caacactcag tggctaatga                                               20

<210> SEQ ID NO 1165
<211> LENGTH: 20
<212> TYPE: DNA
<213> ORGANISM: homo sapiens

<400> SEQUENCE: 1165
actcagtggc taatgaaggt                                               20

<210> SEQ ID NO 1166
<211> LENGTH: 20
<212> TYPE: DNA
<213> ORGANISM: homo sapiens

<400> SEQUENCE: 1166
ctagcttgag aattatatcc                                               20
```

<210> SEQ ID NO 1167
<211> LENGTH: 20
<212> TYPE: DNA
<213> ORGANISM: homo sapiens

<400> SEQUENCE: 1167
tttctttctt catgttgtcc                                           20

<210> SEQ ID NO 1168
<211> LENGTH: 20
<212> TYPE: DNA
<213> ORGANISM: homo sapiens

<400> SEQUENCE: 1168
ggacaacatg aagaaagaaa                                           20

<210> SEQ ID NO 1169
<211> LENGTH: 20
<212> TYPE: DNA
<213> ORGANISM: homo sapiens

<400> SEQUENCE: 1169
gaatgcagta cagaaccaga                                           20

<210> SEQ ID NO 1170
<211> LENGTH: 20
<212> TYPE: DNA
<213> ORGANISM: homo sapiens

<400> SEQUENCE: 1170
tttctatcat cacagccgtc                                           20

<210> SEQ ID NO 1171
<211> LENGTH: 20
<212> TYPE: DNA
<213> ORGANISM: homo sapiens

<400> SEQUENCE: 1171
acggctgtga tgatagaaat                                           20

<210> SEQ ID NO 1172
<211> LENGTH: 20
<212> TYPE: DNA
<213> ORGANISM: homo sapiens

<400> SEQUENCE: 1172
cggctgtgat gatagaaata                                           20

<210> SEQ ID NO 1173
<211> LENGTH: 20
<212> TYPE: DNA
<213> ORGANISM: homo sapiens

<400> SEQUENCE: 1173
aaacctgttg aaccaaacag                                           20

<210> SEQ ID NO 1174
<211> LENGTH: 20
<212> TYPE: DNA
<213> ORGANISM: homo sapiens

<400> SEQUENCE: 1174

```
gctccgctgt ttggttcaac                                            20

<210> SEQ ID NO 1175
<211> LENGTH: 20
<212> TYPE: DNA
<213> ORGANISM: homo sapiens

<400> SEQUENCE: 1175
accaaacagc ggagcaaacg                                            20

<210> SEQ ID NO 1176
<211> LENGTH: 20
<212> TYPE: DNA
<213> ORGANISM: homo sapiens

<400> SEQUENCE: 1176
tccgcgtttg ctccgctgtt                                            20

<210> SEQ ID NO 1177
<211> LENGTH: 20
<212> TYPE: DNA
<213> ORGANISM: homo sapiens

<400> SEQUENCE: 1177
aacgcggaag ttaactgatg                                            20

<210> SEQ ID NO 1178
<211> LENGTH: 20
<212> TYPE: DNA
<213> ORGANISM: homo sapiens

<400> SEQUENCE: 1178
ctagcttgag aattatatcc                                            20

<210> SEQ ID NO 1179
<211> LENGTH: 20
<212> TYPE: DNA
<213> ORGANISM: homo sapiens

<400> SEQUENCE: 1179
tttctttctt catgttgtcc                                            20

<210> SEQ ID NO 1180
<211> LENGTH: 20
<212> TYPE: DNA
<213> ORGANISM: homo sapiens

<400> SEQUENCE: 1180
ggacaacatg aagaaagaaa                                            20

<210> SEQ ID NO 1181
<211> LENGTH: 20
<212> TYPE: DNA
<213> ORGANISM: homo sapiens

<400> SEQUENCE: 1181
gaatgcagta cagaaccaga                                            20

<210> SEQ ID NO 1182
<211> LENGTH: 20
<212> TYPE: DNA
<213> ORGANISM: homo sapiens

<400> SEQUENCE: 1182
```

```
tttctatcat cacagccgtc                                          20

<210> SEQ ID NO 1183
<211> LENGTH: 20
<212> TYPE: DNA
<213> ORGANISM: homo sapiens

<400> SEQUENCE: 1183
acggctgtga tgatagaaat                                          20

<210> SEQ ID NO 1184
<211> LENGTH: 20
<212> TYPE: DNA
<213> ORGANISM: homo sapiens

<400> SEQUENCE: 1184
cggctgtgat gatagaaata                                          20

<210> SEQ ID NO 1185
<211> LENGTH: 20
<212> TYPE: DNA
<213> ORGANISM: homo sapiens

<400> SEQUENCE: 1185
aaacctgttg aaccaaacag                                          20

<210> SEQ ID NO 1186
<211> LENGTH: 20
<212> TYPE: DNA
<213> ORGANISM: homo sapiens

<400> SEQUENCE: 1186
gctccgctgt ttggttcaac                                          20

<210> SEQ ID NO 1187
<211> LENGTH: 20
<212> TYPE: DNA
<213> ORGANISM: homo sapiens

<400> SEQUENCE: 1187
accaaacagc ggagcaaacg                                          20

<210> SEQ ID NO 1188
<211> LENGTH: 20
<212> TYPE: DNA
<213> ORGANISM: homo sapiens

<400> SEQUENCE: 1188
tccgcgtttg ctccgctgtt                                          20

<210> SEQ ID NO 1189
<211> LENGTH: 20
<212> TYPE: DNA
<213> ORGANISM: homo sapiens

<400> SEQUENCE: 1189
aacgcggaag ttaactgatg                                          20

<210> SEQ ID NO 1190
<211> LENGTH: 20
<212> TYPE: DNA
<213> ORGANISM: homo sapiens
```

```
<400> SEQUENCE: 1190
tacaagtttc ctagaaaaga                                               20

<210> SEQ ID NO 1191
<211> LENGTH: 20
<212> TYPE: DNA
<213> ORGANISM: homo sapiens

<400> SEQUENCE: 1191
tagctagcac cttctttttct                                              20

<210> SEQ ID NO 1192
<211> LENGTH: 20
<212> TYPE: DNA
<213> ORGANISM: homo sapiens

<400> SEQUENCE: 1192
agaaaagaag gtgctagcta                                               20

<210> SEQ ID NO 1193
<211> LENGTH: 20
<212> TYPE: DNA
<213> ORGANISM: homo sapiens

<400> SEQUENCE: 1193 cttctttat tgactgtagt                                                20

<210> SEQ ID NO 1194
<211> LENGTH: 20
<212> TYPE: DNA
<213> ORGANISM: homo sapiens

<400> SEQUENCE: 1194
agaagagaaa gatcagctac                                               20

<210> SEQ ID NO 1195
<211> LENGTH: 20
<212> TYPE: DNA
<213> ORGANISM: homo sapiens

<400> SEQUENCE: 1195
ttcaatgatg gaattttgct                                               20

<210> SEQ ID NO 1196
<211> LENGTH: 20
<212> TYPE: DNA
<213> ORGANISM: homo sapiens

<400> SEQUENCE: 1196
tttttctagt tcttcaatga                                               20

<210> SEQ ID NO 1197
<211> LENGTH: 20
<212> TYPE: DNA
<213> ORGANISM: homo sapiens

<400> SEQUENCE: 1197
aaaaaaaata gtgactgcca                                               20

<210> SEQ ID NO 1198
<211> LENGTH: 20
<212> TYPE: DNA
<213> ORGANISM: homo sapiens
```

```
<400> SEQUENCE: 1198
aagaactgaa ttattcaccg                                               20

<210> SEQ ID NO 1199
<211> LENGTH: 20
<212> TYPE: DNA
<213> ORGANISM: homo sapiens

<400> SEQUENCE: 1199
gaagcagcaa catgatctca                                               20

<210> SEQ ID NO 1200
<211> LENGTH: 20
<212> TYPE: DNA
<213> ORGANISM: homo sapiens

<400> SEQUENCE: 1200
tgtaaactta cagtttgatg                                               20

<210> SEQ ID NO 1201
<211> LENGTH: 20
<212> TYPE: DNA
<213> ORGANISM: homo sapiens

<400> SEQUENCE: 1201 ctattttta aaagcagcta                                                20

<210> SEQ ID NO 1202
<211> LENGTH: 20
<212> TYPE: DNA
<213> ORGANISM: homo sapiens

<400> SEQUENCE: 1202
gttcttcttt agcaacagtg                                               20

<210> SEQ ID NO 1203
<211> LENGTH: 20
<212> TYPE: DNA
<213> ORGANISM: homo sapiens

<400> SEQUENCE: 1203
tgttcttctt tagcaacagt                                               20

<210> SEQ ID NO 1204
<211> LENGTH: 20
<212> TYPE: DNA
<213> ORGANISM: homo sapiens

<400> SEQUENCE: 1204
ttgttcttct ttagcaacag                                               20

<210> SEQ ID NO 1205
<211> LENGTH: 20
<212> TYPE: DNA
<213> ORGANISM: homo sapiens

<400> SEQUENCE: 1205
tgtgctgaag tattcaaatc                                               20

<210> SEQ ID NO 1206
<211> LENGTH: 20
<212> TYPE: DNA
```

```
<213> ORGANISM: homo sapiens

<400> SEQUENCE: 1206
aaatcaggac acaccacgaa                                              20

<210> SEQ ID NO 1207
<211> LENGTH: 20
<212> TYPE: DNA
<213> ORGANISM: homo sapiens

<400> SEQUENCE: 1207
taacgtgtag atgccattcg                                              20

<210> SEQ ID NO 1208
<211> LENGTH: 20
<212> TYPE: DNA
<213> ORGANISM: homo sapiens

<400> SEQUENCE: 1208
tgatctcttc tgtagaatta                                              20

<210> SEQ ID NO 1209
<211> LENGTH: 20
<212> TYPE: DNA
<213> ORGANISM: homo sapiens

<400> SEQUENCE: 1209
ttgatctctt ctgtagaatt                                              20

<210> SEQ ID NO 1210
<211> LENGTH: 20
<212> TYPE: DNA
<213> ORGANISM: homo sapiens

<400> SEQUENCE: 1210
taattctaca gaagagatca                                              20

<210> SEQ ID NO 1211
<211> LENGTH: 20
<212> TYPE: DNA
<213> ORGANISM: homo sapiens

<400> SEQUENCE: 1211
ctacagaaga gatcaaggtg                                              20

<210> SEQ ID NO 1212
<211> LENGTH: 20
<212> TYPE: DNA
<213> ORGANISM: homo sapiens

<400> SEQUENCE: 1212
tttgcaggcc tactgtgaca                                              20

<210> SEQ ID NO 1213
<211> LENGTH: 20
<212> TYPE: DNA
<213> ORGANISM: homo sapiens

<400> SEQUENCE: 1213
gcctactgtg acatggaagc                                              20

<210> SEQ ID NO 1214
<211> LENGTH: 20
```

```
<212> TYPE: DNA
<213> ORGANISM: homo sapiens

<400> SEQUENCE: 1214
tccagcttcc atgtcacagt                                        20

<210> SEQ ID NO 1215
<211> LENGTH: 20
<212> TYPE: DNA
<213> ORGANISM: homo sapiens

<400> SEQUENCE: 1215
tactgtgaca tggaagctgg                                        20

<210> SEQ ID NO 1216
<211> LENGTH: 20
<212> TYPE: DNA
<213> ORGANISM: homo sapiens

<400> SEQUENCE: 1216
tgtgacatgg aagctggagg                                        20

<210> SEQ ID NO 1217
<211> LENGTH: 20
<212> TYPE: DNA
<213> ORGANISM: homo sapiens

<400> SEQUENCE: 1217
gacatggaag ctggaggagg                                        20

<210> SEQ ID NO 1218
<211> LENGTH: 20
<212> TYPE: DNA
<213> ORGANISM: homo sapiens

<400> SEQUENCE: 1218
acatggaagc tggaggaggc                                        20

<210> SEQ ID NO 1219
<211> LENGTH: 20
<212> TYPE: DNA
<213> ORGANISM: homo sapiens

<400> SEQUENCE: 1219
tggaagctgg aggaggcggg                                        20

<210> SEQ ID NO 1220
<211> LENGTH: 20
<212> TYPE: DNA
<213> ORGANISM: homo sapiens

<400> SEQUENCE: 1220
gacaattatt cagcgacgtg                                        20

<210> SEQ ID NO 1221
<211> LENGTH: 20
<212> TYPE: DNA
<213> ORGANISM: homo sapiens

<400> SEQUENCE: 1221
attattcagc gacgtgagga                                        20

<210> SEQ ID NO 1222
```

```
<211> LENGTH: 20
<212> TYPE: DNA
<213> ORGANISM: homo sapiens

<400> SEQUENCE: 1222
atggcagcgt tgattttcag                                               20

<210> SEQ ID NO 1223
<211> LENGTH: 20
<212> TYPE: DNA
<213> ORGANISM: homo sapiens

<400> SEQUENCE: 1223
gcgttgattt tcagaggact                                               20

<210> SEQ ID NO 1224
<211> LENGTH: 20
<212> TYPE: DNA
<213> ORGANISM: homo sapiens

<400> SEQUENCE: 1224
gacttggaaa gaatataaag                                               20

<210> SEQ ID NO 1225
<211> LENGTH: 20
<212> TYPE: DNA
<213> ORGANISM: homo sapiens

<400> SEQUENCE: 1225
ggaaagaata taaagtggta                                               20

<210> SEQ ID NO 1226
<211> LENGTH: 20
<212> TYPE: DNA
<213> ORGANISM: homo sapiens

<400> SEQUENCE: 1226
cagggatttg gtaacccttc                                               20

<210> SEQ ID NO 1227
<211> LENGTH: 20
<212> TYPE: DNA
<213> ORGANISM: homo sapiens

<400> SEQUENCE: 1227
gtaacccttc aggagaatat                                               20

<210> SEQ ID NO 1228
<211> LENGTH: 20
<212> TYPE: DNA
<213> ORGANISM: homo sapiens

<400> SEQUENCE: 1228
cccttcagga gaatattggc                                               20

<210> SEQ ID NO 1229
<211> LENGTH: 20
<212> TYPE: DNA
<213> ORGANISM: homo sapiens

<400> SEQUENCE: 1229
ccagccaata ttctcctgaa                                               20
```

```
<210> SEQ ID NO 1230
<211> LENGTH: 20
<212> TYPE: DNA
<213> ORGANISM: homo sapiens

<400> SEQUENCE: 1230
ccttcaggag aatattggct                                              20

<210> SEQ ID NO 1231
<211> LENGTH: 20
<212> TYPE: DNA
<213> ORGANISM: homo sapiens

<400> SEQUENCE: 1231
cccagccaat attctcctga                                              20

<210> SEQ ID NO 1232
<211> LENGTH: 20
<212> TYPE: DNA
<213> ORGANISM: homo sapiens

<400> SEQUENCE: 1232
ttaaaataca ccttaaagac                                              20

<210> SEQ ID NO 1233
<211> LENGTH: 20
<212> TYPE: DNA
<213> ORGANISM: homo sapiens

<400> SEQUENCE: 1233
taaaatacac cttaaagact                                              20

<210> SEQ ID NO 1234
<211> LENGTH: 20
<212> TYPE: DNA
<213> ORGANISM: homo sapiens

<400> SEQUENCE: 1234
atacacctta aagactggga                                              20

<210> SEQ ID NO 1235
<211> LENGTH: 20
<212> TYPE: DNA
<213> ORGANISM: homo sapiens

<400> SEQUENCE: 1235
tacaccttaa agactgggaa                                              20

<210> SEQ ID NO 1236
<211> LENGTH: 20
<212> TYPE: DNA
<213> ORGANISM: homo sapiens

<400> SEQUENCE: 1236
cattcccttc ccagtcttta                                              20

<210> SEQ ID NO 1237
<211> LENGTH: 20
<212> TYPE: DNA
<213> ORGANISM: homo sapiens

<400> SEQUENCE: 1237
taaagactgg gaagggaatg                                              20
```

-continued

```
<210> SEQ ID NO 1238
<211> LENGTH: 20
<212> TYPE: DNA
<213> ORGANISM: homo sapiens

<400> SEQUENCE: 1238
caagtgaaga actcaattat                                                 20

<210> SEQ ID NO 1239
<211> LENGTH: 20
<212> TYPE: DNA
<213> ORGANISM: homo sapiens

<400> SEQUENCE: 1239
gcttacagga ttcaccttaa                                                 20

<210> SEQ ID NO 1240
<211> LENGTH: 20
<212> TYPE: DNA
<213> ORGANISM: homo sapiens

<400> SEQUENCE: 1240
attcacctta aaggacttac                                                 20

<210> SEQ ID NO 1241
<211> LENGTH: 20
<212> TYPE: DNA
<213> ORGANISM: homo sapiens

<400> SEQUENCE: 1241
ttcaccttaa aggacttaca                                                 20

<210> SEQ ID NO 1242
<211> LENGTH: 20
<212> TYPE: DNA
<213> ORGANISM: homo sapiens

<400> SEQUENCE: 1242
ctgtccctgt aagtccttta                                                 20

<210> SEQ ID NO 1243
<211> LENGTH: 20
<212> TYPE: DNA
<213> ORGANISM: homo sapiens

<400> SEQUENCE: 1243
aaaggactta cagggacagc                                                 20

<210> SEQ ID NO 1244
<211> LENGTH: 20
<212> TYPE: DNA
<213> ORGANISM: homo sapiens

<400> SEQUENCE: 1244
gctgatgctg cttattttgc                                                 20

<210> SEQ ID NO 1245
<211> LENGTH: 20
<212> TYPE: DNA
<213> ORGANISM: homo sapiens

<400> SEQUENCE: 1245
ataagcagca tcagccaacc                                                 20
```

<210> SEQ ID NO 1246
<211> LENGTH: 20
<212> TYPE: DNA
<213> ORGANISM: homo sapiens

<400> SEQUENCE: 1246
tgctaaaatc atttcctggt    20

<210> SEQ ID NO 1247
<211> LENGTH: 20
<212> TYPE: DNA
<213> ORGANISM: homo sapiens

<400> SEQUENCE: 1247
tttgtgctaa aatcatttcc    20

<210> SEQ ID NO 1248
<211> LENGTH: 20
<212> TYPE: DNA
<213> ORGANISM: homo sapiens

<400> SEQUENCE: 1248
aggaaatgat tttagcacaa    20

<210> SEQ ID NO 1249
<211> LENGTH: 20
<212> TYPE: DNA
<213> ORGANISM: homo sapiens

<400> SEQUENCE: 1249
aatgatttta gcacaaagga    20

<210> SEQ ID NO 1250
<211> LENGTH: 20
<212> TYPE: DNA
<213> ORGANISM: homo sapiens

<400> SEQUENCE: 1250
aaatgttcac aaatgctaac    20

<210> SEQ ID NO 1251
<211> LENGTH: 20
<212> TYPE: DNA
<213> ORGANISM: homo sapiens

<400> SEQUENCE: 1251
tgttcacaaa tgctaacagg    20

<210> SEQ ID NO 1252
<211> LENGTH: 20
<212> TYPE: DNA
<213> ORGANISM: homo sapiens

<400> SEQUENCE: 1252
cacaaatgct aacaggaggt    20

<210> SEQ ID NO 1253
<211> LENGTH: 20
<212> TYPE: DNA
<213> ORGANISM: homo sapiens

<400> SEQUENCE: 1253
acaaatgcta acaggaggta                                           20

<210> SEQ ID NO 1254
<211> LENGTH: 20
<212> TYPE: DNA
<213> ORGANISM: homo sapiens

<400> SEQUENCE: 1254
ggctggtggt ttgatgcatg                                           20

<210> SEQ ID NO 1255
<211> LENGTH: 20
<212> TYPE: DNA
<213> ORGANISM: homo sapiens

<400> SEQUENCE: 1255
tgtggtcctt ccaacttgaa                                           20

<210> SEQ ID NO 1256
<211> LENGTH: 20
<212> TYPE: DNA
<213> ORGANISM: homo sapiens

<400> SEQUENCE: 1256
tacattccgt tcaagttgga                                           20

<210> SEQ ID NO 1257
<211> LENGTH: 20
<212> TYPE: DNA
<213> ORGANISM: homo sapiens

<400> SEQUENCE: 1257
atagtacatt ccgttcaagt                                           20

<210> SEQ ID NO 1258
<211> LENGTH: 20
<212> TYPE: DNA
<213> ORGANISM: homo sapiens

<400> SEQUENCE: 1258
acggaatgta ctatccacag                                           20

<210> SEQ ID NO 1259
<211> LENGTH: 20
<212> TYPE: DNA
<213> ORGANISM: homo sapiens

<400> SEQUENCE: 1259
ttatttgtgt tctgcctctg                                           20

<210> SEQ ID NO 1260
<211> LENGTH: 20
<212> TYPE: DNA
<213> ORGANISM: homo sapiens

<400> SEQUENCE: 1260
cagaacacaa ataagttcaa                                           20

<210> SEQ ID NO 1261
<211> LENGTH: 20
<212> TYPE: DNA
<213> ORGANISM: homo sapiens

<400> SEQUENCE: 1261

| | |
|---|---|
| ataagttcaa cggcattaaa | 20 |

<210> SEQ ID NO 1262
<211> LENGTH: 20
<212> TYPE: DNA
<213> ORGANISM: homo sapiens

<400> SEQUENCE: 1262

| | |
|---|---|
| acggcattaa atggtactac | 20 |

<210> SEQ ID NO 1263
<211> LENGTH: 20
<212> TYPE: DNA
<213> ORGANISM: homo sapiens

<400> SEQUENCE: 1263

| | |
|---|---|
| attaaatggt actactggaa | 20 |

<210> SEQ ID NO 1264
<211> LENGTH: 20
<212> TYPE: DNA
<213> ORGANISM: homo sapiens

<400> SEQUENCE: 1264

| | |
|---|---|
| tggtactact ggaaaggctc | 20 |

<210> SEQ ID NO 1265
<211> LENGTH: 20
<212> TYPE: DNA
<213> ORGANISM: homo sapiens

<400> SEQUENCE: 1265

| | |
|---|---|
| aggctcaggc tattcgctca | 20 |

<210> SEQ ID NO 1266
<211> LENGTH: 20
<212> TYPE: DNA
<213> ORGANISM: homo sapiens

<400> SEQUENCE: 1266

| | |
|---|---|
| tggtcggatc atcatggttg | 20 |

<210> SEQ ID NO 1267
<211> LENGTH: 20
<212> TYPE: DNA
<213> ORGANISM: homo sapiens

<400> SEQUENCE: 1267

| | |
|---|---|
| atctgctggt cggatcatca | 20 |

<210> SEQ ID NO 1268
<211> LENGTH: 20
<212> TYPE: DNA
<213> ORGANISM: homo sapiens

<400> SEQUENCE: 1268

| | |
|---|---|
| atgtttagaa atctgctggt | 20 |

<210> SEQ ID NO 1269
<211> LENGTH: 20
<212> TYPE: DNA
<213> ORGANISM: homo sapiens

<400> SEQUENCE: 1269
tgggatgttt agaaatctgc                                           20

<210> SEQ ID NO 1270
<211> LENGTH: 20
<212> TYPE: DNA
<213> ORGANISM: homo sapiens

<400> SEQUENCE: 1270
aggctaccta agaggatgag                                           20

<210> SEQ ID NO 1271
<211> LENGTH: 20
<212> TYPE: DNA
<213> ORGANISM: homo sapiens

<400> SEQUENCE: 1271
gaggatgagc ggtgctccga                                           20

<210> SEQ ID NO 1272
<211> LENGTH: 20
<212> TYPE: DNA
<213> ORGANISM: homo sapiens

<400> SEQUENCE: 1272
atgagcggtg ctccgacggc                                           20

<210> SEQ ID NO 1273
<211> LENGTH: 20
<212> TYPE: DNA
<213> ORGANISM: homo sapiens

<400> SEQUENCE: 1273
tgagcggtgc tccgacggcc                                           20

<210> SEQ ID NO 1274
<211> LENGTH: 20
<212> TYPE: DNA
<213> ORGANISM: homo sapiens

<400> SEQUENCE: 1274
gagcggtgct ccgacggccg                                           20

<210> SEQ ID NO 1275
<211> LENGTH: 20
<212> TYPE: DNA
<213> ORGANISM: homo sapiens

<400> SEQUENCE: 1275
atcagggctg ccccggccgt                                           20

<210> SEQ ID NO 1276
<211> LENGTH: 20
<212> TYPE: DNA
<213> ORGANISM: homo sapiens

<400> SEQUENCE: 1276
gcagagcatc agggctgccc                                           20

<210> SEQ ID NO 1277
<211> LENGTH: 20
<212> TYPE: DNA
<213> ORGANISM: homo sapiens

```
<400> SEQUENCE: 1277
ggtggcggcg cagagcatca                                               20

<210> SEQ ID NO 1278
<211> LENGTH: 20
<212> TYPE: DNA
<213> ORGANISM: homo sapiens

<400> SEQUENCE: 1278
cggtggcggc gcagagcatc                                               20

<210> SEQ ID NO 1279
<211> LENGTH: 20
<212> TYPE: DNA
<213> ORGANISM: homo sapiens

<400> SEQUENCE: 1279
gctcagtagc acggcggtgg                                               20

<210> SEQ ID NO 1280
<211> LENGTH: 20
<212> TYPE: DNA
<213> ORGANISM: homo sapiens

<400> SEQUENCE: 1280
agcgctcagt agcacggcgg                                               20

<210> SEQ ID NO 1281
<211> LENGTH: 20
<212> TYPE: DNA
<213> ORGANISM: homo sapiens

<400> SEQUENCE: 1281
ctgagcgctc agtagcacgg                                               20

<210> SEQ ID NO 1282
<211> LENGTH: 20
<212> TYPE: DNA
<213> ORGANISM: homo sapiens

<400> SEQUENCE: 1282
cgccgtgcta ctgagcgctc                                               20

<210> SEQ ID NO 1283
<211> LENGTH: 20
<212> TYPE: DNA
<213> ORGANISM: homo sapiens

<400> SEQUENCE: 1283
gccgtgctac tgagcgctca                                               20

<210> SEQ ID NO 1284
<211> LENGTH: 20
<212> TYPE: DNA
<213> ORGANISM: homo sapiens

<400> SEQUENCE: 1284
gccctgagcg ctcagtagca                                               20

<210> SEQ ID NO 1285
<211> LENGTH: 20
<212> TYPE: DNA
```

```
<213> ORGANISM: homo sapiens

<400> SEQUENCE: 1285
gtgctactga gcgctcaggg                                              20

<210> SEQ ID NO 1286
<211> LENGTH: 20
<212> TYPE: DNA
<213> ORGANISM: homo sapiens

<400> SEQUENCE: 1286
cgcggcgact tggactgcac                                              20

<210> SEQ ID NO 1287
<211> LENGTH: 20
<212> TYPE: DNA
<213> ORGANISM: homo sapiens

<400> SEQUENCE: 1287
gcgcggcgac ttggactgca                                              20

<210> SEQ ID NO 1288
<211> LENGTH: 20
<212> TYPE: DNA
<213> ORGANISM: homo sapiens

<400> SEQUENCE: 1288
ggacgcaaag cgcggcgact                                              20

<210> SEQ ID NO 1289
<211> LENGTH: 20
<212> TYPE: DNA
<213> ORGANISM: homo sapiens

<400> SEQUENCE: 1289
agtcgccgcg ctttgcgtcc                                              20

<210> SEQ ID NO 1290
<211> LENGTH: 20
<212> TYPE: DNA
<213> ORGANISM: homo sapiens

<400> SEQUENCE: 1290
gtcgccgcgc tttgcgtcct                                              20

<210> SEQ ID NO 1291
<211> LENGTH: 20
<212> TYPE: DNA
<213> ORGANISM: homo sapiens

<400> SEQUENCE: 1291
tcgtcccagg acgcaaagcg                                              20

<210> SEQ ID NO 1292
<211> LENGTH: 20
<212> TYPE: DNA
<213> ORGANISM: homo sapiens

<400> SEQUENCE: 1292
caggacattc atctcgtccc                                              20

<210> SEQ ID NO 1293
<211> LENGTH: 20
```

<212> TYPE: DNA
<213> ORGANISM: homo sapiens

<400> SEQUENCE: 1293
ctgggacgag atgaatgtcc                                              20

<210> SEQ ID NO 1294
<211> LENGTH: 20
<212> TYPE: DNA
<213> ORGANISM: homo sapiens

<400> SEQUENCE: 1294
gagatgaatg tcctggcgca                                              20

<210> SEQ ID NO 1295
<211> LENGTH: 20
<212> TYPE: DNA
<213> ORGANISM: homo sapiens

<400> SEQUENCE: 1295
gctgcaggag tccgtgcgcc                                              20

<210> SEQ ID NO 1296
<211> LENGTH: 20
<212> TYPE: DNA
<213> ORGANISM: homo sapiens

<400> SEQUENCE: 1296
gcgcacggac tcctgcagct                                              20

<210> SEQ ID NO 1297
<211> LENGTH: 20
<212> TYPE: DNA
<213> ORGANISM: homo sapiens

<400> SEQUENCE: 1297
cggactcctg cagctcggcc                                              20

<210> SEQ ID NO 1298
<211> LENGTH: 20
<212> TYPE: DNA
<213> ORGANISM: homo sapiens

<400> SEQUENCE: 1298
ggactcctgc agctcggcca                                              20

<210> SEQ ID NO 1299
<211> LENGTH: 20
<212> TYPE: DNA
<213> ORGANISM: homo sapiens

<400> SEQUENCE: 1299
gactcctgca gctcggccag                                              20

<210> SEQ ID NO 1300
<211> LENGTH: 20
<212> TYPE: DNA
<213> ORGANISM: homo sapiens

<400> SEQUENCE: 1300 gcagccctg gccgagctgc                                               20

<210> SEQ ID NO 1301

```
-continued

<211> LENGTH: 20
<212> TYPE: DNA
<213> ORGANISM: homo sapiens

<400> SEQUENCE: 1301
ccaggggctg cgcgaacacg                                            20

<210> SEQ ID NO 1302
<211> LENGTH: 20
<212> TYPE: DNA
<213> ORGANISM: homo sapiens

<400> SEQUENCE: 1302
ccgcgtgttc gcgcagcccc                                            20

<210> SEQ ID NO 1303
<211> LENGTH: 20
<212> TYPE: DNA
<213> ORGANISM: homo sapiens

<400> SEQUENCE: 1303
cagcgcgctc agctgactgc                                            20

<210> SEQ ID NO 1304
<211> LENGTH: 20
<212> TYPE: DNA
<213> ORGANISM: homo sapiens

<400> SEQUENCE: 1304
ccgcagtcag ctgagcgcgc                                            20

<210> SEQ ID NO 1305
<211> LENGTH: 20
<212> TYPE: DNA
<213> ORGANISM: homo sapiens

<400> SEQUENCE: 1305
ccagcgcgct cagctgactg                                            20

<210> SEQ ID NO 1306
<211> LENGTH: 20
<212> TYPE: DNA
<213> ORGANISM: homo sapiens

<400> SEQUENCE: 1306
gtcagctgag cgcgctggag                                            20

<210> SEQ ID NO 1307
<211> LENGTH: 20
<212> TYPE: DNA
<213> ORGANISM: homo sapiens

<400> SEQUENCE: 1307
gagcggcgcc tgagcgcgtg                                            20

<210> SEQ ID NO 1308
<211> LENGTH: 20
<212> TYPE: DNA
<213> ORGANISM: homo sapiens

<400> SEQUENCE: 1308
agcggcgcct gagcgcgtgc                                            20
```

```
<210> SEQ ID NO 1309
<211> LENGTH: 20
<212> TYPE: DNA
<213> ORGANISM: homo sapiens

<400> SEQUENCE: 1309
aggcggaccc gcacgcgctc                                              20

<210> SEQ ID NO 1310
<211> LENGTH: 20
<212> TYPE: DNA
<213> ORGANISM: homo sapiens

<400> SEQUENCE: 1310
cgcgtgcggg tccgcctgtc                                              20

<210> SEQ ID NO 1311
<211> LENGTH: 20
<212> TYPE: DNA
<213> ORGANISM: homo sapiens

<400> SEQUENCE: 1311
gcgtgcgggt ccgcctgtca                                              20

<210> SEQ ID NO 1312
<211> LENGTH: 20
<212> TYPE: DNA
<213> ORGANISM: homo sapiens

<400> SEQUENCE: 1312
gtccgcctgt cagggaaccg                                              20

<210> SEQ ID NO 1313
<211> LENGTH: 20
<212> TYPE: DNA
<213> ORGANISM: homo sapiens

<400> SEQUENCE: 1313
tccgcctgtc agggaaccga                                              20

<210> SEQ ID NO 1314
<211> LENGTH: 20
<212> TYPE: DNA
<213> ORGANISM: homo sapiens

<400> SEQUENCE: 1314
ccgcctgtca gggaaccgag                                              20

<210> SEQ ID NO 1315
<211> LENGTH: 20
<212> TYPE: DNA
<213> ORGANISM: homo sapiens

<400> SEQUENCE: 1315
cccctcggtt ccctgacagg                                              20

<210> SEQ ID NO 1316
<211> LENGTH: 20
<212> TYPE: DNA
<213> ORGANISM: homo sapiens

<400> SEQUENCE: 1316 ggaccccctcg gttccctgac                                             20
```

```
<210> SEQ ID NO 1317
<211> LENGTH: 20
<212> TYPE: DNA
<213> ORGANISM: homo sapiens

<400> SEQUENCE: 1317
cgggaggtcg gtggacccct                                              20

<210> SEQ ID NO 1318
<211> LENGTH: 20
<212> TYPE: DNA
<213> ORGANISM: homo sapiens

<400> SEQUENCE: 1318
aggggctaac gggaggtcgg                                              20

<210> SEQ ID NO 1319
<211> LENGTH: 20
<212> TYPE: DNA
<213> ORGANISM: homo sapiens

<400> SEQUENCE: 1319
ctcaggggct aacgggaggt                                              20

<210> SEQ ID NO 1320
<211> LENGTH: 20
<212> TYPE: DNA
<213> ORGANISM: homo sapiens

<400> SEQUENCE: 1320
ggctctcagg ggctaacggg                                              20

<210> SEQ ID NO 1321
<211> LENGTH: 20
<212> TYPE: DNA
<213> ORGANISM: homo sapiens

<400> SEQUENCE: 1321
tcccgttagc ccctgagagc                                              20

<210> SEQ ID NO 1322
<211> LENGTH: 20
<212> TYPE: DNA
<213> ORGANISM: homo sapiens

<400> SEQUENCE: 1322
cccgttagcc cctgagagcc                                              20

<210> SEQ ID NO 1323
<211> LENGTH: 20
<212> TYPE: DNA
<213> ORGANISM: homo sapiens

<400> SEQUENCE: 1323
cccggctctc aggggctaac                                              20

<210> SEQ ID NO 1324
<211> LENGTH: 20
<212> TYPE: DNA
<213> ORGANISM: homo sapiens

<400> SEQUENCE: 1324
acccggctct caggggctaa                                              20
```

<210> SEQ ID NO 1325
<211> LENGTH: 20
<212> TYPE: DNA
<213> ORGANISM: homo sapiens

<400> SEQUENCE: 1325
gttagcccct gagagccggg                           20

<210> SEQ ID NO 1326
<211> LENGTH: 20
<212> TYPE: DNA
<213> ORGANISM: homo sapiens

<400> SEQUENCE: 1326
agggtccacc cggctctcag                           20

<210> SEQ ID NO 1327
<211> LENGTH: 20
<212> TYPE: DNA
<213> ORGANISM: homo sapiens

<400> SEQUENCE: 1327
cagggtccac ccggctctca                           20

<210> SEQ ID NO 1328
<211> LENGTH: 20
<212> TYPE: DNA
<213> ORGANISM: homo sapiens

<400> SEQUENCE: 1328
tcagggtcca cccggctctc                           20

<210> SEQ ID NO 1329
<211> LENGTH: 20
<212> TYPE: DNA
<213> ORGANISM: homo sapiens

<400> SEQUENCE: 1329
tgagagccgg gtggaccctg                           20

<210> SEQ ID NO 1330
<211> LENGTH: 20
<212> TYPE: DNA
<213> ORGANISM: homo sapiens

<400> SEQUENCE: 1330
gaaggacctc agggtccacc                           20

<210> SEQ ID NO 1331
<211> LENGTH: 20
<212> TYPE: DNA
<213> ORGANISM: homo sapiens

<400> SEQUENCE: 1331
gcaggctgtg aaggacctca                           20

<210> SEQ ID NO 1332
<211> LENGTH: 20
<212> TYPE: DNA
<213> ORGANISM: homo sapiens

<400> SEQUENCE: 1332
tgcaggctgt gaaggacctc                                              20

<210> SEQ ID NO 1333
<211> LENGTH: 20
<212> TYPE: DNA
<213> ORGANISM: homo sapiens

<400> SEQUENCE: 1333
tgaggtcctt cacagcctgc                                              20

<210> SEQ ID NO 1334
<211> LENGTH: 20
<212> TYPE: DNA
<213> ORGANISM: homo sapiens

<400> SEQUENCE: 1334
cacgtacctg caggctgtga                                              20

<210> SEQ ID NO 1335
<211> LENGTH: 20
<212> TYPE: DNA
<213> ORGANISM: homo sapiens

<400> SEQUENCE: 1335
ccctggggac acgtacctgc                                              20

<210> SEQ ID NO 1336
<211> LENGTH: 20
<212> TYPE: DNA
<213> ORGANISM: homo sapiens

<400> SEQUENCE: 1336
ccctccccag acacaactca                                              20

<210> SEQ ID NO 1337
<211> LENGTH: 20
<212> TYPE: DNA
<213> ORGANISM: homo sapiens

<400> SEQUENCE: 1337
tgagccttga gttgtgtctg                                              20

<210> SEQ ID NO 1338
<211> LENGTH: 20
<212> TYPE: DNA
<213> ORGANISM: homo sapiens

<400> SEQUENCE: 1338
ctgagccttg agttgtgtct                                              20

<210> SEQ ID NO 1339
<211> LENGTH: 20
<212> TYPE: DNA
<213> ORGANISM: homo sapiens

<400> SEQUENCE: 1339
tctgagcctt gagttgtgtc                                              20

<210> SEQ ID NO 1340
<211> LENGTH: 20
<212> TYPE: DNA
<213> ORGANISM: homo sapiens

<400> SEQUENCE: 1340
aactcaaggc tcagaacagc                                              20

<210> SEQ ID NO 1341
<211> LENGTH: 20
<212> TYPE: DNA
<213> ORGANISM: homo sapiens

<400> SEQUENCE: 1341
gatccagcaa ctcttccaca                                              20

<210> SEQ ID NO 1342
<211> LENGTH: 20
<212> TYPE: DNA
<213> ORGANISM: homo sapiens

<400> SEQUENCE: 1342
ccagcaactc ttccacaagg                                              20

<210> SEQ ID NO 1343
<211> LENGTH: 20
<212> TYPE: DNA
<213> ORGANISM: homo sapiens

<400> SEQUENCE: 1343
ccaccttgtg gaagagttgc                                              20

<210> SEQ ID NO 1344
<211> LENGTH: 20
<212> TYPE: DNA
<213> ORGANISM: homo sapiens

<400> SEQUENCE: 1344
gctgctgctg ggccaccttg                                              20

<210> SEQ ID NO 1345
<211> LENGTH: 20
<212> TYPE: DNA
<213> ORGANISM: homo sapiens

<400> SEQUENCE: 1345
acaaggtggc ccagcagcag                                              20

<210> SEQ ID NO 1346
<211> LENGTH: 20
<212> TYPE: DNA
<213> ORGANISM: homo sapiens

<400> SEQUENCE: 1346
ggcccagcag cagcggcacc                                              20

<210> SEQ ID NO 1347
<211> LENGTH: 20
<212> TYPE: DNA
<213> ORGANISM: homo sapiens

<400> SEQUENCE: 1347
ctccaggtgc cgctgctgct                                              20

<210> SEQ ID NO 1348
<211> LENGTH: 20
<212> TYPE: DNA
<213> ORGANISM: homo sapiens

```
<400> SEQUENCE: 1348
tctccaggtg ccgctgctgc                                          20

<210> SEQ ID NO 1349
<211> LENGTH: 20
<212> TYPE: DNA
<213> ORGANISM: homo sapiens

<400> SEQUENCE: 1349
ttcgcaggtg ctgcttctcc                                          20

<210> SEQ ID NO 1350
<211> LENGTH: 20
<212> TYPE: DNA
<213> ORGANISM: homo sapiens

<400> SEQUENCE: 1350
tttgcagatg ctgaattcgc                                          20

<210> SEQ ID NO 1351
<211> LENGTH: 20
<212> TYPE: DNA
<213> ORGANISM: homo sapiens

<400> SEQUENCE: 1351
aattcagcat ctgcaaagcc                                          20

<210> SEQ ID NO 1352
<211> LENGTH: 20
<212> TYPE: DNA
<213> ORGANISM: homo sapiens

<400> SEQUENCE: 1352
cccttgatcc tagggttacc                                          20

<210> SEQ ID NO 1353
<211> LENGTH: 20
<212> TYPE: DNA
<213> ORGANISM: homo sapiens

<400> SEQUENCE: 1353
cccatcctag tttggcctcc                                          20

<210> SEQ ID NO 1354
<211> LENGTH: 20
<212> TYPE: DNA
<213> ORGANISM: homo sapiens

<400> SEQUENCE: 1354
gtggtccagg aggccaaact                                          20

<210> SEQ ID NO 1355
<211> LENGTH: 20
<212> TYPE: DNA
<213> ORGANISM: homo sapiens

<400> SEQUENCE: 1355
ctaggtgctt gtggtccagg                                          20

<210> SEQ ID NO 1356
<211> LENGTH: 20
<212> TYPE: DNA
<213> ORGANISM: homo sapiens
```

```
<400> SEQUENCE: 1356
ggtctaggtg cttgtggtcc                                               20

<210> SEQ ID NO 1357
<211> LENGTH: 20
<212> TYPE: DNA
<213> ORGANISM: homo sapiens

<400> SEQUENCE: 1357
ccacaagcac ctagaccatg                                               20

<210> SEQ ID NO 1358
<211> LENGTH: 20
<212> TYPE: DNA
<213> ORGANISM: homo sapiens

<400> SEQUENCE: 1358
cctcatggtc taggtgcttg                                               20

<210> SEQ ID NO 1359
<211> LENGTH: 20
<212> TYPE: DNA
<213> ORGANISM: homo sapiens

<400> SEQUENCE: 1359
caagcaccta gaccatgagg                                               20

<210> SEQ ID NO 1360
<211> LENGTH: 20
<212> TYPE: DNA
<213> ORGANISM: homo sapiens

<400> SEQUENCE: 1360
gcttggccac ctcatggtct                                               20

<210> SEQ ID NO 1361
<211> LENGTH: 20
<212> TYPE: DNA
<213> ORGANISM: homo sapiens

<400> SEQUENCE: 1361
gggcaggctt ggccacctca                                               20

<210> SEQ ID NO 1362
<211> LENGTH: 20
<212> TYPE: DNA
<213> ORGANISM: homo sapiens

<400> SEQUENCE: 1362
ccaagcctgc ccgaagaaag                                               20

<210> SEQ ID NO 1363
<211> LENGTH: 20
<212> TYPE: DNA
<213> ORGANISM: homo sapiens

<400> SEQUENCE: 1363
cctctttctt cgggcaggct                                               20

<210> SEQ ID NO 1364
<211> LENGTH: 20
<212> TYPE: DNA
```

<213> ORGANISM: homo sapiens

<400> SEQUENCE: 1364
ggcagcctct ttcttcgggc                                                    20

<210> SEQ ID NO 1365
<211> LENGTH: 20
<212> TYPE: DNA
<213> ORGANISM: homo sapiens

<400> SEQUENCE: 1365
ctcgggcagc ctctttcttc                                                    20

<210> SEQ ID NO 1366
<211> LENGTH: 20
<212> TYPE: DNA
<213> ORGANISM: homo sapiens

<400> SEQUENCE: 1366
tctcgggcag cctctttctt                                                    20

<210> SEQ ID NO 1367
<211> LENGTH: 20
<212> TYPE: DNA
<213> ORGANISM: homo sapiens

<400> SEQUENCE: 1367
aagaaagagg ctgcccgaga                                                    20

<210> SEQ ID NO 1368
<211> LENGTH: 20
<212> TYPE: DNA
<213> ORGANISM: homo sapiens

<400> SEQUENCE: 1368
tcaactggct gggccatctc                                                    20

<210> SEQ ID NO 1369
<211> LENGTH: 20
<212> TYPE: DNA
<213> ORGANISM: homo sapiens

<400> SEQUENCE: 1369
gtcaactggc tgggccatct                                                    20

<210> SEQ ID NO 1370
<211> LENGTH: 20
<212> TYPE: DNA
<213> ORGANISM: homo sapiens

<400> SEQUENCE: 1370
gatggcccag ccagttgacc                                                    20

<210> SEQ ID NO 1371
<211> LENGTH: 20
<212> TYPE: DNA
<213> ORGANISM: homo sapiens

<400> SEQUENCE: 1371
gtgagccggg tcaactggct                                                    20

<210> SEQ ID NO 1372
<211> LENGTH: 20

```
<212> TYPE: DNA
<213> ORGANISM: homo sapiens

<400> SEQUENCE: 1372
tgtgagccgg gtcaactggc                                                  20

<210> SEQ ID NO 1373
<211> LENGTH: 20
<212> TYPE: DNA
<213> ORGANISM: homo sapiens

<400> SEQUENCE: 1373
acattgtgag ccgggtcaac                                                  20

<210> SEQ ID NO 1374
<211> LENGTH: 20
<212> TYPE: DNA
<213> ORGANISM: homo sapiens

<400> SEQUENCE: 1374
ggcggctgac attgtgagcc                                                  20

<210> SEQ ID NO 1375
<211> LENGTH: 20
<212> TYPE: DNA
<213> ORGANISM: homo sapiens

<400> SEQUENCE: 1375
aggcggctga cattgtgagc                                                  20

<210> SEQ ID NO 1376
<211> LENGTH: 20
<212> TYPE: DNA
<213> ORGANISM: homo sapiens

<400> SEQUENCE: 1376
gcagacactc acggtgcagg                                                  20

<210> SEQ ID NO 1377
<211> LENGTH: 20
<212> TYPE: DNA
<213> ORGANISM: homo sapiens

<400> SEQUENCE: 1377
ggggcagaca ctcacggtgc                                                  20

<210> SEQ ID NO 1378
<211> LENGTH: 20
<212> TYPE: DNA
<213> ORGANISM: homo sapiens

<400> SEQUENCE: 1378
atctcccttc agggctgccc                                                  20

<210> SEQ ID NO 1379
<211> LENGTH: 20
<212> TYPE: DNA
<213> ORGANISM: homo sapiens

<400> SEQUENCE: 1379
tctcccttca gggctgccca                                                  20

<210> SEQ ID NO 1380
```

-continued

```
<211> LENGTH: 20
<212> TYPE: DNA
<213> ORGANISM: homo sapiens

<400> SEQUENCE: 1380
agggctgccc agggattgcc                                                   20

<210> SEQ ID NO 1381
<211> LENGTH: 20
<212> TYPE: DNA
<213> ORGANISM: homo sapiens

<400> SEQUENCE: 1381
aacagctcct ggcaatccct                                                   20

<210> SEQ ID NO 1382
<211> LENGTH: 20
<212> TYPE: DNA
<213> ORGANISM: homo sapiens

<400> SEQUENCE: 1382
gaacagctcc tggcaatccc                                                   20

<210> SEQ ID NO 1383
<211> LENGTH: 20
<212> TYPE: DNA
<213> ORGANISM: homo sapiens

<400> SEQUENCE: 1383
ggattgccag gagctgttcc                                                   20

<210> SEQ ID NO 1384
<211> LENGTH: 20
<212> TYPE: DNA
<213> ORGANISM: homo sapiens

<400> SEQUENCE: 1384
tgccaggagc tgttccaggt                                                   20

<210> SEQ ID NO 1385
<211> LENGTH: 20
<212> TYPE: DNA
<213> ORGANISM: homo sapiens

<400> SEQUENCE: 1385
ccaggagctg ttccaggttg                                                   20

<210> SEQ ID NO 1386
<211> LENGTH: 20
<212> TYPE: DNA
<213> ORGANISM: homo sapiens

<400> SEQUENCE: 1386
ccccaacctg gaacagctcc                                                   20

<210> SEQ ID NO 1387
<211> LENGTH: 20
<212> TYPE: DNA
<213> ORGANISM: homo sapiens

<400> SEQUENCE: 1387
agctgttcca ggttggggag                                                   20
```

-continued

```
<210> SEQ ID NO 1388
<211> LENGTH: 20
<212> TYPE: DNA
<213> ORGANISM: homo sapiens

<400> SEQUENCE: 1388
cactctgcct ctccccaacc                                               20

<210> SEQ ID NO 1389
<211> LENGTH: 20
<212> TYPE: DNA
<213> ORGANISM: homo sapiens

<400> SEQUENCE: 1389
caggttgggg agaggcagag                                               20

<210> SEQ ID NO 1390
<211> LENGTH: 20
<212> TYPE: DNA
<213> ORGANISM: homo sapiens

<400> SEQUENCE: 1390
actatttgaa atccagcctc                                               20

<210> SEQ ID NO 1391
<211> LENGTH: 20
<212> TYPE: DNA
<213> ORGANISM: homo sapiens

<400> SEQUENCE: 1391
ctatttgaaa tccagcctca                                               20

<210> SEQ ID NO 1392
<211> LENGTH: 20
<212> TYPE: DNA
<213> ORGANISM: homo sapiens

<400> SEQUENCE: 1392
tatttgaaat ccagcctcag                                               20

<210> SEQ ID NO 1393
<211> LENGTH: 20
<212> TYPE: DNA
<213> ORGANISM: homo sapiens

<400> SEQUENCE: 1393
atggcggaga ccctgaggc                                                20

<210> SEQ ID NO 1394
<211> LENGTH: 20
<212> TYPE: DNA
<213> ORGANISM: homo sapiens

<400> SEQUENCE: 1394
aaaaatggcg gagacccctg                                               20

<210> SEQ ID NO 1395
<211> LENGTH: 20
<212> TYPE: DNA
<213> ORGANISM: homo sapiens

<400> SEQUENCE: 1395 tcagggtct ccgccatttt                                                20
```

<210> SEQ ID NO 1396
<211> LENGTH: 20
<212> TYPE: DNA
<213> ORGANISM: homo sapiens

<400> SEQUENCE: 1396
ttgcagttca ccaaaaatgg                                        20

<210> SEQ ID NO 1397
<211> LENGTH: 20
<212> TYPE: DNA
<213> ORGANISM: homo sapiens

<400> SEQUENCE: 1397
atcttgcagt tcaccaaaaa                                        20

<210> SEQ ID NO 1398
<211> LENGTH: 20
<212> TYPE: DNA
<213> ORGANISM: homo sapiens

<400> SEQUENCE: 1398
gtgaactgca agatgacctc                                        20

<210> SEQ ID NO 1399
<211> LENGTH: 20
<212> TYPE: DNA
<213> ORGANISM: homo sapiens

<400> SEQUENCE: 1399
actgcaagat gacctcaggt                                        20

<210> SEQ ID NO 1400
<211> LENGTH: 20
<212> TYPE: DNA
<213> ORGANISM: homo sapiens

<400> SEQUENCE: 1400
ctgcaagatg acctcaggta                                        20

<210> SEQ ID NO 1401
<211> LENGTH: 20
<212> TYPE: DNA
<213> ORGANISM: homo sapiens

<400> SEQUENCE: 1401
ggactaacac accctacctg                                        20

<210> SEQ ID NO 1402
<211> LENGTH: 20
<212> TYPE: DNA
<213> ORGANISM: homo sapiens

<400> SEQUENCE: 1402
gtacctttct gggcagatgg                                        20

<210> SEQ ID NO 1403
<211> LENGTH: 20
<212> TYPE: DNA
<213> ORGANISM: homo sapiens

<400> SEQUENCE: 1403
ctttctgggc agatggaggc                                        20

<210> SEQ ID NO 1404
<211> LENGTH: 20
<212> TYPE: DNA
<213> ORGANISM: homo sapiens

<400> SEQUENCE: 1404
gaggctggac agtaattcag					20

<210> SEQ ID NO 1405
<211> LENGTH: 20
<212> TYPE: DNA
<213> ORGANISM: homo sapiens

<400> SEQUENCE: 1405
gtaattcaga ggcgccacga					20

<210> SEQ ID NO 1406
<211> LENGTH: 20
<212> TYPE: DNA
<213> ORGANISM: homo sapiens

<400> SEQUENCE: 1406
gaggcgccac gatggctcag					20

<210> SEQ ID NO 1407
<211> LENGTH: 20
<212> TYPE: DNA
<213> ORGANISM: homo sapiens

<400> SEQUENCE: 1407
tgaagtccac tgagccatcg					20

<210> SEQ ID NO 1408
<211> LENGTH: 20
<212> TYPE: DNA
<213> ORGANISM: homo sapiens

<400> SEQUENCE: 1408
atggctcagt ggacttcaac					20

<210> SEQ ID NO 1409
<211> LENGTH: 20
<212> TYPE: DNA
<213> ORGANISM: homo sapiens

<400> SEQUENCE: 1409
cagtggactt caaccggccc					20

<210> SEQ ID NO 1410
<211> LENGTH: 20
<212> TYPE: DNA
<213> ORGANISM: homo sapiens

<400> SEQUENCE: 1410
agtggacttc aaccggccct					20

<210> SEQ ID NO 1411
<211> LENGTH: 20
<212> TYPE: DNA
<213> ORGANISM: homo sapiens

<400> SEQUENCE: 1411
ccggccctgg gaagcctaca                                               20

<210> SEQ ID NO 1412
<211> LENGTH: 20
<212> TYPE: DNA
<213> ORGANISM: homo sapiens

<400> SEQUENCE: 1412
ccttgtaggc ttcccagggc                                               20

<210> SEQ ID NO 1413
<211> LENGTH: 20
<212> TYPE: DNA
<213> ORGANISM: homo sapiens

<400> SEQUENCE: 1413
gccctgggaa gcctacaagg                                               20

<210> SEQ ID NO 1414
<211> LENGTH: 20
<212> TYPE: DNA
<213> ORGANISM: homo sapiens

<400> SEQUENCE: 1414
ccctgggaag cctacaaggc                                               20

<210> SEQ ID NO 1415
<211> LENGTH: 20
<212> TYPE: DNA
<213> ORGANISM: homo sapiens

<400> SEQUENCE: 1415
cccgccttgt aggcttccca                                               20

<210> SEQ ID NO 1416
<211> LENGTH: 20
<212> TYPE: DNA
<213> ORGANISM: homo sapiens

<400> SEQUENCE: 1416
cctgggaagc ctacaaggcg                                               20

<210> SEQ ID NO 1417
<211> LENGTH: 20
<212> TYPE: DNA
<213> ORGANISM: homo sapiens

<400> SEQUENCE: 1417
ccccgccttg taggcttccc                                               20

<210> SEQ ID NO 1418
<211> LENGTH: 20
<212> TYPE: DNA
<213> ORGANISM: homo sapiens

<400> SEQUENCE: 1418
gaagcctaca aggcggggtt                                               20

<210> SEQ ID NO 1419
<211> LENGTH: 20
<212> TYPE: DNA
<213> ORGANISM: homo sapiens

<400> SEQUENCE: 1419
aagcctacaa ggcggggttt                                           20

<210> SEQ ID NO 1420
<211> LENGTH: 20
<212> TYPE: DNA
<213> ORGANISM: homo sapiens

<400> SEQUENCE: 1420
agcctacaag gcggggtttg                                           20

<210> SEQ ID NO 1421
<211> LENGTH: 20
<212> TYPE: DNA
<213> ORGANISM: homo sapiens

<400> SEQUENCE: 1421
atccccaaac cccgccttgt                                           20

<210> SEQ ID NO 1422
<211> LENGTH: 20
<212> TYPE: DNA
<213> ORGANISM: homo sapiens

<400> SEQUENCE: 1422
gcggggtttg gggatcccca                                           20

<210> SEQ ID NO 1423
<211> LENGTH: 20
<212> TYPE: DNA
<213> ORGANISM: homo sapiens

<400> SEQUENCE: 1423
ggtttgggga tccccacggt                                           20

<210> SEQ ID NO 1424
<211> LENGTH: 20
<212> TYPE: DNA
<213> ORGANISM: homo sapiens

<400> SEQUENCE: 1424
cactagaaac acctaccgtg                                           20

<210> SEQ ID NO 1425
<211> LENGTH: 20
<212> TYPE: DNA
<213> ORGANISM: homo sapiens

<400> SEQUENCE: 1425
ccactagaaa cacctaccgt                                           20

<210> SEQ ID NO 1426
<211> LENGTH: 20
<212> TYPE: DNA
<213> ORGANISM: homo sapiens

<400> SEQUENCE: 1426
ctcccactcc aggcgagttc                                           20

<210> SEQ ID NO 1427
<211> LENGTH: 20
<212> TYPE: DNA
<213> ORGANISM: homo sapiens -continued

<400> SEQUENCE: 1427
cactccaggc gagttctggc                                               20

<210> SEQ ID NO 1428
<211> LENGTH: 20
<212> TYPE: DNA
<213> ORGANISM: homo sapiens

<400> SEQUENCE: 1428
actccaggcg agttctggct                                               20

<210> SEQ ID NO 1429
<211> LENGTH: 20
<212> TYPE: DNA
<213> ORGANISM: homo sapiens

<400> SEQUENCE: 1429
agacccagcc agaactcgcc                                               20

<210> SEQ ID NO 1430
<211> LENGTH: 20
<212> TYPE: DNA
<213> ORGANISM: homo sapiens

<400> SEQUENCE: 1430
aggcgagttc tggctgggtc                                               20

<210> SEQ ID NO 1431
<211> LENGTH: 20
<212> TYPE: DNA
<213> ORGANISM: homo sapiens

<400> SEQUENCE: 1431
gttctggctg ggtctggaga                                               20

<210> SEQ ID NO 1432
<211> LENGTH: 20
<212> TYPE: DNA
<213> ORGANISM: homo sapiens

<400> SEQUENCE: 1432
ggagaaggtg catagcatca                                               20

<210> SEQ ID NO 1433
<211> LENGTH: 20
<212> TYPE: DNA
<213> ORGANISM: homo sapiens

<400> SEQUENCE: 1433
gagaaggtgc atagcatcac                                               20

<210> SEQ ID NO 1434
<211> LENGTH: 20
<212> TYPE: DNA
<213> ORGANISM: homo sapiens

<400> SEQUENCE: 1434
agaaggtgca tagcatcacg                                               20

<210> SEQ ID NO 1435
<211> LENGTH: 20
<212> TYPE: DNA
<213> ORGANISM: homo sapiens

<400> SEQUENCE: 1435
gaaggtgcat agcatcacgg                                         20

<210> SEQ ID NO 1436
<211> LENGTH: 20
<212> TYPE: DNA
<213> ORGANISM: homo sapiens

<400> SEQUENCE: 1436
gggggaccgc aacagccgcc                                         20

<210> SEQ ID NO 1437
<211> LENGTH: 20
<212> TYPE: DNA
<213> ORGANISM: homo sapiens

<400> SEQUENCE: 1437
gcacggccag gcggctgttg                                         20

<210> SEQ ID NO 1438
<211> LENGTH: 20
<212> TYPE: DNA
<213> ORGANISM: homo sapiens

<400> SEQUENCE: 1438
gccgcctggc cgtgcagctg                                         20

<210> SEQ ID NO 1439
<211> LENGTH: 20
<212> TYPE: DNA
<213> ORGANISM: homo sapiens

<400> SEQUENCE: 1439
ccgcctggcc gtgcagctgc                                         20

<210> SEQ ID NO 1440
<211> LENGTH: 20
<212> TYPE: DNA
<213> ORGANISM: homo sapiens

<400> SEQUENCE: 1440
cccgcagctg cacggccagg                                         20

<210> SEQ ID NO 1441
<211> LENGTH: 20
<212> TYPE: DNA
<213> ORGANISM: homo sapiens

<400> SEQUENCE: 1441
agtcccgcag ctgcacggcc                                         20

<210> SEQ ID NO 1442
<211> LENGTH: 20
<212> TYPE: DNA
<213> ORGANISM: homo sapiens

<400> SEQUENCE: 1442
tggccgtgca gctgcgggac                                         20

<210> SEQ ID NO 1443
<211> LENGTH: 20
<212> TYPE: DNA

-continued

<213> ORGANISM: homo sapiens

<400> SEQUENCE: 1443
ggccgtgcag ctgcgggact                                           20

<210> SEQ ID NO 1444
<211> LENGTH: 20
<212> TYPE: DNA
<213> ORGANISM: homo sapiens

<400> SEQUENCE: 1444
atcccagtcc cgcagctgca                                           20

<210> SEQ ID NO 1445
<211> LENGTH: 20
<212> TYPE: DNA
<213> ORGANISM: homo sapiens

<400> SEQUENCE: 1445
gtgcagctgc gggactggga                                           20

<210> SEQ ID NO 1446
<211> LENGTH: 20
<212> TYPE: DNA
<213> ORGANISM: homo sapiens

<400> SEQUENCE: 1446
cacggagaac tgcagcaact                                           20

<210> SEQ ID NO 1447
<211> LENGTH: 20
<212> TYPE: DNA
<213> ORGANISM: homo sapiens

<400> SEQUENCE: 1447
gctgcagttc tccgtgcacc                                           20

<210> SEQ ID NO 1448
<211> LENGTH: 20
<212> TYPE: DNA
<213> ORGANISM: homo sapiens

<400> SEQUENCE: 1448
ctgcagttct ccgtgcacct                                           20

<210> SEQ ID NO 1449
<211> LENGTH: 20
<212> TYPE: DNA
<213> ORGANISM: homo sapiens

<400> SEQUENCE: 1449
cagttctccg tgcacctggg                                           20

<210> SEQ ID NO 1450
<211> LENGTH: 20
<212> TYPE: DNA
<213> ORGANISM: homo sapiens

<400> SEQUENCE: 1450
ctccgtgcac ctgggtggcg                                           20

<210> SEQ ID NO 1451
<211> LENGTH: 20

```
<212> TYPE: DNA
<213> ORGANISM: homo sapiens

<400> SEQUENCE: 1451
gtcctcgcca cccaggtgca                                              20

<210> SEQ ID NO 1452
<211> LENGTH: 20
<212> TYPE: DNA
<213> ORGANISM: homo sapiens

<400> SEQUENCE: 1452
gcacctgggt ggcgaggaca                                              20

<210> SEQ ID NO 1453
<211> LENGTH: 20
<212> TYPE: DNA
<213> ORGANISM: homo sapiens

<400> SEQUENCE: 1453
aggccgtgtc ctcgccaccc                                              20

<210> SEQ ID NO 1454
<211> LENGTH: 20
<212> TYPE: DNA
<213> ORGANISM: homo sapiens

<400> SEQUENCE: 1454
tgcagtgagc tgcaggctat                                              20

<210> SEQ ID NO 1455
<211> LENGTH: 20
<212> TYPE: DNA
<213> ORGANISM: homo sapiens

<400> SEQUENCE: 1455
cctgcagctc actgcacccg                                              20

<210> SEQ ID NO 1456
<211> LENGTH: 20
<212> TYPE: DNA
<213> ORGANISM: homo sapiens

<400> SEQUENCE: 1456
ccacgggtgc agtgagctgc                                              20

<210> SEQ ID NO 1457
<211> LENGTH: 20
<212> TYPE: DNA
<213> ORGANISM: homo sapiens

<400> SEQUENCE: 1457
cagctcactg cacccgtggc                                              20

<210> SEQ ID NO 1458
<211> LENGTH: 20
<212> TYPE: DNA
<213> ORGANISM: homo sapiens

<400> SEQUENCE: 1458
tgcacccgtg gccggccagc                                              20

<210> SEQ ID NO 1459
```

```
<211> LENGTH: 20
<212> TYPE: DNA
<213> ORGANISM: homo sapiens

<400> SEQUENCE: 1459
gcacccgtgg ccggccagct                                               20

<210> SEQ ID NO 1460
<211> LENGTH: 20
<212> TYPE: DNA
<213> ORGANISM: homo sapiens

<400> SEQUENCE: 1460
gcgcccagct ggccggccac                                               20

<210> SEQ ID NO 1461
<211> LENGTH: 20
<212> TYPE: DNA
<213> ORGANISM: homo sapiens

<400> SEQUENCE: 1461
ggcgcccagc tggccggcca                                               20

<210> SEQ ID NO 1462
<211> LENGTH: 20
<212> TYPE: DNA
<213> ORGANISM: homo sapiens

<400> SEQUENCE: 1462
ggtggtggcg cccagctggc                                               20

<210> SEQ ID NO 1463
<211> LENGTH: 20
<212> TYPE: DNA
<213> ORGANISM: homo sapiens

<400> SEQUENCE: 1463
ggacggtggt ggcgcccagc                                               20

<210> SEQ ID NO 1464
<211> LENGTH: 20
<212> TYPE: DNA
<213> ORGANISM: homo sapiens

<400> SEQUENCE: 1464
gccaccaccg tcccacccag                                               20

<210> SEQ ID NO 1465
<211> LENGTH: 20
<212> TYPE: DNA
<213> ORGANISM: homo sapiens

<400> SEQUENCE: 1465
gccgctgggt gggacggtgg                                               20

<210> SEQ ID NO 1466
<211> LENGTH: 20
<212> TYPE: DNA
<213> ORGANISM: homo sapiens

<400> SEQUENCE: 1466
gaggccgctg ggtgggacgg                                               20
```

```
<210> SEQ ID NO 1467
<211> LENGTH: 20
<212> TYPE: DNA
<213> ORGANISM: homo sapiens

<400> SEQUENCE: 1467
ggagaggccg ctgggtggga                                              20

<210> SEQ ID NO 1468
<211> LENGTH: 20
<212> TYPE: DNA
<213> ORGANISM: homo sapiens

<400> SEQUENCE: 1468
gtacggagag gccgctgggt                                              20

<210> SEQ ID NO 1469
<211> LENGTH: 20
<212> TYPE: DNA
<213> ORGANISM: homo sapiens

<400> SEQUENCE: 1469
ggtacggaga ggccgctggg                                              20

<210> SEQ ID NO 1470
<211> LENGTH: 20
<212> TYPE: DNA
<213> ORGANISM: homo sapiens

<400> SEQUENCE: 1470
aagggtacgg agaggccgct                                              20

<210> SEQ ID NO 1471
<211> LENGTH: 20
<212> TYPE: DNA
<213> ORGANISM: homo sapiens

<400> SEQUENCE: 1471
gaagggtacg gagaggccgc                                              20

<210> SEQ ID NO 1472
<211> LENGTH: 20
<212> TYPE: DNA
<213> ORGANISM: homo sapiens

<400> SEQUENCE: 1472
aagtggagaa gggtacggag                                              20

<210> SEQ ID NO 1473
<211> LENGTH: 20
<212> TYPE: DNA
<213> ORGANISM: homo sapiens

<400> SEQUENCE: 1473
tctccgtacc cttctccact                                              20

<210> SEQ ID NO 1474
<211> LENGTH: 20
<212> TYPE: DNA
<213> ORGANISM: homo sapiens

<400> SEQUENCE: 1474
ctccgtaccc ttctccactt                                              20
```

```
<210> SEQ ID NO 1475
<211> LENGTH: 20
<212> TYPE: DNA
<213> ORGANISM: homo sapiens

<400> SEQUENCE: 1475
gtcccaagtg gagaagggta                                              20

<210> SEQ ID NO 1476
<211> LENGTH: 20
<212> TYPE: DNA
<213> ORGANISM: homo sapiens

<400> SEQUENCE: 1476
acccttctcc acttgggacc                                              20

<210> SEQ ID NO 1477
<211> LENGTH: 20
<212> TYPE: DNA
<213> ORGANISM: homo sapiens

<400> SEQUENCE: 1477
tcctggtccc aagtggagaa                                              20

<210> SEQ ID NO 1478
<211> LENGTH: 20
<212> TYPE: DNA
<213> ORGANISM: homo sapiens

<400> SEQUENCE: 1478
atcctggtcc caagtggaga                                              20

<210> SEQ ID NO 1479
<211> LENGTH: 20
<212> TYPE: DNA
<213> ORGANISM: homo sapiens

<400> SEQUENCE: 1479
gtcgtgatcc tggtcccaag                                              20

<210> SEQ ID NO 1480
<211> LENGTH: 20
<212> TYPE: DNA
<213> ORGANISM: homo sapiens

<400> SEQUENCE: 1480
accaggatca cgacctccgc                                              20

<210> SEQ ID NO 1481
<211> LENGTH: 20
<212> TYPE: DNA
<213> ORGANISM: homo sapiens

<400> SEQUENCE: 1481
ccaggatcac gacctccgca                                              20

<210> SEQ ID NO 1482
<211> LENGTH: 20
<212> TYPE: DNA
<213> ORGANISM: homo sapiens

<400> SEQUENCE: 1482
ccctgcggag gtcgtgatcc                                              20
```

<210> SEQ ID NO 1483
<211> LENGTH: 20
<212> TYPE: DNA
<213> ORGANISM: homo sapiens

<400> SEQUENCE: 1483
cgcagttctt gtccctgcgg                                            20

<210> SEQ ID NO 1484
<211> LENGTH: 20
<212> TYPE: DNA
<213> ORGANISM: homo sapiens

<400> SEQUENCE: 1484
tggcgcagtt cttgtccctg                                            20

<210> SEQ ID NO 1485
<211> LENGTH: 20
<212> TYPE: DNA
<213> ORGANISM: homo sapiens

<400> SEQUENCE: 1485
aactgcgcca agagcctctc                                            20

<210> SEQ ID NO 1486
<211> LENGTH: 20
<212> TYPE: DNA
<213> ORGANISM: homo sapiens

<400> SEQUENCE: 1486
ctgctcacca gagaggctct                                            20

<210> SEQ ID NO 1487
<211> LENGTH: 20
<212> TYPE: DNA
<213> ORGANISM: homo sapiens

<400> SEQUENCE: 1487
gcagggcctg ctcaccagag                                            20

<210> SEQ ID NO 1488
<211> LENGTH: 20
<212> TYPE: DNA
<213> ORGANISM: homo sapiens

<400> SEQUENCE: 1488
ccctgacccc ggcaggaggc                                            20

<210> SEQ ID NO 1489
<211> LENGTH: 20
<212> TYPE: DNA
<213> ORGANISM: homo sapiens

<400> SEQUENCE: 1489
tgaccccggc aggaggctgg                                            20

<210> SEQ ID NO 1490
<211> LENGTH: 20
<212> TYPE: DNA
<213> ORGANISM: homo sapiens

<400> SEQUENCE: 1490

-continued ccggcaggag gctggtggtt                                              20

<210> SEQ ID NO 1491
<211> LENGTH: 20
<212> TYPE: DNA
<213> ORGANISM: homo sapiens

<400> SEQUENCE: 1491
gttgaggttg gaatggctgc                                              20

<210> SEQ ID NO 1492
<211> LENGTH: 20
<212> TYPE: DNA
<213> ORGANISM: homo sapiens

<400> SEQUENCE: 1492
tgcagccatt ccaacctcaa                                              20

<210> SEQ ID NO 1493
<211> LENGTH: 20
<212> TYPE: DNA
<213> ORGANISM: homo sapiens

<400> SEQUENCE: 1493
actggccgtt gaggttggaa                                              20

<210> SEQ ID NO 1494
<211> LENGTH: 20
<212> TYPE: DNA
<213> ORGANISM: homo sapiens

<400> SEQUENCE: 1494
gaagtactgg ccgttgaggt                                              20

<210> SEQ ID NO 1495
<211> LENGTH: 20
<212> TYPE: DNA
<213> ORGANISM: homo sapiens

<400> SEQUENCE: 1495
agcggaagta ctggccgttg                                              20

<210> SEQ ID NO 1496
<211> LENGTH: 20
<212> TYPE: DNA
<213> ORGANISM: homo sapiens

<400> SEQUENCE: 1496
gtgggatgga gcggaagtac                                              20

<210> SEQ ID NO 1497
<211> LENGTH: 20
<212> TYPE: DNA
<213> ORGANISM: homo sapiens

<400> SEQUENCE: 1497
tccgctccat cccacagcag                                              20

<210> SEQ ID NO 1498
<211> LENGTH: 20
<212> TYPE: DNA
<213> ORGANISM: homo sapiens

<400> SEQUENCE: 1498
gccgctgctg tgggatggag                    20

<210> SEQ ID NO 1499
<211> LENGTH: 20
<212> TYPE: DNA
<213> ORGANISM: homo sapiens

<400> SEQUENCE: 1499
cttctgccgc tgctgtggga                    20

<210> SEQ ID NO 1500
<211> LENGTH: 20
<212> TYPE: DNA
<213> ORGANISM: homo sapiens

<400> SEQUENCE: 1500
taagcttctg ccgctgctgt                    20

<210> SEQ ID NO 1501
<211> LENGTH: 20
<212> TYPE: DNA
<213> ORGANISM: homo sapiens

<400> SEQUENCE: 1501
ttaagcttct gccgctgctg                    20

<210> SEQ ID NO 1502
<211> LENGTH: 20
<212> TYPE: DNA
<213> ORGANISM: homo sapiens

<400> SEQUENCE: 1502
gcagcggcag aagcttaaga                    20

<210> SEQ ID NO 1503
<211> LENGTH: 20
<212> TYPE: DNA
<213> ORGANISM: homo sapiens

<400> SEQUENCE: 1503
cagcggcaga agcttaagaa                    20

<210> SEQ ID NO 1504
<211> LENGTH: 20
<212> TYPE: DNA
<213> ORGANISM: homo sapiens

<400> SEQUENCE: 1504
agcttaagaa gggaatcttc                    20

<210> SEQ ID NO 1505
<211> LENGTH: 20
<212> TYPE: DNA
<213> ORGANISM: homo sapiens

<400> SEQUENCE: 1505
agggaatctt ctggaagacc                    20

<210> SEQ ID NO 1506
<211> LENGTH: 20
<212> TYPE: DNA
<213> ORGANISM: homo sapiens

```
<400> SEQUENCE: 1506
gaatcttctg gaagacctgg                                          20

<210> SEQ ID NO 1507
<211> LENGTH: 20
<212> TYPE: DNA
<213> ORGANISM: homo sapiens

<400> SEQUENCE: 1507
aatcttctgg aagacctggc                                          20

<210> SEQ ID NO 1508
<211> LENGTH: 20
<212> TYPE: DNA
<213> ORGANISM: homo sapiens

<400> SEQUENCE: 1508
atcttctgga agacctggcg                                          20

<210> SEQ ID NO 1509
<211> LENGTH: 20
<212> TYPE: DNA
<213> ORGANISM: homo sapiens

<400> SEQUENCE: 1509
cgggtagtag cggccccgcc                                          20

<210> SEQ ID NO 1510
<211> LENGTH: 20
<212> TYPE: DNA
<213> ORGANISM: homo sapiens

<400> SEQUENCE: 1510
gggccgctac tacccgctgc                                          20

<210> SEQ ID NO 1511
<211> LENGTH: 20
<212> TYPE: DNA
<213> ORGANISM: homo sapiens

<400> SEQUENCE: 1511
tggcctgcag cgggtagtag                                          20

<210> SEQ ID NO 1512
<211> LENGTH: 20
<212> TYPE: DNA
<213> ORGANISM: homo sapiens

<400> SEQUENCE: 1512
acatggtggt ggcctgcagc                                          20

<210> SEQ ID NO 1513
<211> LENGTH: 20
<212> TYPE: DNA
<213> ORGANISM: homo sapiens

<400> SEQUENCE: 1513
aacatggtgg tggcctgcag                                          20

<210> SEQ ID NO 1514
<211> LENGTH: 20
<212> TYPE: DNA
<213> ORGANISM: homo sapiens
```

```
<400> SEQUENCE: 1514
gggctggatc aacatggtgg                                                   20

<210> SEQ ID NO 1515
<211> LENGTH: 20
<212> TYPE: DNA
<213> ORGANISM: homo sapiens

<400> SEQUENCE: 1515
catgggctgg atcaacatgg                                                   20

<210> SEQ ID NO 1516
<211> LENGTH: 20
<212> TYPE: DNA
<213> ORGANISM: homo sapiens

<400> SEQUENCE: 1516
caccatgttg atccagccca                                                   20

<210> SEQ ID NO 1517
<211> LENGTH: 20
<212> TYPE: DNA
<213> ORGANISM: homo sapiens

<400> SEQUENCE: 1517
tgccatgggc tggatcaaca                                                   20

<210> SEQ ID NO 1518
<211> LENGTH: 20
<212> TYPE: DNA
<213> ORGANISM: homo sapiens

<400> SEQUENCE: 1518
gatccagccc atggcagcag                                                   20

<210> SEQ ID NO 1519
<211> LENGTH: 20
<212> TYPE: DNA
<213> ORGANISM: homo sapiens

<400> SEQUENCE: 1519
ctgcctctgc tgccatgggc                                                   20

<210> SEQ ID NO 1520
<211> LENGTH: 20
<212> TYPE: DNA
<213> ORGANISM: homo sapiens

<400> SEQUENCE: 1520
gaggctgcct ctgctgccat                                                   20

<210> SEQ ID NO 1521
<211> LENGTH: 20
<212> TYPE: DNA
<213> ORGANISM: homo sapiens

<400> SEQUENCE: 1521
ggaggctgcc tctgctgcca                                                   20

<210> SEQ ID NO 1522
<211> LENGTH: 20
<212> TYPE: DNA
```

```
<213> ORGANISM: homo sapiens

<400> SEQUENCE: 1522
ggcccagcca ggacgctagg                                            20

<210> SEQ ID NO 1523
<211> LENGTH: 12
<212> TYPE: RNA
<213> ORGANISM: Artificial Sequence
<220> FEATURE:
<223> OTHER INFORMATION: first complementary domain of Streptococcus
      pyogenes

<400> SEQUENCE: 1523
guuuuagagc ua                                                    12

<210> SEQ ID NO 1524
<211> LENGTH: 25
<212> TYPE: RNA
<213> ORGANISM: Artificial Sequence
<220> FEATURE:
<223> OTHER INFORMATION: first complementary domain of Campylobacter
      jejuni

<400> SEQUENCE: 1524
guuuuagucc cuuuuuaaau uucuu                                      25

<210> SEQ ID NO 1525
<211> LENGTH: 9
<212> TYPE: RNA
<213> ORGANISM: Artificial Sequence
<220> FEATURE:
<223> OTHER INFORMATION: first complementary domain of Parcubacteria
      bacterium

<400> SEQUENCE: 1525 uuuguagau                                                        9

<210> SEQ ID NO 1526
<211> LENGTH: 14
<212> TYPE: RNA
<213> ORGANISM: Artificial Sequence
<220> FEATURE:
<223> OTHER INFORMATION: second complementary domain of Streptococcus
      pyogenes

<400> SEQUENCE: 1526
uagcaaguua aaau                                                  14

<210> SEQ ID NO 1527
<211> LENGTH: 25
<212> TYPE: RNA
<213> ORGANISM: Artificial Sequence
<220> FEATURE:
<223> OTHER INFORMATION: second complementary domain of Campylobacter
      jejuni

<400> SEQUENCE: 1527
aagaaauuua aaagggacu aaaau                                       25

<210> SEQ ID NO 1528
<211> LENGTH: 6
<212> TYPE: RNA
<213> ORGANISM: Artificial Sequence
<220> FEATURE:
<223> OTHER INFORMATION: U6_tail domain
```

```
<400> SEQUENCE: 1528 uuuuuu                                                              6

<210> SEQ ID NO 1529
<211> LENGTH: 4
<212> TYPE: RNA
<213> ORGANISM: Artificial Sequence
<220> FEATURE:
<223> OTHER INFORMATION: H1_tail domain

<400> SEQUENCE: 1529 uuuu                                                                4

<210> SEQ ID NO 1530
<211> LENGTH: 13
<212> TYPE: RNA
<213> ORGANISM: Artificial Sequence
<220> FEATURE:
<223> OTHER INFORMATION: first complementary domain of Streptococcus
      pyogenes including (X)n
<220> FEATURE:
<221> NAME/KEY: misc_feature
<222> LOCATION: (13)..(13)
<223> OTHER INFORMATION: n may be 5-15 bases and may be any of A, T, U,
      and G

<400> SEQUENCE: 1530
guuuuagagc uan                                                     13

<210> SEQ ID NO 1531
<211> LENGTH: 26
<212> TYPE: RNA
<213> ORGANISM: Artificial Sequence
<220> FEATURE:
<223> OTHER INFORMATION: first complementary domain of Campylobacter
      jejuni including (X)n
<220> FEATURE:
<221> NAME/KEY: misc_feature
<222> LOCATION: (26)..(26)
<223> OTHER INFORMATION: n may be 5-15 bases and may be any of A, T, U,
      and G

<400> SEQUENCE: 1531
guuuuagucc cuuuuuaaau uucuun                                       26

<210> SEQ ID NO 1532
<211> LENGTH: 10
<212> TYPE: RNA
<213> ORGANISM: Artificial Sequence
<220> FEATURE:
<223> OTHER INFORMATION: first complementary domain of Parcubacteria
      bacterium including (X)n
<220> FEATURE:
<221> NAME/KEY: misc_feature
<222> LOCATION: (1)..(1)
<223> OTHER INFORMATION: n may be 1-5 bases and may be any of A, T, U,
      and G

<400> SEQUENCE: 1532 nuuuguagau                                                         10

<210> SEQ ID NO 1533
<211> LENGTH: 16
<212> TYPE: RNA
<213> ORGANISM: Artificial Sequence
<220> FEATURE:
<223> OTHER INFORMATION: second complementary domain of Streptococcus
      pyogenes including (X)n and/or (X)m
<220> FEATURE:
```

```
<221> NAME/KEY: misc_feature
<222> LOCATION: (1)..(1)
<223> OTHER INFORMATION: n may be 1-5 bases and may be any of A, T, U,
      and G
<220> FEATURE:
<221> NAME/KEY: misc_feature
<222> LOCATION: (16)..(16)
<223> OTHER INFORMATION: n may be 1-6 bases and may be any of A, T, U,
      and G

<400> SEQUENCE: 1533
nuagcaaguu aaaaun                                                       16

<210> SEQ ID NO 1534
<211> LENGTH: 27
<212> TYPE: RNA
<213> ORGANISM: Artificial Sequence
<220> FEATURE:
<223> OTHER INFORMATION: second complementary domain of Campylobacter
      jejuni (X)n and/or (X)m
<220> FEATURE:
<221> NAME/KEY: misc_feature
<222> LOCATION: (1)..(1)
<223> OTHER INFORMATION: n may be 1-15 bases and may be any of A, T, U,
      and G
<220> FEATURE:
<221> NAME/KEY: misc_feature
<222> LOCATION: (27)..(27)
<223> OTHER INFORMATION: n may be 1-15 bases and may be any of A, T, U,
      and G

<400> SEQUENCE: 1534
naagaaauuu aaaagggac uaaaaun                                            27

<210> SEQ ID NO 1535
<211> LENGTH: 11
<212> TYPE: RNA
<213> ORGANISM: Artificial Sequence
<220> FEATURE:
<223> OTHER INFORMATION: second complementary domain of Parcubacteria
      bacterium

<400> SEQUENCE: 1535
aaauuucuac u                                                            11

<210> SEQ ID NO 1536
<211> LENGTH: 16
<212> TYPE: PRT
<213> ORGANISM: Artificial Sequence
<220> FEATURE:
<223> OTHER INFORMATION: NLS derived from nucleoplasmin

<400> SEQUENCE: 1536

Lys Arg Pro Ala Ala Thr Lys Lys Ala Gly Gln Ala Lys Lys Lys Lys
1               5                   10                  15

<210> SEQ ID NO 1537
<211> LENGTH: 9
<212> TYPE: PRT
<213> ORGANISM: Artificial Sequence
<220> FEATURE:
<223> OTHER INFORMATION: c-myc NLS

<400> SEQUENCE: 1537

Pro Ala Ala Lys Arg Val Lys Leu Asp
1               5

<210> SEQ ID NO 1538
<211> LENGTH: 11
```

```
<212> TYPE: PRT
<213> ORGANISM: Artificial Sequence
<220> FEATURE:
<223> OTHER INFORMATION: c-myc NLS

<400> SEQUENCE: 1538

Arg Gln Arg Arg Asn Glu Leu Lys Arg Ser Pro
1               5                   10

<210> SEQ ID NO 1539
<211> LENGTH: 38
<212> TYPE: PRT
<213> ORGANISM: Artificial Sequence
<220> FEATURE:
<223> OTHER INFORMATION: hRNPA1 M9 NLS

<400> SEQUENCE: 1539

Asn Gln Ser Ser Asn Phe Gly Pro Met Lys Gly Gly Asn Phe Gly Gly
1               5                   10                  15

Arg Ser Ser Gly Pro Tyr Gly Gly Gly Gln Tyr Phe Ala Lys Pro
            20                  25                  30

Arg Asn Gln Gly Gly Tyr
        35

<210> SEQ ID NO 1540
<211> LENGTH: 42
<212> TYPE: PRT
<213> ORGANISM: Artificial Sequence
<220> FEATURE:
<223> OTHER INFORMATION: importin-alpha-derived IBB domain sequence

<400> SEQUENCE: 1540

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 1541
<211> LENGTH: 8
<212> TYPE: PRT
<213> ORGANISM: Artificial Sequence
<220> FEATURE:
<223> OTHER INFORMATION: myoma T protein sequence

<400> SEQUENCE: 1541

Val Ser Arg Lys Arg Pro Arg Pro
1               5

<210> SEQ ID NO 1542
<211> LENGTH: 8
<212> TYPE: PRT
<213> ORGANISM: Artificial Sequence
<220> FEATURE:
<223> OTHER INFORMATION: myoma T protein sequence

<400> SEQUENCE: 1542

Pro Pro Lys Lys Ala Arg Glu Asp
1               5

<210> SEQ ID NO 1543
<211> LENGTH: 8
<212> TYPE: PRT
<213> ORGANISM: Artificial sequence
```

```
<220> FEATURE:
<223> OTHER INFORMATION: human p53

<400> SEQUENCE: 1543

Pro Gln Pro Lys Lys Lys Pro Leu
1               5

<210> SEQ ID NO 1544
<211> LENGTH: 12
<212> TYPE: PRT
<213> ORGANISM: Artificial Sequence
<220> FEATURE:
<223> OTHER INFORMATION: mouse c-able IV

<400> SEQUENCE: 1544

Ser Ala Leu Ile Lys Lys Lys Lys Lys Met Ala Pro
1               5                   10

<210> SEQ ID NO 1545
<211> LENGTH: 7
<212> TYPE: PRT
<213> ORGANISM: Artificial Sequence
<220> FEATURE:
<223> OTHER INFORMATION: Influenza virus NS1

<400> SEQUENCE: 1545

Pro Lys Gln Lys Lys Arg Lys
1               5

<210> SEQ ID NO 1546
<211> LENGTH: 10
<212> TYPE: PRT
<213> ORGANISM: Artificial Sequence
<220> FEATURE:
<223> OTHER INFORMATION: hepatitus virus delta-antigen

<400> SEQUENCE: 1546

Arg Lys Leu Lys Lys Lys Ile Lys Lys Leu
1               5                   10

<210> SEQ ID NO 1547
<211> LENGTH: 10
<212> TYPE: PRT
<213> ORGANISM: Artificial Sequence
<220> FEATURE:
<223> OTHER INFORMATION: mouse Mx1

<400> SEQUENCE: 1547

Arg Glu Lys Lys Lys Phe Leu Lys Arg Arg
1               5                   10

<210> SEQ ID NO 1548
<211> LENGTH: 20
<212> TYPE: PRT
<213> ORGANISM: Artificial Sequence
<220> FEATURE:
<223> OTHER INFORMATION: poly(ADP-ribose) polymerase

<400> SEQUENCE: 1548

Lys Arg Lys Gly Asp Glu Val Asp Gly Val Asp Glu Val Ala Lys Lys
1               5                   10                  15

Lys Ser Lys Lys
            20

<210> SEQ ID NO 1549
<211> LENGTH: 17
```

```
<212> TYPE: PRT
<213> ORGANISM: Artificial Sequence
<220> FEATURE:
<223> OTHER INFORMATION: steroid hormone receptor glucocorticoid

<400> SEQUENCE: 1549

Arg Lys Cys Leu Gln Ala Gly Met Asn Leu Glu Ala Arg Lys Thr Lys
1               5                   10                  15
Lys

<210> SEQ ID NO 1550
<211> LENGTH: 5
<212> TYPE: PRT
<213> ORGANISM: Artificial sequence
<220> FEATURE:
<223> OTHER INFORMATION: influenza virus NS1

<400> SEQUENCE: 1550

Asp Arg Leu Arg Arg
1               5

<210> SEQ ID NO 1551
<211> LENGTH: 34
<212> TYPE: RNA
<213> ORGANISM: Artificial Sequence
<220> FEATURE:
<223> OTHER INFORMATION: tail domain of Streptococcus pyogenes

<400> SEQUENCE: 1551
uuaucaacuu gaaaaagugg caccgagucg gugc                              34

<210> SEQ ID NO 1552
<211> LENGTH: 35
<212> TYPE: RNA
<213> ORGANISM: Artificial Sequence
<220> FEATURE:
<223> OTHER INFORMATION: tail domain of Streptococcus pyogenes
<220> FEATURE:
<221> NAME/KEY: misc_feature
<222> LOCATION: (35)..(35)
<223> OTHER INFORMATION: n may be 1-15 nucleotides and may be A, T, U,
      or G

<400> SEQUENCE: 1552
uuaucaacuu gaaaaagugg caccgagucg gugcn                             35

<210> SEQ ID NO 1553
<211> LENGTH: 38
<212> TYPE: RNA
<213> ORGANISM: Artificial Sequence
<220> FEATURE:
<223> OTHER INFORMATION: tail domain of Campylobacter jejuni

<400> SEQUENCE: 1553
gggacucugc gggguuacaa uccccuaaaa ccgcuuuu                          38

<210> SEQ ID NO 1554
<211> LENGTH: 39
<212> TYPE: RNA
<213> ORGANISM: Artificial Sequence
<220> FEATURE:
<223> OTHER INFORMATION: tail domain of Campylobacter jejuni
<220> FEATURE:
<221> NAME/KEY: misc_feature
<222> LOCATION: (39)..(39)
<223> OTHER INFORMATION: n may be 1-15 base and may be A, T, U, or G

<400> SEQUENCE: 1554
```

```
gggacucugc gggguuacaa uccccuaaaa ccgcuuuun                                    39
```

<210> SEQ ID NO 1555
<211> LENGTH: 22
<212> TYPE: RNA
<213> ORGANISM: Artificial Sequence
<220> FEATURE:
<223> OTHER INFORMATION: first complementary domain of Streptococcus
      thermophilus

<400> SEQUENCE: 1555

```
guuuuagagc uguguuguuu cg                                                     22
```

<210> SEQ ID NO 1556
<211> LENGTH: 24
<212> TYPE: RNA
<213> ORGANISM: Artificial Sequence
<220> FEATURE:
<223> OTHER INFORMATION: second complementary domain of Streptococcus
      thermophilus

<400> SEQUENCE: 1556

```
cgaaacaaca cagcgaguua aaau                                                   24
```

<210> SEQ ID NO 1557
<211> LENGTH: 12
<212> TYPE: RNA
<213> ORGANISM: Artificial Sequence
<220> FEATURE:
<223> OTHER INFORMATION: proximal domain of Streptococcus pyogenes

<400> SEQUENCE: 1557

```
aaggcuaguc cg                                                                12
```

<210> SEQ ID NO 1558
<211> LENGTH: 13
<212> TYPE: RNA
<213> ORGANISM: Artificial Sequence
<220> FEATURE:
<223> OTHER INFORMATION: proximal domain of Streptococcus pyogenes
<220> FEATURE:
<221> NAME/KEY: misc_feature
<222> LOCATION: (13)..(13)
<223> OTHER INFORMATION: n may be 1-15 bases and may be A, T, U, or G

<400> SEQUENCE: 1558

```
aaggcuaguc cgn                                                               13
```

<210> SEQ ID NO 1559
<211> LENGTH: 11
<212> TYPE: RNA
<213> ORGANISM: Artificial Sequence
<220> FEATURE:
<223> OTHER INFORMATION: proximal domain of Campylobacter jejuni

<400> SEQUENCE: 1559

```
aaagaguuug c                                                                 11
```

<210> SEQ ID NO 1560
<211> LENGTH: 12
<212> TYPE: RNA
<213> ORGANISM: Artificial Sequence
<220> FEATURE:
<223> OTHER INFORMATION: proximal domain of Campylobacter jejuni
<220> FEATURE:
<221> NAME/KEY: misc_feature
<222> LOCATION: (12)..(12)

```
<223> OTHER INFORMATION: n is a, c, g, or u

<400> SEQUENCE: 1560
aaagaguuug cn                                                          12

<210> SEQ ID NO 1561
<211> LENGTH: 13
<212> TYPE: RNA
<213> ORGANISM: Artificial Sequence
<220> FEATURE:
<223> OTHER INFORMATION: proximal domain of Streptococcus thermophilus

<400> SEQUENCE: 1561
aaggcuuagu ccg                                                         13

<210> SEQ ID NO 1562
<211> LENGTH: 38
<212> TYPE: RNA
<213> ORGANISM: Artificial Sequence
<220> FEATURE:
<223> OTHER INFORMATION: tail domain of Streptococcus thermophilus

<400> SEQUENCE: 1562
uacucaacuu gaaaaggugg caccgauucg guguuuuu                              38

<210> SEQ ID NO 1563
<211> LENGTH: 13
<212> TYPE: RNA
<213> ORGANISM: Artificial Sequence
<220> FEATURE:
<223> OTHER INFORMATION: second complementary domain of Parcubacteria
      bacterium
<220> FEATURE:
<221> NAME/KEY: misc_feature
<222> LOCATION: (1)..(1)
<223> OTHER INFORMATION: n may be 1-10 bases and may be any of A, T, U,
      and G
<220> FEATURE:
<221> NAME/KEY: misc_feature
<222> LOCATION: (13)..(13)
<223> OTHER INFORMATION: n may be 1-6 bases and may be any of A, T, U,
      and G

<400> SEQUENCE: 1563
naaauuucua cun                                                         13

<210> SEQ ID NO 1564
<211> LENGTH: 57
<212> TYPE: DNA
<213> ORGANISM: Artificial Sequence
<220> FEATURE:
<223> OTHER INFORMATION: TS14 5'-3'

<400> SEQUENCE: 1564
atcttgcatc ggaccagtcg cgctgacgga cagacagaca gacaccgccc ccagccc         57

<210> SEQ ID NO 1565
<211> LENGTH: 57
<212> TYPE: DNA
<213> ORGANISM: Artificial Sequence
<220> FEATURE:
<223> OTHER INFORMATION: TS14 3'-5'

<400> SEQUENCE: 1565
tagaacgtag cctggtcagc gcgactgcct gtctgtctgt ctgtggcggg ggtcggg         57

<210> SEQ ID NO 1566
```

```
<211> LENGTH: 56
<212> TYPE: DNA
<213> ORGANISM: Artificial Sequence
<220> FEATURE:
<223> OTHER INFORMATION: TS5 5'-3'

<400> SEQUENCE: 1566
ttttactcat ccatgtgacc atgaggaaat gagagaaatg cttacacaca gaaatg        56

<210> SEQ ID NO 1567
<211> LENGTH: 56
<212> TYPE: DNA
<213> ORGANISM: Artificial Sequence
<220> FEATURE:
<223> OTHER INFORMATION: TS5 3'-5'

<400> SEQUENCE: 1567
catttctgtg tgtaagcatt tctctcattt cctcatggtc acatggatga gtaaaa        56

<210> SEQ ID NO 1568
<211> LENGTH: 30
<212> TYPE: DNA
<213> ORGANISM: Artificial Sequence
<220> FEATURE:
<223> OTHER INFORMATION: VEGFA-CjCas9 OT1

<400> SEQUENCE: 1568
agacgaactg acagacagac agacaaacag                                      30

<210> SEQ ID NO 1569
<211> LENGTH: 30
<212> TYPE: DNA
<213> ORGANISM: Artificial Sequence
<220> FEATURE:
<223> OTHER INFORMATION: VEGFa-CjCas9 On

<400> SEQUENCE: 1569
agtcgcgctg acggacagac agacagacac                                      30

<210> SEQ ID NO 1570
<211> LENGTH: 30
<212> TYPE: DNA
<213> ORGANISM: Artificial Sequence
<220> FEATURE:
<223> OTHER INFORMATION: HIF1a-CjCas9 OT2

<400> SEQUENCE: 1570
aacccagaag agagtaatca acctgtacac                                      30

<210> SEQ ID NO 1571
<211> LENGTH: 30
<212> TYPE: DNA
<213> ORGANISM: Artificial Sequence
<220> FEATURE:
<223> OTHER INFORMATION: HIF1a-CjCas9 OT1

<400> SEQUENCE: 1571
atgaggaaat ggagataaat gctcaaacac                                      30

<210> SEQ ID NO 1572
<211> LENGTH: 30
<212> TYPE: DNA
<213> ORGANISM: Artificial Sequence
<220> FEATURE:
<223> OTHER INFORMATION: HIF1a-CjCas9 On

<400> SEQUENCE: 1572
```

```
catgaggaaa tgagagaaat gcttacacac                                        30

<210> SEQ ID NO 1573
<211> LENGTH: 50
<212> TYPE: DNA
<213> ORGANISM: Homo sapiens

<400> SEQUENCE: 1573
tcatccatgt gaccatgagg aaatgagaga aatgcttaca cacagaaatg                  50

<210> SEQ ID NO 1574
<211> LENGTH: 50
<212> TYPE: DNA
<213> ORGANISM: Macaque

<400> SEQUENCE: 1574
tcatccatgt gaccatgagg aaatgagaga aatgcttaca cacagaaatg                  50

<210> SEQ ID NO 1575
<211> LENGTH: 50
<212> TYPE: DNA
<213> ORGANISM: Marmoset

<400> SEQUENCE: 1575
tcatccatgt gaccatgagg aaatgagaga aatgcttaca cacagaaatg                  50

<210> SEQ ID NO 1576
<211> LENGTH: 50
<212> TYPE: DNA
<213> ORGANISM: Pig

<400> SEQUENCE: 1576
tcatccgtgc gaccatgagg aaatgagaga aatgcttaca cacagaaatg                  50

<210> SEQ ID NO 1577
<211> LENGTH: 50
<212> TYPE: DNA
<213> ORGANISM: Dog

<400> SEQUENCE: 1577
tcatccatgt gaccatgagg aaatgagaga aatgcttaca cacagaaatg                  50

<210> SEQ ID NO 1578
<211> LENGTH: 50
<212> TYPE: DNA
<213> ORGANISM: Mouse

<400> SEQUENCE: 1578
tcatccatgt gaccatgagg aaatgagaga aatgcttaca cacagaaatg                  50
```

What is claimed is:

1. A method for artificially manipulating an hypoxia-inducible factor 1-alpha (HIF1A) gene in a cell, comprising introducing a composition to the cell,
   in which the composition comprises
   i) an editor protein or a nucleic acid encoding the editor protein, wherein the editor protein is *Campylobacter jejuni* Cas9 protein; and
   ii) a guide nucleic acid capable of targeting a target sequence, or a nucleic acid encoding the guide nucleic acid,
      wherein the target sequence is selected from SEQ ID NOs: 18, 19, 20, 26, and 29 present within the HIF1A gene on a genome in the cell and a protospacer-adjacent motif (PAM), wherein the PAM sequence is contiguous 8 nucleotide sequence that exists in the genome in the 3' direction of the target sequence, which is NNNNRYAC, wherein each N is independently A, T, C or G, R is A or G, and Y is C or T,
   wherein the guide nucleic acid comprises a guide domain capable of targeting a target sequence, and a sequence in which a first complementary domain, a linker domain, a second complementary domain, a proximal domain and a tail domain are linked in a direction of 5' to 3';

wherein the guide nucleic acid and the editor protein form a complex and induces a double strand break in nucleic acid of the HIF1A gene, and wherein the composition induces an indel mutation by NHEJ mechanism within the HIF1A gene in the cell.

2. The method of claim 1, wherein the composition is formed in a viral vector system.

3. The method of claim 2, wherein the viral vector includes one or more selected from a retrovirus, a lentivirus, an adenovirus, adeno-associated virus (AAV), a vaccinia virus, a poxvirus and a herpes simplex virus.

4. The method of claim 1, wherein the composition is a ribonucleoprotein which is a complex of a guide nucleic acid and an editor protein, wherein the guide nucleic acid is a guide RNA.

5. The method of claim 2, wherein the cell is from a subject suffering from an ocular neovascularization disease.

6. The method of claim 5, wherein the ocular neovascularization disease is diabetic retinopathy, macular degeneration, ischemic retinopathy or retinopathy of prematurity.

7. The method of claim 1, wherein the introducing is performed in vivo, ex vivo or in vitro.

8. A method for treating an ocular neovascularization disease, comprising introducing or administering a composition to a subject having the ocular neovascularization disease wherein the ocular neovascularization disease is selected from the group consisting of diabetic retinopathy, macular degeneration, ischemic retinopathy, and retinopathy of prematurity, in which the composition comprises
i) an editor protein or a nucleic acid encoding the editor protein, wherein the editor protein is *Campylobacter jejuni* Cas9 protein; and ii) a guide nucleic acid capable of targeting a target sequence, or a nucleic acid encoding the guide nucleic acid, wherein the target sequence is selected from SEQ ID NOs: 18, 19, 20, 26, and 29 which is present within a HIF1A gene on a genome in the cell and a proto-spacer-adjacent motif (PAM), wherein the PAM sequence is contiguous 8 nucleotide sequence that exists in the genome in the 3' direction of the target sequence, which is NNNN-RYAC, wherein each N is independently A, T, C or G, R is A or G, and Y is C or T, wherein the guide nucleic acid comprises
a guide domain capable of targeting the target sequence, and a sequence in which a first complementary domain, a linker domain, a second complementary domain, a proximal domain and a tail domain are linked in a direction of 5' to 3', wherein the guide nucleic acid and the editor protein form a complex and induces a double strand break in nucleic acid of the HIF1A gene, wherein the composition is formed in an adeno-associated virus (AAV) vector system, and wherein the composition induces an indel mutation by NHEJ (Non-homologous end joining) mechanism within the HIF1A gene in the cell.

9. The method of claim 8, wherein the AAV is AAV9.

10. The method of claim 8, wherein the composition is in the form of a ribonucleoprotein which is a complex of a guide nucleic acid and an editor protein, wherein the guide nucleic acid is a guide RNA.

11. The method of claim 8, wherein the composition is introduced or administered intravitreally.

* * * * *